(12) United States Patent
Hachtel et al.

(10) Patent No.: US 8,686,150 B2
(45) Date of Patent: Apr. 1, 2014

(54) 6-(4-HYDROXY-PHENYL)-3-ALKYL-1H-PYRAZOLO[3,4-B]PYRIDINE-4-CARBOXYLIC ACID AMIDE DERIVATIVES AS KINASE INHIBITORS

(71) Applicant: Sanofi, Paris (FR)

(72) Inventors: Stephanie Hachtel, Frankfurt am Main (DE); Oliver Plettenburg, Frankfurt am Main (DE); Christian Schoenau, Frankfurt am Main (DE); Matthias Loehn, Frankfurt am Main (DE); Stefania Pfeiffer-Marek, Frankfurt am Main (DE); Maria Mendez-Perez, Frankfurt am Main (DE); Aimo Kannt, Frankfurt am Main (DE); Juergen Dedio, Frankfurt am Main (DE); Markus Kohlmann, Frankfurt am Main (DE); Alexander Schiffer, Frankfurt am Main (DE); Guillaume Begis, Paris (FR); Olivier Duclos, Paris (FR); Frederic Jeannot, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/628,216

(22) Filed: Sep. 27, 2012

(65) Prior Publication Data

US 2013/0085128 A1  Apr. 4, 2013

(30) Foreign Application Priority Data

Sep. 27, 2011 (EP) ...................................... 11306228

(51) Int. Cl.
C07D 231/54 (2006.01)
A61K 31/44 (2006.01)

(52) U.S. Cl.
USPC ........... 546/120; 546/119; 546/118; 546/113; 546/112; 546/26; 514/303; 514/300; 514/299; 514/279; 514/277

(58) Field of Classification Search
None
See application file for complete search history.

(56) References Cited

U.S. PATENT DOCUMENTS

| | | | |
|---|---|---|---|
| 2008/0182844 A1* | 7/2008 | Bjergarde et al. ......... | 514/234.2 |
| 2012/0245170 A1* | 9/2012 | Bedjeguelal et al. ...... | 514/234.2 |
| 2013/0065894 A1 | 3/2013 | Loehn et al. | |
| 2013/0150340 A1 | 6/2013 | Plettenburg et al. | |

FOREIGN PATENT DOCUMENTS

| | | |
|---|---|---|
| AU | 617324 | 12/1988 |
| EP | 296110 | 12/1988 |
| EP | 657458 | 12/1994 |
| EP | 1354882 | 10/2003 |
| WO | WO 95/17182 | 6/1995 |
| WO | WO 00/58307 | 10/2000 |
| WO | WO 02/38561 | 5/2002 |
| WO | WO 2005/009389 | 2/2005 |
| WO | WO 2005/028480 | 3/2005 |
| WO | WO 2005/058307 | 6/2005 |
| WO | WO 2008/125945 | 10/2008 |
| WO | WO 2008/144253 | 11/2008 |
| WO | WO 2010/011772 | 1/2010 |
| WO | WO 2010/129668 | 11/2010 |

OTHER PUBLICATIONS

International Search Report for WO2013/045413 dated Apr. 4, 2013.
Non Final Office Action as mailed on Aug. 6, 2013, in U.S. Appl. No. 13/230,365.
Chemical Abstract Services (CAS) STN Records, Apr. 13, 2011-Apr. 17, 2011, American Chemical Society.

* cited by examiner

Primary Examiner — Brandon Fetterolf
Assistant Examiner — Theodore R West

(57) ABSTRACT

The present invention relates to pyrazolo[3,4-b]pyridine compounds of the formula I,

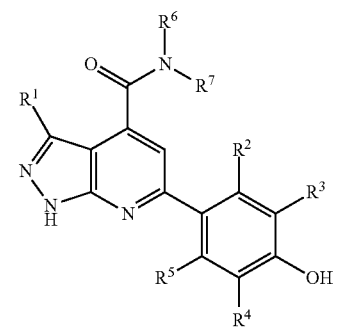

in which $R^1$, $R^2$, $R^3$, $R^4$, $R^5$, $R^6$ and $R^7$ are defined as indicated below. The compounds of the formula I are kinase inhibitors, and are useful for the treatment of diseases associated with diabetes and diabetic complications, such as, diabetic nephropathy, diabetic neuropathy and diabetic retinopathy, for example. The invention furthermore relates to the use of compounds of the formula I, in particular as active ingredients in pharmaceuticals, and pharmaceutical compositions comprising them.

11 Claims, No Drawings

6-(4-HYDROXY-PHENYL)-3-ALKYL-1H-PYRAZOLO[3,4-B]PYRIDINE-4-CARBOXYLIC ACID AMIDE DERIVATIVES AS KINASE INHIBITORS

BACKGROUND OF THE INVENTION

Protein kinase C (PKC) comprises a family of several related isoenzymes that function as serine/threonine kinases. PKC plays an important role in intercellular and intracellular signaling, gene expression, and in the control of cell differentiation and growth. Currently, at least ten isoforms of PKC are known which are different in regulation, tissue distribution, and enzymatic specificity (Newton A C. Regulation of the ABC kinases by phosphorylation: protein kinase C as a paradigm. Biochem J 2003; 370(Pt 2):361-371; Newton A C. Protein kinase C; poised to signal. Am J Physiol Endocrinol Metab 2010; 298(3):E395-E402; Nishizuka Y. Studies and prospectives of the protein kinase c family for cellular regulation. Cancer 1989; 63(10):1892-1903; Nishizuka Y. The Albert Lasker Medical Awards. The family of protein kinase C for signal transduction. JAMA 1989; 262(13):1826-1833). The PKC family of isoenzymes are grouped into three subclasses based on the domain composition of the regulatory moiety: (1) conventional PKCs (alpha, beta-II, and beta-I), (2) novel PKCs (delta, epsilon, gamma, eta and theta) and (3) atypical PKCs (zeta and iota/lambda) (Newton A C. Regulation of the ABC kinases by phosphorylation: protein kinase C as a paradigm. Biochem J 2003; 370(Pt 2):361-371; Mellor H, Parker P J. The extended protein kinase C superfamily. Biochem J 1998; 332 (Pt 2):281-292). PKC is a membrane-associated enzyme that is regulated by several distinct factors, such as membrane phospholipids, calcium, and membrane lipids, e.g. diacylglycerol (Newton A C. Regulation of the ABC kinases by phosphorylation: protein kinase C as a paradigm. Biochem J 2003; 370(Pt 2):361-371; Newton A C. Protein kinase C: poised to signal. Am J Physiol Endocrinol Metab 2010; 298(3):E395-E402; Mellor H, Parker P J. The extended protein kinase C superfamily. Biochem J 1998; 332 (Pt 2):281-292; Kishimoto A, Kikkawa U, Ogita K, Shearman M S, Nishizuka Y. The protein kinase C family in the brain: heterogeneity and its implications. Ann N Y Acad Sci 1989; 568: 181-186; Nishizuka Y. Calcium, phospholipid turnover and trans-membrane signalling. Philos Trans R Soc Land B Biol Sci 1983; 302(1108):101-112.). All PKC isoforms have an autoinhibitory pseudosubstrate sequence that is N-terminal to the C1 domain, which functions as a diacylglycerol sensor. Atypical PKCs have a diacylglycerol non-responsive C1 domain. Conventional PKCs have a C2 domain that serves as a $Ca^{2+}$-regulated phospholipid-binding module. The C2 domain in novel PKCs binds neither $Ca^{2+}$ nor membrane phospholipids. Based on the structural differences conventional PKCs require membrane phospholipids, calcium and diacylglycerol for complete activation. Novel PKCs do not require calcium but diacylglycerol for activation. The zeta and iota/lambda forms of PKC are independent of both calcium and diacylglycerol for their activation (Newton A C. Regulation of the ABC kinases by phosphorylation: protein kinase C as a paradigm. Biochem J 2003; 370(Pt 2):361-371; Newton A C. Lipid activation of protein kinases. Lipid Res 2009; 50 Suppl:S266-S271).

PKC is involved in the regulation of smooth muscle contractility. Upon stimulation PKC phosphorylates the regulatory myosin light chain ($MLC_{20}$) and inhibits the myosin associated phosphatase (MYPT). Phosphorylation of $MLC_{20}$ and inhibition of MYPT leads to an increased activity of the acto-myosin complex and to vasoconstriction in different vascular beds, e.g. resistance-sized, retinal, cerebral, coronary, conduit arteries and veins (Merkel L A, Rivera L M, Colussi D J, Perrone M H. Protein kinase C and vascular smooth muscle contractility: effects of inhibitors and down-regulation. J Pharmacol Exp Ther 1991; 257(1):134-140; Sehic E, Malik K U. Influence of protein kinase C activators on vascular tone and adrenergic neuroeffector events in the isolated rat kidney. J Pharmacol Exp Ther 1989; 251(2):634-639.). Overexpressed or overactivated PKC detrimentally affects heart function. Upon activation PKC affects the intracellular calcium homeostasis which results in reduced myocardial contractility and relaxation of the myocardium. Overall this effect leads to myocardial contractile insufficiency (Connelly K A, Kelly D J, Zhang Y, Prior D L, Advani A, Cox A J, Thai K, Krum H, Gilbert R E. Inhibition of protein kinase C-beta by ruboxistaurin preserves cardiac unction and reduces extracellular matrix production in diabetic cardiomyopathy. Circ Heart Fail 2009; 2(2):129-137). Moreover, activated PKC mediates organ damage during end-organ injuries, e.g. during ischemia in heart (Connelly K A, Kelly D J, Zhang Y, Prior D L, Advani A, Cox A J, Thai K, Krum H, Gilbert R E. Inhibition of protein kinase C-beta by ruboxistaurin preserves cardiac function and reduces extracellular matrix production in diabetic cardiomyopathy, Circ Heart Fail 2009; 2(2):129-137; Hambleton M, Hahn H, Pleger S T, Kuhn M C, Klevitsky R, Carr A N, Kimball T F, Hewett T E, Dorn G W, Koch W J, Molkentin J D. Pharmacological- and gene therapy-based inhibition of protein kinase Calpha/beta enhances cardiac contractility and attenuates heart failure. Circulation 2006; 114(6): 574-582) or kidney (Tuttle K R. Protein kinase C-beta inhibition for diabetic kidney disease. Diabetes Res Cin Pract 2008; 82 Suppl 1:S70-S74; Anderson P W, McGill J B, Tuttle K R. Protein kinase C beta inhibition: the promise for treatment of diabetic nephropathy. Curr Opin Nephrol Hypertens 2007; 16(5):397-402). PKC and especially the PKC-beta II isoform is overexpressed or overactivated in diabetes in various different types of tissue and exerts its deleterious effect to the cells, tissues and end-organs, e.g. kidney (Tuttle K R, Protein kinase C-beta inhibition for diabetic kidney disease. Diabetes Res Clin Pract 2008; 82 Suppl 1:S70-S74; Anderson P W, McGill J B, Tuttle K R. Protein kinase C beta inhibition: the promise for treatment of diabetic nephropathy. Curr Opin Nephrol Hypertens 2007; 16(5):397-402; Tuttle K R, Bakris G L, Toto R D, McGill J B, Hu K, Anderson P W. The effect of ruboxistaurin on nephropathy in type 2 diabetes. Diabetes Care 2005; 28(11):2686-2690; Kelly D J, Zhang Y, Hepper C, Gow R M, Jaworski K, Kemp B E, Wilkinson-Berka J L, Gilbert R E. Protein kinase C beta inhibition attenuates the progression of experimental diabetic nephropathy in the presence of continued hypertension. Diabetes 2003; 52(2):512-518), heart (Connelly K A, Kelly D J, Zhang Y, Prior D L, Advani A, Cox A J, Thai K, Krum H, Gilbert R E. Inhibition of protein kinase C-beta by ruboxistaurin preserves cardiac function and reduces extracellular matrix production in diabetic cardiomyopathy. Circ Heart Fail 2009; 2(2):129-137; Guo M, Wu M H, Korompai F, Yuan S Y. Upregulation of PKC genes and isozymes in cardiovascular tissues during early stages of experimental diabetes. Physiol Genomics 2003; 12(2):139-146), or in tissues like the retina (Aiello L P, Clermont A, Arora V, Davis M D, Sheetz M J, Bursell S E. Inhibition of PKC beta by oral administration of ruboxistaurin is well tolerated and ameliorates diabetes-induced retinal hemodynamic abnormalities in patients. Invest Ophthalmol V is Sci 2006; 47(1):86-92; Aiello L P. The potential role of PKC beta in diabetic retinopathy and macular edema. Surv Ophthalmol 2002; 47 Suppl 2:S263-S269; Kimura M, Ishizawa M, Miura A, Itaya S, Kanoh Y, Yasuda K, Uno Y, Morita H, Ishizuka T. Platelet protein kinase C isoform content in type 2 diabetes complicated with retinopathy and nephropathy. Platelets 2001; 12(3):138-143) or neuronal tissue (Krishnan S T, Rayman G. New treatments for diabetic neuropathy: symptomatic treatments. Curr Diab Rep 2003; 3(6):459-467; Kim H, Sasaki T, Maeda K, Koya D, Kashiwagi A, Yasuda H. Protein kinase Cbeta selective inhibitor LY333531 attenuates diabetic hyperalgesia through ameliorating cGMP level of dorsal root ganglion neurons. Diabetes 2003; 52(8):2102-2109; Cotter M A, Jack A M, Cameron N E. Effects of the protein kinase C beta inhibitor LY333531 on neural and vascular function in rats with streptozotocin-induced diabetes. Clin Sci (Lond) 2002; 103(3):311-321; Nakamura J, Kato K, Hamada Y, Nakayama M, Chaya S, Nakashima E, Naruse K, Kasuya Y, Mizubayashi R, Miwa K, Yasuda Y, Kamiya H, Ienaga K, Sakakibara F, Koh N, Hotta N. A protein kinase C-beta-selective inhibitor ameliorates neural dysfunction in streptozotocin-induced diabetic rats. Diabetes 1999; 48(10):2090-2095) or in platelets (Assert R, Scherk G, Bumbure A, Pirags V, Schatz H, Pfeiffer A F. Regulation of protein kinase C by short term hyperglycaemia in human platelets in vivo and in vitro. Diabetologia 2001; 44(2):188-195; Bynagari-Settipalli Y S, Chari R, Kilpatrick L, Kunapuli S R Protein kinase C—possible therapeutic target to treat cardiovascular diseases. Cardiovasc Hematol Disord Drug Targets 2010; 10(4):292-308; Kimura M, Ishizawa M, Miura A, Itaya S, Kanoh Y, Yasuda K, Uno Y, Morita H, Ishizuka T. Platelet protein kinase C isoform content in type 2 diabetes complicated with retinopathy and nephropathy. Platelets 2001; 12(3):138-143; Oskarsson H J, Hofineyer T G, Coppey L, Yorek M A. Effect of protein kinase C and phospholipase A2 inhibitors on the impaired ability of human diabetic platelets to cause vasodilation, Br J Pharmacol 1999; 127(4):903-908) or induces endothelial dysfunction (Chiasson V L, Quinn M A, Young K J, Mitchell B M. Protein kinase CbetaII-mediated phosphorylation of endothelial nitric oxide synthase threonine 495 mediates the endothelial dysfunction induced by FK506 (tacrolimus). J Pharmacol Exp Ther 2011; 337(3):718-723; Xu Y, Wang S, Feng L, Zhu Q, Xiang P, He B. Blockade of PKC-beta protects HUVEC from advanced glycation end products induced inflammation. Int Immunopharmacol 2010; 10(12):1552-1559; Geraldes P, King G L. Activation of protein kinase C isoforms and its impact on diabetic complications. Circ Res 2010; 106(8):1319-1331; Nacci C, Tarquinio M, Montagnani M. Molecular and clinical aspects of endothelial dysfunction in diabetes. Intern Emerg Med 2009; 4(2):107-116). Furthermore, it has been suggested that PKC signalling is involved in tumour formation (Gonelli A, Mischiati C, Guerrini R, Voltan R, Salvadori S, Zauli G. Perspectives of protein kinase C (PKC) inhibitors as anticancer agents. Mini Rev Med Chem 2009; 9(4):498-509; Ali A S, Ali S, El-Rayes B F, Philip P A, Sarkar F H. Exploitation of protein kinase C: a useful target for cancer therapy. Cancer Treat Rev 2009; 35(1):1-8), e.g. in hematological tumours (Mischiati C, Melloni E, Corallini F, Milani O, Bergamini C, Vaccarezza M. Potential role of PKC inhibitors in the treatment of hematological malignancies. Curr Pharm Des 2008; 14(21):2075-2084; Cheson B D, Zwiebel J A, Dancey J, Murgo A. Novel therapeutic agents for the treatment of myelodysplastic syndromes. Semin Oncol 2000; 27(5):560-577; Deng X, Kornblau S M, Ruvolo P P, May W S, Jr, Regulation of Bcl2 phosphorylation and potential significance for leukemic cell chemoresistance. J Natl Cancer Inst Monogr 2001; (28):30-37), in glioma formation (Baltuch G H, Dooley N P, Villemure J G, Yong V W. Protein kinase C and growth regulation of malignant gliomas. Can J Neurol Sci 1995; 22(4):264-271; Blobe G C, Obeid L M, Hannun Y A. Regulation of protein kinase C and role in cancer biology. Cancer Metastasis Rev 1994; 13(3-4):411-431; Bredel M, Pollack I F. The role of protein kinase C (PKC) in the evolution and proliferation of malignant gliomas, and the application of PKC inhibition as a novel approach to anti-glioma therapy. Acta Neurochir (Wien) 1997; 139(11):1000-1013), in gastric and intestinal cancer (Atten M J, Godoy-Romero E, Attar B M, Milson T, Zopel M, Holian O. Resveratrol regulates cellular PKC alpha and delta to inhibit growth and induce apoptosis in gastric cancer cells. Invest New Drugs 2005; 23(2):111-119; Fahrmann M. Targeting protein kinase C (PKC) in physiology and cancer of the gastric cell system. Curr Med Chem 2008; 15(12):1175-1191), in skin cancer (Birt D F, Yaktine A, Duysen E. Glucocorticoid mediation of dietary energy restriction inhibition of mouse skin carcinogenesis. J Nutr 1999; 129 (2S Suppl):571S-574S; Birt O F, Przybyszewski J, Wang W, Stewart J, Liu Y. Identification of molecular targets for dietary energy restriction prevention of skin carcinogenesis: an idea cultivated by Edward Bresnick. J Cell Biochem 2004; 91(2):258-264), lung cancer (Herbst R S, Oh Y, Wagle A, Lahn M. Enzastaurin, a protein kinase Cbeta-selective inhibitor, and its potential application as an anticancer agent in lung cancer. Clin Cancer Res 2007; 13(15 Pt. 2):s4641-s4646; Herbst R S. Targeted therapy in non-small-cell lung cancer. Oncology (Williston Park) 2002; 16(9 Suppl 9):19-24) and others. PKC is an important signal transducer of events in autoimmune responses, e.g. in T-cell (Birchall A M, Bishop J, Bradshaw D, Cline A, Coffey J, Elliott L H, Gibson V M, Greenham A, Hallam T J, Harris W. Ro 32-0432, a selective and orally active inhibitor of protein kinase C prevents T-cell activation. J Pharmacol Exp Ther 1994; 268 (2):922-929; Isakov N, Altman A. Protein kinase C(theta) in T cell activation. Annu Rev Immunol 2002; 20:761-794) or B-cell (Shinohara H, Kurosaki T. Comprehending the complex connection between PKCbeta, TAK1, and IKK in BCR signaling. Immunol Rev 2009; 232(1):300-318; Venkataraman C, Chen X C, Na S, Lee L, Neote K, Tan S L. Selective role of PKCbeta enzymatic function in regulating cell survival mediated by B cell antigen receptor cross-linking. Immunol Lett 2006; 105(1):83-89) linked autoimmune signalling, and in inflammatory processes. The above mentioned effects of the PKC-mediated signalling leads to induction or promotion of the progression of asthma (Boschelli D H. Small molecule inhibitors of PKCTheta as potential antiinflammatory therapeutics. Curr Top Med Chem 2009; 9(7): 640-654), chronic obstructive pulmonary disease (Mercer B A, D'Armiento J M. Emerging role of MAP kinase pathways as therapeutic targets in COPD. Int J Chron Obstruct Pulmon Dis 2006; 1(2):137-150; Adcock 1M, Chung K F, Caramori G, Ito K. Kinase inhibitors and airway inflammation. Eur J Pharmacol 2006; 533(1-3):118-132; Dempsey E C, Cool C D, Littler C M. Lung disease and PKCs. Pharmacol Res 2007; 55(6):545-559; Ishii M, Kurachi Y. Muscarinic acetylcholine receptors. Curr Pharm Des 2006; 12(28):3573-3581; Medina-Tato D A, Watson M L, Ward S G. Leukocyte navigation mechanisms as targets in airway diseases. Drug Discov Today 2006; 11(19-20):866-879), pulmonary hypertension (Agbani E O, Coats P, Mills A, Wadsworth R M. Peroxynitrite stimulates pulmonary artery endothelial and smooth muscle cell proliferation: involvement of ERK and PKC. Pulm Pharmacol Ther 2011; 24(1):100-109; Littler C M, Wehling C A, Wick M J, Fagan K A, Cool C D, Messing R O, Dempsey E C. Divergent contractile and structural responses of the murine PKC-epsilon null pulmonary circulation to chronic hypoxia. Am J Physiol Lung Cell Mol Physiol 2005; 289(6):L1083-L1093), retinopathy, like retinal ischemia and neovascularization (Galvez M I. Protein kinase C inhibitors in the treatment of diabetic retinopathy. Review. Curr Pharm Biotechnol 2011; 12(3):386-391; Schwartz S G, Flynn H W, Jr., Aiello L P. Ruboxistaurin mesilate hydrate for diabetic retinopathy. Drugs Today (Barc) 2009; 45(4):269-274), nephropathy, including hypertension-induced (Kelly D J, Edgley A J, Zhang Y, Thai K, Tan S M, Cox A J, Advani A, Connelly K A, Whiteside C I, Gilbert R E, Protein kinase C-beta inhibition attenuates the progression of nephropathy in non-diabetic kidney disease. Nephrol Dial Transplant 2009; 24(6):1782-1790; Hayashi K, Wakino S, Ozawa Y, Homma K, Kanda T, Okubo K, Takamatsu Tatematsu S, Kumagai H, Saruta T. Role of protein kinase C in Ca channel blocker-induced renal arteriolar dilation in spontaneously hypertensive rats—studies in the isolated perfused hydronephrotic kidney. Keio J Med 2005; 54(2):102-108; Kelly D J, Zhang Y, Hepper C, Gow R M, Jaworski K, Kemp B E, Wilkinson-Berka J L, Gilbert R E. Protein kinase C beta inhibition attenuates the progression of experimental diabetic nephropathy in the presence of continued hypertension. Diabetes 2003; 52(2):512-518), non-hypertension-induced, and diabetic nephropathies (Danis R P, Sheetz M J. Ruboxistaurin: PKC-beta inhibition for complications of diabetes. Expert Opin Pharmacother 2009; 10(17):2913-2925; Tuttle K R. Protein kinase C-beta inhibition for diabetic kidney disease. Diabetes Res Clin Pract 2008; 82 Suppl 1:S70-S74), renal failure (Danis R P, Sheetz M J. Ruboxistaurin: PKC-beta inhibition for complications of diabetes. Expert Opin Pharmacother 2009: 10(17):2913-2925: Yamagishi S; Fukami K, Ueda S; Okuda S. Molecular mechanisms of diabetic nephropathy and its therapeutic intervention. Curr Drug Targets 2007; 8(8):952-959) and myocardial infarction (Bynagari-Settipalli Y S, Chari R, Kilpatrick L, Kunapuli S P. Protein kinase C—possible therapeutic target to treat cardiovascular diseases. Cardiovasc Hematol Disord Drug Targets 2010; 10(4):292-308; Rohilla A, Singh G, Singh M, Bala kP. Possible involvement of PKC-delta in the abrogated cardioprotective potential of ischemic preconditioning in hyperhomocysteinemic rat hearts. Biomed Pharmacother 2010; 64(3):195-202; Liu Q, Chen X, Macdonnell S M, Kranias E G, Lorenz J N, Leitges M, Houser S R, Molkentin J D. Protein kinase C{alpha}, but not PKC{beta} or PKC {gamma}, regulates contractility and heart failure susceptibility: implications for ruboxistaurin as a novel therapeutic approach. Circ Res 2009: 105(2):194-200; Yonezawa T, Kurata R, Kimura M, Inoko H. PKC delta and epsilon in drug targeting and therapeutics. Recent Pat DNA Gene Seq 2009; 3(2):96-101) cardiac hypertrophy and failure (Ferreira J C, Brum P C, Mochly-Rosen D. betaIIPKC and epsilon PKC isozymes as potential pharmacological targets in cardiac hypertrophy and heart failure. J Mol Cell Cardiol 2010; Palaniyandi S S, Sun L, Ferreira J C, Mochly-Rosen D. Protein kinase C in heart failure: a therapeutic target? Cardiovasc Res 2009; 82(2): 229-239), coronary heart disease, artherosclerosis, restenosis (Ding R Q, Tsao J, Chai H, Mochly-Rosen D, Zhou W. Therapeutic potential for protein kinase C inhibitor in vascular restenosis. J Cardiovasc Pharmacol Ther 2011; 16(2):160-167; Schleicher E, Friess U. Oxidative stress, AGE, and atherosclerosis. Kidney Int Suppl 2007; (106):S17-S26), diabetes, diabetic complications, glucose utilization and metabolic syndrome (Bynagari-Settipalli Y S, Chari R, Kilpatrick L, Kunapuli S R Protein kinase C possible therapeutic target to treat cardiovascular diseases. Cardiovasc Hematol Disord Drug Targets 2010; 10(4):292-308; Geraldes P, King G L. Activation of protein kinase C isoforms and its impact on diabetic complications. Circ Res 2010; 106(8):1319-1331; Danis R P, Sheetz M J. Ruboxistaurin: PKC-beta inhibition for complications of diabetes. Expert Opin Pharmacother 2009; 10(17):2913-2925), immune diseases (Baier G, Wagner J. PKC inhibitors: potential in T cell-dependent immune diseases. Curr Opin Cell Biol 2009; 21(2):262-267; Mecklenbrauker I, Saijo K, Zheng N Y, Leitges M, Tarakhovsky A. Protein kinase Cdelta controls self-antigen-induced B-cell tolerance. Nature 2002; 416(6883):860-865: Wilkinson S E, Hallam T J. Protein kinase C: is its pivotal role in cellular activation over-stated? Trends Pharmacol Sci 1994; 15(2):53-57; Costello R, Mawas C, Olive D. Differential immunosuppressive effects of metabolic inhibitors on T-lymphocyte activation, Eur Cytokine Netw 1993; 4(2):139-146), like psoriasis (Sommerer C, Zeier M. AEB071—a promising immunosuppressive agent. Clin Transplant 2009; 23 Suppl 21:15-18; Rasmussen H H, Celis J E. Evidence for an altered protein kinase C (PKC) signaling pathway in psoriasis. J Invest Dermatol 1993; 101(4):560-566; Fisher G J, Tavakkol A, Leach K, Burns O, Basta P, Loomis C, Griffiths C E, Cooper K D, Reynolds N J, Elder J T, Differential expression of protein kinase C isoenzymes in normal and psoriatic adult human skin: reduced expression of protein kinase C-beta H in psoriasis. J Invest Dermatol 1993; 101(4):553-559), rheumatoid arthritis (Healy A M, Izmailova E, Fitzgerald M, Walker R, Hattersley M, Silva M, Siebert E, Terkelsen J, Picarella O, Pickard M D, LeClair B, Chandra S, Jaffee B. PKC-theta-deficient mice are protected from Th1-dependent antigen-induced arthritis. J Immunol 2006; 177(3):1886-1893; Ji J D, Tassiulas I, Park-Min K H, Aydin A, Mecklenbrauker I, Tarakhovsky A, Pricop L, Salmon J E, Ivashkiv L B. Inhibition of interleukin 10 signaling after Fc receptor ligation and during rheumatoid arthritis. J Exp Med 2003; 197(11):1573-1583; Kehlen A, Thiele K, Riemann D, Langner J. Expression, modulation and signalling of IL-17 receptor in fibroblast-like synoviocytes of patients with rheumatoid arthritis. Clin Exp Immunol 2002; 127(3):539-546), or other autoimmune disorders (Zanin-Zhorov A, Dustin M L, Blazar B R. PKC-theta function at the immunological synapse: prospects for therapeutic targeting. Trends Immunol 2011; 32(8):358-363), central nervous system disorders (Liang J, Takeuchi H, Jin S, Noda M, Li H, Doi Y, Kawanokuchi J, Sonobe Y, Mizuno T, Suzumura A. Glutamate induces neurotrophic factor production from microglia via protein kinase C pathway. Brain Res 2010; 1322:8-23; Bastianetto S, Zheng W H, Quirion R. Neuroprotective abilities of resveratrol and other red wine constituents against nitric oxide-related toxicity in cultured hippocampal neurons. Br J Pharmacol 2000; 131(4):711-720), cerebral ischemia or cerebral vasospasm (Bu X, Zhang N, Yang X, Liu Y, Du J, Liang J, Xu Q, Li J. Proteomic analysis of cPKCbetaII-interacting proteins involved in HPC-induced neuroprotection against cerebral ischemia of mice. J Neurochem 2011; 117(2):346-356), neuropathies and pain, e.g. neuropathic pain (Nakajima A, Tsuboi Y, Suzuki I, Honda K, Shinoda M, Kondo M, Matsuura S, Shibuta K, Yasuda M, Shimizu N, Iwata K. PKC-gamma in Vc and C1/C2 is involved in trigeminal neuropathic pain. J Dent Res 2011; 90(6):177-781; Malmberg A B, Chen C, Tonegawa S, Basbaum A I. Preserved acute pain and reduced neuropathic pain in mice lacking PKCgamma. Science 1997; 278(5336):279-283), cancer development and progression, neoplasia where inhibition of protein kinase C has been shown to inhibit tumor cell growth and metastasis (Kim J, Thorne S H, Sun L, Huang B, Mochly-Rosen D. Sustained inhibition of PKCalpha reduces intravasation and lung seeding during mammary tumor metastasis in an in vivo mouse model. Oncogene 2011; 30(3):323-333; Spindler K L, Lindebjerg J, Lahn M, Kjaer-Frifeldt S, Jakobsen A. Protein kinase C-beta II (PKC-beta II) expression in patients with colorectal cancer. Int J Colorectal Dis 2009; 24(6):641-645;

Guo K, Li Y, Kang X, Sun L, Cui J, Gao D, Liu Y. Role of PKCbeta in hepatocellular carcinoma cells migration and invasion in vitro: a potential therapeutic target. Clin Exp Metastasis 2009; 26(3):189-195), angiogenesis (Nakamura S, Chikaraishi Y, Tsuruma K, Shirnazawa M, Hare H. Ruboxistaurin, a PKCbeta inhibitor, inhibits retinal neovascularization via suppression of phosphorylation of ERK1/2 and Akt. Exp Eye Res 2010; 90(1):137-145; Ali A S, Ah S, El-Rayes B F, Philip P A, Sarkar F H. Exploitation of protein kinase C: a useful target for cancer therapy. Cancer Treat Rev 2009; 35(1):1-8; Tekle C, Giovannetti E, Sigmond J, Graff J R, Smid K, Peters G J. Molecular pathways involved in the synergistic interaction of the PKC beta inhibitor enzastaurin with the antifolate pemeterxed in non-small cell lung cancer cells. Br J Cancer 2008; 99(5):750-759; Mischiati C, Melloni E, Corallini F, Miani O, Bergamini C, Vaccarezza M. Potential role of PKC inhibitors in the treatment of hematological malignancies, Curr Pharm Des 2008; 14(21):2075-2084), platelet disorders leading to thrombosis (Gilio K, Harper M T, Cosemans J M, Konopatskaya O, Munnix I C, Prinzen L, Leitges M, Liu Q, Molkentin J D, Heemskerk J W, Poole A W. Functional divergence of platelet protein kinase C (PKC) isoforms in thrombus formation on collagen. J Bid Chem 2010; 285(30):23410-23419; Chari R, Getz T, Nagy B, Jr., Bhavaraju K, Mao Y, Bynagari Y S, Murugappan S, Nakayama K, Kunapuli S P. Protein kinase C[delta] differentially regulates platelet functional responses. Arterioscler Thromb Vasc Bid 2009; 29(5):699-705; Nagy B, Jr., Bhavaraju K, Getz T, Bynagari Y S, Kim S, Kunapuli S P. Impaired activation of platelets lacking protein kinase C-theta isoform. Blood 2009; 113(11):2557-2567; Harper M T, Poole A W. Isoform-specific functions of protein kinase C: the platelet paradigm. Biochem Sac Trans 2007; 35(Pt 5):1005-1008; Strehi A, Munnix I C, Kuijpers M J, van der Meijden P E, Cosemans J M, Feijge M A, Nieswandt B, Heemskerk J W. Dual role of platelet protein kinase C in thrombus formation: stimulation of pro-aggregatory and suppression of procoagulant activity in platelets. J Biol Chem 2007; 282(10):7046-7055; London F S. The protein kinase C inhibitor RO318220 potentiates thrombin-stimulated platelet-supported prothrombinase activity. Blood 2003; 102(7):2472-2481; Wheeler-Jones C P, Patel Y, Kakkar V V, Krishnamurthi S. Translocation of protein kinase C (PKC) in stimulated platelets: a role for aggregation in PKC degradation. Br J Pharmacol 1989; 98 Suppl:845P), and leukocyte aggregation (Hu H, Zhang W, Li N. Glycoprotein IIb/IIIa inhibition attenuates platelet-activating factor-induced platelet activation by reducing protein kinase C activity. J Thromb Haemost 2003; 1(8):1805-1812; Kotovuori A, Pessa-Morikawa T, Kotovuori P, Nortamo P, Gahmberg C G. ICAM-2 and a peptide from its binding domain are efficient activators of leukocyte adhesion and integrin affinity. J Immunol 1999; 162(11):6613-6620; Lorenz H M, Lagoo A S, Hardy K J. The cell and molecular basis of leukocyte common antigen (CD45)-triggered, lymphocyte function-associated antigen-1-/intercellular adhesion molecule-1-dependent, leukocyte adhesion. Blood 1994; 83(7):1862-1870).

Until now, mainly staurosporine derivatives have been described as PKC inhibitors in the prior art, for example Ruboxistaurin (e.g. EP 657458), Enzastaurin (e.g. WO 9517182), Midostaurin (e.g. EP 296110) or Sotrastaurin (e.g. WO 2002038561). Only very few PKCβ inhibitors, which are not derived from staurosporine have been described, such as 3-amido-pyrrolo[3,4-c]pyrazole-5(1H,4H,6H)carbaldehydes in WO 2008125945. However, there continues to be a need for further effective low molecular weight PKCβ inhibitors, in particular in view of safety and selectivity. The present invention satisfies this need by providing the pyrazolo[3,4-b]pyridine compounds of the formula I.

Pyrazolo[3,4-b]pyridine derivatives which are useful for pharmaceutical applications, have already been disclosed, for example in WO 2005028480 (Neurogen Corp. and Aventis Pharmaceuticals Inc.), in WO 2005009389 (Exelixis Inc.) or in WO 2000058307 (Neurogen Corp.).

SUMMARY OF THE INVENTION

The present invention relates to pyrazolo[3,4-b]pyridine compounds of the formula I,

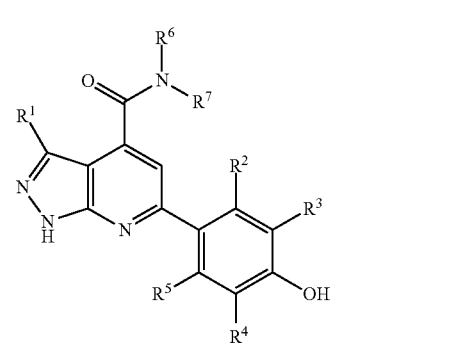

in which $R^1$, $R^2$, $R^3$, $R^4$, $R^5$, $R^6$ and $R^7$ are defined as indicated below. The compounds of the formula I are kinase inhibitors, and are useful for the treatment of diseases associated with diabetes and diabetic complications, e.g., diabetic nephropathy, diabetic neuropathy and diabetic retinopathy, for example. The invention furthermore relates to the use of compounds of the formula I, in particular as active ingredients in pharmaceuticals, and pharmaceutical compositions comprising them.

DETAILED DESCRIPTION OF THE INVENTION

Accordingly, a subject of the present invention is a compound of the formula I or the use of a compound of the formula I,

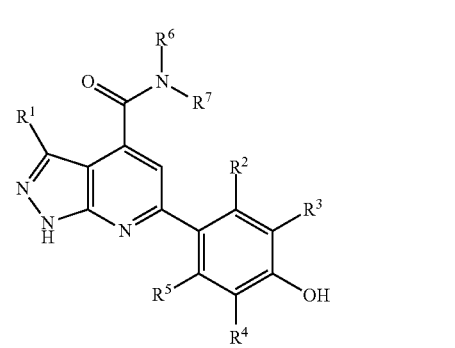

wherein
$R^1$ is $(C_1-C_4)$-alkyl, cyclopropyl, or $CF_3$;
$R^2$ is H, $(C_1-C_4)$-alkyl, halogen or O—$(C_1-C_4)$-alkyl;
$R^3$ is H, $(C_1-C_4)$-alkyl, halogen or O—$(C_1-C_4)$-alkyl;
$R^4$ is H or halogen;
$R^5$ is H, halogen or $(C_1-C_4)$-alkyl;
$R^6$ is H, $(C_1-C_4)$-alkyl or $(C_1-C_4)$-alkylene-phenyl;

R⁷ is
a) $(C_0-C_6)$-alkyl which is mono-substituted by
  i) a 3- to 8-membered monocyclic heterocycle comprising a ring nitrogen atom and optionally one further ring heteroatom selected from the group consisting of nitrogen and oxygen, which is unsubstituted or substituted by one to five identical or different substituents selected from the group consisting of
    ia) F,
    ib) $(C_1-C_4)$-alkyl, which is unsubstituted or one to fivefold substituted by F.
    ic) O—$(C_1-C_4)$-alkyl, which is unsubstituted or one to fivefold substituted by F,
    id) phenyl, which is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F,
    ie) $(C_1-C_4)$-alkylene-phenyl, which is unsubstituted or one to fivefold substituted by F,
    if) $(C_3-C_8)$-cycloalkyl,
    ig) oxo (=O), and
    ih) (CO)—$(C_1-C_4)$-alkyl, and
    ij) $(C_0-C_2)$-alkylene-NH—$(C_1-C_4)$-alkyl, $(C_0-C_2)$-alkylene-N($(C_1-C_4)$-alkyl)$_2$;
    and wherein $(C_0-C_6)$-alkyl can be further mono-substituted by phenyl or pyridyl, wherein phenyl or pyridyl is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F;
  ii) $(C_3-C_8)$-cycloalkyl which is substituted by one to two identical or different substituents selected from the group consisting of NH$_2$, NH($(C_1-C_4)$-alkyl) and N($(C_1-C_4)$-alkyl)$_2$, and wherein $(C_3-C_8)$-cycloalkyl can be further substituted by one to three identical or different substituents selected from the group consisting of
    iia) F,
    iib) $(C_1-C_4)$-alkyl, wherein $(C_1-C_4)$-alkyl is unsubstituted or one to fivefold substituted by F,
    iic) O—$(C_1-C_4)$-alkyl, which is unsubstituted or one to fivefold substituted by F,
    iid) phenyl, which is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F, and
    iie) $(C_1-C_4)$-alkylene-phenyl, which is unsubstituted or one to fivefold substituted by F;
  or
  iii) NR⁸R⁹, wherein
    R⁸ is H or $(C_1-C_4)$-alkyl, and
    R⁹ is H or $(C_1-C_6)$-alkyl,
    and wherein $(C_0-C_6)$-alkyl can be further mono-substituted by phenyl, phenylene-$(C_1-C_4)$-alkyl or phenylene-O—$(C_1-C_4)$-alkyl;
b) a bicyclic $(C_6-C_{11})$-cycloalkyl group, which is mono-substituted by $(C_0-C_2)$-alkylene-NH$_2$, $(C_0-C_2)$-alkylene-NH—$(C_1-C_4)$-alkyl, or $(C_0-C_2)$-alkylene-N($(C_1-C_4)$-alkyl)$_2$;
c) a fused bicyclic $(C_6-C_{10})$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F;
d) a spiro bicyclic $(C_7-C_{11})$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F;
e) a bridged bicyclic $(C_7-C_9)$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F; or
f) a tricyclic $(C_{11}-C_{15})$-heterocycloalkyl group containing one nitrogen atom, which is attached via a carbon atom and which consists of a spiro bicyclic ring with an additional fused phenyl ring, and which is unsubstituted or substituted by one or two identical or different substituents selected from the group consisting of F and $(C_1-C_4)$-alkyl, which is unsubstituted or one to fivefold substituted by F;
or
R⁶ and R⁷ together with the N-atom carrying them denote
a) a 1,4-piperazinyl of the formula

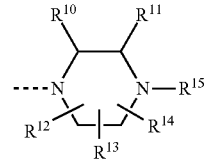

wherein
R¹⁰ is H, or $(C_0-C_6)$-alkyl, which is unsubstituted or one to fivefold substituted by F, or mono-substituted by a substituent selected from the group consisting of
  i) O—$(C_1-C_4)$-alkyl, which is unsubstituted or one to fivefold substituted by F,
  ii) $(C_3-C_6)$-cycloalkyl,
  iii) phenyl, which is unsubstituted or substituted by one to two identical or different substituents selected from the group consisting of halogen, CF$_3$, O—$(C_1-C_4)$-alkyl, OCF$_3$, and $(C_1-C_4)$-alkyl,
  iv) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, CF$_3$, O—$(C_1-C_4)$-alkyl, OCF$_3$, and $(C_1-C_4)$-alkyl,
  v) benzo[1,3]dioxole, and
  vi) CO—R¹⁶;
R¹¹ is H or $(C_0-C_6)$-alkyl, which is unsubstituted or one to fivefold substituted by F or mono-substituted by a substituent selected from the group consisting of
  i) CO—R¹⁷,
  ii) $(C_3-C_6)$-cycloalkyl,
  iii) phenyl, which is unsubstituted or substituted by one to two identical or different substituents selected from the group consisting of halogen, CF$_3$, O—$(C_1-C_4)$-alkyl, OCF$_3$, and $(C_1-C_4)$-alkyl,
  iv) O—$(C_1-C_4)$-alkyl, which is unsubstituted or one to fivefold substituted by F, v) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, $CF_3$, $OCF_3$, and $(C_1-C_4)$-alkyl, and vi) oxo (=O);

$R^{12}$ is H, $(C_1-C_6)$-alkyl, which is unsubstituted or one to fivefold substituted by F, or phenyl;

$R^{13}$ is H or $(C_1-C_6)$-alkyl;

$R^{14}$ is H or $(C_1-C_4)$-alkyl;

$R^{15}$ is H, $(C_1-C_6)$-alkyl, $(C_3-C_6)$-cycloalkyl or CO—$R^{18}$, wherein $(C_1-C_6)$-alkyl is unsubstituted or one to fivefold substituted by F, or mono-substituted by a substituent selected from the group consisting of $SO_2$—$(C_1-C_4)$-alkyl, phenyl, a 5- to 6-membered monocyclic heterocyclic ring comprising one heteroatom selected from the group consisting of nitrogen and oxygen, a 5- to 6-membered monocyclic heteroaromatic ring comprising one heteroatom selected from the group consisting of nitrogen and oxygen;

$R^{16}$ is O—$(C_1-C_4)$-alkyl or NH—$(C_1-C_6)$-alkyl;

$R^{17}$ is O—$(C_1-C_4)$-alkyl;

$R^{18}$ is $(C_1-C_4)$-alkyl, $NH_2$, phenyl, a 5- to 6-membered monocyclic heteroaromatic ring comprising one heteroatom selected from the group consisting of nitrogen and oxygen, or a 5- to 6-membered monocyclic heteroaromatic ring comprising one heteroatom selected from the group consisting of nitrogen and oxygen, where phenyl can be further mono-substituted by $(C_1-C_4)$-alkyl or O—$(C_1-C_4)$-alkyl;

b) a four to seven membered monocyclic heterocycloalkyl group containing a nitrogen atom, which is attached via said nitrogen and which is mono-substituted by $(C_0-C_6)$-alkylene-$NH_2$, $(C_0-C_6)$-alkylene-NH—$(C_1-C_4)$-alkyl, $(C_0-C_6)$-alkylene-NH-phenyl, $(C_0-C_6)$-alkylene-N($(C_1-C_4)$-alkyl$)_2$, or $(C_0-C_6)$-alkylene-N($(C_1-C_4)$-alkyl)(phenyl); and wherein said heterocycloalkyl group can be further mono-substituted by $(C_1-C_6)$-alkyl, which is unsubstituted or one to fivefold substituted by F, CO—O $(C_1-C_4)$-alkyl or phenyl;

c) a 1,4-diazepanyl, which is unsubstituted or mono-substituted by $(C_1-C_6)$-alkyl, wherein $(C_1-C_6)$-alkyl is unsubstituted or one to fivefold substituted by F, CO-phenyl, or CO-pyridyl;

d) a fused bicyclic $(C_6-C_{10})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or substituted by one to two identical or different substituents selected from the group consisting of F, $(C_0-C_2)$-alkylene-phenyl, oxo (=O) and $(C_1-C_4)$-alkyl, wherein $(C_1-C_4)$-alkyl is unsubstituted or one to fivefold substituted by F;

e) a spiro bicyclic $(C_7-C_{11})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or mono- or di-substituted by F or $(C_1-C_4)$-alkyl, which is unsubstituted or one to fivefold substituted by F;

f) a bridged bicyclic $(C_7-C_9)$-heterocycloalkyl group containing one nitrogen atom, which is attached via said nitrogen atom, which is mono-substituted by $(C_0-C_2)$-alkylene-$NH_2$, $(C_0-C_2)$-alkylene-NH—$(C_1-C_4)$-alkyl, $(C_0-C_2)$-alkylene-N($(C_1-C_4)$-alkyl$)_2$ g) a bridged bicyclic $(C_7-C_9)$-heterocycloalkyl group containing two nitrogen atoms, which is attached via a nitrogen atom; and which is unsubstituted or substituted by one to four identical or different substituents selected from the group consisting of the group consisting of F, OH, and $(C_1-C_4)$-alkyl, which is unsubstituted or one to fivefold substituted by F;

or h) a tricyclic $(C_{11}-C_{15})$-heterocycloalkyl group containing two nitrogen atoms, which is attached via a nitrogen atom and which consists of a spiro bicyclic ring with an additional fused phenyl ring, and which is unsubstituted or substituted by one or two identical or different substituents selected from the group consisting of F and $(C_1-C_4)$-alkyl, which is unsubstituted or one to fivefold substituted by F; in any of its stereoisomeric forms, or a mixture of stereoisomeric forms in any ratio, or a physiologically acceptable salt thereof, or a physiologically acceptable solvate of any of them.

In one embodiment the following compounds are disclaimed from the compounds covered by formula I as defined above:

(20) ((S)-2-Ethyl-piperazin-1-yl)-[6-(4-hydroxy-phenyl)-3-methyl-1H-pyrazolo[3,4-b]pyridin-4-yl]-methanone,

(21) [6-(4-Hydroxy-phenyl)-3-methyl-1H-pyrazolo[3,4-b]pyridin-4-yl]-((R)-2-methoxymethyl-piperazin-1-yl)-methanone,

(22) 6-(4-Hydroxy-phenyl)-3-methyl-1H-pyrazolo[3,4-b]pyridine-4-carboxylic acid phenethyl-(R)-piperidin-3-yl-amide,

(26) [6-(4-Hydroxy-phenyl)-3-methyl-1H-pyrazolo[3,4-b]pyridin-4-yl]-(2-phenyl-piperazin-1-yl)-methanone,

(32) (2-Benzo[1,3]dioxol-5-yl-piperazin-yl)-[6-(4-hydroxyphenyl)-3-methyl-1H-pyrazolo[3,4-b]pyridin-4-yl]-methanone,

(41) 6-(4-Hydroxy-phenyl)-3-methyl-1H-pyrazolo[3,4-b]pyridine-4-carboxylic acid (4-methyl-piperidin-4-yl)-amide, (373) 6-(4-Hydroxy-phenyl)-3-methyl-1H-pyrazolo[3,4-b]pyridine-4-carboxylic acid (2,3-dihydro-spiro[1H-indene-1,4'-piperidin]-3-yl)-amide, (374) [6-(4-Hydroxy-phenyl)-3-methyl-1H-pyrazolo[3,4-b]pyridin-4-yl]-(2-pyridin-3-yl-piperazin-1-yl)-methanone, (375) (3-Benzyl-piperazin-1-yl)-[6-(4-hydroxy-phenyl)-3-methyl-1H-pyrazolo[3,4-b]pyridin-4-yl]-methanone,

(27) [6-(4-Hydroxy-phenyl)-3-methyl-1H-pyrazolo[3,4-b]pyridin-4-yl]-((S)-2-phenyl-piperazin-1-yl)-methanone.

(28) [6-(4-Hydroxy-phenyl)-3-methyl-1H-pyrazolo[3,4-b]pyridin-4-yl]-((R)-2-phenyl-piperazin-1-yl)-methanone.

In another group of embodiments

A) $R^1$ is $(C_1-C_4)$-alkyl;

$R^2$ is H, halogen or $(C_1-C_4)$-alkyl;

$R^3$ is H or halogen;

$R^4$ is H;

$R^5$ is H;

$R^6$ is H;

$R^7$ is a) $(C_0-C_6)$-alkyl which is mono-substituted by i) a 3- to 8-membered monocyclic heterocycle comprising a ring nitrogen atom and optionally one further ring heteroatom selected from the group consisting of nitrogen and oxygen, which is unsubstituted or substituted by one to five identical or different substituents selected from the group consisting of ia) F, ib) $(C_1-C_4)$-alkyl, which is unsubstituted or one to fivefold substituted by F, ic) O—($C_1$-$C_4$)-alkyl, which is unsubstituted or one to fivefold substituted by F,
id) phenyl, which is unsubstituted or substituted by one to two identical or different substituents selected from the group consisting of halogen and ($C_1$-$C_4$)-alkyl, wherein ($C_1$-$C_4$)-alkyl is unsubstituted or one to fivefold substituted by F,
ie) ($C_1$-$C_4$)-alkylene-phenyl, which is unsubstituted or one to fivefold substituted by F,
if) ($C_3$-$C_8$)-cycloalkyl,
ig) oxo (=O), and
ih) (CO)—($C_1$-$C_4$)-alkyl,
and wherein ($C_0$-$C_6$)-alkyl can be further mono-substituted by phenyl or pyridyl, wherein phenyl or pyridyl is unsubstituted or substituted by one to two identical or different substituents selected from the group consisting of halogen and ($C_1$-$C_4$)-alkyl, wherein ($C_1$-$C_4$)-alkyl is unsubstituted or one to fivefold substituted by F;
ii) ($C_3$-$C_8$)-cycloalkyl which is substituted by one to two identical or different substituents selected from the group consisting of $NH_2$, NH(($C_1$-$C_4$)-alkyl) and N(($C_1$-$C_4$)-alkyl)$_2$, and wherein ($C_3$-$C_8$)-cycloalkyl can be further substituted by one to three identical or different substituents selected from the group consisting of
iia) F,
iib) ($C_1$-$C_4$)-alkyl, wherein ($C_1$-$C_4$)-alkyl is unsubstituted or one to fivefold substituted by F,
iic) O—($C_1$-$C_4$)-alkyl, which is unsubstituted or one to fivefold substituted by F,
iid) phenyl, which is unsubstituted or substituted by one to two identical or different substituents selected from the group consisting of halogen and ($C_1$-$C_4$)-alkyl, wherein ($C_1$-$C_4$)-alkyl is unsubstituted or one to fivefold substituted by F, and
iie) ($C_1$-$C_4$)-alkylene-phenyl, which is unsubstituted or one to fivefold substituted by F;
or
iii) $NR^8R^9$, wherein
$R^8$ is H or ($C_1$-$C_4$)-alkyl, and
$R^9$ is H or ($C_1$-$C_6$)-alkyl,
and wherein ($C_0$-$C_6$)-alkyl can be further mono-substituted by phenyl, phenylene-($C_1$-$C_4$)-alkyl or phenylene-O—($C_1$-$C_4$)-alkyl;
b) a bicyclic ($C_6$-$C_{11}$)-cycloalkyl group, which is mono-substituted by ($C_0$-$C_2$)-alkylene-$NH_2$, ($C_0$-$C_2$)-alkylene-NH—($C_1$-$C_4$)-alkyl, ($C_0$-$C_2$)-alkylene-N(($C_1$-$C_4$)-alkyl)$_2$;
c) a fused bicyclic ($C_6$-$C_{10}$)-heterocycloalkyl group containing one nitrogen atom, which is attached via a carbon atom and which is unsubstituted or substituted by one or two identical or different substituents selected from the group consisting of F and ($C_1$-$C_4$)-alkyl, which is unsubstituted or one to fivefold substituted by F;
d) a spiro bicyclic ($C_7$-$C_{11}$)-heterocycloalkyl group containing one nitrogen atom, which is attached via a carbon atom and which is unsubstituted or substituted by one or two identical or different substituents selected from the group consisting of F and ($C_1$-$C_4$)-alkyl, which is unsubstituted or one to fivefold substituted by F;
e) a bridged bicyclic ($C_7$-$C_9$)-heterocycloalkyl group containing one nitrogen atom, which is attached via a carbon atom and which is unsubstituted or substituted by one or two identical or different substituents selected from the group consisting of F and ($C_1$-$C_4$)-alkyl, which is unsubstituted or one to fivefold substituted by F; or
f) a tricyclic ($C_{11}$-$C_{15}$)-heterocycloalkyl group containing one nitrogen atom, which is attached via a carbon atom and which consists of a spiro bicyclic ring with an additional fused phenyl ring, and which is unsubstituted or substituted by one or two identical or different substituents selected from the group consisting of F and ($C_1$-$C_4$)-alkyl, which is unsubstituted or one to fivefold substituted by F;
or
B) R is ($C_1$-$C_4$)-alkyl;
$R^2$ is H;
$R^3$ is H or halogen;
$R^4$ is H;
$R^5$ is H;
$R^6$ is ($C_1$-$C_4$)-alkyl or ($C_1$-$C_4$)-alkylene-phenyl;
$R^7$ is a 5- to 6-membered monocyclic heterocycle comprising a ring nitrogen atom, which is attached via a carbon atom, ($C_1$-$C_4$)-alkylene-$NH_2$, or ($C_1$-$C_4$)-alkylene-NH—($C_1$-$C_4$)-alkyl;
or
C) $R^1$ is ($C_1$-$C_4$)-alkyl;
$R^2$ is H, ($C_1$-$C_4$)-alkyl, halogen or O—($C_1$-$C_4$)-alkyl;
$R^3$ is H, ($C_1$-$C_4$)-alkyl, halogen or O—($C_1$-$C_4$)-alkyl;
$R^4$ is H or halogen;
$R^5$ is H, halogen or ($C_1$-$C_4$)-alkyl;
$R^6$ and $R^7$ together with the N-atom carrying them denote
a) a 1,4-piperazinyl of the formula

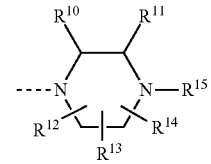

wherein
$R^{10}$ is H, or ($C_0$-$C_6$)-alkyl, which is unsubstituted or one to fivefold substituted by F, or mono-substituted by a substituent selected from the group consisting of
i) O—($C_1$-$C_{11}$)-alkyl, which is unsubstituted or one to fivefold substituted by F,
ii) ($C_3$-$C_6$)-cycloalkyl,
iii) phenyl, which is unsubstituted or substituted by one to two identical or different substituents selected from the group consisting of halogen, $CF_3$, O—($C_1$-$C_4$)-alkyl, $OCF_3$, and ($C_1$-$C_4$)-alkyl,
iv) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, $CF_3$, O—($C_1$-$C_4$)-alkyl, $OCF_3$, and ($C_1$-$C_4$)-alkyl,
v) benzo[1,3]dioxole, and
vi) CO—$R^{16}$;
$R^{11}$ is H or ($C_0$-$C_6$)-alkyl, which is unsubstituted or one to fivefold substituted by F or mono-substituted by a substituent selected from the group consisting of
i) CO—$R^{17}$,
ii) ($C_3$-$C_6$)-cycloalkyl,
iii) phenyl, which is unsubstituted or substituted by one to two identical or different substituents selected from the group consisting of halogen, $CF_3$, $OCF_3$, and ($C_1$-$C_4$)-alkyl, iv) O—$(C_1$-$C_4)$-alkyl, which is unsubstituted or one to fivefold substituted by F, v) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, $CF_3$, O—$(C_1$-$C_4)$-alkyl, $OCF_3$, and $(C_1$-$C_4)$-alkyl, and vi) oxo (=O);

$R^{12}$ is H, $(C_1$-$C_6)$-alkyl, which is unsubstituted or one to fivefold substituted by F, or phenyl;

$R^{13}$ is H or $(C_1$-$C_6)$-alkyl;

$R^{14}$ is H or $(C_1$-$C_4)$-alkyl;

$R^{15}$ is H, $(C_1$-$C_6)$-alkyl, $(C_3$-$C_6)$-cycloalkyl or CO—$R^{18}$, wherein $(C_1$-$C_6)$-alkyl is unsubstituted or one to fivefold substituted by F, or mono-substituted by a substituent selected from the group consisting of $SO_2$—$(C_1$-$C_4)$-alkyl, phenyl, a 5- to 6-membered monocyclic heterocyclic ring comprising one heteroatom selected from the group consisting of nitrogen and oxygen, a 5- to 6-membered monocyclic heteroaromatic ring comprising one heteroatom selected from the group consisting of nitrogen and oxygen;

$R^{16}$ is O—$(C_1$-$C_4)$-alkyl or NH—$(C_1$-$C_6)$-alkyl;

$R^{17}$ is O—$(C_1$-$C_4)$-alkyl;

$R^{18}$ is $(C_1$-$C_4)$-alkyl, $NH_2$, phenyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen, where phenyl can be further mono-substituted by $(C_1$-$C_4)$-alkyl or O—$(C_1$-$C_4)$-alkyl;

b) a four to seven membered monocyclic heterocycloalkyl group containing a nitrogen atom, which is attached via said nitrogen and which is mono-substituted by $(C_0$-$C_6)$-alkylene-$NH_2$, $(C_0$-$C_6)$-alkylene-NH—$(C_1$-$C_4)$-alkyl, $(C_0$-$C_6)$-alkylene-NH-phenyl, $(C_0$-$C_6)$-alkylene-N($(C_1$-$C_4)$-alkyl$)_2$, or $(C_0$-$C_6)$-alkylene-N($(C_1$-$C_4)$-alkyl)(phenyl); and wherein said heterocycloalkyl group can be further mono-substituted by $(C_1$-$C_6)$-alkyl, which is unsubstituted or one to fivefold substituted by F, CO—O—$(C_1$-$C_4)$-alkyl or phenyl;

c) a 1,4-diazepanyl, which is unsubstituted or mono-substituted by $(C_1$-$C_6)$-alkyl, wherein $(C_1$-$C_6)$-alkyl is unsubstituted or one to fivefold substituted by F, CO-phenyl, or CO-pyridyl;

d) a fused bicyclic $(C_6$-$C_{10})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or substituted by one to two identical or different substituents selected from the group consisting of F, $(C_0$-$C_2)$-alkylene-phenyl, oxo (=O) and $(C_1$-$C_4)$-alkyl, wherein $(C_1$-$C_4)$-alkyl is unsubstituted or one to fivefold substituted by F;

e) a spiro bicyclic $(C_7$-$C_{11})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or mono- or di-substituted by F or $(C_1$-$C_4)$-alkyl, which is unsubstituted or one to fivefold substituted by F;

f) a bridged bicyclic $(C_7$-$C_9)$-heterocycloalkyl group containing one nitrogen atom, which is attached via said nitrogen atom, which is mono-substituted by $(C_0$-$C_2)$-alkylene-$NH_2$, $(C_0$-$C_2)$-alkylene-NH—$(C_1$-$C_4)$-alkyl, $(C_0$-$C_2)$-alkylene-N($(C_1$-$C_4)$-alkyl$)_2$ g) a bridged bicyclic $(C_7$-$C_9)$-heterocycloalkyl group containing two nitrogen atoms, which is attached via a nitrogen atom; and which is unsubstituted or substituted by one to four identical or different substituents selected from the group consisting of F, OH, and $(C_1$-$C_4)$-alkyl, which is unsubstituted or one to fivefold substituted by F; or h) a tricyclic $(C_{11}$-$C_{15})$-heterocycloalkyl group containing two nitrogen atoms, which is attached via a nitrogen atom and which consists of a spiro bicyclic ring with an additional fused phenyl ring, and which is unsubstituted or substituted by one or two identical or different substituents selected from the group consisting of F and $(C_1$-$C_4)$-alkyl, which is unsubstituted or one to fivefold substituted by F;

or

D) $R^1$ is $CF_3$;

$R^2$ is H;

$R^3$ is H;

$R^4$ is H;

$R^5$ is H;

$R^6$ is H and $R^7$ is a) 3-azetidyl or 3-piperidyl;

b) a bridged bicyclic $(C_7$-$C_9)$-heterocycloalkyl group containing one nitrogen atom, which is attached via a carbon atom and which is unsubstituted or substituted by one or two identical or different substituents selected from the group consisting of F and $(C_1$-$C_4)$-alkyl, which is unsubstituted or one to fivefold substituted by F;

or $R^6$ and $R^7$ together with the N-atom carrying them denote a) a 1,4-piperazinyl or a 1,4-diazepanyl, which are unsubstituted or mono-substituted by $(C_1$-$C_4)$-alkyl;

b) a 1-pyrrolidinyl or a 1-piperidyl, which are mono-substituted by $NH_2$, NH$(C_1$-$C_4)$-alkyl), or N($(C_1$-$C_4)$-alkyl$)_2$);

c) a fused bicyclic $(C_6$-$C_{10})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or substituted by one to two identical or different substituents selected from the group consisting of F, $(C_0$-$C_2)$-alkylene-phenyl, oxo and $(C_1$-$C_4)$-alkyl, wherein $(C_1$-$C_4)$-alkyl is unsubstituted or one to fivefold substituted by F;

d) a spiro bicyclic $(C_7$-$C_{11})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or mono- or di-substituted by F or $(C_1$-$C_4)$-alkyl, which is unsubstituted or one to fivefold substituted by F;

or

E) $R^1$ is cyclopropyl;

$R^2$ is H;

$R^3$ is H;

$R^4$ is H;

$R^5$ is H;

R⁶ and R⁷ together with the N-atom carrying them denote a 1,4-piperazinyl, which is unsubstituted or substituted by one to two identical or different substituents selected from the group consisting of $(C_1-C_4)$-alkyl and phenyl.

In another group of embodiments

A) $R^1$ is $(C_1-C_4)$-alkyl;
   $R^2$ is H, halogen or $(C_1-C_4)$-alkyl;
   $R^3$ is H or halogen;
   $R^4$ is H;
   $R^5$ is H;
   $R^6$ is H;
   $R^7$ is
   a) $(C_0-C_6)$-alkyl which is mono-substituted by
      i) a 3- to 8-membered monocyclic heterocycle comprising a ring nitrogen atom and optionally one further ring heteroatom selected from the group consisting of nitrogen and oxygen, which is unsubstituted or substituted by one to five identical or different substituents selected from the group consisting of $(C_1-C_4)$-alkyl, O—$(C_1-C_4)$-alkyl, phenyl, phenylene-$(C_1-C_4)$-alkyl, $(C_1-C_4)$-alkylene-phenyl, $(C_3-C_8)$-cycloalkyl, oxo (=O), and (CO)—$(C_1-C_4)$-alkyl, and wherein $(C_0-C_6)$-alkyl can be further mono-substituted by phenyl or pyridyl;
      ii) $(C_3-C_8)$-cycloalkyl which is substituted by one to two identical or different substituents selected from the group consisting of $NH_2$ and $N((C_1-C_4)$-alkyl$)_2$;
      iii) $NR^8R^9$, wherein
         $R^8$ is H or $(C_1-C_4)$-alkyl, and
         $R^9$ is H or $(C_1-C_6)$-alkyl,
         and wherein $(C_0-C_6)$-alkyl can be further mono-substituted by phenyl, phenylene-$(C_1-C_4)$-alkyl or phenylene-O—$(C_1-C_4)$-alkyl;
   or
   $R^7$ is
   b) a bicyclic $(C_7)$-cycloalkyl group, which is mono-substituted by —$NH_2$, or —$CH_2$—$NH_2$;
   c) a fused bicyclic $(C_6)$-heterocycloalkyl group containing one nitrogen atom, which is attached via a carbon atom
   d) a spiro bicyclic $(C_9)$-heterocycloalkyl group containing one nitrogen atom, which is attached via a carbon atom;
   e) a bridged bicyclic $(C_8-C_9)$-heterocycloalkyl group containing one nitrogen atom, which is attached via a carbon atom and which is unsubstituted or monosubstituted by $CH_3$;
   f) a tricyclic $(C_{14})$-heterocycloalkyl group containing one nitrogen atom, which is attached via a carbon atom and which consists of a spiro bicyclic ring with an additional fused phenyl ring;
or
B) $R^1$ is $(C_1-C_4)$-alkyl;
   $R^2$ is H;
   $R^3$ is H or halogen;
   $R^4$ is H;
   $R^5$ is H;
   $R^6$ is $(C_1-C_4)$-alkyl or $(C_1-C_4)$-alkylene-phenyl;
   $R^7$ is a 5- to 6-membered monocyclic heterocycle comprising a ring nitrogen atom, which is attached via a carbon atom, $(C_1-C_4)$-alkylene-$NH_2$, or $(C_1-C_4)$-alkylene-NH—$(C_1-C_4)$-alkyl;
or
C) $R^1$ is $(C_1-C_4)$-alkyl;
   $R^2$ is H, $(C_1-C_4)$-alkyl, halogen or O—$(C_1-C_4)$-alkyl;
   $R^3$ is H, $(C_1-C_4)$-alkyl, halogen or O—$(C_1-C_4)$-alkyl;
   $R^4$ is H or halogen;
   $R^5$ is H, halogen or $(C_1-C_4)$-alkyl;
   $R^6$ and $R^7$ together with the N-atom carrying them denote a) a 1,4-piperazinyl of the formula

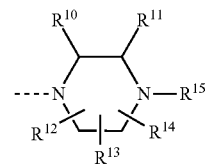

wherein $R^{10}$ is H, or $(C_0-C_6)$-alkyl, which is unsubstituted or substituted threefold by F or mono-substituted by O—$(C_1-C_4)$-alkyl, phenyl; a 5- to 6-membered monocyclic heteroaromatic ring comprising one heteroatom selected from the group consisting of nitrogen, oxygen, and sulphur, benzo[1,3]dioxole or CO—$R^{16}$;
   wherein phenyl is unsubstituted or substituted by one to two identical or different substituents selected from the group consisting of halogen, $CF_3$, O—$(C_1-C_4)$-alkyl, and $(C_1-C_4)$-alkyl;

$R^{11}$ is H or $(C_0-C_6)$-alkyl, which is unsubstituted or substituted threefold by F or mono-substituted by CO—$R^{17}$, $(C_3-C_4)$-cycloalkyl, phenyl, O—$(C_1-C_4)$-alkyl or oxo (=O);

$R^{12}$ is H, $(C_1-C_6)$-alkyl or phenyl;

$R^{13}$ is H or $(C_1-C_6)$-alkyl;

$R^{14}$ is H or $(C_1-C_4)$-alkyl;

$R^{15}$ is H, $(C_1-C_6)$-alkyl, $(C_3-C_6)$-cycloalkyl or CO—$R^{18}$, where $(C_1-C_0)$-alkyl is unsubstituted or mono-substituted by $SO_2$—$(C_1-C_4)$-alkyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen;

$R^{16}$ is O—$(C_1-C_4)$-alkyl or NH—$(C_1-C_6)$-alkyl;

$R^{17}$ is O—$(C_1-C_4)$-alkyl;

$R^{18}$ is $(C_1-C_4)$-alkyl, $NH_2$; phenyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen, where phenyl can be further mono-substituted by $(C_1-C_4)$-alkyl or O—$(C_1-C_4)$-alkyl;

b) a 1-azetidinyl, which is mono-substituted by $NH_2$ or $(C_1-C_6)$-alkylene-$NH_2$;

c) a 1-pyrrolidinyl, which is mono-substituted by $NR^{19}R^{20}$ or $(C_3-C_4)$-alkylene-amine, wherein $R^{19}$ is H, $(C_1-C_4)$-alkyl or phenyl;

$R^{20}$ is H or $(C_1-C_4)$-alkyl, and 1-pyrrolidinyl can be further mono-substituted by $(C_1-C_6)$-alkyl or $CF_3$;

d) a 1-piperidyl, which is mono-substituted by $NR^{21}R^{22}$ or $(C_1-C_4)$-alkyl-$NH_2$, wherein $R^{21}$ is H or $(C_1-C_4)$-alkyl;

$R^{22}$ is H;

and 1-piperidyl can be further mono-substituted by $(C_1-C_6)$-alkyl, CO—O—$(C_1-C_4)$-alkyl or phenyl;

e) a 1,4-diazepanyl of the formula

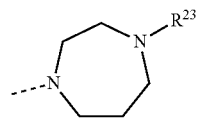

wherein
R$^{23}$ is H, (C$_1$-C$_6$)-alkyl or CO-4-pyridyl;
f) a fused bicyclic (C$_8$-C$_{10}$)-heterocycloalkyl group containing two nitrogen atoms, which is attached via a nitrogen atom and which can contain one further sulphur atom, wherein said heterocycloalkyl group is unsubstituted or substituted by one to two identical or different substituents selected from the group consisting of CH$_3$, phenyl, methylene-phenyl or oxo (=O);
g) a spiro bicyclic (C$_8$-C$_{11}$)-heterocycloalkyl group containing two nitrogen atoms, which is attached via a nitrogen atom and which can contain one further oxygen atom, wherein said heterocycloalkyl group is unsubstituted or mono- or di-substituted by CH$_3$;
h) a bridged bicyclic (C$_8$)-heterocycloalkyl group containing one nitrogen atom, which is attached via said nitrogen atom, which is substituted by NH$_2$;
i) a bridged bicyclic (C$_7$-C$_9$)-heterocycloalkyl group containing two nitrogen atoms, which is attached via a nitrogen atom; and which is unsubstituted or substituted by one to four identical or different substituents selected from the group consisting of CH$_3$, C$_2$H$_5$ and OH;
j) a tricyclic (C$_{14}$)-heterocycloalkyl group containing two nitrogen atoms, which is attached via a nitrogen atom and which consists of a spiro bicyclic ring with an additional fused phenyl ring;

or
D) R$^1$ is CF$_3$;
R$^2$ is H;
R$^3$ is H;
R$^4$ is H;
R$^5$ is H;
R$^6$ is H and
R$^7$ is a) 3-azetidyl or 3-piperidyl;
b) a bridged bicyclic (C$_8$)-heterocycloalkyl group containing one nitrogen atom, which is attached via a carbon atom;

or
R$^6$ and R$^4$ together with the N-atom carrying them denote
a) a 1,4-piperazinyl or a 1,4-diazepanyl, which are unsubstituted or mono-substituted by (C$_1$-C$_4$)-alkyl;
b) a 1-pyrrolidinyl or a 1-piperidyl, which are mono-substituted by NH$_2$ or NH((C$_1$-C$_4$)-alkyl);
c) a fused bicyclic (C$_8$)-heterocycloalkyl group containing two nitrogen atoms, which is attached via a nitrogen atom;
d) a spiro bicyclic (C$_9$-C$_{11}$)-heterocycloalkyl group containing two nitrogen atoms, which is attached via a nitrogen atom;

or
E) R$^1$ is cyclopropyl;
R$^2$ is H;
R$^3$ is H;
R$^4$ is H;
R$^5$ is H;
R$^5$ and R$^7$ together with the N-atom carrying them denote a 1,4-piperazinyl, which is unsubstituted or substituted by one to two identical or different substituents selected from the group consisting of (C$_1$-C$_4$)-alkyl and phenyl.

In another group of embodiments
A) R$^1$ is CH$_3$;
R$^2$ is H, F or CH$_3$;
R$^3$ is H or F;
R$^4$ is H;
R$^5$ is H;
R$^6$ is H;
R$^7$ is
a) (C$_0$-C$_6$)-alkyl which is mono-substituted by
i) azetidyl, pyrrolidinyl, piperidyl, piperazinyl or morpholinyl, which are unsubstituted or substituted by one to five identical or different substituents selected from the group consisting of CH$_3$, C$_2$H$_5$, C$_3$H$_7$, O—CH$_3$, O—C$_2$H$_5$, phenyl, phenylene-methyl, methylene-phenyl, ethylene-phenyl, cyclohexyl, oxo (=O), and (CO)—CH$_3$, and wherein (C$_0$-C$_6$)-alkyl can be further mono-substituted by phenyl or pyridyl;
ii) (C$_3$-C$_8$)-cycloalkyl which is substituted by one to two identical or different substituents selected from the group consisting of and N(CH$_3$)$_2$;
iii) NR$^8$R$^9$, wherein
R$^3$ is H or CH$_3$, and
R$^9$ is H, CH$_3$, CH(CH$_3$)$_2$ or C(CH$_3$)$_3$,
and wherein (C$_0$-C$_6$)-alkyl can be further mono-substituted by phenyl, phenylene-methyl or phenylene-O-methyl;

or
R$^7$ is
b) a fused bicyclic ring selected from the group consisting of

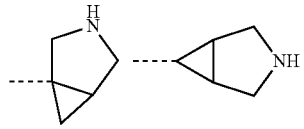

c) a spiro bicyclic ring selected from the group consisting of

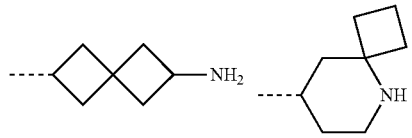

d) a bridged bicyclic ring selected from the group consisting of

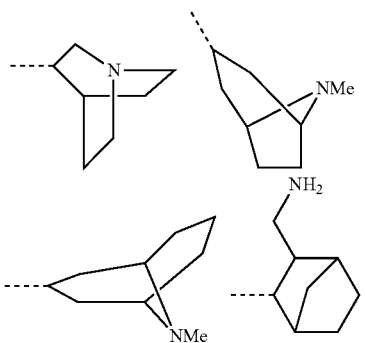

e) a spiro bicyclic ring with a fused ring selected from the group consisting of

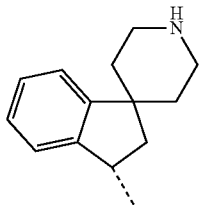

or
B) $R^1$ is $CH_3$;
  $R^2$ is H;
  $R^3$ is H or F;
  $R^4$ is H;
  $R^5$ is H;
  $R^6$ is $CH_3$ or $(CH_2)_2$-phenyl;
  $R^7$ is 4-piperidyl, 4-methyl-4-piperidyl, 3-piperidyl, or t-butyl-aminoethylene;
or
C) $R^1$ is $CH_3$;
  $R^2$ is H, $CH_3$, F, Cl or O—$CH_3$;
  $R^3$ is H, $CH_3$, F, $C_{1-10}$—$CH_3$ or O—$C_2H_5$;
  $R^4$ is H or F;
  $R^5$ is H, F or $CH_3$;
  $R^6$ and $R^7$ together with the N-atom carrying them denote
  a) a 1,4-piperazinyl of the formula

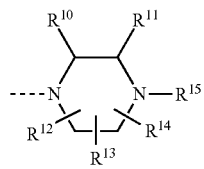

wherein
  $R^{10}$ is H, or $(C_0\text{-}C_4)$-alkyl, which is unsubstituted or substituted threefold by F or mono-substituted by O—$CH_3$, phenyl, pyridyl, furyl, thienyl, benzo[1,3]dioxole or CO—$R^{16}$;
    wherein phenyl is unsubstituted or substituted by one to two identical or different substituents selected from the group consisting of F, Cl, Br, $CF_3$, O—$CH_3$, and $CH(CH_3)_2$;
  $R^{11}$ is H or $(C_0\text{-}C_4)$-alkyl, which is unsubstituted or substituted threefold by F or mono-substituted by CO—$R^{17}$, cyclopropyl, phenyl, O—$CH_3$ or oxo (=O);
  $R^{12}$ is H, $(C_1\text{-}C_4)$-alkyl or phenyl;
  $R^{13}$ is H or $(C_1\text{-}C_4)$-alkyl;
  $R^{14}$ is H or $CH_3$;
  $R^{15}$ is H, cyclobutyl or CO—$R^{18}$, where $(C_1\text{-}C_4)$-alkyl is unsubstituted or mono-substituted by $SO_2$—$CH_3$, 4-piperidyl, 2-pyridyl, 4-tetrahydropyranyl or 3-tetrahydrofuryl;
  $R^{16}$ is O—$CH_3$ or NH—$(C_1\text{-}C_4)$-alkyl;
  $R^{17}$ is O—$CH_3$;
  $R^{18}$ is $CH_3$, $NH_2$, phenyl, 3-furyl, 2-tetrahydrofuryl or 1-pyrrolidinyl, where phenyl can be further mono-substituted by $CH_3$ or O—$CH_3$;
  b) a 1-azetidinyl, which is mono-substituted by $NH_2$ or $(C_1\text{-}C_4)$-alkylene-$NH_2$;

c) a 1-pyrrolidinyl, which is mono-substituted by $NR^{19}R^{20}$ or 1-cyclopropylamine, wherein
  $R^{19}$ is H, $CH_3$ or phenyl;
  $R^{20}$ is H or $CH_3$,
    and 1-pyrrolidinyl can be further mono-substituted by $(C_1\text{-}C_4)$-alkyl or $CF_3$;
d) a 1-piperidyl, which is mono-substituted by $NR^{21}R^{22}$ or $CH_2$—$NH_2$, wherein
  $R^{21}$ is H or $CH_3$;
  $R^{22}$ is H;
    and 1-piperidyl can be further mono-substituted by $(C_1\text{-}C_4)$-alkyl, CO—$OCH_3$ or phenyl;
e) a 1,4-diazepanyl of the formula

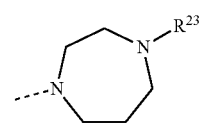

wherein
  $R^{23}$ is H, $(C_1\text{-}C_4)$-alkyl or CO-4-pyridyl;
f) a fused bicyclic ring selected from the group consisting of

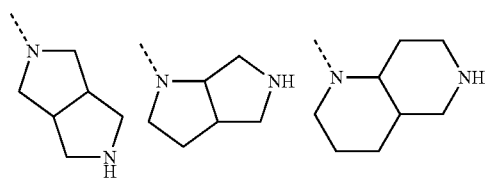

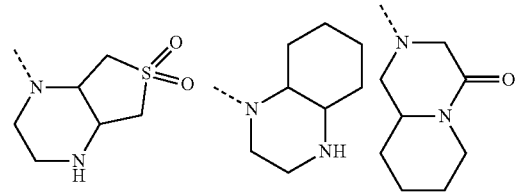

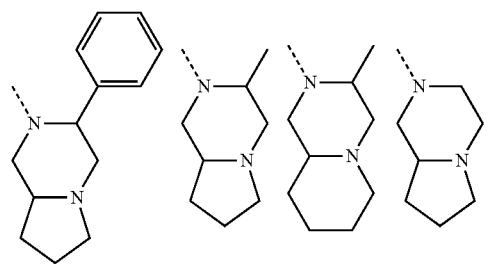

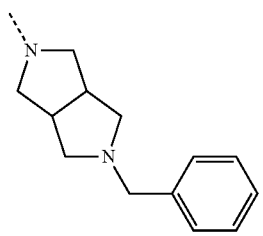

g) a spiro bicyclic ring selected from the group consisting of

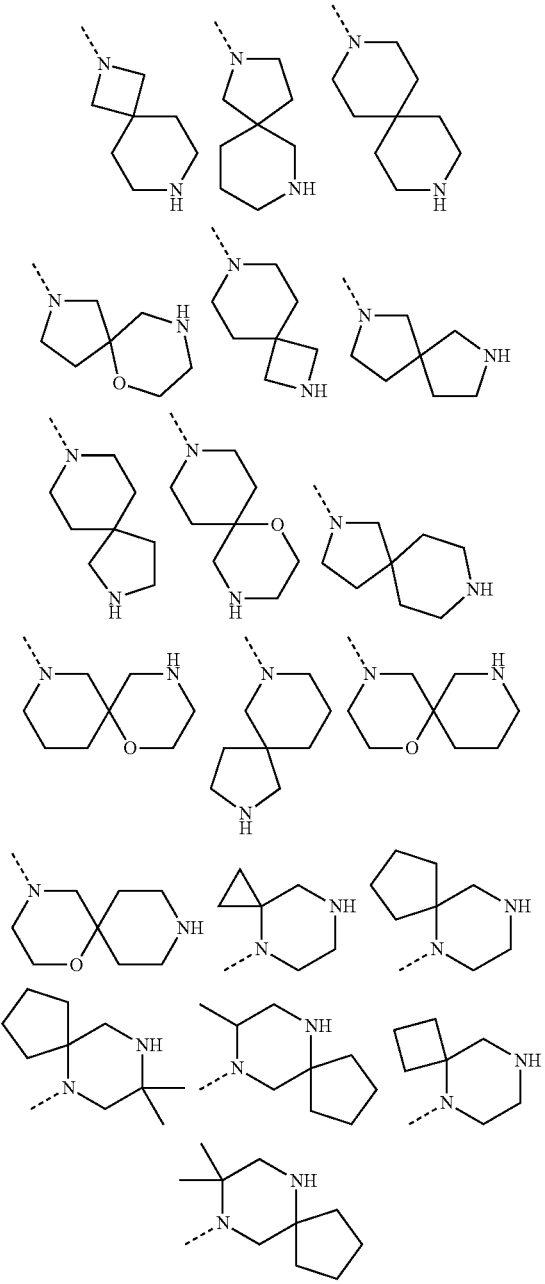

h) a bridged bicyclic ring selected from the group consisting of

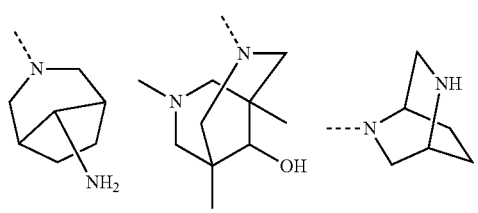

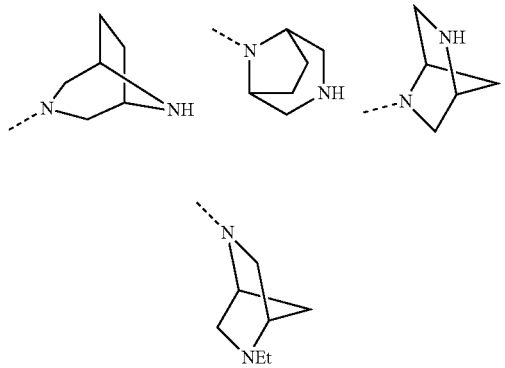

i) a spiro bicyclic ring with a fused ring selected from the group consisting of

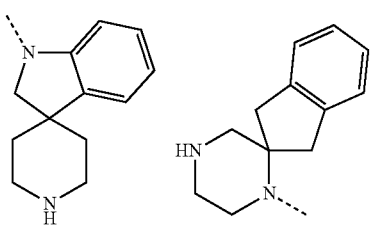

or
D) $R^1$ is $CF_3$;
$R^2$ is H;
$R^3$ is H;
$R^4$ is H;
$R^5$ is H;
$R^6$ is H and
$R^7$ is a) 3-azetidyl or 3-piperidyl;
b) a bridged bicyclic ring selected from the group consisting of

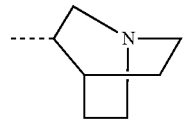

or
$R^6$ and $R^7$ together with the N-atom carrying them denote
a) a 1,4-piperazinyl or a 1,4-diazepanyl, which are unsubstituted or mono-substituted by $CH_3$ or $C_2H_5$;
b) a 1-pyrrolidinyl or a 1-piperidyl, which are mono-substituted by $NH_2$ or $NH(CH_3)$;
c) a fused bicyclic ring selected from the group consisting of

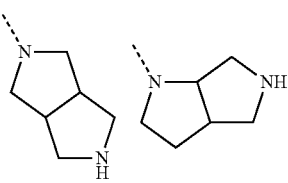

d) a spiro bicyclic ring selected from the group consisting of

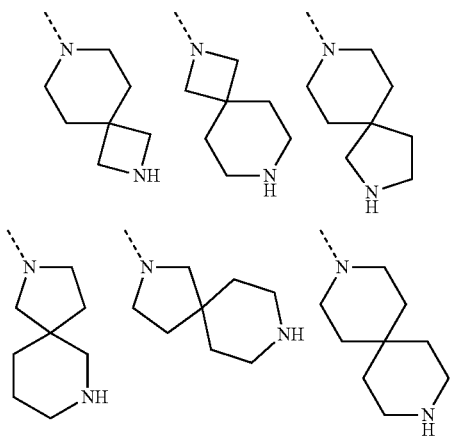

or

E) $R^1$ is $C_2H_5$;
   $R^2$ is H;
   $R^3$ is H or F;
   $R^4$ is H;
   $R^5$ is H;
   $R^6$ is H and
   $R^7$ is a) 3-azetidyl, 3-piperidyl, 4-piperidyl or methylene-2-pyrrolidinyl, which are unsubstituted or mono-substituted by $CH_3$, $C_2H_5$, $OCH_3$, or oxo (=O);
   b) cyclohexyl, which is mono-substituted by $NH_2$;
   c) a bridged bicyclic ring selected from the group consisting of

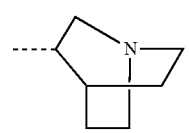 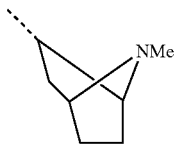 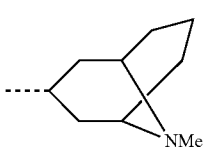

d) a spiro bicyclic ring selected from the group consisting of

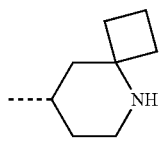

e) a spiro bicyclic ring with a fused ring selected from the group consisting of

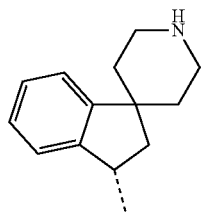

or
$R^6$ is $CH_3$ and
$R^7$ is 4-methyl-4-piperidyl;
or
$R^6$ and $R^7$ together with the N-atom carrying them denote
   a) a 1,4-piperazinyl or a 1,4-diazepanyl, which are unsubstituted or mono-substituted by $CH_3$ or $C_2H_5$;
   b) a 1-azetidinyl, a 1-pyrrolidinyl or a 1-piperidyl, which are mono-substituted by $NH_2$, $NH(CH_3)$ or $N(CH_3)_2$;
   c) a fused bicyclic ring selected from the group consisting of

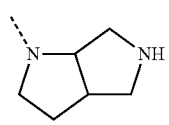

d) a spina bicyclic ring selected from the group consisting of

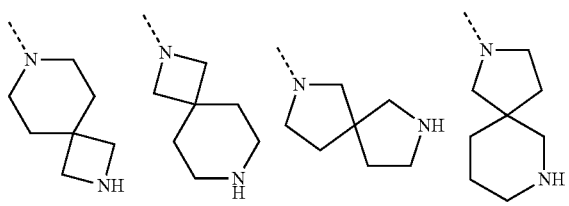

e) a bridged bicyclic ring selected from the group consisting of

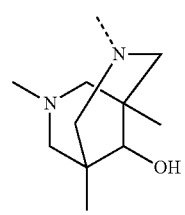

or
F) $R^1$ is propyl or cyclopropyl;
   $R^2$ is H;
   $R^3$ is H;
   $R^4$ is H;
   $R^5$ is H;
   $R^6$ and $R^7$ together with the N-atom carrying them denote a 1,4-piperazinyl, which is unsubstituted or substituted by one to two identical or different substituents selected from the group consisting of $CH_3$ and phenyl.
In another group of embodiments
A) $R^1$ is $CH_3$;

R² is H, F, or CH₃;
R³ is H or F;
R⁴ is H;
R⁵ is H;
R⁶ is H;
R⁷ is
a) 3-azetidinyl,
   3-pyrrolidinyl, which is unsubstituted or mono-substituted by CH₃, C₃H₇, O—CH₃, O—C₂H₅, phenyl, phenylene-methyl or methylene-phenyl, 3-piperidyl, which is unsubstituted or mono-substituted by CH₃, C₂H₅, or C₃H₇,
   4-piperidyl, which is unsubstituted or mono-substituted by CH₃, C₂H₅, C₃H₇, phenyl, methylene-phenyl, ethylene-phenyl, cyclohexyl, oxo (=O), and (CO)—CH₃,
b) (C₃-C₆)-cycloalkyl which is mono-substituted by NH₂ or N(CH₃)₂
c) (C₁)-alkyl which is mono-substituted by
   i) 3-azetidinyl,
      2-pyrrolidinyl; which is unsubstituted or mono-substituted by oxo (=O),
      2-piperidyl,
      3-piperidyl, which is unsubstituted or mono-substituted by C₂H₅;
   ii) (C₆-C₇)-cycloalkyl; which is mono-substituted by NH₂;
d) (C₂-C₄)-alkyl which is mono-substituted by 1-pyrrolidinyl, 2-pyrrolidinyl, 1-piperazinyl, 1-morpholinyl, 4-piperidyl, which are unsubstituted or mono-substituted by CH₃ or phenyl; and wherein (C₂-C₄)-alkyl can be further mono-substituted by phenyl or pyridyl;
e) (C₂-C₆)-alkyl which is mono-substituted by NR²⁴R²⁵, wherein
   R²⁴ is H or CH₃, and
   R²⁵ is H, CH₃ or CH(CH₃)₂,
   and wherein (C₂-C₆)-alkyl can be further mono-substituted by phenyl, phenylene-methyl or phenylene-O-methyl;
or
R⁷ is
f) a fused bicyclic ring selected from the group consisting of

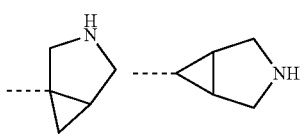

g) a spiro bicyclic ring selected from the group consisting of

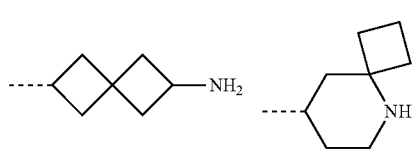

h) abridged bicyclic ring consisting of

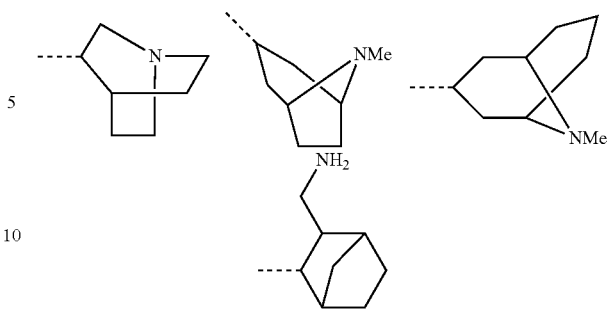

i) a spiro bicyclic ring with a fused ring selected from the group consisting of

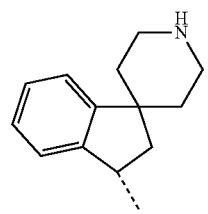

or
B) R¹ is CH₃;
   R² is H;
   R³ is H, F;
   R⁴ is H;
   R⁵ is H;
   R⁶ is CH₃, or (CH₂)₂-phenyl;
   R⁷ is 4-piperidyl, 4-methyl-4-piperidyl, 3-piperidyl, or t-butyl-aminoethylene;
or
C) R¹ is CH₃;
   R² is H, CH₃, F, Cl, or O—CH₃;
   R³ is H, CH₃, F, C₁₋₁₀—CH₃, or O—C₂H₅;
   R⁴ is H, or F;
   R⁵ is H, F, or CH₃;
   R⁶ and R⁷ together with the N-atom carrying them denote
   a) a 1,4-piperazinyl of the formula

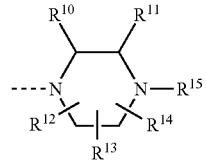

wherein
R¹⁰ is
   i) H,
   ii) (C₁-C₄)-alkyl, which is unsubstituted or substituted threefold by F or mono-substituted by O—CH₃, or CO—R²⁶;
      wherein R²⁶ is O—CH₃, or NH—(C₁-C₄)-alkyl;
   iii) phenyl, pyridyl, furyl, thienyl, or benzo[1,3]dioxole, wherein phenyl is unsubstituted or substituted by one to two identical or different substituents selected from the group consisting of F, Cl, Br, CF₃, O—CH₃, and CH(CH₃)₂;
R¹¹ is H, or (C₁-C₄)-alkyl, which is unsubstituted or substituted threefold by F, cyclopropyl, phenyl, methylene-phenyl, CH₂OCH₃, or COOCH₃;

$R^{12}$ is H, $(C_1-C_4)$-alkyl, or phenyl;
$R^{13}$ is H, or $(C_1-C_4)$-alkyl;
$R^{14}$ is H, or $CH_3$;
$R^{15}$ is H, $(C_1-C_4)$-alkyl, cyclobutyl, or $CO-R^{18}$, where $(C_1-C_4)$-alkyl is unsubstituted or mono-substituted by $SO_2-CH_3$, 4-piperidyl, 2-pyridyl, 4-tetrahydropyranyl, or 3-tetrahydrofuryl;
$R^{16}$ is $O-CH_3$, or $NH-(C_1-C_4)$-alkyl;
$R^{17}$ is $O-CH_3$;
$R^{18}$ is $CH_3$, $NH_2$, phenyl, 3-furyl, 2-tetrahydrofuryl, or 1-pyrrolidinyl, where phenyl can be further mono-substituted by $CH_3$ or $O-CH_3$;
b) a 1-azetidinyl, which is mono-substituted by $NH_2$ or $CH_2-NH_2$;
c) a 1-pyrrolidinyl, which is mono-substituted by $NR^{19}R^{20}$ or 1-cyclopropylamine, wherein
$R^{19}$ is H, $CH_3$, or phenyl;
$R^{20}$ is H, or $CH_3$,
and 1-pyrrolidinyl can be further mono-substituted by $(C_1-C_4)$-alkyl or $CF_3$;
d) a 1-piperidyl, which is mono-substituted by $NR^{21}R^{22}$ or $CH_2-NH_2$, wherein
$R^{21}$ is H, or $CH_3$;
$R^{22}$ is H;
and 1-piperidyl can be further mono-substituted by $(C_1-C_4)$-alkyl, $CO-OCH_3$ or phenyl;
e) a 1,4-diazepanyl of the formula

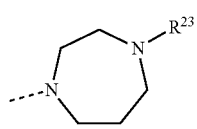

wherein
$R^{23}$ is H, $CH_3$, $C_2H_5$, or CO-4-pyridyl;
f) a fused bicyclic ring selected from the group consisting of

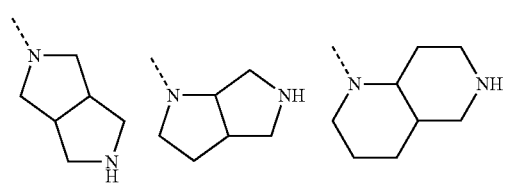

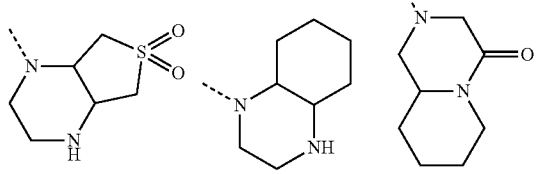

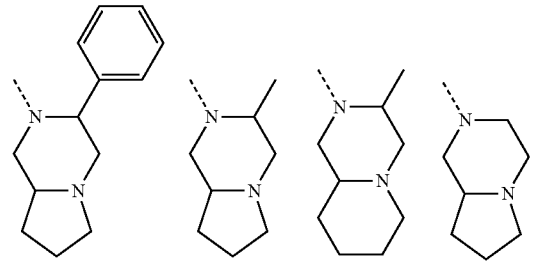

g) a spiro bicyclic ring selected from the group consisting of

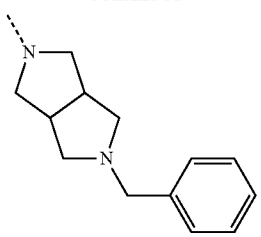

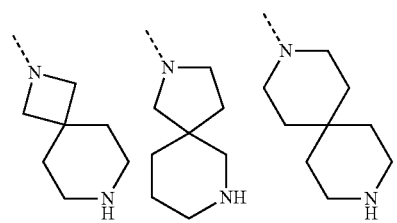

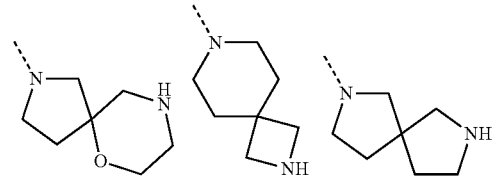

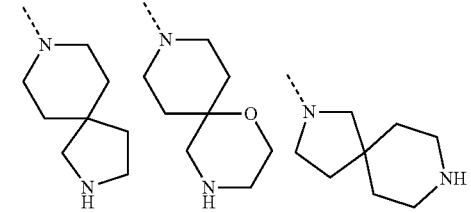

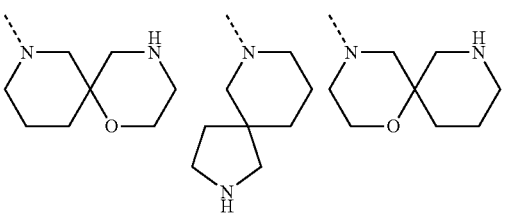

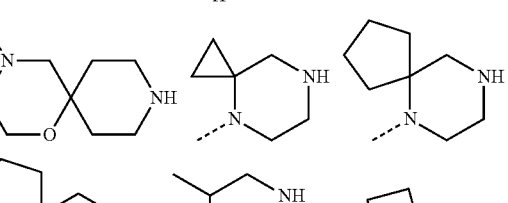

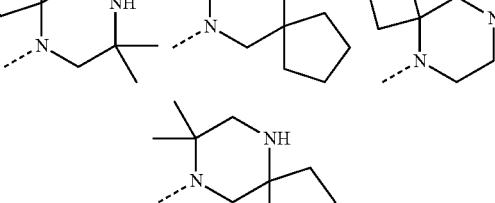

h) a bridged bicyclic ring selected from the group consisting of

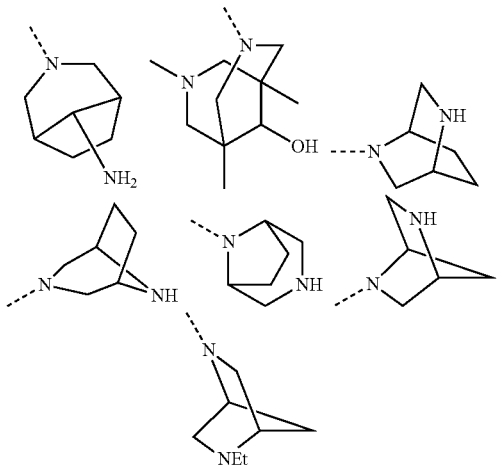

i) a spiro bicyclic ring with a fused ring selected from the group consisting of

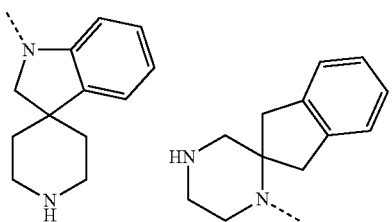

or

D) R¹ is CF₃;
R² is H;
R³ is H;
R⁴ is H;
R⁵ is H;
R⁶ is H and
R⁷ is a) 3-azetidyl, or 3-piperidyl;
b) a bridged bicyclic ring selected from the group consisting of

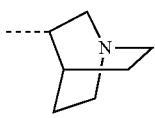

or

R⁶ and R⁷ together with the N-atom carrying them denote
a) a 1,4-piperazinyl or a 1,4-diazepanyl, which are unsubstituted or mono-substituted by CH₃ or C₂H₅;
b) a 1-pyrrolidinyl or a 1-piperidyl, which is mono-substituted by NH₂ or NH(CH₃);
c) a fused bicyclic ring selected from the group consisting of

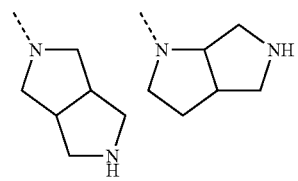

d) a spiro bicyclic ring selected from the group consisting of

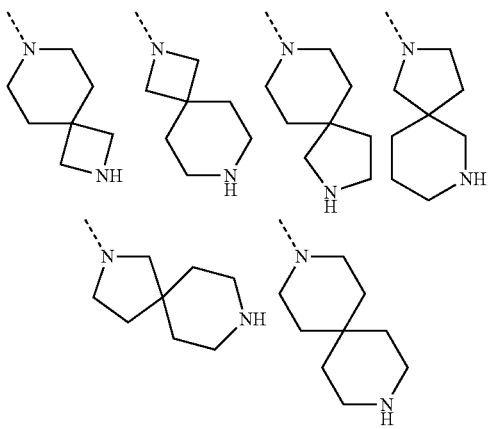

or

E) R¹ is C₂H₅;
R² is H;
R³ is H, or F;
R⁴ is H;
R⁵ is H;
R⁶ is H and
R⁷ is a) 3-azetidyl, 3-pyrrolidinyl, 3-piperidyl, 4-piperidyl or methylene-2-pyrrolidinyl, which are unsubstituted or mono-substituted by CH₃, C₂H₅, OCH₃, or oxo (=O);
b) cyclohexyl, which is mono-substituted by NH-7;
c) abridged bicyclic ring selected from the group consisting of

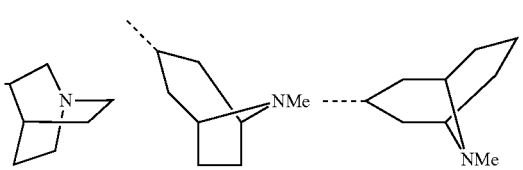

d) a spiro bicyclic ring selected from the group consisting of

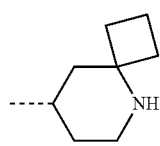

e) a spiro bicyclic ring with a fused ring selected from the group consisting of

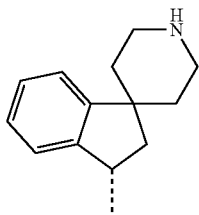

or
$R^6$ is $CH_3$ and
$R^7$ is 4-methyl-4-piperidyl;
or
$R^6$ and $R^7$ together with the N-atom carrying them denote
a) a 1,4-piperazinyl or a 1,4-diazepanyl, which are unsubstituted or mono-substituted by $CH_3$ or $C_2H_5$;
b) a 1-azetidinyl, a 1-pyrrolidinyl or a 1-piperidyl, which are mono-substituted by $NH_2$, $NH(CH_3)$ or $N(CH_3)_2$;
c) a fused bicyclic ring selected from the group consisting of

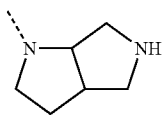

d) a spiro bicyclic ring selected from the group consisting of

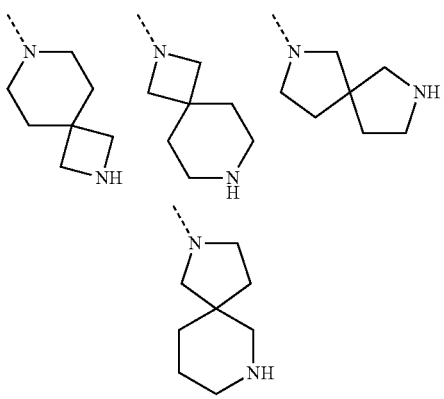

e) a bridged bicyclic ring selected from the group consisting of

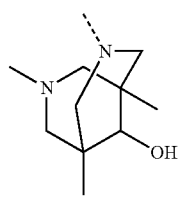

or
F) $R^1$ is propyl or cyclopropyl;
$R^2$ is H;
$R^3$ is H;
$R^4$ is H;
$R^5$ is H;
$R^6$ and $R^7$ together with the N-atom carrying them denote a 1,4-piperazinyl, which is unsubstituted or substituted by one to two identical or different substituents selected from the group consisting of $CH_3$ and phenyl.

In another group of embodiments
A) $R^1$ is $CH_3$;
$R^2$ is H, F, or $CH_3$;
$R^3$ is H or F;
$R^4$ is H;
$R^5$ is H;
$R^6$ is H;
$R^1$ is
a) 3-azetidinyl,
3-pyrrolidinyl, which is unsubstituted or mono-substituted by $CH_3$, $C_3H_7$, O—$CH_3$, O—$C_2H_5$, phenyl, phenylene-methyl or methylene-phenyl, 3-piperidyl, which is unsubstituted or mono-substituted by $CH_3$, $C_2H_5$, or $C_3H_7$,
4-piperidyl, which is unsubstituted or mono-substituted by $CH_3$, $C_2H_5$, $C_3H_7$; phenyl, methylene-phenyl, ethylene-phenyl, cyclohexyl, oxo (=O), and (O)—$CH_3$,
b) ($C_3$-$C_6$)-cycloalkyl which is mono-substituted by $NH_2$ or $N(CH_3)_2$
c) ($C_1$)-alkyl which is mono-substituted by
i) 3-azetidinyl,
2-pyrrolidinyl, which is unsubstituted or mono-substituted by oxo (=O),
2-piperidyl,
3-piperidyl, which is unsubstituted or mono-substituted by $C_2H_5$;
ii) ($C_6$-$C_7$)-cycloalkyl, which is mono-substituted by $NH_2$;
d) ($C_2$-$C_4$)-alkyl which is mono-substituted by 1-pyrrolidinyl, 2-pyrrolidinyl, 1-piperazinyl; 1-morpholinyl, 4-piperidyl; which are unsubstituted or mono-substituted by $CH^3$ or phenyl; and wherein ($C_2$-$C_4$)-alkyl can be further mono-substituted by phenyl or pyridyl;
e) ($C_2$-$C_6$)-alkyl which is mono-substituted by $NR^{24}R^{25}$, wherein
$R^{24}$ is H or $CH_3$, and
$R^{25}$ is H, $CH_3$ or $CH(CH_3)_2$,
and wherein ($C_2$-$C_6$)-alkyl can be further mono-substituted by phenyl, phenylene-methyl or phenylene-O-methyl;
or
B) $R^1$ is $CH_3$;
$R^2$ is H;
$R^3$ is H, F;
$R^4$ is H;
$R^5$ is H;
$R^6$ is $CH_3$,
$R^7$ is 4-piperidyl, 4-methyl-4-piperidyl;
or
C) $R^1$ is $CH_3$;
$R^2$ is H, $CH_3$, F, Cl;
$R^3$ is H, $CH_3$, F, Cl;
$R^4$ is H, or F;
$R^5$ is H, F, or CH3;

$R^6$ and $R^7$ together with the N-atom carrying them denote
a) a 1,4-piperazinyl of the formula

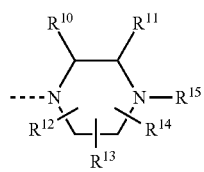

wherein
$R^{10}$ is
  i) H,
  ii) $(C_1-C_4)$-alkyl, which is unsubstituted or substituted threefold by F or mono-substituted by O—$CH_3$, or CO—$R^{26}$;
    wherein $R^{26}$ is O—$CH_3$, or NH—$(C_1-C_4)$-alkyl;
  iii) phenyl, pyridyl, furyl, thienyl, or benzo[1,3]dioxole, wherein phenyl is unsubstituted or substituted by one to two identical or different substituents selected from the group consisting of F, Cl, Br, $CF_3$, O—$CH_3$, and $CH(CH_3)_2$;
$R^{11}$ is H, or $(C_1-C_4)$-alkyl, which is unsubstituted or substituted threefold by F, cyclopropyl, phenyl, methylenephenyl, $CH_2OCH_3$, or $COOCH_3$;
$R^{12}$ is H, $(C_1-C_4)$-alkyl, or phenyl;
$R^{13}$ is H, or $(C_1-C_4)$-alkyl;
$R^{14}$ is H, or $CH_3$;
$R^{15}$ is H, $(C_1-C_4)$-alkyl, cyclobutyl, or CO—$R^{18}$, where $(C_1-C_4)$-alkyl is unsubstituted or mono-substituted by $SO_2$—$CH_3$, 4-piperidyl, 2-pyridyl, 4-tetrahydropyranyl, or 3-tetrahydrofuryl;
$R^{16}$ is O—$CH_3$, or NH—$(C_1-C_4)$-alkyl;
$R^{17}$ is O—$CH_3$;
$R^{18}$ is $CH_3$, $NH_2$, phenyl, 3-furyl, 2-tetrahydrofuryl, or 1-pyrrolidinyl, where phenyl can be further mono-substituted by $CH_3$ or O—$CH_3$;
b) a 1-azetidinyl, which is mono-substituted by $NH_2$ or $CH_2$—$NH_2$;
c) a 1-pyrrolidinyl, which is mono-substituted by $NR^{19}R^{20}$ or 1-cyclopropylamine, wherein
$R^{19}$ is H, $CH_3$, or phenyl;
$R^{20}$ is H, or $CH_3$,
  and 1-pyrrolidinyl can be further mono-substituted by $(C_1-C_4)$-alkyl or $CF_3$;
d) a 1-piperidyl, which is mono-substituted by $NR^{21}R^{22}$ or $CH_2$—$NH_2$, wherein
$R^{21}$ is H, or $CH_3$;
$R^{22}$ is H;
  and 1-piperidyl can be further mono-substituted by $(C_1-C_4)$-alkyl, CO—$OCH_3$ or phenyl;
e) a 1,4-diazepanyl of the formula

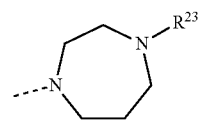

wherein
$R^{23}$ is H, $CH_3$, $C_2H_5$, or CO-4-pyridyl;
f) a fused bicyclic ring selected from the group consisting of

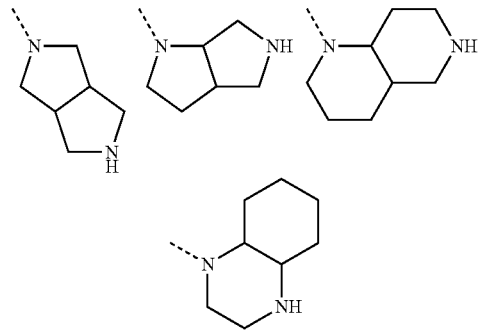

g) a spiro bicyclic ring selected from the group consisting of

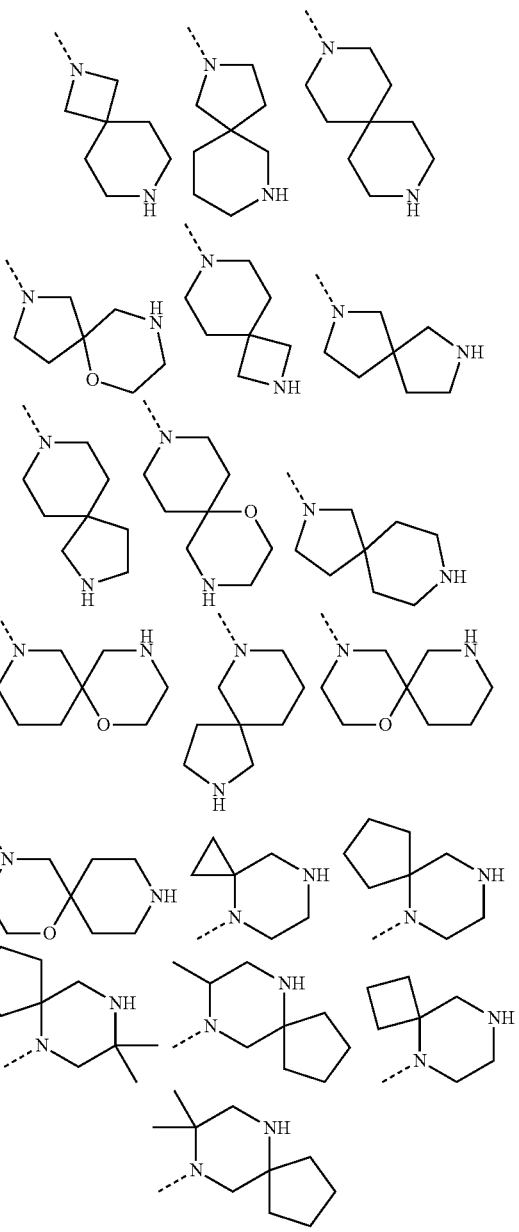

h) a bridged bicyclic ring selected from the group consisting of

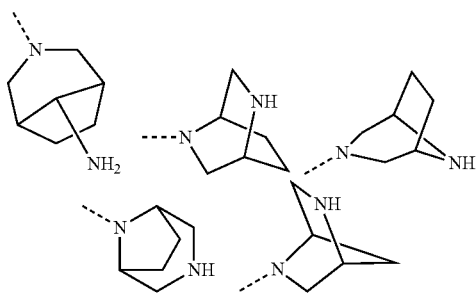

or
D) $R^1$ is $CF_3$;
$R^2$ is H;
$R^3$ is H;
$R^4$ is H;
$R^5$ is H;
$R^6$ is H and
$R^7$ is 3-azetidyl, or 3-piperidyl;
or
$R^6$ and $R^7$ together with the N-atom carrying them denote
a) a 1,4-piperazinyl or a 1,4-diazepanyl, which are unsubstituted or mono-substituted by $CH_3$ or $C_2H_5$;
b) a 1-pyrrolidinyl or a 1-piperidyl, which is mono-substituted by $NH_2$ or $NH(CH_3)$;
c) a fused bicyclic ring consisting of

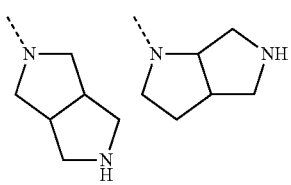

d) a spiro bicyclic ring selected from the group consisting of

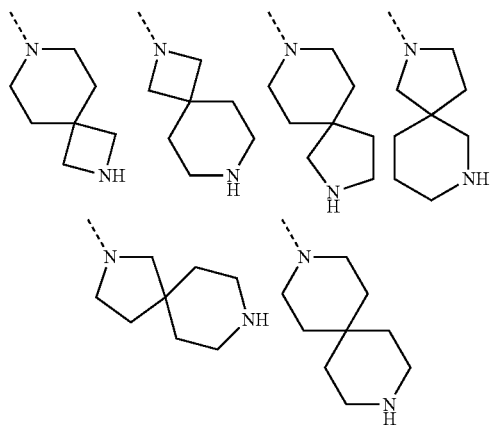

or
E) $R^1$ is $C_2H_5$;
$R^2$ is H;
$R^3$ is H;

$R^4$ is H;
$R^5$ is H;
$R^6$ is H and
$R^7$ is a) 3-azetidyl, 3-pyrrolidinyl, 3-piperidyl, 4-piperidyl or methylene-2-pyrrolidinyl, which are unsubstituted or mono-substituted by $CH_3$, $C_2H_5$, $OCH_3$, or oxo (=O);
b) cyclohexyl, which is mono-substituted by $NH_2$;
or
$R^6$ is $CH_3$ and
$R^7$ is 4-methyl-4-piperidyl;
or
$R^6$ and $R^7$ together with the N-atom carrying them denote
a) a 1,4-piperazinyl or a 1,4-diazepanyl, which are unsubstituted or mono-substituted by $CH_3$ or $C_2H_5$;
b) a 1-azetidinyl, a 1-pyrrolidinyl or a 1-piperidyl, which are mono-substituted by $NH_2$, $NH(CH_3)$ or $N(CH_3)_2$;
c) a fused bicyclic ring selected from the group consisting of

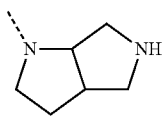

d) a spiro bicyclic ring selected from the group consisting of

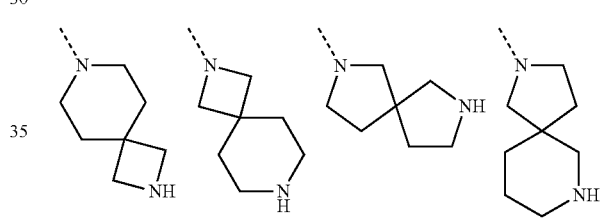

or
F) $R^1$ is propyl or cyclopropyl;
$R^2$ is H;
$R^3$ is H;
$R^4$ is H;
$R^5$ is H;
$R^6$ and $R^7$ together with the N-atom carrying them denote a 1,4-piperazinyl, which is unsubstituted or substituted by one to two identical or different substituents selected from the group consisting of $CH_3$ and phenyl.

In another group of embodiments
A) $R^1$ is $CH_3$;
$R^2$ is H, F, or $CH_3$;
$R^3$ is H or F;
$R^4$ is H;
$R^5$ is H;
$R^6$ is H; and
$R^7$ is
a) 3-azetidinyl,
3-pyrrolidinyl, which is unsubstituted or mono-substituted by $CH_3$, $C_3H_7$, O—$CH_3$, O—$C_2H_5$, phenyl, phenylene-methyl or methylene-phenyl,
3-piperidyl, which is unsubstituted or mono-substituted by $CH_3$, $C_2H_5$, or $C_3H_7$,
4-piperidyl, which is unsubstituted or mono-substituted by $CH_3$, $C_2H_5$, $C_3H_7$, phenyl, methylene-phenyl, ethylene-phenyl, cyclohexyl, oxo (=O), and (O)—$CH_3$, b) $(C_3-C_6)$-cycloalkyl which is mono-substituted by $NH_2$ or $N(CH_3)_2$
c) $(C_1)$-alkyl which is mono-substituted by
  i) 3-azetidinyl,
    2-pyrrolidinyl, which is unsubstituted or mono-substituted by oxo (=O),
    2-piperidyl,
    3-piperidyl, which is unsubstituted or mono-substituted by $C_2H_5$;
  ii) $(C_6-C_7)$-cycloalkyl, which is mono-substituted by $NH_2$;
d) $(C_2-C_4)$-alkyl which is mono-substituted by 1-pyrrolidinyl, 2-pyrrolidinyl, 1-piperazinyl, 1-morpholinyl, 4-piperidyl, which are unsubstituted or mono-substituted by $CH_3$ or phenyl; and wherein $(C_2-C_4)$-alkyl can be further mono-substituted by phenyl or pyridyl;
e) $(C_2-C_6)$-alkyl which is mono-substituted by $NR^{24}R^{25}$; wherein
  $R^{24}$ is H or $CH_3$, and
  $R^{25}$ is H, $CH_3$ or $CH(CH_3)_2$,
  and wherein $(C_2-C_6)$-alkyl can be further mono-substituted by phenyl, phenylene-methyl or phenylene-O-methyl;

or
$R^6$ and $R^7$ together with the N-atom carrying them denote
a) a 1,4-piperazinyl of the formula

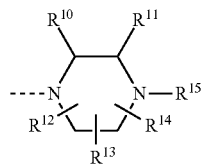

wherein
$R^{10}$ is
  i) H,
  ii) $(C_1-C_4)$-alkyl, which is unsubstituted or substituted threefold by F or mono-substituted by $O-CH_3$, or $CO-R^{26}$;
    wherein $R^{26}$ is $O-CH_3$, or $NH-(C_1-C_4)$-alkyl;
  iii) phenyl, pyridyl, furyl, thienyl, or benzo[1,3]dioxole, wherein phenyl is unsubstituted or substituted by one to two identical or different substituents selected from the group consisting of F, Cl, Br, $CF_3$, $O-CH_3$, and $CH(CH_3)_2$;
$R^{11}$ is H, or $(C_1-C_4)$-alkyl, which is unsubstituted or substituted threefold by F, cyclopropyl, phenyl, methylene-phenyl, $CH_2OCH_3$, or $COOCH_3$;
$R^{12}$ is H, $(C_1-C_4)$-alkyl, or phenyl;
$R^{13}$ is H, or $(C_1-C_4)$-alkyl;
$R^{14}$ is H, or $CH_3$;
$R^{15}$ is H, $(C_1-C_4)$-alkyl, cyclobutyl, or $CO-R^{18}$, where $(C_1-C_4)$-alkyl is unsubstituted or mono-substituted by $SO_2-CH_3$, 4-piperidyl, 2-pyridyl, 4-tetrahydropyranyl, or 3-tetrahydrofuryl;
$R^{16}$ is $O-CH_3$, or $NH-(C_1-C_4)$-alkyl;
$R^{17}$ is $O-CH_3$;
$R^{18}$ is $CH_3$, $NH_2$, phenyl, 3-furyl, 2-tetrahydrofuryl, or 1-pyrrolidinyl, where phenyl can be further mono-substituted by $CH_3$ or $O-CH_3$;
b) a 1-azetidinyl, which is mono-substituted by $NH_2$ or $CH_2-NH_2$;
c) a 1-pyrrolidinyl, which is mono-substituted by $NR^{19}R^{20}$ or 1-cyclopropylamine, wherein
$R^{19}$ is H, $CH_3$, or phenyl;
$R^{20}$ is H, or $CH_3$,
  and 1-pyrrolidinyl can be further mono-substituted by $(C_1-C_4)$-alkyl or $CF_3$;
d) a 1-piperidyl, which is mono-substituted by $NR^{21}R^{22}$ or $CH_2-NH_2$, wherein
$R^{21}$ is H, or $CH_3$;
$R^{22}$ is H;
  and 1-piperidyl can be further mono-substituted by $(C_1-C_4)$-alkyl, $CO-OCH_3$ or phenyl;
e) a 1,4-diazepanyl of the formula

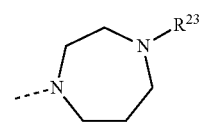

wherein
$R^{23}$ is H, $CH_3$, $C_2H_5$, or CO-4-pyridyl;
f) a fused bicyclic ring selected from the group consisting of

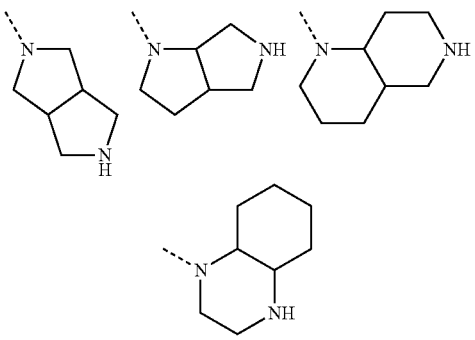

g) a spiro bicyclic ring selected from the group consisting of

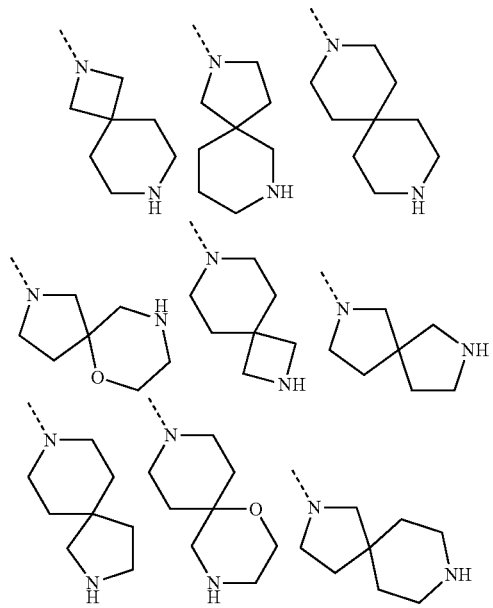

-continued

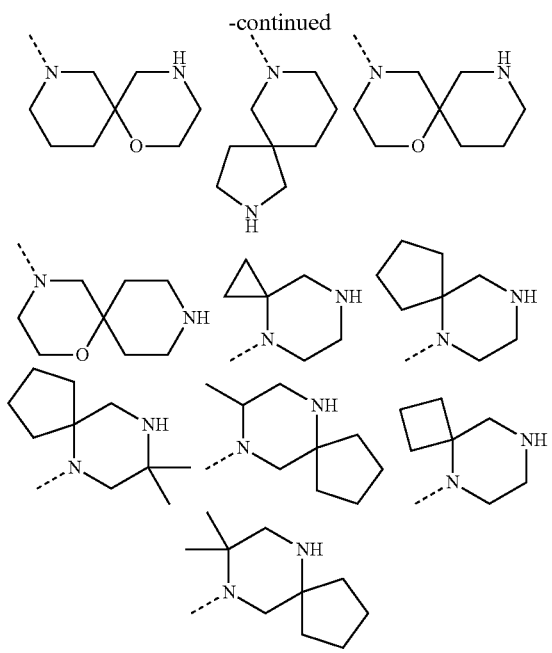

h) a bridged bicyclic ring consisting of

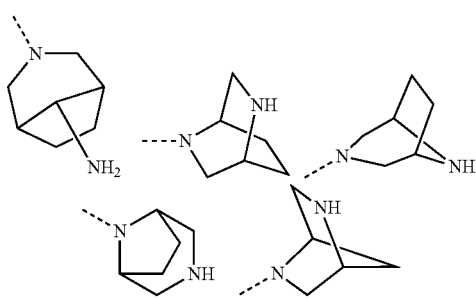

or

B) $R^1$ is $CF_3$, or $C_2H_5$;
  $R^2$ is H;
  $R^3$ is H;
  $R^4$ is H;
  $R^5$ is H;
  $R^6$ is H and
  $R^7$ is 3-azetidyl, or 3-piperidyl;
or
$R^6$ and $R^7$ together with the N-atom carrying them denote
  a) a 1,4-piperazinyl or a 1,4-diazepanyl, which are unsubstituted or mono-substituted by $CH_3$ or $C_2H_5$;
  b) a 1-pyrrolidinyl or a 1-piperidyl, which is mono-substituted by $NH_2$ or $NH(CH_3)$;
  c) a fused bicyclic ring selected from the group consisting of

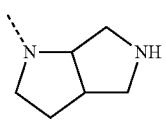

d) a spiro bicyclic ring selected from the group consisting of

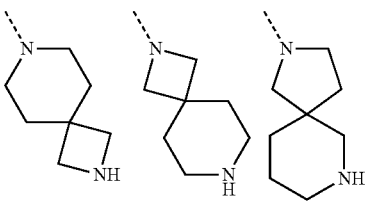

or

C) $R^1$ is propyl or cyclopropyl;
  $R^2$ is H;
  $R^3$ is H;
  $R^4$ is H;
  $R^5$ is H;
  $R^6$ and $R^7$ together with the N-atom carrying them denote a 1,4-piperazinyl, which is unsubstituted or substituted by one to two identical or different substituents selected from the group consisting of $CH_3$ and phenyl.

In another group of embodiments

A) $R^1$ is $CH_3$;
  $R^2$ is H, F, or $CH_3$;
  $R^3$ is H or F;
  $R^4$ is H;
  $R^5$ is H;
  $R^6$ is H; and
  $R^7$ is
  a) 3-pyrrolidinyl, which is unsubstituted or mono-substituted by $CH_3$, $C_3H_7$, O—$CH_3$, O—$C_2H_4$, phenyl or methylene-phenyl,
    3-piperidyl, which is unsubstituted or mono-substituted by $CH_3$, $C_2H_5$, or $C_3H_7$,
    4-piperidyl, which is unsubstituted or mono-substituted by $CH_3$, $C_2H_5$, $C_3H_7$, phenyl, methylene-phenyl;
  b) $(C_3-C_6)$-cycloalkyl which is mono-substituted by $NH_2$ or $N(CH_3)_2$
  c) $(C_1)$-alkyl which is mono-substituted by
    i) 2-pyrrolidinyl,
      2-piperidyl,
      3-piperidyl, which is unsubstituted or mono-substituted by $C_2H_5$;
    ii) $(C_6-C_7)$-cycloalkyl, which is mono-substituted by $NH_2$;
  d) $(C_2-C_4)$-alkyl which is mono-substituted by 1-pyrrolidinyl, 2-pyrrolidinyl, 1-piperazinyl, 1-morpholinyl, 4-piperidyl, which are unsubstituted or mono-substituted by $CH_3$ or phenyl; and wherein $(C_2-C_4)$-alkyl can be further mono-substituted by phenyl or pyridyl;
  e) $(C_2-C_6)$-alkyl which is mono-substituted by $NR^{24}R^{25}$, wherein
    $R^{24}$ is H or $CH_3$, and
    $R^{25}$ is H, $CH_3$ or $CH(CH_3)_2$,
    and wherein $(C_2-C_6)$-alkyl can be further mono-substituted by phenyl;

or

R⁶ and R⁷ together with the N-atom carrying them denote a) a 1,4-piperazinyl of the formula

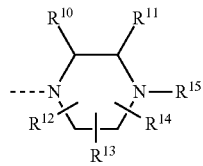

wherein
R¹⁰ is
  i) H,
  ii) (C₁-C₃)-alkyl, CF₃
  iii) phenyl, 3-pyridyl, 2-furyl, 2-thienyl, wherein phenyl is unsubstituted or substituted by one to two identical or different substituents selected from the group consisting of F, Cl, and CF₃;
R¹¹ is H, (C₁-C₄)-alkyl, CF₃, cyclopropyl, or phenyl;
R¹² is H, (C₁-C₃)-alkyl, or phenyl;
R¹³ is H, or (C₁-C₄)-alkyl;
R¹⁴ is H, or CH₃;
R¹⁵ is H;
b) a 1-pyrrolidinyl, which is mono-substituted by NR¹⁹R²⁰, wherein
R¹⁹ is H, CH₃;
R²⁰ is H, or CH₃,
  and 1-pyrrolidinyl can be further mono-substituted by (C₁-C₄)-alkyl or CF₃;
c) a 1-piperidyl, which is mono-substituted by NR²¹R²² or CH₂—NH₂, wherein
R²¹ is H, or CH₃;
R²² is H;
  and 1-piperidyl can be further mono-substituted by (C₁-C₄)-alkyl, or phenyl;
d) a 1,4-diazepanyl of the formula

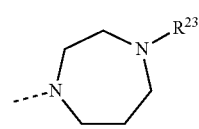

wherein
R²³ is H;
e) a fused bicyclic ring selected from the group consisting of

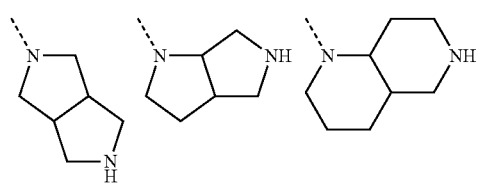

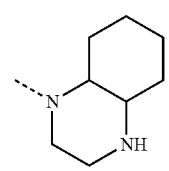

f) a spiro bicyclic ring selected from the group consisting of

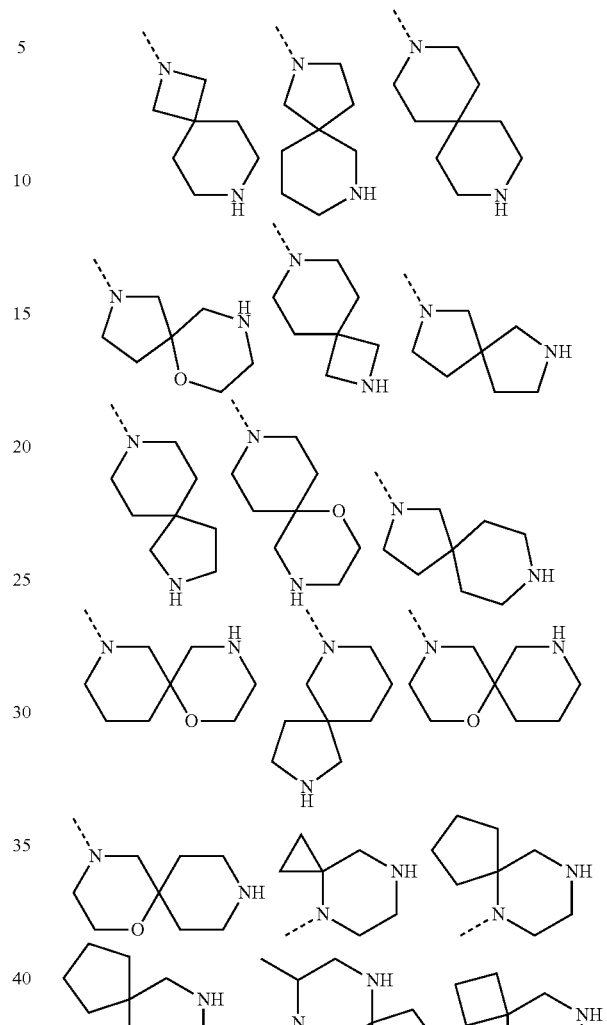

or
B) R¹ is CF₃, or C₇H₅;
R² is H;
R³ is H;
R⁴ is H;
R⁵ is H;
R⁶ is H and
R⁷ is 3-azetidyl, or 3-piperidyl;
or
R⁶ and R⁷ together with the N-atom carrying them denote
  a) a 1,4-piperazinyl or a 1,4-diazepanyl, which are unsubstituted or mono-substituted by CH₃ or C₂H₅;
  b) a 1-pyrrolidinyl or a 1-piperidyl; which is mono-substituted by NH₂ or NH(CH₃);
  c) a fused bicyclic ring selected from the group consisting of

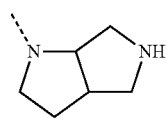

d) a spiro bicyclic ring selected from the group consisting of

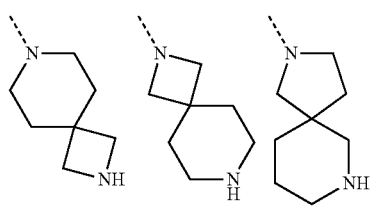

or

C) $R^1$ is propyl or cyclopropyl;
$R^2$ is H;
$R^3$ is H;
$R^4$ is H;
$R^5$ is H;
$R^6$ and $R^7$ together with the N-atom carrying them denote a 1,4-piperazinyl, which is unsubstituted or substituted by one to two identical or different substituents selected from the group consisting of $CH_3$ and phenyl.

In another group of embodiments
$R^1$ is $CH_3$, $CF_3$, $C_2H_5$, propyl or cyclopropyl;
$R^2$ is H, $CH_3$, F, Cl or O—$CH_3$;
$R^3$ is H, $CH_3$, F, $C_{1-10}$—$CH_3$ or O—$C_2H_5$;
$R^4$ is H or F;
$R^5$ is H, F or $CH_3$;
$R^5$ is H, $CH_3$ or $(CH_2)_2$-phenyl;
$R^7$ is a) $(C_0-C_6)$-alkyl which is mono-substituted by
  i) azetidyl, pyrrolidinyl, piperidyl, piperazinyl or morpholinyl, which are unsubstituted or substituted by one to five identical or different substituents selected from the group consisting of $CH_3$, $C_2H_5$, $C_3H_7$, O—$CH_3$, O—$C_2H_5$, phenyl, phenylene-methyl, methylene-phenyl, ethylene-phenyl, cyclohexyl, oxo (=O), and (O)—$CH_3$, and wherein $(C_0-C_6)$-alkyl can be further mono-substituted by phenyl or pyridyl;
  ii) $(C_3-C_8)$-cycloalkyl which is substituted by one to two identical or different substituents selected from the group consisting of and $N(CH_3)_2$;
  iii) $NR^8R^9$, wherein
    $R^3$ is H or $CH_3$, and
    $R^9$ is H, $CH_3$, $CH(CH_3)_2$ or $C(CH_3)_3$,
    and wherein $(C_0-C_6)$-alkyl can be further mono-substituted by phenyl, phenylene-methyl or phenylene-O-methyl;

or
$R^7$ is
b) a fused bicyclic ring selected from the group consisting of

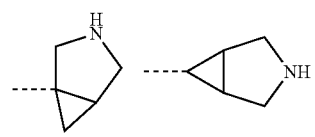

c) a spiro bicyclic ring selected from the group consisting of

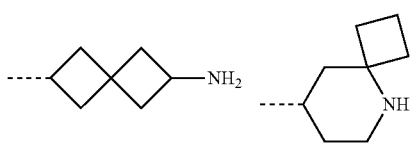

d) a bridged bicyclic ring selected from the group consisting of

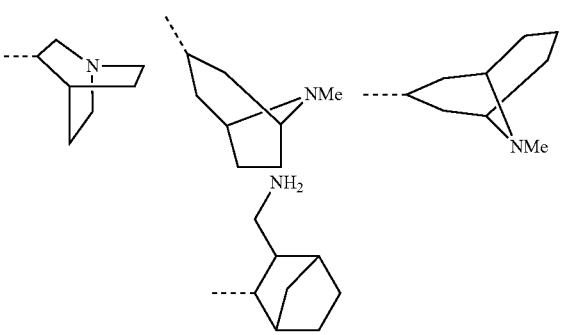

e) a spiro bicyclic ring with a fused ring selected from the group consisting of

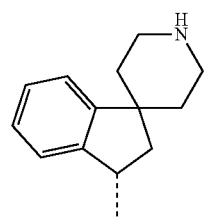

or
$R^6$ and $R^7$ together with the N-atom carrying them denote
a) a 1,4-piperazinyl of the formula

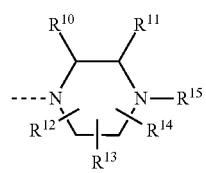

wherein
$R^{10}$ is H, or $(C_0-C_4)$-alkyl, which is unsubstituted or substituted threefold by F or mono-substituted by O—$CH_3$, phenyl, pyridyl, furyl, thienyl, benzo[1,3]dioxole or CO—$R^{16}$;

wherein phenyl is unsubstituted or substituted by one to two identical or different substituents selected from the group consisting of F, Cl, Br, CF$_3$, O—CH$_3$, and CH(CH$_3$)$_2$;

$R^{11}$ is H or (C$_0$-C$_4$)-alkyl, which is unsubstituted or substituted threefold by F or mono-substituted by CO—R$^{17}$, cyclopropyl, phenyl, O—CH$_3$ or oxo (=O);

$R^{12}$ is H, (C$_1$-C$_4$)-alkyl or phenyl;

$R^{13}$ is H or (C$_1$-C$_4$)-alkyl;

$R^{14}$ is H or CH$_3$;

$R^{15}$ is H, (C$_1$-C$_4$)-alkyl, cyclobutyl or CO—R$^{18}$, where (C$_1$-C$_4$)-alkyl is unsubstituted or mono-substituted by SO$_2$—CH$_3$, 4-piperidyl, 2-pyridyl, 4-tetrahydropyranyl or 3-tetrahydrofuryl;

$R^{16}$ is O—CH$_3$ or NH—(C$_1$-C$_4$)-alkyl;

$R^{17}$ is O—CH$_3$;

$R^{18}$ is CH$_3$, NH$_2$, phenyl, 3-furyl, 2-tetrahydrofuryl or 1-pyrrolidinyl where phenyl can be further mono-substituted by CH$_3$ or O—CH$_3$;

b) a 1-azetidinyl, which is mono-substituted by NH$_2$ or (C$_1$-C$_4$)-alkylene-NH$_2$;

c) a 1-pyrrolidinyl, which is mono-substituted by NR$^{19}$R$^{20}$ or 1-cyclopropylamine, wherein $R^{19}$ is H, CH$_3$ or phenyl;

$R^{20}$ is H or CH$_3$, and 1-pyrrolidinyl can be further mono-substituted by (C$_1$-C$_4$)-alkyl or CF$_3$;

d) a 1-piperidyl, which is mono-substituted by NR$^{21}$R$^{22}$ or CH$_2$—NH$_2$, wherein $R^{21}$ is H or CH$_3$;

$R^{22}$ is H;

and 1-piperidyl can be further mono-substituted by (C$_1$-C$_4$)-alkyl, CO—OCH$_3$ or phenyl;

e) a 1,4-diazepanyl of the formula

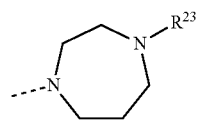

wherein $R^{23}$ is H, (C$_1$-C$_4$)-alkyl or CO-4-pyridyl;

f) a fused bicyclic ring selected from the group consisting of

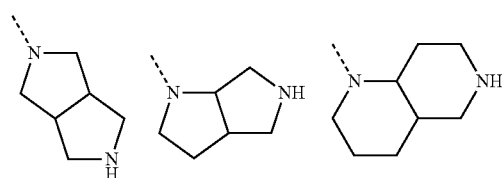

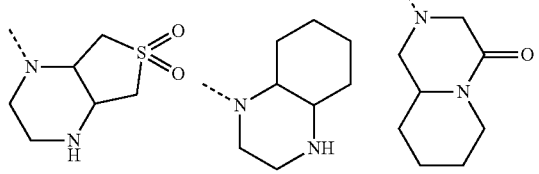

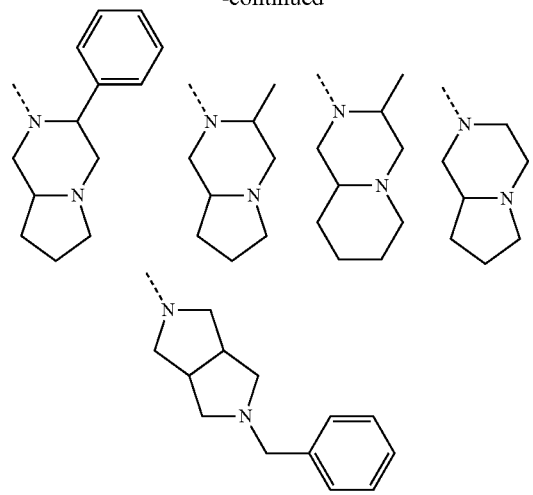

g) a spiro bicyclic ring selected from the group consisting of

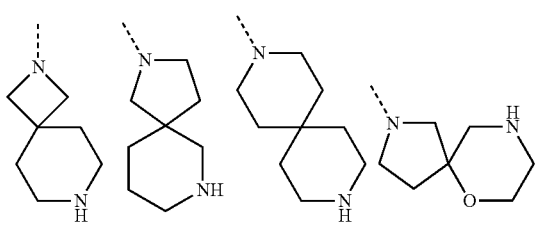

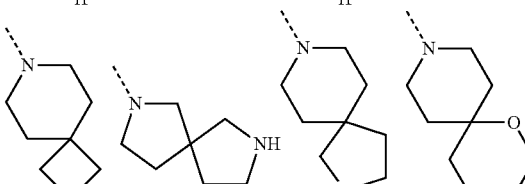

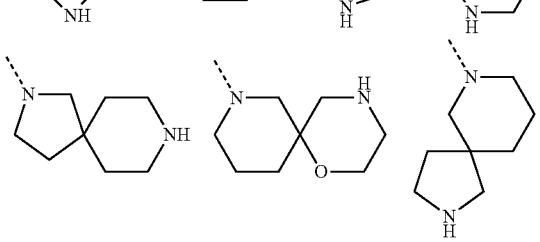

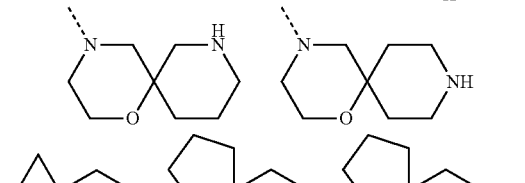

h) a bridged bicyclic ring selected from the group consisting of

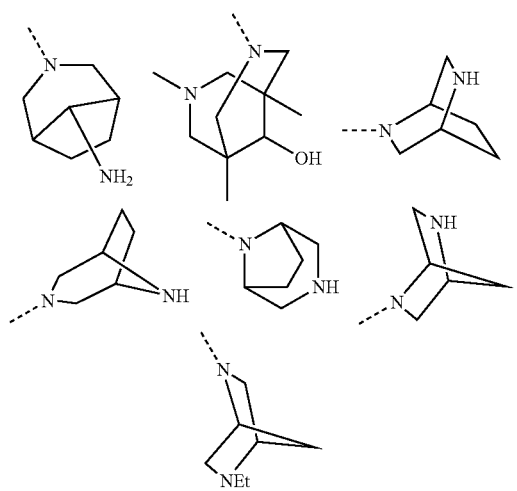

i) a spiro bicyclic ring with a fused ring selected from the group consisting of

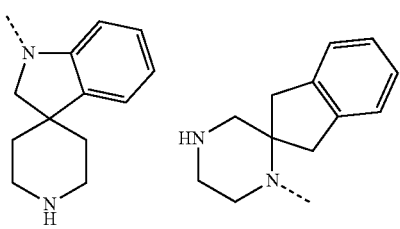

In another group of embodiments
R$^1$ is CH$_3$, CF$_3$, C$_2$H$_5$, propyl or cyclopropyl;
R$^2$ is H, CH$_3$, F, Cl or O—CH$_3$;
R$^3$ is H, CH$_3$, F, C$_{1-10}$—CH$_3$ or O—C$_2$H$_5$;
R$^4$ is H or F;
R$^5$ is H, F or CH$_3$;
R$^6$ is H or CH$_3$;
R$^7$ is
a) (C$_0$-C$_6$)-alkyl which is mono-substituted by
  i) azetidyl, pyrrolidinyl, piperidyl, piperazinyl or morpholinyl, which are unsubstituted or substituted by one to five identical or different substituents selected from the group consisting of CH$_3$, C$_2$H$_5$, C$_3$H$_7$, O—CH$_3$, O—C$_2$H$_5$, phenyl, phenylene-methyl, methylene-phenyl, ethylene-phenyl, cyclohexyl, oxo (=O), and (O)—CH$_3$, and wherein (C$_0$-C$_6$)-alkyl can be further mono-substituted by phenyl or pyridyl;
  ii) (C$_3$-C$_3$)-cycloalkyl which is substituted by one to two identical or different substituents selected from the group consisting of NH$_2$ and N(CH$_3$)$_2$;
  iii) NR$^8$R$^9$, wherein
    R$^8$ is H or CH$_3$, and
    R$^9$ is H, CH$_3$, CH(CH$_3$)$_2$ or C(CH$_3$)$_3$,
    and wherein (C$_0$-C$_6$)-alkyl can be further mono-substituted by phenyl, phenylene-methyl or phenylene-O-methyl;
or
R$^7$ is
b) a fused bicyclic ring selected from the group consisting of

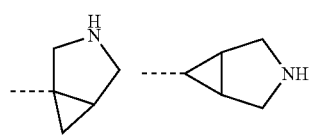

c) a spiro bicyclic ring selected from the group consisting of

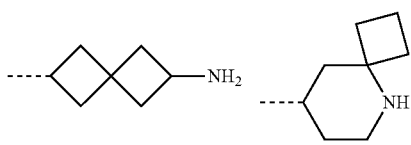

d) a bridged bicyclic ring selected from the group consisting of

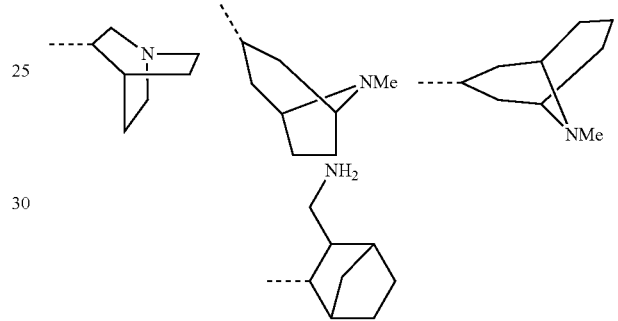

e) a spiro bicyclic ring with a fused ring selected from the group consisting of

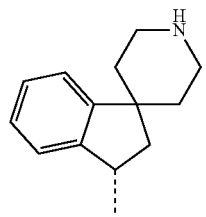

or
R$^6$ and R$^7$ together with the N-atom carrying them denote
a) a 1,4-piperazinyl of the formula

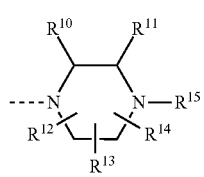

wherein
R$^{10}$ is H, or (C$_0$-C$_4$)-alkyl, which is unsubstituted or substituted threefold by F or mono-substituted by O—CH$_3$, phenyl, pyridyl, furyl, thienyl, benzo[1,3]dioxole or CO—R$^{16}$;

wherein phenyl is unsubstituted or substituted by one to two identical or different substituents selected from the group consisting of F, Cl, Br, $CF_3$, $O-CH_3$, and $CH(CH_3)_2$;

$R^{11}$ is H or $(C_0-C_4)$-alkyl, which is unsubstituted or substituted threefold by F or mono-substituted by $CO-R^{17}$, cyclopropyl, phenyl, $O-CH_3$ or oxo (=O);

$R^{12}$ is H, $(C_1-C_4)$-alkyl or phenyl;

$R^{13}$ is H or $(C_1-C_4)$-alkyl;

$R^{14}$ is H or $CH_3$;

$R^{15}$ is H, $(C_1-C_4)$-alkyl, cyclobutyl or $CO-R^{18}$, where $(C_1-C_4)$-alkyl is unsubstituted or mono-substituted by $SO_2-CH_3$, 4-piperidyl, 2-pyridyl, 4-tetrahydropyranyl or 3-tetrahydrofuryl;

$R^{16}$ is $O-CH_3$ or $NH-(C_1-C_4)$-alkyl;

$R^{17}$ is $O-CH_3$;

$R^{18}$ is $CH_3$, $NH_2$, phenyl, 3-furyl, 2-tetrahydrofuryl or 1-pyrrolidinyl where phenyl can be further mono-substituted by $CH_3$ or $O-CH_3$;

b) a 1-azetidinyl, which is mono-substituted by $NH_2$ or $(C_1-C_4)$-alkylene-$NH_2$;

c) a 1-pyrrolidinyl, which is mono-substituted by $NR^{19}R^{20}$ or 1-cyclopropylamine, wherein $R^{19}$ is H, $CH_3$ or phenyl;

$R^{20}$ is H or $CH_3$, and 1-pyrrolidinyl can be further mono-substituted by $(C_1-C_4)$-alkyl or $CF_3$;

d) a 1-piperidyl, which is mono-substituted by $NR^{21}R^{22}$ or $CH_2-NH_2$, wherein $R^{21}$ is H or $CH_3$;

$R^{22}$ is H;

and 1-piperidyl can be further mono-substituted by $(C_1-C_4)$-alkyl, $CO-OCH_3$ or phenyl;

e) a 1,4-diazepanyl of the formula

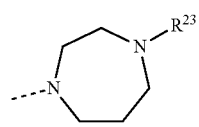

wherein $R^{23}$ is H, $(C_1-C_4)$-alkyl or CO-4-pyridyl;

f) a fused bicyclic ring selected from the group consisting of

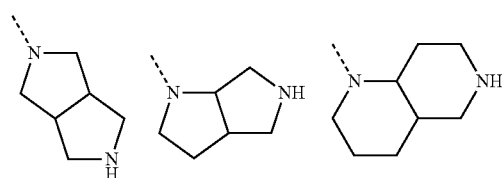

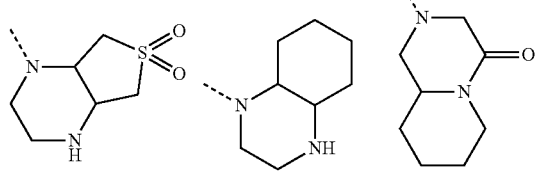

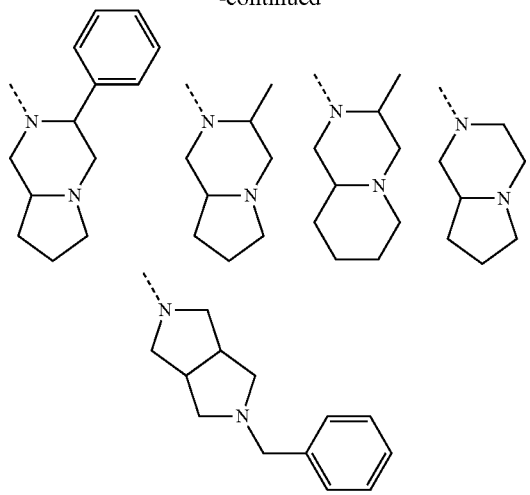

g) a spiro bicyclic ring selected from the group consisting of

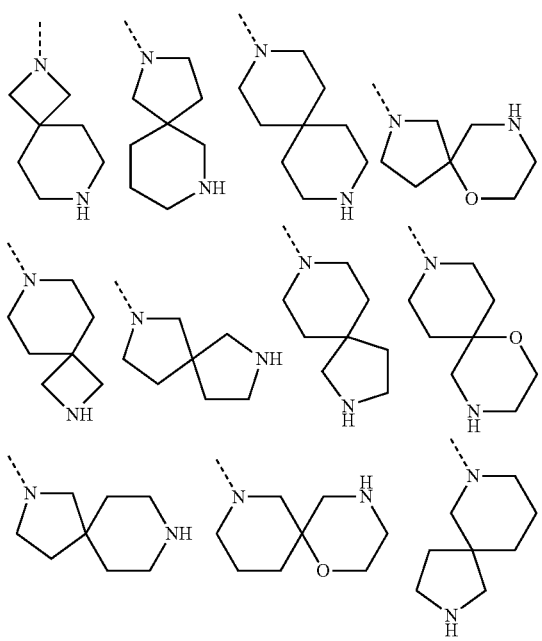

h) a bridged bicyclic ring selected from the group consisting of

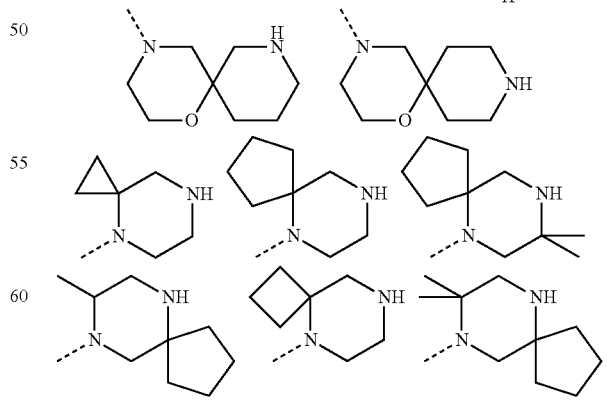

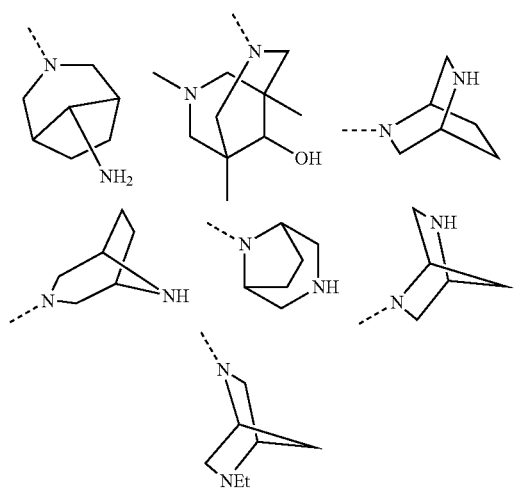

i) a spiro bicyclic ring with a fused ring selected from the group consisting of

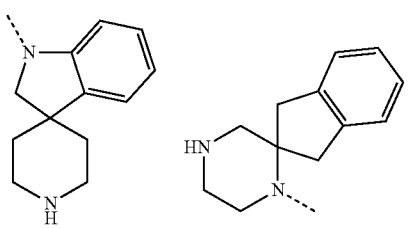

In another group of embodiments $R^1$ is $CF_3$, $C_2H_5$ Propyl or cyclopropyl;

$R^2$ is H;

$R^3$ is H or F;

$R^4$ is H;

$R^6$ is H;

$R^6$ is H and $R^7$ is a) 3-azetidyl, 3-pyrrolidinyl, 3-piperidyl, 4-piperidyl or methylene-2-pyrrolidinyl, which are unsubstituted or mono-substituted by $CH_3$, $C_2H_5$, $OCH_3$, or oxo (=O);

b) cyclohexyl, which is mono-substituted by $NH_2$;

c) a bridged bicyclic ring selected from the group consisting of

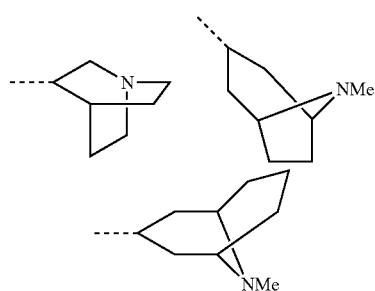

d) a spiro bicyclic ring selected from the group consisting of

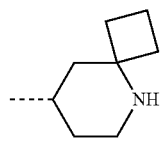

e) a spiro bicyclic ring with a fused ring selected from the group consisting of

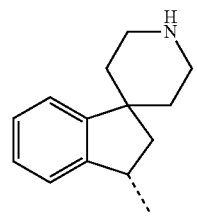

or $R^6$ is $CH_3$ and $R^7$ is 4-methyl-4-piperidyl;

or $R^6$ and $R^7$ together with the N-atom carrying them denote a) a 1,4-piperazinyl or a 1,4-diazepanyl, which are unsubstituted or substituted by one to two identical or different substituents selected from the group consisting of $CH_3$, $C_2H_5$ and phenyl b) a 1-azetidinyl, a 1-pyrrolidinyl or a 1-piperidyl, which are mono-substituted by NH—) $NH(CH_3)$ or $N(CH_3)_2$;

c) a fused bicyclic ring selected from the group consisting of

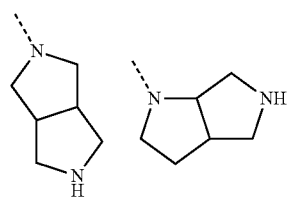

d) a spiro bicyclic ring selected from the group consisting of

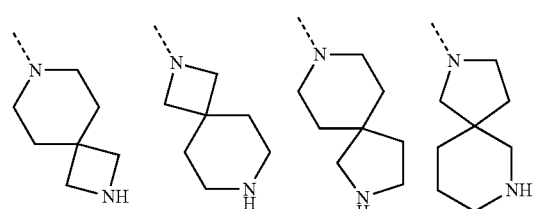

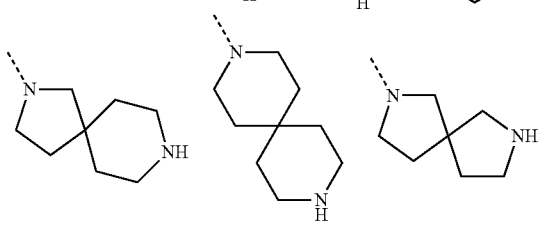

e) a bridged bicyclic ring selected from the group consisting of

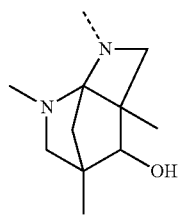

In another group of embodiments
$R^1$ is $CH_3$;
$R^2$ is H, $CH_3$, F, Cl or O—$CH_3$;
$R^3$ is H, $CH_3$, F, $C_{1-10}$—$CH_3$ or O—$C_2H_5$;
$R^4$ is H or F;
$R^5$ is H, F or $CH_3$;
$R^6$ is H, $CH_3$ or $(CH_2)_2$-phenyl;
$R^7$ is a) $(C_0\text{-}C_6)$-alkyl which is mono-substituted by
   i) azetidyl, pyrrolidinyl, piperidyl, piperazinyl or morpholinyl, which are unsubstituted or substituted by one to five identical or different substituents selected from the group consisting of $CH_3$, $C_2H_5$, $C_3H_7$, O—$CH_3$, O—$C_2H_5$, phenyl, phenylene-methyl, methylene-phenyl, ethylene-phenyl, cyclohexyl, oxo (=O), and (O)—$CH_3$, and wherein $(C_0\text{-}C_6)$-alkyl can be further mono-substituted by phenyl or pyridyl;
   ii) $(C_3\text{-}C_8)$-cycloalkyl which is substituted by one to two identical or different substituents selected from the group consisting of $NH_2$ and $N(CH_3)_2$;
   iii) $NR^8R^9$, wherein
      $R^8$ is H or $CH_3$, and
      $R^9$ is H, $CH_3$, $CH(CH_3)$—, or $C(CH_3)_3$,
      and wherein $(C_0\text{-}C_6)$-alkyl can be further mono-substituted by phenyl, phenylene-methyl or phenylene-O-methyl;

or
$R^7$ is b) a fused bicyclic ring selected from the group consisting of

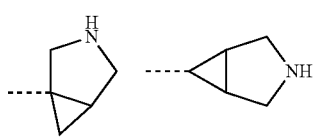

c) a spiro bicyclic ring selected from the group consisting of

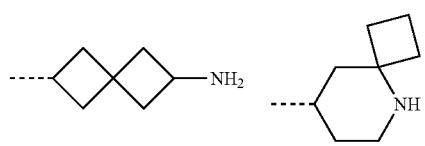

d) a bridged bicyclic ring consisting of

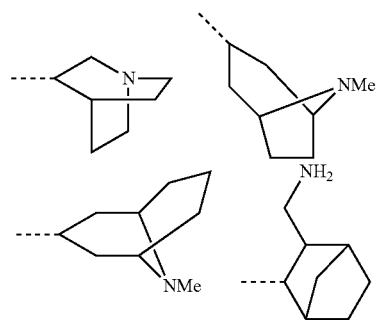

e) a spiro bicyclic ring with a fused ring selected from the group consisting of

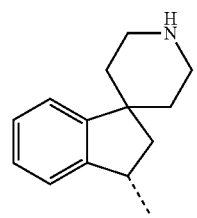

or
$R^6$ and $R^7$ together with the N-atom carrying them denote
a) a 1,4-piperazinyl of the formula

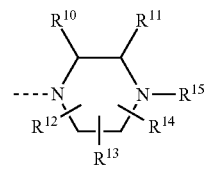

wherein
$R^{10}$ is H, or $(C_0\text{-}C_4)$-alkyl, which is unsubstituted or substituted threefold by F or mono-substituted by O—$CH_3$, phenyl, pyridyl, furyl, thienyl, benzo[1,3]dioxole or CO—$R^{16}$;
   wherein phenyl is unsubstituted or substituted by one to two identical or different substituents selected from the group consisting of F, Cl, Br, $CF_3$, O—$CH_3$, and $CH(CH_3)_2$;
$R^{11}$ is H or $(C_0\text{-}C_4)$-alkyl, which is unsubstituted or substituted threefold by F or mono-substituted by CO—$R^{17}$, cyclopropyl, phenyl, O—$CH_3$ or oxo (=O);
$R^{12}$ is H, $(C_1\text{-}C_4)$-alkyl or phenyl;
$R^{13}$ is H or $(C_1\text{-}C_4)$-alkyl;
$R^{14}$ is H or $CH_3$;
$R^{15}$ is H, $(C_1\text{-}C_4)$-alkyl, cyclobutyl or CO—$R^{18}$, where $(C_1\text{-}C_4)$-alkyl is unsubstituted or mono-substituted by $SO_2$—$CH_3$, 4-piperidyl, 2-pyridyl, 4-tetrahydropyranyl or 3-tetrahydrofuryl;
$R^{16}$ is O—$CH_3$ or NH—$(C_1\text{-}C_4)$-alkyl;
$R^{17}$ is O—$CH_3$;
$R^{18}$ is $CH_3$, $NH_2$, phenyl, 3-furyl, 2-tetrahydrofuryl or 1-pyrrolidinyl, where phenyl can be further mono-substituted by $CH_3$ or O—$(CH_3)$;

b) a 1-azetidinyl, which is mono-substituted by $NH_2$ or $(C_1\text{-}C_4)$-alkylene-$NH_2$;

c) a 1-pyrrolidinyl, which is mono-substituted by $NR^{19}R^{20}$ or 1-cyclopropylamine, wherein $R^{19}$ is H, $CH_3$ or phenyl;

$R^{20}$ is H or $CH_3$, and 1-pyrrolidinyl can be further mono-substituted by $(C_1-C_4)$-alkyl or $CF_3$;

d) a 1-piperidyl, which is mono-substituted by $NR^{21}R^{22}$ or $CH_2-NH_2$, wherein $R^{21}$ is H or $CH_3$;

$R^{22}$ is H;

and 1-piperidyl can be further mono-substituted by $(C_1-C_1)$-alkyl, $CO-OCH_3$ or phenyl;

e) a 1,4-diazepanyl of the formula

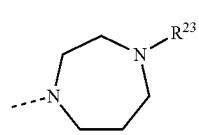

wherein $R^{23}$ is H, $(C_1-C_4)$-alkyl or CO-4-pyridyl;

f) a fused bicyclic ring selected from the group consisting of

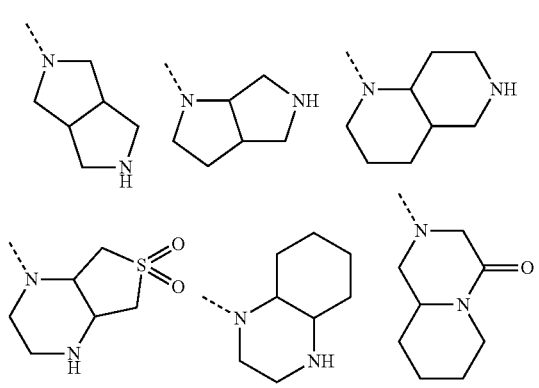

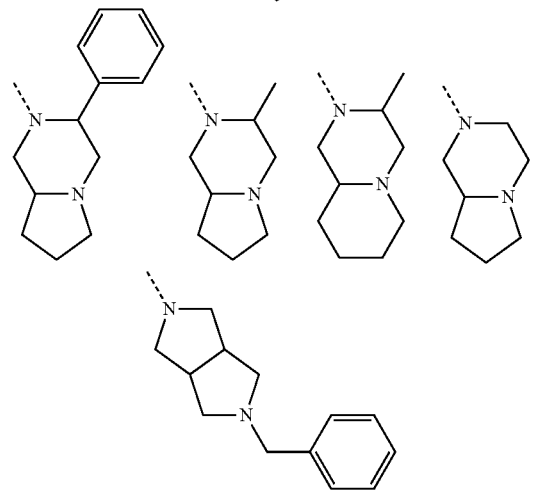

g) a spiro bicyclic ring selected from the group consisting of

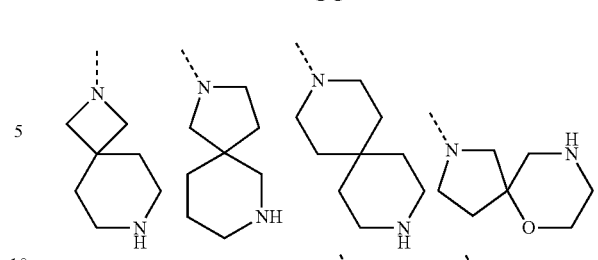

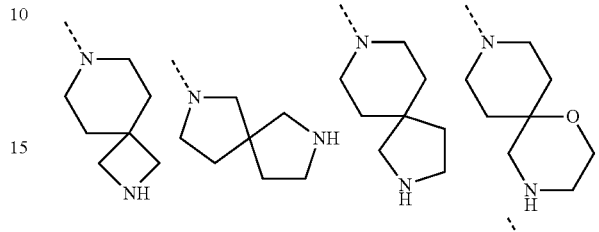

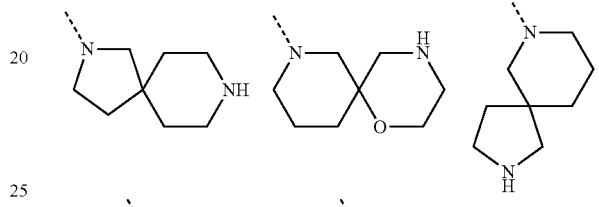

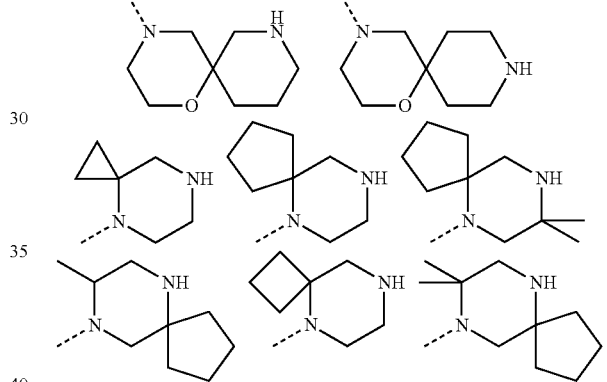

h) a bridged bicyclic ring selected from the group consisting of

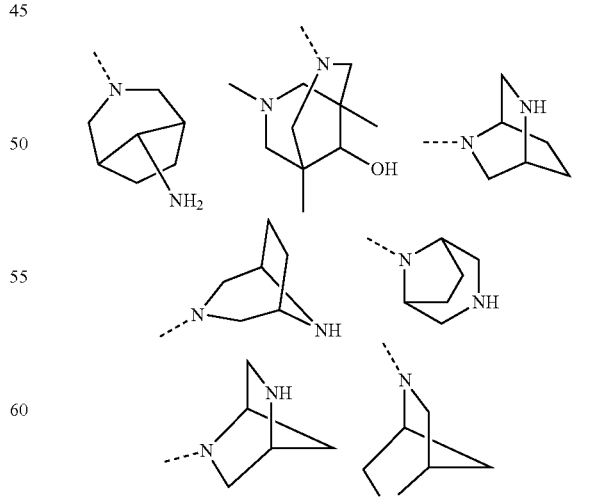

i) a spiro bicyclic ring with a fused ring selected from the group consisting of

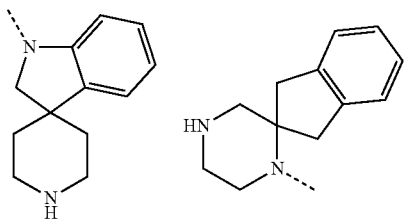

In another group of embodiments

R¹ is $CH_3$;

R² is H, $CH_3$, F, Cl or O—$CH_3$;

R³ is H, $CH_3$, F, Cl, O—$CH_3$ or O—$C_2H_5$;

R⁴ is H or F;

R⁵ is H, F or $CH_3$;

R⁶ is H;

R⁷ is a) ($C_0$-$C_6$)-alkyl which is mono-substituted by azetidyl, pyrrolidinyl, piperidyl, piperazinyl or morpholinyl, which are unsubstituted or substituted by one to five identical or different substituents selected from the group consisting of $CH_3$, $C_2H_5$, $C_3H_7$, O—$CH_3$, O—$C_2H_5$, phenyl, phenylene-methyl, methylene-phenyl, ethylene-phenyl, cyclohexyl, oxo (=O), and (CO)—$CH_3$, and wherein ($C_0$-$C_6$)-alkyl can be further mono-substituted by phenyl or pyridyl;

ii) ($C_3$-$C_8$)-cycloalkyl which is substituted by one to two identical or different substituents selected from the group consisting of and $N(CH_3)_2$;

iii) $NR^8R^9$, wherein

R⁸ is H or $CH_3$, and

R⁹ is H, $CH_3$, $CH(CH_3)_2$ or $C(CH_3)_3$, and wherein ($C_0$-$C_6$)-alkyl can be further mono-substituted by phenyl, phenylene-methyl or phenylene-O-methyl;

or

R⁷ is b) a fused bicyclic ring selected from the group consisting of

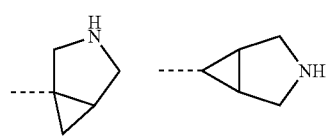

c) a spiro bicyclic ring selected from the group consisting of

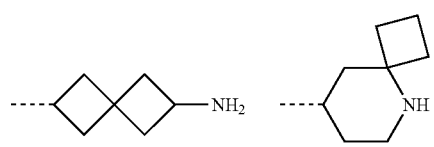

d) a bridged bicyclic ring consisting of

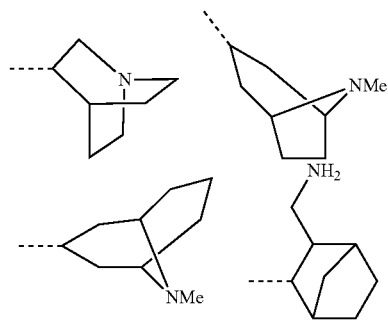

e) a spiro bicyclic ring with a fused ring selected from the group consisting of

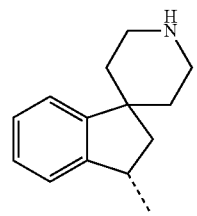

or

R⁶ and R⁷ together with the N-atom carrying them denote a) a 1,4-piperazinyl of the formula

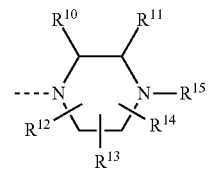

wherein

R¹⁰ is H, or ($C_0$-$C_4$)-alkyl, which is unsubstituted or substituted threefold by F or mono-substituted by O—$CH_3$, phenyl, pyridyl, furyl, thienyl, benzo[1,3]dioxole or CO—$R^{16}$;

wherein phenyl is unsubstituted or substituted by one to two identical or different substituents selected from the group consisting of F, Cl, Br, $CF_3$, O—$CH_3$, and $CH(CH_3)_2$;

R¹¹ is H or ($C_0$-$C_4$)-alkyl, which is unsubstituted or substituted threefold by F or mono-substituted by CO—$R^{17}$, cyclopropyl, phenyl, O—$CH_3$ or oxo (=O);

R¹² is H, ($C_1$-$C_4$)-alkyl or phenyl;

R¹³ is H or ($C_1$-$C_4$)-alkyl;

R¹⁴ is H or $CH_3$;

R¹⁵ is H, ($C_1$-$C_4$)-alkyl, cyclobutyl or CO—$R^{18}$, where ($C_1$-$C_4$)-alkyl is unsubstituted or mono-substituted by $SO_2$—$CH_3$, 4-piperidyl, 2-pyridyl, 4-tetrahydropyranyl or 3-tetrahydrofuryl;

R¹⁶ is O—$CH_3$ or NH—($C_1$-$C_4$)-alkyl;

R¹⁷ is O—$CH_3$;

R¹⁸ is $CH_3$, $NH_2$, phenyl, 3-furyl, 2-tetrahydrofuryl or 1-pyrrolidinyl here phenyl can be further mono-substituted by $CH_3$ or O—$CH_3$;

b) a 1-azetidinyl, which is mono-substituted by $NH_2$ or ($C_1$-$C_4$)-alkylene-$NH_2$;

c) a 1-pyrrolidinyl, which is mono-substituted by NR$^{19}$R$^{20}$ or 1-cyclopropylamine, wherein R$^{19}$ is H, CH$_3$ or phenyl;

R$^{20}$ is H or CH$_3$, and 1-pyrrolidinyl can be further mono-substituted by (C$_1$-C$_4$)-alkyl or CF$_3$;

d) a 1-piperidyl, which is mono-substituted by NR$^{21}$R$^{22}$ or CH$_2$—NH$_2$, wherein R$^{21}$ is H or CH$_3$;

R$^{22}$ is H;

and 1-piperidyl can be further mono-substituted by (C$_1$-C$_4$)-alkyl, CO—OCH$_3$ or phenyl;

e) a 1,4-diazepanyl of the formula

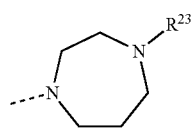

wherein

R$^{23}$ is H, (C$_1$-C$_4$)-alkyl or CO-4-pyridyl;

f) a fused bicyclic ring selected from the group consisting of

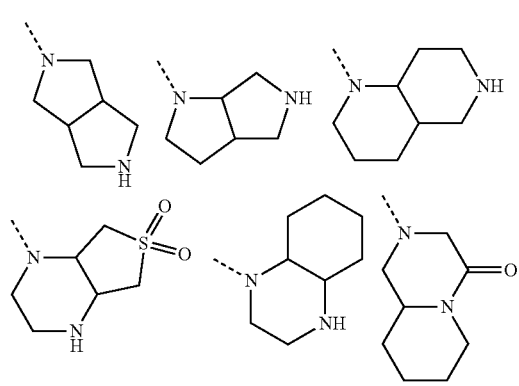

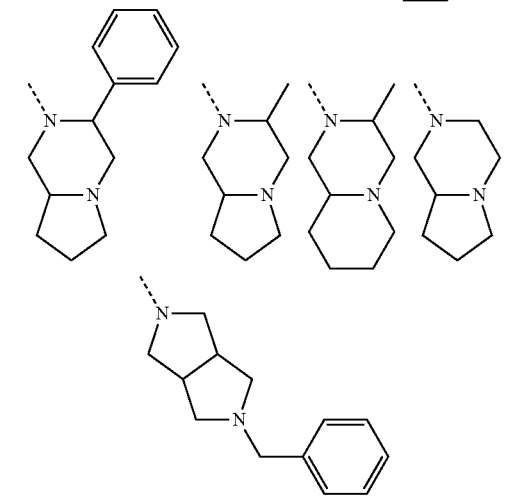

g) a spiro bicyclic ring selected from the group consisting of

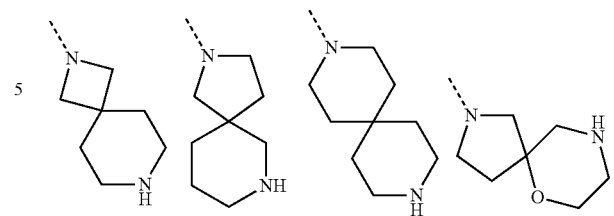

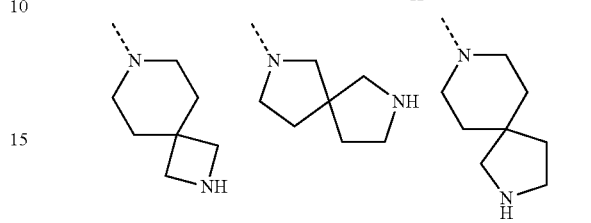

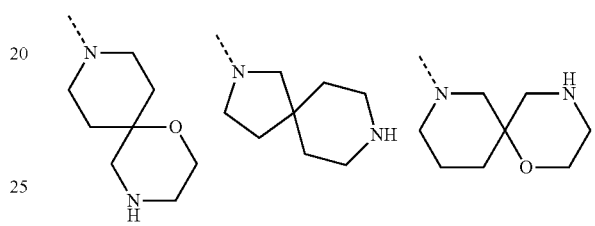

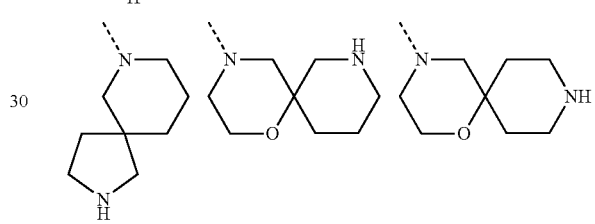

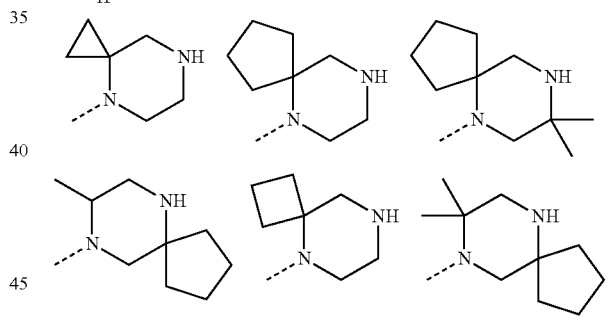

h) a bridged bicyclic ring selected from the group consisting of

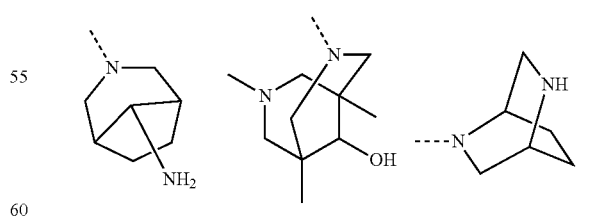

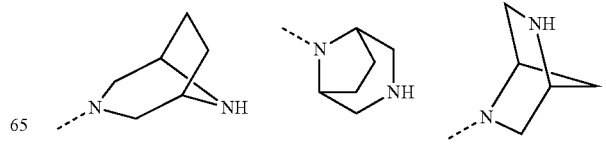

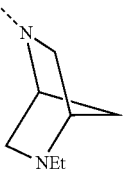

i) a spiro bicyclic ring with a fused ring selected from the group consisting of

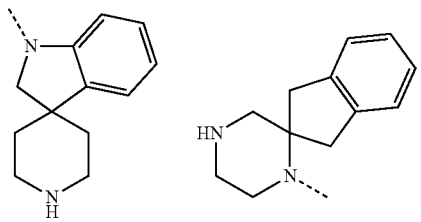

In another group of embodiments
$R^1$ is $(C_1-C_4)$-alkyl; or in a another embodiment $CH_3$;
$R^2$ is H, halogen or $(C_1-C_4)$-alkyl; or in another embodiment H, F, or $CH_3$;
$R^3$ is H or halogen; or in another embodiment H or F;
$R^4$ is H;
$R^5$ is H;
$R^6$ is H; and
$R^7$ is
a) $(C_0-C_6)$-alkyl which is mono-substituted by
  i) a 3- to 8-membered monocyclic heterocycle comprising a ring nitrogen atom and optionally one further ring heteroatom selected from the group consisting of nitrogen and oxygen, which is unsubstituted or substituted by one to five identical or different substituents selected from the group consisting of
    ia) F,
    ib) $(C_1-C_4)$-alkyl, which is unsubstituted or one to fivefold substituted by F,
    ic) O—$(C_1-C_4)$-alkyl, which is unsubstituted or one to fivefold substituted by F,
    id) phenyl, which is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F,
    ie) $(C_1-C_4)$-alkylene-phenyl, which is unsubstituted or one to fivefold substituted by F,
    if) $(C_3-C_8)$-cycloalkyl,
    ie) oxo (=O), and
    ig) (CO)—$(C_1-C_4)$-alkyl,
    and wherein $(C_0-C_6)$-alkyl can be further mono-substituted by phenyl or pyridyl, wherein phenyl or pyridyl is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F;
  ii) $(C_3-C_8)$-cycloalkyl which is substituted by one to two identical or different substituents selected from the group consisting of $NH_2$, $NH((C_1-C_4)$-alkyl) and $N((C_1-C_4)$-alkyl)$_2$, and wherein $(C_3-C_8)$-cycloalkyl can be further substituted by one to three identical or different substituents selected from the group consisting of
    iia) F,
    iib) $(C_1-C_4)$-alkyl, wherein $(C_1-C_4)$-alkyl is unsubstituted or one to fivefold substituted by F,
    iic) O—$(C_1-C_4)$-alkyl, which is unsubstituted or one to fivefold substituted by F.
    iid) phenyl, which is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F, and
    iie) $(C_1-C_4)$-alkylene-phenyl, which is unsubstituted or one to fivefold substituted by F;
    or
  iii) $NR^8R^9$, wherein
    $R^8$ is H or $(C_1-C_4)$-alkyl, and
    $R^9$ is H or $(C_1-C_6)$-alkyl,
    and wherein $(C_0-C_6)$-alkyl can be further mono-substituted by phenyl, phenylene-$(C_1-C_4)$-alkyl or phenylene-O—$(C_1-C_4)$-alkyl;
b) a bicyclic $(C_6-C_{11})$-cycloalkyl group, which is mono-substituted by $(C_0-C_2)$-alkylene-$NH_2$, $(C_0-C_2)$-alkylene-NH—$(C_1-C_4)$-alkyl, $(C_0-C_2)$-alkylene-N($(C_1-C_4)$-alkyl)$_2$;
c) a fused bicyclic $(C_6-C_{10})$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F;
d) a spiro bicyclic $(C_7-C_{11})$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F;
e) a bridged bicyclic $(C_7-C_9)$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F; or
f) a tricyclic $(C_{11}-C_{15})$-heterocycloalkyl group containing one nitrogen atom, which is attached via a carbon atom and which consists of a spiro bicyclic ring with an additional fused phenyl ring, and which is unsubstituted or substituted by one or two identical or different substituents selected from the group consisting of F and $(C_1-C_4)$-alkyl, which is unsubstituted or one to fivefold substituted by F;
or in another embodiment
$R^7$ is
a) $(C_0-C_6)$-alkyl which is mono-substituted by
  i) a 3- to 8-membered monocyclic heterocycle comprising a ring nitrogen atom and optionally one further ring heteroatom selected from the group consisting of nitrogen and oxygen, which is unsubstituted or substituted by one to five identical or different substituents selected from the group consisting of $(C_1-C_4)$-alkyl, O—$(C_1-C_4)$-alkyl, phenyl, phenylene-$(C_1-C_4)$-alkyl, $(C_1-C_4)$-alkylene-phenyl, $(C_3-C_8)$-cycloalkyl, oxo (=O), and (CO)—$(C_1-C_4)$-alkyl, and wherein $(C_0-C_6)$-alkyl can be further mono-substituted by phenyl or pyridyl;
  ii) $(C_3-C_8)$-cycloalkyl which is substituted by one to two identical or different substituents selected from the group consisting of $NH_2$ and $N((C_1-C_4)$-alkyl)$_2$;

iii) NR⁸R⁹, wherein
R⁸ is H or ($C_1$-$C_4$)-alkyl, and
R⁹ is H or ($C_1$-$C_6$)-alkyl,
and wherein ($C_0$-$C_6$)-alkyl can be further mono-substituted by phenyl, phenylene-($C_1$-$C_4$)-alkyl or phenylene-O—($C_1$-$C_4$)-alkyl;
or
R⁷ is
b) a bicyclic ($C_7$)-cycloalkyl group, which is mono-substituted by —$NH_2$, or —$CH_2$—$NH_2$;
c) a fused bicyclic ($C_6$)-heterocycloalkyl group containing one nitrogen atom, which is attached via a carbon atom
d) a spiro bicyclic ($C_9$)-heterocycloalkyl group containing one nitrogen atom, which is attached via a carbon atom;
e) a bridged bicyclic ($C_8$-$C_9$)-heterocycloalkyl group containing one nitrogen atom, which is attached via a carbon atom and which is unsubstituted or monosubstituted by $CH_3$;
f) a tricyclic ($C_{14}$)-heterocycloalkyl group containing one nitrogen atom, which is attached via a carbon atom and which consists of a spiro bicyclic ring with an additional fused phenyl ring;
or in another embodiment
R⁷ is
a) ($C_0$-$C_6$)-alkyl which is mono-substituted by
i) azetidyl, pyrrolidinyl, piperidyl, piperazinyl or morpholinyl, which are unsubstituted or substituted by one to five identical or different substituents selected from the group consisting of $CH_3$, $C_2H_5$, $C_3H_7$, O—$CH_3$, O—$C_7H_5$, phenyl, phenylene-methyl, methylene-phenyl, ethylene-phenyl, cyclohexyl, oxo (=O), and (CO)—$CH_3$, and wherein ($C_0$-$C_6$)-alkyl can be further mono-substituted by phenyl or pyridyl;
ii) ($C_3$-$C_8$)-cycloalkyl which is substituted by one to two identical or different substituents selected from the group consisting of $NH_2$ and N($CH_3$)$_2$;
iii) NR⁸R⁹, wherein
R⁸ is H or $CH_3$, and
R⁹ is H, $CH_3$, CH($CH_3$)$_2$ or C($CH_3$)$_3$,
and wherein ($C_0$-$C_6$)-alkyl can be further mono-substituted by phenyl, phenylene-methyl or phenylene-O-methyl;
or
R⁷ is
b) a fused bicyclic ring selected from the group consisting of

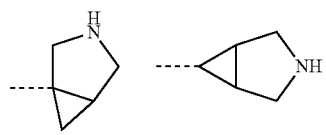

c) a spiro bicyclic ring selected from the group consisting of

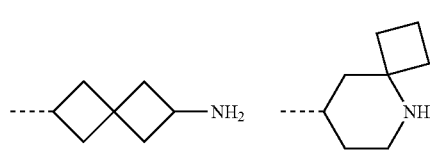

d) a bridged bicyclic ring selected from the group consisting of

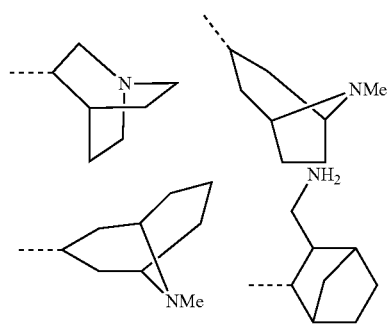

e) a spiro bicyclic ring with a fused ring selected from the group consisting of

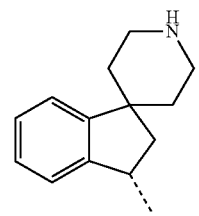

or in another embodiment
R⁷ is
a) 3-azetidinyl,
3-pyrrolidinyl, which is unsubstituted or mono-substituted by $CH_3$, $C_3H_7$, O—$CH_3$, O—$C_2H_5$, phenyl, phenylene-methyl or methylene-phenyl, 3-piperidyl, which is unsubstituted or mono-substituted by $CH_3$, $C_2H_5$, or $C_3H_7$,
4-piperidyl, which is unsubstituted or mono-substituted by $CH_3$, $C_2H_5$, $C_3H_7$, phenyl, methylene-phenyl, ethylene-phenyl, cyclohexyl, oxo and (O)—$CH_3$,
b) ($C_3$-$C_6$)-cycloalkyl which is mono-substituted by $NH_2$ or N($CH_3$)$_2$
c) ($C_1$)-alkyl which is mono-substituted by
i) 3-azetidinyl,
2-pyrrolidinyl, which is unsubstituted or mono-substituted by oxo (=O),
2-piperidyl,
3-piperidyl, which is unsubstituted or mono-substituted by $C_2H_5$;
ii) ($C_6$-$C_7$)-cycloalkyl, which is mono-substituted by $NH_2$;
d) ($C_2$-$C_4$)-alkyl which is mono-substituted by 1-pyrrolidinyl, 2-pyrrolidinyl, 1-piperazinyl, 1-morpholinyl, 4-piperidyl, which are unsubstituted or mono-substituted by CH, or phenyl; and wherein ($C_2$-$C_4$)-alkyl can be further mono-substituted by phenyl or pyridyl;
e) ($C_2$-$C_5$)-alkyl which is mono-substituted by NR²⁴R²⁵, wherein
R²⁴ is H or $CH_3$, and
R²⁵ is H, $CH_3$ or CH($CH_3$)$_2$,
and wherein ($C_2$-$C_6$)-alkyl can be further mono-substituted by phenyl, phenylene-methyl or phenylene-O-methyl;
or
R⁷ is
a) a fused bicyclic ring selected from the group consisting of

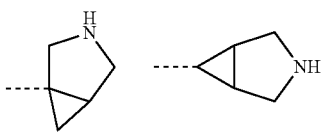

b) a spiro bicyclic ring selected from the group consisting of

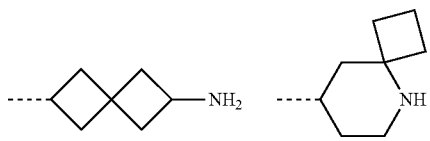

c) a bridged bicyclic ring selected from the group consisting of

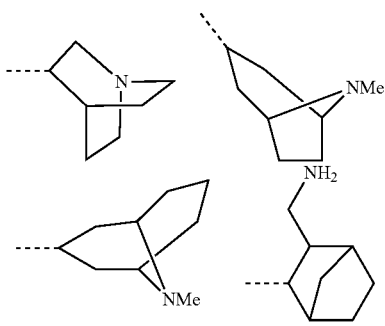

d) a spiro bicyclic ring with a fused ring selected from the group consisting of

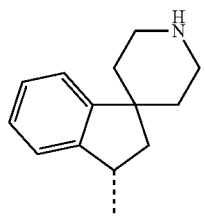

or in another embodiment
R$^7$ is
a) 3-pyrrolidinyl, which is unsubstituted or mono-substituted by CH$_3$, C$_3$H$_7$, O—CH$_3$, O—C$_2$H$_5$, phenyl or methylene-phenyl,
   3-piperidyl, which is unsubstituted or mono-substituted by CH$_3$, C$_2$H$_5$, or C$_3$H$_7$,
   4-piperidyl, which is unsubstituted or mono-substituted by CH$_3$, C$_2$H$_5$, or C$_3$H$_7$, phenyl, methylene-phenyl;
b) (C$_3$-C$_6$)-cycloalkyl which is mono-substituted by NH$_2$ or N(CH$_3$)$_2$
c) (C$_1$)-alkyl which is mono-substituted by
  i) 2-pyrrolidinyl,
    2-piperidyl,
    3-piperidyl, which is unsubstituted or mono-substituted by C$_2$H$_5$;
  ii) (C$_6$-C$_7$)-cycloalkyl, which is mono-substituted by NH$_2$;

d) (C$_2$-C$_4$)-alkyl which is mono-substituted by 1-pyrrolidinyl, 2-pyrrolidinyl, 1-piperazinyl, 1-morpholinyl, 4-piperidyl, which are unsubstituted or mono-substituted by CH$_3$ or phenyl; and wherein (C$_2$-C$_4$)-alkyl can be further mono-substituted by phenyl or pyridyl;
e) (C$_2$-C$_6$)-alkyl which is mono-substituted by NR$^{24}$R$^{25}$, wherein
R$^{24}$ is H or CH$_3$, and
R$^{25}$ is H, CH$_3$ or CH(CH$_3$)$_2$,
and wherein (C$_2$-C$_6$)-alkyl can be further mono-substituted by phenyl.
In another embodiment
R$^1$ is (C$_1$-C$_4$)-alkyl; or in another embodiment CH$_3$, or in another embodiment CF$_3$, or C$_2$H$_5$;
R$^2$ is H;
R$^3$ is H or halogen; or in another embodiment H or F;
R$^4$ is H;
R$^5$ is H;
R$^6$ is (C$_1$-C$_4$)-alkyl or (C$_1$-C$_4$)-alkylene-phenyl; or in another embodiment CH3 or (CH$_2$)$_2$-phenyl; or in another embodiment CH$_3$; and
R$^7$ is a 5- to 6-membered monocyclic heterocycle comprising a ring nitrogen atom, which is attached via a carbon atom, (C$_1$-C$_4$)-alkylene-NH$_2$, or (C$_1$-C$_4$)-alkylene-NH—(C$_1$-C$_4$)-alkyl;
or in another embodiment
R$^7$ is 4-piperidyl, 4-methyl-4-piperidyl, 3-piperidyl, or t-butyl-aminoethylene;
or in another embodiment
R$^7$ is 4-piperidyl, 4-methyl-4-piperidyl.
In another embodiment
R$^1$ is (C$_1$-C$_4$)-alkyl; or in another embodiment CH$_3$;
R$^2$ is H, (C$_1$-C$_4$)-alkyl, halogen or O—(C$_1$-C$_4$)-alkyl; or in another embodiment H, CH$_3$, F, Cl or O—CH$_3$; or in another embodiment H, CH$_3$, F, Cl;
R$^3$ is H, (C$_1$-C$_4$)-alkyl, halogen or O—(C$_1$-C$_4$)-alkyl; or in another embodiment H, CH$_3$, F, C$_{1-10}$—CH$_3$ or O—C$_2$H$_5$; or in another embodiment H, CH$_3$, F, Cl;
R$^4$ is H or halogen; or in another embodiment H or F;
R$^5$ is H, halogen or (C$_1$-C$_4$)-alkyl; or in another embodiment H, F or CH$_3$; and
R$^6$ and R$^7$ together with the N-atom carrying them denote
a) a 1,4-piperazinyl of the formula

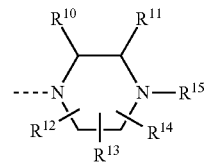

wherein
R$^{10}$ is H, or (C$_0$-C$_4$)-alkyl, which is unsubstituted or one to fivefold substituted by F, or mono-substituted by a substituent selected from the group consisting of
  i) O—(C$_1$-C$_4$)-alkyl, which is unsubstituted or one to fivefold substituted by F,
  ii) (C$_3$-C$_6$)-cycloalkyl,
  iii) phenyl, which is unsubstituted or substituted by one to two identical or different substituents selected from the group consisting of halogen, CF$_3$, OCF$_3$, and (C$_1$-C$_4$)-alkyl,
  iv) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, $CF_3$, $O—(C_1-C_4)$-alkyl, $OCF_3$, and $(C_1-C_4)$-alkyl,
  v) benzo[1,3]dioxole, and
  vi) $CO—R^{16}$;
$R^{11}$ is H or $(C_0-C_6)$-alkyl, which is unsubstituted or one to fivefold substituted by F or mono-substituted by a substituent selected from the group consisting of
  i) $CO—R^{17}$,
  ii) $(C_3-C_6)$-cycloalkyl,
  iii) phenyl, which is unsubstituted or substituted by one to two identical or different substituents selected from the group consisting of halogen, $CF_3$, $O—(C_1-C_4)$-alkyl, $OCF_3$, and $(C_1-C_4)$-alkyl,
  iv) $O—(C_1-C_4)$-alkyl, which is unsubstituted or one to fivefold substituted by F,
  v) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, $CF_3$, $O—(C_1-C_4)$-alkyl, $OCF_3$, and $(C_1-C_4)$-alkyl, and
  vi) oxo (=O);
$R^{12}$ is H, $(C_1-C_6)$-alkyl, which is unsubstituted or one to fivefold substituted by F, or phenyl;
$R^{13}$ is H or $(C_1-C_6)$-alkyl;
$R^{14}$ is H or $(C_1-C_4)$-alkyl;
$R^{15}$ is H, $(C_3-C_6)$-cycloalkyl or $CO—R^{18}$, wherein $(C_1-C_6)$-alkyl is unsubstituted or one to fivefold substituted by F, or mono-substituted by a substituent selected from the group consisting of $SO_2—(C_1-C_4)$-alkyl, phenyl, a 5- to 6-membered monocyclic heterocyclic ring comprising one heteroatom selected from the group consisting of nitrogen and oxygen, a 5- to 6-membered monocyclic heteroaromatic ring comprising one heteroatom selected from the group consisting of nitrogen and oxygen;
$R^{16}$ is $O—(C_1-C_4)$-alkyl or $NH—(C_1-C_6)$-alkyl;
$R^{17}$ is $O—(C_1-C_4)$-alkyl;
$R^{18}$ is $(C_1-C_4)$-alkyl, $NH_2$, phenyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen, where phenyl can be further mono-substituted by $(C_1-C_4)$-alkyl or $O—(C_1-C_4)$-alkyl;
b) a four to seven membered monocyclic heterocycloalkyl group containing a nitrogen atom, which is attached via said nitrogen and which is mono-substituted by $(C_0-C_6)$-alkylene-$NH_2$, $(C_0-C_6)$-alkylene-$NH—(C_1-C_4)$-alkyl, $(C_0-C_6)$-alkylene-NH-phenyl, $(C_0-C_6)$-alkylene-$N((C_1-C_4)$-alkyl$)_2$, or $(C_0-C_6)$-alkylene-$N((C_1-C_4)$-alkyl)(phenyl); and wherein said heterocycloalkyl group can be further mono-substituted by (C alkyl, which is unsubstituted or one to fivefold substituted by F, $CO—O—(C_1-C_4)$-alkyl or phenyl;
c) a 1,4-diazepanyl, which is unsubstituted or mono-substituted by $(C_1-C_6)$-alkyl, wherein $(C_1-C_6)$-alkyl is unsubstituted or one to fivefold substituted by F,
  CO-phenyl, or
  CO-pyridyl;
d) a fused bicyclic $(C_6-C_{10})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or substituted by one to two identical or different substituents selected from the group consisting of F, $(C_0-C_2)$-alkylene-phenyl, oxo (=O), and $(C_1-C_4)$-alkyl, wherein $(C_1-C_4)$-alkyl is unsubstituted or one to fivefold substituted by F;
e) a spiro bicyclic $(C_7-C_{11})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or mono- or di-substituted by F or $(C_1-C_4)$-alkyl, which is unsubstituted or one to fivefold substituted by F;
f) a bridged bicyclic $(C_7-C_9)$-heterocycloalkyl group containing one nitrogen atom, which is attached via said nitrogen atom, which is mono-substituted by $(C_0-C_2)$-alkylene-$NH_2$, $(C_0-C_2)$-alkylene-$NH—(C_1-C_4)$-alkyl, $(C_0-C_2)$-alkylene-$N((C_1-C_4)$-alkyl$)_2$;
g) a bridged bicyclic $(C_7-C_9)$-heterocycloalkyl group containing two nitrogen atoms, which is attached via a nitrogen atom; and which is unsubstituted or substituted by one to four identical or different substituents selected from the group consisting of F, OH, and $(C_1-C_4)$-alkyl, which is unsubstituted or one to fivefold substituted by F; or
h) a tricyclic $(C_{11}-C_{15})$-heterocycloalkyl group containing two nitrogen atoms, which is attached via a nitrogen atom and which consists of a spiro bicyclic ring with an additional fused phenyl ring, and which is unsubstituted or substituted by one or two identical or different substituents selected from the group consisting of F and $(C_1-C_4)$-alkyl, which is unsubstituted or one to fivefold substituted by F;
or in another embodiment
$R^6$ and $R^7$ together with the N-atom carrying them denote
a) a 1,4-piperazinyl of the formula

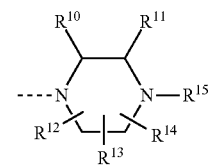

wherein
$R^{10}$ is H, or $(C_0-C_6)$-alkyl, which is unsubstituted or substituted threefold by F or mono-substituted by $O—(C_1-C_4)$-alkyl, phenyl, a 5- to 6-membered monocyclic heteroaromatic ring comprising one heteroatom selected from the group consisting of nitrogen, oxygen, and sulphur, benzo[1,3]dioxole or $CO—R^{16}$;
  wherein phenyl is unsubstituted or substituted by one to two identical or different substituents selected from the group consisting of halogen, $CF_3$, $O—(C_1-C_4)$-alkyl, and $(C_1-C_4)$-alkyl;
$R^{11}$ is H or $(C_0-C_6)$-alkyl, which is unsubstituted or substituted threefold by F or mono-substituted by $CO—R^{17}$, $(C_3-C_4)$-cycloalkyl, phenyl, $O—(C_1-C_4)$-alkyl or oxo (=O);
$R^{12}$ is H, $(C_1-C_6)$-alkyl or phenyl;
$R^{13}$ is H or $(C_1-C_6)$-alkyl;
$R^{14}$ is H or $(C_1-C_4)$-alkyl;

$R^{15}$ is H, $(C_1-C_6)$-alkyl, $(C_3-C_6)$-cycloalkyl or CO—$R^{18}$, where $(C_1-C_6)$-alkyl is unsubstituted or mono-substituted by $SO_2$—$(C_1-C_4)$-alkyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen;

$R^{16}$ is O—$(C_1-C_4)$-alkyl or NH—$(C_1-C_6)$-alkyl;

$R^{17}$ is O—$(C_1-C_4)$-alkyl;

$R^{18}$ is $(C_1-C_4)$-alkyl, $NH_2$, phenyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen, where phenyl can be further mono-substituted by $(C_1-C_4)$-alkyl or O—$(C_1-C_4)$-alkyl;

b) a 1-azetidinyl, which is mono-substituted by $NH_2$ or $(C_1-C_6)$-alkylene-$NH_2$;

c) a 1-pyrrolidinyl, which is mono-substituted by $NR^{19}R^{20}$ or $(C_3-C_4)$-alkylene-amine, wherein $R^{19}$ is H, $(C_1-C_4)$-alkyl or phenyl;

$R^{20}$ is H or $(C_1-C_4)$-alkyl, and 1-pyrrolidinyl can be further mono-substituted by $(C_1-C_6)$-alkyl or $CF_3$;

d) a 1-piperidyl, which is mono-substituted by $NR^{21}R^{22}$ or $(C_1-C_4)$-alkyl-$NH_2$, wherein $R^{21}$ is H or $(C_1-C_4)$-alkyl;

$R^{22}$ is H;

and 1-piperidyl can be further mono-substituted by $(C_1-C_6)$-alkyl, CO—O—$(C_1-C_4)$-alkyl or phenyl;

e) a 1,4-diazepanyl of the formula

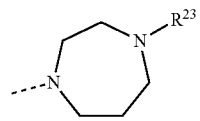

wherein
$R^{23}$ is H, $(C_1-C_6)$-alkyl or CO-4-pyridyl;

f) a fused bicyclic $(C_8-C_{10})$-heterocycloalkyl group containing two nitrogen atoms, which is attached via a nitrogen atom and which can contain one further sulphur atom, wherein said heterocycloalkyl group is unsubstituted or substituted by one to two identical or different substituents selected from the group consisting of $CH_3$, phenyl, methylene-phenyl or oxo (=O);

g) a spiro bicyclic $(C_8-C_{11})$-heterocycloalkyl group containing two nitrogen atoms, which is attached via a nitrogen atom and which can contain one further oxygen atom, wherein said heterocycloalkyl group is unsubstituted or mono- or di-substituted by $CH_3$;

h) a bridged bicyclic $(C_8)$-heterocycloalkyl group containing one nitrogen atom, which is attached via said nitrogen atom, which is substituted by $NH_2$;

i) a bridged bicyclic $(C_7-C_9)$-heterocycloalkyl group containing two nitrogen atoms, which is attached via a nitrogen atom; and which is unsubstituted or substituted by one to four identical or different substituents selected from the group consisting of $CH_3$, $C_2H_5$ and OH;

j) a tricyclic $(C_{14})$-heterocycloalkyl group containing two nitrogen atoms, which is attached via a nitrogen atom and which consists of a spiro bicyclic ring with an additional fused phenyl ring;

or in another embodiment $R^6$ and $R^7$ together with the N-atom carrying them denote a) a 1,4-piperazinyl of the formula

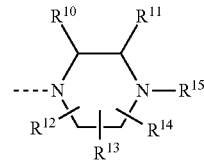

wherein $R^{10}$ is H, or $(C_0-C_4)$-alkyl, which is unsubstituted or substituted threefold by F or mono-substituted by O—$CH_3$, phenyl, pyridyl, furyl, thienyl, benzo[1,3]dioxole or CO—$R^{16}$;

wherein phenyl is unsubstituted or substituted by one to two identical or different substituents selected from the group consisting of F, Cl, Br, $CF_3$, O—$CH_3$, and $CH(CH_3)_2$;

$R^{11}$ is H or $(C_0-C_4)$-alkyl, which is unsubstituted or substituted threefold by F or mono-substituted by CO—$R^{17}$, cyclopropyl, phenyl, O—$CH_3$ or oxo (=O);

$R^{12}$ is H, $(C_1-C_4)$-alkyl or phenyl;

$R^{13}$ is H or $(C_1-C_4)$-alkyl;

$R^{14}$ is H or $CH_3$;

$R^{15}$ is H, $(C_1-C_4)$-alkyl, cyclobutyl or CO—$R^{18}$, where $(C_1-C_4)$-alkyl is unsubstituted or mono-substituted by $SO_2$—$CH_3$, 2-pyridyl, 4-tetrahydropyranyl or 3-tetrahydrofuryl;

$R^{16}$ is O—$CH_3$ or NH—$(C_1-C_4)$-alkyl;

$R^{17}$ is O—$CH_3$;

$R^{18}$ is $CH_3$, $NH_2$, phenyl, 3-furyl, 2-tetrahydrofuryl or 1-pyrrolidinyl, where phenyl can be further mono-substituted by $CH_3$ or O—$CH_3$;

b) a 1-azetidinyl, which is mono-substituted by $NH_2$ or $(C_1-C_4)$-alkylene-$NH_2$;

c) a 1-pyrrolidinyl, which is mono-substituted by $NR^{19}R^{20}$ or 1-cyclopropylamine, wherein $R^{19}$ is H, $CH_3$ or phenyl;

$R^{20}$ is H or $CH_3$, and 1-pyrrolidinyl can be further mono-substituted by $(C_1-C_4)$-alkyl or $CF_3$;

d) a 1-piperidyl, which is mono-substituted by $NR^{21}R^{22}$ or $CH_2$—$NH_2$, wherein $R^{21}$ is H or $CH_3$;

$R^{22}$ is H;

and 1-piperidyl can be further mono-substituted by $(C_1-C_4)$-alkyl, CO—$OCH_3$ or phenyl;

e) a 1,4-diazepanyl of the formula

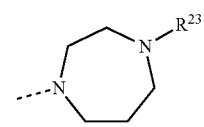

wherein $R^{23}$ is H, $(C_1-C_4)$-alkyl or CO-4-pyridyl;

f) a fused bicyclic ring selected from the group consisting of

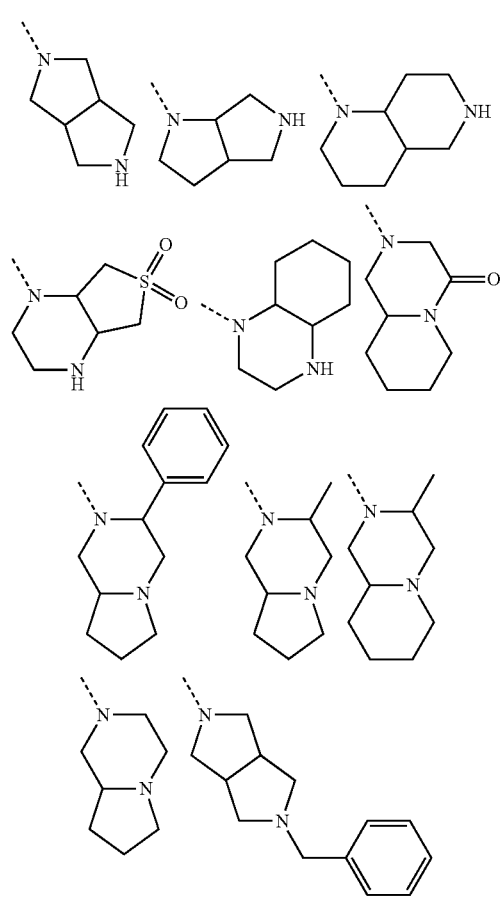
g) a spiro bicyclic ring selected from the group consisting of
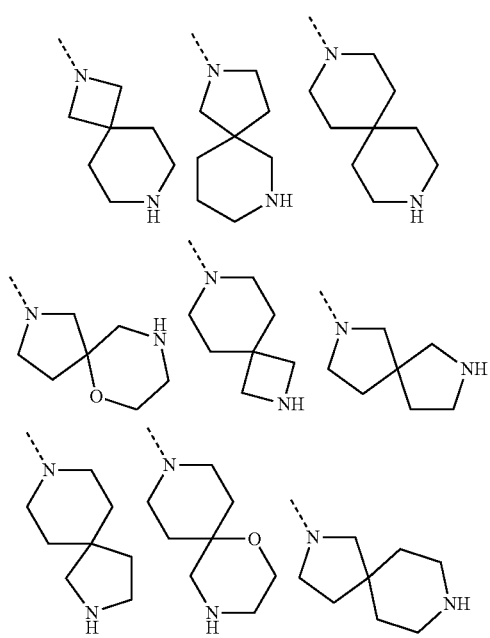
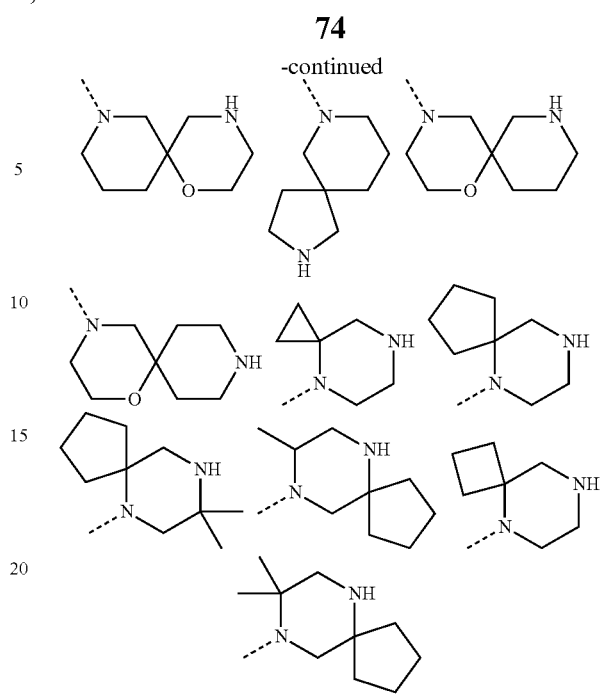
h) abridged bicyclic ring selected from the group consisting of
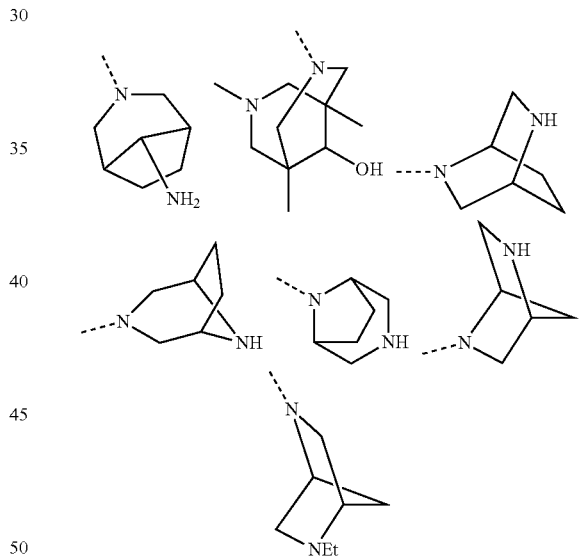
i) a spiro bicyclic ring with a fused ring selected from the group consisting of
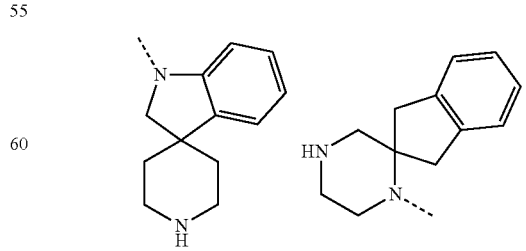
or in another embodiment
$R^6$ and $R^7$ together with the N-atom carrying them denote a) a 1,4-piperazinyl of the formula

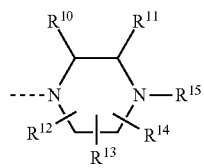

wherein
R$^{10}$ is
  i) H,
  ii) (C$_1$-C$_4$)-alkyl, which is unsubstituted or substituted threefold by F or mono-substituted by O—CH$_3$, or CO—R$^{26}$;
    wherein R$^{26}$ is O—CH$_3$, or NH—(C$_1$-C$_4$)-alkyl;
  iii) phenyl, pyridyl, fury, thienyl, or benzo[1,3]dioxole, wherein phenyl is unsubstituted or substituted by one to two identical or different substituents selected from the group consisting of F, Cl, Br, CF$_3$, O—CH$_3$, and CH(CH$_3$)$_2$;
R$^{11}$ is H, or (C$_1$-C$_4$)-alkyl, which is unsubstituted or substituted threefold by F, cyclopropyl, phenyl, methylenephenyl, CH$_2$OCH$_3$, or COOCH$_3$;
R$^{12}$ is H, (C$_1$-C$_4$)-alkyl, or phenyl;
R$^{13}$ is H, or (C$_1$-C$_4$)-alkyl;
R$^{14}$ is H, or CH$_3$;
R$^{15}$ is H, (C$_1$-C$_4$)-alkyl, cyclobutyl, or CO—R$^{18}$, where (C$_1$-C$_4$)-alkyl is unsubstituted or mono-substituted by SO$_2$—CH$_3$, 4-piperidyl, 2-pyridyl, 4-tetrahydropyranyl, or 3-tetrahydrofuryl;
R$^{16}$ is O—CH$_3$, or NH—(C$_1$-C$_4$)-alkyl;
R$^{17}$ is O—CH$_3$;
R$^{18}$ is CH$_3$, NH$_2$, phenyl, 3-hurl, 2-tetrahydrofuryl, or 1-pyrrolidinyl, where phenyl can be further mono-substituted by CH$_3$ or O—CH$_3$;
b) a 1-azetidinyl, which is mono-substituted by NH$_2$ or CH$_2$—NH$_2$;
c) a 1-pyrrolidinyl, which is mono-substituted by NR$^{19}$R$^{20}$ or 1-cyclopropylamine, wherein
R$^{19}$ is H, CH$_3$, or phenyl;
R$^{20}$ is H, or CH$_3$,
  and 1-pyrrolidinyl can be further mono-substituted by (C$_1$-C$_4$)-alkyl or CF$_3$;
d) a 1-piperidyl, which is mono-substituted by NR$^{21}$R$^{22}$ or CH$_2$—NH$_2$, wherein
R$^{21}$ is H, or CH$_3$;
R$^{22}$ is H;
  and 1-piperidyl can be further mono-substituted by (C$_1$-C$_4$)-alkyl, CO—OCH$_3$ or phenyl;
e) a 1,4-diazepanyl of the formula

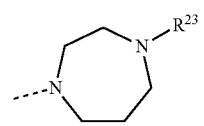

wherein
R$^{23}$ is H, CH$_3$, C$_2$H$_5$, or CO-4-pyridyl;
f) a fused bicyclic ring selected from the group consisting of

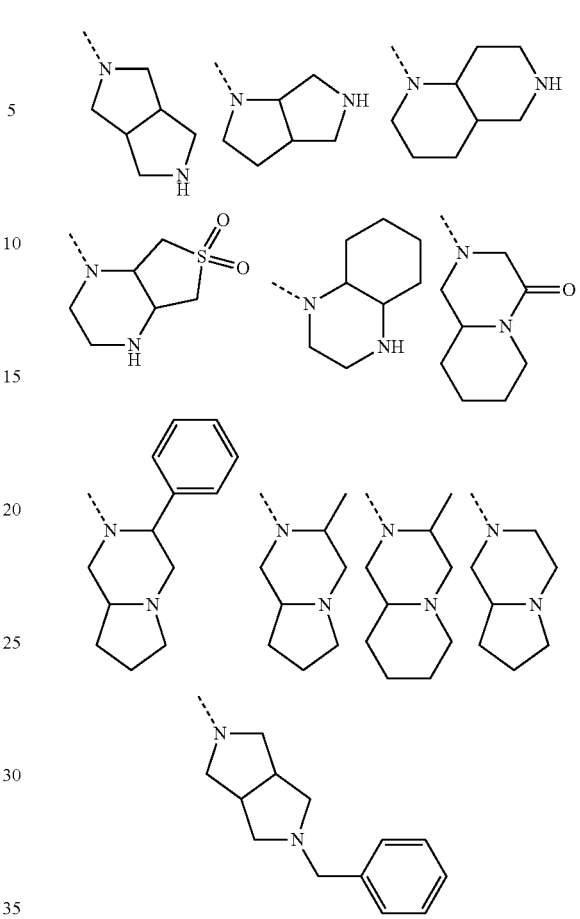

g) a spiro bicyclic ring selected from the group consisting of

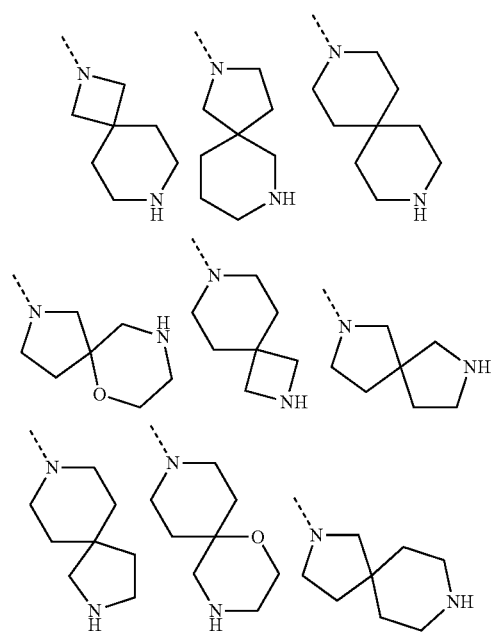

-continued

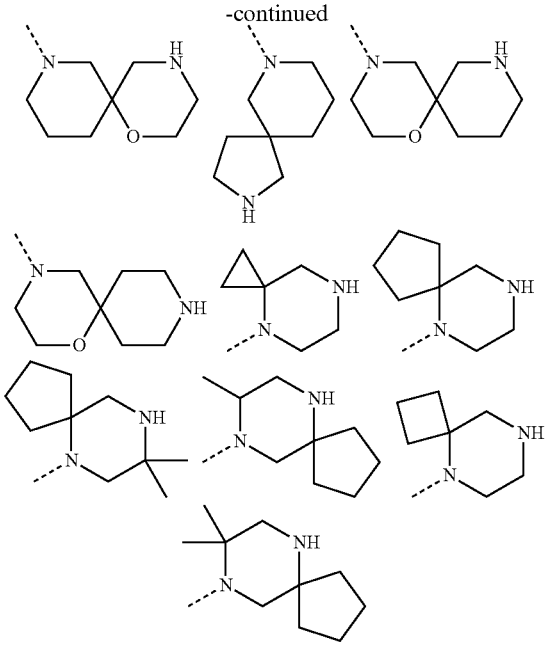

h) a bridged bicyclic ring selected from the group consisting of

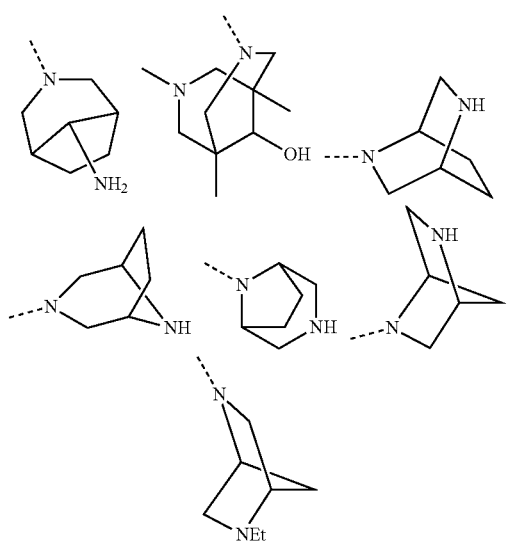

i) a spiro bicyclic ring with a fused ring selected from the group consisting of

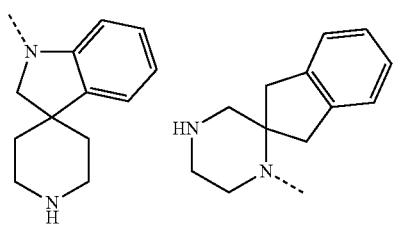

or in another embodiment
$R^6$ and $R^7$ together with the N-atom carrying them denote a) a 1,4-piperazinyl of the formula

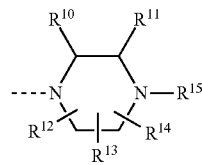

wherein
$R^{10}$ is
  i) H,
  ii) $(C_1\text{-}C_4)$-alkyl, which is unsubstituted or substituted threefold by F or mono-substituted by O—$CH_3$, or CO—$R^{26}$;
    wherein $R^{26}$ is O—$CH_3$, or NH—$(C_1\text{-}C_4)$-alkyl;
  iii) phenyl, pyridyl, fury, thienyl, or benzo[1,3]dioxole, wherein phenyl is unsubstituted or substituted by one to two identical or different substituents selected from the group consisting of F, Cl, Br, $CF_3$, O—$CH_3$, and $CH(CH_3)_2$;
$R^{11}$ is H, or $(C_1\text{-}C_4)$-alkyl, which is unsubstituted or substituted threefold by F, cyclopropyl, phenyl, methylenephenyl, $CH_2OCH_3$, or $COOCH_3$;
$R^{12}$ is H, $(C_1\text{-}C_4)$-alkyl, or phenyl;
$R^{13}$ is H, or $(C_1\text{-}C_4)$-alkyl;
$R^{14}$ is H, or $CH_3$;
$R^{15}$ is H, $(C_1\text{-}C_4)$-alkyl, cyclobutyl, or CO—$R^{18}$, where $(C_1\text{-}C_4)$-alkyl is unsubstituted or mono-substituted by $SO_2$—$CH_3$, 4-piperidyl, 2-pyridyl, 4-tetrahydropyranyl, or 3-tetrahydrofuryl;
$R^{16}$ is O—$CH_3$, or NH—$(C_1\text{-}C_4)$-alkyl;
$R^{17}$ is O—$CH_3$;
$R^{18}$ is $CH_3$, $NH_2$, phenyl, 3-furyl, 2-tetrahydrofuryl, or 1-pyrrolidinyl, where phenyl can be further mono-substituted by $CH_3$ or O—$CH_3$;
b) a 1-azetidinyl, which is mono-substituted by $NH_2$ or $CH_2$—$NH_2$;
c) a 1-pyrrolidinyl, which is mono-substituted by $NR^{19}R^{20}$ or 1-cyclopropylamine, wherein
$R^{19}$ is H, $CH_3$, or phenyl;
$R^{20}$ is H, or $CH_3$, and 1-pyrrolidinyl can be further mono-substituted by $(C_1\text{-}C_4)$-alkyl or $CF_3$;
d) a 1-piperidyl, which is mono-substituted by $NR^{21}R^{22}$ or $CH_2$—$NH_2$, wherein
$R^{21}$ is H, or $CH_3$;
$R^{22}$ is H;
and 1-piperidyl can be further mono-substituted by $(C_1\text{-}C_4)$-alkyl, CO—$OCH_3$ or phenyl;
e) a 1,4-diazepanyl of the formula

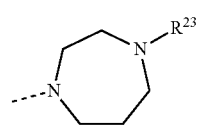

wherein
$R^{23}$ is H, $CH_3$, $C_2H_5$, or CO-4-pyridyl;
f) a fused bicyclic ring selected from the group consisting of

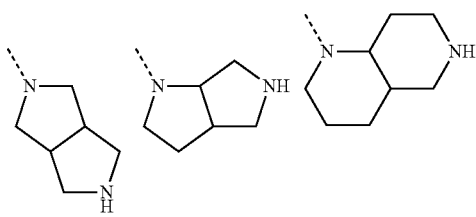

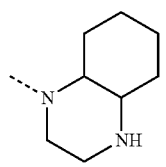

g) a spiro bicyclic ring selected from the group consisting of

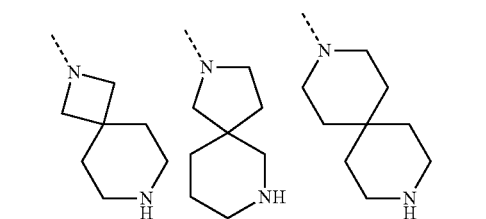

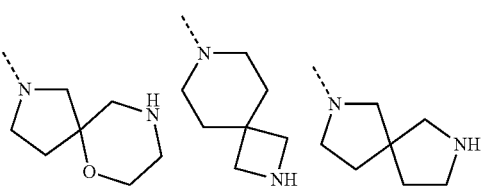

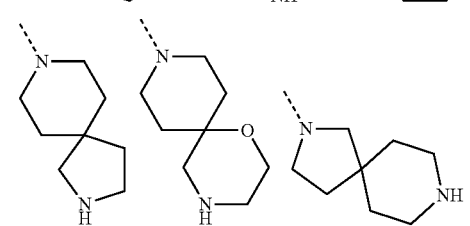

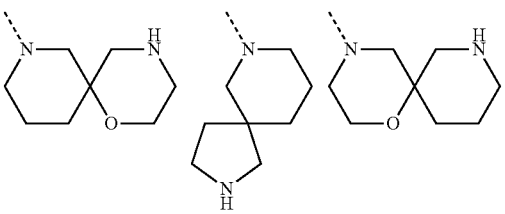

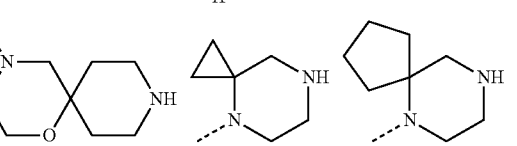

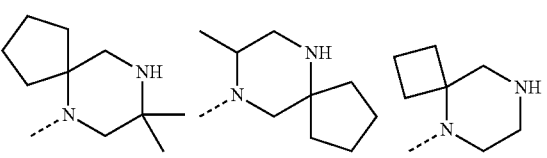

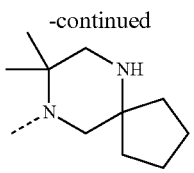

h) a bridged bicyclic ring selected from the group consisting of

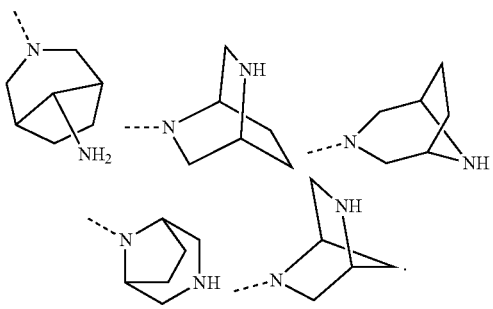

In another embodiment
$R^1$ is $CF_3$;
$R^2$ is H;
$R^3$ is H;
$R^4$ is H;
$R^5$ is H;
$R^6$ is H and
$R^7$ is a) 3-azetidyl or 3-piperidyl;

b) a bridged bicyclic $(C_7\text{-}C_9)$-heterocycloalkyl group containing one nitrogen atom, which is attached via a carbon atom and which is unsubstituted or substituted by one or two identical or different substituents selected from the group consisting of F and (C alkyl, which is unsubstituted or one to fivefold substituted by F;

or $R^6$ and $R^7$ together with the N-atom carrying them denote a) a 1,4-piperazinyl or a 1,4-diazepanyl, which are unsubstituted or mono-substituted by $(C_1\text{-}C_4)$-alkyl;

b) a 1-pyrrolidinyl or a 1-piperidyl, which are mono-substituted by NH2, NH(($C_1\text{-}C_4$)-alkyl), or N(($C_1\text{-}C_4$)-alkyl)$_2$;

c) a fused bicyclic $(C_6\text{-}C_{10})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or substituted by one to two identical or different substituents selected from the group consisting of F, $(C_0\text{-}C_2)$-alkylene-phenyl, oxo and $(C_1\text{-}C_4)$-alkyl, wherein $(C_1\text{-}C_4)$-alkyl is unsubstituted or one to fivefold substituted by F;

d) a spiro bicyclic $(C_7\text{-}C_{11})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or mono- or di-substituted by F or ($C_1$-$C_4$)-alkyl, which is unsubstituted or one to fivefold substituted by F;

or in another embodiment

R⁶ is H and

R⁷ is a) 3-azetidyl or 3-piperidyl;
b) a bridged bicyclic (C₈)-heterocycloalkyl group containing one nitrogen atom, which is attached via a carbon atom;

or

R⁶ and R⁷ together with the N-atom carrying them denote a) a 1,4-piperazinyl or a 1,4-diazepanyl, which are unsubstituted or mono-substituted by (C₁-C₄)-alkyl;
b) a 1-pyrrolidinyl or a 1-piperidyl, which are mono-substituted by NH₂ or NH((C₁-C₄)-alkyl);
c) a fused bicyclic (C₈)-heterocycloalkyl group containing two nitrogen atoms, which is attached via a nitrogen atom;
d) a spiro bicyclic (C₉-C₁₁)-heterocycloalkyl group containing two nitrogen atoms, which is attached via a nitrogen atom;

or in another embodiment

R⁶ is H and

R⁷ is a) 3-azetidyl or 3-piperidyl;
b) a bridged bicyclic ring selected from the group consisting of

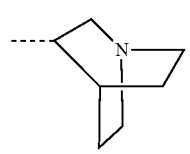

or

R⁶ and R⁷ together with the N-atom carrying them denote a) a 1,4-piperazinyl or a 1,4-diazepanyl, which are unsubstituted or mono-substituted by CH₃ or C₂H₅;
b) a 1-pyrrolidinyl or a 1-piperidyl, which are mono-substituted by NH₂ or NH(CH₃);
c) a fused bicyclic ring selected from the group consisting of

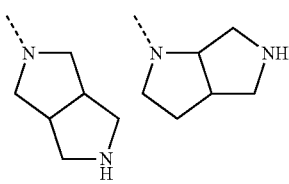

d) a spiro bicyclic ring selected from the group consisting of

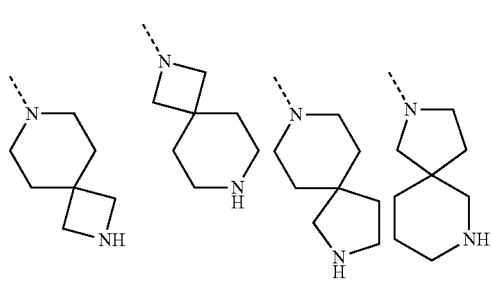

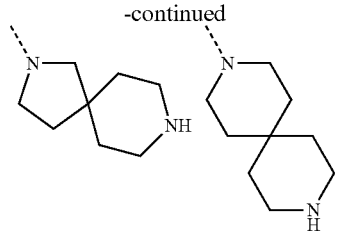

or in another embodiment

R⁶ is H and

R⁷ is 3-azetidyl, or 3-piperidyl;

or

R⁶ and R⁷ together with the N-atom carrying them denote a) a 1,4-piperazinyl or a 1,4-diazepanyl, which are unsubstituted or mono-substituted by CH₃ or C₂H₅;
b) a 1-pyrrolidinyl or a 1-piperidyl, which is mono-substituted by NH₂ or NH(CH₃);
c) a fused bicyclic ring selected from the group consisting of

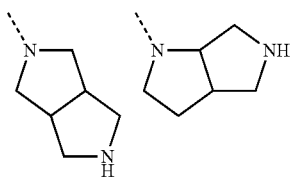

d) a spiro bicyclic ring selected from the group consisting of

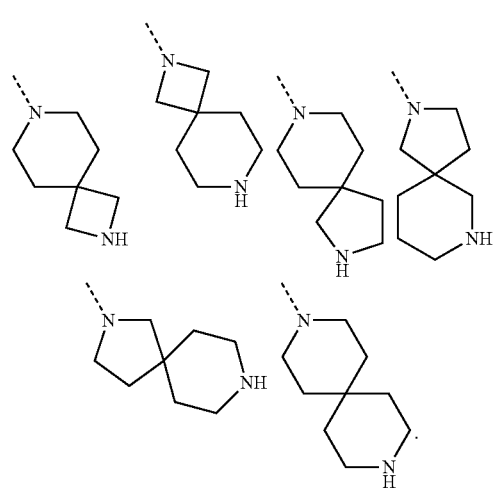

In another embodiment

R¹ is (C₁-C₄)-alkyl; in another embodiment C₂H₅;

R² is H;

R³ is H or halogen; in another embodiment H or F; or in another embodiment H;

R⁴ is H;

R⁵ is H;

R⁶ is H and

R⁷ is a) 3-azetidyl, 3-pyrrolidinyl, 3-piperidyl, 4-piperidyl or (C₁-C₄)-alkylene-2-pyrrolidinyl, which are unsubstituted or mono-substituted by (C₁-C₄)-alkyl, O—(C₁-C₄)-alkyl, or oxo (═O);

b) (C$_3$-C$_6$)-cycloalkyl, which is mono-substituted by NH$_2$;

c) a bridged bicyclic ring selected from the group

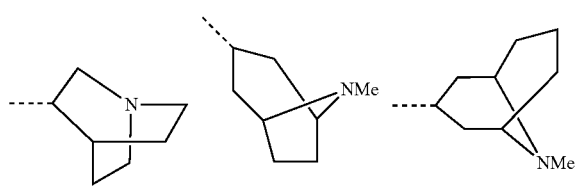

d) a spiro bicyclic ring selected from the group consisting of

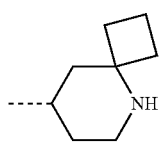

e) a spiro bicyclic ring with a fused ring selected from the group consisting of

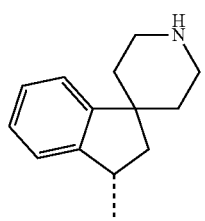

or

R$^6$ is (C$_1$-C$_4$)-alkyl and

R$^7$ is 4-(C$_1$-C$_4$)-alkyl-4-piperidyl;

or

R$^6$ and R$^7$ together with the N-atom carrying them denote a) a 1,4-piperazinyl or a 1,4-diazepanyl, which are unsubstituted or mono-substituted by (C$_1$-C$_4$)-alkyl;

b) a 1-azetidinyl, a 1-pyrrolidinyl or a 1-piperidyl, which are mono-substituted by NH$_2$, NH((C$_1$-C$_4$)-alkyl) or N((C$_1$-C$_4$)-alkyl)$_2$;

c) a fused bicyclic ring selected from the group consisting of

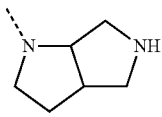

d) a spiro bicyclic ring selected from the group consisting of

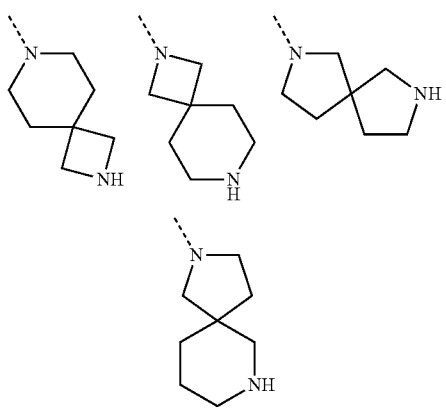

e) a bridged bicyclic ring selected from the group consisting of

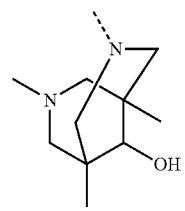

or in another embodiment

R$^6$ is H and

R$^7$ is a) 3-azetidyl, 3-pyrrolidinyl, 3-piperidyl, 4-piperidyl or methylene-2-pyrrolidinyl, which are unsubstituted or mono-substituted by CH$_3$, C$_2$H$_5$, OCH$_3$, or oxo (=O);

b) cyclohexyl, which is mono-substituted by NH$_2$;

c) a bridged bicyclic ring selected from the group consisting of

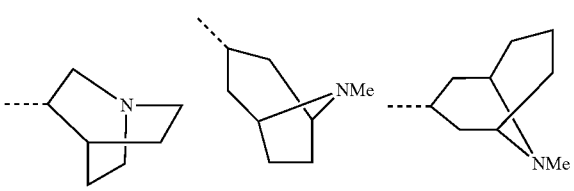

d) a spiro bicyclic ring selected from the group consisting of

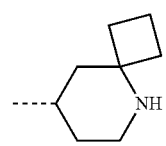

e) a spiro bicyclic ring with a fused ring selected from the group consisting of

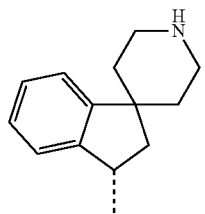

or
R⁶CH₃ and
R⁷ is 4-methyl-4-piperidyl;
or
R⁶ and R⁷ together with the N-atom carrying them denote
  a) a 1,4-piperazinyl or a 1,4-diazepanyl, which are unsubstituted or mono-substituted by $CH_3$ or $C_2H_5$;
  b) a 1-azetidinyl, a 1-pyrrolidinyl or a 1-piperidyl, which are mono-substituted by $NH_2$, $NH(CH_3)$ or $N(CH_3)_2$;
  c) a fused bicyclic ring selected from the group consisting of

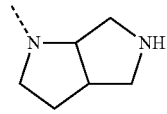

d) a spiro bicyclic ring selected from the group consisting of

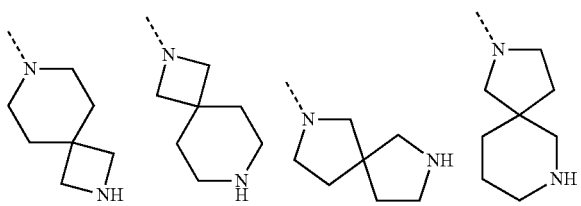

e) a bridged bicyclic ring selected from the group consisting of

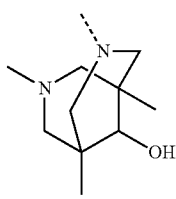

or in another embodiment

R⁶ is H and
R⁷ is a) 3-azetidyl, 3-pyrrolidinyl, 3-piperidyl, 4-piperidyl or methylene-2-pyrrolidinyl, which are unsubstituted or mono-substituted by $CH_3$, $C_2H_5$, $OCH_3$, or oxo (=O);
  b) cyclohexyl, which is mono-substituted by $NH_2$;
or
R⁶ is $CH_3$ and
R⁷ is 4-methyl-4-piperidyl;
or
R⁶ and R⁷ together with the N-atom carrying them denote
  a) a 1,4-piperazinyl or a 1,4-diazepanyl, which are unsubstituted or mono-substituted by $CH_3$ or $C_2H_5$;
  b) a 1-azetidinyl, a 1-pyrrolidinyl or a 1-piperidyl, which are mono-substituted by $NH_2$, $NH(CH_3)$ or $N(CH_3)_2$;
  c) a fused bicyclic ring selected from the group

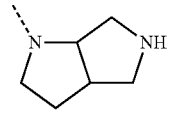

d) a spiro bicyclic ring selected from the group

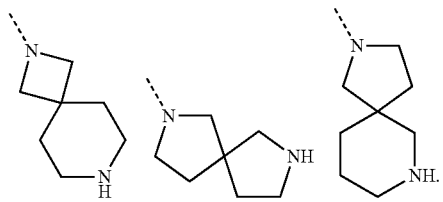

In another embodiment
R¹ is propyl or cyclopropyl;
R² is H;
R³ is H;
R⁴ is H;
R⁵ is H;
R⁶ and R⁷ together with the N-atom carrying them denote a 1,4-piperazinyl, which is unsubstituted or substituted by one to two identical or different substituents selected from the group consisting of $CH_3$ and phenyl.

In another embodiment pounds of the formula I are encompassed selected from the group consisting of 1  [6-(4-Hydroxy-phenyl)-3-methyl-1H-pyrazolo[3,4-b]pyridin-4-yl]-(2-methyl-2-phenyl-piperazin-1-yl)-methanone
2  [3-Ethyl-6-(3-fluoro-4-hydroxy-phenyl)-1H-pyrazolo[3,4-b]pyridin-4-yl]-piperazin-1-yl-methanone
3  [3-Ethyl-6-(4-hydroxy-phenyl)-1H-pyrazolo[3,4-b]pyridin-4-yl]-piperazin-1-yl-methanone
4  [6-(4-Hydroxy-phenyl)-3-propyl-1H-pyrazolo[3,4-b]pyridin-4-yl]-piperazin-1-yl-methanone
5  [6-(4-Hydroxy-phenyl)-3-trifluoromethyl-1H-pyrazolo[3,4-b]pyridin-4-yl]-piperazin-1-yl-methanone
6  [6-(2-Chloro-4-hydroxy-phenyl)-3-methyl-1H-pyrazolo[3,4-b]pyridin-4-yl]-piperazin-1-yl-methanone

| | |
|---|---|
| 7 | [6-(3-Fluoro-4-hydroxy-phenyl)-3-methyl-1H-pyrazolo[3,4-b]pyridin-4-yl]-piperazin-1-yl-methanone |
| 8 | [6-(4-Hydroxy-3-methyl-phenyl)-3-methyl-1H-pyrazolo[3,4-b]pyridin-4-yl]-piperazin-1-yl-methanone |
| 9 | [6-(3-Chloro-4-hydroxy-phenyl)-3-methyl-1H-pyrazolo[3,4-b]pyridin-4-yl]-piperazin-1-yl-methanone |
| 10 | [6-(4-Hydroxy-3-methoxy-phenyl)-3-methyl-1H-pyrazolo[3,4-b]pyridin-4-yl]-piperazin-1-yl-methanone |
| 11 | [6-(2-Fluoro-4-hydroxy-phenyl)-3-methyl-1H-pyrazolo[3,4-b]pyridin-4-yl]-piperazin-1-yl-methanone |
| 12 | [6-(3,5-Difluoro-4-hydroxy-phenyl)-3-methyl-1H-pyrazolo[3,4-b]pyridin-4-yl]-piperazin-1-yl-methanone |
| 13 | [6-(4-Hydroxy-2-methyl-phenyl)-3-methyl-1H-pyrazolo[3,4-b]pyridin-4-yl]-piperazin-1-yl-methanone |
| 14 | [6-(4-Hydroxy-2-methoxy-phenyl)-3-methyl-1H-pyrazolo[3,4-b]pyridin-4-yl]-piperazin-1-yl-methanone |
| 15 | [6-(3-Ethoxy-4-hydroxy-phenyl)-3-methyl-1H-pyrazolo[3,4-b]pyridin-4-yl]-piperazin-1-yl-methanone |
| 16 | [6-(3,5-Difluoro-4-hydroxy-phenyl)-3-methyl-1H-pyrazolo[3,4-b]pyridin-4-yl]-((S)-2-methyl-piperazin-1-yl)-methanone |
| 17 | [6-(4-Hydroxy-2-methyl-phenyl)-3-methyl-1H-pyrazolo[3,4-b]pyridin-4-yl]-((S)-2-methyl-piperazin-1-yl)-methanone |
| 18 | [6-(4-Hydroxy-2-methoxy-phenyl)-3-methyl-1H-pyrazolo[3,4-b]pyridin-4-yl]-((S)-2-methyl-piperazin-1-yl)-methanone |
| 19 | 2,5-Diaza-bicyclo[2.2.1]hept-2-yl-[6-(4-hydroxy-phenyl)-3-methyl-1H-pyrazolo[3,4-b]pyridin-4-yl]-methanone |
| 20 | ((S)-2-Ethyl-piperazin-1-yl)-[6-(4-hydroxy-phenyl)-3-methyl-1H-pyrazolo[3,4-b]pyridin-4-yl]-methanone |
| 21 | [6-(4-Hydroxy-phenyl)-3-methyl-1H-pyrazolo[3,4-b]pyridin-4-yl]-((R)-2-methoxymethyl-piperazin-1-yl)-methanone |
| 22 | 6-(4-Hydroxy-phenyl)-3-methyl-1H-pyrazolo[3,4-b]pyridine-4-carboxylic acid phenethyl-(R)-piperidin-3-yl-amide |
| 23 | [6-(4-Hydroxy-phenyl)-3-methyl-1H-pyrazolo[3,4-b]pyridin-4-yl]-((R)-2-methyl-piperazin-1-yl)-methanone |
| 24 | ((3R,5S)-3,5-Dimethyl-piperazin-1-yl)-[6-(4-hydroxy-phenyl)-3-methyl-1H-pyrazolo[3,4-b]pyridin-4-yl]-methanone |
| 25 | [6-(4-Hydroxy-phenyl)-3-methyl-1H-pyrazolo[3,4-b]pyridin-4-yl]-(3-phenyl-piperazin-1-yl)-methanone |
| 26 | [6-(4-Hydroxy-phenyl)-3-methyl-1H-pyrazolo[3,4-b]pyridin-4-yl]-(2-phenyl-piperazin-1-yl)-methanone |
| 27 | [6-(4-Hydroxy-phenyl)-3-methyl-1H-pyrazolo[3,4-b]pyridin-4-yl]-((S)-2-phenyl-piperazin-1-yl)-methanone |
| 28 | [6-(4-Hydroxy-phenyl)-3-methyl-1H-pyrazolo[3,4-b]pyridin-4-yl]-((R)-2-phenyl-piperazin-1-yl)-methanone |
| 29 | [2-(3,4-Dichloro-phenyl)-piperazin-1-yl]-[6-(4-hydroxy-phenyl)-3-methyl-1H-pyrazolo[3,4-b]pyridin-4-yl]-methanone |
| 30 | (2-Furan-2-yl-piperazin-1-yl)-[6-(4-hydroxy-phenyl)-3-methyl-1H-pyrazolo[3,4-b]pyridin-4-yl]-methanone |
| 31 | [6-(4-Hydroxy-phenyl)-3-methyl-1H-pyrazolo[3,4-b]pyridin-4-yl]-(2-thiophen-2-yl-piperazin-1-yl)-methanone |
| 32 | (2-Benzo[1,3]dioxol-5-yl-piperazin-1-yl)-[6-(4-hydroxy-phenyl)-3-methyl-1H-pyrazolo[3,4-b]pyridin-4-yl]-methanone |
| 33 | [3-(1-Amino-1-methyl-ethyl)-azetidin-1-yl]-[6-(4-hydroxy-phenyl)-3-methyl-1H-pyrazolo[3,4-b]pyridin-4-yl]-methanone |
| 34 | (4-Aminomethyl-4-phenyl-piperidin-1-yl)-[6-(4-hydroxy-phenyl)-3-methyl-1H-pyrazolo[3,4-b]pyridin-4-yl]-methanone |
| 35 | 6-(4-Hydroxy-phenyl)-3-methyl-1H-pyrazolo[3,4-b]pyridine-4-carboxylic acid (2-pyrrolidin-1-yl-ethyl)-amide |
| 36 | [6-(4-Hydroxy-phenyl)-3-methyl-1H-pyrazolo[3,4-b]pyridin-4-yl]-(4-isopropyl-piperazin-1-yl)-methanone |
| 37 | [6-(4-Hydroxy-phenyl)-3-methyl-1H-pyrazolo[3,4-b]pyridin-4-yl]-(4-methyl-piperazin-1-yl)-methanone |
| 38 | 6-(4-Hydroxy-phenyl)-3-methyl-1H-pyrazolo[3,4-b]pyridine-4-carboxylic acid (2-dimethylamino-ethyl)-amide |
| 39 | (4-Cyclobutyl-piperazin-1-yl)-[6-(4-hydroxy-phenyl)-3-methyl-1H-pyrazolo[3,4-b]pyridin-4-yl]-methanone |
| 40 | 6-(4-Hydroxy-phenyl)-3-methyl-1H-pyrazolo[3,4-b]pyridine-4-carboxylic acid (2-tert-butylamino-ethyl)-methyl-amide |
| 41 | 6-(4-Hydroxy-phenyl)-3-methyl-1H-pyrazolo[3,4-b]pyridine-4-carboxylic acid (4-methyl-piperidin-4-yl)-amide |
| 42 | (1,3-Dihydro-spiro[indene-2,2'-piperazin]-1'-yl)-[6-(4-hydroxy-phenyl)-3-methyl-1H-pyrazolo[3,4-b]pyridin-4-yl]-methanone |
| 43 | 6-(4-Hydroxy-phenyl)-3-methyl-1H-pyrazolo[3,4-b]pyridine-4-carboxylic acid (4-methyl-pyrrolidin-3-yl)-amide |
| 44 | 6-(4-Hydroxy-phenyl)-3-methyl-1H-pyrazolo[3,4-b]pyridine-4-carboxylic acid (4-ethoxy-pyrrolidin-3-yl)-amide |
| 45 | 6-(4-Hydroxy-phenyl)-3-methyl-1H-pyrazolo[3,4-b]pyridine-4-carboxylic acid (4-phenyl-pyrrolidin-3-yl)-amide |
| 46 | (4-Amino-4-propyl-piperidin-1-yl)-[6-(4-hydroxy-phenyl)-3-methyl-1H-pyrazolo[3,4-b]pyridin-4-yl]-methanone |

| | -continued |
|---|---|
| 47 | (3-Amino-3-propyl-pyrrolidin-1-yl)-[6-(4-hydroxy-phenyl)-3-methyl-1H-pyrazolo[3,4-b]pyridin-4-yl]-methanone |
| 48 | (3-Amino-3-propyl-piperidin-1-yl)-[6-(4-hydroxy-phenyl)-3-methyl-1H-pyrazolo[3,4-b]pyridin-4-yl]-methanone |
| 49 | 6-(4-Hydroxy-phenyl)-3-methyl-1H-pyrazolo[3,4-b]pyridine-4-carboxylic acid (4-ethyl-piperidin-4-yl)-amide |
| 50 | 6-(4-Hydroxy-phenyl)-3-methyl-1H-pyrazolo[3,4-b]pyridine-4-carboxylic acid (2-isopropylamino-ethyl)-amide |
| 51 | 6-(4-Hydroxy-phenyl)-3-methyl-1H-pyrazolo[3,4-b]pyridine-4-carboxylic acid [2-amino-1-(3-methoxy-phenyl)-ethyl]-amide |
| 52 | 6-(4-Hydroxy-phenyl)-3-methyl-1H-pyrazolo[3,4-b]pyridine-4-carboxylic acid (2-amino-1-p-tolyl-ethyl)-amide |
| 53 | [6-(4-Hydroxy-phenyl)-3-methyl-1H-pyrazolo[3,4-b]pyridin-4-yl]-piperazin-1-yl-methanone |
| 54 | 4-[6-(4-Hydroxy-phenyl)-3-methyl-1H-pyrazolo[3,4-b]pyridine-4-carbonyl]-piperazine-1-carboxylic acid amide |
| 55 | [3-Cyclopropyl-6-(4-hydroxy-phenyl)-1H-pyrazolo[3,4-b]pyridin-4-yl]-piperazin-1-yl-methanone |
| 56 | (2,2-Dimethyl-piperazin-1-yl)-[6-(2-fluoro-4-hydroxy-phenyl)-3-methyl-1H-pyrazolo[3,4-b]pyridin-4-yl]-methanone |
| 57 | [6-(2-Fluoro-4-hydroxy-phenyl)-3-methyl-1H-pyrazolo[3,4-b]pyridin-4-yl]-((R)-2-phenyl-piperazin-1-yl)-methanone |
| 58 | [6-(2-Fluoro-4-hydroxy-phenyl)-3-methyl-1H-pyrazolo[3,4-b]pyridin-4-yl]-(4-methylamino-piperidin-1-yl)-methanone |
| 59 | ((S)-3-Aminomethyl-piperidin-1-yl)-[6-(2-fluoro-4-hydroxy-phenyl)-3-methyl-1H-pyrazolo[3,4-b]pyridin-4-yl]-methanone |
| 60 | [6-(2-Fluoro-4-hydroxy-phenyl)-3-methyl-1H-pyrazolo[3,4-b]pyridin-4-yl]-(2-trifluoromethyl-piperazin-1-yl)-methanone |
| 61 | 6-(2-Fluoro-4-hydroxy-phenyl)-3-methyl-1H-pyrazolo[3,4-b]pyridine-4-carboxylic acid (1-amino-cycloheptylmethyl)-amide |
| 62 | 6-(2-Fluoro-4-hydroxy-phenyl)-3-methyl-1H-pyrazolo[3,4-b]pyridine-4-carboxylic acid (3-ethyl-piperidin-3-yl)-amide |
| 63 | [6-(2-Fluoro-4-hydroxy-phenyl)-3-methyl-1H-pyrazolo[3,4-b]pyridin-4-yl]-(2,2,5,5-tetramethyl-piperazin-1-yl)-methanone |
| 64 | (4,7-Diaza-spiro[2.5]oct-4-yl)-[6-(2-fluoro-4-hydroxy-phenyl)-3-methyl-1H-pyrazolo[3,4-b]pyridin-4-yl]-methanone |
| 65 | 6-(2-Fluoro-4-hydroxy-phenyl)-3-methyl-1H-pyrazolo[3,4-b]pyridine-4-carboxylic acid (3-amino-1-ethyl-propyl)-amide |
| 66 | 6-(2-Fluoro-4-hydroxy-phenyl)-3-methyl-1H-pyrazolo[3,4-b]pyridine-4-carboxylic acid (3-amino-1,1-dimethyl-propyl)-amide |
| 67 | 6-(2-Fluoro-4-hydroxy-phenyl)-3-methyl-1H-pyrazolo[3,4-b]pyridine-4-carboxylic acid (3-amino-3-methyl-butyl)-amide |
| 68 | [6-(4-Hydroxy-phenyl)-3-methyl-1H-pyrazolo[3,4-b]pyridin-4-yl]-((S)-3-propyl-piperazin-1-yl)-methanone |
| 69 | [6-(4-Hydroxy-phenyl)-3-methyl-1H-pyrazolo[3,4-b]pyridin-4-yl]-[2-(4-methoxy-phenyl)-piperazin-1-yl]-methanone |
| 70 | [6-(4-Hydroxy-phenyl)-3-methyl-1H-pyrazolo[3,4-b]pyridin-4-yl]-(5-methyl-2-phenyl-piperazin-1-yl)-methanone |
| 71 | 2,5-Diaza-bicyclo[2.2.2]oct-2-yl-[6-(4-hydroxy-phenyl)-3-methyl-1H-pyrazolo[3,4-b]pyridin-4-yl]-methanone |
| 72 | [6-(4-Hydroxy-phenyl)-3-methyl-1H-pyrazolo[3,4-b]pyridin-4-yl]-[2-(3-methoxy-phenyl)-piperazin-1-yl]-methanone |
| 73 | (trans-2,5-Dimethyl-piperazin-1-yl)-[6-(4-hydroxy-phenyl)-3-methyl-1H-pyrazolo[3,4-b]pyridin-4-yl]-methanone |
| 74 | 6-(4-Hydroxy-phenyl)-3-methyl-1H-pyrazolo[3,4-b]pyridine-4-carboxylic acid piperidin-4-ylamide |
| 75 | [1,4]Diazepan-1-yl-[6-(4-hydroxy-phenyl)-3-methyl-1H-pyrazolo[3,4-b]pyridin-4-yl]-methanone |
| 76 | (3-Amino-piperidin-1-yl)-[6-(4-hydroxy-phenyl)-3-methyl-1H-pyrazolo[3,4-b]pyridin-4-yl]-methanone |
| 77 | 6-(4-Hydroxy-phenyl)-3-methyl-1H-pyrazolo[3,4-b]pyridine-4-carboxylic acid (trans-4-amino-cyclohexyl)-amide |
| 78 | 6-(4-Hydroxy-phenyl)-3-methyl-1H-pyrazolo[3,4-b]pyridine-4-carboxylic acid ((trans)-4-methoxy-pyrrolidin-3-yl)-amide |
| 79 | [6-(4-Hydroxy-phenyl)-3-methyl-1H-pyrazolo[3,4-b]pyridin-4-yl]-[2-(2-methoxy-phenyl)-piperazin-1-yl]-methanone |
| 80 | (4,7-Diaza-spiro[2.5]oct-4-yl)-[6-(4-hydroxy-phenyl)-3-methyl-1H-pyrazolo[3,4-b]pyridin-4-yl]-methanone |
| 81 | ((2R,5S)-2,5-Dimethyl-piperazin-1-yl)-[6-(4-hydroxy-phenyl)-3-methyl-1H-pyrazolo[3,4-b]pyridin-4-yl]-methanone |
| 82 | [(S)-2-(3-Fluoro-phenyl)-piperazin-1-yl]-[6-(4-hydroxy-phenyl)-3-methyl-1H-pyrazolo[3,4-b]pyridin-4-yl]-methanone |
| 83 | ((2R,5R)-2,5-Dimethyl-piperazin-1-yl)-[6-(4-hydroxy-phenyl)-3-methyl-1H-pyrazolo[3,4-b]pyridin-4-yl]-methanone |
| 84 | [2-(4-Fluoro-phenyl)-piperazin-1-yl]-[6-(4-hydroxy-phenyl)-3-methyl-1H-pyrazolo[3,4-b]pyridin-4-yl]-methanone |
| 85 | [2-(2,3-Difluoro-phenyl)-piperazin-1-yl]-[6-(4-hydroxy-phenyl)-3-methyl-1H-pyrazolo[3,4-b]pyridin-4-yl]-methanone |
| 86 | (3-Cyclopropyl-piperazin-1-yl)-[6-(4-hydroxy-phenyl)-3-methyl-1H-pyrazolo[3,4-b]pyridin-4-yl]-methanone |

-continued

| | |
|---|---|
| 87 | [2-(3,5-Difluoro-phenyl)-piperazin-1-yl]-[6-(4-hydroxy-phenyl)-3-methyl-1H-pyrazolo[3,4-b]pyridin-4-yl]-methanone |
| 88 | ((2S,5S)-2,5-Dimethyl-piperazin-1-yl)-[6-(4-hydroxy-phenyl)-3-methyl-1H-pyrazolo[3,4-b]pyridin-4-yl]-methanone |
| 89 | [2-(4-Bromo-phenyl)-piperazin-1-yl]-[6-(4-hydroxy-phenyl)-3-methyl-1H-pyrazolo[3,4-b]pyridin-4-yl]-methanone |
| 90 | (3-Aminomethyl-azetidin-1-yl)-[6-(4-hydroxy-phenyl)-3-methyl-1H-pyrazolo[3,4-b]pyridin-4-yl]-methanone |
| 91 | [2-(3-Fluoro-phenyl)-piperazin-1-yl]-[6-(4-hydroxy-phenyl)-3-methyl-1H-pyrazolo[3,4-b]pyridin-4-yl]-methanone |
| 92 | [2-(3,4-Difluoro-phenyl)-piperazin-1-yl]-[6-(4-hydroxy-phenyl)-3-methyl-1H-pyrazolo[3,4-b]pyridin-4-yl]-methanone |
| 93 | [6-(4-Hydroxy-phenyl)-3-methyl-1H-pyrazolo[3,4-b]pyridin-4-yl]-[2-(2-trifluoromethyl-phenyl)-piperazin-1-yl]-methanone |
| 94 | [6-(4-Hydroxy-phenyl)-3-methyl-1H-pyrazolo[3,4-b]pyridin-4-yl]-[2-(4-isopropyl-phenyl)-piperazin-1-yl]-methanone |
| 95 | [2-(2-Fluoro-phenyl)-piperazin-1-yl]-[6-(4-hydroxy-phenyl)-3-methyl-1H-pyrazolo[3,4-b]pyridin-4-yl]-methanone |
| 96 | [2-(2,4-Difluoro-phenyl)-piperazin-1-yl]-[6-(4-hydroxy-phenyl)-3-methyl-1H-pyrazolo[3,4-b]pyridin-4-yl]-methanone |
| 97 | [6-(4-Hydroxy-phenyl)-3-methyl-1H-pyrazolo[3,4-b]pyridin-4-yl]-[2-(4-trifluoromethyl-phenyl)-piperazin-1-yl]-methanone |
| 98 | 6-(4-Hydroxy-phenyl)-3-methyl-1H-pyrazolo[3,4-b]pyridine-4-carboxylic acid (azetidin-3-ylmethyl)-amide |
| 99 | [6-(4-Hydroxy-phenyl)-3-methyl-1H-pyrazolo[3,4-b]pyridin-4-yl]-[2-(3-trifluoromethyl-phenyl)-piperazin-1-yl]-methanone |
| 100 | [2-(2,6-Difluoro-phenyl)-piperazin-1-yl]-[6-(4-hydroxy-phenyl)-3-methyl-1H-pyrazolo[3,4-b]pyridin-4-yl]-methanone |
| 101 | [2-(3-Bromo-phenyl)-piperazin-1-yl]-[6-(4-hydroxy-phenyl)-3-methyl-1H-pyrazolo[3,4-b]pyridin-4-yl]-methanone |
| 102 | [2-(2-Chloro-phenyl)-piperazin-1-yl]-[6-(4-hydroxy-phenyl)-3-methyl-1H-pyrazolo[3,4-b]pyridin-4-yl]-methanone |
| 103 | 6-(4-Hydroxy-phenyl)-3-methyl-1H-pyrazolo[3,4-b]pyridine-4-carboxylic acid (cis-4-amino-cyclohexyl)-amide |
| 104 | 6-(4-Hydroxy-phenyl)-3-methyl-1H-pyrazolo[3,4-b]pyridine-4-carboxylic acid (2-amino-1-phenyl-ethyl)-amide |
| 105 | 6-(4-Hydroxy-phenyl)-3-methyl-1H-pyrazolo[3,4-b]pyridine-4-carboxylic acid (cis-4-amino-cyclohexylmethyl)-amide |
| 106 | 6-(4-Hydroxy-phenyl)-3-methyl-1H-pyrazolo[3,4-b]pyridine-4-carboxylic acid pyrrolidin-3-ylamide |
| 107 | 6-(4-Hydroxy-phenyl)-3-methyl-1H-pyrazolo[3,4-b]pyridine-4-carboxylic acid [2-amino-1-(4-fluoro-phenyl)-ethyl]-amide |
| 108 | (6,9-Diaza-spiro[4.5]dec-6-yl)-[6-(4-hydroxy-phenyl)-3-methyl-1H-pyrazolo[3,4-b]pyridin-4-yl]-methanone |
| 109 | [6-(4-Hydroxy-phenyl)-3-methyl-1H-pyrazolo[3,4-b]pyridin-4-yl]-(4-methylamino-piperidin-1-yl)-methanone |
| 110 | ((S)-3-Aminomethyl-piperidin-1-yl)-[6-(4-hydroxy-phenyl)-3-methyl-1H-pyrazolo[3,4-b]pyridin-4-yl]-methanone |
| 111 | 3,8-Diaza-bicyclo[3.2.1]oct-3-yl-[6-(4-hydroxy-phenyl)-3-methyl-1H-pyrazolo[3,4-b]pyridin-4-yl]-methanone |
| 112 | ((2S,5R)-2,5-Dimethyl-piperazin-1-yl)-[6-(4-hydroxy-phenyl)-3-methyl-1H-pyrazolo[3,4-b]pyridin-4-yl]-methanone |
| 113 | [6-(4-Hydroxy-phenyl)-3-methyl-1H-pyrazolo[3,4-b]pyridin-4-yl]-(2,5,5-trimethyl-piperazin-1-yl)-methanone |
| 114 | [6-(4-Hydroxy-phenyl)-3-methyl-1H-pyrazolo[3,4-b]pyridin-4-yl]-(2-trifluoromethyl-piperazin-1-yl)-methanone |
| 115 | 6-(4-Hydroxy-phenyl)-3-methyl-1H-pyrazolo[3,4-b]pyridine-4-carboxylic acid (3-ethyl-piperidin-3-yl)-amide |
| 116 | 6-(4-Hydroxy-phenyl)-3-methyl-1H-pyrazolo[3,4-b]pyridine-4-carboxylic acid (1-amino-cycloheptylmethyl)-amide |
| 117 | (3-Amino-3-methyl-piperidin-1-yl)-[6-(4-hydroxy-phenyl)-3-methyl-1H-pyrazolo[3,4-b]pyridin-4-yl]-methanone |
| 118 | 6-(4-Hydroxy-phenyl)-3-methyl-1H-pyrazolo[3,4-b]pyridine-4-carboxylic acid (4-propyl-piperidin-4-yl)-amide |
| 119 | 6-(4-Hydroxy-phenyl)-3-methyl-1H-pyrazolo[3,4-b]pyridine-4-carboxylic acid (trans-4-p-tolyl-pyrrolidin-3-yl)-amide |
| 120 | 6-(4-Hydroxy-phenyl)-3-methyl-1H-pyrazolo[3,4-b]pyridine-4-carboxylic acid ((1R,2R)-2-amino-cyclopentyl)-amide |
| 121 | [6-(4-Hydroxy-phenyl)-3-methyl-1H-pyrazolo[3,4-b]pyridin-4-yl]-(2,2,5,5-tetramethyl-piperazin-1-yl)-methanone |
| 122 | (3-Amino-3-methyl-pyrrolidin-1-yl)-[6-(4-hydroxy-phenyl)-3-methyl-1H-pyrazolo[3,4-b]pyridin-4-yl]-methanone |
| 123 | 6-(4-Hydroxy-phenyl)-3-methyl-1H-pyrazolo[3,4-b]pyridine-4-carboxylic acid (trans-2-amino-cyclohexyl)-amide |
| 124 | 6-(4-Hydroxy-phenyl)-3-methyl-1H-pyrazolo[3,4-b]pyridine-4-carboxylic acid (3-propyl-piperidin-3-yl)-amide |
| 125 | 6-(4-Hydroxy-phenyl)-3-methyl-1H-pyrazolo[3,4-b]pyridine-4-carboxylic acid (3-propyl-pyrrolidin-3-yl)-amide |
| 126 | 6-(4-Hydroxy-phenyl)-3-methyl-1H-pyrazolo[3,4-b]pyridine-4-carboxylic acid (cis-2-amino-cyclohexyl)-amide |

| | |
|---|---|
| 127 | 6-(4-Hydroxy-phenyl)-3-methyl-1H-pyrazolo[3,4-b]pyridine-4-carboxylic acid (3-amino-1-ethyl-propyl)-amide |
| 128 | 6-(4-Hydroxy-phenyl)-3-methyl-1H-pyrazolo[3,4-b]pyridine-4-carboxylic acid (3-amino-1,1-dimethyl-propyl)-amide |
| 129 | 6-(4-Hydroxy-phenyl)-3-methyl-1H-pyrazolo[3,4-b]pyridine-4-carboxylic acid (3-amino-3-methyl-butyl)-amide |
| 130 | 6-(4-Hydroxy-phenyl)-3-methyl-1H-pyrazolo[3,4-b]pyridine-4-carboxylic acid (trans-4-amino-cyclohexylmethyl)-amide |
| 131 | 6-(4-Hydroxy-phenyl)-3-methyl-1H-pyrazolo[3,4-b]pyridine-4-carboxylic acid (3-amino-1-phenyl-propyl)-amide |
| 132 | 6-(4-Hydroxy-phenyl)-3-methyl-1H-pyrazolo[3,4-b]pyridine-4-carboxylic acid (2-dimethylamino-1-phenyl-ethyl)-amide |
| 133 | 6-(4-Hydroxy-phenyl)-3-methyl-1H-pyrazolo[3,4-b]pyridine-4-carboxylic acid (2-amino-2-methyl-propyl)-amide |
| 134 | 6-(4-Hydroxy-phenyl)-3-methyl-1H-pyrazolo[3,4-b]pyridine-4-carboxylic acid (2-amino-1,1,2-trimethyl-propyl)-amide |
| 135 | [6-(2,6-Difluoro-4-hydroxy-phenyl)-3-methyl-1H-pyrazolo[3,4-b]pyridin-4-yl]-(2,2-dimethyl-piperazin-1-yl)-methanone |
| 136 | [2-(3,5-Difluoro-phenyl)-piperazin-1-yl]-[6-(4-hydroxy-2-methyl-phenyl)-3-methyl-1H-pyrazolo[3,4-b]pyridin-4-yl]-methanone |
| 137 | [2-(4-Bromo-phenyl)-piperazin-1-yl]-[6-(4-hydroxy-2-methyl-phenyl)-3-methyl-1H-pyrazolo[3,4-b]pyridin-4-yl]-methanone |
| 138 | [2-(4-Fluoro-phenyl)-piperazin-1-yl]-[6-(4-hydroxy-2-methyl-phenyl)-3-methyl-1H-pyrazolo[3,4-b]pyridin-4-yl]-methanone |
| 139 | [2-(2,3-Difluoro-phenyl)-piperazin-1-yl]-[6-(4-hydroxy-2-methyl-phenyl)-3-methyl-1H-pyrazolo[3,4-b]pyridin-4-yl]-methanone |
| 140 | [6-(4-Hydroxy-2-methyl-phenyl)-3-methyl-1H-pyrazolo[3,4-b]pyridin-4-yl]-[2-(4-methoxy-phenyl)-piperazin-1-yl]-methanone |
| 141 | [(S)-2-(3-Fluoro-phenyl)-piperazin-1-yl]-[6-(4-hydroxy-2-methyl-phenyl)-3-methyl-1H-pyrazolo[3,4-b]pyridin-4-yl]-methanone |
| 142 | (2,2-Dimethyl-piperazin-1-yl)-[6-(4-hydroxy-2-methyl-phenyl)-3-methyl-1H-pyrazolo[3,4-b]pyridin-4-yl]-methanone |
| 143 | 6-(4-Hydroxy-2-methyl-phenyl)-3-methyl-1H-pyrazolo[3,4-b]pyridine-4-carboxylic acid ((3S,4S)-4-methoxy-pyrrolidin-3-yl)-amide |
| 144 | [6-(4-Hydroxy-2-methyl-phenyl)-3-methyl-1H-pyrazolo[3,4-b]pyridin-4-yl]-(2-trifluoromethyl-piperazin-1-yl)-methanone |
| 145 | [6-(4-Hydroxy-2-methyl-phenyl)-3-methyl-1H-pyrazolo[3,4-b]pyridin-4-yl]-((S)-3-methyl-piperazin-1-yl)-methanone |
| 146 | [6-(4-Hydroxy-2-methyl-phenyl)-3-methyl-1H-pyrazolo[3,4-b]pyridin-4-yl]-[2-(3-methoxy-phenyl)-piperazin-1-yl]-methanone |
| 147 | [2-(3-Fluoro-phenyl)-piperazin-1-yl]-[6-(4-hydroxy-2-methyl-phenyl)-3-methyl-1H-pyrazolo[3,4-b]pyridin-4-yl]-methanone |
| 148 | 6-(4-Hydroxy-2-methyl-phenyl)-3-methyl-1H-pyrazolo[3,4-b]pyridine-4-carboxylic acid (1-amino-cycloheptylmethyl)-amide |
| 149 | 6-(4-Hydroxy-2-methyl-phenyl)-3-methyl-1H-pyrazolo[3,4-b]pyridine-4-carboxylic acid (3-ethyl-piperidin-3-yl)-amide |
| 150 | [6-(4-Hydroxy-2-methyl-phenyl)-3-methyl-1H-pyrazolo[3,4-b]pyridin-4-yl]-((R)-2-phenyl-piperazin-1-yl)-methanone |
| 151 | [2-(2-Fluoro-phenyl)-piperazin-1-yl]-[6-(4-hydroxy-2-methyl-phenyl)-3-methyl-1H-pyrazolo[3,4-b]pyridin-4-yl]-methanone |
| 152 | [2-(2,4-Difluoro-phenyl)-piperazin-1-yl]-[6-(4-hydroxy-2-methyl-phenyl)-3-methyl-1H-pyrazolo[3,4-b]pyridin-4-yl]-methanone |
| 153 | [2-(2-Chloro-phenyl)-piperazin-1-yl]-[6-(4-hydroxy-2-methyl-phenyl)-3-methyl-1H-pyrazolo[3,4-b]pyridin-4-yl]-methanone |
| 154 | [6-(4-Hydroxy-2-methyl-phenyl)-3-methyl-1H-pyrazolo[3,4-b]pyridin-4-yl]-[2-(4-trifluoromethyl-phenyl)-piperazin-1-yl]-methanone |
| 155 | [6-(4-Hydroxy-2-methyl-phenyl)-3-methyl-1H-pyrazolo[3,4-b]pyridin-4-yl]-(2,2,5,5-tetramethyl-piperazin-1-yl)-methanone |
| 156 | (2,2-Dimethyl-piperazin-1-yl)-[6-(4-hydroxy-2,6-dimethyl-phenyl)-3-methyl-1H-pyrazolo[3,4-b]pyridin-4-yl]-methanone |
| 157 | [3-Cyclopropyl-6-(4-hydroxy-phenyl)-1H-pyrazolo[3,4-b]pyridin-4-yl]-(2,2-dimethyl-piperazin-1-yl)-methanone |
| 158 | [3-Cyclopropyl-6-(4-hydroxy-phenyl)-1H-pyrazolo[3,4-b]pyridin-4-yl]-((R)-2-phenyl-piperazin-1-yl)-methanone |
| 159 | 3-Ethyl-6-(4-hydroxy-phenyl)-1H-pyrazolo[3,4-b]pyridine-4-carboxylic acid (1-aza-bicyclo[2.2.2]oct-3-yl)-amide |
| 160 | (3-Amino-azetidin-1-yl)-[3-ethyl-6-(4-hydroxy-phenyl)-1H-pyrazolo[3,4-b]pyridin-4-yl]-methanone |
| 161 | 3-Ethyl-6-(4-hydroxy-phenyl)-1H-pyrazolo[3,4-b]pyridine-4-carboxylic acid ((3S,4S)-4-methoxy-pyrrolidin-3-yl)-amide |
| 162 | (S)-3-Ethyl-6-(4-hydroxy-phenyl)-1H-pyrazolo[3,4-b]pyridine-4-carboxylic acid (1-aza-bicyclo[2.2.2]oct-3-yl)-amide |
| 163 | 3-Ethyl-6-(4-hydroxy-phenyl)-1H-pyrazolo[3,4-b]pyridine-4-carboxylic acid (8-methyl-8-aza-bicyclo[3.2.1]oct-3-yl)-amide |
| 164 | 3-Ethyl-6-(4-hydroxy-phenyl)-1H-pyrazolo[3,4-b]pyridine-4-carboxylic acid ((3R)-8-methyl-8-aza-bicyclo[3.2.1]oct-3-yl)-amide |
| 165 | [3-Ethyl-6-(4-hydroxy-phenyl)-1H-pyrazolo[3,4-b]pyridin-4-yl]-(3-methyl-piperazin-1-yl)-methanone |
| 166 | (4-Amino-piperidin-1-yl)-[3-ethyl-6-(4-hydroxy-phenyl)-1H-pyrazolo[3,4-b]pyridin-4-yl]-methanone |

| | |
|---|---|
| 167 | [3-Ethyl-6-(4-hydroxy-phenyl)-1H-pyrazolo[3,4-b]pyridin-4-yl]-(hexahydro-pyrrolo[3,4-b]pyrrol-1-yl)-methanone |
| 168 | 3-Ethyl-6-(4-hydroxy-phenyl)-1H-pyrazolo[3,4-b]pyridine-4-carboxylic acid (5-aza-spiro[3.5]non-8-yl)-amide |
| 169 | (2,7-Diaza-spiro[3.5]non-2-yl)-[3-ethyl-6-(4-hydroxy-phenyl)-1H-pyrazolo[3,4-b]pyridin-4-yl]-methanone |
| 170 | 3-Ethyl-6-(4-hydroxy-phenyl)-1H-pyrazolo[3,4-b]pyridine-4-carboxylic acid (3-amino-cyclohexyl)-amide |
| 171 | (2,7-Diaza-spiro[3.5]non-7-yl)-[3-ethyl-6-(4-hydroxy-phenyl)-1H-pyrazolo[3,4-b]pyridin-4-yl]-methanone |
| 172 | (2,7-Diaza-spiro[4.4]non-2-yl)-[3-ethyl-6-(4-hydroxy-phenyl)-1H-pyrazolo[3,4-b]pyridin-4-yl]-methanone |
| 173 | (2,7-Diaza-spiro[4.5]dec-2-yl)-[3-ethyl-6-(4-hydroxy-phenyl)-1H-pyrazolo[3,4-b]pyridin-4-yl]-methanone |
| 174 | 3-Ethyl-6-(4-hydroxy-phenyl)-1H-pyrazolo[3,4-b]pyridine-4-carboxylic acid methyl-(1-methyl-piperidin-4-yl)-amide |
| 175 | 3-Ethyl-6-(4-hydroxy-phenyl)-1H-pyrazolo[3,4-b]pyridine-4-carboxylic acid (1-ethyl-piperidin-3-yl)-amide |
| 176 | ((R)-3-Dimethylamino-pyrrolidin-1-yl)-[3-ethyl-6-(4-hydroxy-phenyl)-1H-pyrazolo[3,4-b]pyridin-4-yl]-methanone |
| 177 | ((S)-3-Dimethylamino-pyrrolidin-1-yl)-[3-ethyl-6-(4-hydroxy-phenyl)-1H-pyrazolo[3,4-b]pyridin-4-yl]-methanone |
| 178 | [3-Ethyl-6-(4-hydroxy-phenyl)-1H-pyrazolo[3,4-b]pyridin-4-yl]-(3-methylamino-pyrrolidin-1-yl)-methanone |
| 179 | [3-Ethyl-6-(4-hydroxy-phenyl)-1H-pyrazolo[3,4-b]pyridin-4-yl]-((1S,5R)-9-hydroxy-1,5,7-trimethyl-3,7-diaza-bicyclo[3.3.1]non-3-yl)-methanone |
| 180 | 3-Ethyl-6-(4-hydroxy-phenyl)-1H-pyrazolo[3,4-b]pyridine-4-carboxylic acid (1-methyl-piperidin-3-yl)-amide |
| 181 | 3-Ethyl-6-(4-hydroxy-phenyl)-1H-pyrazolo[3,4-b]pyridine-4-carboxylic acid (2,3-dihydrospiro[1H-indene-1,4'-piperidin]-3-yl)-amide |
| 182 | 3-Ethyl-6-(4-hydroxy-phenyl)-1H-pyrazolo[3,4-b]pyridine-4-carboxylic acid (1-methyl-piperidin-4-yl)-amide |
| 183 | 3-Ethyl-6-(4-hydroxy-phenyl)-1H-pyrazolo[3,4-b]pyridine-4-carboxylic acid azetidin-3-ylamide |
| 184 | 3-Ethyl-6-(4-hydroxy-phenyl)-1H-pyrazolo[3,4-b]pyridine-4-carboxylic acid (9-methyl-9-aza-bicyclo[3.3.1]non-3-yl)-amide |
| 185 | 3-Ethyl-6-(4-hydroxy-phenyl)-1H-pyrazolo[3,4-b]pyridine-4-carboxylic acid ((R)-6-oxo-piperidin-3-yl)-amide |
| 186 | 3-Ethyl-6-(4-hydroxy-phenyl)-1H-pyrazolo[3,4-b]pyridine-4-carboxylic acid (5-oxo-pyrrolidin-2-ylmethyl)-amide |
| 187 | (4-Ethyl-[1,4]diazepan-1-yl)-[3-ethyl-6-(4-hydroxy-phenyl)-1H-pyrazolo[3,4-b]pyridin-4-yl]-methanone |
| 188 | [6-(4-Hydroxy-phenyl)-3-methyl-1H-pyrazolo[3,4-b]pyridin-4-yl]-((S)-2-methyl-piperazin-1-yl)-methanone |
| 189 | [6-(4-Hydroxy-phenyl)-3-methyl-1H-pyrazolo[3,4-b]pyridin-4-yl]-((R)-3-methyl-piperazin-1-yl)-methanone |
| 190 | [6-(4-Hydroxy-phenyl)-3-methyl-1H-pyrazolo[3,4-b]pyridin-4-yl]-((S)-3-methyl-piperazin-1-yl)-methanone |
| 191 | 6-(4-Hydroxy-phenyl)-3-methyl-1H-pyrazolo[3,4-b]pyridine-4-carboxylic acid (6-amino-spiro[3.3]hept-2-yl)-amide |
| 192 | (Hexahydro-pyrrolo[3,4-c]pyrrol-2-yl)-[6-(4-hydroxy-phenyl)-3-methyl-1H-pyrazolo[3,4-b]pyridin-4-yl]-methanone |
| 193 | 6-(4-Hydroxy-phenyl)-3-methyl-1H-pyrazolo[3,4-b]pyridine-4-carboxylic acid (2-aza-bicyclo[2.2.1]hept-5-yl)-amide |
| 194 | (2,3-Dimethyl-piperazin-1-yl)-[6-(4-hydroxy-phenyl)-3-methyl-1H-pyrazolo[3,4-b]pyridin-4-yl]-methanone |
| 195 | [6-(4-Hydroxy-phenyl)-3-methyl-1H-pyrazolo[3,4-b]pyridin-4-yl]-((R)-3-propyl-piperazin-1-yl)-methanone |
| 196 | [6-(4-Hydroxy-phenyl)-3-methyl-1H-pyrazolo[3,4-b]pyridin-4-yl]-(3-trifluoromethyl-piperazin-1-yl)-methanone |
| 197 | {1-[6-(4-Hydroxy-phenyl)-3-methyl-1H-pyrazolo[3,4-b]pyridine-4-carbonyl]-piperazin-2-yl}-acetic acid methyl ester |
| 198 | (3,3-Dimethyl-piperazin-1-yl)-[6-(4-hydroxy-phenyl)-3-methyl-1H-pyrazolo[3,4-b]pyridin-4-yl]-methanone |
| 199 | (2,2-Dimethyl-piperazin-1-yl)-[6-(4-hydroxy-phenyl)-3-methyl-1H-pyrazolo[3,4-b]pyridin-4-yl]-methanone |
| 200 | (S)-[6-(4-Hydroxy-phenyl)-3-methyl-1H-pyrazolo[3,4-b]pyridine-4-carboxylic acid (1-aza-bicyclo[2.2.2]oct-3-yl)-amide |
| 201 | 6-(4-Hydroxy-phenyl)-3-methyl-1H-pyrazolo[3,4-b]pyridine-4-carboxylic acid ((3R)-8-methyl-8-aza-bicyclo[3.2.1]oct-3-yl)-amide |
| 202 | [6-(4-Hydroxy-phenyl)-3-methyl-1H-pyrazolo[3,4-b]pyridin-4-yl]-((S)-2-isopropyl-piperazin-1-yl)-methanone |
| 203 | [(R)-3-(1-Amino-cyclopropyl)-pyrrolidin-1-yl]-[6-(4-hydroxy-phenyl)-3-methyl-1H-pyrazolo[3,4-b]pyridin-4-yl]-methanone |
| 204 | 6-(4-Hydroxy-phenyl)-3-methyl-1H-pyrazolo[3,4-b]pyridine-4-carboxylic acid (5-aza-spiro[3.5]non-8-yl)-amide |
| 205 | 6-(4-Hydroxy-phenyl)-3-methyl-1H-pyrazolo[3,4-b]pyridine-4-carboxylic acid [(R)-3-azabicyclo[3.1.0]hexan-1-yl]-amide |
| 206 | (R)-1-[6-(4-Hydroxy-phenyl)-3-methyl-1H-pyrazolo[3,4-b]pyridine-4-carbonyl]-piperazine-2-carboxylic acid methyl ester |

| | |
|---|---|
| 207 | 6-(4-Hydroxy-phenyl)-3-methyl-1H-pyrazolo[3,4-b]pyridine-4-carboxylic acid (1-aza-bicyclo[2.2.2]oct-3-yl)-amide |
| 208 | 6-(4-Hydroxy-phenyl)-3-methyl-1H-pyrazolo[3,4-b]pyridine-4-carboxylic acid ((R)-6-oxo-piperidin-3-yl)-amide |
| 209 | ((S)-3-Butyl-piperazin-1-yl)-[6-(4-hydroxy-phenyl)-3-methyl-1H-pyrazolo[3,4-b]pyridin-4-yl]-methanone |
| 210 | ((S)-3-Ethyl-piperazin-1-yl)-[6-(4-hydroxy-phenyl)-3-methyl-1H-pyrazolo[3,4-b]pyridin-4-yl]-methanone |
| 211 | (R)-4-[6-(4-Hydroxy-phenyl)-3-methyl-1H-pyrazolo[3,4-b]pyridine-4-carbonyl]-piperazine-2-carboxylic acid methyl ester |
| 212 | [6-(4-Hydroxy-phenyl)-3-methyl-1H-pyrazolo[3,4-b]pyridin-4-yl]-((R)-3-methoxymethyl-piperazin-1-yl)-methanone |
| 213 | 6-(4-Hydroxy-phenyl)-3-methyl-1H-pyrazolo[3,4-b]pyridine-4-carboxylic acid ((3S,4S)-4-methoxy-pyrrolidin-3-yl)-amide |
| 214 | 6-(4-Hydroxy-phenyl)-3-methyl-1H-pyrazolo[3,4-b]pyridine-4-carboxylic acid (3-azabicyclo[3.1.0]hex-6-yl)-amide |
| 215 | [6-(4-Hydroxy-phenyl)-3-methyl-1H-pyrazolo[3,4-b]pyridin-4-yl]-((S)-3-isobutyl-piperazin-1-yl)-methanone |
| 216 | 6-(4-Hydroxy-phenyl)-3-methyl-1H-pyrazolo[3,4-b]pyridine-4-carboxylic acid (pyrrolidin-3-ylmethyl)-amide |
| 217 | (2-Benzyl-piperazin-1-yl)-[6-(4-hydroxy-phenyl)-3-methyl-1H-pyrazolo[3,4-b]pyridin-4-yl]-methanone |
| 218 | 6-(4-Hydroxy-phenyl)-3-methyl-1H-pyrazolo[3,4-b]pyridine-4-carboxylic acid [2-(1-methyl-pyrrolidin-2-yl)-ethyl]-amide |
| 219 | 6-(4-Hydroxy-phenyl)-3-methyl-1H-pyrazolo[3,4-b]pyridine-4-carboxylic acid (8-methyl-8-aza-bicyclo[3.2.1]oct-3-yl)-amide |
| 220 | 6-(4-Hydroxy-phenyl)-3-methyl-1H-pyrazolo[3,4-b]pyridine-4-carboxylic acid (1-methyl-piperidin-4-yl)-amide |
| 221 | [6-(4-Hydroxy-phenyl)-3-methyl-1H-pyrazolo[3,4-b]pyridin-4-yl]-(3-methyl-piperazin-1-yl)-methanone |
| 222 | 6-(4-Hydroxy-phenyl)-3-methyl-1H-pyrazolo[3,4-b]pyridine-4-carboxylic acid (R)-piperidin-3-ylamide |
| 223 | 6-(4-Hydroxy-phenyl)-3-methyl-1H-pyrazolo[3,4-b]pyridine-4-carboxylic acid (9-methyl-9-aza-bicyclo[3.3.1]non-3-yl)-amide |
| 224 | ((R)-2-Benzyl-piperazin-1-yl)-[6-(4-hydroxy-phenyl)-3-methyl-1H-pyrazolo[3,4-b]pyridin-4-yl]-methanone |
| 225 | ((S)-2-Benzyl-piperazin-1-yl)-[6-(4-hydroxy-phenyl)-3-methyl-1H-pyrazolo[3,4-b]pyridin-4-yl]-methanone |
| 226 | (Hexahydro-pyrrolo[3,4-b]pyrrol-1-yl)-[6-(4-hydroxy-phenyl)-3-methyl-1H-pyrazolo[3,4-b]pyridin-4-yl]-methanone |
| 227 | (8-Amino-3-aza-bicyclo[3.2.1]oct-3-yl)-[6-(4-hydroxy-phenyl)-3-methyl-1H-pyrazolo[3,4-b]pyridin-4-yl]-methanone |
| 228 | 6-(4-Hydroxy-phenyl)-3-methyl-1H-pyrazolo[3,4-b]pyridine-4-carboxylic acid (3-aminomethyl-bicyclo[2.2.1]hept-2-yl)-amide |
| 229 | [6-(4-Hydroxy-phenyl)-3-methyl-1H-pyrazolo[3,4-b]pyridin-4-yl]-(cis-4-methyl-3-methylamino-piperidin-1-yl)-methanone |
| 230 | [6-(4-Hydroxy-phenyl)-3-methyl-1H-pyrazolo[3,4-b]pyridin-4-yl]-(octahydro-[1,6]naphthyridin-1-yl)-methanone |
| 231 | 6-(4-Hydroxy-phenyl)-3-methyl-1H-pyrazolo[3,4-b]pyridine-4-carboxylic acid (4-amino-cyclohexyl)-amide |
| 232 | (S)-1-[6-(4-Hydroxy-phenyl)-3-methyl-1H-pyrazolo[3,4-b]pyridine-4-carbonyl]-piperazine-2-carboxylic acid tert-butylamide |
| 233 | [6-(4-Hydroxy-phenyl)-3-methyl-1H-pyrazolo[3,4-b]pyridin-4-yl]-((S)-3-isopropyl-piperazin-1-yl)-methanone |
| 234 | (2,7-Diaza-spiro[3.5]non-2-yl)-[6-(4-hydroxy-phenyl)-3-methyl-1H-pyrazolo[3,4-b]pyridin-4-yl]-methanone |
| 235 | (2,7-Diaza-spiro[4.5]dec-2-yl)-[6-(4-hydroxy-phenyl)-3-methyl-1H-pyrazolo[3,4-b]pyridin-4-yl]-methanone |
| 236 | (3,9-Diaza-spiro[5.5]undec-3-yl)-[6-(4-hydroxy-phenyl)-3-methyl-1H-pyrazolo[3,4-b]pyridin-4-yl]-methanone |
| 237 | 6-(4-Hydroxy-phenyl)-3-methyl-1H-pyrazolo[3,4-b]pyridine-4-carboxylic acid (2,3-dihydro-spiro[1H-indene-1,4'-piperidin]-3-yl)-amide |
| 238 | ((R)-3-Dimethylamino-pyrrolidin-1-yl)-[6-(4-hydroxy-phenyl)-3-methyl-1H-pyrazolo[3,4-b]pyridin-4-yl]-methanone |
| 239 | ((S)-3-Dimethylamino-pyrrolidin-1-yl)-[6-(4-hydroxy-phenyl)-3-methyl-1H-pyrazolo[3,4-b]pyridin-4-yl]-methanone |
| 240 | [6-(4-Hydroxy-phenyl)-3-methyl-1H-pyrazolo[3,4-b]pyridin-4-yl]-(3-methylamino-pyrrolidin-1-yl)-methanone |
| 241 | 6-(4-Hydroxy-phenyl)-3-methyl-1H-pyrazolo[3,4-b]pyridine-4-carboxylic acid methyl-piperidin-4-yl-amide |
| 242 | 6-(4-Hydroxy-phenyl)-3-methyl-1H-pyrazolo[3,4-b]pyridine-4-carboxylic acid piperidin-3-ylamide |
| 243 | 6-(4-Hydroxy-phenyl)-3-methyl-1H-pyrazolo[3,4-b]pyridine-4-carboxylic acid (piperidin-3-ylmethyl)-amide |
| 244 | 6-(4-Hydroxy-phenyl)-3-methyl-1H-pyrazolo[3,4-b]pyridine-4-carboxylic acid (3-methylamino-propyl)-amide |
| 245 | 6-(4-Hydroxy-phenyl)-3-methyl-1H-pyrazolo[3,4-b]pyridine-4-carboxylic acid (piperidin-2-ylmethyl)-amide |
| 246 | ((S)-3-Amino-pyrrolidin-1-yl)-[6-(4-hydroxy-phenyl)-3-methyl-1H-pyrazolo[3,4-b]pyridin-4-yl]-methanone |

| | -continued |
|---|---|
| 247 | (3-Amino-azetidin-1-yl)-[6-(4-hydroxy-phenyl)-3-methyl-1H-pyrazolo[3,4-b]pyridin-4-yl]-methanone |
| 248 | 6-(4-Hydroxy-phenyl)-3-methyl-1H-pyrazolo[3,4-b]pyridine-4-carboxylic acid azetidin-3-ylamide |
| 249 | (4-Amino-piperidin-1-yl)-[6-(4-hydroxy-phenyl)-3-methyl-1H-pyrazolo[3,4-b]pyridin-4-yl]-methanone |
| 250 | (3aR,6aS)-Hexahydro-pyrrolo[3,4-c]pyrrol-2-yl-[6-(4-hydroxy-phenyl)-3-methyl-1H-pyrazolo[3,4-b]pyridin-4-yl]-methanone |
| 251 | 6-(4-Hydroxy-phenyl)-3-methyl-1H-pyrazolo[3,4-b]pyridine-4-carboxylic acid (trans-2-amino-cyclopropyl)-amide |
| 252 | 6-(4-Hydroxy-phenyl)-3-methyl-1H-pyrazolo[3,4-b]pyridine-4-carboxylic acid (trans-3-amino-cyclobutyl)-amide |
| 253 | [6-(4-Hydroxy-phenyl)-3-methyl-1H-pyrazolo[3,4-b]pyridin-4-yl]-(6-oxa-2,9-diaza-spiro[4.5]dec-2-yl)-methanone |
| 254 | 6-(4-Hydroxy-phenyl)-3-methyl-1H-pyrazolo[3,4-b]pyridine-4-carboxylic acid (3-amino-cyclohexyl)-amide |
| 255 | (2,7-Diaza-spiro[3.5]non-7-yl)-[6-(4-hydroxy-phenyl)-3-methyl-1H-pyrazolo[3,4-b]pyridin-4-yl]-methanone |
| 256 | (2,7-Diaza-spiro[4.4]non-2-yl)-[6-(4-hydroxy-phenyl)-3-methyl-1H-pyrazolo[3,4-b]pyridin-4-yl]-methanone |
| 257 | (2,8-Diaza-spiro[4.5]dec-8-yl)-[6-(4-hydroxy-phenyl)-3-methyl-1H-pyrazolo[3,4-b]pyridin-4-yl]-methanone |
| 258 | [6-(4-Hydroxy-phenyl)-3-methyl-1H-pyrazolo[3,4-b]pyridin-4-yl]-(1-oxa-4,8-diaza-spiro[5.5]undec-4-yl)-methanone |
| 259 | [6-(4-Hydroxy-phenyl)-3-methyl-1H-pyrazolo[3,4-b]pyridin-4-yl]-(1-oxa-4,9-diaza-spiro[5.5]undec-9-yl)-methanone |
| 260 | (2,8-Diaza-spiro[4.5]dec-2-yl)-[6-(4-hydroxy-phenyl)-3-methyl-1H-pyrazolo[3,4-b]pyridin-4-yl]-methanone |
| 261 | [6-(4-Hydroxy-phenyl)-3-methyl-1H-pyrazolo[3,4-b]pyridin-4-yl]-(1-oxa-4,9-diaza-spiro[5.5]undec-4-yl)-methanone |
| 262 | [6-(4-Hydroxy-phenyl)-3-methyl-1H-pyrazolo[3,4-b]pyridin-4-yl]-(1-oxa-4,8-diaza-spiro[5.5]undec-8-yl)-methanone |
| 263 | (2,7-Diaza-spiro[4.5]dec-7-yl)-[6-(4-hydroxy-phenyl)-3-methyl-1H-pyrazolo[3,4-b]pyridin-4-yl]-methanone |
| 264 | (3-Amino-pyrrolidin-1-yl)-[6-(4-hydroxy-phenyl)-3-methyl-1H-pyrazolo[3,4-b]pyridin-4-yl]-methanone |
| 265 | 1-{4-[6-(4-Hydroxy-phenyl)-3-methyl-1H-pyrazolo[3,4-b]pyridine-4-carbonyl]-piperazin-1-yl}-ethanone |
| 266 | 2-[6-(4-Hydroxy-phenyl)-3-methyl-1H-pyrazolo[3,4-b]pyridine-4-carbonyl]-octahydro-pyrido[1,2-a]pyrazin-4-one |
| 267 | [6-(4-Hydroxy-phenyl)-3-methyl-1H-pyrazolo[3,4-b]pyridin-4-yl]-[4-(4-methyl-benzoyl)-piperazin-1-yl]-methanone |
| 268 | (5-Ethyl-2,5-diaza-bicyclo[2.2.1]hept-2-yl)-[6-(4-hydroxy-phenyl)-3-methyl-1H-pyrazolo[3,4-b]pyridin-4-yl]-methanone |
| 269 | [6-(4-Hydroxy-phenyl)-3-methyl-1H-pyrazolo[3,4-b]pyridin-4-yl]-(4-methyl-[1,4]diazepan-1-yl)-methanone |
| 270 | 6-(4-Hydroxy-phenyl)-3-methyl-1H-pyrazolo[3,4-b]pyridine-4-carboxylic acid (3-amino-2,2-dimethyl-propyl)-amide |
| 271 | [6-(4-Hydroxy-phenyl)-3-methyl-1H-pyrazolo[3,4-b]pyridin-4-yl]-[4-(2-methanesulfonyl-ethyl)-piperazin-1-yl]-methanone |
| 272 | 6-(4-Hydroxy-phenyl)-3-methyl-1H-pyrazolo[3,4-b]pyridine-4-carboxylic acid methyl-(1-methyl-piperidin-4-yl)-amide |
| 273 | 6-(4-Hydroxy-phenyl)-3-methyl-1H-pyrazolo[3,4-b]pyridine-4-carboxylic acid (1-ethyl-piperidin-3-yl)-amide |
| 274 | [6-(4-Hydroxy-phenyl)-3-methyl-1H-pyrazolo[3,4-b]pyridin-4-yl]-((1S,5R)-9-hydroxy-1,5,7-trimethyl-3,7-diaza-bicyclo[3.3.1]non-3-yl)-methanone |
| 275 | 6-(4-Hydroxy-phenyl)-3-methyl-1H-pyrazolo[3,4-b]pyridine-4-carboxylic acid (1-methyl-piperidin-3-yl)-amide |
| 276 | 6-(4-Hydroxy-phenyl)-3-methyl-1H-pyrazolo[3,4-b]pyridine-4-carboxylic acid (1,2,2,6,6-pentamethyl-piperidin-4-yl)-amide |
| 277 | 6-(4-Hydroxy-phenyl)-3-methyl-1H-pyrazolo[3,4-b]pyridine-4-carboxylic acid (1-acetyl-piperidin-4-yl)-amide |
| 278 | 6-(4-Hydroxy-phenyl)-3-methyl-1H-pyrazolo[3,4-b]pyridine-4-carboxylic acid (5-oxo-pyrrolidin-2-ylmethyl)-amide |
| 279 | 6-(4-Hydroxy-phenyl)-3-methyl-1H-pyrazolo[3,4-b]pyridine-4-carboxylic acid (1-cyclohexyl-piperidin-4-yl)-amide |
| 280 | [6-(4-Hydroxy-phenyl)-3-methyl-1H-pyrazolo[3,4-b]pyridin-4-yl]-[4-(tetrahydro-furan-2-carbonyl)-piperazin-1-yl]-methanone |
| 281 | (4-Ethyl-[1,4]diazepan-1-yl)-[6-(4-hydroxy-phenyl)-3-methyl-1H-pyrazolo[3,4-b]pyridin-4-yl]-methanone |
| 282 | [6-(4-Hydroxy-phenyl)-3-methyl-1H-pyrazolo[3,4-b]pyridin-4-yl]-(3-phenyl-hexahydro-pyrrolo[1,2-a]pyrazin-2-yl)-methanone |
| 283 | 4-Amino-1-[6-(4-hydroxy-phenyl)-3-methyl-1H-pyrazolo[3,4-b]pyridine-4-carbonyl]-piperidine-4-carboxylic acid methyl ester |
| 284 | [6-(4-Hydroxy-phenyl)-3-methyl-1H-pyrazolo[3,4-b]pyridin-4-yl]-(3-methyl-hexahydro-pyrrolo[1,2-a]pyrazin-2-yl)-methanone |
| 285 | [6-(4-Hydroxy-phenyl)-3-methyl-1H-pyrazolo[3,4-b]pyridin-4-yl]-(3-methyl-octahydro-pyrido[1,2-a]pyrazin-2-yl)-methanone |
| 286 | 6-(4-Hydroxy-phenyl)-3-methyl-1H-pyrazolo[3,4-b]pyridine-4-carboxylic acid (2-methyl-2-pyridin-2-yl-3-pyrrolidin-1-yl-propyl)-amide |

| | |
|---|---|
| 287 | [6-(4-Hydroxy-phenyl)-3-methyl-1H-pyrazolo[3,4-b]pyridin-4-yl]-(4-piperidin-1-ylmethyl-piperidin-1-yl)-methanone |
| 288 | 6-(3-Fluoro-4-hydroxy-phenyl)-3-methyl-1H-pyrazolo[3,4-b]pyridine-4-carboxylic acid (6-amino-spiro[3.3]hept-2-yl)-amide |
| 289 | [6-(3-Fluoro-4-hydroxy-phenyl)-3-methyl-1H-pyrazolo[3,4-b]pyridin-4-yl]-(hexahydro-pyrrolo[3,4-c]pyrrol-2-yl)-methanone |
| 290 | [6-(3-Fluoro-4-hydroxy-phenyl)-3-methyl-1H-pyrazolo[3,4-b]pyridin-4-yl]-((S)-3-methyl-piperazin-1-yl)-methanone |
| 291 | [6-(3-Fluoro-4-hydroxy-phenyl)-3-methyl-1H-pyrazolo[3,4-b]pyridin-4-yl]-((R)-3-propyl-piperazin-1-yl)-methanone |
| 292 | ((S)-3-Amino-pyrrolidin-1-yl)-[6-(3-fluoro-4-hydroxy-phenyl)-3-methyl-1H-pyrazolo[3,4-b]pyridin-4-yl]-methanone |
| 293 | [6-(3-Fluoro-4-hydroxy-phenyl)-3-methyl-1H-pyrazolo[3,4-b]pyridin-4-yl]-((S)-3-propyl-piperazin-1-yl)-methanone |
| 294 | ((S)-3-Butyl-piperazin-1-yl)-[6-(3-fluoro-4-hydroxy-phenyl)-3-methyl-1H-pyrazolo[3,4-b]pyridin-4-yl]-methanone |
| 295 | ((S)-3-Ethyl-piperazin-1-yl)-[6-(3-fluoro-4-hydroxy-phenyl)-3-methyl-1H-pyrazolo[3,4-b]pyridin-4-yl]-methanone |
| 296 | (6,6-Dioxo-octahydro-6lambda6-thieno[3,4-b]pyrazin-1-yl)-[6-(3-fluoro-4-hydroxy-phenyl)-3-methyl-1H-pyrazolo[3,4-b]pyridin-4-yl]-methanone |
| 297 | (R)-4-[6-(3-Fluoro-4-hydroxy-phenyl)-3-methyl-1H-pyrazolo[3,4-b]pyridine-4-carbonyl]-piperazine-2-carboxylic acid methyl ester |
| 298 | [6-(3-Fluoro-4-hydroxy-phenyl)-3-methyl-1H-pyrazolo[3,4-b]pyridin-4-yl]-((R)-3-methoxymethyl-piperazin-1-yl)-methanone |
| 299 | 6-(3-Fluoro-4-hydroxy-phenyl)-3-methyl-1H-pyrazolo[3,4-b]pyridine-4-carboxylic acid (2,3-dihydro-spiro[1H-indene-1,4'-piperidin]-3-yl)-amide |
| 300 | (2-Benzyl-piperazin-1-yl)-[6-(3-fluoro-4-hydroxy-phenyl)-3-methyl-1H-pyrazolo[3,4-b]pyridin-4-yl]-methanone |
| 301 | 6-(3-Fluoro-4-hydroxy-phenyl)-3-methyl-1H-pyrazolo[3,4-b]pyridine-4-carboxylic acid (8-methyl-8-aza-bicyclo[3.2.1]oct-3-yl)-amide |
| 302 | 6-(3-Fluoro-4-hydroxy-phenyl)-3-methyl-1H-pyrazolo[3,4-b]pyridine-4-carboxylic acid azetidin-3-ylamide |
| 303 | [6-(3-Fluoro-4-hydroxy-phenyl)-3-methyl-1H-pyrazolo[3,4-b]pyridin-4-yl]-(3-methyl-piperazin-1-yl)-methanone |
| 304 | (4-Amino-piperidin-1-yl)-[6-(3-fluoro-4-hydroxy-phenyl)-3-methyl-1H-pyrazolo[3,4-b]pyridin-4-yl]-methanone |
| 305 | 6-(3-Fluoro-4-hydroxy-phenyl)-3-methyl-1H-pyrazolo[3,4-b]pyridine-4-carboxylic acid (R)-piperidin-3-ylamide |
| 306 | [6-(3-Fluoro-4-hydroxy-phenyl)-3-methyl-1H-pyrazolo[3,4-b]pyridin-4-yl]-(3aR,6aS)-hexahydro-pyrrolo[3,4-c]pyrrol-2-yl-methanone |
| 307 | 6-(3-Fluoro-4-hydroxy-phenyl)-3-methyl-1H-pyrazolo[3,4-b]pyridine-4-carboxylic acid (trans-2-amino-cyclopropyl)-amide |
| 308 | [6-(3-Fluoro-4-hydroxy-phenyl)-3-methyl-1H-pyrazolo[3,4-b]pyridin-4-yl]-(hexahydro-pyrrolo[3,4-b]pyrrol-1-yl)-methanone |
| 309 | 6-(3-Fluoro-4-hydroxy-phenyl)-3-methyl-1H-pyrazolo[3,4-b]pyridine-4-carboxylic acid (trans-3-amino-cyclobutyl)-amide |
| 310 | (8-Amino-3-aza-bicyclo[3.2.1]oct-3-yl)-[6-(3-fluoro-4-hydroxy-phenyl)-3-methyl-1H-pyrazolo[3,4-b]pyridin-4-yl]-methanone |
| 311 | 6-(3-Fluoro-4-hydroxy-phenyl)-3-methyl-1H-pyrazolo[3,4-b]pyridine-4-carboxylic acid (3-aminomethyl-bicyclo[2.2.1]hept-2-yl)-amide |
| 312 | [6-(3-Fluoro-4-hydroxy-phenyl)-3-methyl-1H-pyrazolo[3,4-b]pyridin-4-yl]-(cis-4-methyl-3-methylamino-piperidin-1-yl)-methanone |
| 313 | [6-(3-Fluoro-4-hydroxy-phenyl)-3-methyl-1H-pyrazolo[3,4-b]pyridin-4-yl]-((S)-2-methyl-piperazin-1-yl)-methanone |
| 314 | [6-(3-Fluoro-4-hydroxy-phenyl)-3-methyl-1H-pyrazolo[3,4-b]pyridin-4-yl]-(3-trifluoromethyl-piperazin-1-yl)-methanone |
| 315 | (3-Amino-azetidin-1-yl)-[6-(3-fluoro-4-hydroxy-phenyl)-3-methyl-1H-pyrazolo[3,4-b]pyridin-4-yl]-methanone |
| 316 | 6-(3-Fluoro-4-hydroxy-phenyl)-3-methyl-1H-pyrazolo[3,4-b]pyridine-4-carboxylic acid [2-(1-methyl-pyrrolidin-2-yl)-ethyl]-amide |
| 317 | (S)-6-(3-Fluoro-4-hydroxy-phenyl)-3-methyl-1H-pyrazolo[3,4-b]pyridine-4-carboxylic acid (1-aza-bicyclo[2.2.2]oct-3-yl)-amide |
| 318 | 6-(3-Fluoro-4-hydroxy-phenyl)-3-methyl-1H-pyrazolo[3,4-b]pyridine-4-carboxylic acid (3R)-8-methyl-8-aza-bicyclo[3.2.1]oct-3-yl)-amide |
| 319 | 6-(3-Fluoro-4-hydroxy-phenyl)-3-methyl-1H-pyrazolo[3,4-b]pyridine-4-carboxylic acid (1-methyl-piperidin-4-yl)-amide |
| 320 | [6-(3-Fluoro-4-hydroxy-phenyl)-3-methyl-1H-pyrazolo[3,4-b]pyridin-4-yl]-((S)-2-isopropyl-piperazin-1-yl)-methanone |
| 321 | ((R)-2-Benzyl-piperazin-1-yl)-[6-(3-fluoro-4-hydroxy-phenyl)-3-methyl-1H-pyrazolo[3,4-b]pyridin-4-yl]-methanone |
| 322 | [(R)-3-(1-Amino-cyclopropyl)-pyrrolidin-1-yl]-[6-(3-fluoro-4-hydroxy-phenyl)-3-methyl-1H-pyrazolo[3,4-b]pyridin-4-yl]-methanone |
| 323 | [6-(3-Fluoro-4-hydroxy-phenyl)-3-methyl-1H-pyrazolo[3,4-b]pyridin-4-yl]-(6-oxa-2,9-diaza-spiro[4.5]dec-2-yl)-methanone |
| 324 | [6-(3-Fluoro-4-hydroxy-phenyl)-3-methyl-1H-pyrazolo[3,4-b]pyridin-4-yl]-(octahydro-[1,6]naphthyridin-1-yl)-methanone |
| 325 | (S)-1-[6-(3-Fluoro-4-hydroxy-phenyl)-3-methyl-1H-pyrazolo[3,4-b]pyridine-4-carbonyl]-piperazine-2-carboxylic acid tert-butylamide |
| 326 | [6-(3-Fluoro-4-hydroxy-phenyl)-3-methyl-1H-pyrazolo[3,4-b]pyridin-4-yl]-((S)-3-isopropyl-piperazin-1-yl)-methanone |

| | |
|---|---|
| 327 | [6-(3-Fluoro-4-hydroxy-phenyl)-3-methyl-1H-pyrazolo[3,4-b]pyridin-4-yl]-(2-pyridin-3-yl-piperazin-1-yl)-methanone |
| 328 | (R)-1-[6-(3-Fluoro-4-hydroxy-phenyl)-3-methyl-1H-pyrazolo[3,4-b]pyridine-4-carbonyl]-piperazine-2-carboxylic acid methyl ester |
| 329 | (2,7-Diaza-spiro[3.5]non-7-yl)-[6-(3-fluoro-4-hydroxy-phenyl)-3-methyl-1H-pyrazolo[3,4-b]pyridin-4-yl]-methanone |
| 330 | (1,2-Dihydro-5-spiro[3H-indole-3,4'-piperidin]-1-yl)-[6-(3-fluoro-4-hydroxy-phenyl)-3-methyl-1H-pyrazolo[3,4-b]pyridin-4-yl]-methanone |
| 331 | 6-(3-Fluoro-4-hydroxy-phenyl)-3-methyl-1H-pyrazolo[3,4-b]pyridine-4-carboxylic acid methyl-(1-methyl-piperidin-4-yl)-amide |
| 332 | 6-(3-Fluoro-4-hydroxy-phenyl)-3-methyl-1H-pyrazolo[3,4-b]pyridine-4-carboxylic acid (1-ethyl-piperidin-3-yl)-amide |
| 333 | 6-(3-Fluoro-4-hydroxy-phenyl)-3-methyl-1H-pyrazolo[3,4-b]pyridine-4-carboxylic acid (1-aza-bicyclo[2.2.2]oct-3-yl)-amide |
| 334 | [6-(3-Fluoro-4-hydroxy-phenyl)-3-methyl-1H-pyrazolo[3,4-b]pyridin-4-yl]-((1S,5R)-9-hydroxy-1,5,7-trimethyl-3,7-diaza-bicyclo[3.3.1]non-3-yl)-methanone |
| 335 | 6-(3-Fluoro-4-hydroxy-phenyl)-3-methyl-1H-pyrazolo[3,4-b]pyridine-4-carboxylic acid methyl-piperidin-4-yl-amide |
| 336 | (3-Amino-pyrrolidin-1-yl)-[6-(3-fluoro-4-hydroxy-phenyl)-3-methyl-1H-pyrazolo[3,4-b]pyridin-4-yl]-methanone |
| 337 | [6-(3-Fluoro-4-hydroxy-phenyl)-3-methyl-1H-pyrazolo[3,4-b]pyridin-4-yl]-((R)-3-methyl-piperazin-1-yl)-methanone |
| 338 | 6-(3-Fluoro-4-hydroxy-phenyl)-3-methyl-1H-pyrazolo[3,4-b]pyridine-4-carboxylic acid (4-amino-cyclohexyl)-amide |
| 339 | (2,7-Diaza-spiro[3.5]non-2-yl)-[6-(3-fluoro-4-hydroxy-phenyl)-3-methyl-1H-pyrazolo[3,4-b]pyridin-4-yl]-methanone |
| 340 | (2,7-Diaza-spiro[4.4]non-2-yl)-[6-(3-fluoro-4-hydroxy-phenyl)-3-methyl-1H-pyrazolo[3,4-b]pyridin-4-yl]-methanone |
| 341 | (2,8-Diaza-spiro[4.5]dec-8-yl)-[6-(3-fluoro-4-hydroxy-phenyl)-3-methyl-1H-pyrazolo[3,4-b]pyridin-4-yl]-methanone |
| 342 | [6-(3-Fluoro-4-hydroxy-phenyl)-3-methyl-1H-pyrazolo[3,4-b]pyridin-4-yl]-(1-oxa-4,9-diaza-spiro[5.5]undec-9-yl)-methanone |
| 343 | (2,8-Diaza-spiro[4.5]dec-2-yl)-[6-(3-fluoro-4-hydroxy-phenyl)-3-methyl-1H-pyrazolo[3,4-b]pyridin-4-yl]-methanone |
| 344 | [6-(3-Fluoro-4-hydroxy-phenyl)-3-methyl-1H-pyrazolo[3,4-b]pyridin-4-yl]-(1-oxa-4,9-diaza-spiro[5.5]undec-4-yl)-methanone |
| 345 | [6-(3-Fluoro-4-hydroxy-phenyl)-3-methyl-1H-pyrazolo[3,4-b]pyridin-4-yl]-(1-oxa-4,8-diaza-spiro[5.5]undec-8-yl)-methanone |
| 346 | (2,7-Diaza-spiro[4.5]dec-7-yl)-[6-(3-fluoro-4-hydroxy-phenyl)-3-methyl-1H-pyrazolo[3,4-b]pyridin-4-yl]-methanone |
| 347 | ((R)-3-Dimethylamino-pyrrolidin-1-yl)-[6-(3-fluoro-4-hydroxy-phenyl)-3-methyl-1H-pyrazolo[3,4-b]pyridin-4-yl]-methanone |
| 348 | ((S)-3-Dimethylamino-pyrrolidin-1-yl)-[6-(3-fluoro-4-hydroxy-phenyl)-3-methyl-1H-pyrazolo[3,4-b]pyridin-4-yl]-methanone |
| 349 | 6-(3-Fluoro-4-hydroxy-phenyl)-3-methyl-1H-pyrazolo[3,4-b]pyridine-4-carboxylic acid piperidin-3-ylamide |
| 350 | 6-(3-Fluoro-4-hydroxy-phenyl)-3-methyl-1H-pyrazolo[3,4-b]pyridine-4-carboxylic acid (2-aza-bicyclo[2.2.1]hept-5-yl)-amide |
| 351 | [6-(3-Fluoro-4-hydroxy-phenyl)-3-methyl-1H-pyrazolo[3,4-b]pyridin-4-yl]-((S)-3-isobutyl-piperazin-1-yl)-methanone |
| 352 | (2,3-Dimethyl-piperazin-1-yl)-[6-(3-fluoro-4-hydroxy-phenyl)-3-methyl-1H-pyrazolo[3,4-b]pyridin-4-yl]-methanone |
| 353 | {1-[6-(3-Fluoro-4-hydroxy-phenyl)-3-methyl-1H-pyrazolo[3,4-b]pyridine-4-carbonyl]-piperazin-2-yl}-acetic acid methyl ester |
| 354 | 6-(3-Fluoro-4-hydroxy-phenyl)-3-methyl-1H-pyrazolo[3,4-b]pyridine-4-carboxylic acid (pyrrolidin-3-ylmethyl)-amide |
| 355 | 6-(3-Fluoro-4-hydroxy-phenyl)-3-methyl-1H-pyrazolo[3,4-b]pyridine-4-carboxylic acid (1-methyl-piperidin-3-yl)-amide |
| 356 | 1-{4-[6-(3-Fluoro-4-hydroxy-phenyl)-3-methyl-1H-pyrazolo[3,4-b]pyridine-4-carbonyl]-piperazin-1-yl}-ethanone |
| 357 | 6-(3-Fluoro-4-hydroxy-phenyl)-3-methyl-1H-pyrazolo[3,4-b]pyridine-4-carboxylic acid (1-acetyl-piperidin-4-yl)-amide |
| 358 | (5-Ethyl-2,5-diaza-bicyclo[2.2.1]hept-2-yl)-[6-(3-fluoro-4-hydroxy-phenyl)-3-methyl-1H-pyrazolo[3,4-b]pyridin-4-yl]-methanone |
| 359 | 6-(3-Fluoro-4-hydroxy-phenyl)-3-methyl-1H-pyrazolo[3,4-b]pyridine-4-carboxylic acid (5-oxo-pyrrolidin-2-ylmethyl)-amide |
| 360 | 6-(3-Fluoro-4-hydroxy-phenyl)-3-methyl-1H-pyrazolo[3,4-b]pyridine-4-carboxylic acid (1-cyclohexyl-piperidin-4-yl)-amide |
| 361 | (R)-6-(3-Fluoro-4-hydroxy-phenyl)-3-methyl-1H-pyrazolo[3,4-b]pyridine-4-carboxylic acid (1-aza-bicyclo[2.2.2]oct-3-yl)-amide |
| 362 | 6-(3-Fluoro-4-hydroxy-phenyl)-3-methyl-1H-pyrazolo[3,4-b]pyridine-4-carboxylic acid [2-methyl-2-(4-methyl-piperazin-1-yl)-propyl]-amide |
| 363 | 6-(3-Fluoro-4-hydroxy-phenyl)-3-methyl-1H-pyrazolo[3,4-b]pyridine-4-carboxylic acid (3-amino-2,2-dimethyl-propyl)-amide |
| 364 | 6-(3-Fluoro-4-hydroxy-phenyl)-3-methyl-1H-pyrazolo[3,4-b]pyridine-4-carboxylic acid (1,2,2,6,6-pentamethyl-piperidin-4-yl)-amide |
| 365 | [6-(3-Fluoro-4-hydroxy-phenyl)-3-methyl-1H-pyrazolo[3,4-b]pyridin-4-yl]-(4-methyl-[1,4]diazepan-1-yl)-methanone |

-continued

| | |
|---|---|
| 366 | (4-Ethyl-[1,4]diazepan-1-yl)-[6-(3-fluoro-4-hydroxy-phenyl)-3-methyl-1H-pyrazolo[3,4-b]pyridin-4-yl]-methanone |
| 367 | 6-(3-Fluoro-4-hydroxy-phenyl)-3-methyl-1H-pyrazolo[3,4-b]pyridine-4-carboxylic acid (piperidin-2-ylmethyl)-amide |
| 368 | 4-[6-(3-Fluoro-4-hydroxy-phenyl)-3-methyl-1H-pyrazolo[3,4-b]pyridine-4-carbonyl]-6-isopropyl-piperazin-2-one |
| 369 | [6-(3-Fluoro-4-hydroxy-phenyl)-3-methyl-1H-pyrazolo[3,4-b]pyridin-4-yl]-(3-phenyl-hexahydro-pyrrolo[1,2-a]pyrazin-2-yl)-methanone |
| 370 | 6-(3-Fluoro-4-hydroxy-phenyl)-3-methyl-1H-pyrazolo[3,4-b]pyridine-4-carboxylic acid (2-pyridin-2-yl-2-pyrrolidin-1-yl-propyl)-amide |
| 371 | 6-(3-Fluoro-4-hydroxy-phenyl)-3-methyl-1H-pyrazolo[3,4-b]pyridine-4-carboxylic acid (2-methyl-2-pyridin-2-yl-3-pyrrolidin-1-yl-propyl)-amide |
| 372 | [6-(4-Hydroxy-phenyl)-3-methyl-1H-pyrazolo[3,4-b]pyridin-4-yl]-(4-methyl-2-phenyl-piperazin-1-yl)-methanone |
| 373 | 6-(4-Hydroxy-phenyl)-3-methyl-1H-pyrazolo[3,4-b]pyridine-4-carboxylic acid (2,3-dihydro-spiro[1H-indene-1,4'-piperidin]-3-yl)-amide |
| 374 | [6-(4-Hydroxy-phenyl)-3-methyl-1H-pyrazolo[3,4-b]pyridin-4-yl]-(2-pyridin-3-yl-piperazin-1-yl)-methanone |
| 375 | (3-Benzyl-piperazin-1-yl)-[6-(4-hydroxy-phenyl)-3-methyl-1H-pyrazolo[3,4-b]pyridin-4-yl]-methanone |
| 376 | 6-(4-Hydroxy-phenyl)-3-methyl-1H-pyrazolo[3,4-b]pyridine-4-carboxylic acid [2-dimethylamino-2-(4-methoxy-phenyl)-ethyl]-amide |
| 377 | 6-(4-Hydroxy-phenyl)-3-methyl-1H-pyrazolo[3,4-b]pyridine-4-carboxylic acid (1-phenyl-2-pyrrolidin-1-yl-ethyl)-amide |
| 378 | [2-(4-Chloro-phenyl)-piperazin-1-yl]-[6-(4-hydroxy-phenyl)-3-methyl-1H-pyrazolo[3,4-b]pyridin-4-yl]-methanone |
| 379 | {4-[6-(4-Hydroxy-phenyl)-3-methyl-1H-pyrazolo[3,4-b]pyridine-4-carbonyl]-piperazin-1-yl}-pyrrolidin-1-yl-methanone |
| 380 | [4-(Furan-3-carbonyl)-piperazin-1-yl]-[6-(4-hydroxy-phenyl)-3-methyl-1H-pyrazolo[3,4-b]pyridin-4-yl]-methanone |
| 381 | [6-(4-Hydroxy-phenyl)-3-methyl-1H-pyrazolo[3,4-b]pyridin-4-yl]-[4-(2-methoxy-benzoyl)-piperazin-1-yl]-methanone |
| 382 | 6-(4-Hydroxy-phenyl)-3-methyl-1H-pyrazolo[3,4-b]pyridine-4-carboxylic acid (1-phenethyl-piperidin-4-yl)-amide |
| 383 | (S)-Hexahydro-pyrrolo[1,2-a]pyrazin-2-yl-[6-(4-hydroxy-phenyl)-3-methyl-1H-pyrazolo[3,4-b]pyridin-4-yl]-methanone |
| 384 | 6-(4-Hydroxy-phenyl)-3-methyl-1H-pyrazolo[3,4-b]pyridine-4-carboxylic acid (1-benzyl-pyrrolidin-3-yl)-amide |
| 385 | [6-(4-Hydroxy-phenyl)-3-methyl-1H-pyrazolo[3,4-b]pyridin-4-yl]-(3-phenylamino-pyrrolidin-1-yl)-methanone |
| 386 | (5-Benzyl-hexahydro-pyrrolo[3,4-c]pyrrol-2-yl)-[6-(4-hydroxy-phenyl)-3-methyl-1H-pyrazolo[3,4-b]pyridin-4-yl]-methanone |
| 387 | [6-(4-Hydroxy-phenyl)-3-methyl-1H-pyrazolo[3,4-b]pyridin-4-yl]-[4-(pyridine-4-carbonyl)-[1,4]diazepan-1-yl]-methanone |
| 388 | 6-(4-Hydroxy-phenyl)-3-methyl-1H-pyrazolo[3,4-b]pyridine-4-carboxylic acid [2-(3-phenyl-pyrrolidin-1-yl)-ethyl]-amide |
| 389 | 6-(4-Hydroxy-phenyl)-3-methyl-1H-pyrazolo[3,4-b]pyridine-4-carboxylic acid (2-pyrrolidin-1-yl-propyl)-amide |
| 390 | 6-(4-Hydroxy-phenyl)-3-methyl-1H-pyrazolo[3,4-b]pyridine-4-carboxylic acid [2-(4-phenyl-piperidin-1-yl)-ethyl]-amide |
| 391 | 6-(4-Hydroxy-phenyl)-3-methyl-1H-pyrazolo[3,4-b]pyridine-4-carboxylic acid (2-phenyl-2-pyrroiidin-1-yl-ethyl)-amide |
| 392 | 6-(4-Hydroxy-phenyl)-3-methyl-1H-pyrazolo[3,4-b]pyridine-4-carboxylic acid (1-benzyl-piperidin-4-yl)-amide |
| 393 | 6-(4-Hydroxy-phenyl)-3-methyl-1H-pyrazolo[3,4-b]pyridine-4-carboxylic acid (2-phenyl-2-piperazin-1-yl-ethyl)-amide |
| 394 | 6-(4-Hydroxy-phenyl)-3-methyl-1H-pyrazolo[3,4-b]pyridine-4-carboxylic acid (2-morpholin-4-yl-2-phenyl-ethyl)-amide |
| 395 | 6-(4-Hydroxy-phenyl)-3-methyl-1H-pyrazolo[3,4-b]pyridine-4-carboxylic acid (2-piperidin-4-yl-ethyl)-amide |
| 396 | 6-(4-Hydroxy-phenyl)-3-methyl-1H-pyrazolo[3,4-b]pyridine-4-carboxylic acid (4-dimethylamino-cyclohexyl)-amide |
| 397 | [6-(4-Hydroxy-phenyl)-3-trifluoromethyl-1H-pyrazolo[3,4-b]pyridin-4-yl]-((S)-3-methyl-piperazin-1-yl)-methanone |
| 398 | 6-(4-Hydroxy-phenyl)-3-trifluoromethyl-1H-pyrazolo[3,4-b]pyridine-4-carboxylic acid (R)-piperidin-3-ylamide |
| 399 | (4-Amino-piperidin-1-yl)-[6-(4-hydroxy-phenyl)-3-trifluoromethyl-1H-pyrazolo[3,4-b]pyridin-4-yl]-methanone |
| 400 | (Hexahydro-pyrrolo[3,4-c]pyrrol-2-yl)-[6-(4-hydroxy-phenyl)-3-trifluoromethyl-1H-pyrazolo[3,4-b]pyridin-4-yl]-methanone |
| 401 | [6-(4-Hydroxy-phenyl)-3-trifluoromethyl-1H-pyrazolo[3,4-b]pyridin-4-yl]-((R)-3-methyl-piperazin-1-yl)-methanone |
| 402 | 6-(4-Hydroxy-phenyl)-3-trifluoromethyl-1H-pyrazolo[3,4-b]pyridine-4-carboxylic acid azetidin-3-ylamide |
| 403 | (2,7-Diaza-spiro[3.5]non-2-yl)-[6-(4-hydroxy-phenyl)-3-trifluoromethyl-1H-pyrazolo[3,4-b]pyridin-4-yl]-methanone |
| 404 | ((S)-3-Amino-pyrrolidin-1-yl)-[6-(4-hydroxy-phenyl)-3-trifluoromethyl-1H-pyrazolo[3,4-b]pyridin-4-yl]-methanone |
| 405 | (2,7-Diaza-spiro[3.5]non-7-yl)-[6-(4-hydroxy-phenyl)-3-trifluoromethyl-1H-pyrazolo[3,4-b]pyridin-4-yl]-methanone |

| | |
|---|---|
| 406 | [6-(4-Hydroxy-phenyl)-3-trifluoromethyl-1H-pyrazolo[3,4-b]pyridin-4-yl]-(3-methylamino-pyrrolidin-1-yl)-methanone |
| 407 | (2,7-Diaza-spiro[4.5]dec-2-yl)-[6-(4-hydroxy-phenyl)-3-trifluoromethyl-1H-pyrazolo[3,4-b]pyridin-4-yl]-methanone |
| 408 | (Hexahydro-pyrrolo[3,4-b]pyrrol-1-yl)-[6-(4-hydroxy-phenyl)-3-trifluoromethyl-1H-pyrazolo[3,4-b]pyridin-4-yl]-methanone |
| 409 | (2,8-Diaza-spiro[4.5]dec-2-yl)-[6-(4-hydroxy-phenyl)-3-trifluoromethyl-1H-pyrazolo[3,4-b]pyridin-4-yl]-methanone |
| 410 | (2,8-Diaza-spiro[4.5]dec-8-yl)-[6-(4-hydroxy-phenyl)-3-trifluoromethyl-1H-pyrazolo[3,4-b]pyridin-4-yl]-methanone |
| 411 | (3,9-Diaza-spiro[5.5]undec-3-yl)-[6-(4-hydroxy-phenyl)-3-trifluoromethyl-1H-pyrazolo[3,4-b]pyridin-4-yl]-methanone |
| 412 | 6-(4-Hydroxy-phenyl)-3-trifluoromethyl-1H-pyrazolo[3,4-b]pyridine-4-carboxylic acid [(S)-1-aza-bicyclo[2.2.2]oct-3-yl]-amide |
| 413 | 6-(4-Hydroxy-phenyl)-3-trifluoromethyl-1H-pyrazolo[3,4-b]pyridine-4-carboxylic acid [(R)-1-aza-bicyclo[2.2.2]oct-3-yl]-amide |
| 414 | (4-Ethyl-[1,4]diazepan-1-yl)-[6-(4-hydroxy-phenyl)-3-trifluoromethyl-1H-pyrazolo[3,4-b]pyridin-4-yl]-methanone |
| 415 | (4-Amino-4-phenyl-piperidin-1-yl)-[6-(2-fluoro-4-hydroxy-phenyl)-3-methyl-1H-pyrazolo[3,4-b]pyridin-4-yl]-methanone |
| 416 | (4-Amino-4-ethyl-piperidin-1-yl)-[6-(2-fluoro-4-hydroxy-phenyl)-3-methyl-1H-pyrazolo[3,4-b]pyridin-4-yl]-methanone |
| 417 | 3,8-Diaza-bicyclo[3.2.1]oct-8-yl-[6-(2-fluoro-4-hydroxy-phenyl)-3-methyl-1H-pyrazolo[3,4-b]pyridin-4-yl]-methanone |
| 418 | (4-Amino-4-methyl-piperidin-1-yl)-[6-(2-fluoro-4-hydroxy-phenyl)-3-methyl-1H-pyrazolo[3,4-b]pyridin-4-yl]-methanone |
| 419 | [6-(2-Fluoro-4-hydroxy-phenyl)-3-methyl-1H-pyrazolo[3,4-b]pyridin-4-yl]-(3aR,6aS)-hexahydro-pyrrolo[3,4-c]pyrrol-2-yl-methanone |
| 420 | [6-(2-Fluoro-4-hydroxy-phenyl)-3-methyl-1H-pyrazolo[3,4-b]pyridin-4-yl]-((R)-3-propyl-piperazin-1-yl)-methanone |
| 421 | [6-(2-Fluoro-4-hydroxy-phenyl)-3-methyl-1H-pyrazolo[3,4-b]pyridin-4-yl]-(3-phenyl-piperazin-1-yl)-methanone |
| 422 | [6-(2-Fluoro-4-hydroxy-phenyl)-3-methyl-1H-pyrazolo[3,4-b]pyridin-4-yl]-((S)-3-propyl-piperazin-1-yl)-methanone |
| 423 | (3-Cyclopropyl-piperazin-1-yl)-[6-(2-fluoro-4-hydroxy-phenyl)-3-methyl-1H-pyrazolo[3,4-b]pyridin-4-yl]-methanone |
| 424 | [6-(2-Fluoro-4-hydroxy-phenyl)-3-methyl-1H-pyrazolo[3,4-b]pyridin-4-yl]-((S)-3-methyl-piperazin-1-yl)-methanone |
| 425 | (3,3-Dimethyl-piperazin-1-yl)-[6-(2-fluoro-4-hydroxy-phenyl)-3-methyl-1H-pyrazolo[3,4-b]pyridin-4-yl]-methanone |
| 426 | [6-(2-Fluoro-4-hydroxy-phenyl)-3-methyl-1H-pyrazolo[3,4-b]pyridin-4-yl]-((R)-3-methyl-piperazin-1-yl)-methanone |
| 427 | [6-(2-Fluoro-4-hydroxy-phenyl)-3-methyl-1H-pyrazolo[3,4-b]pyridin-4-yl]-(2,5,5-trimethyl-piperazin-1-yl)-methanone |
| 428 | ((2R,5R)-2,5-Dimethyl-piperazin-1-yl)-[6-(2-fluoro-4-hydroxy-phenyl)-3-methyl-1H-pyrazolo[3,4-b]pyridin-4-yl]-methanone |
| 429 | ((2S,5R)-2,5-Dimethyl-piperazin-1-yl)-[6-(2-fluoro-4-hydroxy-phenyl)-3-methyl-1H-pyrazolo[3,4-b]pyridin-4-yl]-methanone |
| 430 | ((2S,5S)-2,5-Dimethyl-piperazin-1-yl)-[6-(2-fluoro-4-hydroxy-phenyl)-3-methyl-1H-pyrazolo[3,4-b]pyridin-4-yl]-methanone |
| 431 | ((S)-2-Ethyl-piperazin-1-yl)-[6-(2-fluoro-4-hydroxy-phenyl)-3-methyl-1H-pyrazolo[3,4-b]pyridin-4-yl]-methanone |
| 432 | (3-Amino-3-trifluoromethyl-pyrrolidin-1-yl)-[6-(2-fluoro-4-hydroxy-phenyl)-3-methyl-1H-pyrazolo[3,4-b]pyridin-4-yl]-methanone |
| 433 | (6,9-Diaza-spiro[4.5]dec-6-yl)-[6-(2-fluoro-4-hydroxy-phenyl)-3-methyl-1H-pyrazolo[3,4-b]pyridin-4-yl]-methanone |
| 434 | [6-(2-Fluoro-4-hydroxy-phenyl)-3-methyl-1H-pyrazolo[3,4-b]pyridin-4-yl]-(2,2,5-trimethyl-piperazin-1-yl)-methanone |
| 435 | [6-(2-Fluoro-4-hydroxy-phenyl)-3-methyl-1H-pyrazolo[3,4-b]pyridin-4-yl]-(2-methyl-2-phenyl-piperazin-1-yl)-methanone |
| 436 | (2,2-Diethyl-piperazin-1-yl)-[6-(2-fluoro-4-hydroxy-phenyl)-3-methyl-1H-pyrazolo[3,4-b]pyridin-4-yl]-methanone |
| 437 | (8,8-Dimethyl-6,9-diaza-spiro[4.5]dec-6-yl)-[6-(2-fluoro-4-hydroxy-phenyl)-3-methyl-1H-pyrazolo[3,4-b]pyridin-4-yl]-methanone |
| 438 | [6-(2-Fluoro-4-hydroxy-phenyl)-3-methyl-1H-pyrazolo[3,4-b]pyridin-4-yl]-(8-methyl-6,9-diaza-spiro[4.5]dec-6-yl)-methanone |
| 439 | (5,8-Diaza-spiro[3.5]non-5-yl)-[6-(2-fluoro-4-hydroxy-phenyl)-3-methyl-1H-pyrazolo[3,4-b]pyridin-4-yl]-methanone |
| 440 | 6-(2-Fluoro-4-hydroxy-phenyl)-3-methyl-1H-pyrazolo[3,4-b]pyridine-4-carboxylic acid (4-phenyl-piperidin-4-yl)-amide |
| 441 | (2,5-Dipropyl-piperazin-1-yl)-[6-(2-fluoro-4-hydroxy-phenyl)-3-methyl-1H-pyrazolo[3,4-b]pyridin-4-yl]-methanone |
| 442 | ((cis)-2,3-Dimethyl-piperazin-1-yl)-[6-(2-fluoro-4-hydroxy-phenyl)-3-methyl-1H-pyrazolo[3,4-b]pyridin-4-yl]-methanone |
| 443 | [6-(2-Fluoro-4-hydroxy-phenyl)-3-methyl-1H-pyrazolo[3,4-b]pyridin-4-yl]-(4aS,8aS)-octahydro-quinoxalin-1-yl-methanone |
| 444 | (2,6-Dimethyl-piperazin-1-yl)-[6-(2-fluoro-4-hydroxy-phenyl)-3-methyl-1H-pyrazolo[3,4-b]pyridin-4-yl]-methanone |
| 445 | (2,5-Diethyl-piperazin-1-yl)-[6-(2-fluoro-4-hydroxy-phenyl)-3-methyl-1H-pyrazolo[3,4-b]pyridin-4-yl]-methanone |

-continued

| | |
|---|---|
| 446 | ((2S,5R)-5-Ethyl-2-methyl-piperazin-1-yl)-[6-(2-fluoro-4-hydroxy-phenyl)-3-methyl-1H-pyrazolo[3,4-b]pyridin-4-yl]-methanone |
| 447 | [6-(2-Fluoro-4-hydroxy-phenyl)-3-methyl-1H-pyrazolo[3,4-b]pyridin-4-yl]-(trans-2-methyl-5-phenyl-piperazin-1-yl)-methanone |
| 448 | [6-(2-Fluoro-4-hydroxy-phenyl)-3-methyl-1H-pyrazolo[3,4-b]pyridin-4-yl]-((2S,5R)-2-methyl-5-propyl-piperazin-1-yl)-methanone |
| 449 | (2-Ethyl-2,5,5-trimethyl-piperazin-1-yl)-[6-(2-fluoro-4-hydroxy-phenyl)-3-methyl-1H-pyrazolo[3,4-b]pyridin-4-yl]-methanone |
| 450 | (2,2-Diethyl-5,5-dimethyl-piperazin-1-yl)-[6-(2-fluoro-4-hydroxy-phenyl)-3-methyl-1H-pyrazolo[3,4-b]pyridin-4-yl]-methanone |
| 451 | (8,8-Dimethyl-6,9-diaza-spiro[4.5]dec-9-yl)-[6-(2-fluoro-4-hydroxy-phenyl)-3-methyl-1H-pyrazolo[3,4-b]pyridin-4-yl]-methanone |
| 452 | ((2S,5R)-2,5-Dimethyl-4-pyridin-2-ylmethyl-piperazin-1-yl)-[6-(2-fluoro-4-hydroxy-phenyl)-3-methyl-1H-pyrazolo[3,4-b]pyridin-4-yl]-methanone |
| 453 | ((2S,5R)-2,5-Dimethyl-4-piperidin-4-ylmethyl-piperazin-1-yl)-[6-(2-fluoro-4-hydroxy-phenyl)-3-methyl-1H-pyrazolo[3,4-b]pyridin-4-yl]-methanone |
| 454 | [(2S,5R)-2,5-Dimethyl-4-(tetrahydro-pyran-4-ylmethyl)-piperazin-1-yl]-[6-(2-fluoro-4-hydroxy-phenyl)-3-methyl-1H-pyrazolo[3,4-b]pyridin-4-yl]-methanone |
| 455 | [(2S,5R)-2,5-Dimethyl-4-(tetrahydro-furan-3-ylmethyl)-piperazin-1-yl]-[6-(2-fluoro-4-hydroxy-phenyl)-3-methyl-1H-pyrazolo[3,4-b]pyridin-4-yl]-methanone |
| 456 | [6-(4-Hydroxy-phenyl)-3-methyl-1H-pyrazolo[3,4-b]pyridin-4-yl]-((R)-3-phenyl-piperazin-1-yl)-methanone |
| 457 | [6-(4-Hydroxy-phenyl)-3-methyl-1H-pyrazolo[3,4-b]pyridin-4-yl]-((S)-3-phenyl-piperazin-1-yl)-methanone |
| 458 | [6-(4-Hydroxy-phenyl)-3-methyl-1H-pyrazolo[3,4-b]pyridin-4-yl]-((2S,5R)-5-methyl-2-phenyl-piperazin-1-yl)-methanone |
| 459 | [6-(4-Hydroxy-phenyl)-3-methyl-1H-pyrazolo[3,4-b]pyridin-4-yl]-((2R,5S)-5-methyl-2-phenyl-piperazin-1-yl)-methanone |
| 460 | [6-(2-Fluoro-4-hydroxy-phenyl)-3-methyl-1H-pyrazolo[3,4-b]pyridin-4-yl]-((2S,5R)-2-methyl-5-phenyl-piperazin-1-yl)-methanone |
| 461 | [6-(2-Fluoro-4-hydroxy-phenyl)-3-methyl-1H-pyrazolo[3,4-b]pyridin-4-yl]-((2R,5S)-2-methyl-5-phenyl-piperazin-1-yl)-methanone |

In another embodiment compounds of the formula I are encompassed selected from the group consisting of

| | |
|---|---|
| 1 | [6-(4-Hydroxy-phenyl)-3-methyl-1H-pyrazolo[3,4-b]pyridin-4-yl]-(2-methyl-2-phenyl-piperazin-1-yl)-methanone |
| 2 | [3-Ethyl-6-(3-fluoro-4-hydroxy-phenyl)-1H-pyrazolo[3,4-b]pyridin-4-yl]-piperazin-1-yl-methanone |
| 3 | [3-Ethyl-6-(4-hydroxy-phenyl)-1H-pyrazolo[3,4-b]pyridin-4-yl]-piperazin-1-yl-methanone |
| 4 | [6-(4-Hydroxy-phenyl)-3-propyl-1H-pyrazolo[3,4-b]pyridin-4-yl]-piperazin-1-yl-methanone |
| 5 | [6-(4-Hydroxy-phenyl)-3-trifluoromethyl-1H-pyrazolo[3,4-b]pyridin-4-yl]-piperazin-1-yl-methanone |
| 6 | [6-(2-Chloro-4-hydroxy-phenyl)-3-methyl-1H-pyrazolo[3,4-b]pyridin-4-yl]-piperazin-1-yl-methanone |
| 7 | [6-(3-Fluoro-4-hydroxy-phenyl)-3-methyl-1H-pyrazolo[3,4-b]pyridin-4-yl]-piperazin-1-yl-methanone |
| 8 | [6-(4-Hydroxy-3-methyl-phenyl)-3-methyl-1H-pyrazolo[3,4-b]pyridin-4-yl]-piperazin-1-yl-methanone |
| 9 | [6-(3-Chloro-4-hydroxy-phenyl)-3-methyl-1H-pyrazolo[3,4-b]pyridin-4-yl]-piperazin-1-yl-methanone |
| 10 | [6-(4-Hydroxy-3-methoxy-phenyl)-3-methyl-1H-pyrazolo[3,4-b]pyridin-4-yl]-piperazin-1-yl-methanone |
| 11 | [6-(2-Fluoro-4-hydroxy-phenyl)-3-methyl-1H-pyrazolo[3,4-b]pyridin-4-yl]-piperazin-1-yl-methanone |
| 12 | [6-(3,5-Difluoro-4-hydroxy-phenyl)-3-methyl-1H-pyrazolo[3,4-b]pyridin-4-yl]-piperazin-1-yl-methanone |
| 13 | [6-(4-Hydroxy-2-methyl-phenyl)-3-methyl-1H-pyrazolo[3,4-b]pyridin-4-yl]-piperazin-1-yl-methanone |
| 14 | [6-(4-Hydroxy-2-methoxy-phenyl)-3-methyl-1H-pyrazolo[3,4-b]pyridin-4-yl]-piperazin-1-yl-methanone |
| 15 | [6-(3-Ethoxy-4-hydroxy-phenyl)-3-methyl-1H-pyrazolo[3,4-b]pyridin-4-yl]-piperazin-1-yl-methanone |
| 16 | [6-(3,5-Difluoro-4-hydroxy-phenyl)-3-methyl-1H-pyrazolo[3,4-b]pyridin-4-yl]-((S)-2-methyl-piperazin-1-yl)-methanone |
| 17 | [6-(4-Hydroxy-2-methyl-phenyl)-3-methyl-1H-pyrazolo[3,4-b]pyridin-4-yl]-((S)-2-methyl-piperazin-1-yl)-methanone |
| 18 | [6-(4-Hydroxy-2-methoxy-phenyl)-3-methyl-1H-pyrazolo[3,4-b]pyridin-4-yl]-((S)-2-methyl-piperazin-1-yl)-methanone |

-continued

| | |
|---|---|
| 19 | 2,5-Diaza-bicyclo[2.2.1]hept-2-yl-[6-(4-hydroxy-phenyl)-3-methyl-1H-pyrazolo[3,4-b]pyridin-4-yl]-methanone |
| 23 | [6-(4-Hydroxy-phenyl)-3-methyl-1H-pyrazolo[3,4-b]pyridin-4-yl]-((R)-2-methyl-piperazin-1-yl)-methanone |
| 24 | ((3R,5S)-3,5-Dimethyl-piperazin-1-yl)-[6-(4-hydroxy-phenyl)-3-methyl-1H-pyrazolo[3,4-b]pyridin-4-yl]-methanone |
| 25 | [6-(4-Hydroxy-phenyl)-3-methyl-1H-pyrazolo[3,4-b]pyridin-4-yl]-(3-phenyl-piperazin-1-yl)-methanone |
| 29 | [2-(3,4-Dichloro-phenyl)-piperazin-1-yl]-[6-(4-hydroxy-phenyl)-3-methyl-1H-pyrazolo[3,4-b]pyridin-4-yl]-methanone |
| 30 | (2-Furan-2-yl-piperazin-1-yl)-[6-(4-hydroxy-phenyl)-3-methyl-1H-pyrazolo[3,4-b]pyridin-4-yl]-methanone |
| 31 | [6-(4-Hydroxy-phenyl)-3-methyl-1H-pyrazolo[3,4-b]pyridin-4-yl]-(2-thiophen-2-yl-piperazin-1-yl)-methanone |
| 33 | [3-(1-Amino-1-methyl-ethyl)-azetidin-1-yl]-[6-(4-hydroxy-phenyl)-3-methyl-1H-pyrazolo[3,4-b]pyridin-4-yl]-methanone |
| 34 | (4-Aminomethyl-4-phenyl-piperidin-1-yl)-[6-(4-hydroxy-phenyl)-3-methyl-1H-pyrazolo[3,4-b]pyridin-4-yl]-methanone |
| 35 | 6-(4-Hydroxy-phenyl)-3-methyl-1H-pyrazolo[3,4-b]pyridine-4-carboxylic acid (2-pyrrolidin-1-yl-ethyl)-amide |
| 36 | [6-(4-Hydroxy-phenyl)-3-methyl-1H-pyrazolo[3,4-b]pyridin-4-yl]-(4-isopropyl-piperazin-1-yl)-methanone |
| 37 | [6-(4-Hydroxy-phenyl)-3-methyl-1H-pyrazolo[3,4-b]pyridin-4-yl]-(4-methyl-piperazin-1-yl)-methanone |
| 38 | 6-(4-Hydroxy-phenyl)-3-methyl-1H-pyrazolo[3,4-b]pyridine-4-carboxylic acid (2-dimethylamino-ethyl)-amide |
| 39 | (4-Cyclobutyl-piperazin-1-yl)-[6-(4-hydroxy-phenyl)-3-methyl-1H-pyrazolo[3,4-b]pyridin-4-yl]-methanone |
| 40 | 6-(4-Hydroxy-phenyl)-3-methyl-1H-pyrazolo[3,4-b]pyridine-4-carboxylic acid (2-tert-butylamino-ethyl)-methyl-amide |
| 42 | (1,3-Dihydro-spiro[indene-2,2'-piperazin]-1'-yl)-[6-(4-hydroxy-phenyl)-3-methyl-1H-pyrazolo[3,4-b]pyridin-4-yl]-methanone |
| 43 | 6-(4-Hydroxy-phenyl)-3-methyl-1H-pyrazolo[3,4-b]pyridine-4-carboxylic acid (4-methyl-pyrrolidin-3-yl)-amide |
| 44 | 6-(4-Hydroxy-phenyl)-3-methyl-1H-pyrazolo[3,4-b]pyridine-4-carboxylic acid (4-ethoxy-pyrrolidin-3-yl)-amide |
| 45 | 6-(4-Hydroxy-phenyl)-3-methyl-1H-pyrazolo[3,4-b]pyridine-4-carboxylic acid (4-phenyl-pyrrolidin-3-yl)-amide |
| 46 | (4-Amino-4-propyl-piperidin-1-yl)-[6-(4-hydroxy-phenyl)-3-methyl-1H-pyrazolo[3,4-b]pyridin-4-yl]-methanone |
| 47 | (3-Amino-3-propyl-pyrrolidin-1-yl)-[6-(4-hydroxy-phenyl)-3-methyl-1H-pyrazolo[3,4-b]pyridin-4-yl]-methanone |
| 48 | (3-Amino-3-propyl-piperidin-1-yl)-[6-(4-hydroxy-phenyl)-3-methyl-1H-pyrazolo[3,4-b]pyridin-4-yl]-methanone |
| 49 | 6-(4-Hydroxy-phenyl)-3-methyl-1H-pyrazolo[3,4-b]pyridine-4-carboxylic acid (4-ethyl-piperidin-4-yl)-amide |
| 50 | 6-(4-Hydroxy-phenyl)-3-methyl-1H-pyrazolo[3,4-b]pyridine-4-carboxylic acid (2-isopropylamino-ethyl)-amide |
| 51 | 6-(4-Hydroxy-phenyl)-3-methyl-1H-pyrazolo[3,4-b]pyridine-4-carboxylic acid [2-amino-1-(3-methoxy-phenyl)-ethyl]-amide |
| 52 | 6-(4-Hydroxy-phenyl)-3-methyl-1H-pyrazolo[3,4-b]pyridine-4-carboxylic acid (2-amino-1-p-tolyl-ethyl)-amide |
| 53 | [6-(4-Hydroxy-phenyl)-3-methyl-1H-pyrazolo[3,4-b]pyridin-4-yl]-piperazin-1-yl-methanone |
| 54 | 4-[6-(4-Hydroxy-phenyl)-3-methyl-1H-pyrazolo[3,4-b]pyridine-4-carbonyl]-piperazine-1-carboxylic acid amide |
| 55 | [3-Cyclopropyl-6-(4-hydroxy-phenyl)-1H-pyrazolo[3,4-b]pyridin-4-yl]-piperazin-1-yl-methanone |
| 56 | (2,2-Dimethyl-piperazin-1-yl)-[6-(2-fluoro-4-hydroxy-phenyl)-3-methyl-1H-pyrazolo[3,4-b]pyridin-4-yl]-methanone |
| 57 | [6-(2-Fluoro-4-hydroxy-phenyl)-3-methyl-1H-pyrazolo[3,4-b]pyridin-4-yl]-((R)-2-phenyl-piperazin-1-yl)-methanone |
| 58 | [6-(2-Fluoro-4-hydroxy-phenyl)-3-methyl-1H-pyrazolo[3,4-b]pyridin-4-yl]-(4-methylamino-piperidin-1-yl)-methanone |
| 59 | ((S)-3-Aminomethyl-piperidin-1-yl)-[6-(2-fluoro-4-hydroxy-phenyl)-3-methyl-1H-pyrazolo[3,4-b]pyridin-4-yl]-methanone |
| 60 | [6-(2-Fluoro-4-hydroxy-phenyl)-3-methyl-1H-pyrazolo[3,4-b]pyridin-4-yl]-(2-trifluoromethyl-piperazin-1-yl)-methanone |
| 61 | 6-(2-Fluoro-4-hydroxy-phenyl)-3-methyl-1H-pyrazolo[3,4-b]pyridine-4-carboxylic acid (1-amino-cycloheptylmethyl)-amide |
| 62 | 6-(2-Fluoro-4-hydroxy-phenyl)-3-methyl-1H-pyrazolo[3,4-b]pyridine-4-carboxylic acid (3-ethyl-piperidin-3-yl)-amide |
| 63 | [6-(2-Fluoro-4-hydroxy-phenyl)-3-methyl-1H-pyrazolo[3,4-b]pyridin-4-yl]-(2,2,5,5-tetramethyl-piperazin-1-yl)-methanone |
| 64 | (4,7-Diaza-spiro[2.5]oct-4-yl)-[6-(2-fluoro-4-hydroxy-phenyl)-3-methyl-1H-pyrazolo[3,4-b]pyridin-4-yl]-methanone |
| 65 | 6-(2-Fluoro-4-hydroxy-phenyl)-3-methyl-1H-pyrazolo[3,4-b]pyridine-4-carboxylic acid (3-amino-1-ethyl-propyl)-amide |
| 66 | 6-(2-Fluoro-4-hydroxy-phenyl)-3-methyl-1H-pyrazolo[3,4-b]pyridine-4-carboxylic acid (3-amino-1,1-dimethyl-propyl)-amide |

-continued

| | |
|---|---|
| 67 | 6-(2-Fluoro-4-hydroxy-phenyl)-3-methyl-1H-pyrazolo[3,4-b]pyridine-4-carboxylic acid (3-amino-3-methyl-butyl)-amide |
| 68 | [6-(4-Hydroxy-phenyl)-3-methyl-1H-pyrazolo[3,4-b]pyridin-4-yl]-((S)-3-propyl-piperazin-1-yl)-methanone |
| 69 | [6-(4-Hydroxy-phenyl)-3-methyl-1H-pyrazolo[3,4-b]pyridin-4-yl]-[2-(4-methoxy-phenyl)-piperazin-1-yl]-methanone |
| 70 | [6-(4-Hydroxy-phenyl)-3-methyl-1H-pyrazolo[3,4-b]pyridin-4-yl]-(5-methyl-2-phenyl-piperazin-1-yl)-methanone |
| 71 | 2,5-Diaza-bicyclo[2.2.2]oct-2-yl-[6-(4-hydroxy-phenyl)-3-methyl-1H-pyrazolo[3,4-b]pyridin-4-yl]-methanone |
| 72 | [6-(4-Hydroxy-phenyl)-3-methyl-1H-pyrazolo[3,4-b]pyridin-4-yl]-[2-(3-methoxy-phenyl)-piperazin-1-yl]-methanone |
| 73 | (trans-2,5-Dimethyl-piperazin-1-yl)-[6-(4-hydroxy-phenyl)-3-methyl-1H-pyrazolo[3,4-b]pyridin-4-yl]-methanone |
| 74 | 6-(4-Hydroxy-phenyl)-3-methyl-1H-pyrazolo[3,4-b]pyridine-4-carboxylic acid piperidin-4-ylamide |
| 75 | [1,4]Diazepan-1-yl-[6-(4-hydroxy-phenyl)-3-methyl-1H-pyrazolo[3,4-b]pyridin-4-yl]-methanone |
| 76 | (3-Amino-piperidin-1-yl)-[6-(4-hydroxy-phenyl)-3-methyl-1H-pyrazolo[3,4-b]pyridin-4-yl]-methanone |
| 77 | 6-(4-Hydroxy-phenyl)-3-methyl-1H-pyrazolo[3,4-b]pyridine-4-carboxylic acid (trans-4-amino-cyclohexyl)-amide |
| 78 | 6-(4-Hydroxy-phenyl)-3-methyl-1H-pyrazolo[3,4-b]pyridine-4-carboxylic acid ((trans)-4-methoxy-pyrrolidin-3-yl)-amide |
| 79 | [6-(4-Hydroxy-phenyl)-3-methyl-1H-pyrazolo[3,4-b]pyridin-4-yl]-[2-(2-methoxy-phenyl)-piperazin-1-yl]-methanone |
| 80 | (4,7-Diaza-spiro[2.5]oct-4-yl)-[6-(4-hydroxy-phenyl)-3-methyl-1H-pyrazolo[3,4-b]pyridin-4-yl]-methanone |
| 81 | ((2R,5S)-2,5-Dimethyl-piperazin-1-yl)-[6-(4-hydroxy-phenyl)-3-methyl-1H-pyrazolo[3,4-b]pyridin-4-yl]-methanone |
| 82 | [(S)-2-(3-Fluoro-phenyl)-piperazin-1-yl]-[6-(4-hydroxy-phenyl)-3-methyl-1H-pyrazolo[3,4-b]pyridin-4-yl]-methanone |
| 83 | ((2R,5R)-2,5-Dimethyl-piperazin-1-yl)-[6-(4-hydroxy-phenyl)-3-methyl-1H-pyrazolo[3,4-b]pyridin-4-yl]-methanone |
| 84 | [2-(4-Fluoro-phenyl)-piperazin-1-yl]-[6-(4-hydroxy-phenyl)-3-methyl-1H-pyrazolo[3,4-b]pyridin-4-yl]-methanone |
| 85 | [2-(2,3-Difluoro-phenyl)-piperazin-1-yl]-[6-(4-hydroxy-phenyl)-3-methyl-1H-pyrazolo[3,4-b]pyridin-4-yl]-methanone |
| 86 | (3-Cyclopropyl-piperazin-1-yl)-[6-(4-hydroxy-phenyl)-3-methyl-1H-pyrazolo[3,4-b]pyridin-4-yl]-methanone |
| 87 | [2-(3,5-Difluoro-phenyl)-piperazin-1-yl]-[6-(4-hydroxy-phenyl)-3-methyl-1H-pyrazolo[3,4-b]pyridin-4-yl]-methanone |
| 88 | ((2S,5S)-2,5-Dimethyl-piperazin-1-yl)-[6-(4-hydroxy-phenyl)-3-methyl-1H-pyrazolo[3,4-b]pyridin-4-yl]-methanone |
| 89 | [2-(4-Bromo-phenyl)-piperazin-1-yl]-[6-(4-hydroxy-phenyl)-3-methyl-1H-pyrazolo[3,4-b]pyridin-4-yl]-methanone |
| 90 | (3-Aminomethyl-azetidin-1-yl)-[6-(4-hydroxy-phenyl)-3-methyl-1H-pyrazolo[3,4-b]pyridin-4-yl]-methanone |
| 91 | [2-(3-Fluoro-phenyl)-piperazin-1-yl]-[6-(4-hydroxy-phenyl)-3-methyl-1H-pyrazolo[3,4-b]pyridin-4-yl]-methanone |
| 92 | [2-(3,4-Difluoro-phenyl)-piperazin-1-yl]-[6-(4-hydroxy-phenyl)-3-methyl-1H-pyrazolo[3,4-b]pyridin-4-yl]-methanone |
| 93 | [6-(4-Hydroxy-phenyl)-3-methyl-1H-pyrazolo[3,4-b]pyridin-4-yl]-[2-(2-trifluoromethyl-phenyl)-piperazin-1-yl]-methanone |
| 94 | [6-(4-Hydroxy-phenyl)-3-methyl-1H-pyrazolo[3,4-b]pyridin-4-yl]-[2-(4-isopropyl-phenyl)-piperazin-1-yl]-methanone |
| 95 | [2-(2-Fluoro-phenyl)-piperazin-1-yl]-[6-(4-hydroxy-phenyl)-3-methyl-1H-pyrazolo[3,4-b]pyridin-4-yl]-methanone |
| 96 | [2-(2,4-Difluoro-phenyl)-piperazin-1-yl]-[6-(4-hydroxy-phenyl)-3-methyl-1H-pyrazolo[3,4-b]pyridin-4-yl]-methanone |
| 97 | [6-(4-Hydroxy-phenyl)-3-methyl-1H-pyrazolo[3,4-b]pyridin-4-yl]-[2-(4-trifluoromethyl-phenyl)-piperazin-1-yl]-methanone |
| 98 | 6-(4-Hydroxy-phenyl)-3-methyl-1H-pyrazolo[3,4-b]pyridine-4-carboxylic acid (azetidin-3-ylmethyl)-amide |
| 99 | [6-(4-Hydroxy-phenyl)-3-methyl-1H-pyrazolo[3,4-b]pyridin-4-yl]-[2-(3-trifluoromethyl-phenyl)-piperazin-1-yl]-methanone |
| 100 | [2-(2,6-Difluoro-phenyl)-piperazin-1-yl]-[6-(4-hydroxy-phenyl)-3-methyl-1H-pyrazolo[3,4-b]pyridin-4-yl]-methanone |
| 101 | [2-(3-Bromo-phenyl)-piperazin-1-yl]-[6-(4-hydroxy-phenyl)-3-methyl-1H-pyrazolo[3,4-b]pyridin-4-yl]-methanone |
| 102 | [2-(2-Chloro-phenyl)-piperazin-1-yl]-[6-(4-hydroxy-phenyl)-3-methyl-1H-pyrazolo[3,4-b]pyridin-4-yl]-methanone |
| 103 | 6-(4-Hydroxy-phenyl)-3-methyl-1H-pyrazolo[3,4-b]pyridine-4-carboxylic acid (cis-4-amino-cyclohexyl)-amide |
| 104 | 6-(4-Hydroxy-phenyl)-3-methyl-1H-pyrazolo[3,4-b]pyridine-4-carboxylic acid (2-amino-1-phenyl-ethyl)-amide |
| 105 | 6-(4-Hydroxy-phenyl)-3-methyl-1H-pyrazolo[3,4-b]pyridine-4-carboxylic acid (cis-4-amino-cyclohexylmethyl)-amide |
| 106 | 6-(4-Hydroxy-phenyl)-3-methyl-1H-pyrazolo[3,4-b]pyridine-4-carboxylic acid pyrrolidin-3-ylamide |

| | |
|---|---|
| 107 | 6-(4-Hydroxy-phenyl)-3-methyl-1H-pyrazolo[3,4-b]pyridine-4-carboxylic acid [2-amino-1-(4-fluoro-phenyl)-ethyl]-amide |
| 108 | (6,9-Diaza-spiro[4.5]dec-6-yl)-[6-(4-hydroxy-phenyl)-3-methyl-1H-pyrazolo[3,4-b]pyridin-4-yl]-methanone |
| 109 | [6-(4-Hydroxy-phenyl)-3-methyl-1H-pyrazolo[3,4-b]pyridin-4-yl]-(4-methylamino-piperidin-1-yl)-methanone |
| 110 | ((S)-3-Aminomethyl-piperidin-1-yl)-[6-(4-hydroxy-phenyl)-3-methyl-1H-pyrazolo[3,4-b]pyridin-4-yl]-methanone |
| 111 | 3,8-Diaza-bicyclo[3.2.1]oct-3-yl-[6-(4-hydroxy-phenyl)-3-methyl-1H-pyrazolo[3,4-b]pyridin-4-yl]-methanone |
| 112 | ((2S,5R)-2,5-Dimethyl-piperazin-1-yl)-[6-(4-hydroxy-phenyl)-3-methyl-1H-pyrazolo[3,4-b]pyridin-4-yl]-methanone |
| 113 | [6-(4-Hydroxy-phenyl)-3-methyl-1H-pyrazolo[3,4-b]pyridin-4-yl]-(2,5,5-trimethyl-piperazin-1-yl)-methanone |
| 114 | [6-(4-Hydroxy-phenyl)-3-methyl-1H-pyrazolo[3,4-b]pyridin-4-yl]-(2-trifluoromethyl-piperazin-1-yl)-methanone |
| 115 | 6-(4-Hydroxy-phenyl)-3-methyl-1H-pyrazolo[3,4-b]pyridine-4-carboxylic acid (3-ethyl-piperidin-3-yl)-amide |
| 116 | 6-(4-Hydroxy-phenyl)-3-methyl-1H-pyrazolo[3,4-b]pyridine-4-carboxylic acid (1-amino-cycloheptylmethyl)-amide |
| 117 | (3-Amino-3-methyl-piperidin-1-yl)-[6-(4-hydroxy-phenyl)-3-methyl-1H-pyrazolo[3,4-b]pyridin-4-yl]-methanone |
| 118 | 6-(4-Hydroxy-phenyl)-3-methyl-1H-pyrazolo[3,4-b]pyridine-4-carboxylic acid (4-propyl-piperidin-4-yl)-amide |
| 119 | 6-(4-Hydroxy-phenyl)-3-methyl-1H-pyrazolo[3,4-b]pyridine-4-carboxylic acid (trans-4-p-tolyl-pyrrolidin-3-yl)-amide |
| 120 | 6-(4-Hydroxy-phenyl)-3-methyl-1H-pyrazolo[3,4-b]pyridine-4-carboxylic acid ((1R,2R)-2-amino-cyclopentyl)-amide |
| 121 | [6-(4-Hydroxy-phenyl)-3-methyl-1H-pyrazolo[3,4-b]pyridin-4-yl]-(2,2,5,5-tetramethyl-piperazin-1-yl)-methanone |
| 122 | (3-Amino-3-methyl-pyrrolidin-1-yl)-[6-(4-hydroxy-phenyl)-3-methyl-1H-pyrazolo[3,4-b]pyridin-4-yl]-methanone |
| 123 | 6-(4-Hydroxy-phenyl)-3-methyl-1H-pyrazolo[3,4-b]pyridine-4-carboxylic acid (trans-2-amino-cyclohexyl)-amide |
| 124 | 6-(4-Hydroxy-phenyl)-3-methyl-1H-pyrazolo[3,4-b]pyridine-4-carboxylic acid (3-propyl-piperidin-3-yl)-amide |
| 125 | 6-(4-Hydroxy-phenyl)-3-methyl-1H-pyrazolo[3,4-b]pyridine-4-carboxylic acid (3-propyl-pyrrolidin-3-yl)-amide |
| 126 | 6-(4-Hydroxy-phenyl)-3-methyl-1H-pyrazolo[3,4-b]pyridine-4-carboxylic acid (cis-2-amino-cyclohexyl)-amide |
| 127 | 6-(4-Hydroxy-phenyl)-3-methyl-1H-pyrazolo[3,4-b]pyridine-4-carboxylic acid (3-amino-1-ethyl-propyl)-amide |
| 128 | 6-(4-Hydroxy-phenyl)-3-methyl-1H-pyrazolo[3,4-b]pyridine-4-carboxylic acid (3-amino-1,1-dimethyl-propyl)-amide |
| 129 | 6-(4-Hydroxy-phenyl)-3-methyl-1H-pyrazolo[3,4-b]pyridine-4-carboxylic acid (3-amino-3-methyl-butyl)-amide |
| 130 | 6-(4-Hydroxy-phenyl)-3-methyl-1H-pyrazolo[3,4-b]pyridine-4-carboxylic acid (trans-4-amino-cyclohexylmethyl)-amide |
| 131 | 6-(4-Hydroxy-phenyl)-3-methyl-1H-pyrazolo[3,4-b]pyridine-4-carboxylic acid (3-amino-1-phenyl-propyl)-amide |
| 132 | 6-(4-Hydroxy-phenyl)-3-methyl-1H-pyrazolo[3,4-b]pyridine-4-carboxylic acid (2-dimethylamino-1-phenyl-ethyl)-amide |
| 133 | 6-(4-Hydroxy-phenyl)-3-methyl-1H-pyrazolo[3,4-b]pyridine-4-carboxylic acid (2-amino-2-methyl-propyl)-amide |
| 134 | 6-(4-Hydroxy-phenyl)-3-methyl-1H-pyrazolo[3,4-b]pyridine-4-carboxylic acid (2-amino-1,1,2-trimethyl-propyl)-amide |
| 135 | [6-(2,6-Difluoro-4-hydroxy-phenyl)-3-methyl-1H-pyrazolo[3,4-b]pyridin-4-yl]-(2,2-dimethyl-piperazin-1-yl)-methanone |
| 136 | [2-(3,5-Difluoro-phenyl)-piperazin-1-yl]-[6-(4-hydroxy-2-methyl-phenyl)-3-methyl-1H-pyrazolo[3,4-b]pyridin-4-yl]-methanone |
| 137 | [2-(4-Bromo-phenyl)-piperazin-1-yl]-[6-(4-hydroxy-2-methyl-phenyl)-3-methyl-1H-pyrazolo[3,4-b]pyridin-4-yl]-methanone |
| 138 | [2-(4-Fluoro-phenyl)-piperazin-1-yl]-[6-(4-hydroxy-2-methyl-phenyl)-3-methyl-1H-pyrazolo[3,4-b]pyridin-4-yl]-methanone |
| 139 | [2-(2,3-Difluoro-phenyl)-piperazin-1-yl]-[6-(4-hydroxy-2-methyl-phenyl)-3-methyl-1H-pyrazolo[3,4-b]pyridin-4-yl]-methanone |
| 140 | [6-(4-Hydroxy-2-methyl-phenyl)-3-methyl-1H-pyrazolo[3,4-b]pyridin-4-yl]-[2-(4-methoxy-phenyl)-piperazin-1-yl]-methanone |
| 141 | [(S)-2-(3-Fluoro-phenyl)-piperazin-1-yl]-[6-(4-hydroxy-2-methyl-phenyl)-3-methyl-1H-pyrazolo[3,4-b]pyridin-4-yl]-methanone |
| 142 | (2,2-Dimethyl-piperazin-1-yl)-[6-(4-hydroxy-2-methyl-phenyl)-3-methyl-1H-pyrazolo[3,4-b]pyridin-4-yl]-methanone |
| 143 | 6-(4-Hydroxy-2-methyl-phenyl)-3-methyl-1H-pyrazolo[3,4-b]pyridine-4-carboxylic acid ((3S,4S)-4-methoxy-pyrrolidin-3-yl)-amide |
| 144 | [6-(4-Hydroxy-2-methyl-phenyl)-3-methyl-1H-pyrazolo[3,4-b]pyridin-4-yl]-(2-trifluoromethyl-piperazin-1-yl)-methanone |
| 145 | [6-(4-Hydroxy-2-methyl-phenyl)-3-methyl-1H-pyrazolo[3,4-b]pyridin-4-yl]-((S)-3-methyl-piperazin-1-yl)-methanone |
| 146 | [6-(4-Hydroxy-2-methyl-phenyl)-3-methyl-1H-pyrazolo[3,4-b]pyridin-4-yl]-[2-(3-methoxy-phenyl)-piperazin-1-yl]-methanone |

| | |
|---|---|
| 147 | [2-(3-Fluoro-phenyl)-piperazin-1-yl]-[6-(4-hydroxy-2-methyl-phenyl)-3-methyl-1H-pyrazolo[3,4-b]pyridin-4-yl]-methanone |
| 148 | 6-(4-Hydroxy-2-methyl-phenyl)-3-methyl-1H-pyrazolo[3,4-b]pyridine-4-carboxylic acid (1-amino-cycloheptylmethyl)-amide |
| 149 | 6-(4-Hydroxy-2-methyl-phenyl)-3-methyl-1H-pyrazolo[3,4-b]pyridine-4-carboxylic acid (3-ethyl-piperidin-3-yl)-amide |
| 150 | [6-(4-Hydroxy-2-methyl-phenyl)-3-methyl-1H-pyrazolo[3,4-b]pyridin-4-yl]-((R)-2-phenyl-piperazin-1-yl)-methanone |
| 151 | [2-(2-Fluoro-phenyl)-piperazin-1-yl]-[6-(4-hydroxy-2-methyl-phenyl)-3-methyl-1H-pyrazolo[3,4-b]pyridin-4-yl]-methanone |
| 152 | [2-(2,4-Difluoro-phenyl)-piperazin-1-yl]-[6-(4-hydroxy-2-methyl-phenyl)-3-methyl-1H-pyrazolo[3,4-b]pyridin-4-yl]-methanone |
| 153 | [2-(2-Chloro-phenyl)-piperazin-1-yl]-[6-(4-hydroxy-2-methyl-phenyl)-3-methyl-1H-pyrazolo[3,4-b]pyridin-4-yl]-methanone |
| 154 | [6-(4-Hydroxy-2-methyl-phenyl)-3-methyl-1H-pyrazolo[3,4-b]pyridin-4-yl]-[2-(4-trifluoromethyl-phenyl)-piperazin-1-yl]-methanone |
| 155 | [6-(4-Hydroxy-2-methyl-phenyl)-3-methyl-1H-pyrazolo[3,4-b]pyridin-4-yl]-(2,2,5,5-tetramethyl-piperazin-1-yl)-methanone |
| 156 | (2,2-Dimethyl-piperazin-1-yl)-[6-(4-hydroxy-2,6-dimethyl-phenyl)-3-methyl-1H-pyrazolo[3,4-b]pyridin-4-yl]-methanone |
| 157 | [3-Cyclopropyl-6-(4-hydroxy-phenyl)-1H-pyrazolo[3,4-b]pyridin-4-yl]-(2,2-dimethyl-piperazin-1-yl)-methanone |
| 158 | [3-Cyclopropyl-6-(4-hydroxy-phenyl)-1H-pyrazolo[3,4-b]pyridin-4-yl]-((R)-2-phenyl-piperazin-1-yl)-methanone |
| 159 | 3-Ethyl-6-(4-hydroxy-phenyl)-1H-pyrazolo[3,4-b]pyridine-4-carboxylic acid (1-aza-bicyclo[2.2.2]oct-3-yl)-amide |
| 160 | (3-Amino-azetidin-1-yl)-[3-ethyl-6-(4-hydroxy-phenyl)-1H-pyrazolo[3,4-b]pyridin-4-yl]-methanone |
| 161 | 3-Ethyl-6-(4-hydroxy-phenyl)-1H-pyrazolo[3,4-b]pyridine-4-carboxylic acid ((3S,4S)-4-methoxy-pyrrolidin-3-yl)-amide |
| 162 | (S)-3-Ethyl-6-(4-hydroxy-phenyl)-1H-pyrazolo[3,4-b]pyridine-4-carboxylic acid (1-aza-bicyclo[2.2.2]oct-3-yl)-amide |
| 163 | 3-Ethyl-6-(4-hydroxy-phenyl)-1H-pyrazolo[3,4-b]pyridine-4-carboxylic acid (8-methyl-8-aza-bicyclo[3.2.1]oct-3-yl)-amide |
| 164 | 3-Ethyl-6-(4-hydroxy-phenyl)-1H-pyrazolo[3,4-b]pyridine-4-carboxylic acid ((3R)-8-methyl-8-aza-bicyclo[3.2.1]oct-3-yl)-amide |
| 165 | [3-Ethyl-6-(4-hydroxy-phenyl)-1H-pyrazolo[3,4-b]pyridin-4-yl]-(3-methyl-piperazin-1-yl)-methanone |
| 166 | (4-Amino-piperidin-1-yl)-[3-ethyl-6-(4-hydroxy-phenyl)-1H-pyrazolo[3,4-b]pyridin-4-yl]-methanone |
| 167 | [3-Ethyl-6-(4-hydroxy-phenyl)-1H-pyrazolo[3,4-b]pyridin-4-yl]-(hexahydro-pyrrolo[3,4-b]pyrrol-1-yl)-methanone |
| 168 | 3-Ethyl-6-(4-hydroxy-phenyl)-1H-pyrazolo[3,4-b]pyridine-4-carboxylic acid (5-aza-spiro[3.5]non-8-yl)-amide |
| 169 | (2,7-Diaza-spiro[3.5]non-2-yl)-[3-ethyl-6-(4-hydroxy-phenyl)-1H-pyrazolo[3,4-b]pyridin-4-yl]-methanone |
| 170 | 3-Ethyl-6-(4-hydroxy-phenyl)-1H-pyrazolo[3,4-b]pyridine-4-carboxylic acid (3-amino-cyclohexyl)-amide |
| 171 | (2,7-Diaza-spiro[3.5]non-7-yl)-[3-ethyl-6-(4-hydroxy-phenyl)-1H-pyrazolo[3,4-b]pyridin-4-yl]-methanone |
| 172 | (2,7-Diaza-spiro[4.4]non-2-yl)-[3-ethyl-6-(4-hydroxy-phenyl)-1H-pyrazolo[3,4-b]pyridin-4-yl]-methanone |
| 173 | (2,7-Diaza-spiro[4.5]dec-2-yl)-[3-ethyl-6-(4-hydroxy-phenyl)-1H-pyrazolo[3,4-b]pyridin-4-yl]-methanone |
| 174 | 3-Ethyl-6-(4-hydroxy-phenyl)-1H-pyrazolo[3,4-b]pyridine-4-carboxylic acid methyl-(1-methyl-piperidin-4-yl)-amide |
| 175 | 3-Ethyl-6-(4-hydroxy-phenyl)-1H-pyrazolo[3,4-b]pyridine-4-carboxylic acid (1-ethyl-piperidin-3-yl)-amide |
| 176 | ((R)-3-Dimethylamino-pyrrolidin-1-yl)-[3-ethyl-6-(4-hydroxy-phenyl)-1H-pyrazolo[3,4-b]pyridin-4-yl]-methanone |
| 177 | ((S)-3-Dimethylamino-pyrrolidin-1-yl)-[3-ethyl-6-(4-hydroxy-phenyl)-1H-pyrazolo[3,4-b]pyridin-4-yl]-methanone |
| 178 | [3-Ethyl-6-(4-hydroxy-phenyl)-1H-pyrazolo[3,4-b]pyridin-4-yl]-(3-methylamino-pyrrolidin-1-yl)-methanone |
| 179 | [3-Ethyl-6-(4-hydroxy-phenyl)-1H-pyrazolo[3,4-b]pyridin-4-yl]-((1S,5R)-9-hydroxy-1,5,7-trimethyl-3,7-diaza-bicyclo[3.3.1]non-3-yl)-methanone |
| 180 | 3-Ethyl-6-(4-hydroxy-phenyl)-1H-pyrazolo[3,4-b]pyridine-4-carboxylic acid (1-methyl-piperidin-3-yl)-amide |
| 181 | 3-Ethyl-6-(4-hydroxy-phenyl)-1H-pyrazolo[3,4-b]pyridine-4-carboxylic acid (2,3-dihydrospiro[1H-indene-1,4'-piperidin]-3-yl)-amide |
| 182 | 3-Ethyl-6-(4-hydroxy-phenyl)-1H-pyrazolo[3,4-b]pyridine-4-carboxylic acid (1-methyl-piperidin-4-yl)-amide |
| 183 | 3-Ethyl-6-(4-hydroxy-phenyl)-1H-pyrazolo[3,4-b]pyridine-4-carboxylic acid azetidin-3-ylamide |
| 184 | 3-Ethyl-6-(4-hydroxy-phenyl)-1H-pyrazolo[3,4-b]pyridine-4-carboxylic acid (9-methyl-9-aza-bicyclo[3.3.1]non-3-yl)-amide |
| 185 | 3-Ethyl-6-(4-hydroxy-phenyl)-1H-pyrazolo[3,4-b]pyridine-4-carboxylic acid ((R)-6-oxo-piperidin-3-yl)-amide |
| 186 | 3-Ethyl-6-(4-hydroxy-phenyl)-1H-pyrazolo[3,4-b]pyridine-4-carboxylic acid (5-oxo-pyrrolidin-2-ylmethyl)-amide |

| | |
|---|---|
| 187 | (4-Ethyl-[1,4]diazepan-1-yl)-[3-ethyl-6-(4-hydroxy-phenyl)-1H-pyrazolo[3,4-b]pyridin-4-yl]-methanone |
| 188 | [6-(4-Hydroxy-phenyl)-3-methyl-1H-pyrazolo[3,4-b]pyridin-4-yl]-((S)-2-methyl-piperazin-1-yl)-methanone |
| 189 | [6-(4-Hydroxy-phenyl)-3-methyl-1H-pyrazolo[3,4-b]pyridin-4-yl]-((R)-3-methyl-piperazin-1-yl)-methanone |
| 190 | [6-(4-Hydroxy-phenyl)-3-methyl-1H-pyrazolo[3,4-b]pyridin-4-yl]-((S)-3-methyl-piperazin-1-yl)-methanone |
| 191 | 6-(4-Hydroxy-phenyl)-3-methyl-1H-pyrazolo[3,4-b]pyridine-4-carboxylic acid (6-amino-spiro[3.3]hept-2-yl)-amide |
| 192 | (Hexahydro-pyrrolo[3,4-c]pyrrol-2-yl)-[6-(4-hydroxy-phenyl)-3-methyl-1H-pyrazolo[3,4-b]pyridin-4-yl]-methanone |
| 193 | 6-(4-Hydroxy-phenyl)-3-methyl-1H-pyrazolo[3,4-b]pyridine-4-carboxylic acid (2-aza-bicyclo[2.2.1]hept-5-yl)-amide |
| 194 | (2,3-Dimethyl-piperazin-1-yl)-[6-(4-hydroxy-phenyl)-3-methyl-1H-pyrazolo[3,4-b]pyridin-4-yl]-methanone |
| 195 | [6-(4-Hydroxy-phenyl)-3-methyl-1H-pyrazolo[3,4-b]pyridin-4-yl]-((R)-3-propyl-piperazin-1-yl)-methanone |
| 196 | [6-(4-Hydroxy-phenyl)-3-methyl-1H-pyrazolo[3,4-b]pyridin-4-yl]-(3-trifluoromethyl-piperazin-1-yl)-methanone |
| 197 | {1-[6-(4-Hydroxy-phenyl)-3-methyl-1H-pyrazolo[3,4-b]pyridine-4-carbonyl]-piperazin-2-yl}-acetic acid methyl ester |
| 198 | (3,3-Dimethyl-piperazin-1-yl)-[6-(4-hydroxy-phenyl)-3-methyl-1H-pyrazolo[3,4-b]pyridin-4-yl]-methanone |
| 199 | (2,2-Dimethyl-piperazin-1-yl)-[6-(4-hydroxy-phenyl)-3-methyl-1H-pyrazolo[3,4-b]pyridin-4-yl]-methanone |
| 200 | (S)-[6-(4-Hydroxy-phenyl)-3-methyl-1H-pyrazolo[3,4-b]pyridine-4-carboxylic acid (1-aza-bicyclo[2.2.2]oct-3-yl)-amide |
| 201 | 6-(4-Hydroxy-phenyl)-3-methyl-1H-pyrazolo[3,4-b]pyridine-4-carboxylic acid ((3R)-8-methyl-8-aza-bicyclo[3.2.1]oct-3-yl)-amide |
| 202 | [6-(4-Hydroxy-phenyl)-3-methyl-1H-pyrazolo[3,4-b]pyridin-4-yl]-((S)-2-isopropyl-piperazin-1-yl)-methanone |
| 203 | [(R)-3-(1-Amino-cyclopropyl)-pyrrolidin-1-yl]-[6-(4-hydroxy-phenyl)-3-methyl-1H-pyrazolo[3,4-b]pyridin-4-yl]-methanone |
| 204 | 6-(4-Hydroxy-phenyl)-3-methyl-1H-pyrazolo[3,4-b]pyridine-4-carboxylic acid (5-aza-spiro[3.5]non-8-yl)-amide |
| 205 | 6-(4-Hydroxy-phenyl)-3-methyl-1H-pyrazolo[3,4-b]pyridine-4-carboxylic acid [(R)-3-azabicyclo[3.1.0]hexan-1-yl]-amide |
| 206 | (R)-1-[6-(4-Hydroxy-phenyl)-3-methyl-1H-pyrazolo[3,4-b]pyridine-4-carbonyl]-piperazine-2-carboxylic acid methyl ester |
| 207 | 6-(4-Hydroxy-phenyl)-3-methyl-1H-pyrazolo[3,4-b]pyridine-4-carboxylic acid (1-aza-bicyclo[2.2.2]oct-3-yl)-amide |
| 208 | 6-(4-Hydroxy-phenyl)-3-methyl-1H-pyrazolo[3,4-b]pyridine-4-carboxylic acid ((R)-6-oxo-piperidin-3-yl)-amide |
| 209 | ((S)-3-Butyl-piperazin-1-yl)-[6-(4-hydroxy-phenyl)-3-methyl-1H-pyrazolo[3,4-b]pyridin-4-yl]-methanone |
| 210 | ((S)-3-Ethyl-piperazin-1-yl)-[6-(4-hydroxy-phenyl)-3-methyl-1H-pyrazolo[3,4-b]pyridin-4-yl]-methanone |
| 211 | (R)-4-[6-(4-Hydroxy-phenyl)-3-methyl-1H-pyrazolo[3,4-b]pyridine-4-carbonyl]-piperazine-2-carboxylic acid methyl ester |
| 212 | [6-(4-Hydroxy-phenyl)-3-methyl-1H-pyrazolo[3,4-b]pyridin-4-yl]-((R)-3-methoxymethyl-piperazin-1-yl)-methanone |
| 213 | 6-(4-Hydroxy-phenyl)-3-methyl-1H-pyrazolo[3,4-b]pyridine-4-carboxylic acid ((3S,4S)-4-methoxy-pyrrolidin-3-yl)-amide |
| 214 | 6-(4-Hydroxy-phenyl)-3-methyl-1H-pyrazolo[3,4-b]pyridine-4-carboxylic acid (3-azabicyclo[3.1.0]hex-6-yl)-amide |
| 215 | [6-(4-Hydroxy-phenyl)-3-methyl-1H-pyrazolo[3,4-b]pyridin-4-yl]-((S)-3-isobutyl-piperazin-1-yl)-methanone |
| 216 | 6-(4-Hydroxy-phenyl)-3-methyl-1H-pyrazolo[3,4-b]pyridine-4-carboxylic acid (pyrrolidin-3-ylmethyl)-amide |
| 217 | (2-Benzyl-piperazin-1-yl)-[6-(4-hydroxy-phenyl)-3-methyl-1H-pyrazolo[3,4-b]pyridin-4-yl]-methanone |
| 218 | 6-(4-Hydroxy-phenyl)-3-methyl-1H-pyrazolo[3,4-b]pyridine-4-carboxylic acid [2-(1-methyl-pyrrolidin-2-yl)-ethyl]-amide |
| 219 | 6-(4-Hydroxy-phenyl)-3-methyl-1H-pyrazolo[3,4-b]pyridine-4-carboxylic acid (8-methyl-8-aza-bicyclo[3.2.1]oct-3-yl)-amide |
| 220 | 6-(4-Hydroxy-phenyl)-3-methyl-1H-pyrazolo[3,4-b]pyridine-4-carboxylic acid (1-methyl-piperidin-4-yl)-amide |
| 221 | [6-(4-Hydroxy-phenyl)-3-methyl-1H-pyrazolo[3,4-b]pyridin-4-yl]-(3-methyl-piperazin-1-yl)-methanone |
| 222 | 6-(4-Hydroxy-phenyl)-3-methyl-1H-pyrazolo[3,4-b]pyridine-4-carboxylic acid (R)-piperidin-3-ylamide |
| 223 | 6-(4-Hydroxy-phenyl)-3-methyl-1H-pyrazolo[3,4-b]pyridine-4-carboxylic acid (9-methyl-9-aza-bicyclo[3.3.1]non-3-yl)-amide |
| 224 | ((R)-2-Benzyl-piperazin-1-yl)-[6-(4-hydroxy-phenyl)-3-methyl-1H-pyrazolo[3,4-b]pyridin-4-yl]-methanone |
| 225 | ((S)-2-Benzyl-piperazin-1-yl)-[6-(4-hydroxy-phenyl)-3-methyl-1H-pyrazolo[3,4-b]pyridin-4-yl]-methanone |
| 226 | (Hexahydro-pyrrolo[3,4-b]pyrrol-1-yl)-[6-(4-hydroxy-phenyl)-3-methyl-1H-pyrazolo[3,4-b]pyridin-4-yl]-methanone |

-continued

| | |
|---|---|
| 227 | (8-Amino-3-aza-bicyclo[3.2.1]oct-3-yl)-[6-(4-hydroxy-phenyl)-3-methyl-1H-pyrazolo[3,4-b]pyridin-4-yl]-methanone |
| 228 | 6-(4-Hydroxy-phenyl)-3-methyl-1H-pyrazolo[3,4-b]pyridine-4-carboxylic acid (3-aminomethyl-bicyclo[2.2.1]hept-2-yl)-amide |
| 229 | [6-(4-Hydroxy-phenyl)-3-methyl-1H-pyrazolo[3,4-b]pyridin-4-yl]-(cis-4-methyl-3-methylamino-piperidin-1-yl)-methanone |
| 230 | [6-(4-Hydroxy-phenyl)-3-methyl-1H-pyrazolo[3,4-b]pyridin-4-yl]-(octahydro-[1,6]naphthyridin-1-yl)-methanone |
| 231 | 6-(4-Hydroxy-phenyl)-3-methyl-1H-pyrazolo[3,4-b]pyridine-4-carboxylic acid (4-amino-cyclohexyl)-amide |
| 232 | (S)-1-[6-(4-Hydroxy-phenyl)-3-methyl-1H-pyrazolo[3,4-b]pyridine-4-carbonyl]-piperazine-2-carboxylic acid tert-butylamide |
| 233 | [6-(4-Hydroxy-phenyl)-3-methyl-1H-pyrazolo[3,4-b]pyridin-4-yl]-((S)-3-isopropyl-piperazin-1-yl)-methanone |
| 234 | (2,7-Diaza-spiro[3.5]non-2-yl)-[6-(4-hydroxy-phenyl)-3-methyl-1H-pyrazolo[3,4-b]pyridin-4-yl]-methanone |
| 235 | (2,7-Diaza-spiro[4.5]dec-2-yl)-[6-(4-hydroxy-phenyl)-3-methyl-1H-pyrazolo[3,4-b]pyridin-4-yl]-methanone |
| 236 | (3,9-Diaza-spiro[5.5]undec-3-yl)-[6-(4-hydroxy-phenyl)-3-methyl-1H-pyrazolo[3,4-b]pyridin-4-yl]-methanone |
| 237 | 6-(4-Hydroxy-phenyl)-3-methyl-1H-pyrazolo[3,4-b]pyridine-4-carboxylic acid (2,3-dihydro-spiro[1H-indene-1,4'-piperidin]-3-yl)-amide |
| 238 | ((R)-3-Dimethylamino-pyrrolidin-1-yl)-[6-(4-hydroxy-phenyl)-3-methyl-1H-pyrazolo[3,4-b]pyridin-4-yl]-methanone |
| 239 | ((S)-3-Dimethylamino-pyrrolidin-1-yl)-[6-(4-hydroxy-phenyl)-3-methyl-1H-pyrazolo[3,4-b]pyridin-4-yl]-methanone |
| 240 | [6-(4-Hydroxy-phenyl)-3-methyl-1H-pyrazolo[3,4-b]pyridin-4-yl]-(3-methylamino-pyrrolidin-1-yl)-methanone |
| 241 | 6-(4-Hydroxy-phenyl)-3-methyl-1H-pyrazolo[3,4-b]pyridine-4-carboxylic acid methyl-piperidin-4-yl-amide |
| 242 | 6-(4-Hydroxy-phenyl)-3-methyl-1H-pyrazolo[3,4-b]pyridine-4-carboxylic acid piperidin-3-ylamide |
| 243 | 6-(4-Hydroxy-phenyl)-3-methyl-1H-pyrazolo[3,4-b]pyridine-4-carboxylic acid (piperidin-3-ylmethyl)-amide |
| 244 | 6-(4-Hydroxy-phenyl)-3-methyl-1H-pyrazolo[3,4-b]pyridine-4-carboxylic acid (3-methylamino-propyl)-amide |
| 245 | 6-(4-Hydroxy-phenyl)-3-methyl-1H-pyrazolo[3,4-b]pyridine-4-carboxylic acid (piperidin-2-ylmethyl)-amide |
| 246 | ((S)-3-Amino-pyrrolidin-1-yl)-[6-(4-hydroxy-phenyl)-3-methyl-1H-pyrazolo[3,4-b]pyridin-4-yl]-methanone |
| 247 | (3-Amino-azetidin-1-yl)-[6-(4-hydroxy-phenyl)-3-methyl-1H-pyrazolo[3,4-b]pyridin-4-yl]-methanone |
| 248 | 6-(4-Hydroxy-phenyl)-3-methyl-1H-pyrazolo[3,4-b]pyridine-4-carboxylic acid azetidin-3-ylamide |
| 249 | (4-Amino-piperidin-1-yl)-[6-(4-hydroxy-phenyl)-3-methyl-1H-pyrazolo[3,4-b]pyridin-4-yl]-methanone |
| 250 | (3aR,6aS)-Hexahydro-pyrrolo[3,4-c]pyrrol-2-yl-[6-(4-hydroxy-phenyl)-3-methyl-1H-pyrazolo[3,4-b]pyridin-4-yl]-methanone |
| 251 | 6-(4-Hydroxy-phenyl)-3-methyl-1H-pyrazolo[3,4-b]pyridine-4-carboxylic acid (trans-2-amino-cyclopropyl)-amide |
| 252 | 6-(4-Hydroxy-phenyl)-3-methyl-1H-pyrazolo[3,4-b]pyridine-4-carboxylic acid (trans-3-amino-cyclobutyl)-amide |
| 253 | [6-(4-Hydroxy-phenyl)-3-methyl-1H-pyrazolo[3,4-b]pyridin-4-yl]-(6-oxa-2,9-diaza-spiro[4.5]dec-2-yl)-methanone |
| 254 | 6-(4-Hydroxy-phenyl)-3-methyl-1H-pyrazolo[3,4-b]pyridine-4-carboxylic acid (3-amino-cyclohexyl)-amide |
| 255 | (2,7-Diaza-spiro[3.5]non-7-yl)-[6-(4-hydroxy-phenyl)-3-methyl-1H-pyrazolo[3,4-b]pyridin-4-yl]-methanone |
| 256 | (2,7-Diaza-spiro[4.4]non-2-yl)-[6-(4-hydroxy-phenyl)-3-methyl-1H-pyrazolo[3,4-b]pyridin-4-yl]-methanone |
| 257 | (2,8-Diaza-spiro[4.5]dec-8-yl)-[6-(4-hydroxy-phenyl)-3-methyl-1H-pyrazolo[3,4-b]pyridin-4-yl]-methanone |
| 258 | [6-(4-Hydroxy-phenyl)-3-methyl-1H-pyrazolo[3,4-b]pyridin-4-yl]-(1-oxa-4,8-diaza-spiro[5.5]undec-4-yl)-methanone |
| 259 | [6-(4-Hydroxy-phenyl)-3-methyl-1H-pyrazolo[3,4-b]pyridin-4-yl]-(1-oxa-4,9-diaza-spiro[5.5]undec-9-yl)-methanone |
| 260 | (2,8-Diaza-spiro[4.5]dec-2-yl)-[6-(4-hydroxy-phenyl)-3-methyl-1H-pyrazolo[3,4-b]pyridin-4-yl]-methanone |
| 261 | [6-(4-Hydroxy-phenyl)-3-methyl-1H-pyrazolo[3,4-b]pyridin-4-yl]-(1-oxa-4,9-diaza-spiro[5.5]undec-4-yl)-methanone |
| 262 | [6-(4-Hydroxy-phenyl)-3-methyl-1H-pyrazolo[3,4-b]pyridin-4-yl]-(1-oxa-4,8-diaza-spiro[5.5]undec-8-yl)-methanone |
| 263 | (2,7-Diaza-spiro[4.5]dec-7-yl)-[6-(4-hydroxy-phenyl)-3-methyl-1H-pyrazolo[3,4-b]pyridin-4-yl]-methanone |
| 264 | (3-Amino-pyrrolidin-1-yl)-[6-(4-hydroxy-phenyl)-3-methyl-1H-pyrazolo[3,4-b]pyridin-4-yl]-methanone |
| 265 | 1-{4-[6-(4-Hydroxy-phenyl)-3-methyl-1H-pyrazolo[3,4-b]pyridine-4-carbonyl]-piperazin-1-yl}-ethanone |
| 266 | 2-[6-(4-Hydroxy-phenyl)-3-methyl-1H-pyrazolo[3,4-b]pyridine-4-carbonyl]-octahydro-pyrido[1,2-a]pyrazin-4-one |

| | |
|---|---|
| 267 | [6-(4-Hydroxy-phenyl)-3-methyl-1H-pyrazolo[3,4-b]pyridin-4-yl]-[4-(4-methyl-benzoyl)-piperazin-1-yl]-methanone |
| 268 | (5-Ethyl-2,5-diaza-bicyclo[2.2.1]hept-2-yl)-[6-(4-hydroxy-phenyl)-3-methyl-1H-pyrazolo[3,4-b]pyridin-4-yl]-methanone |
| 269 | [6-(4-Hydroxy-phenyl)-3-methyl-1H-pyrazolo[3,4-b]pyridin-4-yl]-(4-methyl-[1,4]diazepan-1-yl)-methanone |
| 270 | 6-(4-Hydroxy-phenyl)-3-methyl-1H-pyrazolo[3,4-b]pyridine-4-carboxylic acid (3-amino-2,2-dimethyl-propyl)-amide |
| 271 | [6-(4-Hydroxy-phenyl)-3-methyl-1H-pyrazolo[3,4-b]pyridin-4-yl]-[4-(2-methanesulfonyl-ethyl)-piperazin-1-yl]-methanone |
| 272 | 6-(4-Hydroxy-phenyl)-3-methyl-1H-pyrazolo[3,4-b]pyridine-4-carboxylic acid methyl-(1-methyl-piperidin-4-yl)-amide |
| 273 | 6-(4-Hydroxy-phenyl)-3-methyl-1H-pyrazolo[3,4-b]pyridine-4-carboxylic acid (1-ethyl-piperidin-3-yl)-amide |
| 274 | [6-(4-Hydroxy-phenyl)-3-methyl-1H-pyrazolo[3,4-b]pyridin-4-yl]-((1S,5R)-9-hydroxy-1,5,7-trimethyl-3,7-diaza-bicyclo[3.3.1]non-3-yl)-methanone |
| 275 | 6-(4-Hydroxy-phenyl)-3-methyl-1H-pyrazolo[3,4-b]pyridine-4-carboxylic acid (1-methyl-piperidin-3-yl)-amide |
| 276 | 6-(4-Hydroxy-phenyl)-3-methyl-1H-pyrazolo[3,4-b]pyridine-4-carboxylic acid (1,2,2,6,6-pentamethyl-piperidin-4-yl)-amide |
| 277 | 6-(4-Hydroxy-phenyl)-3-methyl-1H-pyrazolo[3,4-b]pyridine-4-carboxylic acid (1-acetyl-piperidin-4-yl)-amide |
| 278 | 6-(4-Hydroxy-phenyl)-3-methyl-1H-pyrazolo[3,4-b]pyridine-4-carboxylic acid (5-oxo-pyrrolidin-2-ylmethyl)-amide |
| 279 | 6-(4-Hydroxy-phenyl)-3-methyl-1H-pyrazolo[3,4-b]pyridine-4-carboxylic acid (1-cyclohexyl-piperidin-4-yl)-amide |
| 280 | [6-(4-Hydroxy-phenyl)-3-methyl-1H-pyrazolo[3,4-b]pyridin-4-yl]-[4-(tetrahydro-furan-2-carbonyl)-piperazin-1-yl]-methanone |
| 281 | (4-Ethyl-[1,4]diazepan-1-yl)-[6-(4-hydroxy-phenyl)-3-methyl-1H-pyrazolo[3,4-b]pyridin-4-yl]-methanone |
| 282 | [6-(4-Hydroxy-phenyl)-3-methyl-1H-pyrazolo[3,4-b]pyridin-4-yl]-(3-phenyl-hexahydro-pyrrolo[1,2-a]pyrazin-2-yl)-methanone |
| 283 | 4-Amino-1-[6-(4-hydroxy-phenyl)-3-methyl-1H-pyrazolo[3,4-b]pyridine-4-carbonyl]-piperidine-4-carboxylic acid methyl ester |
| 284 | [6-(4-Hydroxy-phenyl)-3-methyl-1H-pyrazolo[3,4-b]pyridin-4-yl]-(3-methyl-hexahydro-pyrrolo[1,2-a]pyrazin-2-yl)-methanone |
| 285 | [6-(4-Hydroxy-phenyl)-3-methyl-1H-pyrazolo[3,4-b]pyridin-4-yl]-(3-methyl-octahydro-pyrido[1,2-a]pyrazin-2-yl)-methanone |
| 286 | 6-(4-Hydroxy-phenyl)-3-methyl-1H-pyrazolo[3,4-b]pyridine-4-carboxylic acid (2-methyl-2-pyridin-2-yl-3-pyrrolidin-1-yl-propyl)-amide |
| 287 | [6-(4-Hydroxy-phenyl)-3-methyl-1H-pyrazolo[3,4-b]pyridin-4-yl]-(4-piperidin-1-ylmethyl-piperidin-1-yl)-methanone |
| 288 | 6-(3-Fluoro-4-hydroxy-phenyl)-3-methyl-1H-pyrazolo[3,4-b]pyridine-4-carboxylic acid (6-amino-spiro[3.3]hept-2-yl)-amide |
| 289 | [6-(3-Fluoro-4-hydroxy-phenyl)-3-methyl-1H-pyrazolo[3,4-b]pyridin-4-yl]-(hexahydro-pyrrolo[3,4-c]pyrrol-2-yl)-methanone |
| 290 | [6-(3-Fluoro-4-hydroxy-phenyl)-3-methyl-1H-pyrazolo[3,4-b]pyridin-4-yl]-((S)-3-methyl-piperazin-1-yl)-methanone |
| 291 | [6-(3-Fluoro-4-hydroxy-phenyl)-3-methyl-1H-pyrazolo[3,4-b]pyridin-4-yl]-((R)-3-propyl-piperazin-1-yl)-methanone |
| 292 | ((S)-3-Amino-pyrrolidin-1-yl)-[6-(3-fluoro-4-hydroxy-phenyl)-3-methyl-1H-pyrazolo[3,4-b]pyridin-4-yl]-methanone |
| 293 | [6-(3-Fluoro-4-hydroxy-phenyl)-3-methyl-1H-pyrazolo[3,4-b]pyridin-4-yl]-((S)-3-propyl-piperazin-1-yl)-methanone |
| 294 | ((S)-3-Butyl-piperazin-1-yl)-[6-(3-fluoro-4-hydroxy-phenyl)-3-methyl-1H-pyrazolo[3,4-b]pyridin-4-yl]-methanone |
| 295 | ((S)-3-Ethyl-piperazin-1-yl)-[6-(3-fluoro-4-hydroxy-phenyl)-3-methyl-1H-pyrazolo[3,4-b]pyridin-4-yl]-methanone |
| 296 | (6,6-Dioxo-octahydro-6lambda6-thieno[3,4-b]pyrazin-1-yl)-[6-(3-fluoro-4-hydroxy-phenyl)-3-methyl-1H-pyrazolo[3,4-b]pyridin-4-yl]-methanone |
| 297 | (R)-4-[6-(3-Fluoro-4-hydroxy-phenyl)-3-methyl-1H-pyrazolo[3,4-b]pyridine-4-carbonyl]-piperazine-2-carboxylic acid methyl ester |
| 298 | [6-(3-Fluoro-4-hydroxy-phenyl)-3-methyl-1H-pyrazolo[3,4-b]pyridin-4-yl]-((R)-3-methoxymethyl-piperazin-1-yl)-methanone |
| 299 | 6-(3-Fluoro-4-hydroxy-phenyl)-3-methyl-1H-pyrazolo[3,4-b]pyridine-4-carboxylic acid (2,3-dihydro-spiro[1H-indene-1,4'-piperidin]-3-yl)-amide |
| 300 | (2-Benzyl-piperazin-1-yl)-[6-(3-fluoro-4-hydroxy-phenyl)-3-methyl-1H-pyrazolo[3,4-b]pyridin-4-yl]-methanone |
| 301 | 6-(3-Fluoro-4-hydroxy-phenyl)-3-methyl-1H-pyrazolo[3,4-b]pyridine-4-carboxylic acid (8-methyl-8-aza-bicyclo[3.2.1]oct-3-yl)-amide |
| 302 | 6-(3-Fluoro-4-hydroxy-phenyl)-3-methyl-1H-pyrazolo[3,4-b]pyridine-4-carboxylic acid azetidin-3-ylamide |
| 303 | [6-(3-Fluoro-4-hydroxy-phenyl)-3-methyl-1H-pyrazolo[3,4-b]pyridin-4-yl]-(3-methyl-piperazin-1-yl)-methanone |
| 304 | (4-Amino-piperidin-1-yl)-[6-(3-fluoro-4-hydroxy-phenyl)-3-methyl-1H-pyrazolo[3,4-b]pyridin-4-yl]-methanone |
| 305 | 6-(3-Fluoro-4-hydroxy-phenyl)-3-methyl-1H-pyrazolo[3,4-b]pyridine-4-carboxylic acid (R)-piperidin-3-ylamide |
| 306 | [6-(3-Fluoro-4-hydroxy-phenyl)-3-methyl-1H-pyrazolo[3,4-b]pyridin-4-yl]-(3aR,6aS)-hexahydro-pyrrolo[3,4-c]pyrrol-2-yl-methanone |

| | |
|---|---|
| 307 | 6-(3-Fluoro-4-hydroxy-phenyl)-3-methyl-1H-pyrazolo[3,4-b]pyridine-4-carboxylic acid (trans-2-amino-cyclopropyl)-amide |
| 308 | [6-(3-Fluoro-4-hydroxy-phenyl)-3-methyl-1H-pyrazolo[3,4-b]pyridin-4-yl]-(hexahydro-pyrrolo[3,4-b]pyrrol-1-yl)-methanone |
| 309 | 6-(3-Fluoro-4-hydroxy-phenyl)-3-methyl-1H-pyrazolo[3,4-b]pyridine-4-carboxylic acid (trans-3-amino-cyclobutyl)-amide |
| 310 | (8-Amino-3-aza-bicyclo[3.2.1]oct-3-yl)-[6-(3-fluoro-4-hydroxy-phenyl)-3-methyl-1H-pyrazolo[3,4-b]pyridin-4-yl]-methanone |
| 311 | 6-(3-Fluoro-4-hydroxy-phenyl)-3-methyl-1H-pyrazolo[3,4-b]pyridine-4-carboxylic acid (3-aminomethyl-bicyclo[2.2.1]hept-2-yl)-amide |
| 312 | [6-(3-Fluoro-4-hydroxy-phenyl)-3-methyl-1H-pyrazolo[3,4-b]pyridin-4-yl]-(cis-4-methyl-3-methylamino-piperidin-1-yl)-methanone |
| 313 | [6-(3-Fluoro-4-hydroxy-phenyl)-3-methyl-1H-pyrazolo[3,4-b]pyridin-4-yl]-((S)-2-methyl-piperazin-1-yl)-methanone |
| 314 | [6-(3-Fluoro-4-hydroxy-phenyl)-3-methyl-1H-pyrazolo[3,4-b]pyridin-4-yl]-(3-trifluoromethyl-piperazin-1-yl)-methanone |
| 315 | (3-Amino-azetidin-1-yl)-[6-(3-fluoro-4-hydroxy-phenyl)-3-methyl-1H-pyrazolo[3,4-b]pyridin-4-yl]-methanone |
| 316 | 6-(3-Fluoro-4-hydroxy-phenyl)-3-methyl-1H-pyrazolo[3,4-b]pyridine-4-carboxylic acid [2-(1-methyl-pyrrolidin-2-yl)-ethyl]-amide |
| 317 | (S)-6-(3-Fluoro-4-hydroxy-phenyl)-3-methyl-1H-pyrazolo[3,4-b]pyridine-4-carboxylic acid (1-aza-bicyclo[2.2.2]oct-3-yl)-amide |
| 318 | 6-(3-Fluoro-4-hydroxy-phenyl)-3-methyl-1H-pyrazolo[3,4-b]pyridine-4-carboxylic acid (3R)-8-methyl-8-aza-bicyclo[3.2.1]oct-3-yl)-amide |
| 319 | 6-(3-Fluoro-4-hydroxy-phenyl)-3-methyl-1H-pyrazolo[3,4-b]pyridine-4-carboxylic acid (1-methyl-piperidin-4-yl)-amide |
| 320 | [6-(3-Fluoro-4-hydroxy-phenyl)-3-methyl-1H-pyrazolo[3,4-b]pyridin-4-yl]-((S)-2-isopropyl-piperazin-1-yl)-methanone |
| 321 | ((R)-2-Benzyl-piperazin-1-yl)-[6-(3-fluoro-4-hydroxy-phenyl)-3-methyl-1H-pyrazolo[3,4-b]pyridin-4-yl]-methanone |
| 322 | [(R)-3-(1-Amino-cyclopropyl)-pyrrolidin-1-yl]-[6-(3-fluoro-4-hydroxy-phenyl)-3-methyl-1H-pyrazolo[3,4-b]pyridin-4-yl]-methanone |
| 323 | [6-(3-Fluoro-4-hydroxy-phenyl)-3-methyl-1H-pyrazolo[3,4-b]pyridin-4-yl]-(6-oxa-2,9-diaza-spiro[4.5]dec-2-yl)-methanone |
| 324 | [6-(3-Fluoro-4-hydroxy-phenyl)-3-methyl-1H-pyrazolo[3,4-b]pyridin-4-yl]-(octahydro-[1,6]naphthyridin-1-yl)-methanone |
| 325 | (S)-1-[6-(3-Fluoro-4-hydroxy-phenyl)-3-methyl-1H-pyrazolo[3,4-b]pyridine-4-carbonyl]-piperazine-2-carboxylic acid tert-butylamide |
| 326 | [6-(3-Fluoro-4-hydroxy-phenyl)-3-methyl-1H-pyrazolo[3,4-b]pyridin-4-yl]-((S)-3-isopropyl-piperazin-1-yl)-methanone |
| 327 | [6-(3-Fluoro-4-hydroxy-phenyl)-3-methyl-1H-pyrazolo[3,4-b]pyridin-4-yl]-(2-pyridin-3-yl-piperazin-1-yl)-methanone |
| 328 | (R)-1-[6-(3-Fluoro-4-hydroxy-phenyl)-3-methyl-1H-pyrazolo[3,4-b]pyridine-4-carbonyl]-piperazine-2-carboxylic acid methyl ester |
| 329 | (2,7-Diaza-spiro[3.5]non-7-yl)-[6-(3-fluoro-4-hydroxy-phenyl)-3-methyl-1H-pyrazolo[3,4-b]pyridin-4-yl]-methanone |
| 330 | (1,2-Dihydro-5-spiro[3H-indole-3,4'-piperidin]-1-yl)-[6-(3-fluoro-4-hydroxy-phenyl)-3-methyl-1H-pyrazolo[3,4-b]pyridin-4-yl]-methanone |
| 331 | 6-(3-Fluoro-4-hydroxy-phenyl)-3-methyl-1H-pyrazolo[3,4-b]pyridine-4-carboxylic acid methyl-(1-methyl-piperidin-4-yl)-amide |
| 332 | 6-(3-Fluoro-4-hydroxy-phenyl)-3-methyl-1H-pyrazolo[3,4-b]pyridine-4-carboxylic acid (1-ethyl-piperidin-3-yl)-amide |
| 333 | 6-(3-Fluoro-4-hydroxy-phenyl)-3-methyl-1H-pyrazolo[3,4-b]pyridine-4-carboxylic acid (1-aza-bicyclo[2.2.2]oct-3-yl)-amide |
| 334 | [6-(3-Fluoro-4-hydroxy-phenyl)-3-methyl-1H-pyrazolo[3,4-b]pyridin-4-yl]-((1S,5R)-9-hydroxy-1,5,7-trimethyl-3,7-diaza-bicyclo[3.3.1]non-3-yl)-methanone |
| 335 | 6-(3-Fluoro-4-hydroxy-phenyl)-3-methyl-1H-pyrazolo[3,4-b]pyridine-4-carboxylic acid methyl-piperidin-4-yl-amide |
| 336 | (3-Amino-pyrrolidin-1-yl)-[6-(3-fluoro-4-hydroxy-phenyl)-3-methyl-1H-pyrazolo[3,4-b]pyridin-4-yl]-methanone |
| 337 | [6-(3-Fluoro-4-hydroxy-phenyl)-3-methyl-1H-pyrazolo[3,4-b]pyridin-4-yl]-((R)-3-methyl-piperazin-1-yl)-methanone |
| 338 | 6-(3-Fluoro-4-hydroxy-phenyl)-3-methyl-1H-pyrazolo[3,4-b]pyridine-4-carboxylic acid (4-amino-cyclohexyl)-amide |
| 339 | (2,7-Diaza-spiro[3.5]non-2-yl)-[6-(3-fluoro-4-hydroxy-phenyl)-3-methyl-1H-pyrazolo[3,4-b]pyridin-4-yl]-methanone |
| 340 | (2,7-Diaza-spiro[4.4]non-2-yl)-[6-(3-fluoro-4-hydroxy-phenyl)-3-methyl-1H-pyrazolo[3,4-b]pyridin-4-yl]-methanone |
| 341 | (2,8-Diaza-spiro[4.5]dec-8-yl)-[6-(3-fluoro-4-hydroxy-phenyl)-3-methyl-1H-pyrazolo[3,4-b]pyridin-4-yl]-methanone |
| 342 | [6-(3-Fluoro-4-hydroxy-phenyl)-3-methyl-1H-pyrazolo[3,4-b]pyridin-4-yl]-(1-oxa-4,9-diaza-spiro[5.5]undec-9-yl)-methanone |
| 343 | (2,8-Diaza-spiro[4.5]dec-2-yl)-[6-(3-fluoro-4-hydroxy-phenyl)-3-methyl-1H-pyrazolo[3,4-b]pyridin-4-yl]-methanone |
| 344 | [6-(3-Fluoro-4-hydroxy-phenyl)-3-methyl-1H-pyrazolo[3,4-b]pyridin-4-yl]-(1-oxa-4,9-diaza-spiro[5.5]undec-4-yl)-methanone |
| 345 | [6-(3-Fluoro-4-hydroxy-phenyl)-3-methyl-1H-pyrazolo[3,4-b]pyridin-4-yl]-(1-oxa-4,8-diaza-spiro[5.5]undec-8-yl)-methanone |

-continued 346  (2,7-Diaza-spiro[4.5]dec-7-yl)-[6-(3-fluoro-4-hydroxy-phenyl)-3-methyl-1H-pyrazolo[3,4-b]pyridin-4-yl]-methanone
347  ((R)-3-Dimethylamino-pyrrolidin-1-yl)-[6-(3-fluoro-4-hydroxy-phenyl)-3-methyl-1H-pyrazolo[3,4-b]pyridin-4-yl]-methanone
348  ((S)-3-Dimethylamino-pyrrolidin-1-yl)-[6-(3-fluoro-4-hydroxy-phenyl)-3-methyl-1H-pyrazolo[3,4-b]pyridin-4-yl]-methanone
349  6-(3-Fluoro-4-hydroxy-phenyl)-3-methyl-1H-pyrazolo[3,4-b]pyridine-4-carboxylic acid piperidin-3-ylamide
350  6-(3-Fluoro-4-hydroxy-phenyl)-3-methyl-1H-pyrazolo[3,4-b]pyridine-4-carboxylic acid (2-aza-bicyclo[2.2.1]hept-5-yl)-amide
351  [6-(3-Fluoro-4-hydroxy-phenyl)-3-methyl-1H-pyrazolo[3,4-b]pyridin-4-yl]-((S)-3-isobutyl-piperazin-1-yl)-methanone
352  (2,3-Dimethyl-piperazin-1-yl)-[6-(3-fluoro-4-hydroxy-phenyl)-3-methyl-1H-pyrazolo[3,4-b]pyridin-4-yl]-methanone
353  {1-[6-(3-Fluoro-4-hydroxy-phenyl)-3-methyl-1H-pyrazolo[3,4-b]pyridine-4-carbonyl]-piperazin-2-yl}-acetic acid methyl ester
354  6-(3-Fluoro-4-hydroxy-phenyl)-3-methyl-1H-pyrazolo[3,4-b]pyridine-4-carboxylic acid (pyrrolidin-3-ylmethyl)-amide
355  6-(3-Fluoro-4-hydroxy-phenyl)-3-methyl-1H-pyrazolo[3,4-b]pyridine-4-carboxylic acid (1-methyl-piperidin-3-yl)-amide
356  1-{4-[6-(3-Fluoro-4-hydroxy-phenyl)-3-methyl-1H-pyrazolo[3,4-b]pyridine-4-carbonyl]-piperazin-1-yl}-ethanone
357  6-(3-Fluoro-4-hydroxy-phenyl)-3-methyl-1H-pyrazolo[3,4-b]pyridine-4-carboxylic acid (1-acetyl-piperidin-4-yl)-amide
358  (5-Ethyl-2,5-diaza-bicyclo[2.2.1]hept-2-yl)-[6-(3-fluoro-4-hydroxy-phenyl)-3-methyl-1H-pyrazolo[3,4-b]pyridin-4-yl]-methanone
359  6-(3-Fluoro-4-hydroxy-phenyl)-3-methyl-1H-pyrazolo[3,4-b]pyridine-4-carboxylic acid (5-oxo-pyrrolidin-2-ylmethyl)-amide
360  6-(3-Fluoro-4-hydroxy-phenyl)-3-methyl-1H-pyrazolo[3,4-b]pyridine-4-carboxylic acid (1-cyclohexyl-piperidin-4-yl)-amide
361  (R)-6-(3-Fluoro-4-hydroxy-phenyl)-3-methyl-1H-pyrazolo[3,4-b]pyridine-4-carboxylic acid (1-aza-bicyclo[2.2.2]oct-3-yl)-amide
362  6-(3-Fluoro-4-hydroxy-phenyl)-3-methyl-1H-pyrazolo[3,4-b]pyridine-4-carboxylic acid [2-methyl-2-(4-methyl-piperazin-1-yl)-propyl]-amide
363  6-(3-Fluoro-4-hydroxy-phenyl)-3-methyl-1H-pyrazolo[3,4-b]pyridine-4-carboxylic acid (3-amino-2,2-dimethyl-propyl)-amide
364  6-(3-Fluoro-4-hydroxy-phenyl)-3-methyl-1H-pyrazolo[3,4-b]pyridine-4-carboxylic acid (1,2,2,6,6-pentamethyl-piperidin-4-yl)-amide
365  [6-(3-Fluoro-4-hydroxy-phenyl)-3-methyl-1H-pyrazolo[3,4-b]pyridin-4-yl]-(4-methyl-[1,4]diazepan-1-yl)-methanone
366  (4-Ethyl-[1,4]diazepan-1-yl)-[6-(3-fluoro-4-hydroxy-phenyl)-3-methyl-1H-pyrazolo[3,4-b]pyridin-4-yl]-methanone
367  6-(3-Fluoro-4-hydroxy-phenyl)-3-methyl-1H-pyrazolo[3,4-b]pyridine-4-carboxylic acid (piperidin-2-ylmethyl)-amide
368  4-[6-(3-Fluoro-4-hydroxy-phenyl)-3-methyl-1H-pyrazolo[3,4-b]pyridine-4-carbonyl]-6-isopropyl-piperazin-2-one
369  [6-(3-Fluoro-4-hydroxy-phenyl)-3-methyl-1H-pyrazolo[3,4-b]pyridin-4-yl]-(3-phenyl-hexahydro-pyrrolo[1,2-a]pyrazin-2-yl)-methanone
370  6-(3-Fluoro-4-hydroxy-phenyl)-3-methyl-1H-pyrazolo[3,4-b]pyridine-4-carboxylic acid (2-pyridin-2-yl-2-pyrrolidin-1-yl-propyl)-amide
371  6-(3-Fluoro-4-hydroxy-phenyl)-3-methyl-1H-pyrazolo[3,4-b]pyridine-4-carboxylic acid (2-methyl-2-pyridin-2-yl-3-pyrrolidin-1-yl-propyl)-amide
372  [6-(4-Hydroxy-phenyl)-3-methyl-1H-pyrazolo[3,4-b]pyridin-4-yl]-(4-methyl-2-phenyl-piperazin-1-yl)-methanone
376  6-(4-Hydroxy-phenyl)-3-methyl-1H-pyrazolo[3,4-b]pyridine-4-carboxylic acid [2-dimethylamino-2-(4-methoxy-phenyl)-ethyl]-amide
377  6-(4-Hydroxy-phenyl)-3-methyl-1H-pyrazolo[3,4-b]pyridine-4-carboxylic acid (1-phenyl-2-pyrrolidin-1-yl-ethyl)-amide
378  [2-(4-Chloro-phenyl)-piperazin-1-yl]-[6-(4-hydroxy-phenyl)-3-methyl-1H-pyrazolo[3,4-b]pyridin-4-yl]-methanone
379  {4-[6-(4-Hydroxy-phenyl)-3-methyl-1H-pyrazolo[3,4-b]pyridine-4-carbonyl]-piperazin-1-yl}-pyrrolidin-1-yl-methanone
380  [4-(Furan-3-carbonyl)-piperazin-1-yl]-[6-(4-hydroxy-phenyl)-3-methyl-1H-pyrazolo[3,4-b]pyridin-4-yl]-methanone
381  [6-(4-Hydroxy-phenyl)-3-methyl-1H-pyrazolo[3,4-b]pyridin-4-yl]-[4-(2-methoxy-benzoyl)-piperazin-1-yl]-methanone
382  6-(4-Hydroxy-phenyl)-3-methyl-1H-pyrazolo[3,4-b]pyridine-4-carboxylic acid (1-phenethyl-piperidin-4-yl)-amide
383  (S)-Hexahydro-pyrrolo[1,2-a]pyrazin-2-yl-[6-(4-hydroxy-phenyl)-3-methyl-1H-pyrazolo[3,4-b]pyridin-4-yl]-methanone
384  6-(4-Hydroxy-phenyl)-3-methyl-1H-pyrazolo[3,4-b]pyridine-4-carboxylic acid (1-benzyl-pyrrolidin-3-yl)-amide
385  [6-(4-Hydroxy-phenyl)-3-methyl-1H-pyrazolo[3,4-b]pyridin-4-yl]-(3-phenylamino-pyrrolidin-1-yl)-methanone
386  (5-Benzyl-hexahydro-pyrrolo[3,4-c]pyrrol-2-yl)-[6-(4-hydroxy-phenyl)-3-methyl-1H-pyrazolo[3,4-b]pyridin-4-yl]-methanone
387  [6-(4-Hydroxy-phenyl)-3-methyl-1H-pyrazolo[3,4-b]pyridin-4-yl]-[4-(pyridine-4-carbonyl)-[1,4]diazepan-1-yl]-methanone
388  6-(4-Hydroxy-phenyl)-3-methyl-1H-pyrazolo[3,4-b]pyridine-4-carboxylic acid [2-(3-phenyl-pyrrolidin-1-yl)-ethyl]-amide -continued

| | |
|---|---|
| 389 | 6-(4-Hydroxy-phenyl)-3-methyl-1H-pyrazolo[3,4-b]pyridine-4-carboxylic acid (2-pyrrolidin-1-yl-propyl)-amide |
| 390 | 6-(4-Hydroxy-phenyl)-3-methyl-1H-pyrazolo[3,4-b]pyridine-4-carboxylic acid [2-(4-phenyl-piperidin-1-yl)-ethyl]-amide |
| 391 | 6-(4-Hydroxy-phenyl)-3-methyl-1H-pyrazolo[3,4-b]pyridine-4-carboxylic acid (2-phenyl-2-pyrroiidin-1-yl-ethyl)-amide |
| 392 | 6-(4-Hydroxy-phenyl)-3-methyl-1H-pyrazolo[3,4-b]pyridine-4-carboxylic acid (1-benzyl-piperidin-4-yl)-amide |
| 393 | 6-(4-Hydroxy-phenyl)-3-methyl-1H-pyrazolo[3,4-b]pyridine-4-carboxylic acid (2-phenyl-2-piperazin-1-yl-ethyl)-amide |
| 394 | 6-(4-Hydroxy-phenyl)-3-methyl-1H-pyrazolo[3,4-b]pyridine-4-carboxylic acid (2-morpholin-4-yl-2-phenyl-ethyl)-amide |
| 395 | 6-(4-Hydroxy-phenyl)-3-methyl-1H-pyrazolo[3,4-b]pyridine-4-carboxylic acid (2-piperidin-4-yl-ethyl)-amide |
| 396 | 6-(4-Hydroxy-phenyl)-3-methyl-1H-pyrazolo[3,4-b]pyridine-4-carboxylic acid (4-dimethylamino-cyclohexyl)-amide |
| 397 | [6-(4-Hydroxy-phenyl)-3-trifluoromethyl-1H-pyrazolo[3,4-b]pyridin-4-yl]-((S)-3-methyl-piperazin-1-yl)-methanone |
| 398 | 6-(4-Hydroxy-phenyl)-3-trifluoromethyl-1H-pyrazolo[3,4-b]pyridine-4-carboxylic acid (R)-piperidin-3-ylamide |
| 399 | (4-Amino-piperidin-1-yl)-[6-(4-hydroxy-phenyl)-3-trifluoromethyl-1H-pyrazolo[3,4-b]pyridin-4-yl]-methanone |
| 400 | (Hexahydro-pyrrolo[3,4-c]pyrrol-2-yl)-[6-(4-hydroxy-phenyl)-3-trifluoromethyl-1H-pyrazolo[3,4-b]pyridin-4-yl]-methanone |
| 401 | [6-(4-Hydroxy-phenyl)-3-trifluoromethyl-1H-pyrazolo[3,4-b]pyridin-4-yl]-((R)-3-methyl-piperazin-1-yl)-methanone |
| 402 | 6-(4-Hydroxy-phenyl)-3-trifluoromethyl-1H-pyrazolo[3,4-b]pyridine-4-carboxylic acid azetidin-3-ylamide |
| 403 | (2,7-Diaza-spiro[3.5]non-2-yl)-[6-(4-hydroxy-phenyl)-3-trifluoromethyl-1H-pyrazolo[3,4-b]pyridin-4-yl]-methanone |
| 404 | ((S)-3-Amino-pyrrolidin-1-yl)-[6-(4-hydroxy-phenyl)-3-trifluoromethyl-1H-pyrazolo[3,4-b]pyridin-4-yl]-methanone |
| 405 | (2,7-Diaza-spiro[3.5]non-7-yl)-[6-(4-hydroxy-phenyl)-3-trifluoromethyl-1H-pyrazolo[3,4-b]pyridin-4-yl]-methanone |
| 406 | [6-(4-Hydroxy-phenyl)-3-trifluoromethyl-1H-pyrazolo[3,4-b]pyridin-4-yl]-(3-methylamino-pyrrolidin-1-yl)-methanone |
| 407 | (2,7-Diaza-spiro[4.5]dec-2-yl)-[6-(4-hydroxy-phenyl)-3-trifluoromethyl-1H-pyrazolo[3,4-b]pyridin-4-yl]-methanone |
| 408 | (Hexahydro-pyrrolo[3,4-b]pyrrol-1-yl)-[6-(4-hydroxy-phenyl)-3-trifluoromethyl-1H-pyrazolo[3,4-b]pyridin-4-yl]-methanone |
| 409 | (2,8-Diaza-spiro[4.5]dec-2-yl)-[6-(4-hydroxy-phenyl)-3-trifluoromethyl-1H-pyrazolo[3,4-b]pyridin-4-yl]-methanone |
| 410 | (2,8-Diaza-spiro[4.5]dec-8-yl)-[6-(4-hydroxy-phenyl)-3-trifluoromethyl-1H-pyrazolo[3,4-b]pyridin-4-yl]-methanone |
| 411 | (3,9-Diaza-spiro[5.5]undec-3-yl)-[6-(4-hydroxy-phenyl)-3-trifluoromethyl-1H-pyrazolo[3,4-b]pyridin-4-yl]-methanone |
| 412 | 6-(4-Hydroxy-phenyl)-3-trifluoromethyl-1H-pyrazolo[3,4-b]pyridine-4-carboxylic acid [(S)-1-aza-bicyclo[2.2.2]oct-3-yl]-amide |
| 413 | 6-(4-Hydroxy-phenyl)-3-trifluoromethyl-1H-pyrazolo[3,4-b]pyridine-4-carboxylic acid [(R)-1-aza-bicyclo[2.2.2]oct-3-yl]-amide |
| 414 | (4-Ethyl-[1,4]diazepan-1-yl)-[6-(4-hydroxy-phenyl)-3-trifluoromethyl-1H-pyrazolo[3,4-b]pyridin-4-yl]-methanone |
| 415 | (4-Amino-4-phenyl-piperidin-1-yl)-[6-(2-fluoro-4-hydroxy-phenyl)-3-methyl-1H-pyrazolo[3,4-b]pyridin-4-yl]-methanone |
| 416 | (4-Amino-4-ethyl-piperidin-1-yl)-[6-(2-fluoro-4-hydroxy-phenyl)-3-methyl-1H-pyrazolo[3,4-b]pyridin-4-yl]-methanone |
| 417 | 3,8-Diaza-bicyclo[3.2.1]oct-8-yl-[6-(2-fluoro-4-hydroxy-phenyl)-3-methyl-1H-pyrazolo[3,4-b]pyridin-4-yl]-methanone |
| 418 | (4-Amino-4-methyl-piperidin-1-yl)-[6-(2-fluoro-4-hydroxy-phenyl)-3-methyl-1H-pyrazolo[3,4-b]pyridin-4-yl]-methanone |
| 419 | [6-(2-Fluoro-4-hydroxy-phenyl)-3-methyl-1H-pyrazolo[3,4-b]pyridin-4-yl]-(3aR,6aS)-hexahydro-pyrrolo[3,4-c]pyrrol-2-yl-methanone |
| 420 | [6-(2-Fluoro-4-hydroxy-phenyl)-3-methyl-1H-pyrazolo[3,4-b]pyridin-4-yl]-((R)-3-propyl-piperazin-1-yl)-methanone |
| 421 | [6-(2-Fluoro-4-hydroxy-phenyl)-3-methyl-1H-pyrazolo[3,4-b]pyridin-4-yl]-(3-phenyl-piperazin-1-yl)-methanone |
| 422 | [6-(2-Fluoro-4-hydroxy-phenyl)-3-methyl-1H-pyrazolo[3,4-b]pyridin-4-yl]-((S)-3-propyl-piperazin-1-yl)-methanone |
| 423 | (3-Cyclopropyl-piperazin-1-yl)-[6-(2-fluoro-4-hydroxy-phenyl)-3-methyl-1H-pyrazolo[3,4-b]pyridin-4-yl]-methanone |
| 424 | [6-(2-Fluoro-4-hydroxy-phenyl)-3-methyl-1H-pyrazolo[3,4-b]pyridin-4-yl]-((S)-3-methyl-piperazin-1-yl)-methanone |
| 425 | (3,3-Dimethyl-piperazin-1-yl)-[6-(2-fluoro-4-hydroxy-phenyl)-3-methyl-1H-pyrazolo[3,4-b]pyridin-4-yl]-methanone |
| 426 | [6-(2-Fluoro-4-hydroxy-phenyl)-3-methyl-1H-pyrazolo[3,4-b]pyridin-4-yl]-((R)-3-methyl-piperazin-1-yl)-methanone |
| 427 | [6-(2-Fluoro-4-hydroxy-phenyl)-3-methyl-1H-pyrazolo[3,4-b]pyridin-4-yl]-(2,5,5-trimethyl-piperazin-1-yl)-methanone |
| 428 | ((2R,5R)-2,5-Dimethyl-piperazin-1-yl)-[6-(2-fluoro-4-hydroxy-phenyl)-3-methyl-1H-pyrazolo[3,4-b]pyridin-4-yl]-methanone |

-continued

| | |
|---|---|
| 429 | ((2S,5R)-2,5-Dimethyl-piperazin-1-yl)-[6-(2-fluoro-4-hydroxy-phenyl)-3-methyl-1H-pyrazolo[3,4-b]pyridin-4-yl]-methanone |
| 430 | ((2S,5S)-2,5-Dimethyl-piperazin-1-yl)-[6-(2-fluoro-4-hydroxy-phenyl)-3-methyl-1H-pyrazolo[3,4-b]pyridin-4-yl]-methanone |
| 431 | ((S)-2-Ethyl-piperazin-1-yl)-[6-(2-fluoro-4-hydroxy-phenyl)-3-methyl-1H-pyrazolo[3,4-b]pyridin-4-yl]-methanone |
| 432 | (3-Amino-3-trifluoromethyl-pyrrolidin-1-yl)-[6-(2-fluoro-4-hydroxy-phenyl)-3-methyl-1H-pyrazolo[3,4-b]pyridin-4-yl]-methanone |
| 433 | (6,9-Diaza-spiro[4.5]dec-6-yl)-[6-(2-fluoro-4-hydroxy-phenyl)-3-methyl-1H-pyrazolo[3,4-b]pyridin-4-yl]-methanone |
| 434 | [6-(2-Fluoro-4-hydroxy-phenyl)-3-methyl-1H-pyrazolo[3,4-b]pyridin-4-yl]-(2,2,5-trimethyl-piperazin-1-yl)-methanone |
| 435 | [6-(2-Fluoro-4-hydroxy-phenyl)-3-methyl-1H-pyrazolo[3,4-b]pyridin-4-yl]-(2-methyl-2-phenyl-piperazin-1-yl)-methanone |
| 436 | (2,2-Diethyl-piperazin-1-yl)-[6-(2-fluoro-4-hydroxy-phenyl)-3-methyl-1H-pyrazolo[3,4-b]pyridin-4-yl]-methanone |
| 437 | (8,8-Dimethyl-6,9-diaza-spiro[4.5]dec-6-yl)-[6-(2-fluoro-4-hydroxy-phenyl)-3-methyl-1H-pyrazolo[3,4-b]pyridin-4-yl]-methanone |
| 438 | [6-(2-Fluoro-4-hydroxy-phenyl)-3-methyl-1H-pyrazolo[3,4-b]pyridin-4-yl]-(8-methyl-6,9-diaza-spiro[4.5]dec-6-yl)-methanone |
| 439 | (5,8-Diaza-spiro[3.5]non-5-yl)-[6-(2-fluoro-4-hydroxy-phenyl)-3-methyl-1H-pyrazolo[3,4-b]pyridin-4-yl]-methanone |
| 440 | 6-(2-Fluoro-4-hydroxy-phenyl)-3-methyl-1H-pyrazolo[3,4-b]pyridine-4-carboxylic acid (4-phenyl-piperidin-4-yl)-amide |
| 441 | (2,5-Dipropyl-piperazin-1-yl)-[6-(2-fluoro-4-hydroxy-phenyl)-3-methyl-1H-pyrazolo[3,4-b]pyridin-4-yl]-methanone |
| 442 | ((cis)-2,3-Dimethyl-piperazin-1-yl)-[6-(2-fluoro-4-hydroxy-phenyl)-3-methyl-1H-pyrazolo[3,4-b]pyridin-4-yl]-methanone |
| 443 | [6-(2-Fluoro-4-hydroxy-phenyl)-3-methyl-1H-pyrazolo[3,4-b]pyridin-4-yl]-(4aS,8aS)-octahydro-quinoxalin-1-yl-methanone |
| 444 | (2,6-Dimethyl-piperazin-1-yl)-[6-(2-fluoro-4-hydroxy-phenyl)-3-methyl-1H-pyrazolo[3,4-b]pyridin-4-yl]-methanone |
| 445 | (2,5-Diethyl-piperazin-1-yl)-[6-(2-fluoro-4-hydroxy-phenyl)-3-methyl-1H-pyrazolo[3,4-b]pyridin-4-yl]-methanone |
| 446 | ((2S,5R)-5-Ethyl-2-methyl-piperazin-1-yl)-[6-(2-fluoro-4-hydroxy-phenyl)-3-methyl-1H-pyrazolo[3,4-b]pyridin-4-yl]-methanone |
| 447 | [6-(2-Fluoro-4-hydroxy-phenyl)-3-methyl-1H-pyrazolo[3,4-b]pyridin-4-yl]-(trans-2-methyl-5-phenyl-piperazin-1-yl)-methanone |
| 448 | [6-(2-Fluoro-4-hydroxy-phenyl)-3-methyl-1H-pyrazolo[3,4-b]pyridin-4-yl]-((2S,5R)-2-methyl-5-propyl-piperazin-1-yl)-methanone |
| 449 | (2-Ethyl-2,5,5-trimethyl-piperazin-1-yl)-[6-(2-fluoro-4-hydroxy-phenyl)-3-methyl-1H-pyrazolo[3,4-b]pyridin-4-yl]-methanone |
| 450 | (2,2-Diethyl-5,5-dimethyl-piperazin-1-yl)-[6-(2-fluoro-4-hydroxy-phenyl)-3-methyl-1H-pyrazolo[3,4-b]pyridin-4-yl]-methanone |
| 451 | (8,8-Dimethyl-6,9-diaza-spiro[4.5]dec-9-yl)-[6-(2-fluoro-4-hydroxy-phenyl)-3-methyl-1H-pyrazolo[3,4-b]pyridin-4-yl]-methanone |
| 452 | ((2S,5R)-2,5-Dimethyl-4-pyridin-2-ylmethyl-piperazin-1-yl)-[6-(2-fluoro-4-hydroxy-phenyl)-3-methyl-1H-pyrazolo[3,4-b]pyridin-4-yl]-methanone |
| 453 | ((2S,5R)-2,5-Dimethyl-4-piperidin-4-ylmethyl-piperazin-1-yl)-[6-(2-fluoro-4-hydroxy-phenyl)-3-methyl-1H-pyrazolo[3,4-b]pyridin-4-yl]-methanone |
| 454 | [(2S,5R)-2,5-Dimethyl-4-(tetrahydro-pyran-4-ylmethyl)-piperazin-1-yl]-[6-(2-fluoro-4-hydroxy-phenyl)-3-methyl-1H-pyrazolo[3,4-b]pyridin-4-yl]-methanone |
| 455 | [(2S,5R)-2,5-Dimethyl-4-(tetrahydro-furan-3-ylmethyl)-piperazin-1-yl]-[6-(2-fluoro-4-hydroxy-phenyl)-3-methyl-1H-pyrazolo[3,4-b]pyridin-4-yl]-methanone |
| 456 | [6-(4-Hydroxy-phenyl)-3-methyl-1H-pyrazolo[3,4-b]pyridin-4-yl]-((R)-3-phenyl-piperazin-1-yl)-methanone |
| 457 | [6-(4-Hydroxy-phenyl)-3-methyl-1H-pyrazolo[3,4-b]pyridin-4-yl]-((S)-3-phenyl-piperazin-1-yl)-methanone |
| 458 | [6-(4-Hydroxy-phenyl)-3-methyl-1H-pyrazolo[3,4-b]pyridin-4-yl]-((2S,5R)-5-methyl-2-phenyl-piperazin-1-yl)-methanone |
| 459 | [6-(4-Hydroxy-phenyl)-3-methyl-1H-pyrazolo[3,4-b]pyridin-4-yl]-((2R,5S)-5-methyl-2-phenyl-piperazin-1-yl)-methanone |
| 460 | [6-(2-Fluoro-4-hydroxy-phenyl)-3-methyl-1H-pyrazolo[3,4-b]pyridin-4-yl]-((2S,5R)-2-methyl-5-phenyl-piperazin-1-yl)-methanone |
| 461 | [6-(2-Fluoro-4-hydroxy-phenyl)-3-methyl-1H-pyrazolo[3,4-b]pyridin-4-yl]-((2R,5S)-2-methyl-5-phenyl-piperazin-1-yl)-methanone |

Structural elements such as groups, substituents, hetero ring members, numbers or other features, for example alkyl groups, groups like $R^1$, $R^2$, $R^3$ etc., which can occur several times in the compounds of the formula I, can all independently of one another have any of the indicated meanings and can in each case be identical to or different from one another. For example, the alkyl groups in a dialkylamino group can be identical or different.

As used here, the terms "including" and "comprising" are used in their open, non-limiting sense. As used herein, the terms "$(C_1$-$C_8)$" or "$(C_5$-$C_8)$" and so forth, refer to moieties having 1 to 8 or 5 to 8 carbon atoms, respectively. Within terms like "$(C_0$-$C_6)$-alkyl" or "$(C_0$-$C_6)$-alkylen" "$C_0$-alkyl" or "$(C_0)$-alkylen" refer to a bond, or in case of an unsubstituted "$(C_0)$-alkyl" it refers to a hydrogen.

The term "alkyl", as used herein, refers to saturated, monovalent hydrocarbon radicals. The term "alkenyl", as used herein, refers to monovalent hydrocarbon radicals, which contain at least one carbon-carbon double bond, wherein each double bond can have E- or Z-configuration. The term "alkinyl", as used herein, refers to monovalent hydrocarbon radicals, which contain at least one carbon-carbon triple bond. The alkyl, alkenyl and alkynyl groups can be linear, i.e. straight-chain, or branched. This also applies when they are part of other groups, for example alkyloxy groups (=alkoxy groups, O-alkylgroups), alkyloxycarbonyl groups or alkyl-substituted amino groups, or when they are substituted. Depending on the respective definition, the number of carbon atoms in an alkyl group can be 1, 2, 3, 4, 5, 6, 7 or 8, or 1, 2, 3, 4, 5 or 6, or 1, 2, 3 or 4, or 1, 2 or 3. Examples of alkyl are methyl, ethyl, propyl including n-propyl and isopropyl, butyl including n-butyl, sec-butyl, isobutyl and tert-butyl, pentyl including n-pentyl, 1-methylbutyl, isopentyl, neopentyl and tert-pentyl, hexyl including n-hexyl, 3,3-dimethylbutyl and isohexyl, heptyl and octyl. Double bonds and triple bonds in alkenyl groups and alkynyl groups can be present in any positions. In one embodiment of the invention, alkenyl groups contain one double bond and alkynyl groups contain one triple bond. In one embodiment of the invention, an alkenyl group or alkynyl group contains at least three carbon atoms and is bonded to the remainder of the molecule via a carbon atom which is not part of a double bond or triple bond. Examples of alkenyl and alkynyl are ethenyl, prop-1-enyl, prop-2-enyl allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl. Substituted alkyl groups, alkenyl groups and alkynyl groups can be substituted in any positions, provided that the respective compound is sufficiently stable and is suitable for the desired purpose such as use as a drug substance. The prerequisite that a specific group and a compound of the formula I are sufficiently stable and suitable for the desired purpose such as use as a drug substance, applies in general with respect to the definitions of all groups in the compounds of the formula I.

Independently of one another and independently of any other substituents, alkyl groups, divalent alkyl groups, alkenyl groups, alkynyl groups, cycloalkyl groups and heterocycloalkyl groups are optionally substituted by one or more fluorine substituents which can be located in any positions, i.e., the said groups can be unsubstituted by fluorine substituents or substituted by fluorine substituents, for example by 1, 2, 3, 4, 5, 6, 7, 8, 9, 10, 11, 12 or 13, or by 1, 2, 3, 4, 5, 6, 7, 8 or 9, or by 1, 2, 3, 4, 5, 6 or 7, or by 1, 2, 3, 4 or 5, or by 1, 2 or 3, or by 1 or 2, fluorine substituents. Examples of fluorine-substituted said groups are trifluoromethyl, 2-fluoroethyl, 2,2,2-trifluoroethyl, pentafluoroethyl, 3,3,3-trifluoropropyl, 2,2,3,3,3-pentafluoropropyl, 4,4,4-trifluorobutyl, heptafluoroisopropyl, —CHF—, —CF$_2$—, —CF$_2$—CH$_2$—, —CH$_2$—CF$_2$—, —CF$_2$—CF$_2$—, —CF(CH$_3$)—, —C(CF$_3$)$_2$—, —O(CH$_3$)$_2$—CF$_2$—, —CF$_2$—C(CH$_3$)$_2$—, 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Examples of alkyloxy groups in which the alkyl moiety is fluorine-substituted, are trifluoromethoxy, 2,2,2-trifluoroethoxy, pentafluoroethoxy and 3,3,3-trifluoropropoxy.

The term "alkanediyl" or "alkylene", as used herein, refers to saturated, divalent hydrocarbon radicals. The term "alkenediyl", as used herein, refers to divalent hydrocarbon radicals, which contain at least one carbon-carbon double bond, wherein each double bond can have E- or Z-configuration. The term "alkindiyl", as used herein, refers to divalent hydrocarbon carbon radicals, which contain at least one carbon-carbon triple bond. As far as applicable, the preceding explanations regarding alkyl, alkenyl and alkinyl groups apply correspondingly to alkanediyl, alkendiyl and alkindiyl groups, which thus can likewise be linear and branched. Examples of divalent alkyl groups are —CH$_2$— (=methylene), —CH$_2$—CH$_2$—, —CH$_2$—CH$_2$—CH$_2$—, —CH$_2$—CH$_2$—CH$_2$—CH$_2$—, —CH(CH$_3$)—, —C(CH$_3$)$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$—.

The term "cycloalkyl", as used herein, unless otherwise indicated, refers to a monovalent radical of a saturated or partially saturated hydrocarbon ring system, which can be monocyclic, bicyclic or tricyclic, i.e. which can contain one, two or three rings. The bicyclic or tricyclic ring system can be a fused ring system, in which two adjacent rings share two adjacent carbon atoms. The bicyclic or tricyclic ring system can be a spiro ring system or a di-spiro-ringsystem, in which two adjacent rings share a single carbon atom. The tricyclic ring system can also be a bicyclic spiro ring system, to which another ring is fused, that means that the latter ring and the ring in the spiro ring system, to which it is attached, share two adjacent carbon atoms; herein the latter ring can be an aromatic, saturated or partially saturated ring. The bicyclic or tricyclic system can also be a non-fused or bridged ring system, in which two adjacent rings share two non-adjacent carbon atoms. The bicyclic or tricyclic ring can be attached by any ring atom except a spiro- or a bridgehead atom.

In a monocyclic cycloalkyl group the number of ring carbon atoms can be 3, 4, 5, 6, 7 or 8. In one embodiment of the invention, the number of ring carbon atoms in a cycloalkyl group, independently of the number of ring carbon atoms in any other cycloalkyl group, is 3, 4, 5 or 6, in another embodiment 3, 4 or 5, in another embodiment 3 or 4, in another embodiment 3, in another embodiment 5, 6 or 7, in another embodiment 5 or 6, in another embodiment 6 or 7, in another embodiment 5, in another embodiment 6. Examples of cycloalkyl groups are cyclopropyl, cyclobutyl, cyclopentyl, cyclohexyl, cycloheptyl and cyclooctyl.

In a bicyclic cycloalkyl group the number of ring carbon atoms can be 6, 7, 8, 9, 10, 11 or 12. In one embodiment of the invention, the number of ring carbon atoms in a bicyclic cycloalkyl group can be 7, 8, 9, 10 or 11, in another embodiment 8, 9 or 10. In a tricyclic cycloalkyl group the number of ring carbon atoms can be 7, 8, 9, 10, 11, 12, 13, 14 or 15. In one embodiment of the invention, the number of ring carbon atoms in a tricyclic cycloalkyl group can be 10, 11 or 12.

Exemplary bicyclic or tricyclic fused ring cycloalkyls are derived from, but not limited to, the following ring systems: bicyclo[3.1.0]hexane, bicyclo[4.1.0]heptane, bicycle-[5.1.0]octane, bicyclo[3.2.0]heptane, bicyclo[4.2.0]octane, octahydro-pentalene, octahydro-indene, decahydro-azulene, decahydro-naphthalene, decahydro-benzocycloheptene, dodecahydro-heptalene, 1,2,3,3a,4,6a-hexahydro-pentalene, 1,2,3,4-tetrahydro-pentalene, 2,3,3a,4,5,7a-hexahydro-1H-indene, 2,3,3a,4,7,7a-hexahydro-1H-indene, 3a,4,5,6,7,7a-hexahydro-1H-indene, 4,5,6,7-tetrahydro-1H-indene, indane, 1,2,3,4,4a,5,6,8a-octahydro-naphthalene, 1,2,3,4,4a,5,8,8a-octahydro-naphthalene, 1,2,4a,5,8,8a-hexahydro-naphthalene, 1,4,4a,5,8,8a-hexahydro-naphthalene, 1,2,3,4-tetrahydro-naphthalene, 2,3,4,4a,5,6,9,9a-octahydro-1H-benzo-cycloheptene, 2,3,4,4a,5,9a-hexahydro-1H-benzocycloheptene, 4,4a,5,6,7,8,9,9a-octahydro-1H-benzocycloheptene, 6,7,8,9-tetrahydro-5H-benzocycloheptene, 1,2,3,4,5,5a,6,7,8,10a-decahydro-heptalene, dodecahydro-as-indacene and 2,3,3a,4,9,9a-hexahydro-1H-cyclopenta[b]naphthalene:

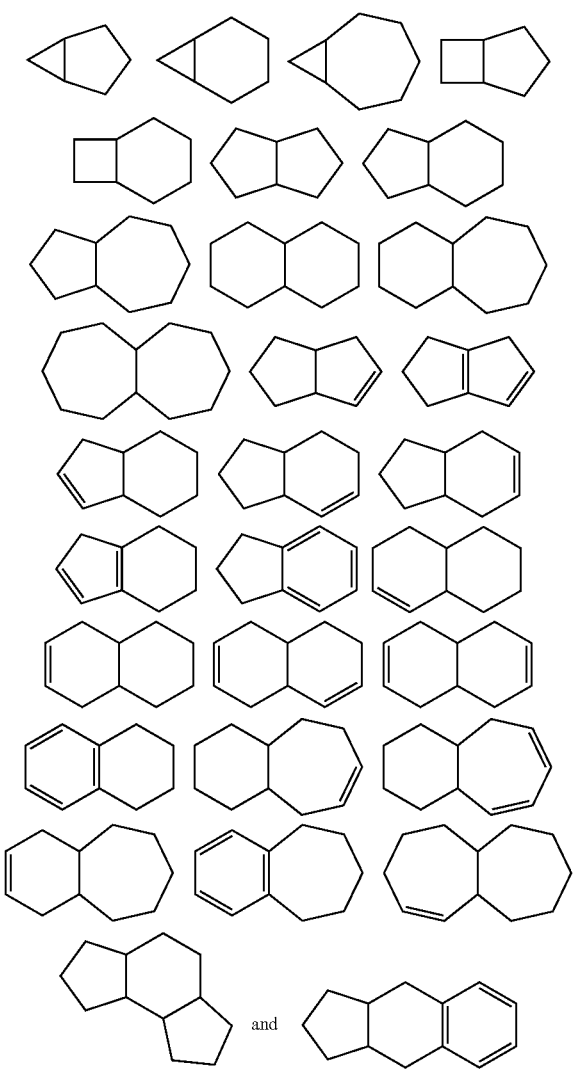

Exemplary bicyclic or tricyclic spiro ring cycloalkyls are derived from, but not limited to, the following ring systems: spiro[2.4]heptane, spiro[2.5]octane, spiro[2.6]nonane, spiro[3.3]heptane, spiro[3.4]octane, spiro[3.5]nonane, spiro[3.6]decane, spiro[4.4]nonane, spiro[4.5]decane, spiro[4.6]undecane, spiro[5.5]undecane, spiro[5.6]dodecane, spiro[6.6]tridecane, dispiro[2.2.4.2]dodecane, dispiro[2.2.3.2]undecane, dispiro[2.1.4.2]undecane and spiro[5.5]undec-2-ene:

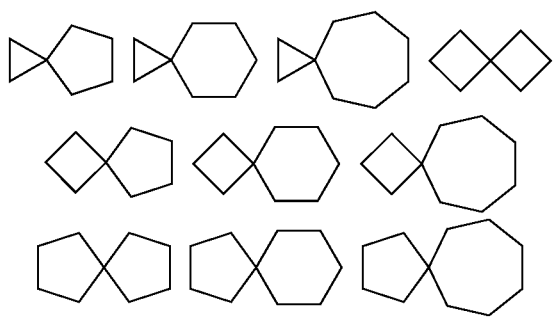

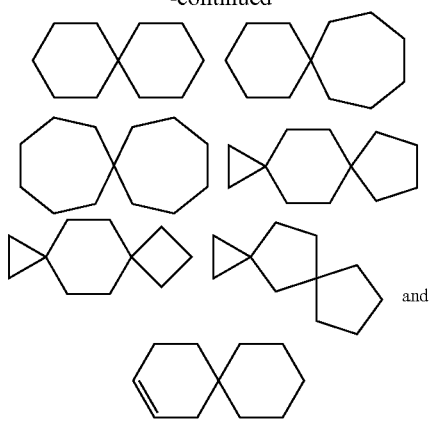

Exemplary cycloalkyls, in which a ring is fused to one ring of a bicyclic spiro system, are derived from, but not limited to, the following ring systems:

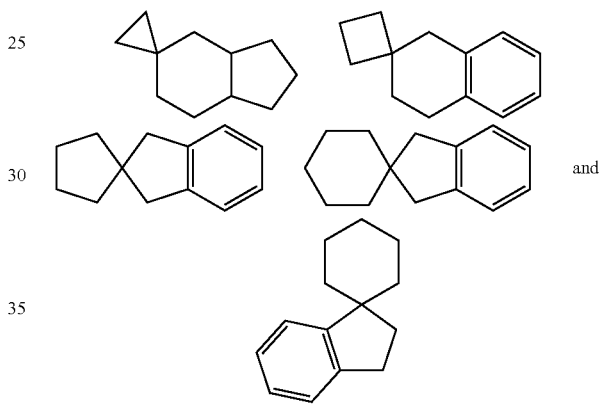

Exemplary non-fused or bridged bicyclic or tricyclic ring cycloalkyls are derived from, but not limited to, the following ring systems: bicyclo[2.2.1]heptane, bicyclo[2.2.2]octane, bicyclo[3.2.1]octane, bicyclo[3.2.2]nonane and adamantane.

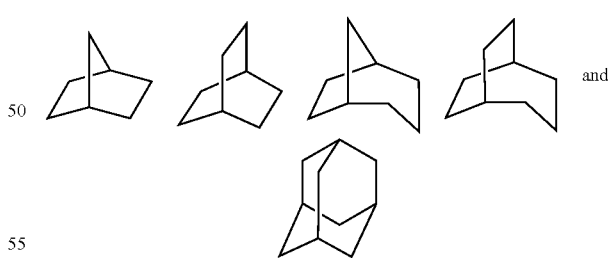

The term "heterocycloalkyl" or "heterocyclyl", as used herein, unless otherwise indicated, refers to a cycloalkyl as defined above, in which 1, 2, 3 or 4 carbon atoms are replaced by nitrogen, oxygen or sulfur atoms, provided that a spiro atom is always a carbon atom and a bridgehead atom is either a carbon or a nitrogen atom and provided that the heterocycloalkyl system is stable and suitable as a subgroup for the desired purpose of the compound of the formula such as use as a drug substance. Depending on the definition of the respective heterocyclic group, in one embodiment of the invention the number of ring heteroatoms which can be present in a heterocyclic group, independently of the number of ring heteroatoms in any other heterocyclic group, is 1, 2, 3 or 4, in another embodiment 1, 2 or 3, in another embodiment 1 or 2, in another embodiment 2, in another embodiment 1, wherein the ring heteroatoms can be identical or different. The heterocycloalkyl group can be attached by any ring carbon atom or saturated ring nitrogen atom, with the exception of spiro- or bridgehead atoms. A ring sulfur atom in a heterocycloalkyl group can carry zero, one or two oxo groups, it is a non-oxidized sulfur atom S in case it does not carry any oxo group, or it is an S(O) group (=sulfoxide group, S-oxide group) in case it carries one oxo group; or it is an $S(O)_2$ group (=sulfone group, S,S-dioxide group) in case it carries two oxo groups.

Exemplary monocyclic heterocycloalkyls are derived from, but not limited to, the following ring systems: aziridine, oxirane, azetidine, oxetane, pyrrolidine, tetrahydrofurane, tetrahydrothiophene, 4,5-dihydrothiazole, piperidine, piperazine, morpholine, thiomorpholine, tetrahydropyran, 1,4-dioxane, 1,4-oxathiane, 1,2,3,6-tetrahydropyridine, azepane, 2,3,4,7-tetrahydro-1H-azepine, 2,7-dihydro-1H-azepine, 1,4-diazepane, 1,4-oxazepane, 1,4-thiazepane and 1,4-dioxepane:

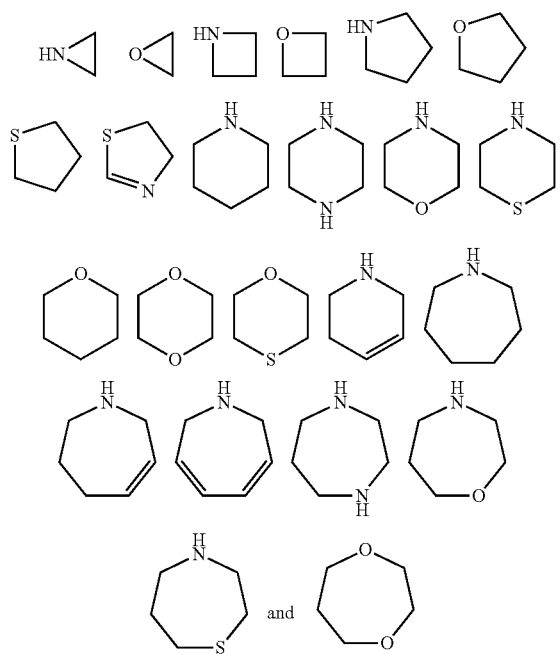

In one embodiment monocyclic heterocycloalkyls are derived from azetidine, pyrrolidine, piperidine, piperazine, morpholine or 1,4-diazepane:

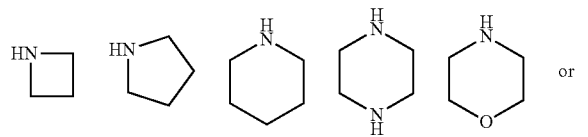

Exemplary bicyclic fused ring heterocycloalkyls are derived from, but not limited to, the following ring systems; 3-aza-bicyclo[3.1.0]hexane, 2-aza-bicyclo[4.1.0]heptane, 2-oxa-5-aza-bicyclo[51.0]octane, 3-aza-bicyclo[3.2.0]heptane, 2-aza-bicyclo[4.2.0]-octane, octahydro-pyrrolo[3,4-c]pyrrole, octahydro-pyrrolo[3,4-b]pyrrole, octahydropyrrolo-[3,4-b]pyridine, octahydro-thieno[3,4-b]pyrazine, octahydro-furo[3,4-b]pyridine, octahydro-cyclopenta[1,4]oxazine, octahydro-pyrrolo[1,2-a]pyrimidine, octahydro-pyrrolo[1,2-a]pyrazine, octahydro-cyclopenta[e][1,4]oxazepine, decahydro-quinoxaline, decahydro-[1,6]naphthyridine, octahydro-benzo[1,4]oxazine, octahydro-benzo[1,4]thiazine, octahydro-pyrido[1,2-a]pyrazine, octahydropyrano-[3,2-b]pyridine, decahydro-1-oxa-9-aza-benzocycloheptene, 1,2,3,3a,6,6a-hexahydro-cyclopenta[b]pyrrole, 5,6-dihydro-4H-cyclopenta[b]thiophene, 2,3,4,4a,7,7a-hexahydro-1H-[2]pyrindine, 2,4a,5,6,7,7a-hexahydro-1H-[1]pyrindine, 2,3,3a,4,7,7a-hexahydro-1H-indole, 1,2,3,4-tetrahydro-quinoxaline, 4,5,6,7-tetrahydro-benzofuran, benzo[1,3]dioxole, 3,4,4a,7,8,8a-hexahydro-2H-benzo[1,4]oxazine, 1,2,3,4,4a,5,8,8a-octahydro-quinoxaline, 4a,5,8,8a-tetrahydro-2H-thiopyrano[3,2-b]pyridine and 1,2,3,4-tetrahydro-[1,5]naphthyridine:

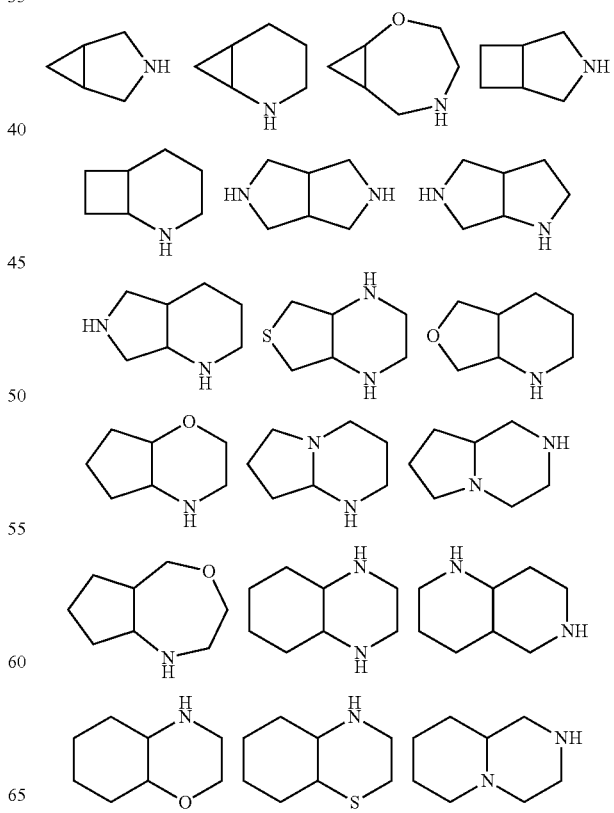

-continued

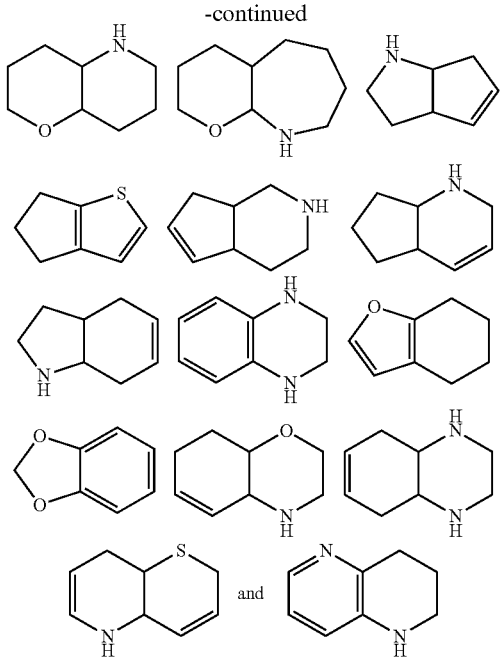

In one embodiment bicyclic fused ring heterocycloalkyls are derived from 3-aza-bicyclo[3.1.0]hexane, octahydro-pyrrolo[3,4-c]pyrrole, octahydro-pyrrolo[3,4-b]pyrrole, octahydro-thieno[3,4-b]pyrazine, octahydro-pyrrolo[1,2-a]pyrazin decahydro-quinoxaline, octahydro-pyrido[1,2-a]pyrazine or decahydro-[1,6]naphthyridine:

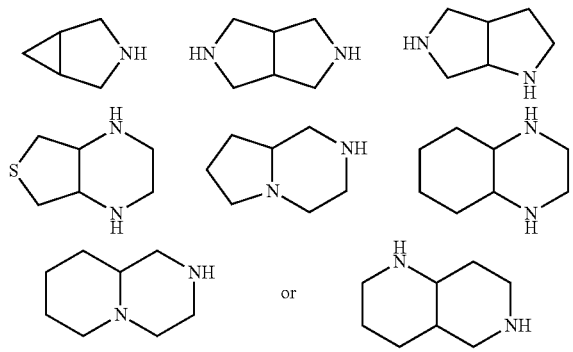

Exemplary bicyclic or tricyclic spiro ring heterocycloalkyls are derived from, but not limited to, the following ring systems: 4-aza-spiro[2.4]heptane, 5-aza-spiro[3.4]-octane, 1-aza-spiro[4,4]nonane, 7-oxa-1-aza-spiro[4.4]nonane, 7-thia-1-aza-spiro[4.4]nonane, 4-aza-spiro[2.5]octane, 5-aza-spiro[2.5]octane, 6-aza-spiro[2.5]-octane, 5-aza-spiro[3.5]nonane, 6-aza-spiro[3.5]nonane, 7-aza-spiro[3.5]nonane, 4,7-diaza-spiro[2.5]octane, 5,8-diaza-spiro[3.5]nonane, 6,9-diaza-spiro[4.5]decane, 1,4-diaza-spiro[5.5]undecane, 2-oxa-6,9-diaza-spiro[4.5]decane, 2-oxa-6-aza-spiro[4.5]decane, 2,7-diaza-spiro[3.5]nonane, 3,9-diaza-spiro[5.5]undecane, 1-oxa-4,9-diaza-spiro[5.5]undecane, 1-oxa-4,8-diaza-spiro[5.5]undecane, 1-thia-4,9-diaza-spiro[5.5]undecane, 1-thia-4,8-diaza-spiro[5.5]undecane, 4,8-diaza-spiro[2.6]nonane, 5,8-diaza-spiro[3.6]decane, 2-aza-spiro[5.5]undec-7-ene, 6,9-diaza-spiro[4.6]undecane, 4-aza-dispiro[2.1.4.2]undecane, 4,10-diaza-dispiro[2.2.3.2]undecane and 4,11-diaza-dispiro[2.2.4.2]dodecane:

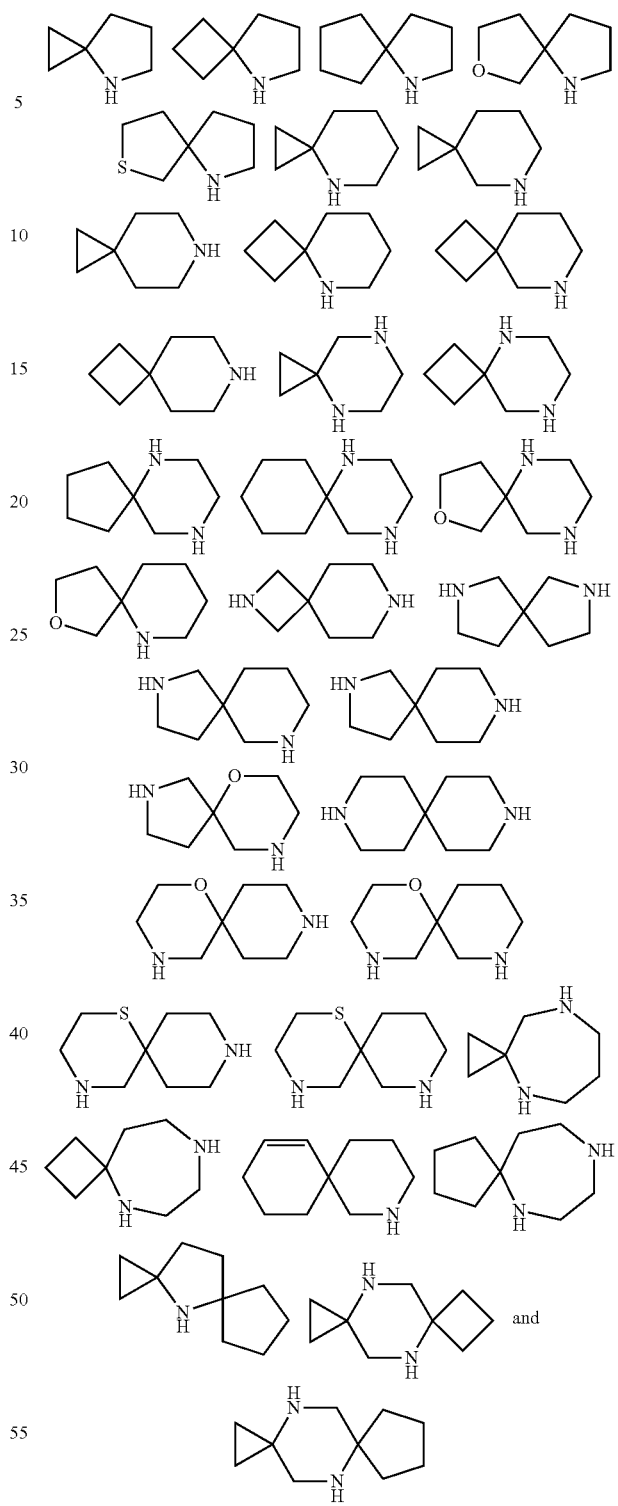

In one embodiment bicyclic or tricyclic spiro ring heterocycloalkyls are derived from 4,7-diaza-spiro[2.5]octane, 6-aza-spiro[3.5]nonane, 5,8-diaza-spiro[3.5]nonane, 6,9-diaza-spiro[4.5]decane, 2,7-diaza-spiro[3,5]nonane, 2,7-diaza-spiro[4.4]nonane, 2,7-diaza-spiro[4.5]decane, 2,8-diaza-spiro[4.5]decane, 6-oxa-2,9-diaza-spiro[4.5]decane, 3,9-diaza-spiro[5.5]undecane, 1-oxa-4,9-diaza-spiro[5.5]undecane or 1-oxa-4,8-diaza-spiro[5,5]undecane:

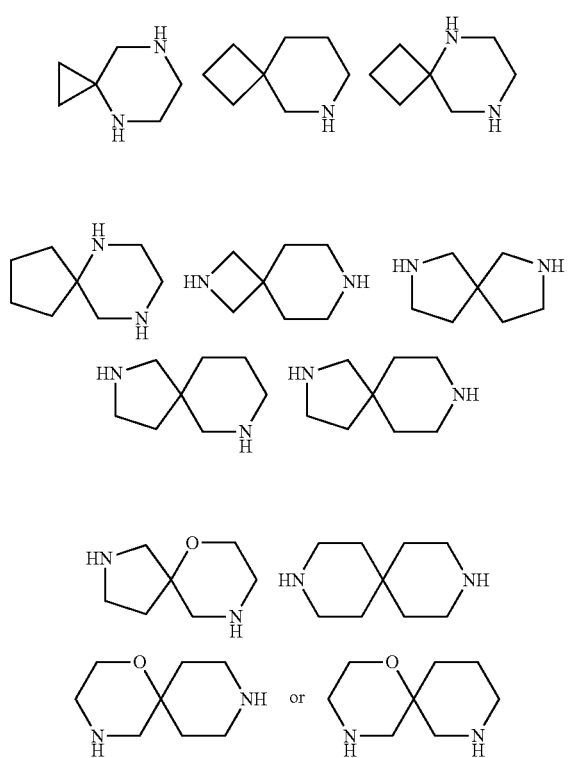

Exemplary heterocycloalkyls, in which a ring is fused to one ring of a bicyclic spiro system, are derived from, but not limited to, the following ring systems: octahydro-spiro[cyclopentane-1,2'(3'H)-quinoxalin], 1',4'-dihydro-spiro[cyclopentane-1,2'(3'H)-quinoxalin], 1',2',4,5-tetrahydro-spiro[furan-3(2H),3'-[3H]-indol], 1,3-dihydro-spiro[indene-2,2'-piperazine], 2,3-dihydro-spiro[1H-indene-1,4'-piperidin] and 1,2-dihydro-5-spiro[3H-indole-3,4'-piperidin]:

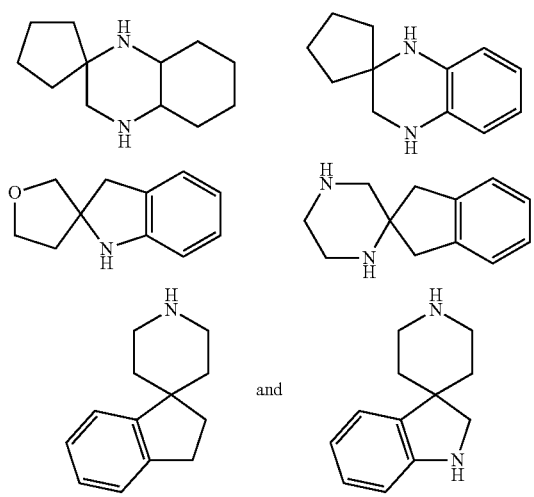

In one embodiment heterocycloalkyls, in which a ring is fused to one ring of a bicyclic spiro system, are derived from 3-dihydro-spiro[indene-2,2'-piperazine], 2,3-dihydro-spiro[1H-indene-1,4'-piperidin] or 1,2-dihydro-5-spiro[3H-indole-3,4'-piperidin]:

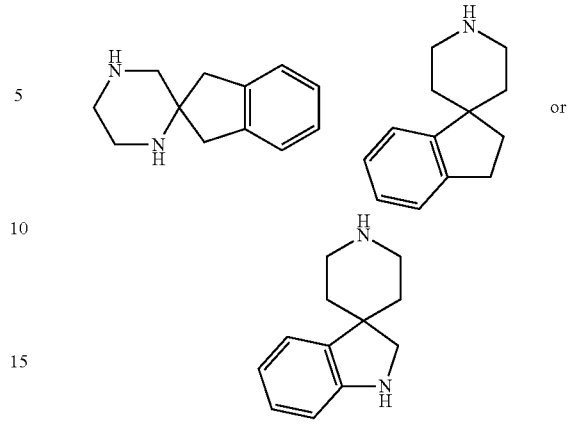

Exemplary non-fused or bridged bicyclic or tricyclic ring heterocycloalkyls are derived from, but not limited to, the following ring systems: 2-aza-bicyclo[2.2.1]heptane, 1-aza-bicyclo[2.2.2]octane, 8-aza-bicyclo[3.2.1]octane, 3-aza-bicyclo[3.2.1]octane, 9-aza-bicyclo[3.3.1]nonane, 2,5-diaza-bicyclo[2.2.1]heptane, 2,5-diaza-bicyclo-[2.2.2]octane, 3,8-diaza-bicyclo[32]octane and 3,7-diaza-bicyclo[3.3.1]nonane:

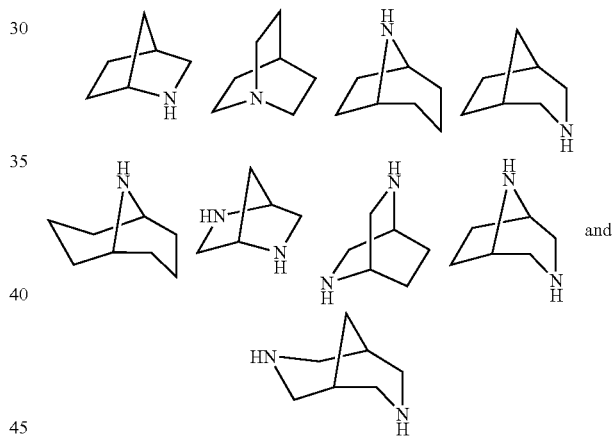

The term "aryl", as used herein, refers to a radical derived from an aromatic hydrocarbon by removal of one hydrogen, such as phenyl or naphthyl naphthalenyl).

The term "heteroaryl" or "hetaryl" as used herein, refers to a radical derived from an aromatic mono- or bicyclic ring system, in which 1, 2, 3, 4 or 5 carbon atoms are replaced by heteroatoms. The ring heteroatoms are generally chosen from N, O and S, wherein N includes ring nitrogen atoms which carry a hydrogen atom or a substituent as well as ring nitrogen atoms which do not carry a hydrogen atom or a substituent. Ring heteroatoms can be located in any position, provided that the heterocyclic system is stable and suitable as a subgroup for the desired purpose of the compound of the formula such as use as a drug substance. Heteroaryl radicals are derived from 5-membered or 6-membered monocyclic rings or 8-membered, 9-membered or 10-membered bicyclic rings, in another embodiment 5-membered or 6-membered monocyclic rings or 9-membered or 10-membered bicyclic rings, in another embodiment 5-membered or 6-membered monocyclic rings.

Exemplary heteroaryl systems are derived from, but not limited to, the following ring systems: pyrrole, furan, thiophene, imidazole, pyrazole, oxazole (=[1,3]oxazole), isoxazole (=[1,2]oxazole), thiazole (=[1,3]thiazole), isothiazole (=[1,2]thiazole), [1,2,3]triazole, [1,2,4]triazole, [1,2,4]oxadiazole, [1,3,4]oxadiazole, [1,2,4]thiadiazole, [1,3,4]thiadiazole, tetrazole, pyridine, pyridazine, pyrimidine, pyrazine, [1,2,3]triazine, [1,2,4]triazine, [1,3,5]triazine, indole, isoindole, benzofuran, benzothiophene [1,3]benzoxazole, [1,3]benzothiazole, benzoimidazole, indazole, quinoline, isoquinoline, cinnoline, quinazoline, quinoxaline, phthalazine, different naphthyridines, [1,8]naphthyridine, different thienopyridines, e.g. thieno[2,3-b]pyridine and purine:

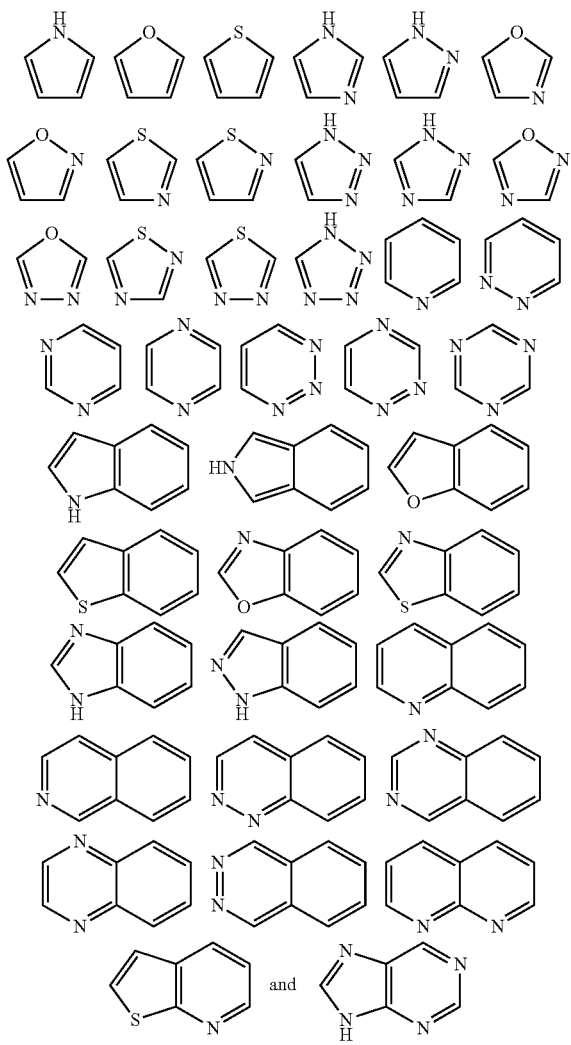

Groups like phenyl, naphthyl (=naphthalenyl) and residues of aromatic heterocycles which are optionally substituted by one or more substituents, can be unsubstituted or substituted, for example by 1, 2, 3, 4 or 5, or by 1, 2, 3 or 4, or by 1, 2 or 3, or by 1 or 2, or by 1, identical or different substituents which can be located in any positions. Aromatic nitrogen heterocycles which in the parent ring system carry a hydrogen atom on a ring nitrogen atom in a 5-membered ring, such as a pyrrole, imidazole, indole or benzoimidazole ring, for example, can be substituted on ring carbon atoms and/or on such ring nitrogen atoms. In one embodiment of the invention, substituents on such ring nitrogen atoms are chosen from $(C_1-C_4)$-alkyl groups, i.e. such ring nitrogen atoms in aromatic heterocycles carry a hydrogen atom or a $(C_1-C_4)$-alkyl substituent. When it is stated with respect to ring nitrogen atoms in aromatic heterocycles and any other heterocycles that they can carry a hydrogen atom or a substituent, such ring nitrogen atoms either carry a hydrogen atom or a substituent or they do not carry a hydrogen atom or substituent. Ring nitrogen atoms which carry a hydrogen atom or a substituent, occur in a nitrogen-containing aromatic 5-membered ring as is present in pyrrole, imidazole, indole or benzoimidazole, for example, and in a non-aromatic ring including a saturated ring. Ring nitrogen atoms which do not carry a hydrogen atom or a substituent unless they are present in positively charged form, including any further ring nitrogen atoms in addition to ring nitrogen atoms which carry a hydrogen atom or a substituent, occur in an aromatic ring as is present in thiazole, imidazole, pyridine or benzoimidazole, for example, and in a non-aromatic ring in which they are part of a double bond, and they occur as ring nitrogen atoms via which a ring is bonded. Suitable ring nitrogen atoms in aromatic heterocycles in the compounds of the formula I, such as the ring nitrogen atom in a pyridine ring or a quinoline ring, can in general also be present as N-oxide or as quaternary salt, for example as N—$(C_1-C_4)$-alkyl salt such as N-methyl salt, wherein in one embodiment of the invention the counter anion in such quaternary salt is a physiologically acceptable anion which is derived from an acid that forms a physiologically acceptable salt.

In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthyl can be 1-naphthyl (=naphthalen-1-yl) or 2-naphthyl (=naphthalen-2-yl). In monosubstituted 1-naphthyl groups, the substituent can be located in the 2-, 3-, 4-, 5-, 6-, 7- or 8-position. In monosubstituted 2-naphthyl groups, the substituent can be located in the 1-, 3-, 4-, 5-, 6-, 7- or 8-position. In disubstituted naphthyl groups, the substituents can likewise be located in any positions both in the ring via which the naphthyl group is bonded and/or in the other ring.

Ring heteroatoms can be located in any positions, provided that the heterocyclic system is known in the art and is stable and suitable as a subgroup for the desired purpose of the compound of the formula I such as use as a drug substance. In one embodiment of the invention, two ring oxygen atoms cannot be present in adjacent ring positions of any heterocycle, in another embodiment two ring heteroatoms chosen from oxygen and sulfur cannot be present in adjacent ring positions of any heterocycle. Substituents on heterocyclic groups can be located in any positions. For example, in a pyridin-2-yl group substituents can be located in the 3-position and/or 4-position and/or 5-position and/or 6-position, in a pyridin-3-yl group substituent can be located in the 2-position and/or 4-position and/or 5-position and/or 6-position, in a pyridin-4-yl group substituents can be located in the 2-position and/or 3-position and/or 5-position and/or 6-position.

Halogen is fluorine, chlorine, bromine or iodine. In one embodiment of the invention, any halogen in a compound of the formula I is independently of any other halogen chosen from fluorine, chlorine and bromine, in another embodiment from fluorine and chlorine, and in yet another embodiment it is fluorine.

When an oxo group is bonded to a carbon atom, it replaces two hydrogen atoms on a carbon atom of the parent system. Thus, if a group in a chain or a ring is substituted by oxo, i.e. by a doubly bonded oxygen atom, it becomes a CO group. Evidently, an oxo group cannot occur as a substituent on a carbon atom in an aromatic ring such as in a phenyl group, for example. When a ring sulfur atom in a heterocyclic group can carry one or two oxo groups, it is a non-oxidized sulfur atom S in case it does not carry any oxo group, or it is an S(O) group (=sulfoxide group, S-oxide group) in case it carries one oxo group, or it is an $S(O)_2$ group (=sulfone group. S,S-dioxide group) in case it carries two oxo groups.

The present invention includes all stereoisomeric forms of the compounds of the formula I and their salts and solvates. With respect to each chiral center, independently of any other chiral center, the compounds of the formula I can be present in S configuration or substantially S configuration, or in R configuration or substantially R configuration, or as a mixture of the S isomer and the R isomer in any ratio. The invention includes all possible enantiomers and diastereomers and mixtures of two or more stereoisomers, for example mixtures of enantiomers and/or diastereomers, in all ratios. Thus, compounds according to the invention which can exist as enantiomers can be present in enantiomerically pure form, both as levorotatory and as dextrorotatory antipodes, and in the form of mixtures of the two enantiomers in all ratios including racemates. In the case of a E/Z isomerism, or cis/trans isomerism, for example on double bonds or rings such as cycloalkyl rings, the invention includes both the E form and Z form, or the cis form and the trans form, as well as mixtures of these forms in all ratios. In one embodiment of the invention, a compound which can occur in two or more stereoisomeric forms is a pure, or substantially pure, individual stereoisomer. The preparation of individual stereoisomers can be carried out, for example, by separation of a mixture of isomers by customary methods, for example by chromatography or crystallization, by the use of stereochemically uniform starting materials in the synthesis, or by stereoselective synthesis. Optionally, a derivatization can be carried out before a separation of stereoisomers. The separation of a mixture of stereoisomers can be carried out at the stage of the compound of the formula I or at the stage of a starting material or an intermediate during the synthesis. The present invention also includes all tautomeric forms of the compounds of the formula I and their salts and solvates.

In case the compounds of the formula I contain one or more acidic and/or basic groups, i.e. salt-forming groups, the invention also includes their corresponding physiologically or toxicologically acceptable salts, i.e. non-toxic salts, in particular their pharmaceutically acceptable salts.

The present invention furthermore includes all solvates of compounds of the formula I, for example hydrates or adducts with alcohols such as ($C_1$-$C_4$)-alkanols, active metabolites of the compounds of the formula I, and also prodrugs and derivatives of the compounds of the formula I which in vitro may not necessarily exhibit pharmacological activity but which in vivo are converted into pharmacologically active compounds, for example esters or amides of carboxylic acid groups.

The compounds of the present invention, PKC inhibitors, can be widely combined with other pharmacologically active compounds, e.g., with all antihypertensives and nephroprotectives, mentioned in the Rote Liste 2011, antidiabetics mentioned in the Rote Liste 2011, chapter 12; all weight-reducing agents/appetite suppressants mentioned in the Rote Liste 2011, chapter 1; all diuretics mentioned in the Rote Liste 2011, chapter 36; all lipid-lowering agents mentioned in the Rote Liste 2011, chapter 58. They can be combined with the inventive compound of the formula especially for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively. Most of the active ingredients mentioned hereinafter are disclosed in the USP Dictionary of USAN and International Drug Names, US Pharmacopeia, Rockville 2006.

Antidiabetics include insulin and insulin derivatives, for example Lantus® (see www.lantus.com) or HMR 1964 or Levemir® (insulin detemir), Humalog® (Insulin Lispro), insulin degludec, insulin aspart, polyethylene glycosidized (PEGylated) Insulin Lispro as described in WO2009152128, Humulin®, VIAject™, SuliXen®, VIAject™ or those as described in WO2005005477 (Novo Nordisk), fast-acting insulins (see U.S. Pat. No. 6,221,633), inhalable insulins, for example Exubera®, Nasulin™ or oral insulins, for example IN-105 (Nobex) or Oral-lyn™ (Generex Biotechnology), or Technosphere® insulin (MannKind) or Cobalamin™ oral insulin or ORMD-0801 or insulins or insulin precursors as described in WO2007128815, WO2007128817, WO2008034881, WO2008049711, WO2008145721, WO2009034117, WO2009060071, WO2009133099 or insulins which can be administered transdermally; additionally included are also those insulin derivatives which are bonded to albumin by a bifunctional linker, as described, for example, in WO2009121884;

GLP-1 derivatives and GLP-1 agonists, for example exenatide or specific formulations thereof, as described, for example, in WO2008061355, WO2009080024, WO2009080032, liraglutide, taspoglutide (R-1583), albiglutide, lixisenatide or those which have been disclosed in WO 98/08871, WO2005027978, WO2006037811, WO2006037810 by Novo Nordisk A/S, in WO 01/04156 by Zealand or in WO 00134331 by Beaufour-Ipsen, pramlintide acetate (Symlin; Amylin Pharmaceuticals), inhalable GLP-1 (MKC-253 from MannKind) AVE-0010, BIM-51077 (R-1583, ITM-077), PC-DAC:exendin-4 (an exendin-4 analog which is bonded covalently to recombinant human albumin), biotinylated exendin (WO2009107900), a specific formulation of exendin-4 as described in US2009238879, CVX-73, CVX-98 and CVx-96 (GLP-1 analogs which are bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists or modulators, as described, for example, in D. Chen et al., Proc. Natl. Acad. Sci, USA 104 (2007) 943, those as described in WO2006124529, WO2007124461, WO2008062457, WO2008082274, WO2008101017, WO2008081418, WO2008112939, WO2008112941, WO2008113601, WO2008116294, WO2008116648, WO2008119238, WO2008148839, US2008299096, WO2008152403, WO2009030738, WO2009030771, WO2009030774, WO2009035540, WO2009058734, WO2009111700, WO2009125424, WO2009129696, WO2009149148, peptides, for example obinepitide (TM-30338), orally active GLP-1 analogs (e.g. NN9924 from Novo Nordisk), amylin receptor agonists, as described, for example, in WO2007104789, WO2009034119, analogs of the human GLP-1, as described in WO2007120899, WO2008022015, WO2008056726, chimeric pegylated peptides containing both GLP-1 and glucagon residues, as described, for example, in WO2008101017, WO2009155257, WO2009155258, glycosylated GLP-1 derivatives as described in WO2009153960, and orally active hypoglycemic ingredients.

Antidiabetics also include gastrin analogs, for example TT-223.

Antidiabetics additionally include poly- or monoclonal antibodies directed, for example, against interleukin 1 beta (IL-1β), for example XOMA-052.

Antidiabetics additionally include peptides which can bind to the human pro-islet peptide (HIP) receptor, as described, for example, in WO2009049222.

Antidiabetics also include agonists of the glucose-dependent insulinotropic polypeptide (GIP) receptor, as described, for example, in WO2006121860.

Antidiabetics also include the glucose-dependent insulinotropic polypeptide (GIP), and also analogous compounds, as described, for example, in WO2008021560, WO2010016935, WO2010016936, WO2010016938, WO2010016940, WO2010016944.

Additionally included are analogs and theivatives of human pancreatic polypeptide, as described, for example, in WO2009007714.

Antidiabetics additionally include encapsulated insulin-producing porcine cells, for example DiabeCell®.

Antidiabetics also include analogs and theivatives of fibroblast growth factor 21 (FGF-21), as described, for example, in WO2009149171, WO2010006214.

The orally active hypoglycemic ingredients preferably include sulfonylureas,
biguanidines,
meglitinides,
oxadiazolidinediones,
thiazolidinediones,
PPAR and RXR modulators,
glucosidase inhibitors,
inhibitors of glycogen phosphorylase,
glucagon receptor antagonists,
glucokinase activators,
inhibitors of fructose 1,6-bisphosphatase,
modulators of glucose transporter 4 (GLUT4),
inhibitors of glutamine:fructose-6-phosphate amidotransferase (GFAT),
GLP-1 agonists,
potassium channel openers, for example pinacidil, cromakalim, diazoxide, diazoxide choline salt, or those as described in R. D. Carr et al., Diabetes 52, 2003, 2513.2518, in J. B. Hansen et al., Current Medicinal Chemistry 11, 2004, 1595-1615, in T. M. Tagmose at al., J. Med. Chem. 47, 2004, 3202-3211 or in M. J. Coghlan at al., J. Med. Chem. 44, 2001, 1627-1653, or those which have been disclosed in WO 97/26265 and WO 99/03861 by Novo Nordisk A/S,
active ingredients which act on the ATP-dependent potassium channel of the beta cells,
inhibitors of dipeptidyl peptidase-IV (DPP-IV),
insulin sensitizers,
inhibitors of liver enzymes involved in stimulating gluconeogenesis and/or
glycogenolysis,
modulators of glucose uptake, of glucose transport and of glucose reabsorption,
modulators of sodium-dependent glucose transporter 1 or 2 (SGLT1, SGLT2),
inhibitors of 11-beta-hydroxysteroid dehydrogenase-1 (11β-HSD1),
inhibitors of protein tyrosine phosphatase-1B (PTP-1B),
nicotinic acid receptor agonists,
inhibitors of hormone-sensitive or endothelial lipases,
inhibitors of acetyl-CoA carboxylase (ACC1 and/or ACC2) or
inhibitors of GSK-3 beta.

Also included are compounds which modify the lipid metabolism, such as active antihyperlipidemic ingredients and active antilipidemic ingredients,
HMG-CoA reductase inhibitors,
farnesoid X receptor (FXR) modulators,
fibrates,
cholesterol reabsorption inhibitors,
CETP inhibitors,
be acid absorption inhibitors,
MTP inhibitors,
estrogen receptor gamma agonists (ERR γ agonists),
sigma-1 receptor antagonists,
antagonists of the somatostatin 5 receptor (SST5 receptor);
compounds which reduce food intake, and
compounds which increase thermogenesis.

In one embodiment of the invention, the compound of the formula I is administered in combination with insulin.

In another embodiment of the invention, the compound of the formula I is administered in combination with an insulin sensitizer, for example PN-2034 or ISIS-113715.

In one embodiment, the compound of the formula I is administered in combination with an active ingredient which acts on the ATP-dependent potassium channel of the beta cells, for example sulfonylureas, for example tolbutamide, glibenclamide, glipizide, gliclazide or glimepiride, or those formulations as described, for example, in EP2103302.

In one embodiment, the compound of the formula I is administered in combination with a tablet which comprises both glimepiride, which is released rapidly, and metformin, which is released over a longer period (as described, for example, in US2007264331, WO2008050987, WO2008062273).

In one embodiment, the compound of the formula I is administered in combination with a biguanide, for example metformin or one of its salts.

In a further embodiment, the compound of the formula I is administered in combination with a guanidine, for example benzylguanidine or one of its salts, or those guanidines as described in WO2009087395.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In a further embodiment, the compound of the formula I is administered in combination with antidiabetic compounds, as described in WO2007095462, WO2007101060, WO2007105650.

In a further embodiment, the compound of the formula I is administered in combination with antihypoglycemic compounds, as described in WO2007137008, WO2008020607.

In one embodiment, the compound of the formula I is administered in combination with a thiazolidinedione, for example troglitazone, ciglitazone, pioglitazone, rosiglitazone or the compounds disclosed in WO 97/41097 by Dr. Reddy's Research Foundation, especially 5-[[4-[(3,4-dihydro-3-methyl-4-oxo-2-quinazolinylmethoxy]-phenyl]methyl]-2,4-thiazolidinedione.

In one embodiment of the invention, the compound of the formula I is administered in combination with a PPAR gamma agonist, for example rosiglitazone, pioglitazone, JTT-501, GI 262570, R-483, CS-011 (rivoglitazone), DRL-17564, DRF-2593 (balaglitazone), INT-131, T-2384, or those as described in WO2005086904, WO2007060992, WO2007100027, WO2007103252. WO2007122970, WO2007138485, WO2008006319, WO2008006969, WO2008010238, WO2008017398, WO2008028188, WO2008066356, WO2008084303, WO2008089461-WO2008089464, WO2008093639, WO2008096769, WO2008096820, WO2008096829, US2008194617, WO2008099944, WO2008108602, WO2008109334, WO2008110062, WO2008126731, WO2008126732, WO2008137105, WO2009005672, WO2009038681, WO2009046606, WO2009080821, WO2009083526. WO2009102226, WO2009128558, WO2009139340.

In one embodiment of the invention, the compound of the formula I is administered in combination with Competact™, a solid combination of pioglitazone hydrochloride with metformin hydrochloride.

In one embodiment of the invention, the compound of the formula I is administered in combination with Tandemact™, a solid combination of pioglitazone with glimepiride.

In a further embodiment of the invention, the compound of the formula I is administered in combination with a solid combination of pioglitazone hydrochloride with an angiotensin U agonist, for example TAK-536.

In one embodiment of the invention, the compound of the formula I is administered in combination with a PPAR alpha agonist or mixed PPAR alpha/PPAR delta agonist, for example GW9578, GW-590735, K-111, LY-674, KRP-101, DRF-10945, LY-518674, CP-900691, BMS-687453, BMS-711939, or those as described in WO2001040207, WO2002096894, WO2005097076, WO2007056771, WO2007087448, WO2007089667, WO2007089557, WO2007102515, WO2007103252, JP2007246474, WO2007118963, WO2007118964, WO2007126043, WO2008006043, WO2008006044, WO2008012470, WO2008035359, WO2008087365, WO2008087366, WO2008087367, WO2008117982, JP2009023975, WO2009033561, WO2009047240, WO2009072581, WO2009080248, WO2009080242, WO2009149819, WO2009149820, WO2009147121, WO2009153496, WO2010008299, WO2010014771.

In one embodiment of the invention, the compound of the formula I is administered in combination with a mixed PPAR alpha/gamma agonist, for example naveglitazar, aleglitazar, LY-510929, ONO-5129, E-3030, AVE 8042, AVE 8134, AVE 0847, AVE 0897, CKD-501 (lobeglitazone sulfate), MBX-213, KY-201, BMS-759509, or as described in WO 00/64888, WO 00/64876, WO03/020269, WO2004024726, WO2007099553, US2007276041, WO2007085135, WO2007085136, WO2007141423, WO2008016175, WO2008053331, WO2008109697, WO2008109700, WO2008108735, WO2009026657, WO2009026658, WO2009149819, WO2009149820 or in J. P. Berger at al., TRENDS in Pharmacological Sciences 28(5), 244-251, 2005.

In one embodiment of the invention, the compound of the formula I is administered in combination with a PPAR delta agonist, for example GW-501516, or as described in WO2006059744, WO2006084176, WO2006029699, WO2007039172-WO2007039178, WO2007071766, WO2007101864, US2007244094, WO2007119887, WO2007141423, US2008004281, WO2008016175, WO2008066356, WO2008071311, WO2008084962, US2008176861, WO2009012650, US2009137671, WO2009080223, WO2009149819, WO2009149820, WO2010000353.

In one embodiment of the invention, the compound of the formula I is administered in combination with a pan-SPPARM (selective PPAR modulator alpha, gamma, delta), for example GFT-505, indeglitazar, or those as described in WO2008035359, WO2009072581.

In one embodiment, the compound of the formula I is administered in combination with metaglidasen or with MBX-2044 or other partial PPAR gamma agonists/antagonists.

In one embodiment, the compound of the formula I is administered in combination with an α-glucosidase inhibitor, for example miglitol or acarbose, or those as described, for example, in WO2007114532, WO2007140230, US2007287674, US2008103201, WO2008065796, WO2008082017, US2009076129.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932, WO2008062739, WO2008099000, WO2008113760, WO2009016118, WO2009016119, WO2009030715, WO2009045830, WO2009045831, WO2009127723.

In another embodiment, the compound of the formula I is administered in combination with an inhibitor of the interaction of liver glycogen phosphorylase with the protein PPP1R3 (GL subunit of glycogen-associated protein phosphatase 1 (PP1)), as described, for example, in WO2009030715.

In one embodiment, the compound of the formula I is administered in combination with glucagon receptor antagonists, for example A-770077 or NNC-25-2504 or as described in WO2004100875, WO2005065680, WO2006086488, WO2007047177, WO2007106181, WO2007111864, WO2007120270, WO2007120284, WO2007123581, WO2007136577, WO2008042223, WO2008098244, WO2009057784, WO2009058662, WO2009058734, WO2009110520, WO2009120530, WO2009140342, WO2010019828.

In a further embodiment, the compound of the formula I is administered in combination with an antisense compound, e.g. ISIS-325568, which inhibits the production of the glucagon receptor.

In one embodiment, the compound of the formula is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847, WO2007061923, WO2007075847, WO2007089512, WO2007104034, WO2007117381, WO2007122482, WO2007125103, WO2007125105, US2007281942, WO2008005914, WO2008005964, WO2008043701, WO2008044777, WO2008047821, US2008096877, WO2008050117, WO2008050101, WO2008059625, US2008146625, WO2008078674, WO2008079787, WO2008084043, WO2008084044, WO2008084872, WO2008089892, WO2008091770, WO2008075073, WO2008084043, WO2008084044, WO2008084872, WO2008084873, WO2008089892, WO2008091770, JP2008189659, WO2008104994, WO2008111473, WO2008116107, WO2008118718, WO2008120754, US2008280875, WO2008136428, WO2008136444, WO2008149382, WO2008154563, WO2008156174, WO2008156757, US2009030046, WO2009018065, WO2009023718, WO2009039944, WO2009042435, WO2009046784, WO2009046802, WO2009047798, WO2009063821, WO2009081782, WO2009082152, WO2009083553, WO2009091014, US2009181981, WO2009092432, WO2009099080, WO2009106203, WO2009106209, WO2009109270, WO2009125873, WO2009127544, WO2009127546, WO2009128481, WO2009133687, WO2009140624, WO2010013161, WO2010015849, WO2010018800.

In one embodiment, the compound of the formula I is administered in combination with an inhibitor of gluconeogenesis, as described, for example, in FR-225654, WO2008053446.

In one embodiment, the compound of the formula I is administered in combination with inhibitors of fructose 1,6-bisphosphatase (FBPase), for example MB-07729, CS-917 (MB-06322) or MB-07803, or those as described in WO2006023515, WO2006104030, WO2007014619, WO2007137962, WO2008019309, WO2008037628, WO2009012039, EP2058308, WO2009068467, WO2009068468.

In one embodiment, the compound of the formula I is administered in combination with modulators of glucose transporter 4 (GLUT4), for example KST-48 (D.-O. Lee et al.: Arzneim.-Forsch. Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidyl peptidase-IV (DPP-IV), for example vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200 (melogliptin), GW-825964X, KRP-104, DP-893, ABT-341, ABT-279 or another salt thereof, S-40010, S-40755, PF-00734200, BI-1356, PHX-1149, DSP-7238, alogliptin benzoate, linagliptin, melogliptin, carmegliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006085685, WO2006090915, WO2006104356, WO2006127530, WO2006111261, US2006890898, US2006803357, US2006303661, WO2007015767 (LY-2463665), WO2007024993, WO2007029086, WO2007063928, WO2007070434, WO2007071738, WO2007071576, WO2007077508, WO2007087231, WO2007097931, WO2007099385, WO2007100374, WO2007112347, WO2007112669, WO2007113226, WO2007113634, WO2007115821, WO2007116092, US2007259900, EP1852108, US2007270492, WO2007126745, WO2007136603, WO2007142253, WO2007148185, WO2008017670, US2008051452, WO2008027273, 102008028662, WO2008029217, JP2008031064, JP2008063256, WO2008033851, WO2008040974, WO2008040995, WO2008060488, WO2008064107, WO2008066070, WO2008077597, JP2008156318, WO2008087560, WO2008089636, WO2008093960, WO2008096841, WO2008101953, WO2008118848, WO2008119005, WO2008119208, WO2008120813, WO2008121506, WO2008130151, WO2008131149, WO2009003681, WO2009014676, WO2009025784, WO2009027276, WO2009037719, WO2009068531, WO2009070314, WO2009065298, WO2009082134, WO2009082881, WO2009084497, WO2009093269, WO2009099171, WO2009099172, WO2009111239, WO2009113423, WO2009116067, US2009247532, WO2010000469, WO2010015664.

In one embodiment, the compound of the formula I is administered in combination with Janumet™, a solid combination of sitagliptin phosphate with metformin hydrochloride.

In one embodiment, the compound of the formula I is administered in combination with Eucreas®, a solid combination of vildagliptin with metformin hydrochloride.

In a further embodiment, the compound of the formula I is administered in combination with a solid combination of alogliptin benzoate with pioglitazone.

In one embodiment, the compound of the formula I is administered in combination with a solid combination of a salt of sitagliptin with metformin hydrochloride.

In one embodiment, the compound of the formula I is administered in combination with a combination of a DPP-IV inhibitor with omega-3 fatty acids or omega-3 fatty acid esters, as described, for example, in WO2007128801.

In one embodiment, the compound of the formula I is administered in combination with a combination of a DPP-IV inhibitor with metformin hydrochloride, as described, for example, in WO2009121945.

In one embodiment, the compound of the formula I is administered in combination with a combination of a DPP-IV inhibitor with a GPR-119 agonist, as described, for example, in WO2009123992.

In one embodiment, the compound of the formula I is administered in combination with a combination of a DPP-IV inhibitor with miglitol, as described, for example, in WO2009139362.

In one embodiment, the compound of the formula I is administered in combination with a solid combination of a salt of sitagliptin with metformin hydrochloride.

In one embodiment, the compound of the formula I is administered in combination with a solid combination of alopliptin benzoate with pioglitazone hydrochloride.

In one embodiment, the compound of the formula I is administered in combination with a substance which enhances insulin secretion, for example KCP-265 (WO2003097064), or those as described in WO2007026761, WO2008045484, US2008194617, WO2009109259, WO2009109341.

In one embodiment, the compound of the formula I is administered in combination with agonists of the glucose-dependent insulinotropic receptor (GDIR), for example APD-668.

In one embodiment of the invention, the compound of the formula I is administered in combination with an ATP citrate lyase inhibitor, for example SB-204990.

In one embodiment, the compound of the formula I is administered in combination with modulators of the sodium-dependent glucose transporter 1 and/or 2 (SGLT1, SGLT2), for example KGA-2727, T-1095, SGL-0010, AVE 2268, SAR 7226, SGL-5083, SGL-5085, SGL-5094, ISIS-388626, sergliflozin, dapagliflozin or remoglifiozin etabonate, canagliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170, WO2007093610, WO2007126117, WO2007128480, WO2007129668, US2007275907, WO2007136116, WO2007143316, WO2007147478, WO2008001864, WO2008002824, WO2008013277, WO2008013280, WO2008013321, WO2008013322, WO2008016132, WO2008020011, JP2008031161, WO2008034859, WO2008042688, WO2008044762, WO2008046497, WO2008049923, WO2008055870, WO2008055940, WO2008069327, WO2008070609, WO2008071288, WO2008072726, WO2008083200, WO2008090209, WO2008090210, WO2008101586, WO2008101939, WO2008116179, WO2008116195, US2008242596, US2008287529, WO2009026537, WO2009049731, WO2009076550, WO2009084531, WO2009096503, WO2009100936, WO2009121939, WO2009124638, WO2009128421, WO2009135673, WO2010009197, WO2010018435, WO2010018438 or by A. L. Handlon in Expert Opin. Ther. Patents (2005) 15(11), 1531-1540.

In a further embodiment of the invention, the compound of the formula I is administered in combination with a solid combination of an SGLT inhibitor with a DPP-IV inhibitor, as described in WO2009091082.

In one embodiment, the compound of the formula I is administered in combination with a stimulator of glucose transport, as described, for example, in WO2008136392, WO2008136393.

In one embodiment, the compound of the formula I is administered in combination with inhibitors of 11-beta-hydroxysteroid dehydrogenase 1 (11β-HSD1), for example BVT-2733, JNJ-25918646, INCB-13739, INCB-20817, D10-92 ((-)-ketoconazole) or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005063247, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138508, WO2006138695, WO2006133926, WO2007003521, WO2007007688, US2007066584, WO2007029021, WO2007047625, WO2007051811, WO2007051810, WO2007057768, WO2007058346, WO2007061661, WO2007068330, WO2007070506, WO2007087150, WO2007092435, WO2007089683, WO2007101270, WO2007105753, WO2007107470, WO2007107550, WO2007111921, US2007207985, US2007208001, WO2007115935, WO2007118185, WO2007122411, WO2007124329, WO2007124337, WO2007124254, WO2007127688, WO2007127693, WO2007127704, WO2007127726, WO2007127763, WO2007127765, WO2007127901, US2007270424, JP2007291075, WO2007130898, WO2007135427, WO2007139992, WO2007144394, WO2007145834, WO2007145835, WO2007146761, WO2008000950, WO2008000951, WO2008003611, WO2008005910, WO2008006702, WO2008006703, WO2008011453, WO2008012532, WO2008024497, WO2008024892, WO2008032164, WO2008034032, WO2008043544, WO2008044656, WO2008046758, WO2008052638, WO2008053194, WO2008071169, WO2008074384, WO2008076336, WO2008076862, WO2008078725, WO2008087654, WO2008088540, WO2008099145, WO2008101885, WO2008101886, WO2008101907, WO2008101914, WO2008106128, WO2008110196, WO2008119017, WO2008120655, WO2008127924, WO2008130951, WO2008134221, WO2008142859, WO2008142986, WO2008157752, WO2009001817, WO2009010416, WO2009017664, WO2009020140, WO2009023180, WO2009023181, WO2009023664, WO2009026422, WO2009038064, WO2009045753, WO2009056881, WO2009059666, WO2009061498, WO2009063061, WO2009070497, WO2009074789, WO2009075835, WO2009090239, WO2009094169, WO2009098997, WO2009090239, WO2009094169, WO2009098501, WO2009100872, WO2009102428, WO2009102460, WO2009102761, WO2009106817, WO2009108332, WO2009112691, WO2009112845, WO2009114173, WO2009117109, US2009264401, WO2009118473, WO2009131669, WO2009132986, WO2009134384, WO2009134387, WO2009134392, WO2009134400, WO2009135581, WO2009138386, WO2010006940, WO2010010157, WO2010010174, WO2010011917.

In one embodiment, the compound of the formula is administered in combination with inhibitors of protein tyrosine phosphatase-1B (PTP-1B), as described, for example, in WO200119830-31, WO200117516, WO2004506446, WO2005012295, WO2005116003, WO2005116003, WO2006007959, DE 10 2004 060542.4, WO2007009911, WO2007028145, WO2007067612-615, WO2007081755, WO2007115058, US2008004325, WO2008033455, WO2008033931, WO2008033932, WO2008033934, WO2008089581, WO2008148744, WO2009032321, WO2009109999, WO2009109998.

In a further embodiment, the compound of the formula I is administered in combination with stimulators of tyrosine kinase B (Trk-B), as described, for example, in WO2010014613.

In a further embodiment, the compound of the formula I is administered in combination with beta 3 agonists (also called beta-3 adrenoceptor agonists), as described, for example, in Physiol. Behav. 2004 Sep. 15; 82(2-3):489-96, J Clin Invest (1998) 101: 2387-93, Curr. Pharma. Des. 2001 September; 7(14):1433-49, Bioorganic & Medicinal Chemistry Letters volume 14, number 13, Jul. 5, 2004, pages 3525-3529 (BMS-201620).

In one embodiment of the invention, the compound of the formula I is administered in combination with an agonist of GPR109A (HM74A receptor agonists; NAR agonists (nicotinic acid receptor agonists)), for example nicotinic acid or extended release niacin in conjunction with MK-0524A (laropiprant) or MK-0524, or those compounds as described in WO2004041274, WO2006045565, WO2006045564, WO2006069242, WO2006085108, WO2006085112, WO2006085113, WO2006124490, WO2006113150, WO2007002557, WO2007017261, WO2007017262, WO2007017265, WO2007015744, WO2007027532, WO2007092364, WO2007120575, WO2007134986, WO2007150025, WO2007150026, WO2008016968, WO2008051403, WO2008086949, WO2008091338, WO2008097535, WO2008099448, US2008234277, WO2008127591.

In another embodiment of the invention, the compound of the formula I is administered in combination with a solid combination of niacin with simvastatin.

In another embodiment of the invention, the compound of the formula I is administered in combination with nicotinic acid or "extended release niacin" in conjunction with MK-0524A (laropiprant).

In a further embodiment of the invention, the compound of the formula I is administered in combination with nicotinic acid or "extended release niacin" in conjunction with MK-0524A (laropiprant) and with simvastatin.

In one embodiment of the invention, the compound of the formula I is administered in combination with nicotinic acid or another nicotinic acid receptor agonist and a prostaglandin DP receptor antagonist, for example those as described in WO2008039882.

In another embodiment of the invention, the compound of the formula I is administered in combination with a solid combination of niacin with meloxicam, as described, for example, in WO2009149056.

In another embodiment of the invention, the compound of the formula I is administered in combination with an agonist of GPR116, as described, for example, in WO2006067531, WO2006067532.

In one embodiment, the compound of the formula I is administered in combination with modulators of GPR40, as described, for example, in WO2007013689, WO2007033002, WO2007106469, WO2007265332, WO2007123225, WO2007131619, WO2007131620, WO2007131621, US2007265332, WO2007131622, WO2007136572, WO2008001931, WO2008030520, WO2008030618, WO2008054674, WO2008054675, WO2008066097, US2008176912, WO2008130514, WO2009038204, WO2009039942, WO2009039943, WO2009048527, WO2009054479, WO2009058237, WO2009111056, WO2010012650.

In one embodiment, the compound of the formula I is administered in combination with modulators of GPR119 (G-protein-coupled glucose-dependent insulinotropic receptor), for example PSN-119-1, PSN-821, PSN-119-2, MBX-2982 or those as described, for example, in WO2004065380, WO2005061489 (PSN-632408), WO2006083491, WO2007003960-62 and WO2007003964, WO2007035355, WO2007116229, WO2007116230, WO2008005569, WO2008005576, WO2008008887, WO2008008895, WO2008025798, WO2008025799, WO2008025800, WO2008070692, WO2008076243, WO200807692, WO2008081204, WO2008081205, WO2008081206, WO2008081207, WO2008081208, WO2008083238, WO2008085316, WO2008109702, WO2008130581, WO2008130584, WO2008130615, WO2008137435, WO2008137436, WO2009012275, WO2009012277, WO2009014910, WO2009034388, WO2009038974, WO2009050522, WO2009050523, WO2009055331, WO2009105715, WO2009105717, WO2009105722, WO2009106561, WO2009106565, WO2009117421, WO2009125434, WO2009126535, WO2009129036, US2009286812, WO2009143049, WO2009150144, WO2010001166, WO2010004343, WO2010004344, WO2010004345, WO2010004346, WO2010004347, WO2010004348, WO2010008739, WO2010006191, WO2010009183, WO2010009195, WO2010009207, WO2010009208, WO2010014593.

In a further embodiment, the compound of the formula I is administered in combination with modulators of GPR120, as described, for example, in EP1688138, WO2008066131, WO2008066131, WO2008103500, WO2008103501 WO2008139879, WO2009038204, WO2009147990, WO2010008831.

In another embodiment, the compound of the formula I is administered in combination with antagonists of GPR105, as described, for example, in WO2009000087, WO2009070873.

In a further embodiment, the compound of the formula I is administered in combination with agonists of GPR43, for example ESN-282.

In one embodiment, the compound of the formula I is administered in combination with inhibitors of hormone-sensitive lipase (HSL) and/or phospholipases, as described, for example, in WO2005073199, WO2006074957, WO2006087309, WO200611121, WO2007042178, WO20079837, WO2008122352, WO2008122357, WO2009009287.

In one embodiment, the compound of the formula I is administered in combination with inhibitors of endothelial lipase, as described, for example, in WO2007110216.

In one embodiment, the compound of the formula I is administered in combination with a phospholipase A2 inhibitor, for example darapladib or A-002, or those as described in WO2008048866, WO20080488867, US2009062369.

In one embodiment, the compound of the formula I is administered in combination with myricitrin, a lipase inhibitor (WO2007119827).

In one embodiment, the compound of the formula I is administered in combination with an inhibitor of glycogen synthase kinase-3 beta (GSK-3 beta), as described, for example, in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117, WO2007073117, WO2007083978, WO2007120102, WO2007122634, WO2007125109, WO2007125110, US2007281949, WO2008002244, WO2008002245, WO2008016123, WO2008023239, WO2008044700, WO2008056266, WO2008057940, WO2008077138, EP1939191, EP1939192, WO2008078196, WO2008094992, WO2008112642, WO2008112651, WO2008113469, WO2008121063, WO2008121064, EP-1992620, EP-1992621, EP1992624, EP-1992625, WO2008130312, WO2009007029, EP2020232, WO2009017452, WO2009035634, WO2009035684, WO2009038385, WO2009095787, WO2009095788, WO2009095789, WO2009095792, WO2009145814, US2009291982, WO2009154697, WO2009156857, WO2009156859, WO2009156860, WO2009156861, WO2009156863, WO2009156864, WO2009156865, WO2010013168, WO2010014794.

In one embodiment, the compound of the formula I is administered in combination with an inhibitor of phosphoenolpyruvate carboxykinase (PEPCK), for example those as described in WO2004074288.

In one embodiment, the compound of the formula I is administered in combination with an inhibitor of phosphoinositide kinase-3 (PI3K), for example those as described in WO2008027584, WO2008070150, WO2008125833, WO2008125835, WO2008125839, WO2009010530, WO2009026345, WO2009071888, WO2009071890, WO2009071895.

In one embodiment, the compound of the formula I is administered in combination with an inhibitor of serum/glucocorticoid-regulated kinase (SGK), as described, for example, in WO2006072354, WO2007093264, WO2008009335, WO2008086854, WO2008138448.

In one embodiment, the compound of the formula is administered in combination with a modulator of the glucocorticoid receptor, as described, for example, in WO2008057855, WO2008057856, WO2008057857, WO2008057859, WO2008057862, WO2008059867, WO2008059866, WO2008059865, WO2008070507, WO2008124665, WO2008124745, WO2008146871, WO2009015067, WO2009040288, WO2009069736, WO2009149139.

In one embodiment, the compound of the formula I is administered in combination with a modulator of the mineralocorticoid receptor (MR), for example drospirenone, or those as described in WO2008104306. WO2008119918.

In one embodiment, the compound of the formula I is administered in combination with an inhibitor of protein kinase C beta (PKC beta), for example ruboxistaurin, or those as described in WO2008096260, WO2008125945.

In one embodiment, the compound of the formula I is administered in combination with an inhibitor of protein kinase D, for example doxazosin (WO2008088006).

In a further embodiment, the compound of the formula I is administered in combination with an activator/modulator of the AMP-activated protein kinase (AMPK), as described, for example, in WO2007062568, WO2008006432, WO2008016278, WO2008016730, WO2008020607, WO2008083124, WO2008136642, WO2009019445, WO2009019446, WO2009019600, WO2009028891, WO2009065131, WO2009076631, WO2009079921, WO2009100130, WO2009124636, WO2009135580, WO2009152909.

In one embodiment, the compound of the formula I is administered in combination with an inhibitor of ceramide kinase, as described, for example, in WO2007112914, WO2007149865.

In a further embodiment, the compound of the formula I is administered in combination with an inhibitor of MAPK-interacting kinase 1 or 2 (MNK1 or 2), as described, for example, in WO2007104053, WO2007115822, WO2008008547, WO2008075741.

In one embodiment, the compound of the formula I is administered in combination with inhibitors of "I-kappaB kinase" (IKK inhibitors), as described, for example, in WO2001000610, WO2001030774, WO2004022057, WO2004022553, WO2005097129, WO2005113544, US2007244140, WO2008099072, WO2008099073, WO2008099073, WO2008099074, WO2008099075, WO2009056693, WO2009075277, WO2009089042, WO2009120801.

In another embodiment, the compound of the formula I is administered in combination with inhibitors of NF-kappaB (NFKB) activation, for example salsalate.

In a further embodiment, the compound of the formula I is administered in combination with inhibitors of ASK-1 (apoptosis signal-regulating kinase 1), as described, for example, in WO2008016131, WO2009123986.

In one embodiment of the invention, the compound of formula I is administered in combination with an HMG-CoA reductase inhibitor such as simvastatin, fluvastatin, pravastatin, lovastatin, atorvastatin, cerivastatin, rosuvastatin, pitavastatin, L-659699, BMS-644950, NCX-6560, or those as described in US2007249583, WO2008083551, WO2009054682.

In a further embodiment of the invention, the compound of the formula I is administered in combination with a farnesoid X receptor (FXR) modulator, for example WAY-362450 or those as described in WO2003099821, WO2005056554, WO2007052843, WO2007070796, WO2007092751, JP2007230909, WO2007095174, WO2007140174, WO2007140183, WO2008000643, WO2008002573, WO2008025539, WO2008025540, JP2008214222, JP2008273847, WO2008157270, US2008299118, US2008300235, WO2009005998, WO2009012125, WO2009027264, WO2009062874, US2009131409, US2009137554, US2009163552, WO2009127321, EP2128158.

In another embodiment of the invention, the compound of the formula I is administered in combination with a ligand of the liver X receptor (LXR), as described, for example, in WO2007092965, WO2008041003, WO2008049047, WO2008065754, WO2008073825, US2008242677, WO2009020683, US2009030082, WO2009021868, US2009069373, WO2009024550, WO2009040289, WO2009086123, WO2009086129, WO2009086130, WO2009086138, WO2009107387, US2009247587, WO2009133692, WO2008138438, WO2009144961, WO2009150109.

In one embodiment of the invention, the compound of the formula I is administered in combination with a fibrate, for example fenofibrate, clofibrate, bezafibrate, or those as described in WO2008093655.

In one embodiment of the invention, the compound of the formula I is administered in combination with fibrates, for example the choline salt of fenofibrate (SLV-348; Trilipix™).

In one embodiment of the invention, the compound of the formula I is administered in combination with fibrates, for example the choline salt of fenofibrate (Trilipix™) and an HMG-CoA reductase inhibitor, for example rosuvastatin.

In a further embodiment of the invention, the compound of the formula I is administered in combination with bezafibrate and diflunisal.

In a further embodiment of the invention, the compound of the formula I is administered in combination with a solid combination of fenofibrate or a salt thereof with simvastatin, rosuvastatin, fluvastatin, lovastatin, cerivastatin, pravastatin, pitavastatin or atorvastatin.

In a further embodiment of the invention, the compound of the formula I is administered in combination with Synordia®, a solid combination of fenofibrate with metformin.

In another embodiment of the invention, the compound of the formula I is administered in combination with a solid combination of metformin with an MTP inhibitor, as described in WO2009090210.

In one embodiment of the invention, the compound of the formula I is administered in combination with a cholesterol reabsorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG), or as described in WO2002050060, WO2002050068, WO2004000803, WO2004000804, WO2004000805, WO2004087655, WO2004097655, WO2005047248, WO2006086562, WO2006102674, WO2006116499, 102006121861, WO2006122186, WO2006122216, WO2006127893, WO2006137794, WO2006137796, WO2006137782, WO2006137793, WO2006137797, WO2006137795, WO2006137792, WO2006138163, WO2007059871, US2007232688, WO2007126358, WO2008033431, WO2008033465, WO2008052658, WO2008057336, WO2008085300, WO2008104875, US2008280836, WO2008108486.

In one embodiment of the invention, the compound of the formula I is administered in combination with an NPC1L1 antagonist, for example those as described in WO2008033464, WO2008033465.

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with atorvastatin.

In one embodiment of the invention, the compound of the formula I is administered in combination with a solid combination of ezetimibe with fenofibrate.

In one embodiment of the invention, the further active ingredient is a diphenylazetidinone derivative, as described, for example, in U.S. Pat. No. 6,992,067 or U.S. Pat. No. 7,205,290.

In a further embodiment of the invention, the further active ingredient is a diphenylazetidinone derivative, as described, for example, in U.S. Pat. No. 6,992,067 or U.S. Pat. No. 7,205,290, combined with a statin, for example simvastatin, fluvastatin, pravastatin, lovastatin, cerivastatin, atorvastatin, pitavastatin or rosuvastatin.

In one embodiment of the invention, the compound of the formula I is administered in combination with a solid combination of lapaquistat, a squalene synthase inhibitor, with atorvastatin.

In a further embodiment of the invention, the compound of the formula I is administered in combination with a conjugate consisting of the HMG-CoA reductase inhibitor atorvastatin with the renin inhibitor aliskiren (WO2009090158).

In one embodiment of the invention, the compound of the formula I is administered in combination with a CETP inhibitor, for example torcetrapib, anacetrapib or JTT-705 (dalcetrapib), or those as described in WO2006002342, WO2006010422, WO2006012093, WO2006073973, WO2006072362, WO2007088996, WO2007088999, US2007185058, US2007185113, US2007185154, US2007185182, WO2006097169, WO2007041494, WO2007090752, WO2007107243, WO2007120621, US2007265252, US2007265304, WO2007128568, WO2007132906, WO2008006257, WO2008009435, WO2008018529, WO2008058961, WO2008058967, WO2008059513. WO2008070496, WO2008115442, WO2008111604, WO2008129951, WO2008141077, US2009118287, WO2009062371, WO2009071509.

In one embodiment of the invention, the compound of the formula I is administered in combination with be acid reabsorption inhibitors (inhibitors of the intestinal be acid transporter (IBAT)) (see, for example, U.S. Pat. No. 6,245,744, U.S. Pat. No. 6,221,897 or WO00/61568), for example HMR 1741, or those as described in DE 10 2005 033099.1 and DE 10 2005 033100.9, DE 10 2006 053635, DE 10 2006 053637, WO2007009655-56, WO2008058628, WO2008058629, WO2008058630, WO2008058631.

In one embodiment, the compound of the formula I is administered in combination with agonists of GPBAR1 (G-protein-coupled be acid receptor 1; TGR5), for example INT-777 or those as described, for example, in US20060199795, WO2007110237, WO2007127505, WO2008009407, WO2008067219, WO2008067222, FR2908310, WO2008091540, WO2008097976, US2009054304, WO2009026241, WO2009146772, WO2010014739, WO2010014836.

In one embodiment, the compound of the formula I is administered in combination with modulators of histone deacetylase, for example ursodeoxycholic acid, as described in WO2009011420.

In one embodiment, the compound of the formula I is administered in combination with inhibitors/modulators of the TRPM5 channel (TRP cation channel M5), as described, for example, in WO2008097504, WO2009038722.

In one embodiment, the compound of the formula I is administered in combination with inhibitors/modulators of the TRPA1 channel (TRP cation channel A1), as described, for example, in US2009176883, WO2009089083, WO2009144548.

In one embodiment, the compound of the formula I is administered in combination with inhibitors/modulators of the TRPV3 channel (TRP cation channel V3), as described, for example, in WO2009084034, WO2009130560.

In one embodiment of the invention, the compound of the formula I is administered in combination with a polymeric bile acid adsorber, for example cholestyramine, colesevelam hydrochloride.

In one embodiment of the invention, the compound of the formula I is administered in combination with colesevelam hydrochloride and metformin or a sulfonylurea or insulin.

In one embodiment of the invention, the compound of the formula I is administered in combination with tocotrienol and insulin or an insulin derivative.

In one embodiment of the invention, the compound of the formula I is administered in combination with a chewing gum comprising phytosterols (Reductol™).

In one embodiment of the invention, the compound of the formula I is administered in combination with an inhibitor of the microsomal triglyceride transfer protein (MIT inhibitor), for example implitapide, BMS-201038, R-103757, AS-1552133, SLx-4090, AEGR-733, STT-130, or those as described in WO2005085226, WO2005121091, WO2006010423, WO2006113910, WO2007143164, WO2008049806, WO2008049808, WO2008090198, WO2008100423, WO2009014674.

In a further embodiment of the invention, the compound of the formula I is administered in combination with a combination of a cholesterol absorption inhibitor, for example ezetimibe, and an inhibitor of the triglyceride transfer protein (MTP inhibitor), for example implitapide, as described in WO2008030382 or in WO2008079398.

In one embodiment of the invention, the compound of the formula I is administered in combination with an active antihypertriglyceridemic ingredient, for example those as described in WO2008032980.

In another embodiment of the invention, the compound of the formula I is administered in combination with an antagonist of the somatostatin 5 receptor (SST5 receptor), for example those as described in WO2006094682.

In one embodiment of the invention, the compound of the formula I is administered in combination with an ACAT inhibitor, for example avasimibe, SMP-797 or KY-382, or those as described in WO2008087029, WO2008087030, WO2008095189, WO2009030746, WO2009030747, WO2009030750, WO2009030752, WO2009070130, WO2009081957, WO2009081957.

In a further embodiment of the invention, the compound of the formula I is administered in combination with an inhibitor of liver carnitine palmitoyltransferase-1 (L-CPT1), as described, for example, in WO2007063012, WO2007096251 (ST-3473), WO2008015081, US2008103182, WO2008074692, WO2008145596, WO2009019199, WO2009156479, WO2010008473.

In another embodiment of the invention, the compound of the formula I is administered in combination with an inhibitor of carnitin O-palmitoyltransferase II (CPT2), as described, for example, in US2009270500, US2009270505, WO2009132978, WO2009132979.

In a further embodiment of the invention, the compound of the formula I is administered in combination with a modulator of serine palmitoyltransferase (SPT), as described, for example, in WO2008031032, WO2008046071, WO2008083280, WO2008084300.

In one embodiment of the invention, the compound of the formula I is administered in combination with a squalene synthetase inhibitor, for example BMS-188494, TAK-475 (lapaquistat acetate), or as described in WO2005077907, JP2007022943, WO2008003424, WO2008132846, WO2008133288, WO2009136396.

In one embodiment of the invention, the compound of the formula I is administered in combination with ISIS-301012 (mipomersen), an antisense oligonucleotide which is capable of regulating the apolipoprotein B gene.

In one embodiment of the invention, the compound of the formula I is administered in combination with apolipoprotein (ApoB) SNALP, a therapeutic product which comprises an siRNA (directed against the ApoB gene).

In one embodiment of the invention, the compound of the formula I is administered in combination with a stimulator of the ApoA-1 gene, as described, for example, in WO2008092231.

In one embodiment of the invention, the compound of the formula I is administered in combination with a modulator of the synthesis of apolipoprotein C-III, for example ISIS-APOCIIIRx.

In one embodiment of the invention, the compound of the formula I is administered in combination with an LDL receptor inducer (see U.S. Pat. No. 6,342,512), for example HMR1171, HMR1586, or those as described in WO2005097738, WO2008020607.

In another embodiment of the invention, the compound of the formula I is administered in combination with an HDL cholesterol-elevating agent, for example those as described in WO2008040651, WO2008099278, WO2009071099, WO2009086096, US2009247550.

In one embodiment of the invention, the compound of the formula I is administered in combination with an ABCA1 expression enhancer, as described, for example, in WO2006072393, WO2008062830, WO2009100326.

In one embodiment of the invention, the compound of the formula I is administered in combination with a lipoprotein lipase modulator, for example ibrolipim (NO-1886).

In one embodiment of the invention, the compound of the formula I is administered in combination with a lipoprotein (a) antagonist, for example gemcabene (CI-1027).

In one embodiment of the invention, the compound of the formula I is administered in combination with a lipase inhibitor, for example orlistat or cetilistat (ATL-962).

In one embodiment of the invention, the compound of the formula I is administered in combination with an adenosine A1 receptor agonist (adenosine A1 R), for example CVT-3619 or those as described, for example, in EP1258247, EP1375508, WO2008028590, WO2008077050, WO2009050199, WO2009080197, WO2009100827, WO2009112155.

In one embodiment of the invention, the compound of the formula I is administered in combination with an adenosine A2B receptor agonist (adenosine A2B R), for example ATL-801.

In another embodiment of the invention, the compound of the formula I is administered in combination with a modulator of adenosine A2A and/or adenosine A3 receptors, as described, for example, in WO2007111954, WO2007121918, WO2007121921, WO2007121923, WO2008070661, WO2009010871.

In a further embodiment of the invention, the compound of the formula I is administered in combination with a ligand of the adenosine A1/A2B receptors, as described, for example, in WO2008064788, WO2008064789, WO2009080198, WO2009100827, WO2009143992.

In one embodiment of the invention, the compound of the formula I is administered in combination with an adenosine A2B receptor antagonist (adenosine A2B R), as described in US2007270433, WO2008027585, WO2008080461, WO2009037463, WO2009037467, WO2009037468, WO2009118759.

In one embodiment, the compound of the formula I is administered in combination with inhibitors of acetyl-CoA carboxylase (ACC1 and/or ACC2), for example those as described in WO199946262, WO200372197, WO2003072197, WO2005044814, WO2005108370, JP2006131559, WO2007011809, WO2007011811, WO2007013691, WO2007095601-603, WO2007119833, WO2008065508, WO2008069500, WO2008070609, WO2008072850, WO2008079610, WO2008088688, WO2008088689, WO2008088692, US2008171761, WO2008090944, JP2008179621, US2008200461, WO2008102749, WO2008103382, WO2008121592, WO2009082346, US2009253725, JP2009196966, WO2009144554, WO2009144555, WO2010003624, WO2010002010.

In another embodiment, the compound of the formula I is administered in combination with modulators of microsomal acyl-CoA:glycerol-3-phosphate acyltransferase 3 (GPAT3, described in WO2007100789) or with modulators of microsomal acyl-CoA:glycerol-3-phosphate acyltransferase 4 (GPAT4, described in WO2007100833) or with modulators of mitochondrial glycerol-3-phosphate O-acyltransferase, described in WO2010005922.

In a further embodiment, the compound of the formula I is administered in combination with modulators of xanthine oxidoreductase (XOR).

In another embodiment, the compound of the formula I is administered in combination with inhibitors of soluble epoxide hydrolase (sEH), as described, for example, in WO2008051873, WO2008051875, WO2008073623, WO2008094869, WO2008112022, WO2009011872, WO2009049154, WO2009049157, WO2009049165, WO2009073772, WO2009097476, WO2009111207, WO2009129508, WO2009151800.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example 4-[(4-aminoquinazolin-2-ylamino)methyl]-cyclohexylmethylnaphthalene-1-sulfonamide hydrochloride (CGP 71683A) or velneperit or those as described in WO2009110510;

NPY-5 receptor antagonists/receptor modulators, such as L-152804 or the compound "NPY-5-BY" from Banyu, or as described, for example, in WO2006001318, WO2007103295, WO2007125952, WO2008026563, WO2008026564, WO2008052769, WO2008092887, WO2008092888, WO2008092891, WO2008129007, WO2008134228, WO2009054434, WO2009095377, WO2009131096;

NPY-4 receptor antagonists, as described, for example, in WO2007038942;

NPY-2 receptor antagonists/modulators, as described, for example, in WO2007038943, WO2009006185, US2009099199, US2009099243, US2009099244, WO2009079593, WO2009079597;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424, WO2006095166, WO2008003947, WO2009080608;

NPY-2 receptor agonists, as described, for example, in WO2009080608;

derivatives of the peptide obestatin, as described by WO2006096847;

CB1 R (cannabinoid receptor 1) antagonists/inverse agonists, for example rimonabant, surinabant (SR147778), SLV-319 (ibipinabant), AVE-1625, taranabant (MK-0364) or salts thereof, otenabant (CP-945,598), rosonabant, V-24343 or those compounds as described in, for example, EP 0656354, WO 00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO2005063761-62, WO2005061509, WO2005077897, WO2006018662, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007018460, WO2007016460, WO2007020502, WO2007026215, WO2007028849, WO2007031720, WO2007031721, WO2007036945, WO2007038045, WO2007039740, US20070015810, WO2007046548, WO2007047737, WO2007057687, WO2007062193, WO2007064272, WO2007079681, WO2007084319, WO2007084450, WO2007086080, EP1816125, US2007213302, WO2007095513, WO2007096764, US2007254863, WO2007119001, WO2007120454, WO2007121687, WO2007123949, US2007259934, WO2007131219, WO2007133820, WO2007136571, WO2007136607, WO2007136571, U.S. Pat. No. 7,297,710, WO2007138050, WO2007139464, WO2007140385, WO2007140439, WO2007146761, WO2007148061, WO2007148062, US2007293509, WO2008004698, WO2008017381, US2008021031, WO2008024284, WO2008031734, WO2008032164, WO2008034032, WO2008035356, WO2008036021, WO2008036022, WO2008039023, WO2998043544, WO2008044111, WO2008048648, EP1921072-A1, WO2008053341, WO2008056377, WO2008059207, WO2008059335, WO2008062424, WO2008068423, WO2008068424, WO2008070305, WO2008070306, WO2008074816, WO2008074982, WO2008075012, WO2008075013, WO2008075019, WO2008075118, WO2008076754, WO2008081009, WO2008084057, EP1944295, US2008090809, US2008090810, WO2008092816, WO2008094473, WO2008094476, WO2008099076, WO2008099139, WO2008101995, US2008207704, WO2008107179, WO2008109027, WO2008112674, WO2008115705, WO2008118414, WO2008119999, WO200812000, WO2008121257, WO2008127585, WO2008129157, WO2008130616, WO2008134300, US2008262066, US2008287505, WO2009005645, WO2009005646, WO2009005671, WO2009023292, WO2009023653, WO2009024819, WO2009033125, EP2042175, WO2009053548-WO2009053553, WO2009054923, WO2009054929, WO2009059264, WO2009073138, WO2009074782, WO2009075691, WO2009078498, WO2009087285, WO2009074782, WO2009097590, WO2009097995, WO2009097996, WO2009097998, WO2009097999, WO2009098000, WO2009106708, US2009239909, WO2009118473, US2009264436, US2009264476, WO2009130234, WO2009131814, WO2009131815, US2009286758, WO2009141532, WO2009141533, WO2009153569, WO2010003760, WO2010012437, WO2010019762;

cannabinoid receptor 1/cannabinoid receptor 2 (CB1,/CB2) modulating compounds, for example delta-9-tetrahydrocannabivarin, or those as described, for example, in WO2007001939, WO2007044215, WO2007047737, WO2007095513, WO2007096764, WO2007112399, WO2007112402, WO2008122618, WO2009007697, WO2009012227, 102009087564, WO2009093018, WO2009095752, WO2009120660, WO2010012964;

cannabinoid receptor 2 (CB2) modulating compounds, for example those as described, for example, in WO2008063625, WO2008157500, WO2009004171, WO2009032754, WO2009055357, WO2009061652, WO2009063495, WO2009067613, WO2009114566;

modulators of FAAH (fatty acid amide hydrolase), as described, for example, in WO2007140005, WO2008019357, WO2008021625, WO2008023720, WO2008030532, WO2008129129, WO2008145839, WO2008145843, WO2008147553, WO2008153752, WO2009011904, WO2009048101, WO2009084970, WO2009105220, WO2009109504, WO2009109743, WO2009117444, WO2009127944, WO2009138416, WO2009151991, WO2009152025, WO2009154785, WO2010005572, WO2010017079; inhibitors of fatty acid synthase (FAS), as described, for example, in WO2008057585, WO2008059214, WO2008075064, WO2008075070, WO2008075077, WO2009079860;

inhibitors of LCE (long chain fatty acid elongase)/long chain fatty acid CoA ligase, as described, for example, in WO2008120653, WO2009038021, WO2009044788, WO2009081789, WO2009099086;

vanilloid-1 receptor modulators (modulators of TRPV1), as described, for example, in WO2007091948, WO2007129188, WO2007133637, WO2008007780, WO2008010061, WO2008007211, WO2008010061, WO2008015335, WO2008018827, WO2008024433, WO2008024438, WO2008032204, WO2008050199, WO2008059339, WO2008059370, WO2008066664, WO2008075150, WO2008090382, WO2008090434, WO2008093024, WO2008107543, WO2008107544, WO2008110863, WO2008125295, WO2008125296, WO2008125337, WO2008125342, WO2008132600, WO2008133973, WO2009010529, WO2009010824, WO2009016241, WO2009023539, WO2009038812, WO2009050348, WO2009055629, WO2009055749, WO2009064449, WO2009081222, WO2009089057, WO2009109710 WO2009112677, WO2009112678, WO2009112679, WO2009121036, WO2009124551, WO2009136625, WO2010002209;

modulators, ligands, antagonists or inverse agonists of the opioid receptors, for example GSK-982 or those as described, for example, in WO2007047397, WO2008021849, WO2008021851, WO2008032156, WO2008059335, WO2008125348, WO2008125349, WO2008142454, WO2009030962, WO2009103552, WO2009115257;

modulators of the "orphan opioid (ORL-1) receptor", as described, for example, in US2008249122, WO2008089201;

agonists of the prostaglandin receptor, for example bimatoprost or those compounds as described in WO2007111806;

MC4 receptor agonists (melanocortin-4 receptor agonists, MC4R agonists, for example N-[2-(3a-benzyl-2-methyl-3-oxo-2,3,3a,4,6,7-hexahydro-pyrazolo[4,3-c]pyridin-5-yl)-1-(4-chlorophenyl)-2-oxoethyl]-1-amino-1,2,3,4-tetrahydronaphthalene-2-carboxamide, (WO 01/91752)) or LB53280, LB53279, LB53278 or THIQ, MB243, RY764, CHIR-785, PT-141, MK-0493, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2004089307, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052, JP2007131570, EP-1842846, WO2007096186, WO2007096763, WO2007141343, WO2008007930, WO2008017852, WO2008039418, WO2008087186, WO2008087187, WO2008087189, WO2008087186-WO2008087190, WO2008090357, WO2008142319, WO2009015867, WO2009061411, US2009076029, US2009131465, WO2009071101, US2009305960, WO2009144432, WO2009151383, WO2010015972;

MC4 receptor modulators (melanocortin-4 receptor modulators), as described, for example, in WO2009010299, WO2009074157;

orexin receptor 1 antagonists (OX1R antagonists), orexin receptor 2 antagonists (OX2R antagonists) or mixed OX1R/OX2R antagonists (e.g. 1-(2-methylbenzoxazol-6-yl)-3-[1,5]naphthyridin-4-ylurea hydrochloride (SB-334867-A), or those as described, for example, in WO200196302, WO200185693, WO2004085403, WO2005075458, WO2006067224, WO2007085718, WO2007088276, WO2007116374, WO2007122591, WO2007126934, WO2007126935, WO2008008517, WO2008008518, WO2008008551, WO2008020405, WO2008026149, WO2008038251, US2008132490, WO2008065626, WO2008078291, WO2008087611, WO2008081399, WO2008108991, WO2008107335, US2008249125, WO2008147518, WO2008150364, WO2009003993, WO2009003997, WO2009011775, WO2009016087, WO2009020642, WO2009058238, US2009186920, US2009203736, WO2009092642, WO2009100994, WO2009104155, WO2009124956, WO2009133522, WO2009156951, WO2010017260);

histamine H3 receptor antagonists/inverse agonists (e.g. 3-cyclohexyl-1-(4,4-dimethyl-1,4,6,7-tetrahydroimidazo [4.5-c]pyridin-5-yl)propan-1-one oxalic acid salt (WO 00/63208), or those as described in WO200064884, WO2005082893, WO2005123716, US2005171181 (e.g. PF-00389027), WO2006107661, WO2007003804, WO2007016496, WO2007020213, WO2007049798, WO2007055418, WO2007057329, WO2007062999, WO2007065820, WO2007068620, WO2007068641, WO2007075629, WO2007080140, WO2007082840, WO2007088450, WO2007088462, WO2007094962, WO2007099423, WO2007100990, WO2007105053, WO2007106349, WO2007110364, WO2007115938, WO2007131907, WO2007133561, US2007270440, WO2007135111, WO2007137955, US2007281923, WO2007137968, WO2007138431, WO2007146122, WO2008005338, WO2008012010, WO2008015125, WO2008045371, EPI 757594. WO2008068173, WO2008068174, US20080171753, WO2008072703, WO2008072724, US2008188484, US2008188486, US2008188487, WO2008109333, WO2008109336, WO2008126886, WO2008154126, WO2008151957, US2008318952, WO2009003003, WO2009013195, WO2009036132, WO2009039431, WO2009045313, WO2009058300, WO2009063953, WO2009067401, WO2009067405, WO2009067406, US2009163464, WO2009100120, WO2009105206, WO2009121812, WO2009126782, WO2010011653, WO2010011657);

histamine H1/histamine H3 modulators, for example betahistine or its dihydrochloride;

modulators of the histamine H3 transporter or of the histamine H3/serotonin transporter, as described; for example; in WO2008002816, WO2008002817, WO2008002818, WO2008002820;

modulators of vesicular monoamine transporter 2 (VMAT2); as described, for example, in WO2009126305;

histamine H4 modulators, as described, for example, in WO2007117399, US2009156613;

CRF antagonists (e.g. [2-methyl-9-(2,4,6-trimethylphenyl)-9H-1,3,9-triazafluoren-4-yl]dipropylamine (WO 00/66585) or those CRF1 antagonists as described in WO2007105113, WO2007133756, WO2008036541, WO2008036579, WO2008083070, WO2010015628, WO2010015655);

CRF BP antagonists (e.g. urocortin);

urocortin agonists;

modulators of the beta-3 adrenoceptor, for example 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as described in JP2006111553, WO2002038543, WO2002038544, WO2007048840-843, WO2008015558, EP1947103, WO2008132162;

MSH (melanocyte-stimulating hormone) agonists;

MCH (melanine-concentrating hormone) receptor antagonists (for example NBI-845, A-761, A-665798, A-798, ATC-0175, T-226296, T-71 (AMG-071, AMG-076), GW-856464, NGD-4715, ATC-0453, ATC-0759, GW-803430, or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649, WO2007092416; WO2007093363-366, WO2007114902, WO2007114916, WO2007141200, WO2007142217, US2007299062, WO2007146758, WO2007146759, WO2008001160, WO2008016811, WO2008020799, WO2008022979, WO2008038692, WO2008041090, WO2008044632, WO2008047544, WO2008061109, WO2008065021, WO2008068265, WO2008071646, WO2008076562, JP2008088120, WO2008086404, WO2008086409, US2008269110, WO2008140239, WO2009021740, US2009011994, US2009082359, WO2009041567, WO2009076387, WO2009089482, WO2009103478, WO2009119726, WO2009120655, WO2009123194, WO2009137270, WO2009146365, WO2009154132);

CCK-A (CCK-1) modulators (for example {2-[4-(4-chloro-2,5-dimethoxyphenyl)-5-(2-cyclohexylethyl)-thiazol-2-ylcarbamoyl]-5,7-dimethylindol-1-yl}acetic acid trifluoroacetic acid salt (WO 99/15525) or SR-146131 (WO 0244150) or SSR-125180) or those as described in WO2005116034, WO2007120655, WO2007120688, WO2007120718, WO2008091631;

serotonin reuptake inhibitors (e.g. dexfenfluramine), or those as described in WO2007148341, WO2008034142, WO2008081477, WO2008120761, WO2008141081, WO2008141082, WO2008145135, WO2008150848, WO2009043834, WO2009077858;

mixed serotonin/dopamine reuptake inhibitors (e.g. bupropion), or those as described in WO2008063673, or solid combinations of bupropion with naltrexone or bupropion with zonisamide;

mixed reuptake inhibitors, for example DOV-21947 or those as described in WO2009016214, WO2009016215, WO2009077584, WO2009098208, WO2009098209, WO2009106769, WO2009109517, WO2009109518, WO2009109519, WO2009109608, WO2009145357, WO2009149258;

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

mixed dopamine/norepinephrine/acetylcholine reuptake inhibitors (e.g. tesofensine), or those as described, for example, in WO2006085118, WO2008150480;

dopamine antagonists, as described, for example, in WO2008079838, WO2008079839, WO2008079847, WO2008079848;

norepinephrine reuptake inhibitors, as described, for example, in US2008076724, WO2009062318;

5-HT1A receptor modulators, as described, for example, in WO2009006227, WO2009137679, WO2009137732;

5-HT2A receptor antagonists, as described, for example, in WO2007138343;

5-HT2C receptor agonists (for example lorcaserine hydrochloride (APD-356) or BVT-933, or those as described in WO200077010, WO200077001-02, WO2005019180, WO2003064423, WO200242304, WO2005035533, WO2005082859, WO2006004937, US2006025601, WO2006028961, WO2006077025, WO2006103511, WO2007028132, WO2007084622, US2007249709; WO2007132841, WO2007140213, WO2008007661, WO2008007664, WO2008009125, WO2008010073, WO2008108445, WO2009063991, WO2009063992, WO2009063993, WO2009079765);

5-HT6 receptor modulators, for example E-6837, BVT-74316, PF-3246799 or PRX-07034, or those as described, for example, in WO2005058858, WO2007054257, WO2007107373, WO2007108569, WO2007108742-744, WO2008003703, WO2008027073, WO2008034815, WO2008054288, EP1947085, WO2008084491, WO2008084492, WO2008092665, WO2008092666, WO2008101247, WO2008110598, WO2008116831, WO2008116833, WO2008117169, WO2008136017, WO2008147812, EP2036888, WO2009013010, WO2009034581, WO2009053997, WO2009056632, WO2009073118, WO2009115515, WO2009135925, WO2009135927, WO2010000456, WO2010012806, EP2145887;

agonists of estrogen receptor gamma (ERRγ agonists), as described, for example, in WO2007131005, WO2008052709;

agonists of estrogen receptor alpha (ERRα/ERR1 agonists), as described, for example, in WO2008109727;

agonists of estrogen receptor beta (ERRβ agonists), as described, for example, in WO2009055734, WO2009100335, WO2009127686;

sigma-1 receptor antagonists, as described, for example, in WO2007098953, WO2007098961, WO2008015266, WO2008055932, WO2008055933, WO2009071657;

muscarin 3 receptor (M3R) antagonists, as described, for example, in WO2007110782, WO2008041184;

bombesin receptor agonists (BRS-3 agonists), as described, for example, in WO2008051404, WO2008051405, WO2008051406, WO2008073311;

galanin receptor antagonists;

growth hormone (e.g. human growth hormone or AOD-9604);

growth hormone releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734, WO2007127457, WO2008008286, WO2009056707;

growth hormone secretagogue receptor modulators (ghrelin modulators), for example WV-2959, WV-3002, WV-2810, WV-2951, or those as described in WO2006012577 (e.g. YIL-781 or YIL-870), WO2007079239, WO2008092681, WO2008145749, WO2008148853, WO2008148854, WO2008148856, WO2009047558, WO2009071283, WO2009115503;

TRH agonists (see, for example, EP 0 462 884);

decoupling protein 2 or 3 modulators (as described, for example, in WO2009128583);

chemical decouplers (e.g. WO2008059023, WO2008059024, WO2008059025, WO2008059026);

leptin receptor agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

leptin receptor modulators, as described, for example, in WO2009019427, WO2009071658, WO2009071668, WO2009071677, WO2009071678, WO2009147211, WO2009147216, WO2009147219, WO2009147221;

DA agonists (bromocriptin, bromocriptin mesylate, doprexin) or those as described in US2009143390;

lipase/amylase inhibitors (e.g. WO 00/40569, WO2008107184, WO2009049428, WO2009125819);

inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538, WO2007060140, JP2007131584, WO2007071966, WO2007126957, WO2007137103, WO2007137107, WO2007138304, WO2007138311, WO2007141502, WO2007141517, WO2007141538, WO2007141545, WO2007144571, WO2008011130, WO2008011131, WO2008039007, WO2008048991, WO2008067257, WO2008099221, WO2008129319, WO2008141976, WO2008148840, WO2008148849, WO2008148851, WO2008148868, WO2009011285, WO2009016462, WO2009024821, US2009076275, WO2009040410, WO2009071483, WO2009081195, WO2009119534, WO2009126624, WO2009126861, WO2010007046, WO2010017040;

inhibitors of monoacylglycerol acyltransferase (2-acylglycerol O-acyltransferase; MGAT), as described, for example, in WO2008038768;

inhibitors of fatty acid synthase (FAS), for example C75, or those as described in WO2004005277, WO2008006113;

inhibitors of stearoyl-CoA delta9 desaturase (SCD1), as described, for example, in WO2007009236, WO2007044085, WO2007046867, WO2007046868, WO20070501124, WO2007056846, WO2007071023, WO2007130075, WO2007134457, WO2007136746, WO2007143597, WO2007143823, WO2007143824, WO2008003753, WO2008017161, WO2008024390, WO2008029266, WO2008036715, WO2008043087, WO2008044767, WO2008046226, WO2008056687, WO2008062276, WO2008064474, WO2008074824, WO2008074832, WO2008074833, WO2008074834, WO2008074835, WO2008089580, WO2008096746, WO2008104524, WO2008116898, US2008249100, WO2008120744, WO2008120759, WO2008123469, WO2008127349, WO2008128335, WO2008135141, WO2008139845, WO2008141455, US20080255130, US2008255161, WO2008141455, WO2009010560, WO2009016216, WO2009012573, WO2009024287, JP2009019013, WO2009037542, WO2009056556, WO2009060053, WO2009060054, WO2009070533, WO2009073973, WO2009103739, WO2009117659, WO2009117676, US2009253693, US2009253738, WO2009124259, WO2009126123, WO2009126527, WO2009129625, WO2009137201, WO2009150196, WO2009156484, WO2010006962, WO2010007482;

inhibitors of fatty acid desaturase 1 (delta5 desaturase), as described, for example, in WO2008089310;

inhibitors of monoglyceride lipase (MGL), as described in WO2008145842;

hypoglycemic/hypertriglyceridemic indoline compounds, as described in WO2008039087, WO2009051119;

inhibitors of "adipocyte fatty acid-binding protein aP2", for example BMS-309403 or those as described in WO2009028248;

activators of adiponectin secretion, as described, for example, in WO2006082978, WO2008105533, WO2008136173;

promoters of adiponectin production, as described, for example, in WO2007125946, WO2008038712;

modified adiponectins, as described, for example, in WO2008121009;

oxyntomodulin or analogs thereof (for example, TKS-1225);

oleoyl-estrone or agonists or partial agonists of the thyroid hormone receptor (thyroid hormone receptor agonists), for example: KB-2115 (eprotirome), QRX-431 (sobetirome) or DITPA, or those as described in WO20058279, WO200172692, WO200194293, WO2003084915, WO2004018421, WO2005092316, WO2007003419, WO2007009913, WO2007039125, WO2007110225, WO2007110226, WO2007128492, WO2007132475, WO2007134864, WO2008001959, WO2008106213, JP2009155261;

or agonists of the thyroid hormone receptor beta (TR-beta), for example MB-07811 or MB-07344, or those as described in WO2008062469.

In one embodiment of the invention, the compound of the formula I is administered in combination with a combination of eprotirome with ezetimibe.

In one embodiment of the invention, the compound of the formula I is administered in combination with an inhibitor of site-1 protease (SIP), for example PF-429242.

In a further embodiment of the invention, the compound of the formula I is administered in combination with a modulator of the "trace amine associated receptor 1" (TAAR, as described, for example, in US2008146523, WO2008092785.

In one embodiment of the invention, the compound of the formula I is administered in combination with an inhibitor of growth factor receptor bound protein 2 (GRB2), as described, for example, in WO2008067270.

In a further embodiment of the invention, the compound of the formula I is administered in combination with an RNAi (siRNA) therapeutic agent directed against PCSK9 (proprotein convertase subtilisin/kexin type 9).

In one embodiment, the compound of the formula I is administered in combination with Omacor® or Lovaza™ (omega-3 fatty acid ester; highly concentrated ethyl ester of eicosapentaenoic acid and of docosahexaenoic acid).

In one embodiment, the compound of the formula is administered in combination with lycopene.

In one embodiment of the invention, the compound of the formula I is administered in combination with an antioxidant, for example OPC-14117, AGI-1067 (succinobucol), probucol, tocopherol, ascorbic acid, β-carotene or selenium, or those as described in WO2009135918.

In one embodiment of the invention, the compound of the formula I is administered in combination with a vitamin, for example vitamin B6 or vitamin B12.

In one embodiment, the compound of the formula I is administered in combination with more than one of the aforementioned compounds, for example in combination with a sulfonylurea and metformin, a sulfonylurea and acarbose, repaglinide and metformin (PrandiMet™), insulin and a sulfonylurea, insulin and metformin, insulin and troglitazone, insulin and lovastatin, etc.

In a further embodiment, the compound of the formula I is administered in combination with an activator of soluble guanylate cyclase (sGC), as described, for example, in WO2009032249.

In another embodiment, the compound of the formula I is administered in combination with an inhibitor of carboanhydrase type 2 (carbonic anhydrase type 2), for example those as described in WO2007065948, WO2009050252.

In another embodiment, the compound of the formula is administered in combination with topiramat or a derivative thereof, as described in WO2008027557, US2009304789.

In a further embodiment, the compound of the formula I is administered in combination with a solid combination of topiramat with phentermin (Qnexa™).

In a further embodiment, the compound of the formula I is administered in combination with an antisense compound, e.g. ISIS-377131, which inhibits the production of the glucocorticoid receptor.

In another embodiment, the compound of the formula I is administered in combination with an aldosterone synthase inhibitor and an antagonist of the glucocorticoid receptor, a cortisol synthesis inhibitor and/or an antagonist of the corticotropin releasing factor, as described, for example, in EP1886695, WO2008119744.

In one embodiment, the compound of the formula I is administered in combination with an agonist of the RUP3 receptor, as described, for example, in WO2007035355, WO2008005576.

In another embodiment, the compound of the formula I is administered in combination with an activator of the gene which codes for ataxia telangiectasia mutated (ATM) protein kinase, for example chloroquine.

In one embodiment, the compound of the formula I is administered in combination with a tau protein kinase 1 inhibitor (TPK1 inhibitor), as described, for example, in WO2007119463, WO2009035159, WO2009035162.

In one embodiment, the compound of the formula I is administered in combination with a "c-Jun N-terminal kinase" inhibitor (JNK inhibitor), for example B1-78D3 or those as described, for example, in WO2007125405, WO2008028860, WO2008118626.

In one embodiment, the compound of the formula I is administered in combination with an endothelin A receptor antagonist, for example avosentan (SPP-301).

In one embodiment, the compound of the formula I is administered in combination with inhibitors of neutral endopeptidase (NEP inhibitors), as described, for example, in WO2009138122, WO2009135526.

In one embodiment, the compound of the formula I is administered in combination with modulators of the glucocorticoid receptor (GR), for example KB-3305 or those compounds as described, for example, in WO2005090336, WO2006071609, WO2006135826, WO2007105766, WO2008120661, WO2009040288, WO2009058944, WO2009108525, WO2009111214.

In one embodiment, the further active ingredient is varenicline tartrate, a partial agonist of the alpha 4-beta 2 nicotinic acetylcholine receptor.

In one embodiment, the further active ingredient is an agonist of the alpha 7-nicotinic acetylcholine receptor, as described, for example, in WO2009018551, WO2009071519, WO2009071576, WO2009071577.

In one embodiment, the further active ingredient is trodusquemine.

In one embodiment, the further active ingredient is a modulator of the enzyme SIRT1 and/or SIRT3 (an $NAD^+$-dependent protein deacetylase); this active ingredient may, for example, be resveratrol in suitable formulations, or those compounds as specified in WO2007019416 (e.g. SRT-1720), WO2008073451, WO2008156866, WO2008156869, WO2009026701, WO2009049018, WO2009058348, WO2009061453, WO2009134973, WO2009146358, WO2010003048.

In one embodiment of the invention, the further active ingredient is DM-71 (N-acetyl-L-cysteine with bethanechol).

In one embodiment, the compound of the formula I is administered in combination with antihypercholesterolemic compounds, as described, for example, in WO2004000803, WO2006000804, WO2004000805, WO2004087655, WO2005113496, WO2007059871, WO2007107587, WO2007111994, WO2008052658, WO2008106600, WO2008113796, US2008280836, WO2009113952, US2009312302.

In a further embodiment, the compound of the formula I is administered in combination with inhibitors of SREBP (sterol regulatory element-binding protein), for example fatostatin, or those as described, for example, in WO2008097835.

In another embodiment, the compound of the formula I is administered in combination with a cyclic peptide agonist of the VPAC2 receptor, as described, for example, in WO2007101146, WO2007133828.

In a further embodiment, the compound of the formula I is administered in combination with an agonist of the endothelin receptor, as described, for example, in WO2007112069.

In a further embodiment, the compound of the formula I is administered in combination with AKP-020 (bis(ethylmaltolato)oxovanadium(IV)).

In another embodiment, the compound of the formula I is administered in combination with tissue-selective androgen receptor modulators (SARM), as described, for example, in WO2007099200, WO2007137874.

In a further embodiment, the compound of the formula I is administered in combination with an AGE (advanced glycation endproduct) inhibitor, as described, for example, in JP2008024673.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment of the invention, the further active ingredient is meterleptin (recombinant methionyl-leptin) combined with pramlintide.

In a further embodiment of the invention, the further active ingredient is the tetrapeptide ISF-402.

In one embodiment, the further active ingredient is dexamphetamine or amphetamine.

In one embodiment, the further active ingredient is fenfluramine or dexfenfluramine. In another embodiment, the further active ingredient is sibutramine or those derivatives as described in WO2008034142.

In one embodiment, the further active ingredient is mazindol or phentermin.

In a further embodiment, the further active ingredient is geniposidic acid (WO2007100104) or derivatives thereof (JP2008106008).

In another embodiment, the further active ingredient is a neuropeptide FF2 agonist, as described, for example, in WO2009038012.

In one embodiment, the further active ingredient is a nasal calcium channel blacker, for example diltiazem, or those as described in U.S. Pat. No. 7,138,107.

In one embodiment, the further active ingredient is an inhibitor of sodium-calcium ion exchange, for example those as described in WO2008028958, WO2008085711.

In a further embodiment, the further active ingredient is a blocker of calcium channels, for example of CaV3.2 or CaV2.2, as described in WO2008033431, WO2008033447, WO2008033356, WO2008033460, WO2008033464, WO2008033465, WO2008033468, WO2008073461.

In one embodiment, the further active ingredient is a modulator of a calcium channel, for example those as described in WO2008073934, WO2008073936, WO2009107660.

In one embodiment, the further active ingredient is an inhibitor of the calcium metabolism, for example those as described in US2009124680.

In one embodiment, the further active ingredient is a blacker of the "T-type calcium channel", as described, for example, in WO2008033431, WO2008110008, US2008280900, WO2008141446, US2009270338, WO2009146540, US2009325979, WO2009146539.

In one embodiment, the further active ingredient is an inhibitor of KCNQ potassium channel 2 or 3, for example those as described in US2008027049, US2008027090.

In one embodiment, the further active ingredient is a modulator of KCNN potassium channel 1, 2 or 3 (modulators of the SK1, SK2 and/or SK3 channel), for example those as described in US2009036475.

In one embodiment, the further active ingredient is an inhibitor of the potassium Kv1.3 on channel, for example those as described in WO2008040057, WO2008040058, WO2008046065, WO2009043117.

In one embodiment, the further active ingredient is a potassium channel modulator, for example those as described in WO2008135447, WO2008135448, WO2008135591, WO2009099820.

In a further embodiment, the further active ingredient is a hyperpolarization-activated cyclic nucleotide-gated (HON) potassium-sodium channel inhibitor, for example those as described in US2009069296.

In another embodiment, the further active ingredient is an inhibitor of the sodium-potassium-2 chloride (NKCCl) cotransporter, for example those as described in WO2009130735.

In another embodiment, the further active ingredient is a voltage-gated sodium channel inhibitor, for example those as described in WO2009049180, WO2009049181.

In another embodiment, the further active ingredient is a modulator of the MCP-1 receptor (monocyte chemoattractant protein-1 (MCP-1)), for example those as described in WO2008014360, WO2008014381.

In one embodiment, the further active ingredient is a modulator of somatostatin receptor 3 (SSTR3), for example those as described in WO2009011836.

In one embodiment, the further active ingredient is a modulator of somatostatin receptor 5 (SSTR5), for example those as described in WO2008019967, US2008064697, US2008249101, WO2008000692, US2008293756, WO2008148710.

In one embodiment, the further active ingredient is a modulator of somatostatin receptor 2 (SSTR2), for example those as described in WO2008051272.

In one embodiment, the further active ingredient is a compound which is capable of reducing the amount of retinal-binding protein 4 (RBP4), for example those as described in WO2009051244, WO2009145286.

In one embodiment, the further active ingredient is an erythropoietin-mimetic peptide which acts as an erythropoietin (EPO) receptor agonist. Such molecules are described, for example, in WO2008042800.

In a further embodiment, the further active ingredient is an anorectic/a hypoglycemic compound, for example those as described in WO2008035305, WO2008035306, WO2008035686.

In one embodiment, the further active ingredient is an inductor of lipoic acid synthetase, for example those as described in WO2008036966, WO2008036967.

In one embodiment, the further active ingredient is a stimulator of endothelial nitric oxide synthase (eNOS), for example those as described in WO2008058641, WO2008074413.

In one embodiment, the further active ingredient is a modulator of carbohydrate and/or lipid metabolism, for example those as described in WO2008059023, WO2008059024, WO2008059025, WO2008059026.

In a further embodiment, the further active ingredient is an angiotensin receptor antagonist, for example those as described in WO2008062905, WO2008067378, WO2008062905.

In one embodiment, the further active ingredient is an agonist of the sphingosine 1-phosphate receptor (SIP), for example those as described in WO2008064315, WO2008074820, WO2008074821, WO2008135522, WO2009019167, WO2009043013, WO2009080663, WO2009085847, WO2009151529, WO2009151621, WO2009151626, WO2009154737.

In one embodiment, the further active ingredient is an agent which retards gastric emptying, for example 4-hydroxyisoleucine (WO2008044770).

In one embodiment, the further active ingredient is a tryptophan-5-hydroxylase inhibitor-1 (TPH1 inhibitor), which modulates gastrointestinal motility, as described, for example, in WO2009014972.

In one embodiment, the further active ingredient is a muscle-relaxing substance, as described, for example, in WO2008090200.

In a further embodiment, the further active ingredient is an inhibitor of monoamine oxidase B (MAO-B), for example those as described in WO2008092091, WO2009066152.

In a further embodiment, the further active ingredient is an inhibitor of monoamine oxidase A (MAO-A), for example those as described in WO2009030968.

In another embodiment, the further active ingredient is an inhibitor of the binding of cholesterol and/or triglycerides to the SCP-2 protein (sterol carrier protein-2), for example those as described in US2008194658.

In a further embodiment, the further active ingredient is a compound which binds to the β-subunit of the trimeric GTP-binding protein, for example those as described in WO2008126920.

In one embodiment, the further active ingredient is a urate anion exchanger inhibitor 1, as described, for example, in WO2009070740.

In one embodiment, the further active ingredient is a modulator of the ATP transporter, as described, for example, in WO2009108657.

In another embodiment, the further active ingredient is lisofyiline, which prevents autoimmune damage to insulin-producing cells.

In yet another embodiment, the further active ingredient is an extract from *Bidens pilosa* with the ingredient cytopiloyne as described in EP1955701.

In one embodiment, the further active ingredient is an inhibitor of glucosylceramide synthase, as described, for example, in WO2008150486.

In a further embodiment of the invention, the further active ingredient is a glycosidase inhibitor, as described, for example, in WO2009117829, WO2009155753.

In another embodiment, the further active ingredient is an ingredient from the plant *Hoodia Gordonii*, as described in US2009042813, EP2044852.

In one embodiment, the further active ingredient is an antidiabetic, for example D-tagatose.

In one embodiment, the further active ingredient is a zinc complex of curcumin, as described in WO2009079902.

In one embodiment, the further active ingredient is an inhibitor of the "cAMP response element binding protein" (CREB), as described in WO2009143391.

In another embodiment, the further active ingredient is an antagonist of the bradykinin B1 receptor, as described in WO2009124746.

In a further embodiment, the further active ingredient is a compound which is capable of modulating diabetic peripheral neuropathy (DPN). Such modulators are, for example, FK-1706 or SB-509, or those as described in WO1989005304, WO2009092129, WO2010002956.

In one embodiment, the further active ingredient is a compound which is capable of modulating diabetic nephropathy. Such compounds are described, for example, in WO2009089545, WO2009153261.

In one embodiment, the further active ingredient is an inhibitor (e.g. an anti-CD38 antibody) of CD38, as described in US2009196825.

In one embodiment, the further active ingredient is an inhibitor of human fibroblast growth factor receptor 4 (FGFR4), as described, for example, in WO2009046141.

In a further embodiment of the invention, the further active ingredient is a compound which protects the beta cell, for example 14-alpha-lipolyl-andrographolide (AL-1).

In yet another embodiment of the invention, the further active ingredient is the INGAP (islet neogenesis associated protein) peptide, a peptide which reestablishes insulin production in patients with diabetes mellitus.

In one embodiment of the invention, the further active ingredient is a modulator of the CFTR (cystic fibrosis transmembrane conductance regulator), as described, for example, in US2009246137, US2009264433, US2009264441, US2009264471, US2009264481, US2009264486, WO2010019239.

In one embodiment of the invention, the further active ingredient is a compound which stimulates/modulates insulin release, for example those as described in WO2009109258, WO2009132739, US2009281057, WO2009157418.

In one embodiment of the invention, the further active ingredient is an extract from *Hippophae rhamnoides*, as described, for example, in WO2009125071.

In one embodiment of the invention, the further active ingredient is an from *Huanglian* and *Ku Ding Cha*, as described, for example, in WO2009133458.

In another embodiment, the further active ingredient is a root extract from *Cipadessa baccifera*, as described in US2009238900.

In one embodiment of the invention, the further active ingredients are borapetoside A and/or borapetoside C, which can be isolated from the plant SDH-V, a species of *Tinospora crispa*, as described, for example, in US2010016213.

In one embodiment, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 September-October), 18(5), 230-6), Caromax® is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered within the scope of protection conferred by the present invention.

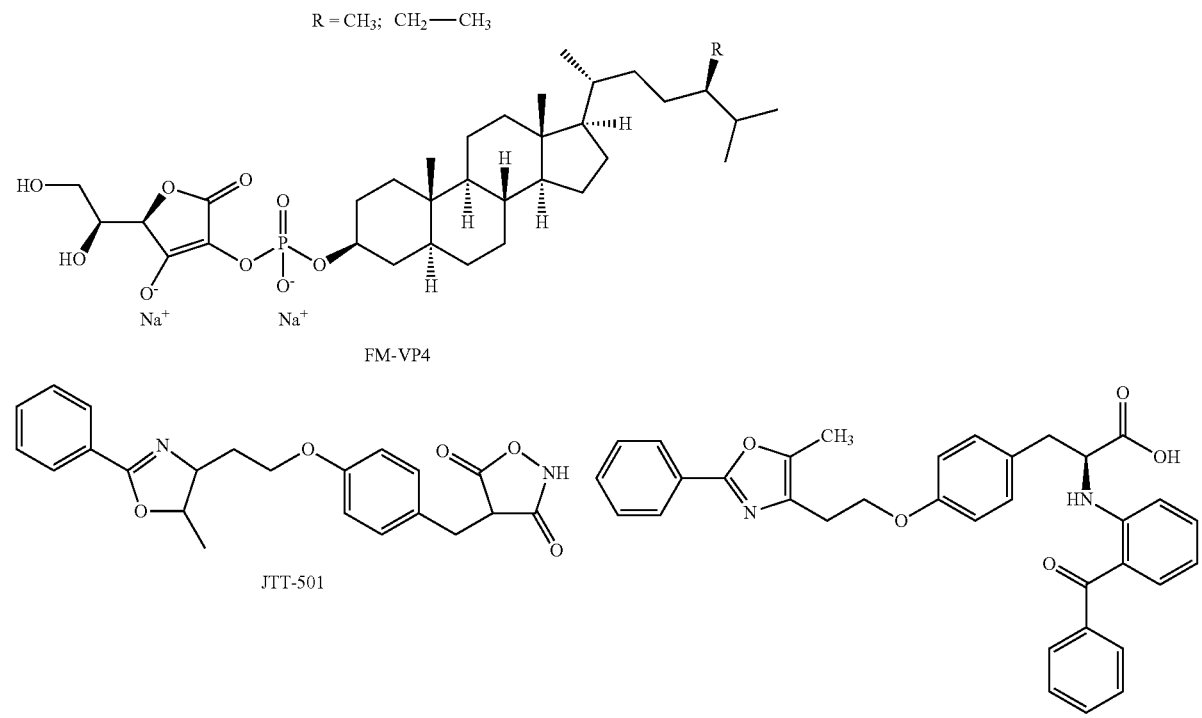

-continued
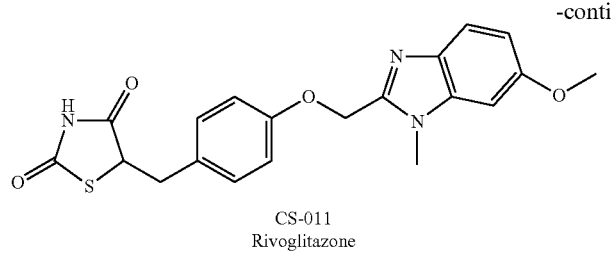
CS-011
Rivoglitazone
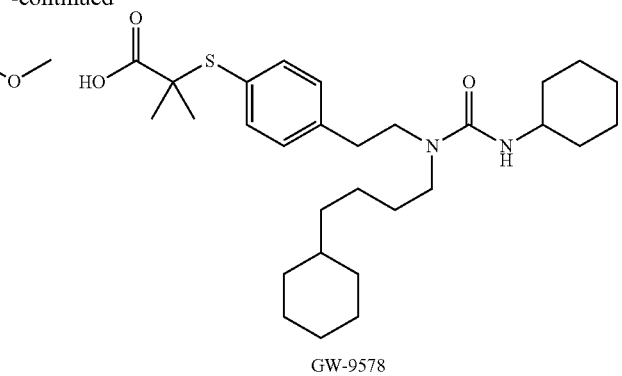
GW-9578
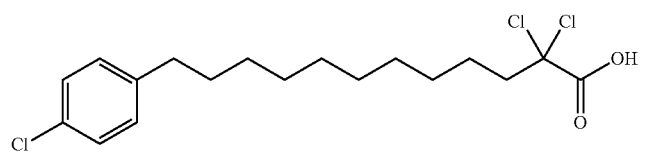
K-111
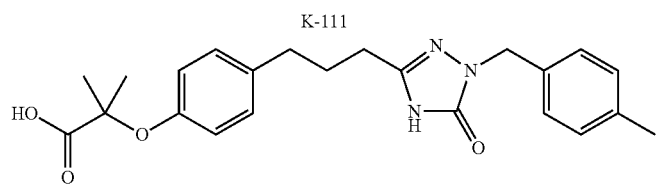
LY-518674
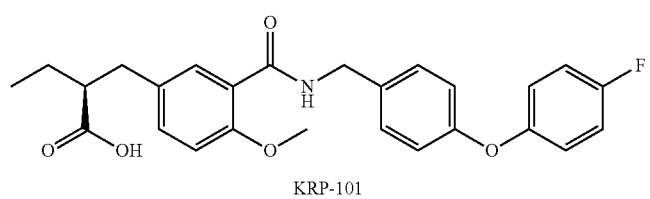
KRP-101
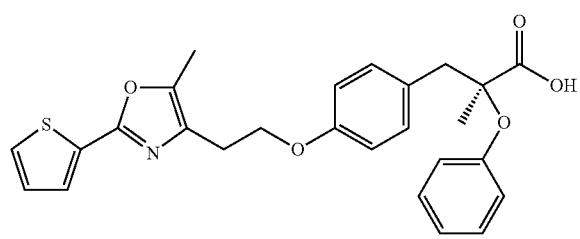
LY-510929
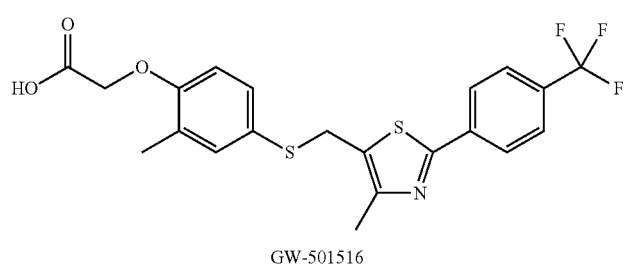
GW-501516

-continued
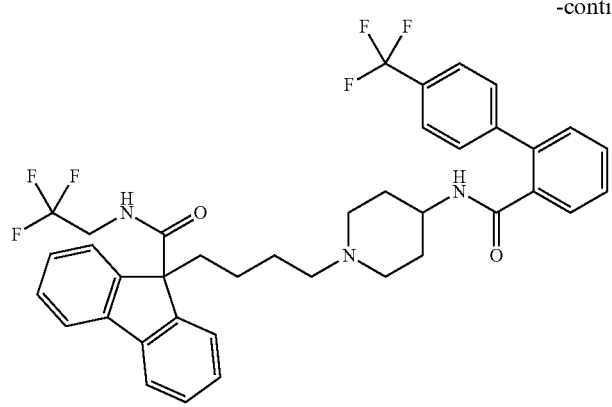
BMS-201038
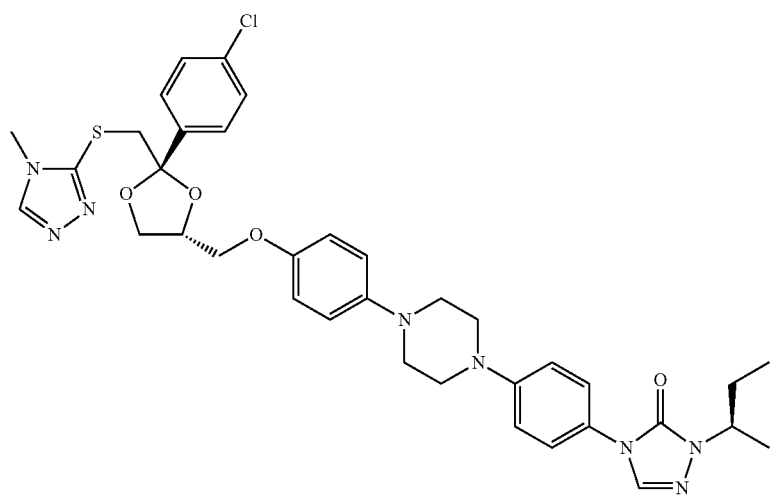
R-103757
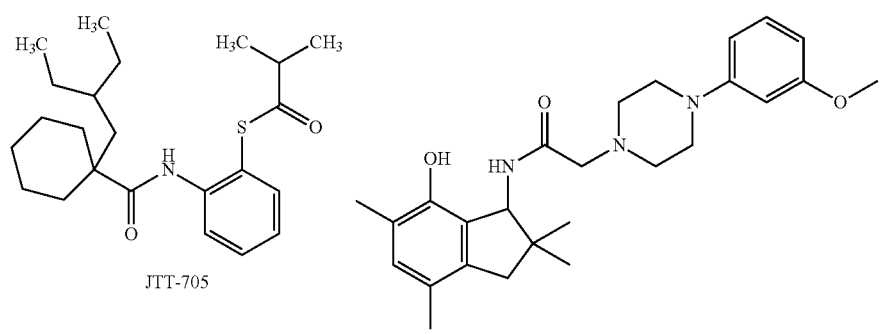
JTT-705    OPC-14117
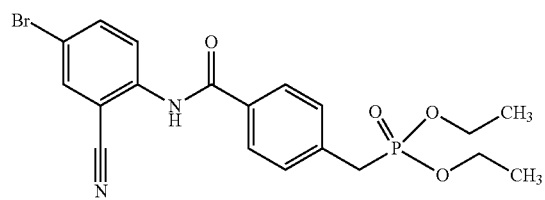
NO-1886
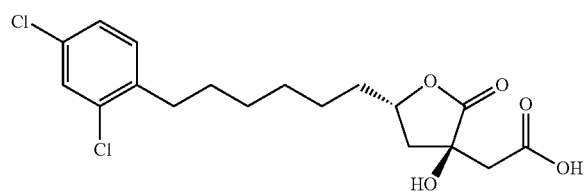
SB-204990

181
-continued
182
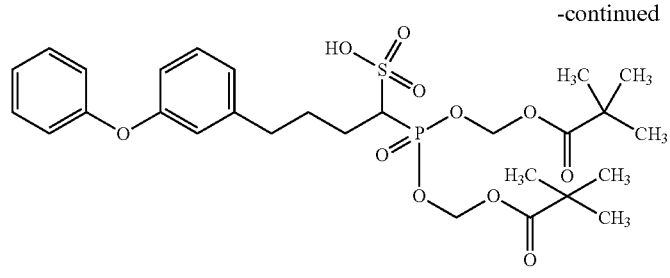
BMS-188494
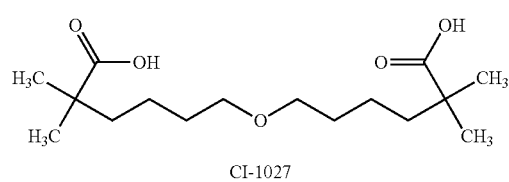
CI-1027
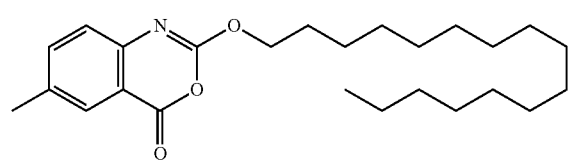
ATL-962
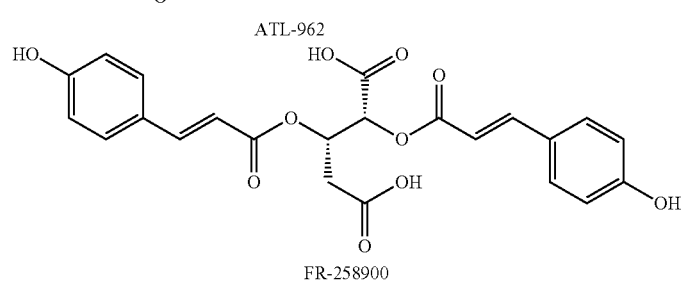
FR-258900
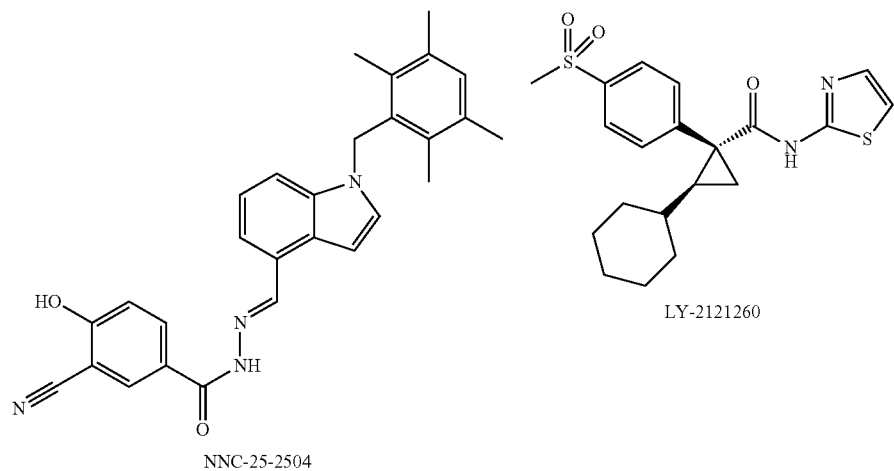
NNC-25-2504
LY-2121260
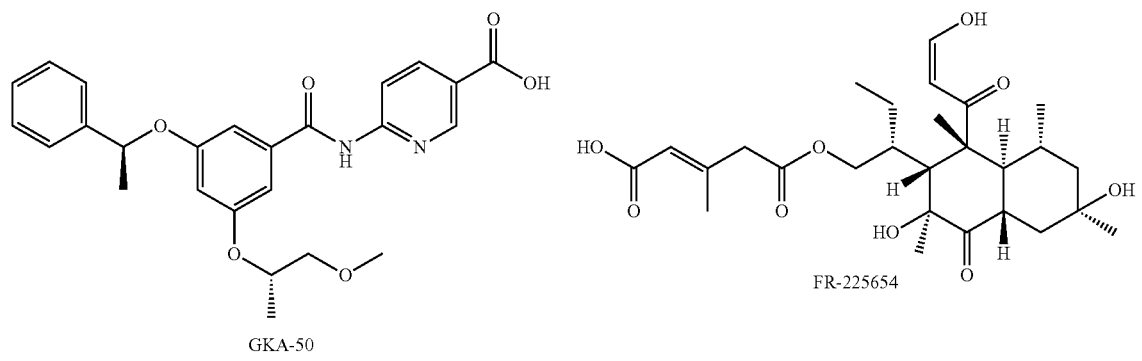
GKA-50
FR-225654

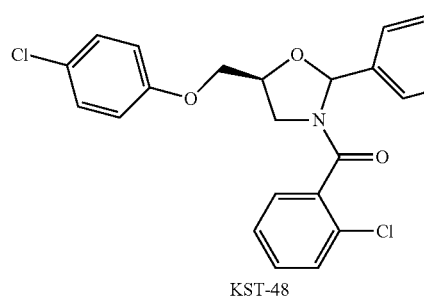
KST-48
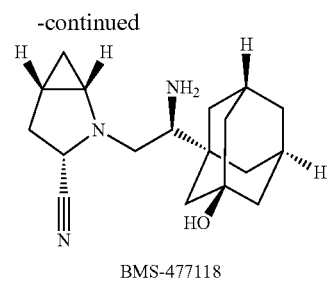
BMS-477118
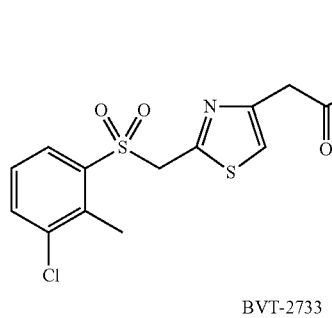
BVT-2733
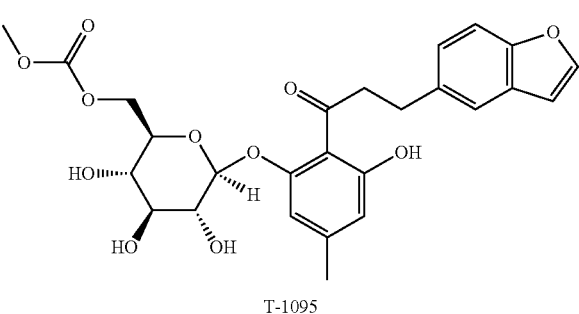
T-1095
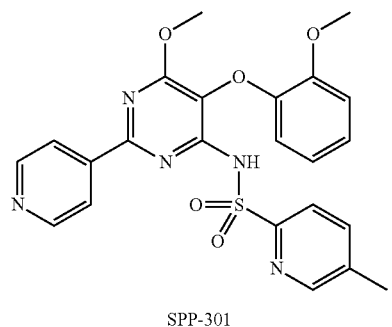
SPP-301
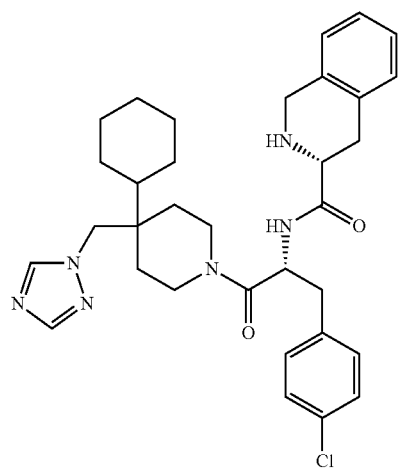
THIQ
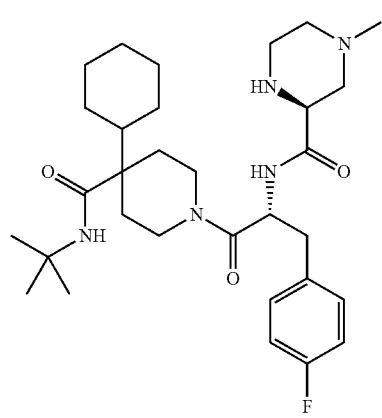
MB243
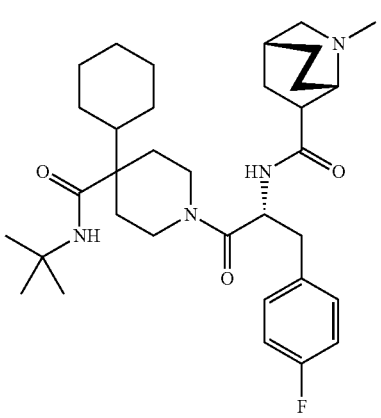
RY764

-continued
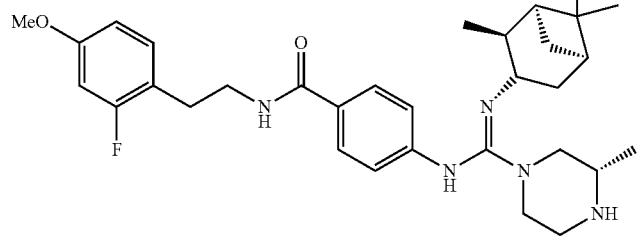
CHIR-785
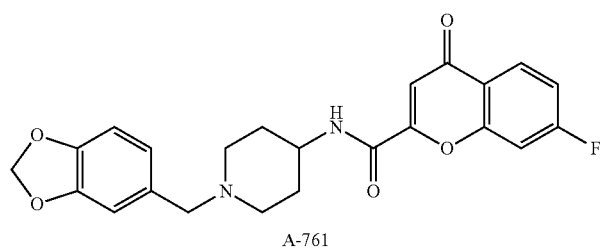
A-761
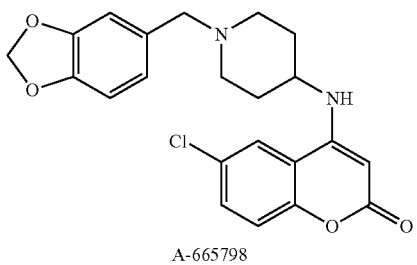
A-665798
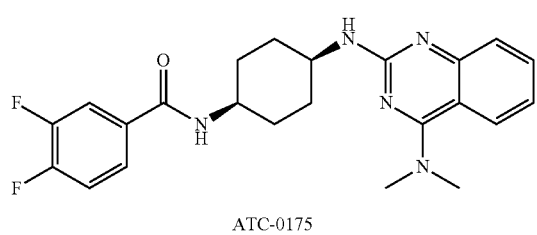
ATC-0175
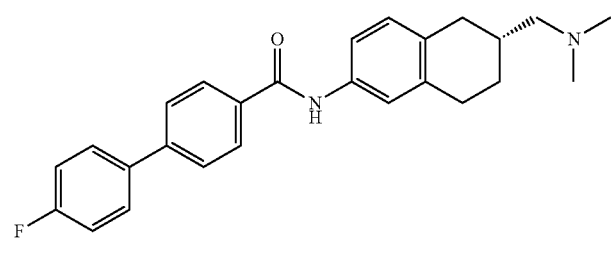
T-226296
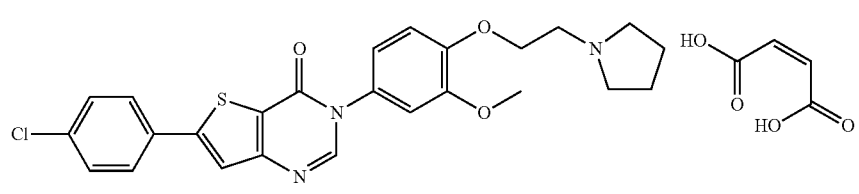
GW-803430
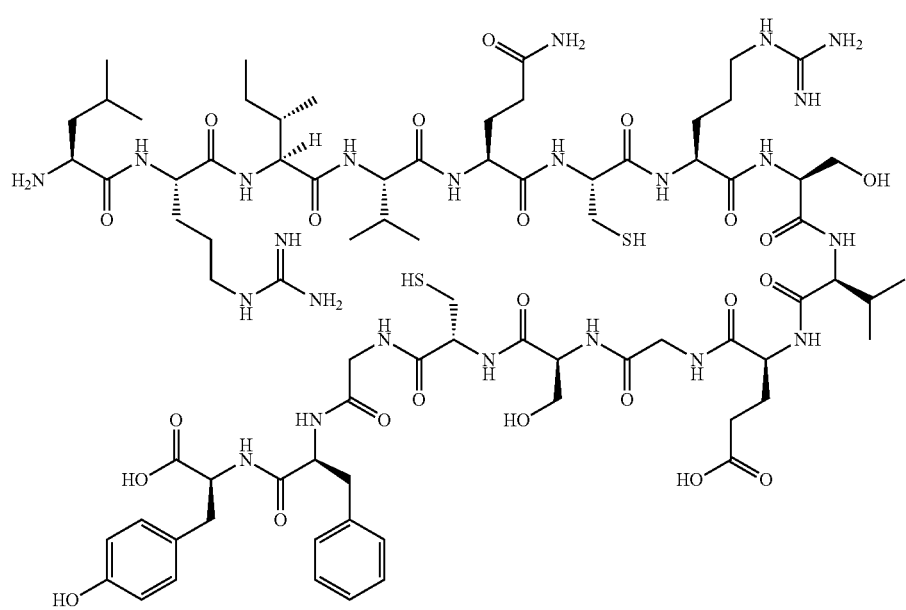
AOD-9604

-continued
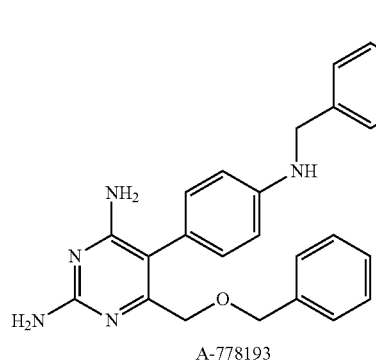
A-778193
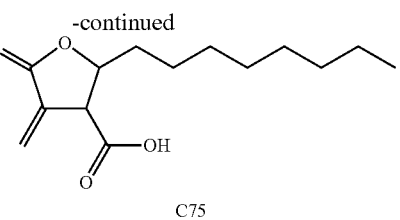
C75
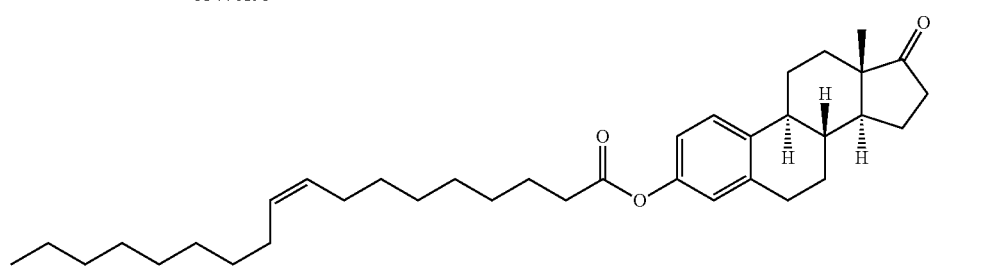
Oleoyl-Estron
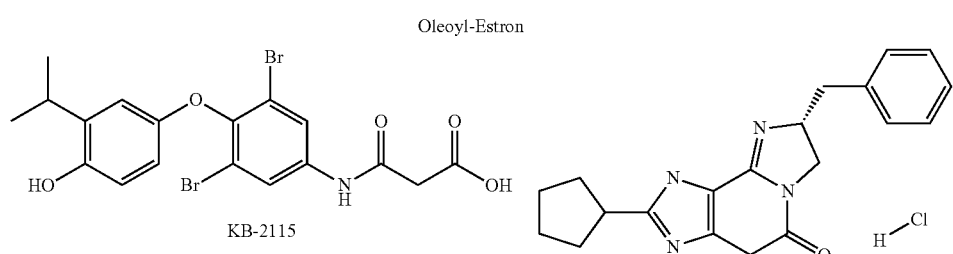
KB-2115
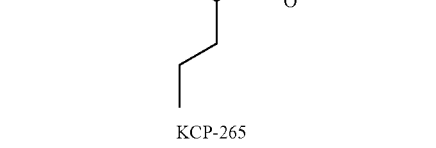
KCP-265
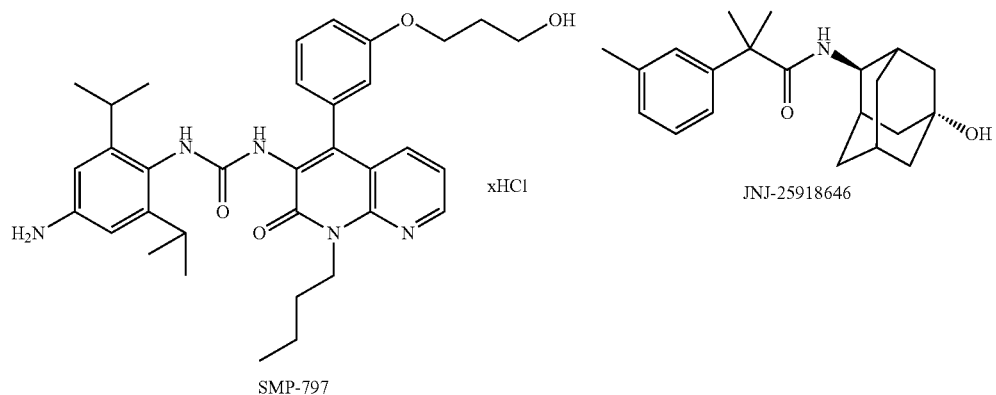
SMP-797  xHCl
JNJ-25918646
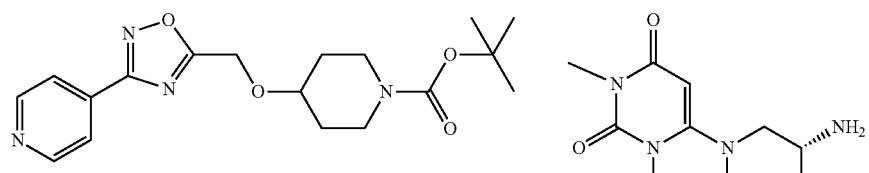
PSN-632408
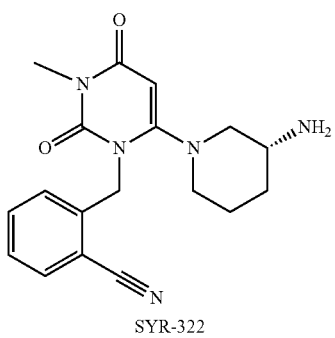
SYR-322

-continued
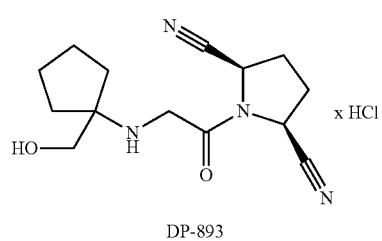
DP-893
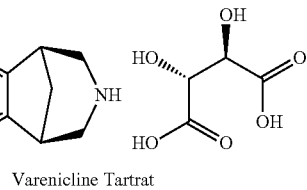
Varenicline Tartrat
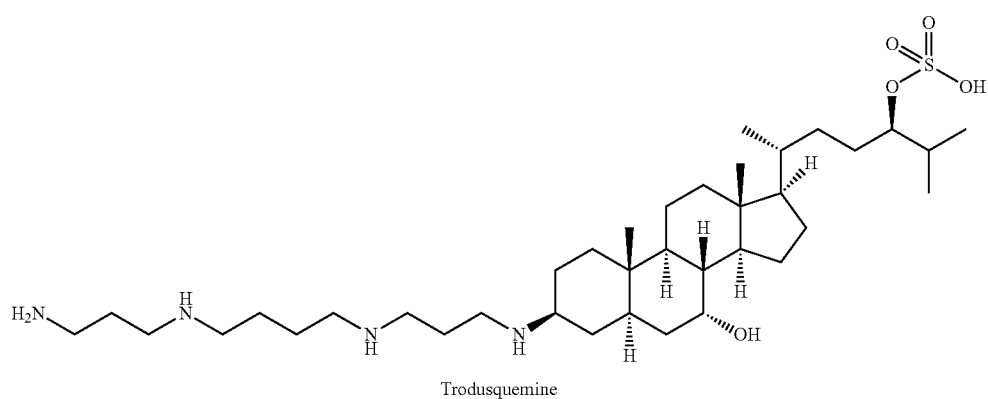
Trodusquemine
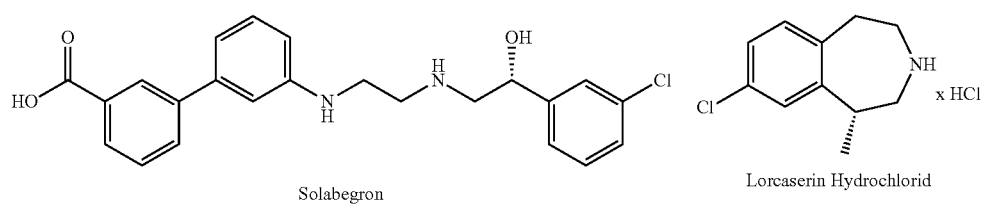
Solabegron                    Lorcaserin Hydrochlorid
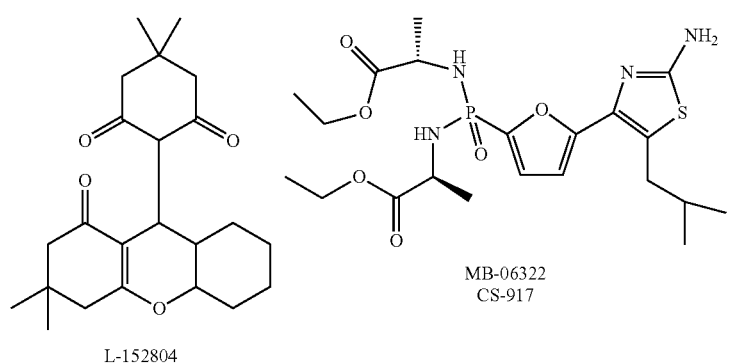
L-152804            MB-06322
                    CS-917
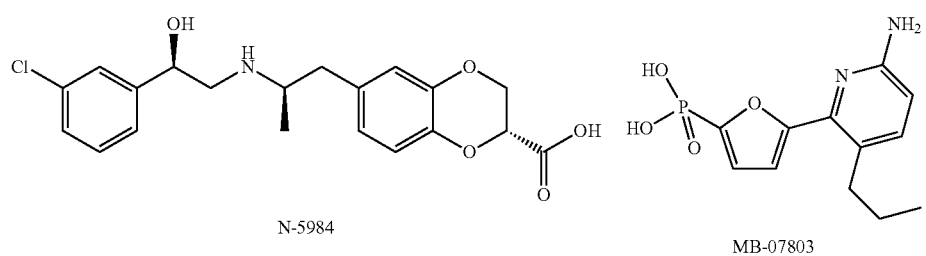
N-5984                  MB-07803

191 192
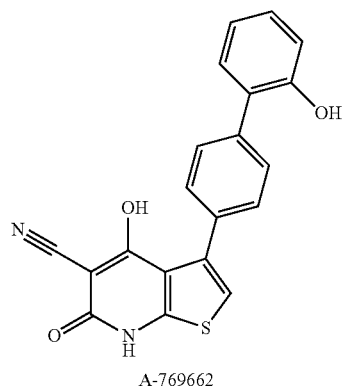
A-769662
-continued
BIM-51077
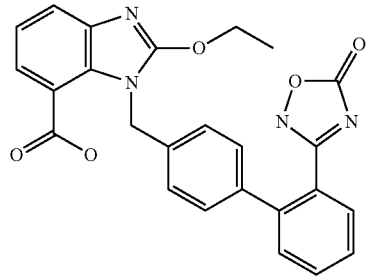
TAK-536
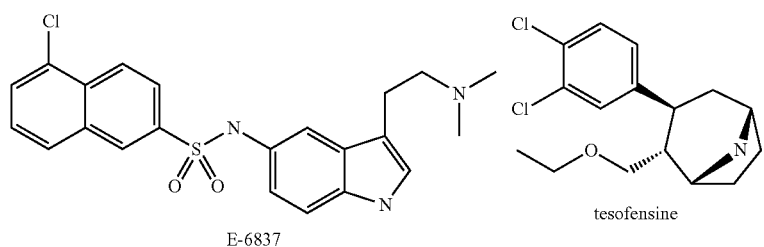
E-6837
tesofensine
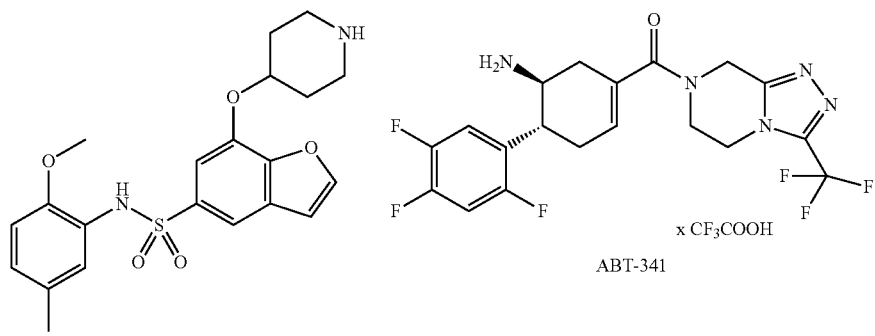
BVT-74316
ABT-341
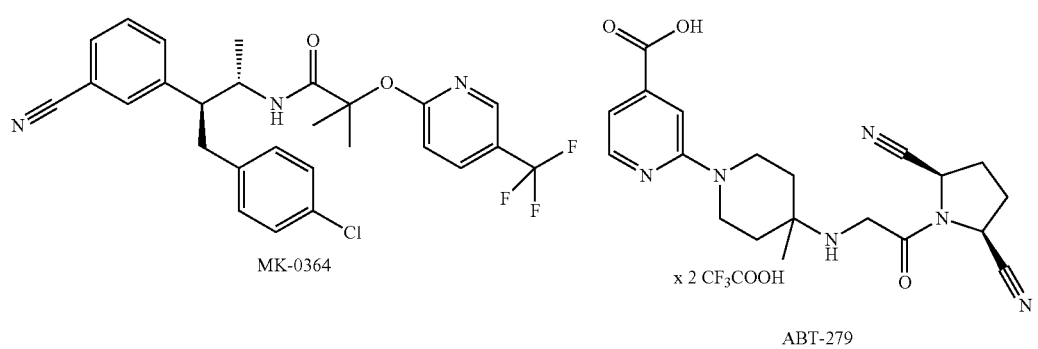
MK-0364
ABT-279

193
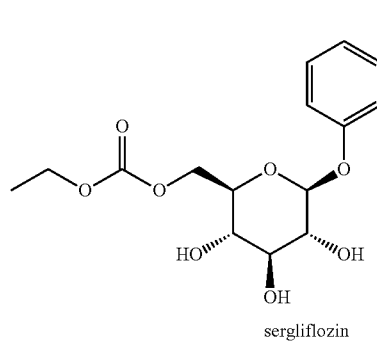
sergliflozin
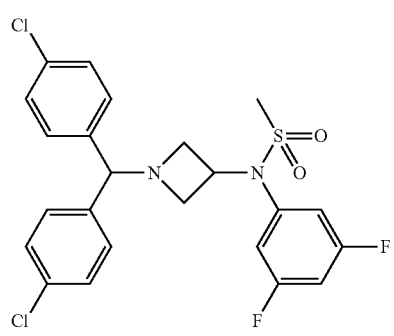
AVE 1625 (proposed INN:drinabant)
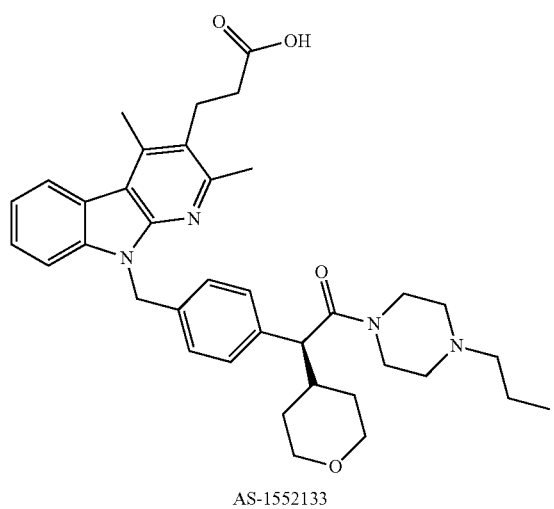
AS-1552133
194
-continued
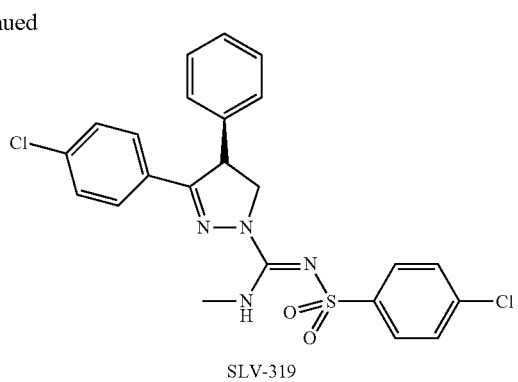
SLV-319
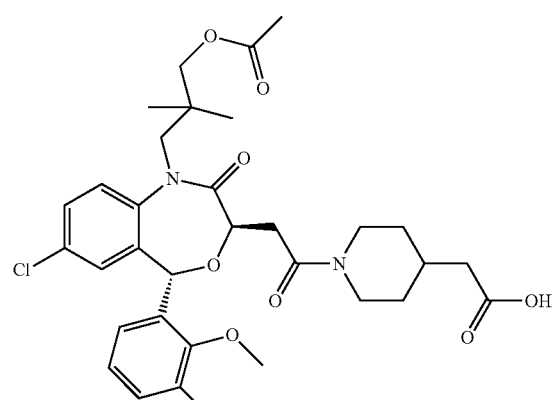
TAK-475 (lapaquistat acetate)
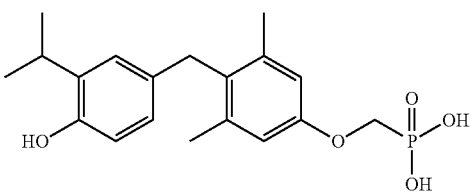
MB-07344
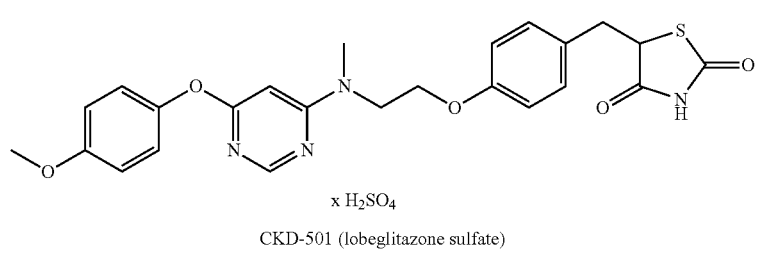
x H₂SO₄
CKD-501 (lobeglitazone sulfate)

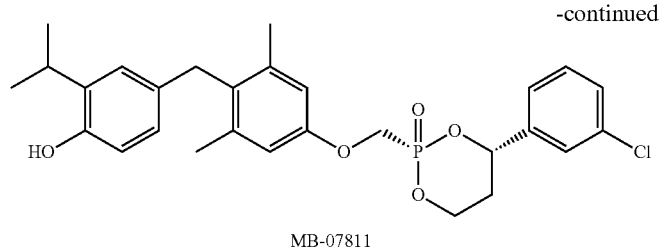
MB-07811
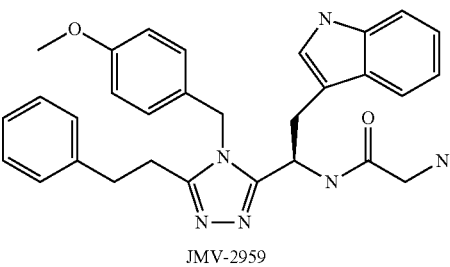
JMV-2959
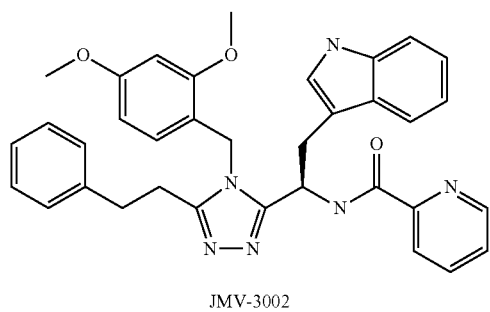
JMV-3002
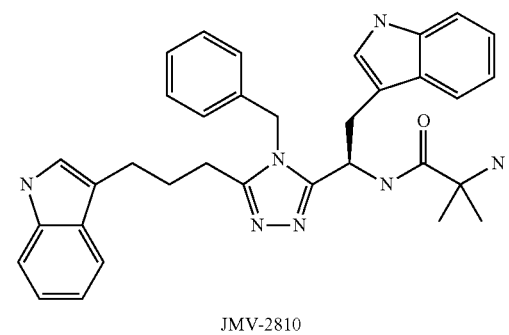
JMV-2810
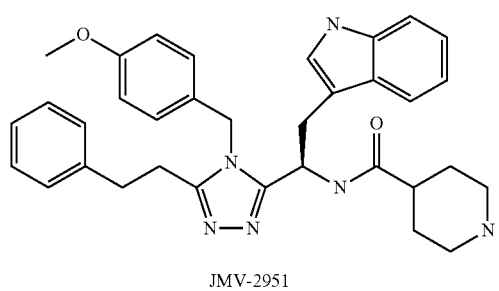
JMV-2951
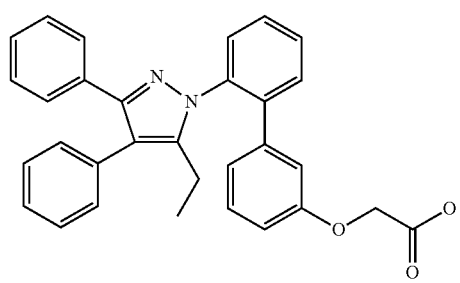
BMS-309403
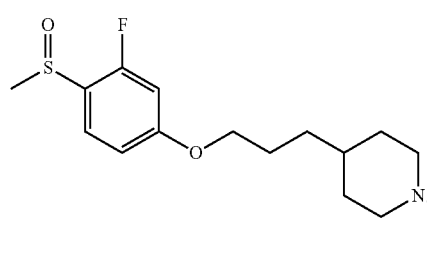
PSN-119-1
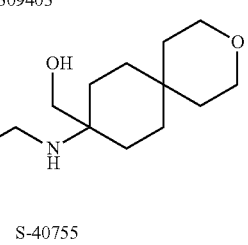
S-40755
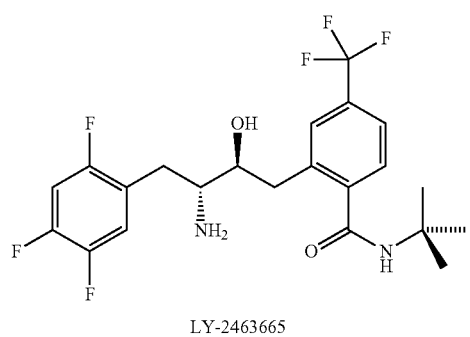
LY-2463665
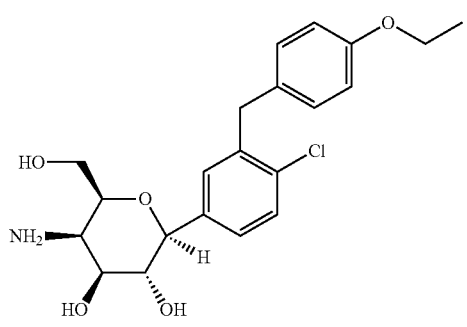
dapagliflozin, BMS-512148

-continued
197
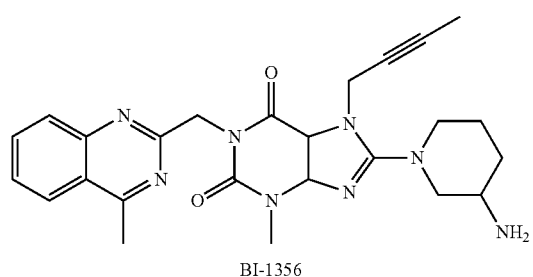
BI-1356
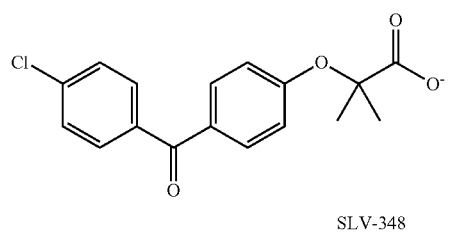
SLV-348
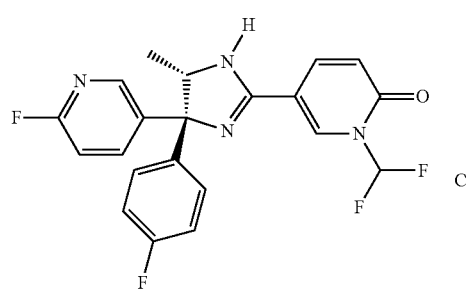
"NPY-5-BY"
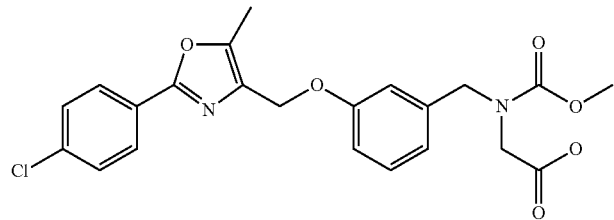
BMS-687453
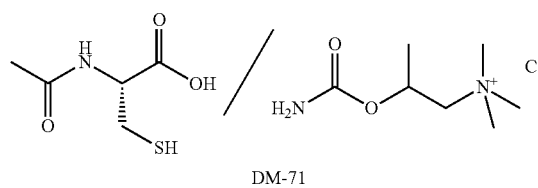
DM-71
198
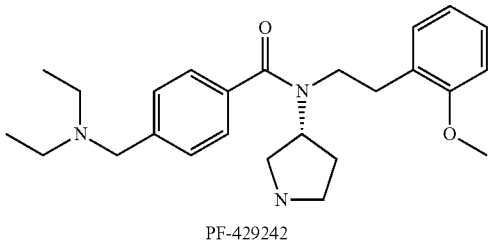
PF-429242
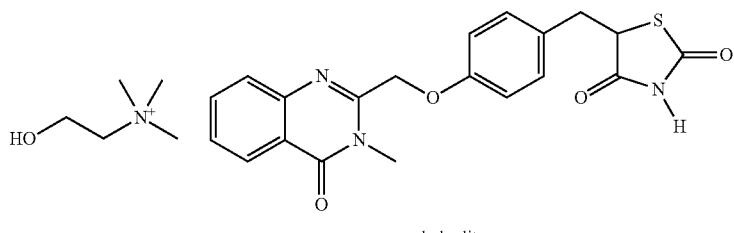
balaglitazone
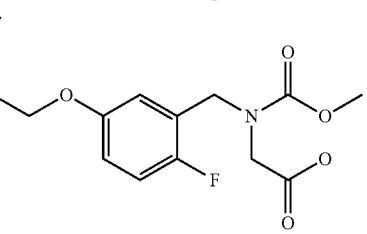
BMS-711939
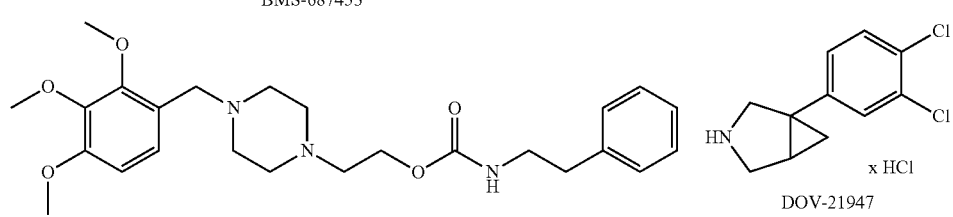
ST-3473    DOV-21947
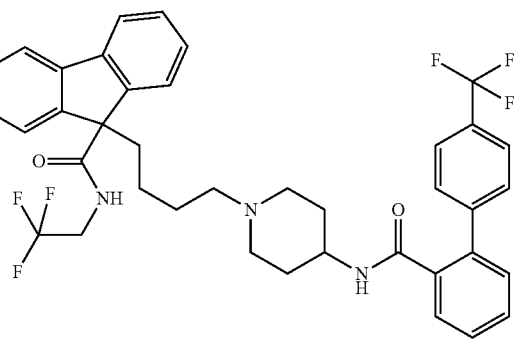
AEGR-733

-continued
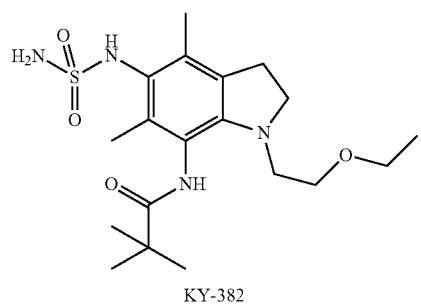
KY-382
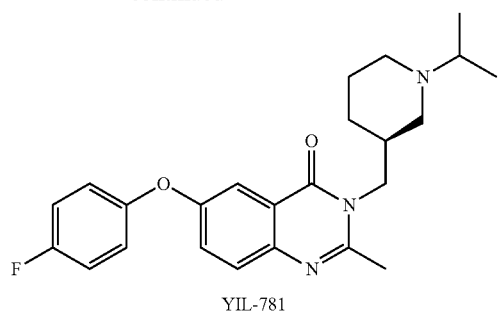
YIL-781
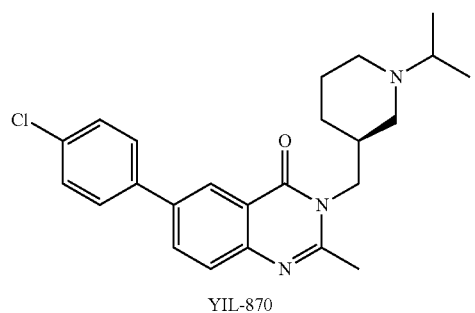
YIL-870
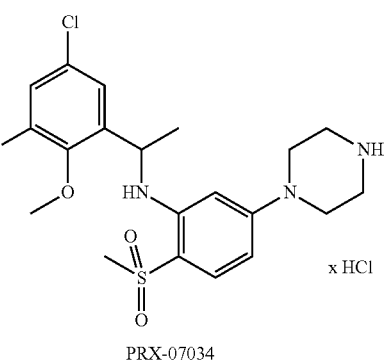
PRX-07034 x HCl
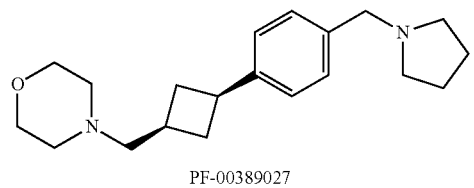
PF-00389027
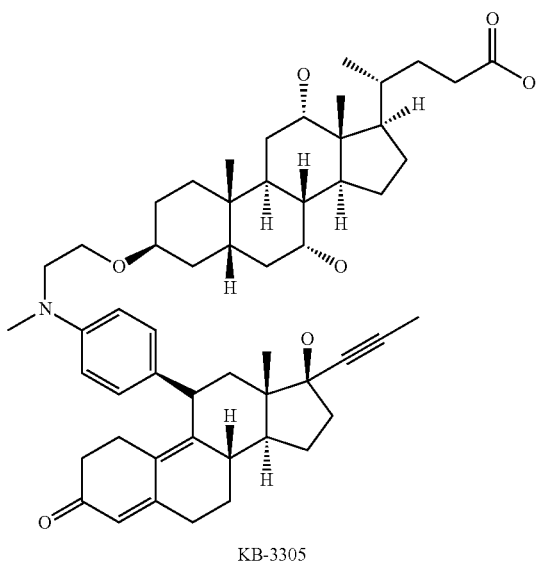
KB-3305
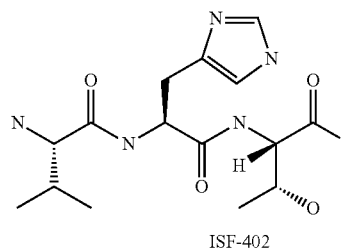
ISF-402
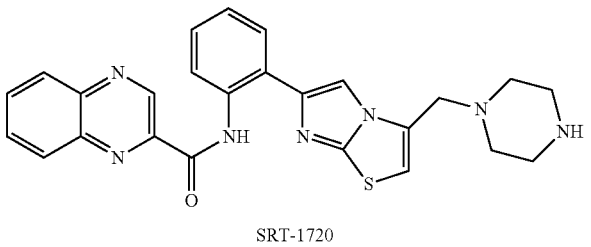
SRT-1720

201
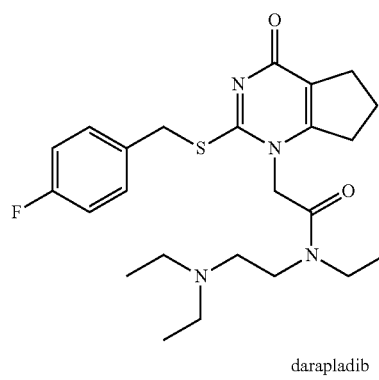
darapladib
202
-continued
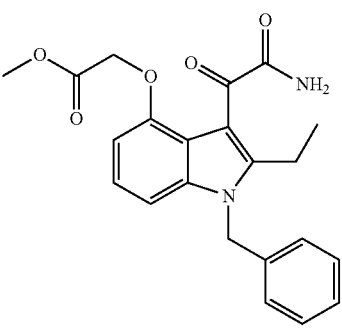
A-002
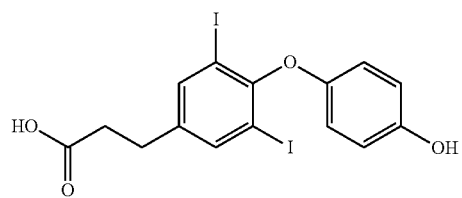
DITPA
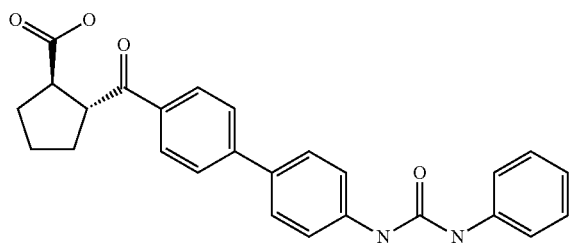
DGAT-1 inhibitor from WO2007137103
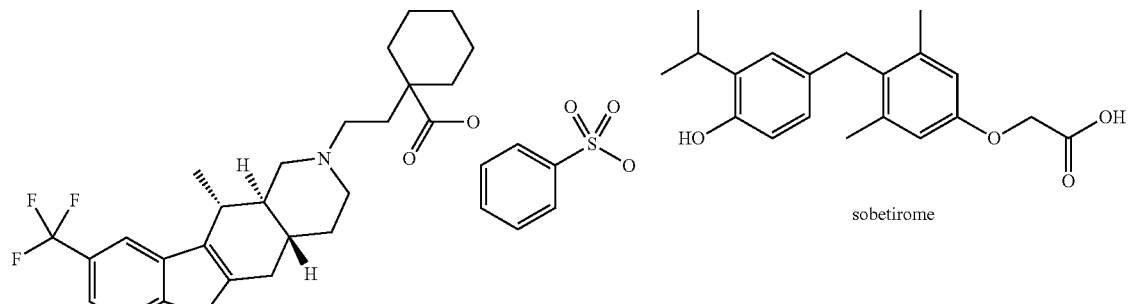
AMG-071
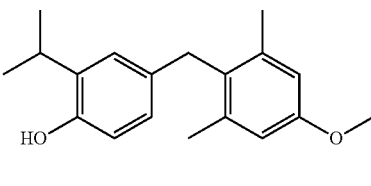
sobetirome
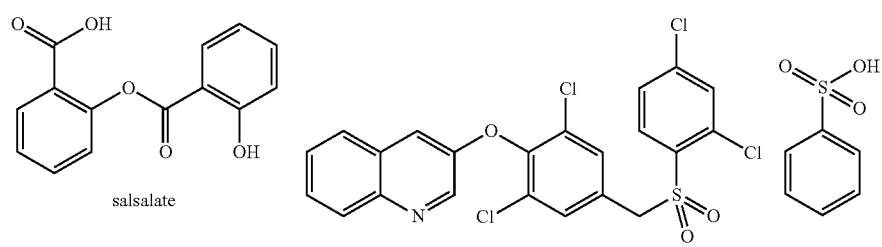
salsalate
INT-131

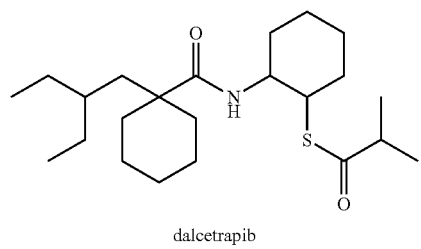
dalcetrapib
-continued
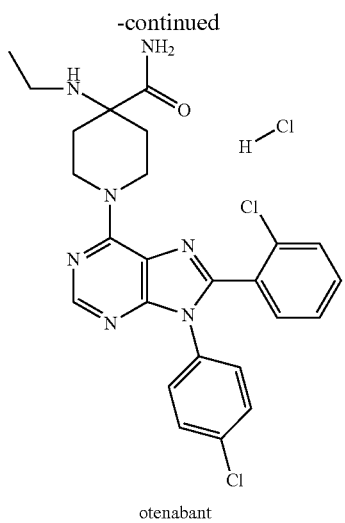
otenabant
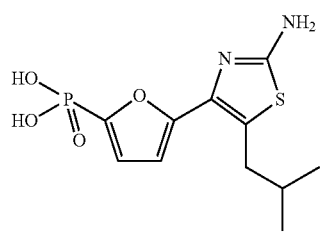
MB-07229
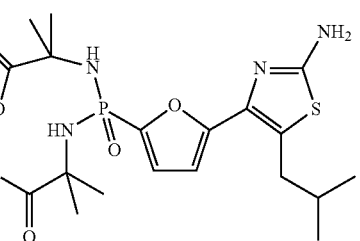
MB-07803
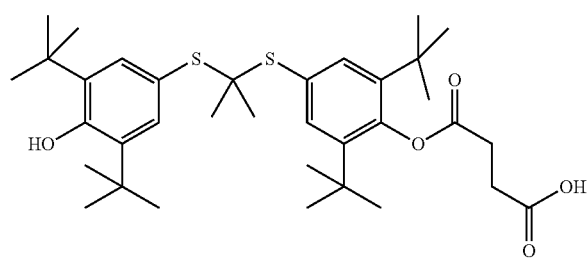
succinobucol
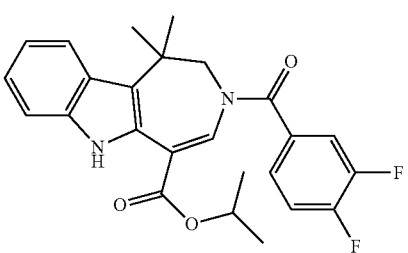
WAY-362450
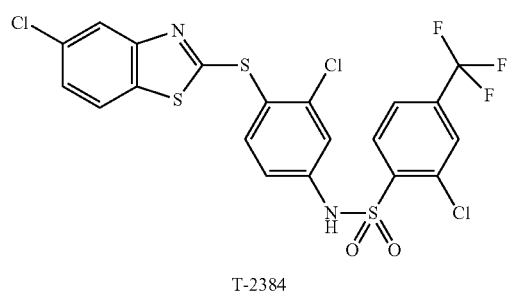
T-2384
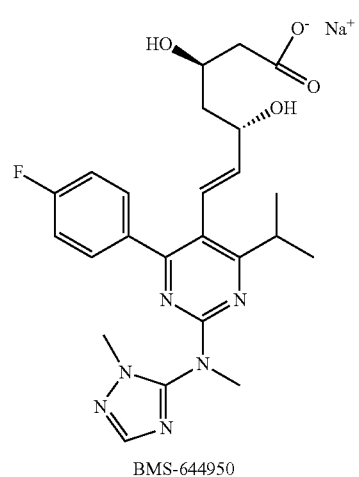
BMS-644950

205
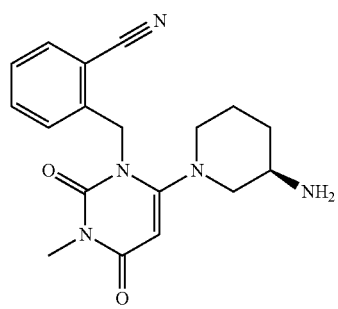
alogliptin benzoate
206
-continued
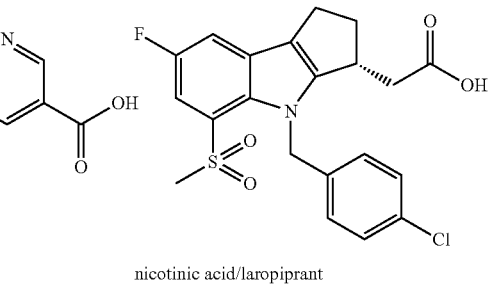
nicotinic acid/laropiprant
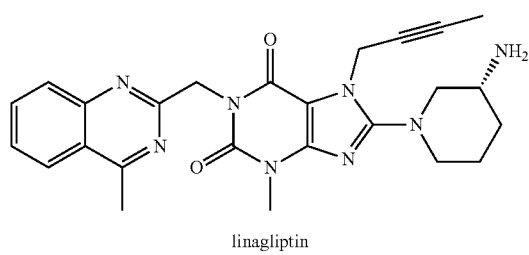
linagliptin
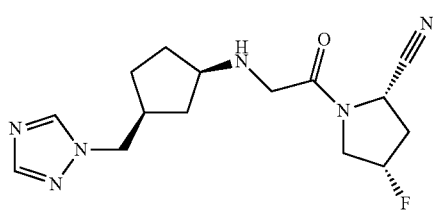
melogliptin
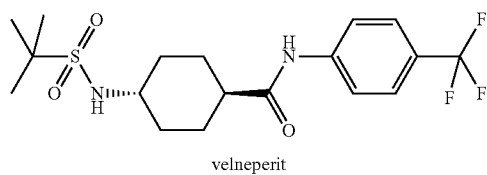
velneperit
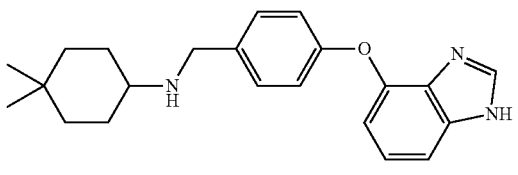
GSK-982
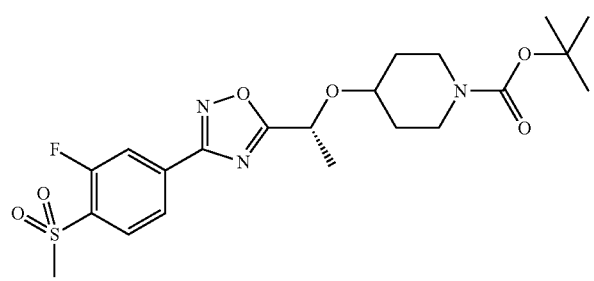
PSN-119-2
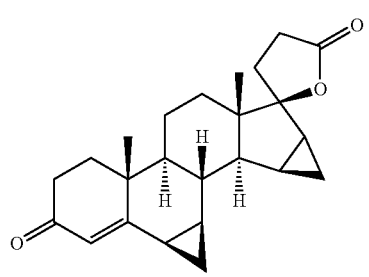
drospirenone
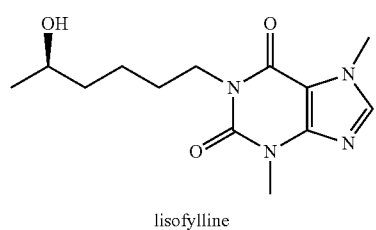
lisofylline
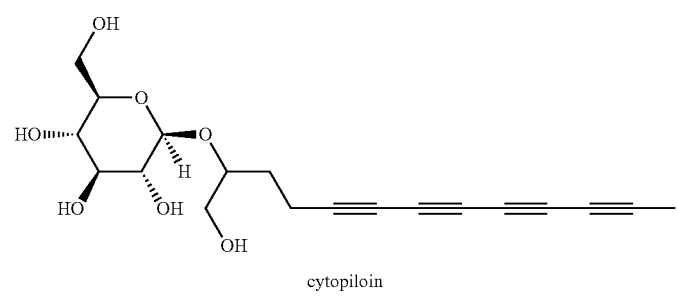
cytopiloin -continued
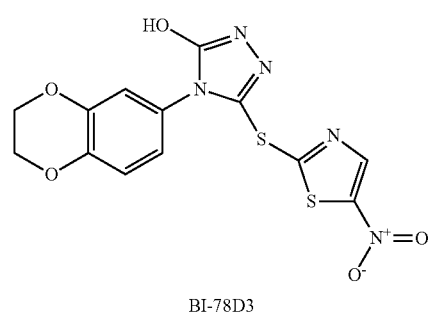
BI-78D3
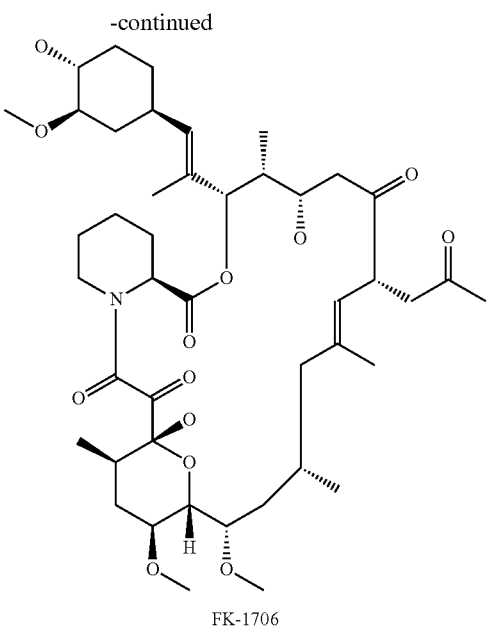
FK-1706
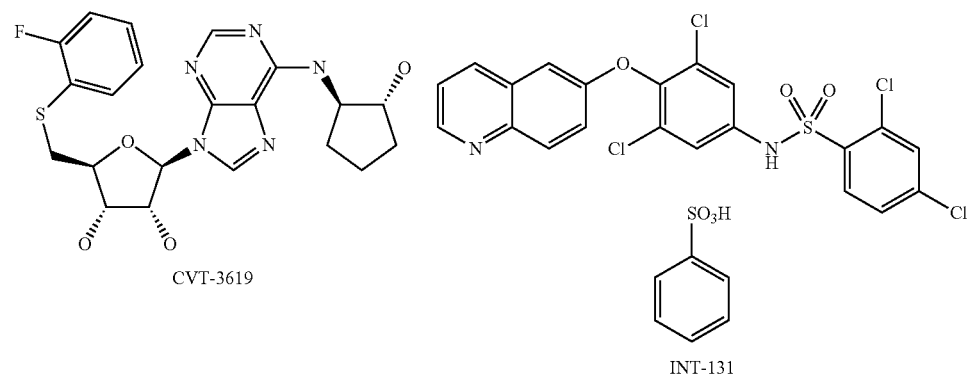
CVT-3619
INT-131
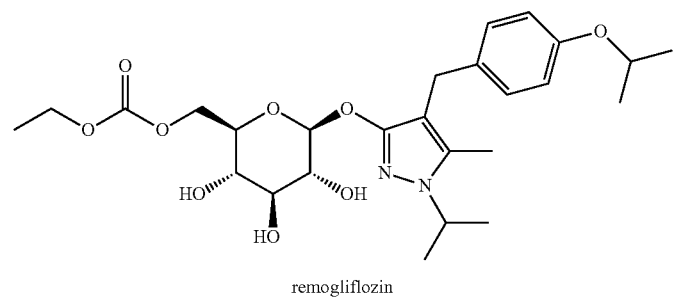
remogliflozin
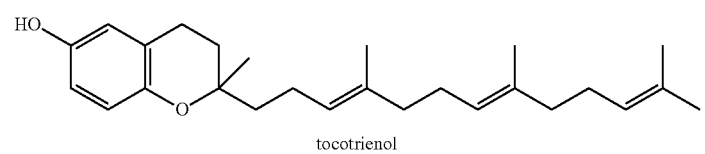
tocotrienol -continued
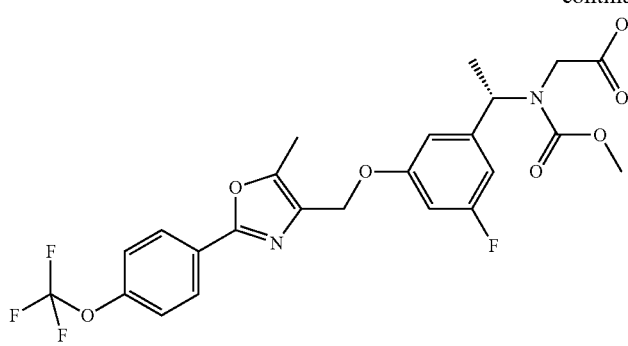
BMS-759509
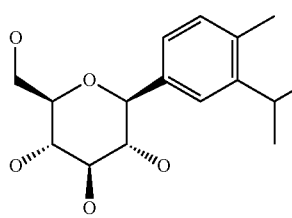
canagliflozin
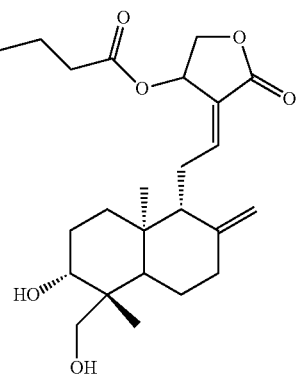
14-alpha-lipolyl-andrographolide (AL-1)
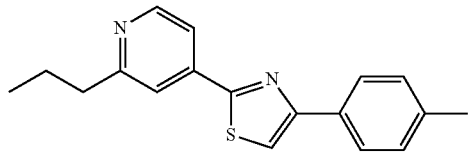
fatostatin
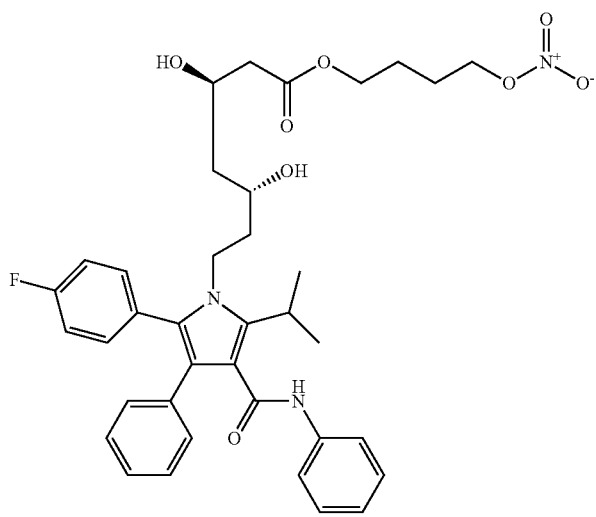
NCX-6560
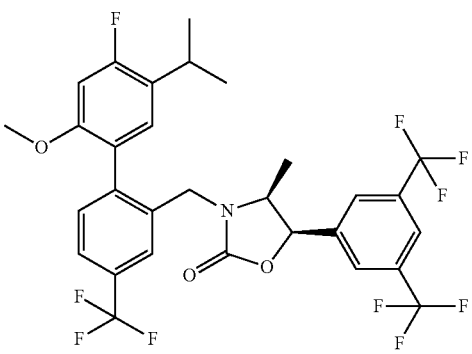
anacetrapib
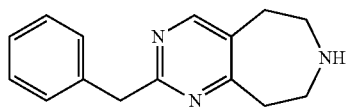
PF-3246799

Also suitable are the following active ingredients for combination preparations:

all antiepileptics specified in the Rote Liste 2011, chapter 15;

all antihypertensives specified in the Rote Liste 2011, chapter 17;

all hypotonics specified in the Rote Liste 2011, chapter 19;

all anticoagulants specified in the Rote Liste 2011, chapter 20;

all arteriosclerosis drugs specified in the Rote Liste 2011, chapter 25;

all beta receptors, calcium channel blockers and inhibitors of the renin angiotensin system specified in the Rote Liste 2011, chapter 27;

all diuretics and perfusion-promoting drugs specified in the Rote Liste 2011, chapter 36 and 37;

all withdrawal drugs/drugs for the treatment of addictive disorders specified in the Rote Liste 2011, chapter 39;

all coronary drugs and gastrointestinal drugs specified in the Rote Liste 2011, chapter 55 and 60;

all migraine drugs, neuropathy preparations and Parkinson's drugs specified in the Rote Liste 2011, chapter 61, 66 and 70.

It will be appreciated that every suitable combination of the compounds of the invention with one or more of the aforementioned compounds and optionally one or more other pharmacologically active substances is considered to be covered within the scope of protection conferred by the present invention.

PKC-inhibitors can be administered to animals, in particular to mammals including humans, as pharmaceuticals by themselves, in mixtures with one another, or in the form of pharmaceutical compositions. The administration can be carried out orally, for example in the form of tablets, film-coated tablets, sugar-coated tablets, granules, hard and soft gelatin capsules, solutions including aqueous, alcoholic and oily solutions, juices, drops, syrups, emulsions or suspensions, rectally, for example in the form of suppositories, or parenterally, for example in the form of solutions for subcutaneous, intramuscular or intravenous injection or infusion, in particular aqueous solutions.

Suitable pharmaceutical compounds for oral administration may be in the form of separate units, for example capsules, cachets, lozenges or tablets, each of which contains a defined amount of the compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surfactant(s)/dispersant(s) in a suitable machine. Molded tablets can be produced by molding the compound, which is in powder form and has been moistened with an inert liquid diluent, in a suitable machine.

Pharmaceutical compositions which are suitable for peroral (sublingual) administration comprise lozenges which contain a compound of formula I with a flavoring, typically sucrose, and gum arabic or tragacanth, and pastilles which comprise the compound in an inert base such as gelatin and glycerol or sucrose and gum arabic.

Coated formulations and coated slow-release formulations, especially acid- and gastric juice-resistant formulations, also belong within the framework of the invention. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Pharmaceutical compositions suitable for rectal administration are preferably in the form of single-dose suppositories. These can be produced by mixing a compound of formula I with one or more conventional solid carriers, for example cocoa butter, and shaping resulting mixture.

Pharmaceutical compositions suitable for parenteral administration comprise preferably sterile aqueous preparations of a compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain 0.1 to 5% by weight of the active compound.

Other suitable administration forms are, for example, percutaneous or topical administration, for example in the form of ointments, creams, tinctures, sprays, powders or transdermal therapeutic systems, or inhalative administration, for example in the form of nasal sprays or aerosol mixtures, or forms such as microcapsules, implants or rods.

Pharmaceutical compositions suitable for topical use on the skin are preferably in the form of ointment, cream, lotion, paste, spray, aerosol or oil. The carriers used may be petrolatum, lanolin, polyethylene glycols, alcohols and combinations of two or more of these substances. The active ingredient is generally present in a concentration of 0.1 to 15% by weight of the composition, for example 0, 5 to 2%.

Transdermal administration is also possible. Pharmaceutical compositions suitable for transdermal uses may be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular option is for the active ingredient to be released by electrotransport or iontophoresis as described, for example, in Pharmaceutical Research, 2(6): 318 (1986).

PKC inhibitors can additionally be used in systems for local drug delivery, for example in coated stents for preventing or reducing in-stent restenosis or by applying them locally by means of a catheter. The appropriate administration form depends, among others, on the disease to be treated and on its severity.

The dosing of PKC inhibitors to achieve the desirable therapeutic effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram of body weight, for example 3-10 mg/kg/day. An intravenous dose may be, for example, in the range from 0.3 mg to 1.0 mg/kg, which can suitably be administered as infusion of 10 ng to 100 ng per kilogram and per minute.

Suitable infusion solutions for these purposes may contain, for example, 0.1 ng to 100 mg, typically 1 ng to 100 mg, per milliliter. Single doses may contain, for example, 1 mg to 10 g of the active ingredient. Thus, ampoules for injections may contain, for example, from 1 mg to 100 mg, and orally administrable single-dose formulations, for example tablets or capsules, may contain, for example, from 1.0 to 1000 mg, typically from 10 to 600 mg. For treatment of the abovementioned conditions, the compounds of the formula I themselves may be used as the compound, but they are preferably present with a compatible carrier in the form of a pharmaceutical composition. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

The present invention provides novel and potent PKC inhibitors. The compounds of the present invention are selective to PKC over other kinases and are isozyme-selective. Selective PKC inhibitors are useful in preventing and treating diseases associated with diabetes and diabetic complications (e.g. diabetic cardiomyopathy, diabetic nephropathy, diabetic micro- and macrovascular complications, diabetic neuropathy and diabetic retinopathy, preferably diabetic nephropathy, diabetic neuropathy and diabetic retinopathy), cardiovascular diseases, diseases associated with hypertension- and non-hypertension-related and ischemic and non-ischemic end-organ damage (e.g. mycardial infarction, coronary heart disease, atherosclerosis, cardiac and renal hypertrophy, stroke), diseases associated with inflammation and fibrosis, central nervous system disorders (e.g. neuropathic pain), dermatological diseases, autoimmune diseases (e.g. psoriasis, type 1 diabetes) and cancer (e.g. hematological tumours, glioma, gastric and intestinal cancer, skin cancer and lung cancer).

Another subject of the present invention are processes for the preparation of the compounds of the formula I and their salts and solvates, by which the compounds are obtainable and which are outlined in the following.

In one process, a compound of the formula II is reacted with a compound of the formula III to give a compound of the formula Ia, which can be a compound of formula I already or which can be converted into a compound of formula I,

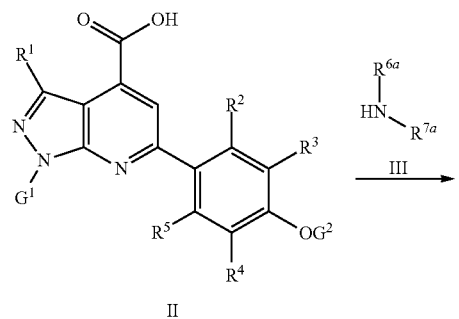

II

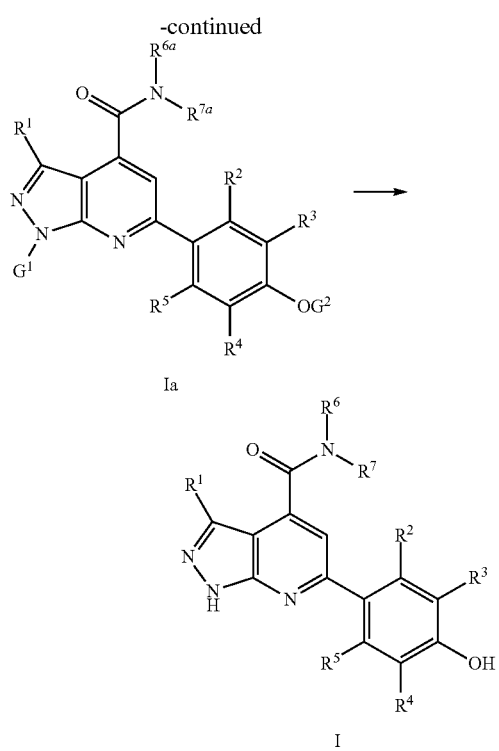

wherein the groups $R^1$, $R^2$, $R^3$, $R^4$, $R^5$, $R^6$ and $R^7$ in the compounds of the formulae II and Ia are defined as in the compounds of the formula I. The groups $R^{6a}$ and $R^{7a}$ in the compounds of formulae Ia and III are, independently of each other, either defined as the groups $R^6$ and $R^7$ in formula I, or they are precursors of the groups $R^6$ and $R^7$ in formula I, they can for example contain functional groups in protected form or functional groups which can be converted to obtain the final groups $R^6$ and $R^7$. The group $G^1$ in the compounds of formulae Ia and II is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group $G^2$ in the compounds of formulae Ia and II is defined as a hydrogen or a protecting group for a phenolic hydroxyl group, such as, for example, a 2-tetrahydropyranyl-group, a benzyl group, a 4-methoxybenzyl or a 2,5-dimethoxybenzyl group.

The compounds of the formula II may also be present in another tautomeric form, especially for compounds, in which $G^1$ is hydrogen, for example in the form of the respective 2H-pyrazolo[3,4-b]pyridine derivatives in which the mobile hydrogen atom, which in formula II is bonded to the ring nitrogen atom in the 1-position of the pyrazolo[3,4-b]pyridine ring system, is bonded to the ring nitrogen atom in the 2-position of the pyrazolo[3,4-b]pyridine ring system. As far as applicable, it applies to all compounds occurring in the preparation of the compounds of the formula I that they can be present in any other tautomeric form than the one represented in their formulae.

The reaction of the compounds of the formulae II and III to form an amide of formula Ia is generally performed in the presence of activating agents, such as CDI, DCC, EDC, HOAt, HOBt, HATU, TOTU, TBTU, BEP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature in this case is generally from −30° C. to 200° C., preferably from −20° C. to 80°, more preferably from 0° C. to 20° C. The reaction time is generally from 15 min to 6 days, preferably from 15 min to 16 h, depending on the composition of the mixture and the chosen temperature range. The acids of formula II can be subjected to the reaction in form of their salts, for example their sodium salts. They can also be transformed into an activated derivative prior to the coupling with the amine, for example into an acid chloride or an acid anhydride by standard transformations. The amines of formula III can be subjected to the reaction in form of their salts, for example as hydrochloride or triflate salts, in which case usually an additional equivalent of the base is added to the reaction. As far as applicable and unless otherwise indicated, it applies to all acidic or basic compounds occurring in the preparation of the compounds of the formula I that they can be present in form of their salts.

A compound of the formula Ia can already be a compound of formula I, if $G^1$ and $G^2$ are both H and if $R^{6a}$ is $R^6$ and $R^{7a}$ is $R^7$. If a compound of formula Ia is not already a compound of formula I, it can be transformed into a compound of formula I in one step or in several steps depending of the meaning of the groups $G^1$, $G^2$, $R^{6a}$ and $R^{7a}$. If the groups $R^{6a}$ and/or $R^{7a}$ contain or if the groups $G^1$ and/or $G^2$ consist of protecting groups that can be cleaved by hydrogenation, e.g. a benzyl group or a 4-methoxybenzyl group, one step in the transformation of a compound of formula Ia to a compound of formula I can be a catalytic hydrogenation or a transfer hydrogenation. If the groups $R^{6a}$ and/or $R^{7a}$ contain or if the groups $G^1$ and/or $G^2$ consist of protecting groups that can be cleaved by treatment with acid, e.g. a 2-tetrahydropyranyl group, a 4-methoxybenzyl group, a 2,4-dimethoxybenzyl group or a tert-butoxycarbonyl group, one step in the transformation of a compound of formula Ia to a compound of formula I can be an acidic deprotection. All deprotection reactions used in the above-described transformation of compounds of the formula Ia, in which the groups $R^{6a}$ and/or $R^{7a}$ contain or in which the groups $G^1$ and/or $G^2$ consist of protecting groups, to compounds of formula I are per se well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

A transformation of a compound of formula Ia, in which the groups $R^{6a}$ and/or $R^{7a}$ are precursors to the groups $R^6$ and/or $R^7$ into a compound of formula I can also include a functionalization or modification of contained functional groups according to standard procedures, for example by esterification, amidation, hydrolysis, etherification, alkylation, acylation, sulfonylation, reduction, oxidation, conversion into salts, and others. For example, a hydroxy group, which may be obtained from a protected hydroxy group by deprotection, can be esterified to give a carboxylic acid ester or a sulfonic acid ester, or etherified. Etherifications of hydroxy groups can favorably be performed by alkylation with the respective halogen compound, for example a bromide or iodide, in the presence of a base, for example an alkaline metal carbonate such potassium carbonate or cesium carbonate in an inert solvent, for example an amide like DMF or NMP or a ketone like acetone or butan-2-one, or with the respective alcohol under the conditions of the Mitsunobu reaction referred to above. A hydroxy group can be converted into a halide by treatment with a halogenating agent. A halogen atom can be replaced with a variety of groups in a substitution reaction which may also be a transition-metal catalyzed reaction. A nitro group can be reduced to an amino group, for example by catalytic hydrogenation. An amino group, which may be obtained from a protected amino group by deprotection, can be modified under standard conditions for alkylation, for example by reaction with a halogen compound or by reductive amination of a carbonyl compound, or for acylation or sulfonylation, for example by reaction with a reactive carboxylic acid derivative, like an acid chloride or anhydride or a sulfonic acid chloride, or with a carboxylic acid in the presence of activating agents, such as CDI, DCC, EDC, HOAt, HOBt, HATU, TOTU, TBTU, BEP or combinations thereof, or for carbamoylation, for example by reaction with an isocyanate. A carboxylic ester group can be hydrolyzed under acidic or basic conditions to give a carboxylic acid. A carboxylic acid group can be activated or converted into a reactive derivative as mentioned afore and reacted with an alcohol or an amine or ammonia to give an ester or amide. A primary amide can be dehydrated to give a nitrile. A sulfur atom, for example in an alkyl-S-group or in a heterocyclic ring, can be oxidized with a peroxide like hydrogen peroxide or a peracid to give a sulfoxide moiety S(O) or a sulfone moiety $S(O)_2$. A carboxylic acid group, carboxylic acid ester group and a ketone group can be reduced to an alcohol, for example by means of a complex hydride such as lithium aluminium hydride, lithium borohydride or sodium borohydride. All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York.

The compounds of the formula II can be obtained by reacting an aminopyrazole compound of the formula IV with a benzaldehyde of formula V and a pyruvic acid derivative of formula VI to give a compound of formula IIa, which can be a compound of formula II already or which can be converted into a compound of formula II,

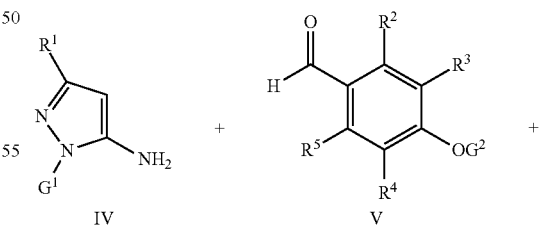

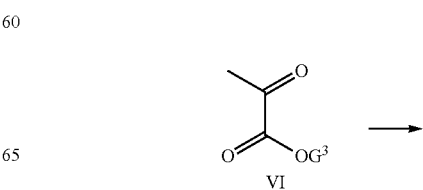

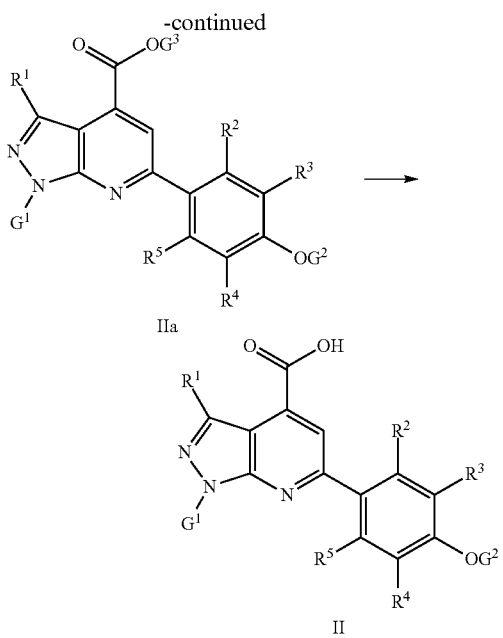

IIa

II wherein the groups $R^1$, $R^2$, $R^3$, $R^4$ and $R^5$ in the compounds of the formulae II, IIa, IV and V are defined as in the compounds of the formula I. The group $G^1$ in the compounds of formulae II, IIa and IV is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group $G^2$ in the compounds of formulae II, IIa and V is defined as a hydrogen or a protecting group for a phenolic hydroxyl group, such as, for example, a 2-tetrahydropyranyl-group, a benzyl group, a 4-methoxybenzyl or a 2,5-dimethoxybenzyl group. The group $G^3$ in the compounds of formulae IIa and VI is hydrogen, or a protecting group for a carboxylic acid, such as, for example methyl, ethyl, propyl, tert-butyl or benzyl, preferably methyl or ethyl.

The reaction of an aminopyrazole compound of the formula IV with a benzaldehyde of formula V and a pyruvic acid derivative of formula VI is generally performed in the presence of acids, for example acetic acid or hydrochloric acid, in an appropriate solvent, for example in an alcohol as ethanol, methanol or iso-propanol or an ether such as tetrahydrofurane, 1,4-dioxane, dibutylether, diisopropylether, methyl-tert-butylether, dimethoxyethane or in water, or in mixtures thereof. The reaction temperature in this case is generally from −30° C. to 200° C., preferably from 0° C. to 150°, more preferably from 0° C. to 80° C. The reaction time is generally from 30 min to 48 h, preferably from 30 mm n to 6 h, depending on the composition of the mixture and the chosen temperature range. Depending on the solvents and conditions applied the preferred regionisomer of formula IIa can be easily isolated by precipitation from the reaction mixture.

A compound of the formula IIa can already be a compound of formula II, if $G^1$ and $G^2$ are identical in the compounds of formula IIa and II and if $G^3$ in the compound of formula IIa is H. If a compound of formula IIa is not already a compound of formula II, it can be transformed into a compound of formula II in one step or in several steps depending of the meaning of the groups $G^1$, $G^2$ and $G^3$. For example, a compound of formula IIa, in which G1 is hydrogen, can be converted into a compound of formula IIa, in which G1 is a protecting group for a pyrazole nitrogen, by a suitable protection reaction, e.g. by the reaction with 3,4-dihydro-2H-pyrane under acidic catalysis. Alternatively, or as an additional step, a compound of formula IIa, in which $G^2$ is hydrogen, can be converted to a compound of formula II, in which $G^2$ is a protecting group for a phenolic hydroxyl group, for example a benzyl group, by a suitable protection reaction, e.g. by the reaction with a benzyl halide such as benzyl bromide or benzyl chloride in the presence of a base such as sodium carbonate. Alternatively or as an additional step, a compound of formula IIa, in which $G^3$ is not hydrogen, but a protecting group for a carboxylic acid, the compound of formula IIa can be reacted to a compound of formula II by a suitable deprotection reaction, e.g. a basic hydrolysis, if G3 is a methyl, ethyl or propyl residue. As it is known to the skilled person the employed protection groups should be chosen in a manner to be compatible with the desired reaction conditions for all subsequent steps. All protection and deprotection reactions used in the above-described transformation of compounds of the formula IIa to compounds of formula II are well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

Alternatively, the compounds of the formula II can be obtained by reacting an aminopyrazole of formula IV with a 2-oxo succinic acid derivative of formula VII (or a tautomer and/or salt thereof) to a compound of formula VIII, the obtained compound of formula VIII is then converted into a compound of formula IXa, which is then reacted with a compound of formula X to give a compound of formula IIa, which can be a compound of formula II already or which can be converted into a compound of formula II,

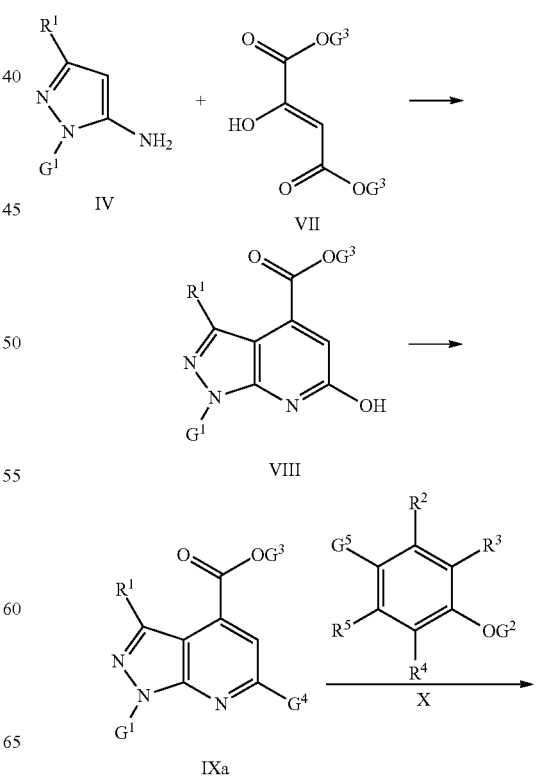

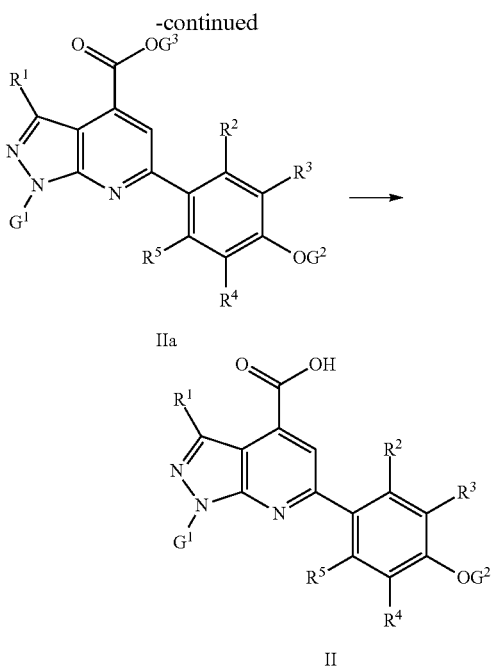

wherein the groups $R^1$, $R^2$, $R^3$, $R^4$ and $R^5$ in the compounds of the formulae II, IIa, IV, VIII, IXa and X are defined as in the compounds of the formula I. The group $G^1$ in the compounds of formulae II, IIa, IV, VIII and IXa is defined as a hydrogen or a protecting group for a pyrrazole nitrogen, such as, for example, a 2-tetrahydropyranyl-group, a benzyl group, a 4-methoxybenzyl or a 2,5-dimethoxybenzyl group. The group $G^2$ in the compounds of formulae IIa and X is defined as a hydrogen or a protecting group for a phenolic hydroxyl group, such as, for example, a 2-tetrahydropyranyl-group, a benzyl group, a 4-methoxybenzyl or a 2,5-dimethoxybenzyl group. The group $G^3$ in the compounds of formulae IIa, VII, VIII and IXa is hydrogen or a protecting group for a carboxylic acid, such as, for example methyl, ethyl, propyl, tert-butyl or benzyl, preferably methyl or ethyl. The group $G^4$ in the compounds of formula IXa is a leaving group that can be replaced in a Suzuki-type reaction, such as a halide, e.g. a bromide or a chloride or as a sulfonate, e.g. a trifluoromethanesulfonate or methanesulfonate. The group $G^5$ in the compounds of formula X is a boronic acid or a boronic ester or cyclic boronic ester.

The reaction of an aminopyrazole of formula IV with a compound of formula VI (or a tautomer and/or salt thereof, e.g. a dialkyl oxalacetate sodium salt) to a compound of formula VIII is generally carried out in the presence of an acid, such as aqueous hydrochloric acid or acetic acid or trifluoro acetic acid at temperatures from about 0° C. to about 200° C., for example at temperatures from about 20° C. to about 120° C. The reaction can be carried out in neat conditions or in a suitable inert solvent. The reaction time is generally from 30 min to 48 h, preferably from 30 min to 16 h. depending on the composition of the mixture and the chosen temperature range. Depending on the solvents and conditions applied the preferred regioisomer of formula VIII can be easily isolated by precipitation from the reaction mixture.

The conversion of a compound of formula VIII to a compound of formula IXa, in which $G^4$ is a halide, for example a bromide or a chloride, is generally carried out by reaction with a phosphorhalide like phosphorous trichloride or phosphorous tribromide or a phosphorous oxyhalide like phosphorous oxychloride or phosphorous oxybromide. The reaction can be carried out in neat conditions or in a suitable inert solvent, for example a hydrocarbon, such as benzene, toluene or xylene, or a chlorinated hydrocarbon, such as chlorobenzene, or a mixture of solvents, at temperatures from about 20° C. to about 200° C., for example at temperatures from about 80° C. to about 120° C., favorably with addition of a base, for example a tertiary amine, such as triethylamine, ethyldiisopropylamine, N-methylmorpholine or 1,8-diazabicyclo[5.4.0]unde-7-ene. The reaction time is generally from 30 min to 48 h, preferably from 30 min to 4 h, depending on the composition of the mixture and the chosen temperature range. The conversion of a compound of Formula VIM to a compound of formula IXa, in which $G^4$ is an alkylsulfonate, e.g. trifluoromethylsulfonate or methylsulfonate, is generally carried out by reaction with an alkanesulfonyl halide, such as methanesulfonyl chloride, or an alkane sulfonic anhydride, such as trifluoromethane sulfonic anhydride. The reaction can be carried out in neat conditions or in a suitable inert solvent, for example a hydrocarbon, such as benzene, toluene or xylene, or a chlorinated hydrocarbon, such as chlorobenzene, or an ether, such as THF, dioxane or DME, or a mixture of solvents, at temperatures from about 0° C. to about 200° C., for example at temperatures from about 20° C. to about 120° C., favorably with addition of a base, for example a tertiary amine, such as triethylamine, ethyldiisopropylamine, N-methylmorpholine or 1,8-diazabicyclo[5.4.0]unde-7-ene. The reaction time is generally from 30 min to 48 h, preferably from 30 min to 4 h, depending on the composition of the mixture and the chosen temperature range.

The reaction of the compound of the formula IXa with compounds of the formula X to a compound of formula IIa is a Suzuki-type reaction and is generally carried out in the presence of catalytic palladium compound, for example a palladium(II) salt such as palladium(II) acetate or palladium(II) chloride, which can be employed in the presence of a phosphine such as tricyclohexylphosphine or triphenylphosphine, or a palladium complex such as tetrakis(triphenylphosphine)palladium(0), palladium(0) bis(tri-tert-butylphosphin) or bis(triphenylphosphine)palladium(II) chloride, and favourably in the presence of a base, for example an alkaline metal carbonate or phosphate such as sodium carbonate or tripotassium phosphate, in an inert solvent, for example a hydrocarbon, such as benzene, toluene or xylene, or an ether, such as THF, dioxane or DME, or water, or a mixture of solvents, at temperatures from about 20° C. to about 200° C., for example at temperatures from about 80° C. to about 120° C. The reaction time is generally from 30 min to 48 h, preferably from 30 min to 16 h, depending on the composition of the mixture and the chosen temperature range.

A compound of the formula IIa can already be a compound of formula II, if $G^1$ and $G^2$ are identical in the compounds of formula IIa and II and if $G^3$ in the compound of formula IIa is H. If a compound of formula IIa is not already a compound of formula II, it can be transformed into a compound of formula II in one step or in several steps depending of the meaning of the groups $G^1$, $G^2$ and $G^3$ as it was described above.

Alternatively, the compounds of the formula II can be obtained by reacting a ketone of formula XI with an oxalic acid derivative of formula XII in a Claisen-type condensation to a compound of formula XIII, which is then reacted with an amino pyrazole compound of formula IV to give a compound of formula IIa, which can be a compound of formula II already or which can be converted into a compound of formula II,

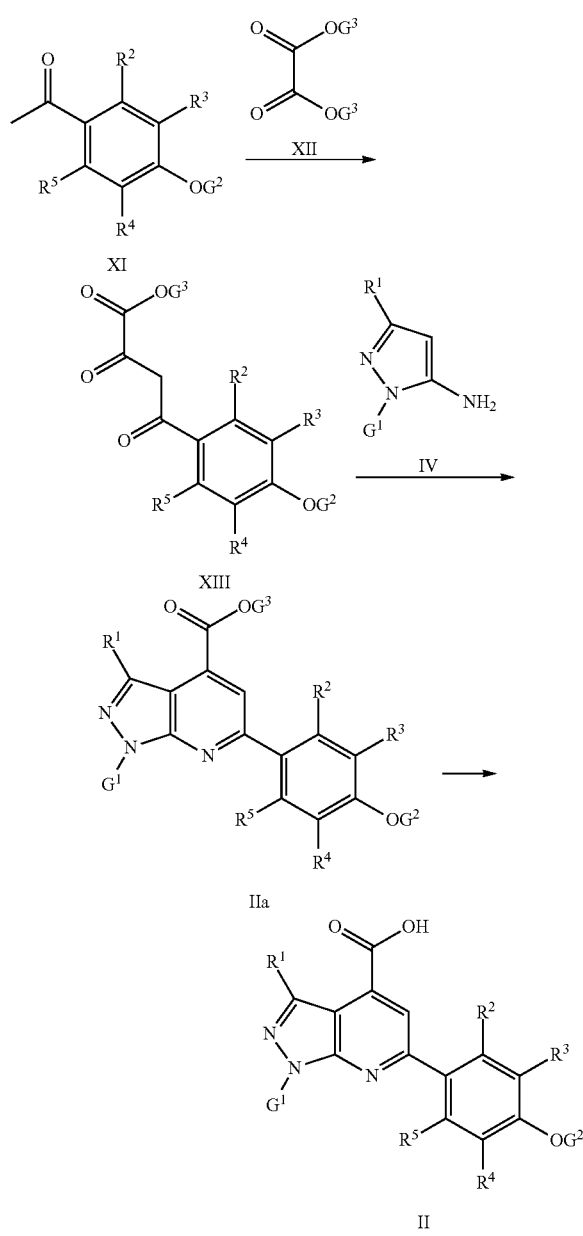

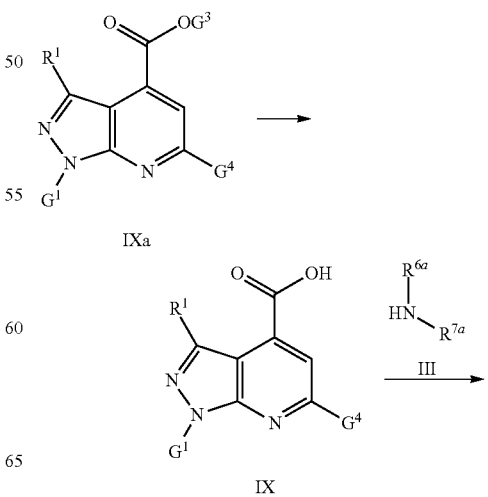

wherein the groups $R^1$, $R^2$, $R^3$, $R^4$ and $R^5$ in the compounds of the formulae IIa, IV, XI and XIII are defined as in the compounds of the formula I. The group $G^1$ in the compounds of formulae II, IIa and IV is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group $G^2$ in the compounds of formulae II, IIa, XI and XIII is defined as a hydrogen or a protecting group for a phenolic hydroxyl group, such as, for example, a 2-tetrahydropyranyl-group, a benzyl group, a 4-methoxybenzyl or a 2,5-dimethoxybenzyl group. The group $G^3$ in the compounds of formulae IIa, VI and XII is hydrogen or a protecting group for a carboxylic acid, such as, for example, methyl, ethyl, propyl, tert-butyl or benzyl, preferably methyl or ethyl.

The Claisen-type condensation of a ketone of formula XI with an oxalic acid derivative of formula XII is generally carried out in the presence of a base, for example an inorganic base such as an alkaline metal hydride, like sodium hydride, or an alkoxide or amide such as sodium methoxide, sodium ethoxide, potassium methoxide, potassium tert-butoxide, sodium amide or lithium diisopropylamide, and in an inert solvent, for example a hydrocarbon or chlorinated hydrocarbon such as benzene, toluene, xylene and chlorobenzene, an ether such as THF, dioxane, dibutyl ether, diisopropyl ether or DME, an alcohol such as methanol, ethanol, isopropanol or tert-butanol, or a mixture of solvents at temperatures from about 0° C. to about 200° C., for example at temperatures from about 20° C. to about 120° C. The reaction time is generally from 30 min to 48 h, preferably from 30 min to 8 h, depending on the composition of the mixture and the chosen temperature range. The compounds of formula XIII can be obtained in form of a tautomer and/or salt, e.g. as sodium 1-methoxycarbonyl-3-oxo-3-aryl-propen-1-olate for compounds of formula XIII, in which $G^3$ is methyl.

The reaction of a compound of formula XIII with an amino pyrazole compound of formula IV to give a compound of the formula IIa is generally carried out in the presence of an acid, for example acetic acid or hydrochloric acid or trifluoro acetic acid. The reaction can be carried out neat or in suitable solvents at temperatures from about 0° C. to about 200° C., for example at temperatures from about 20° C. to about 150° C., preferably from about 80° C. to 120° C. The reaction time is generally from 30 min to 48 h, preferably from 30 min to 16 h, depending on the composition of the mixture and the chosen temperature range. Depending on the solvents and conditions applied the preferred regioisomer of formula IIa can be easily isolated by precipitation from the reaction mixture.

A compound of the formula IIa can already be a compound of formula II, if $G^1$ and $G^2$ are identical in the compounds of formula IIa and H and if $G^3$ in the compound of formula IIa is H. If a compound of formula IIa is not already a compound of formula II, it can be transformed into a compound of formula II in one step or in several steps depending of the meaning of the groups $G^1$, $G^2$ and $G^3$ as it was described above.

In another process for the preparation of compounds of the formula I, a compound of the formula IXa, in which $G^3$ is not hydrogen, is converted into a compound of formula IX, the latter compound is then reacted with a compound of the formula III to give a compound of formula XIV, which is then reacted with a compound of formula X to give a compound of the formula Ia, which can be a compound of formula I already or which can be converted into a compound of formula I,

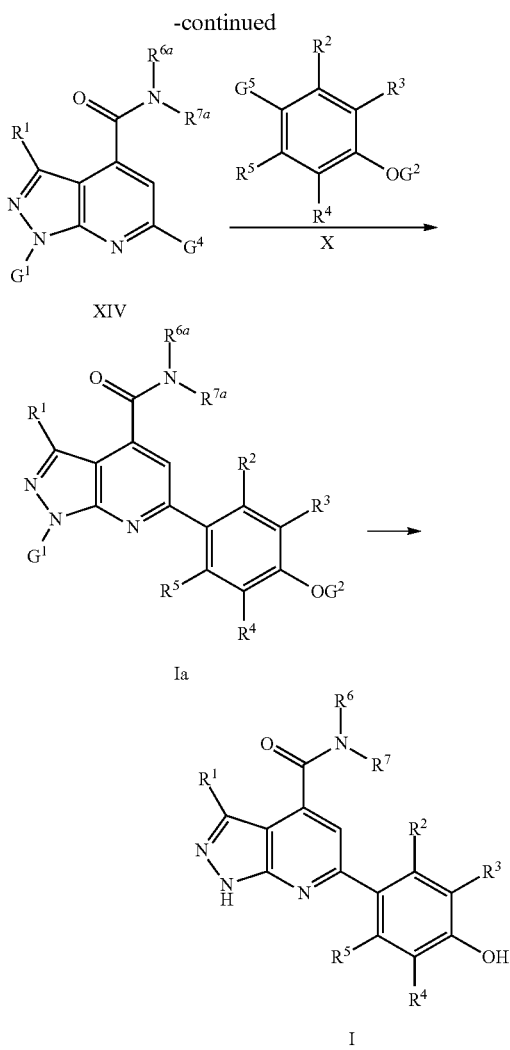

wherein the groups $R^1$, $R^2$, $R^4$, $R^5$ and $R^6$ in the compounds of the formulae Ia, IX, IXa, X and XIV are defined as in the compounds of the formula I. The groups $R^{6a}$ and $R^{7a}$ in the compounds of formulae Ia, III and XIV are, independently of each other, either defined as the groups $R^6$ and $R^7$ in formula I, or they are precursors of the groups $R^6$ and $R^7$ in formula I, they can for example contain functional groups in protected form or functional groups which can be converted to obtain the final groups $R^6$ and $R^7$. The group $G^1$ in the compounds of formulae Ia, IX, IXa and XIV is defined as a hydrogen or a protecting group for a pyrazole nitrogen, such as, for example, a 2-tetrahydropyranyl-group, a benzyl group, a 4-methoxybenzyl or a 2,5-dimethoxybenzyl group. The group $G^2$ in the compounds of formulae Ia and X is defined as a hydrogen or a protecting group for a phenolic hydroxyl group, such as, for example, a 2-tetrahydropyranyl-group, a benzyl group, a 4-methoxybenzyl or a 2,5-dimethoxybenzyl group. The group $G^3$ in the compounds of formula IXa is a protecting group for a carboxylic acid, such as, for example methyl, ethyl, propyl, tert-butyl or benzyl, preferably methyl or ethyl. The group $G^4$ in the compounds of formulae IX, IXa and XIV is a leaving group, that can be replaced in a Suzuki-type reaction, such as a halide, e.g. bromide or chloride or as a sulfonate, e.g. a trifluoromethanesulfonate or a methanesulfonate. The group $G^5$ in the compounds of formula X is a boronic acid or a boronic ester or cyclic boronic ester.

The conversion of a compound of formula IXa, in which $G^3$ is not hydrogen, but a protecting group for a carboxylic acid, to a compound of formula IX is a suitable deprotection reaction, such as a basic hydrolysis, if $G^3$ is a methyl, ethyl or propyl residue, or as an acidic deprotection, if $G^3$ is a tert-butyl group, or as a hydrogenation, if $G^3$ is a benzyl group. As it is known to the skilled person the employed protection groups should chosen in a manner to be compatible with the desired reaction conditions for all subsequent steps. All protection and deprotection reactions used in the above-described transformation of compounds of the formula IX to compounds of formula IX are well known to the skilled person and can be carried out under standard conditions according to, or analogously to, procedures described in the literature, for example in P. J. Kocienski, Protecting Groups, Georg Thieme Verlag, Stuttgart, 1994 or T. W. Greene, P. G. M. Wuts, Protective Groups in Organic Synthesis, John Wiley, New York, 1999).

The reaction of the compounds of the formulae IX and III to form an amide of formula Ia is generally performed in the presence of activating agents, such as CDI, DCC, EDC, HOAt, HOBt, HATU, TOTU, TBTU BEP or combinations thereof, and optionally an additional base, such as TEA, DIPEA or N-methylmorpholin in an appropriate inert solvent, for example a hydrocarbon or a chlorinated hydrocarbon such as benzene, toluene, chlorobenzene, dichloromethane, dichloroethane, chloroform, or an ether such as tetrahydrofurane, 1,4-dioxane, dibutylether, diisopropylether, methyl-tert-butylether, dimethoxyethane, or an ester such as ethyl acetate or ethyl butanoate or an amide such as N,N-dimethylformamide or N,N-dimethylacetamide or N-methyl-pyridone or a in mixture of solvents. The reaction temperature in this case is generally from −30° C. to 200° C., preferably from −20° C. to 80', more preferably from 0° C. to 20° C. The reaction time is generally from 15 min to 6 days, preferably from 15 min to 16 h, depending on the composition of the mixture and the chosen temperature range. The acids of formula IX can be subjected to the reaction in form of their salts, for example their sodium salts. They can also be transformed into an activated derivative prior to the coupling with the amine, for example into an acid chloride or an acid anhydride by standard transformations. The amines of formula III can be subjected to the reaction in form of their salts, for example as hydrochloride or triflate salts, in which case usually an additional equivalent of the base is added to the reaction.

The reaction of the compound of the formula XIV with a compound of the formula X to a compound of formula Ia is a Suzuki-type reaction and is generally carried out in the presence of catalytic palladium compound, for example a palladium(II) salt such as palladium(II) acetate or palladium(II) chloride, which can be employed in the presence of a phosphine such as tricyclohexylphosphine or triphenylphosphine, or a palladium complex such as tetrakis(triphenylphosphine)palladium(0), palladium(0) bis(tri-tert-butylphosphin) or bis(triphenylphosphine)palladium(II) chloride, and favourably in the presence of a base, for example an alkaline metal carbonate or phosphate such as sodium carbonate or tripotassium phosphate, in an inert solvent, for example a hydrocarbon, such as benzene, toluene or xylene, or an ether, such as THF, dioxane or DME, or water, or a mixture of solvents, at temperatures from about 20° C. to about 200° C., for example at temperatures from about 80° C. to about 120° C. The reaction time is generally from 30 min to 48 h, preferably from 30 min to 16 h, depending on the composition of the mixture and the chosen temperature range.

A compound of the formula Ia can already be a compound of formula I, if $G^1$ and $G^2$ are both H and if $R^{6a}$ is $R^6$ and $R^{7a}$ is $R^7$. If a compound of formula Ia is not already a compound of formula I, it can be transformed into a compound of formula I in one step or in several steps depending of the meaning of the groups $G^1$, $G^2$, $R^{6a}$ and $R^{7a}$, as it was described above.

All reactions used in the above-described syntheses of the compounds of the formula I are per se well known to the skilled person and can be carried out under standard conditions according to, or analogously to, procedures described in the literature, for example in Houben-Weyl, Methoden der Organischen Chemie (Methods of Organic Chemistry), Thieme-Verlag, Stuttgart, or Organic Reactions, John Wiley & Sons, New York. If desired, the obtained compounds of the formula I, as well as any intermediate compounds, can be purified by customary purification procedures, for example by recrystallization or chromatography. As already mentioned, all starting compounds and intermediates employed into the above-described syntheses which contain an acidic or basic group, can also be employed in the form of salts, and all intermediates and final target compounds can also be obtained in the form of salts. As likewise mentioned above, depending on the circumstances of the specific case, in order to avoid an unwanted course of a reaction or side reactions during the synthesis of a compound it can generally be necessary or advantageous to temporarily block functional groups by introducing protective groups and deprotect them at a later stage of the synthesis, or to introduce functional groups in the form of precursor groups which later are converted into the desired functional groups. As examples of protecting groups amino-protecting groups may be mentioned which can be acyl groups or alkyloxycarbonyl groups, for example a tert-butyloxycarbonyl group (=Boc) which can be removed by treatment with trifluoroacetic acid (=TFA), a benzyloxycarbonyl group which can be removed by catalytic hydrogenation, or a fluoren-9-ylmethoxycarbonyl group which can be removed by treatment with piperidine, and protecting groups of carboxylic acid groups which can be protected as ester groups, such as tert-butyl esters which can be deprotected by treatment with trifluoroacetic acid, or benzyl esters which can be deprotected by catalytic hydrogenation. As an example of a precursor group the nitro group may be mentioned, which can be converted into an amino group by reduction, for example by catalytic hydrogenation. Such synthesis strategies, and protective groups and precursor groups which are suitable in a specific case, are known to the skilled person.

Another subject of the present invention are the novel starting compounds and intermediates occurring in the synthesis of the compounds of the formula I, including the compounds of the formulae Ia, II, IIa, III, IV, V, VI, VII, VIII, IX, IXa, X, XI, XII, XIII and XIV, wherein $R^1$, $R^2$, $R^3$, $R^4$, $R^5$, $R^6$, $R^7$, $R^{6a}$, $R^{7a}$, $G^2$, $G^3$, $G^4$ and $G^5$ are defined as above, in any of their stereoisomeric forms or a mixture of stereoisomeric forms in any ratio, and their salts, and solvates of any of them, and their use as intermediates. The invention also includes all tautomeric forms of the said intermediates and starting compounds. All explanations given above and embodiments specified above with respect to the compounds of the formula I apply correspondingly to the said intermediates and starting compounds. Another subject of the invention are in particular the novel specific starting compounds and intermediates disclosed herein. Independently thereof whether they are disclosed as a free compound and/or as a specific salt, they are a subject of the invention both in the form of the free compounds and in the form of their salts, and if a specific salt is disclosed, additionally in the form of this specific salt, and in the form of solvates of any of them.

EXEMPLIFICATION

The following examples illustrate the invention.

When example compounds containing a basic group were purified by preparative high pressure liquid chromatography (HPLC) on reversed phase (RP) column material and, as customary, the eluent was a gradient mixture of water and acetonitrile containing trifluoroacetic acid (TFA), they were in part obtained in the form of their acid addition salt with trifluoroacetic acid, depending on the details of the workup such as evaporation or lyophilization conditions. In the names of the example compounds and their structural formulae any such contained trifluoroacetic acid is not specified. When example compounds containing a basic group were obtained after an acidic deprotection step, they were in part obtained in the form of their acid addition salt with hydrochloric acid, depending on the details of the workup such as washing steps with bases or evaporation or lyophilization conditions. In the names of the example compounds and their structural formulae any such contained hydrochloric acid may or may not be specified.

The prepared compounds were in general characterized by spectroscopic data and chromatographic data, in particular mass spectra (MS) and HPLC retention times ($R_t$; in min) which were obtained by combined analytical HPLC/MS characterization (LC/MS), and/or nuclear magnetic resonance (NMR) spectra. In the NMR characterization, the chemical shift δ (in ppm), the number of hydrogen atoms and the multiplicity (s=singlet, d=doublet, dd=double doublet, t=triplet, dt=double triplet, q=quartet, m=multiplet; b=broad) of the peaks is given. In the MS characterization, in general the mass number (m/z) of the peak of the molecular ion M, e.g. $M^+$, or of a related on such as the ion M+1, e.g. $[M+1]^+$, i.e. the protonated molecular ion $[M+H]^+$, which was formed depending on the ionization method used, is given. Generally, the ionization method was electrospray ionization (ESI). The LC/MS conditions used were as follows.

Method LC1:
Column: BEH C18 2.1×50 mm; 1.7 μm; flow: 0.9 ml; solvent A: water+0.1% formic acid; solvent B: acetonitrile+0.08% formic acid; gradient from 95% A+5% B to 5% A+95% B in 1.1 min; then 5% A+95% B for 0.6 min; MS ionisation method: $ESI^+$.

Method LC2:
Column: Waters Xbridge C18 4.6 mm×50 mm, 2.5 μM; flow: 1.3 ml/min; solvent A: water+0.05% TFA; solvent B: methanol+0.05% TFA; gradient from 98% A+2% B for 1 min, then from 98% A+2% B to 5% A+95% B in 4 min, then 5% A+95% B for 1.25 min; MS ionisation method: $ESI^+$.

Method LC3:
Column: Waters Xbridge C18 4.6 mm×50 mm, 2.5 μM; flow: 1.3 ml/mm; solvent A: water+0.1% formic acid; solvent B: acetonitrile+0.1% formic acid; gradient from 97% A+3% B to 40% A+60% B in 3.5 min, then to 2% A+98% B in 0.5 min; then 2% A+98% B for 1.0 min; MS ionisation method: $ESI^+$.

Method LC4:
Column: Phenomenex, 10×2 mm, 1.7 μm; flow: 1.1 ml/min; solvent A: water+0.05% trifluoroacetic acid; solvent B: acetonitrile; gradient; from 93% A+7% B to 5% A+95% B in 1.2 min, then 5% A+95% B for 0.2 min; MS-Ionisation-method: $ESI^+$.

Method LC5:

Column: BEH C18 2.1×50 mm; 1.7 µm, flow: 0.9 ml, solvent A water+0.05% formic acid; solvent B: acetonitrile+0.035% formic acid; gradient from 95% A+5% B to 5% A+95% B in 1.1 min; then 5% A+95% B for 0.6 min; MS ionisation method: ESI$^+$.

Method LC6:

Column; YMC-Pack Jsphere H80 33×2.1 mm, 4 µm; flow: 1.3 ml/min; solvent A: water+0.05% trifluoroacetic acid; solvent B: acetonitrile+0.05% trifluoroacetic acid; gradient from 95% A+5% B to 5% A+95% B in 2.5 min, then to 95% A+5% B in 0.7 min; MS-Ionisationmethod: ESI$^+$.

Method LC7:

Column: YMC-Pack Jsphere H80 33×2.1 mm, 4 µm; flow: 1.3 ml/min; solvent A: water+0.05% trifluoroacetic acid; solvent B: acetonitrile+0.05% trifluoroacetic acid; gradient from 95% A+5% B to 5% A+95% B in 2.5 min, MS-Ionisationmethod: ESI$^+$ Method LC8:

Column Waters Xbridge C18 4.6 mm×50 mm, 2.5 µM; flow: 1.3 ml/mm; solvent A: water+0.1% formic acid; solvent B: acetonitrile+0.1% formic acid; gradient from 97% A+3% B to 40% A+60% B in 3.5 min, then to 2% A+98% B in 0.5 min; then 2% A+98% B for 1.0 min; then to 97% A+3% B in 0.2 min, then 97% A+3% B for 1.3 min; MS ionisation method: ESI$^+$.

Method LC9:

Instrument: Waters UPLC, column: BEN C18, 2.1×50 mm; 1.7 µm, flow: 0.9 ml, solvent A water+0.05% formic acid; solvent B: acetonitrile+0.035% formic acid; gradient from 98% A+2% B to 5% A+95% B in 2 min, then 5% A+95% B for 0.6 min; MS-Ionisationmethod:

Method LC10:

Column: YMC Jsphere H80 33×2.1 mm, 4 µm; flow: 1 ml/min; solvent A: water+0.05% trifluoroacetic acid; solvent B: methanol+0.05% trifluoroacetic acid; gradient 98% A+2% B for 1 min, then from 98% A+2% B to 5% A+95% B in 4.0 min, then 5% A+95% B for 1.25 min; MS ionisation method: ESI$^+$.

Method LC11;

Column: Waters Xbridge C18 4.6 mm×50 mm, 2.5 µM; flow: 1.3 ml/min; solvent A: water+0.05% trifluoroacetic acid; solvent B: acetonitrile+0.05% trifluoroacetic acid; gradient 95% A+5% B for 0.3 min, then from 95% A+5% B to 5% A+95% B in 3.2 min, then 5% A+95% B for 0.5 min; MS ionisation method: ESI$^+$.

Method LC12:

Column: Waters Xbridge C18 4.6 mm×50 mm, 2.5 µM; flow: 1.3 ml/min; solvent A: water+0.1% formic acid; solvent B: acetonitrile+0.08% formic acid; gradient from 97% A+3% B to 40% A+60% B in 3.5 min, then to 2% A+98% B in 0.5 min; then 2% A+98% B for 1.0 min; MS ionisation method: ESI$^+$.

Method LC13:

Column: BEH C18 2.1×50 mm, 1.7 µm; flow 0.8 mL/min; solvent A: water+0.1% formic acid; solvent B: acetonitrile+0.1% formic acid; gradient from 95% A+5% B to 94% A+6% B in 0.05 min; then from 94% A+6% B to 0% A+100% B in 2.45 min; MS ionisation method: ESI$^+$ or ESI$^-$.

Method LC14:

Column BEH C18 2.1×50 mm, 1.7 µm; flow 1.0 ml/min; solvent A: water+0.05% trifluoroacetic acid; solvent B: acetonitrile+0.035% trifluoroacetic acid; gradient: 98% A+2% B for 1.6 min; then from 98% A+2% B to 0% A+100% B in 0.5 min; then 0% A+100% B for 0.4 min; then from 0% A+100% B to 98% A+2% B in 0.5 min; MS ionisation method: ESI$^+$ or ESI$^-$.

Method LC15:

Column: Kromasil C18 50×2.1 mm; 3.5 µm; flow 0.8 mL/min; solvent A: CH3COONH4 5 mM+3% acetonitrile; solvent B: acetonitrile; gradient: 100% A+0% B for 5.5 min; then from 100% A+0% B to 0% A+100% B in 1.5 min; then 0% A+100% B for 0.1 min; then from 0% A+100% B to 100% A+02% B in 2.9 min; MS ionisation method: ESI$^+$ or ESI$^-$.

Method LC16:

Column XBridge 4.6×30 mm, 3 µm, flow 1 ml/min; solvent A: water+0.1% formic acid; solvent B: acetonitrile+ 0.1% formic acidgradient: from 95% A+5% B to 0% A+100% B in 5.5 min; then 0% A+100% B for 1.5 min; MS ionisation method: ESI$^+$ or ESI$^-$.

List of Abbreviations

BEP 2-bromo-1-ethyl-pyridinium tetrafluoroborate

BOC tert.butoxy carbonyl

CDI N,N'-carbonyldiimidazole

DCC 1,3-dicyclohexylcarbodiimide

DCM dichloromethane

DEA diethylamine

DMF N,N-dimethylformamide

EDC 1-(3-dimethylaminopropyl)-3-ethylcarbodiimide hydrochloride

EtOAc ethyl acetate

EtOH ethanol

Exp. No. Example number h hour/s

HOAt 1-hydroxy-aza-benzotriazole

HOBt 1-hydroxy-benzotriazole

HATU N-tetramethyl-uronium hexafluorophosphate

HPLC high pressure liquid chromatography

LC liquid chromatography

MeOH methanol

Min minutes

MS mass spectroscopy $R_t$ retention time r.t. room temperature sep. separation

TBTU [(benzotriazol-1-yloxy)-dimethylamino-methylene] dimethyl-ammonium tetrafluoroborate TEA triethylamine TFA trifluoroacetic acid THF tetrahydrofurane TOTU O-(cyano(ethoxycarbonyl)methyleneamino)-N,N,N',N'-tetramethyluronium tetrafluoroborate

Example 1

[6-(4-Hydroxy-phenyl)-3-methyl-1H-pyrazolo[3,4-b]pyridin-4-yl]-(2-methyl-2-phenyl-piperazin-1-yl)-methanone

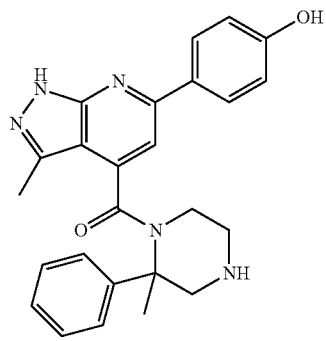 [SMILES: Cc1n[nH]c2nc(-c3ccc(O)cc3)cc(C(=O)N3CCNCC3(C)c3ccccc3)c12]

(a) 6-Hydroxy-3-methyl-1H-pyrazolo[3,4-b]pyridine-4-carboxylic acid ethyl ester

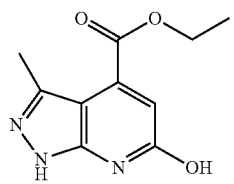 [SMILES: CCOC(=O)c1cc(O)nc2[nH]nc(C)c12]

A mixture of 3-amino-5-methylpyrazole (50.0 g), diethyl oxalate sodium salt (127.3 g) and acetic acid (113 mL) in 1N aqueous hydrochloric acid (625 mL) was stirred at 80° C. for 14 h, then refluxed for 3 h, cooled to r.t., and the precipitate formed was filtered by suction filtration and dried in vacuo at 60° C. The crude product was stirred in 500 mL ethyl acetate at r.t. and the solid was filtered off and dried in air. 40.2 g (35%) of the title compound were obtained as pale yellow solid.

$^1$H-NMR (500 MHz, d6-DMSO): 1.33 (t, 3H), 2.45 (s, 3H), 4.34 (q, 2H), 6.44 (s, 1H), 11.90 (br s, 1H), 13.05 (br s, 1H).
LC/MS (Method LC1): $R_t$=0.91 min; m/z=222.1 [M+H]$^+$.

(b) 6-Chloro-3-methyl-1H-pyrazolo[3,4-b]pyridine-4-carboxylic acid ethyl ester

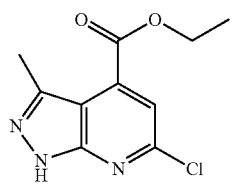 [SMILES: CCOC(=O)c1cc(Cl)nc2[nH]nc(C)c12]

6-Hydroxy-3-methyl-1H-pyrazolo[3,4-b]pyridine-4-carboxylic acid ethyl ester (30.0 g), phosphorous oxychloride (12.6 mL) and 1,8-diazabicyclo[5.4.0]undec-7-ene (22.3 mL) were dissolved in toluene (550 mL) at 0° C. (ice bath), then stirred at 110° C. for 5 h, then cooled to r.t. The mixture was poured into a vigorously stirred solution of potassium acetate (39.9 g) in water (1 l). The aqueous solution was extracted with ethyl acetate, the organic layer was dried over magnesium sulfate and concentrated in vacuo. The crude product was used for the next step without further purification. 28.6 g (88%) of the title compound were obtained.

$^1$H-NMR (500 MHz, d$_6$-DMSO): 1.39 (t, 3H), 2.60 (s, 3H), 4.44 (q, 2H), 7.53 (s, 1H), 13.70 (s, 1H).
LC/MS (Method LC1): $R_t$=1.19 min; m/z=240.1 [M+H]$^+$.

(c) 6-Chloro-3-methyl-1-(tetrahydro-pyran-2-yl)-1H-pyrazolo[3,4-b]pyridine-4-carboxylic acid ethyl ester

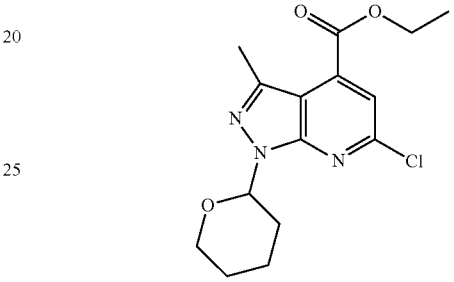

A mixture of 6-chloro-3-methyl-1H-pyrazolo[3,4-b]pyridine-4-carboxylic acid ethyl ester (28.5 g), 3,4-dihydro-2H-pyran (23.7 mL) and p-toluenesulfonic acid monohydrate (6.8 g) in THF (800 mL) was stirred at r.t. until the reaction was complete. The mixture was poured into water (1.5 l) and extracted with ethyle acetate (600 mL). The organic phase was dried over magnesium sulfate and concentrated in a vacuo. The crude product was purified by silica gel chromatography (heptane/ethyl acetate gradient). 37.8 g (98%) of the title compound were obtained.

$^1$H-NMR (500 MHz, d$_6$-DMSO): 1.38 (t, 3H), 1.40-1.61 (m, 2H), 1.70-1.84 (m, 1H), 1.86-1.92 (m, 1H), 1.97-2.06 (m, 1H), 2.37-2.48 (m, 1H), 2.60 (s, 3H), 3.68-3.73 (m, 1H), 3.91-3.96 (m, 1H), 445 (q, 2H), 5.92 (dd, 1H), 7.63 (s, 1H).
LC/MS (Method LC2): $R_t$=4.92 min; m/z=240.1 [M+H—C5H9O]$^+$.

(d) 6-Chloro-3-methyl-1-(tetrahydro-pyran-2-yl)-1H-pyrazolo[3,4-b]pyridine-4-carboxylic acid

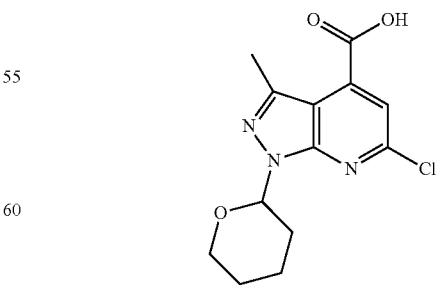

A mixture of 6-chloro-3-methyl-1-(tetrahydro-pyran-2-yl)-1H-pyrazolo[3,4-b]pyridine-4-carboxylic acid ethyl ester (25 g) and 1N sodium hydroxide solution (200 mL) in isopropanol (200 mL) was stirred at r.t. for 3 h. The solvent was distilled off, the residue was taken up in a little water and brought to pH 3-4 with 1N hydrochloric acid. A solid precipitated, which was filtered off and dried in air. 22 g (96%) of the title compound were obtained.

$^1$H-NMR (500 MHz, $d_6$-DMSO): 1.40-1.61 (m, 2H), 1.73-1.84 (m, 1H), 1.86-1.92 (m, 1H), 2.00-2.07 (m, 1H), 2.37-2.48 (m, 1H), 2.62 (s, 3H), 3.66-3.75 (m, 1H), 3.92-3.96 (m, 1H), 5.82 (dd, 1H), 7.58 (s, 1H), 14.2 (br s, 1H).

LC/MS (Method LC1): $R_t$=1.16 min; m/z=296.1 [M+H]$^+$.

(e) 4-[6-Chloro-3-methyl-1-(tetrahydro-pyran-2-yl)-1H-pyrazolo[3,4-b]pyridine-4-carbonyl]-3-methyl-3-phenyl-piperazine-1-carboxylic acid tert-butyl ester

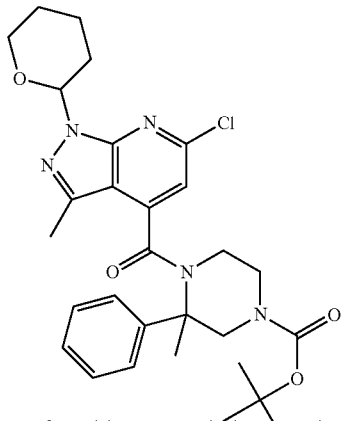

A mixture of 6-chloro-3-methyl-1-(tetrahydro-pyran-2-yl)-1H-pyrazolo[3,4-b]pyridine-4-carboxylic acid (325 mg), 3-methyl-3-phenyl-piperazine-1-carboxylic acid tert-butyl ester (319 mg), DIPEA (0.38 mL) and BEP (331 mg) in DMF (8.1 mL) was stirred at r.t. for 90 min. The mixture was poured into water. A solid precipitated which was filtered off and dried in a desiccator vacuum over sodium hydroxide. 540 mg (89%) of the title compound were obtained.

LC/MS (Method LC1): $R_t$=1.40 min; m/z=554.3 [M+H]$^+$.

(f) 3-Methyl-4-{3-methyl-1-(tetrahydropyran-2-yl)-6-[4-(tetrahydro-pyran-2-yloxy)phenyl]-1H-pyrazolo[3,4-b]pyridine-4-carbonyl}-3-phenyl-piperazine-1-carboxylic acid tert-butyl ester

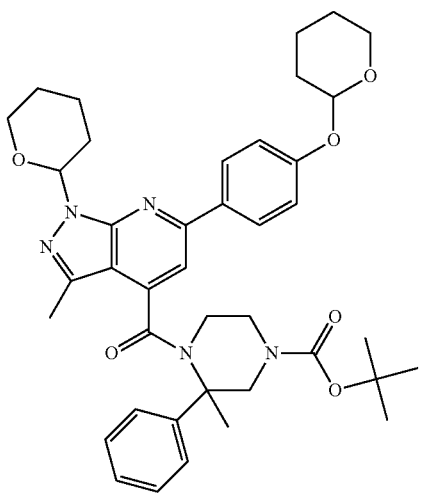 [SMILES: Cc1nn(C2CCCCO2)c2nc(-c3ccc(OC4CCCCO4)cc3)cc(C(=O)N3CCN(C(=O)OC(C)(C)C)CC3(C)c3ccccc3)c12]

4-[6-Chloro-3-methyl-1-(tetrahydro-pyran-2-yl)-1H-pyrazolo[3,4-b]pyridine-4-carbonyl]-3-methyl-3-phenyl-piperazine-1-carboxylic acid tert-butyl ester (255 mg) and 4-(tetrahydro-2H-pyran-2-yloxy)phenylboronic acid (153 mg) were dissolved in DMF/toluene (v/v=1/1, 7.5 mL). After inertisation of the mixture with argon; cesium fluoride (140 mg) and tetrakis(triphenylphosphine)palladium(0) (27 mg) were added. The mixture was stirred at 100° C. overnight. The mixture was filtered through a 0.2 μm membrane syringe filter, the filtrate was diluted with ethyl acetate and washed three times with water (15 mL each) and once with brine (10 mL). The organic phase was dried over magnesium sulfate and concentrated. The residue was absorbed on silica and purified by flash chromatography (heptane/ethylacetate v/v=1/1). 3000 g (94%) of the title compound were obtained.

LC/MS (Method LC1): $R_t$=1.48 min; m/z=696.5 [M+H]$^+$.

(g) [6-(4-Hydroxy-phenyl)-3-methyl-1H-pyrazolo[3,4-b]pyridin-4-yl]-(2-methyl-2-phenyl-piperazin-1-yl)-methanone

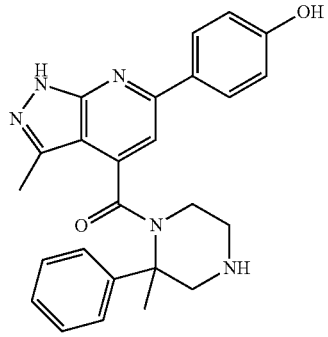 [SMILES: Cc1n[nH]c2nc(-c3ccc(O)cc3)cc(C(=O)N3CCNCC3(C)c3ccccc3)c12]

A mixture of 3-methyl-4-{3-methyl-1-(tetrahydropyran-2-yl)-6-[4-(tetrahydro-pyran-2-yloxy)-phenyl]-1H-pyrazolo[3,4-b]pyridine-4-carbonyl}-3-phenyl-piperazine-1-carboxylic acid tert-butyl ester (300 mg) and HCl (4M in 1,4-dioxane, 104 μL) in dichloromethane (2 mL) was stirred at r.t. overnight. A solid precipitated during the reaction, which was filtered off and dried in air. The sticky solid was triturated with acetonitrile and filtered again, washed with acetonitrile and dried in air. 137 mg (64%) of the title compound were obtained as hydrochloride salt.

LC/MS (Method LC1): $R_t$=0.91 min; m/z=428.3 [M+H]$^+$.

Example 2

[3-Ethyl-6-(3-fluoro-4-hydroxy-phenyl)-1H-pyrazolo[3,4-b]pyridin-4-yl]-piperazin-1-yl-methanone

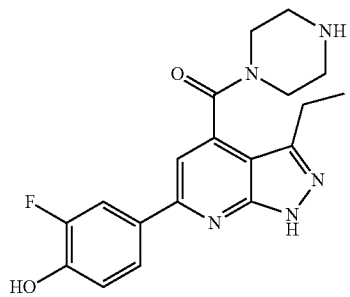 [SMILES: CCc1n[nH]c2nc(-c3ccc(O)c(F)c3)cc(C(=O)N3CCNCC3)c12]

(a) 3-Ethyl-6-(3-fluoro-4-hydroxy-phenyl)-1H-pyrazolo[3,4-b]pyridine-4-carboxylic acid

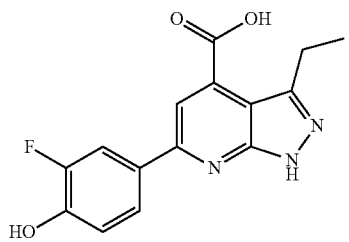 [SMILES: CCc1n[nH]c2nc(-c3ccc(O)c(F)c3)cc(C(=O)O)c12]

A mixture of 5-ethyl-2H-pyrazol-3-ylamine (1 g, 9 mmol), 3-fluoro-4-hydroxybenzaldehyde (1.26 g, 9 mmol), pyruvic acid (0.63 ml, 9 mmol) and glacial acetic acid (14 ml) was heated to reflux under nitrogen for 2 h and then cooled to room temperature. The precipitate was filtered and washed with absolute ethanol to afford the title compound (0.614 g, 23%) as beige solid.
LC/MS (Method LC13): $R_t$=0.93 min; m/z=300 [M−H]⁻.

(b) 4-[3-Ethyl-6-(3-fluoro-4-hydroxy-phenyl)-1H-pyrazolo[3,4-b]pyridine-4-carbonyl]-piperazine-1-carboxylic acid tert-butyl ester

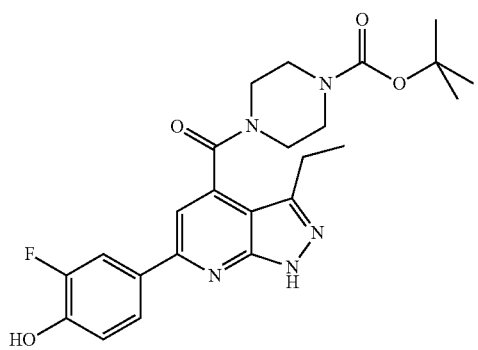 [SMILES: CCc1n[nH]c2nc(-c3ccc(O)c(F)c3)cc(C(=O)N3CCN(C(=O)OC(C)(C)C)CC3)c12]

To a suspension of 3-ethyl-6-(3-fluoro-4-hydroxy-phenyl)-1H-pyrazolo[3,4-b]pyridine-4-carboxylic acid (0.25 g, 0.83 mmol), tert-butyl piperazine-1-carboxylate (0.17 g, 0.91 mmol), 1-hydroxybenzotriazole (0.11 g, 0.83 mmol), and N-(3-dimethylaminopropyl)-N'-ethylcarbodiimide hydrochloride (0.16 g, 0.83 mmol) in anhydrous tetrahydrofurane (5 ml) was added dry N,N-dimethylacetamide (2 ml). The reaction mixture was stirred at room temperature under nitrogen overnight. A solution of saturated sodium hydrogen carbonate was then added, the resulting precipitate was filtered off to afford the title compound (0.25 g, 66%) as a beige solid.
LC/MS (Method LC13): Rt=1.43 min; m/z=470 [M+H]⁺.

(c) [3-Ethyl-6-(3-fluoro-4-hydroxy-phenyl)-1H-pyrazolo[3,4-b]pyridin-4-yl]-piperazin-1-yl-methanone

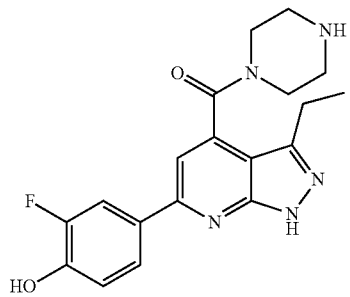 [SMILES: CCc1n[nH]c2nc(-c3ccc(O)c(F)c3)cc(C(=O)N3CCNCC3)c12]

To a solution of 4-[3-ethyl-6-(3-fluoro-4-hydroxy-phenyl)-1H-pyrazolo[3,4-b]pyridine-4-carbonyl]-piperazine-1-carboxylic acid tert-butyl ester (0.23 g, 0.50 mmol) in isopropanol (7 ml) was added 4N HCl in dioxane (1.3 ml). The reaction mixture was heated for 4 hours, diethyl ether was then added, the resulting precipitate was filtered off and washed once with diethyl ether to afford the hydrochloride salt of the title compound (0.19 g, 97%) as a yellow solid.
LC/MS (Method LC14): Rt=0.56 min; m/z=370 [M+H]⁺.

The following pyrazolopyridine derivatives were obtained in a similar fashion as described for Example 2 [3-Ethyl-6-(3-fluoro-4-hydroxy-phenyl)-1H-pyrazolo[3,4-b]pyridin-4-yl]-piperazin-1-yl-methanone step (a), using 5-ethyl-2H-pyrazol-3-ylamine, 5-propyl-2H-pyrazol-3-ylamine, 5-methyl-2H-pyrazol-3-ylamine or 5-trifluoromethyl-2H-pyrazol-3-ylamine and the respective substituted benzaldehydes as starting materials:

| Name | Structure | LC/MS method | m/z [M + H]⁺ [M − H]⁻ | $R_t$ [min] |
|---|---|---|---|---|
| 3-Ethyl-6-(3-fluoro-4-hydroxy-phenyl)-1H-pyrazolo[3,4-b]pyridine-4-carboxylic acid | 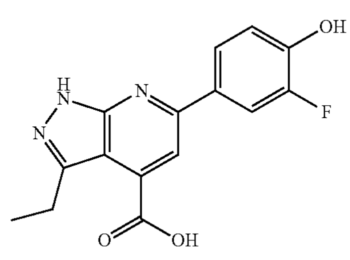 [SMILES: CCc1n[nH]c2nc(-c3ccc(O)c(F)c3)cc(C(=O)O)c12] | LC13 | 300 | 0.93 |

-continued

| Name | Structure | LC/MS method | m/z [M + H]+ [M − H]− | R_t [min] |
|---|---|---|---|---|
| 3-Ethyl-6-(4-hydroxy-phenyl)-1H-pyrazolo[3,4-b]pyridine-4-carboxylic acid | 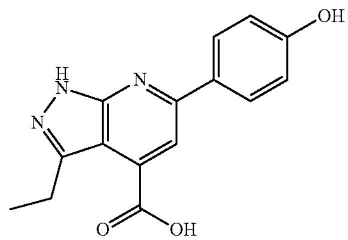 [SMILES: CCc1n[nH]c2nc(-c3ccc(O)cc3)cc(C(=O)O)c12] | LC16 | 283 | 3.57 |
| 6-(4-Hydroxy-phenyl)-3-propyl-1H-pyrazolo[3,4-b]pyridine-4-carboxylic acid | 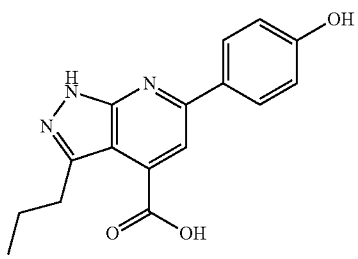 [SMILES: CCCc1n[nH]c2nc(-c3ccc(O)cc3)cc(C(=O)O)c12] | LC13 | 298 | 1.03 |
| 6-(4-Hydroxy-phenyl)-3-trifluoromethyl-1H-pyrazolo[3,4-b]pyridine-4-carboxylic acid | 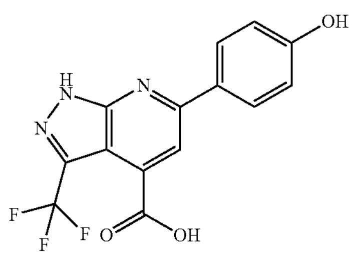 [SMILES: O=C(O)c1cc(-c2ccc(O)cc2)nc2[nH]nc(C(F)(F)F)c12] | LC16 | 323 | 3.95 |
| 6-(2-Chloro-4-hydroxy-phenyl)-3-methyl-1H-pyrazolo[3,4-b]pyridine-4-carboxylic acid | 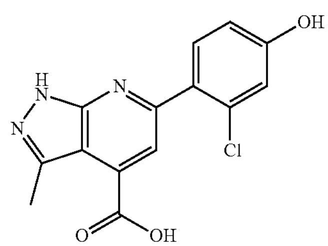 [SMILES: Cc1n[nH]c2nc(-c3ccc(O)cc3Cl)cc(C(=O)O)c12] | LC13 | 302 [M − H]− | 1.07 |
| 6-(4-Hydroxy-phenyl)-3-methyl-1H-pyrazolo[3,4-b]pyridine-4-carboxylic acid | 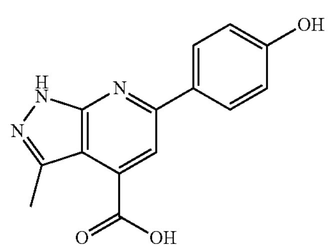 [SMILES: Cc1n[nH]c2nc(-c3ccc(O)cc3)cc(C(=O)O)c12] | LC16 | 269 | 3.34 |
| 6-(3-Fluoro-4-hydroxy-phenyl)-3-methyl-1H-pyrazolo[3,4-b]pyridine-4-carboxylic acid | 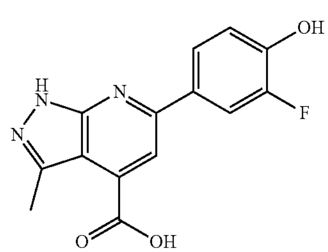 [SMILES: Cc1n[nH]c2nc(-c3ccc(O)c(F)c3)cc(C(=O)O)c12] | LC13 | 288 | 0.88 |

-continued

| Name | Structure | LC/MS method | m/z [M + H]+ [M − H]− | R_t [min] |
|---|---|---|---|---|
| 6-(4-Hydroxy-3-methyl-phenyl)-3-methyl-1H-pyrazolo[3,4-b]pyridine-4-carboxylic acid | 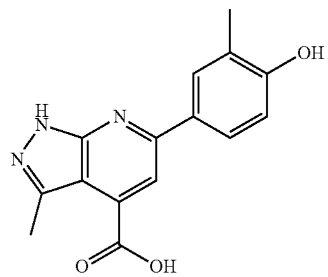 [SMILES: Cc1cc(-c2cc(C(=O)O)c3c(C)n[nH]c3n2)ccc1O] | LC14 | 284 | 0.68 |
| 6-(3-Chloro-4-hydroxy-phenyl)-3-methyl-1H-pyrazolo[3,4-b]pyridine-4-carboxylic acid | 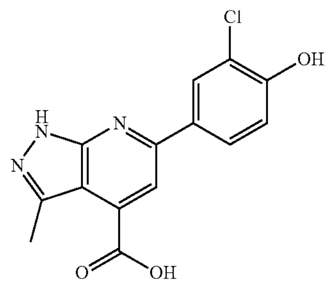 [SMILES: Cc1n[nH]c2nc(-c3ccc(O)c(Cl)c3)cc(C(=O)O)c12] | LC14 | 304 | 0.74 |
| 6-(4-Hydroxy-3-methoxy-phenyl)-3-methyl-1H-pyrazolo[3,4-b]pyridine-4-carboxylic acid | 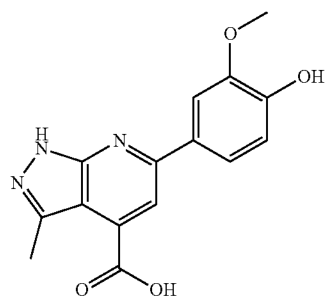 [SMILES: COc1cc(-c2cc(C(=O)O)c3c(C)n[nH]c3n2)ccc1O] | LC14 | 300 | 0.65 |
| 6-(2-Fluoro-4-hydroxy-phenyl)-3-methyl-1H-pyrazolo[3,4-b]pyridine-4-carboxylic acid | 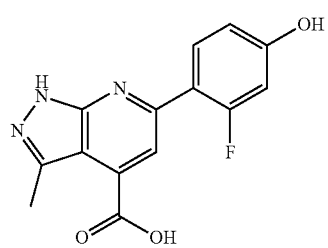 [SMILES: Cc1n[nH]c2nc(-c3ccc(O)cc3F)cc(C(=O)O)c12] | LC14 | 288 | 0.67 |
| 6-(2,6-Difluoro-4-hydroxy-phenyl)-3-methyl-1H-pyrazolo[3,4-b]pyridine-4-carboxylic acid | 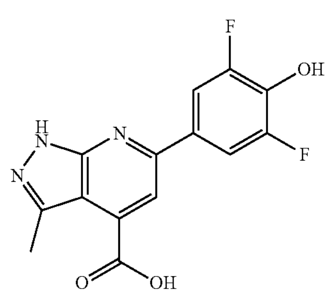 [SMILES: Cc1n[nH]c2nc(-c3cc(F)c(O)c(F)c3)cc(C(=O)O)c12] | LC14 | 306 | 0.72 |

| Name | Structure | LC/MS method | m/z [M + H]⁺ [M − H]⁻ | R_t [min] |
|---|---|---|---|---|
| 6-(4-Hydroxy-2-methyl-phenyl)-3-methyl-1H-pyrazolo[3,4-b]pyridine-4-carboxylic acid | 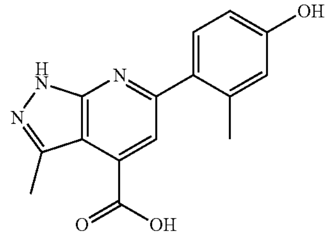 | LC14 | 284 | 0.63 |
| 6-(4-Hydroxy-2-methoxy-phenyl)-3-methyl-1H-pyrazolo[3,4-b]pyridine-4-carboxylic acid | 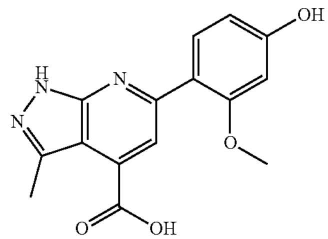 [SMILES: COc1cc(O)ccc1-c1cc(C(=O)O)c2c(C)n[nH]c2n1] | LC13 | 300 | 1.06 |

6-(3-Ethoxy-4-hydroxy-phenyl)-3-methyl-1H-pyrazolo[3,4-b]pyridine-4-carboxylic acid

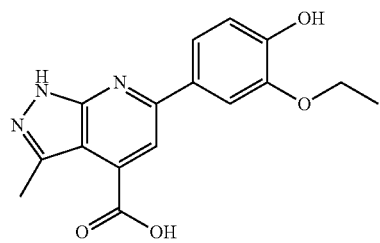 [SMILES: CCOc1cc(-c2cc(C(=O)O)c3c(C)n[nH]c3n2)ccc1O]

The title compound was obtained in a similar fashion as described for Example 2, [3-Ethyl-6-(3-fluoro-4-hydroxy-phenyl)-1H-pyrazolo[3,4-b]pyridin-4-yl]-piperazin-1-yl-methanone, step (a), using 5-methyl-2H-pyrazol-3-ylamine and 3-ethoxy-4-hydroxybenzaldehyde as starting materials.

$^1$H-NMR (400 mHz, d6-DMSO): 1.41 (t, J=7 Hz, 3H); 2.58-2.61 (m, 3H); 4.15 (q, J=7 Hz, 2H); 6.93 (d, J=8 Hz, 1H); 7.62 (dd. J=8, 2 Hz, 1H); 7.73 (d, J=2 Hz, 1H), 7.94 (s, 1H), 9.39 (s, 1H), 13.45 (bs, 2H).

The following examples have been prepared following a similar procedure as described for Example 2, [3-Ethyl-6-(3-fluoro-4-hydroxy-phenyl)-1H-pyrazolo[3,4-b]pyridin-4-yl]-piperazin-1-yl-methanone, steps (b) and (c) using the 1H-pyrazolo[3,4-b]pyridine-4-carboxylic acid intermediates described above and tert-butyl piperazine-1-carboxylate:

| Exp. No. | Name | Structure | LC/MS method | m/z [M + H]⁺ | R_t [min] |
|---|---|---|---|---|---|
| 3 | [3-Ethyl-6-(4-hydroxy-phenyl)-1H-pyrazolo[3,4-b]pyridin-4-yl]-piperazin-1-yl-methanone | 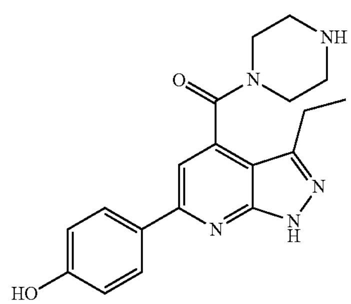 [SMILES: CCc1n[nH]c2nc(-c3ccc(O)cc3)cc(C(=O)N3CCNCC3)c12] | LC14 | 352 | 0.54 |

-continued

| Exp. No. | Name | Structure | LC/MS method | m/z [M + H]+ | R$_t$ [min] |
|---|---|---|---|---|---|
| 4 | [6-(4-Hydroxy-phenyl)-3-propyl-1H-pyrazolo[3,4-b]pyridin-4-yl]-piperazin-1-yl]-methanone | 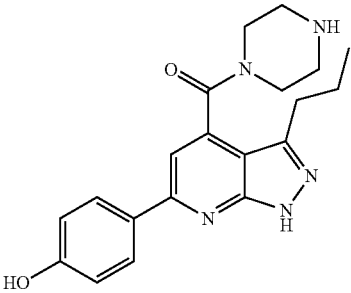 [SMILES: CCCc1n[nH]c2nc(-c3ccc(O)cc3)cc(C(=O)N3CCNCC3)c12] | LC14 | 366 | 0.58 |
| 5 | [6-(4-Hydroxy-phenyl)-3-trifluoromethyl-1H-pyrazolo[3,4-b]pyridin-4-yl]-piperazin-1-yl-methanone | 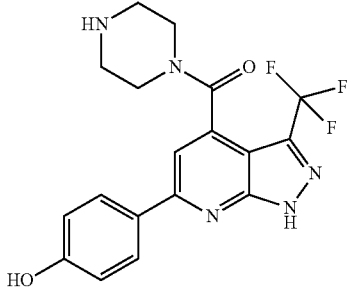 [SMILES: O=C(c1cc(-c2ccc(O)cc2)nc2[nH]nc(C(F)(F)F)c12)N1CCNCC1] | LC14 | 392 | 0.59 |
| 6 | [6-(2-Chloro-4-hydroxy-phenyl)-3-methyl-1H-pyrazolo[3,4-b]pyridin-4-yl]-piperazin-1-yl-methanone | 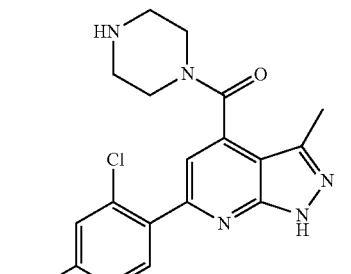 | LC14 | 372 | 0.54 |
| 7 | [6-(3-Fluoro-4-hydroxy-phenyl)-3-methyl-1H-pyrazolo[3,4-b]pyridin-4-yl]-piperazin-1-yl-methanone | 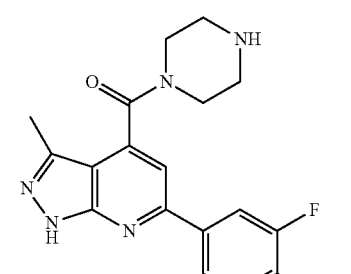 | LC15 | 356 | 2.25 |
| 8 | [6-(4-Hydroxy-3-methyl-phenyl)-3-methyl-1H-pyrazolo[3,4-b]pyridin-4-yl]-piperazin-1-yl-methanone | 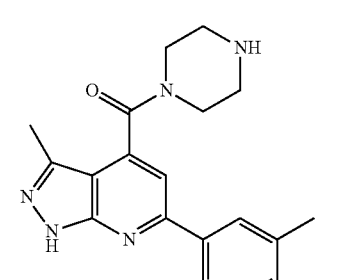 | LC13 | 350 [M − H]− | 2.40 |

-continued

| Exp. No. | Name | Structure | LC/MS method | m/z [M + H]+ | R$_t$ [min] |
|---|---|---|---|---|---|
| 9 | [6-(3-Chloro-4-hydroxy-phenyl)-3-methyl-1H-pyrazolo[3,4-b]pyridin-4-yl]-piperazin-1-yl-methanone | 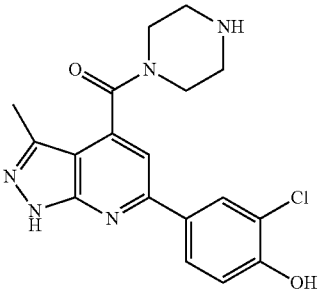 [SMILES: Cc1n[nH]c2nc(-c3ccc(O)c(Cl)c3)cc(C(=O)N3CCNCC3)c12] | LC14 | 372 | 0.57 |
| 10 | [6-(4-Hydroxy-3-methoxy-phenyl)-3-methyl-1H-pyrazolo[3,4-b]pyridin-4-yl]-piperazin-1-yl-methanone | 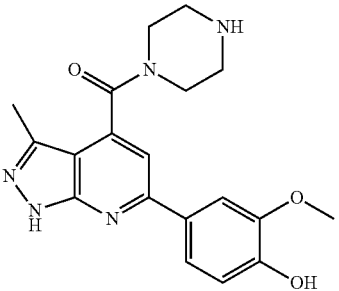 [SMILES: COc1cc(-c2cc(C(=O)N3CCNCC3)c3c(C)n[nH]c3n2)ccc1O] | LC14 | 368 | 0.52 |
| 11 | [6-(2-Fluoro-4-hydroxy-phenyl)-3-methyl-1H-pyrazolo[3,4-b]pyridin-4-yl]-piperazin-1-yl-methanone | 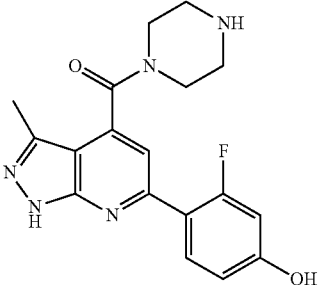 [SMILES: Cc1n[nH]c2nc(-c3ccc(O)cc3F)cc(C(=O)N3CCNCC3)c12] | LC15 | 356 | 2.28 |
| 12 | [6-(3,5-Difluoro-4-hydroxy-phenyl)-3-methyl-1H-pyrazolo[3,4-b]pyridin-4-yl]-piperazin-1-yl-methanone | 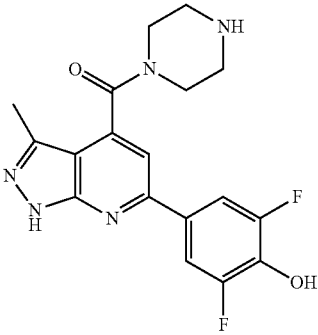 [SMILES: Cc1n[nH]c2nc(-c3cc(F)c(O)c(F)c3)cc(C(=O)N3CCNCC3)c12] | LC15 | 374 | 2.10 |
| 13 | [6-(4-Hydroxy-2-methyl-phenyl)-3-methyl-1H-pyrazolo[3,4-b]pyridin-4-yl]-piperazin-1-yl-methanone | 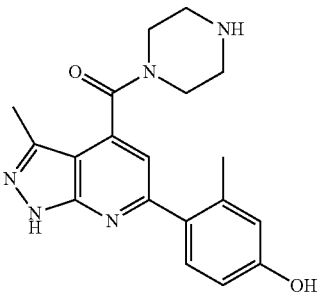 [SMILES: Cc1cc(O)ccc1-c1cc(C(=O)N2CCNCC2)c2c(C)n[nH]c2n1] | LC14 | 352 | 0.51 |

| Exp. No. | Name | Structure | LC/MS method | m/z [M + H]⁺ | R_t [min] |
|---|---|---|---|---|---|
| 14 | [6-(4-Hydroxy-2-methoxy-phenyl)-3-methyl-1H-pyrazolo[3,4-b]pyridin-4-yl]-piperazin-1-yl-methanone | 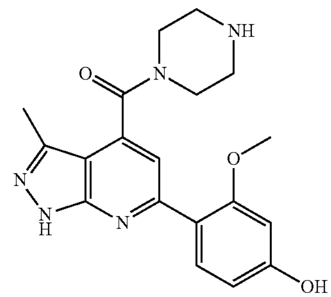 [SMILES: COc1cc(O)ccc1-c1cc(C(=O)N2CCNCC2)c2c(C)n[nH]c2n1] | LC14 | 368 | 0.50 |
| 15 | [6-(3-Ethoxy-4-hydroxy-phenyl)-3-methyl-1H-pyrazolo[3,4-b]pyridin-4-yl]-piperazin-1-yl-methanone | 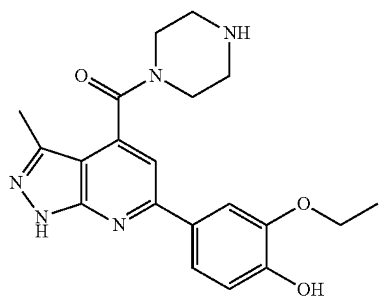 [SMILES: CCOc1cc(-c2cc(C(=O)N3CCNCC3)c3c(C)n[nH]c3n2)ccc1O] | LC14 | 380 [M − H]⁻ | 0.60 |

The following examples have been prepared following a similar procedure as described for Example 2, [3-Ethyl-6-(3-fluoro-4-hydroxy-phenyl)-1H-pyrazolo[3,4-b]pyridin-4-yl]-piperazin-1-yl-methanone, steps (b) and (c) using the 1H-pyrazolo[3,4-b]pyridine-4-carboxylic acid intermediates described above and (S)-3-methyl-piperazine-1-carboxylic acid tert-butyl ester:

| Exp. No. | Name | Structure | LC/MS method | m/z [M + H]⁺ | R_t [min] |
|---|---|---|---|---|---|
| 16 | [6-(3,5-Difluoro-4-hydroxy-phenyl)-3-methyl-1H-pyrazolo[3,4-b]pyridin-4-yl]-((S)-2-methyl-piperazin-1-yl)-methanone | 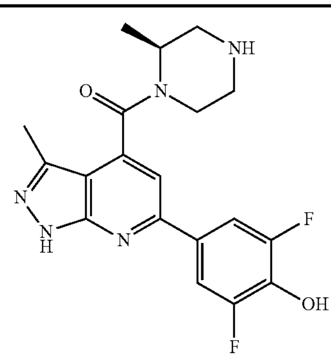 | LC15 | 388 | 2.22 |
| 17 | [6-(4-Hydroxy-2-methyl-phenyl)-3-methyl-1H-pyrazolo[3,4-b]pyridin-4-yl]-((S)-2-methyl-piperazin-1-yl)-methanone | 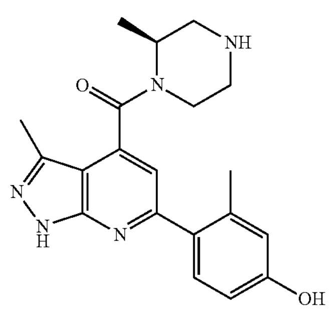 [SMILES: Cc1cc(O)ccc1-c1cc(C(=O)N2CCNC[C@@H]2C)c2c(C)n[nH]c2n1] | LC14 | 366 | 0.53 |

| Exp. No. | Name | Structure | LC/MS method | m/z [M + H]+ | $R_t$ [min] |
|---|---|---|---|---|---|
| 18 | [6-(4-Hydroxy-2-methoxy-phenyl)-3-methyl-1H-pyrazolo[3,4-b]pyridin-4-yl]-((S)-2-methyl-piperazin-1-yl)-methanone | 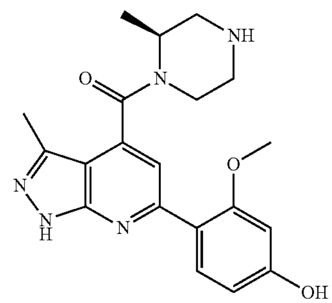 [SMILES: COc1cc(O)ccc1-c1cc(C(=O)N2CCNC[C@@H]2C)c2c(C)n[nH]c2n1] | LC14 | 382 | 0.52 |

The following examples have been prepared following a similar procedure as described for Example 2, [3-Ethyl-6-(3-fluoro-4-hydroxy-phenyl)-1H-pyrazolo[3,4-b]pyridin-4-yl]-piperazin-1-yl-methanone, steps (b) and (c) using 6-(4-Hydroxyphenyl)-3-methyl-1H-pyrazolo[3,4-b]pyridine-4-carboxylic acid and the respective amine precursors

| Exp. No | Name | Structure | LC/MS method | m/z [M + H]+ | $R_t$ [min] |
|---|---|---|---|---|---|
| 19 | 2,5-Diaza-bicyclo[2.2.1]hept-2-yl-[6-(4-hydroxy-phenyl)-3-methyl-1H-pyrazolo[3,4-b]pyridin-4-yl]-methanone | 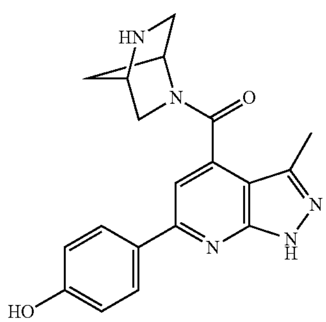 [SMILES: Cc1n[nH]c2nc(-c3ccc(O)cc3)cc(C(=O)N3CC4CC3CN4)c12] | LC14 | 350 | 0.49 |
| 20 | (S)-2-Ethyl-piperazin-1-yl)-[6-(4-hydroxy-phenyl)-3-methyl-1H-pyrazolo[3,4-b]pyridin-4-yl]-methanone | 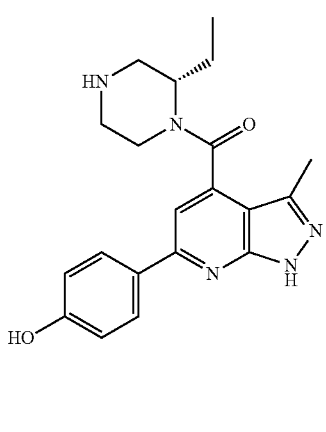 [SMILES: CC[C@H]1CNCCN1C(=O)c1cc(-c2ccc(O)cc2)nc2[nH]nc(C)c12] | LC15 | 366 | 2.52 |

| Exp. No | Name | Structure | LC/MS method | m/z [M + H]+ | R_t [min] |
|---|---|---|---|---|---|
| 21 | [6-(4-Hydroxy-phenyl)-3-methyl-1H-pyrazolo[3,4-b]pyridin-4-yl]-((R)-2-methoxymethyl-piperazin-1-yl)-methanone | 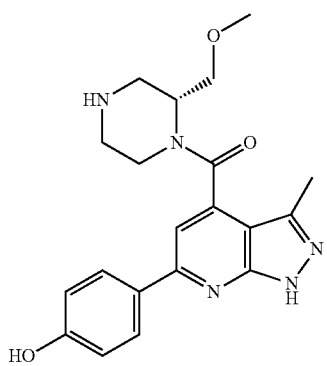 [SMILES: COC[C@H]1CNCCN1C(=O)c1cc(-c2ccc(O)cc2)nc2[nH]nc(C)c12] | LC13 | 382 | 2.42 |
| 22 | 6-(4-Hydroxy-phenyl)-3-methyl-1H-pyrazolo[3,4-b]pyridine-4-carboxylic acid phenethyl-(R)-piperidin-3-yl-amide | 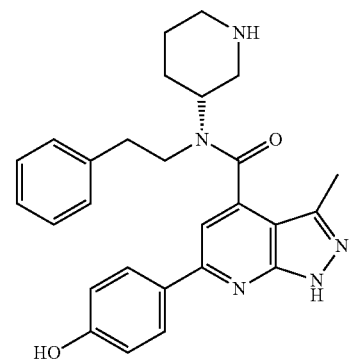 | LC14 | 456 | 0.83 |
| 23 | [6-(4-Hydroxy-phenyl)-3-methyl-1H-pyrazolo[3,4-b]pyridin-4-yl]-((R)-2-methyl-piperazin-1-yl)-methanone | 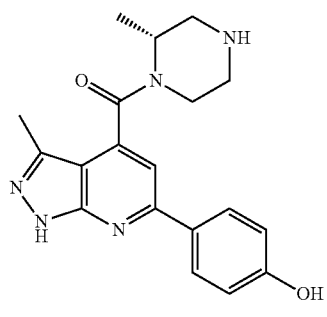 [SMILES: Cc1n[nH]c2nc(-c3ccc(O)cc3)cc(C(=O)N3CCNC[C@H]3C)c12] | LC15 | 352 | 2.32 |
| 24 | ((3R,5S)-3,5-Dimethyl-piperazin-1-yl)-[6-(4-hydroxy-phenyl)-3-methyl-1H-pyrazolo[3,4-b]pyridin-4-yl]-methanone | 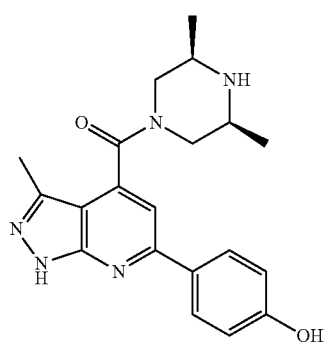 [SMILES: Cc1n[nH]c2nc(-c3ccc(O)cc3)cc(C(=O)N3C[C@@H](C)N[C@@H](C)C3)c12] | LC14 | 366 | 0.53 |

-continued

| Exp. No | Name | Structure | LC/MS method | m/z [M + H]+ | R_t [min] |
|---|---|---|---|---|---|
| 25 | [6-(4-Hydroxy-phenyl)-3-methyl-1H-pyrazolo[3,4-b]pyridin-4-yl]-(3-phenyl-piperazin-1-yl)-methanone | 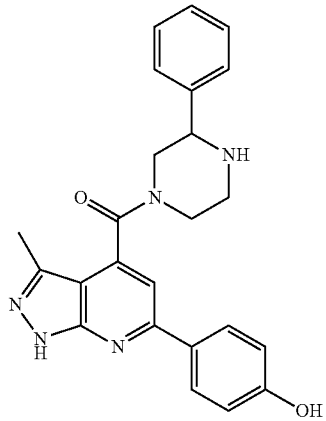 [SMILES: Cc1n[nH]c2nc(-c3ccc(O)cc3)cc(C(=O)N3CCNC(c4ccccc4)C3)c12] | LC14 | 414 | 0.64 |
| 26 | [6-(4-Hydroxy-phenyl)-3-methyl-1H-pyrazolo[3,4-b]pyridin-4-yl]-(2-phenyl-piperazin-1-yl)-methanone | 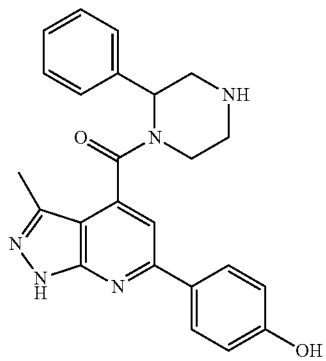 [SMILES: Cc1n[nH]c2nc(-c3ccc(O)cc3)cc(C(=O)N3CCNCC3c3ccccc3)c12] | LC14 | 414 | 0.70 |
| 27 | [6-(4-Hydroxy-phenyl)-3-methyl-1H-pyrazolo[3,4-b]pyridin-4-yl]-((S)-2-phenyl-piperazin-1-yl)-methanone | 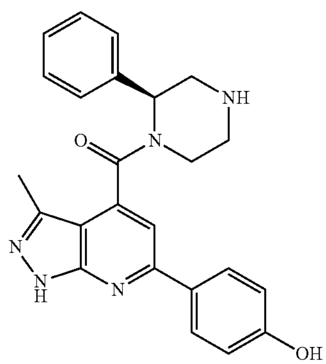 [SMILES: Cc1n[nH]c2nc(-c3ccc(O)cc3)cc(C(=O)N3CCNC[C@@H]3c3ccccc3)c12] | LC14 | 414 | 0.70 |
| 28 | [6-(4-Hydroxy-phenyl)-3-methyl-1H-pyrazolo[3,4-b]pyridin-4-yl]-((R)-2-phenyl-piperazin-1-yl)-methanone | 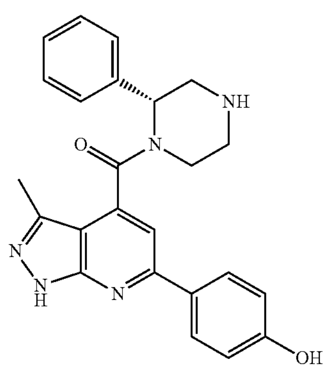 [SMILES: Cc1n[nH]c2nc(-c3ccc(O)cc3)cc(C(=O)N3CCNC[C@H]3c3ccccc3)c12] | LC14 | 414 | 0.70 |

-continued

| Exp. No | Name | Structure | LC/MS method | m/z [M + H]+ | R<sub>t</sub> [min] |
|---|---|---|---|---|---|
| 29 | [2-(3,4-Dichloro-phenyl)-piperazin-1-yl]-[6-(4-hydroxy-phenyl)-3-methyl-1H-pyrazolo[3,4-b]pyridin-4-yl]-methanone | 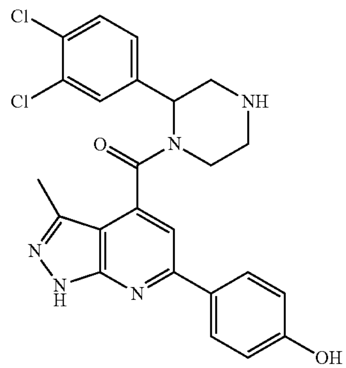 [SMILES: Cc1n[nH]c2nc(-c3ccc(O)cc3)cc(C(=O)N3CCNCC3c3ccc(Cl)c(Cl)c3)c12] | LC14 | 482 | 0.85 |
| 30 | (2-Furan-2-yl-piperazin-1-yl)-[6-(4-hydroxy-phenyl)-3-methyl-1H-pyrazolo[3,4-b]pyridin-4-yl]-methanone | 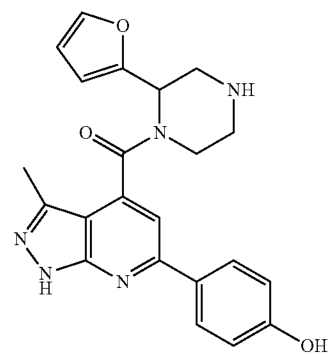 [SMILES: Cc1n[nH]c2nc(-c3ccc(O)cc3)cc(C(=O)N3CCNCC3c3ccco3)c12] | LC14 | 404 | 0.68 |
| 31 | [6-(4-Hydroxy-phenyl)-3-methyl-1H-pyrazolo[3,4-b]pyridin-4-yl]-(2-thiophen-2-yl-piperazin-1-yl)-methanone | 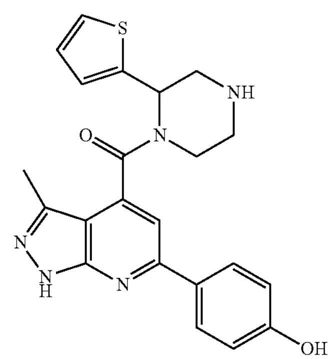 [SMILES: Cc1n[nH]c2nc(-c3ccc(O)cc3)cc(C(=O)N3CCNCC3c3cccs3)c12] | LC14 | 420 | 0.70 |
| 32 | (2-Benzo[1,3]dioxol-5-yl-piperazin-1-yl)-[6-(4-hydroxy-phenyl)-3-methyl-1H-pyrazolo[3,4-b]pyridin-4-yl]-methanone | 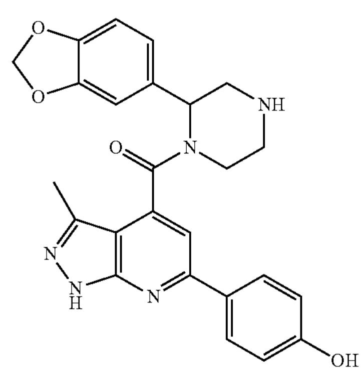 [SMILES: Cc1n[nH]c2nc(-c3ccc(O)cc3)cc(C(=O)N3CCNCC3c3ccc4c(c3)OCO4)c12] | LC15 | 458 | 2.93 |

| Exp. No | Name | Structure | LC/MS method | m/z [M + H]⁺ | R_t [min] |
|---|---|---|---|---|---|
| 33 | [3-(1-Amino-1-methyl-ethyl)-azetidin-1-yl]-[6-(4-hydroxy-phenyl)-3-methyl-1H-pyrazolo[3,4-b]pyridin-4-yl]-methanone | 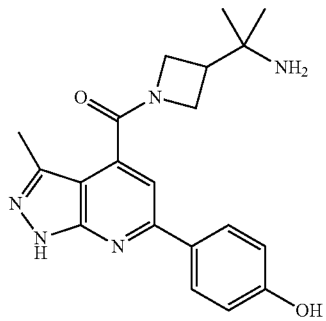 [SMILES: Cc1n[nH]c2nc(-c3ccc(O)cc3)cc(C(=O)N3CC(C(C)(C)N)C3)c12] | LC14 | 366 | 0.52 |
| 34 | (4-Aminomethyl-4-phenyl-piperidin-1-yl)-[6-(4-hydroxy-phenyl)-3-methyl-1H-pyrazolo[3,4-b]pyridin-4-yl]-methanone | 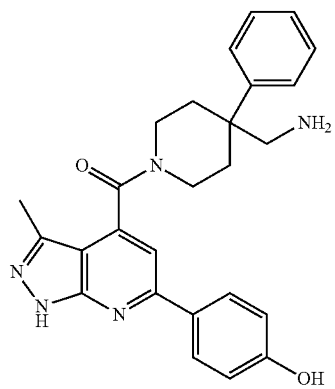 [SMILES: Cc1n[nH]c2nc(-c3ccc(O)cc3)cc(C(=O)N3CCC(CN)(c4ccccc4)CC3)c12] | LC14 | 442 | 0.64 |

The following examples have been prepared following a similar procedure as described for Example 2, [3-Ethyl-6-(3-fluoro-4-hydroxy-phenyl)-1H-pyrazolo[3,4-b]pyridin-4-yl]-piperazin-1-yl-methanone, step (b) using 6-(4-Hydroxy-phenyl)-3-methyl-1H-pyrazolo[3,4-b]pyridine-4-carboxylic acid and the respective amine precursors:

| Exp. No | Name | Structure | LC/MS method | m/z [M + H]⁺ | R_t [min] |
|---|---|---|---|---|---|
| 35 | 6-(4-Hydroxy-phenyl)-3-methyl-1H-pyrazolo[3,4-b]pyridine-4-carboxylic acid (2-pyrrolidin-1-yl-ethyl)-amide | 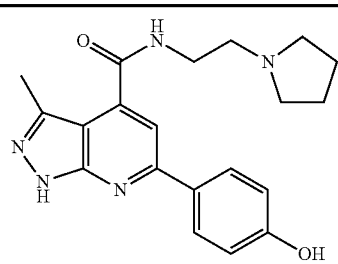 | LC14 | 366 | 0.53 |
| 36 | [6-(4-Hydroxy-phenyl)-3-methyl-1H-pyrazolo[3,4-b]pyridin-4-yl]-(4-isopropyl-piperazin-1-yl)-methanone | 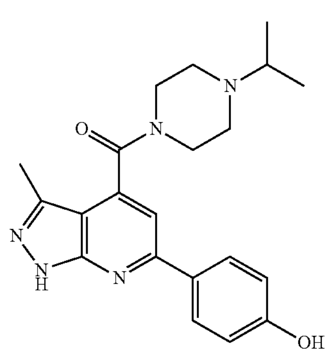 [SMILES: Cc1n[nH]c2nc(-c3ccc(O)cc3)cc(C(=O)N3CCN(C(C)C)CC3)c12] | LC14 | 380 | 0.54 |

-continued

| Exp. No | Name | Structure | LC/MS method | m/z [M + H]+ | R_t [min] |
|---|---|---|---|---|---|
| 37 | [6-(4-Hydroxy-phenyl)-3-methyl-1H-pyrazolo[3,4-b]pyridin-4-yl]-(4-methyl-piperazin-1-yl)-methanone | 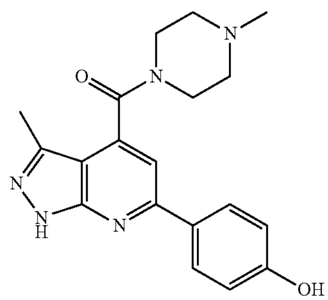 [SMILES: Cc1n[nH]c2nc(-c3ccc(O)cc3)cc(C(=O)N3CCN(C)CC3)c12] | LC14 | 352 | 0.51 |
| 38 | 6-(4-Hydroxy-phenyl)-3-methyl-1H-pyrazolo[3,4-b]pyridine-4-carboxylic acid (2-dimethylamino-ethyl)-amide | 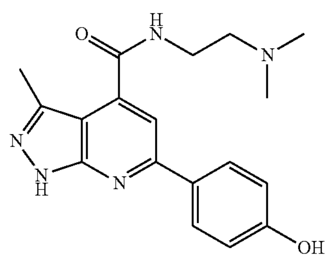 [SMILES: Cc1n[nH]c2nc(-c3ccc(O)cc3)cc(C(=O)NCCN(C)C)c12] | LC15 | 340 | 2.32 |
| 39 | (4-Cyclobutyl-piperazin-1-yl)-[6-(4-hydroxy-phenyl)-3-methyl-1H-pyrazolo[3,4-b]pyridin-4-yl]-methanone | 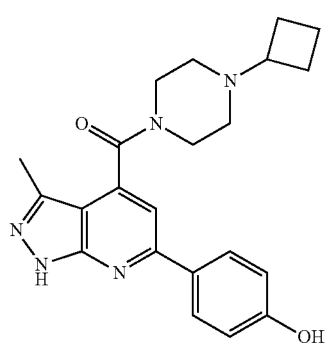 [SMILES: Cc1n[nH]c2nc(-c3ccc(O)cc3)cc(C(=O)N3CCN(C4CCC4)CC3)c12] | LC1 | 392.23 | 0.79 |
| 40 | 6-(4-Hydroxy-phenyl)-3-methyl-1H-pyrazolo[3,4-b]pyridine-4-carboxylic acid (2-tert-butylamino-ethyl)-methyl-amide | 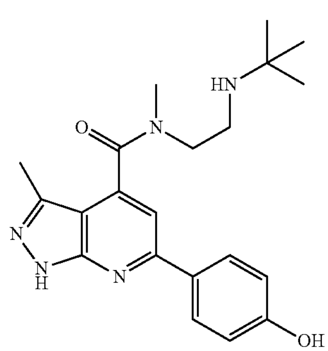 [SMILES: Cc1n[nH]c2nc(-c3ccc(O)cc3)cc(C(=O)N(C)CCNC(C)(C)C)c12] | LC1 | 382.30 | 0.81 |

Example 41

6-(4-Hydroxy-phenyl)-3-methyl-1H-pyrazolo[3,4-b]pyridine-4-carboxylic acid (4-methyl-piperidin-4-yl)-amide

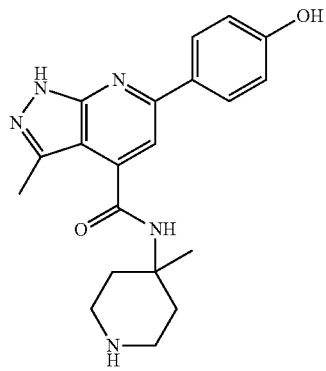 [SMILES: Cc1n[nH]c2nc(-c3ccc(O)cc3)cc(C(=O)NC3(C)CCNCC3)c12]

(a) 6-(4-Hydroxy-phenyl)-3-methyl-1H-pyrazolo[3,4-b]pyridine-4-carboxylic acid methyl ester

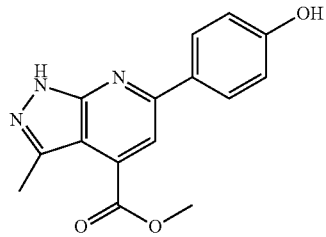 [SMILES: COC(=O)c1cc(-c2ccc(O)cc2)nc2[nH]nc(C)c12]

A mixture of 3-amino-5-methylpyrazole (50.0 g), pyruvic acid methyl ester (58.4 g) and 4-hydroxybenzaldehyde (62.9 mL) in acetic acid/methanol (v/v=1/1, 300 mL) was stirred at 75° C. for 15 h, cooled to r.t.; and the precipitate formed was isolated by suction filtration and dried in vacuo at 60° C. 15 g (10%) of the title compound were obtained as pale yellow solid.

$^1$H-NMR (500 MHz, $d_6$-DMSO): 2.59 (s, 3H), 4.02 (s, 3H), 6.93 (d, 2H), 7.96 (s 2H), 8.04 (d, 2H), 11.9 (s, 1H), 13.4 (s, 1H).

LC/MS (Method LC3): $R_t$=3.55 min; m/z=284.14 [M+H]$^+$.

(b) 6-(4-Hydroxy-phenyl)-3-methyl-1-(tetrahydro-pyran-2-yl)-1H-pyrazolo[3,4-b]pyridine-4-carboxylic acid methyl ester

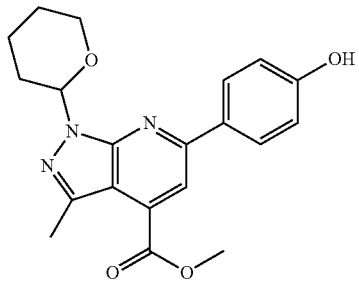 [SMILES: COC(=O)c1cc(-c2ccc(O)cc2)nc2c1c(C)nn2C1CCCCO1]

A mixture of 6-(4-hydroxy-phenyl)-3-methyl-1H-pyrazolo[3,4-b]pyridine-4-carboxylic acid methyl ester (15 g), 3,4-dihydro-2H-pyran (24 mL) and p-toluenesulfonic acid monohydrate (3.0 g) in THF (400 mL) was stirred at r.t. until the reaction was complete. Water was added and the mixture was extracted with ethyl acetate, the combined organic phases were washed with water and brine, dried over magnesium sulfate and concentrated. The residue was chromatographed over a short path column (heptane/ethyl acetate gradient). The product containing fractions were combined, concentrated, and the resulting residue was triturated with ether to give 11 g (57%) of the title compound.

$^1$H-NMR (500 MHz, $d_6$-DMSO): 1.54-168 (m, 2H), 1.78-1.90 (m, 1H), 1.91-1.98 (m, 1H), 2.04-2.12 (m, 1H), 2.45-2.60 (m, 1H), 2.60 (s, 3H), 3.68-3.75 (m, 1H), 3.93-4.02 (m, 1H), 4.02 (s, 3H), 6.10 (dd, 1H), 6.93 (d, 2H), 8.02 (s 2H), 8.12 (d, 2H), 10 (s, 1H).

LC/MS (Method LC1): $R_t$=1.27 min; m/z=368.2 μM'.

(c) 6-(4-Hydroxy-phenyl)-3-methyl-1-(tetrahydro-pyran-2-yl)-1H-pyrazolo[3,4-b]pyridine-4-carboxylic acid

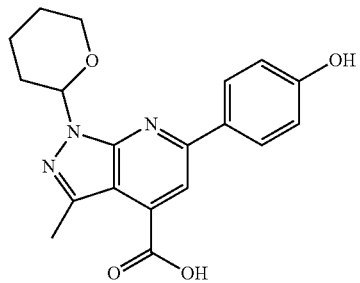 [SMILES: Cc1nn(C2CCCCO2)c2nc(-c3ccc(O)cc3)cc(C(=O)O)c12]

A mixture of 6-(4-hydroxy-phenyl)-3-methyl-1H-pyrazolo[3,4-b]pyridine-4-carboxylic acid methyl ester (10.9 g) and sodium hydroxide solution (1N, 80 mL) in isopropanol (80 mL) was stirred at r.t. for 90 min. The pH was adjusted to 3 with 1N HCl and the mixture was poured onto water. The precipitate formed was filtered off and dried in air to give 10.2 g (97%) of the title compound.

$^1$H-NMR (500 MHz, $d_6$-DMSO): 1.54-1.65 (m, 2H), 1.74-1.86 (m, 1H), 1.87-1.95 (m, 1H), 2.02-2.10 (m, 1H), 2.46-2.57 (m, 1H), 2.60 (s, 3H), 3.68-3.75 (m, 1H), 3.91-4.00 (m, 1H), 6.09 (dd, 1H), 6.93 (d, 2H), 8.00 (s 2H), 8.12 (d, 2H), 9.90 (s, 1H), 13.9 (br, s, 1H).

LC/MS (Method LC1): $R_t$=1.15 min; m/z=354.2 [M+H]$^+$.

(d) 6-(4-Hydroxy-phenyl)-3-methyl-1-(tetrahydro-pyran-2-yl)-1H-pyrazolo[3,4-b]pyridine-4-carboxylic acid (1-benzyl-4-methyl-piperidin-4-yl)-amide

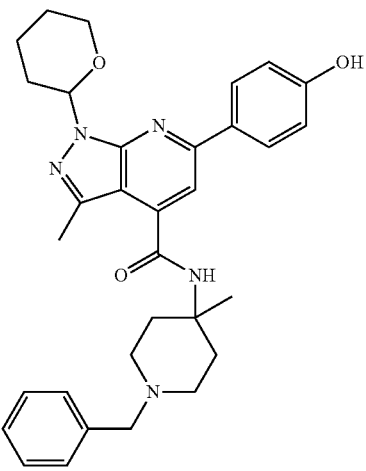 [SMILES: Cc1nn(C2CCCCO2)c2nc(-c3ccc(O)cc3)cc(C(=O)NC3(C)CCN(Cc4ccccc4)CC3)c12]

To a mixture of 6-(4-hydroxy-phenyl)-3-methyl-1-(tetrahydro-pyran-2-yl)-1H-pyrazolo[3,4-b]pyridine-4-carboxylic acid (215 mg), DIPEA (313 μL) and 1-benzyl-4-methyl-piperidin-4-ylamine (175 mg) in dichloroethane (7 mL), which was being stirred at 40° C., was added BEP (200 mg). The mixture was stirred at 40° C. for 60 min, then at r.t. overnight. Water was added and the mixture was extracted with dichloromethane. To the dichloromethane phase 30% sodium methoxide in methanol (0.4 mL) was added and stirred for 30 min. The mixture was filtered and the filtrate was washed with water, dried over magnesium sulfate and concentrated. The residue was chromatographed over silica (dichloromethane/methanol gradient) to give 1420 g (43%) of the title compound.

LC/MS (Method LC2): $R_t$=3.26 min; m/z=540.40 [M+H]$^+$.

(e) 6-(4-Hydroxy-phenyl)-3-methyl-1-(tetrahydro-pyran-2-yl)-1H-pyrazolo[3,4-b]pyridine-4-carboxylic acid (4-methyl-piperidin-4-yl)-amide

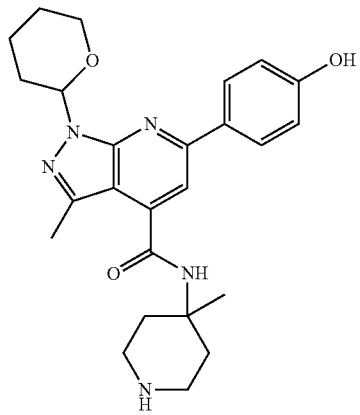 [SMILES: Cc1nn(C2CCCCO2)c2nc(-c3ccc(O)cc3)cc(C(=O)NC3(C)CCNCC3)c12]

To a solution of 6-(4-hydroxy-phenyl)-3-methyl-1-(tetrahydro-pyran-2-yl)-1H-pyrazolo[3,4-b]pyridine-4-carboxylic acid (1-benzyl-4-methyl-piperidin-4-yl)-amide (136 mg) in methanol (2 mL) was added palladium (10% on charcoal, 27 mg). Argon was purged through the mixture, then the mixture was saturated with hydrogen and stirred at r.t. overnight. The catalyst was filtered off, the residue was concentrated in vacuo, the residue was re-dissolved in fresh methanol (2 mL) and fresh palladium (10% on charcoal, 27 mg) was added. The mixture was again stirred at r.t. for 1 week. The catalyst was filtered off, the residue was concentrated in vacuo to give 75 mg (66%) of the title compound.

LC/MS (Method LC1): $R_t$=0.99 min; m/z 450.3 [M+H]$^+$.

(f) 6-(4-Hydroxy-phenyl)-3-methyl-1H-pyrazolo[3,4-b]pyridine-4-carboxylic acid (4-methyl-piperidin-4-yl)-amide

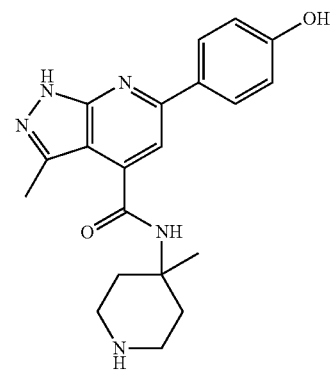 [SMILES: Cc1n[nH]c2nc(-c3ccc(O)cc3)cc(C(=O)NC3(C)CCNCC3)c12]

A solution of 6-(4-hydroxy-phenyl)-3-methyl-1-(tetrahydro-pyran-2-yl)-1H-pyrazolo-[3,4-b]pyridine-4-carboxylic acid (4-methyl-piperidin-4-yl)-amide (75 mg) in THF (1 mL) was added to a stirred solution of HCl (4N in dioxane). The mixture was stirred at r.t. overnight, the precipitate formed was filtered off and washed with ethyl acetate and acetone and dried in air to give 72 mg (99%) of the title compound as hydrochloride LC/MS (Method LC1): $R_t$=0.66 min; m/z=366.3 [M+H]$^+$.

The following pyrazolopyridine derivatives were obtained in a similar fashion as described for Example 41, steps (a)-(c), using the corresponding substituted benzaldehyde starting materials.

| Name | | LC/MS method | m/z [M + H]$^+$ | $R_t$ [min] |
|---|---|---|---|---|
| 6-(2-Fluoro-4-hydroxy-phenyl)-3-methyl-1-(tetrahydro-pyran-2-yl)-1H-pyrazolo[3,4-b]pyridine-4-carboxylic acid | | LC1 | 372.21 | 1.16 |
| 6-(2,6-Difluoro-4-hydroxy-phenyl)-3-methyl-1-(tetrahydro-pyran-2-yl)-1H-pyrazolo[3,4-bipyridine-4-carboxylic acid | | LC1 | 390.14 | 1.18 |

-continued

| Name | LC/MS method | m/z [M + H]+ | R_t [min] |
|---|---|---|---|
| 6-(4-Hydroxy-2-methyl-phenyl)-3-methyl-1-(tetrahydro-pyran-2-yl)-1H-pyrazolo[3,4-b]pyridine-4-carboxylic acid | LC1 | 368.21 | 1.16 |
| 6-(4-Hydroxy-2,6-dimethyl-phenyl)-3-methyl-1-(tetrahydro-pyran-2-yl)-1H-pyrazolo[3,4-b]pyridine-4-carboxylic acid | LC1 | 578.36 | 1.34 |
| 3-Cyclopropyl-6-(4-hydroxy-phenyl)-1-(tetrahydro-pyran-2-yl)-1H-pyrazolo[3,4-b]pyridine-4-carboxylic acid | LC1 | 380.15 | 1.22 |

The following examples have been prepared following a similar procedure as described for Example 41, 6-(4-Hydroxy-phenyl)-3-methyl-1H-pyrazolo[3,4-b]pyridine-4-carboxylic acid (4-methyl-piperidin-4-yl)-amide using the respective amine precursors.

| Exp. No. | Name | Structure | LC/MS method | m/z [M + H]+ | R_t [min] |
|---|---|---|---|---|---|
| 42 | (1,3-Dihydro-spiro[indene-2,2'-piperazin]-1'-yl)-[6-(4-hydroxy-phenyl)-3-methyl-1H-pyrazolo[3,4-b]pyridin-4-yl]-methanone | 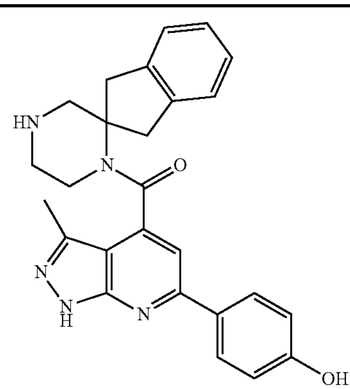 | LC5 | 440.4 | 0.82 |

| Exp. No. | Name | Structure | LC/MS method | m/z [M + H]⁺ | R_t [min] |
|---|---|---|---|---|---|
| 43 | 6-(4-Hydroxy-phenyl)-3-methyl-1H-pyrazolo[3,4-b]pyridine-4-carboxylic acid (4-methyl-pyrrolidin-3-yl)-amide | 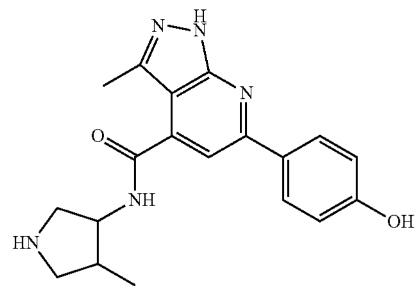 [SMILES: Cc1n[nH]c2nc(-c3ccc(O)cc3)cc(C(=O)NC3CNCC3C)c12] | LC5 | 352.20 | 0.62 |
| 44 | 6-(4-Hydroxy-phenyl)-3-methyl-1H-pyrazolo[3,4-b]pyridine-4-carboxylic acid (4-ethoxy-pyrrolidin-3-yl)-amide | 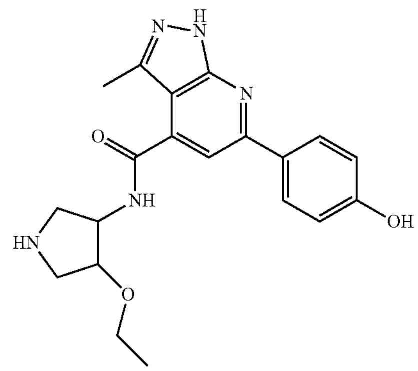 [SMILES: CCOC1CNCC1NC(=O)c1cc(-c2ccc(O)cc2)nc2[nH]nc(C)c12] | LC5 | 382.23 | 0.70 |
| 45 | 6-(4-Hydroxy-phenyl)-3-methyl-1H-pyrazolo[3,4-b]pyridine-4-carboxylic acid (4-phenyl-pyrrolidin-3-yl)-amide | 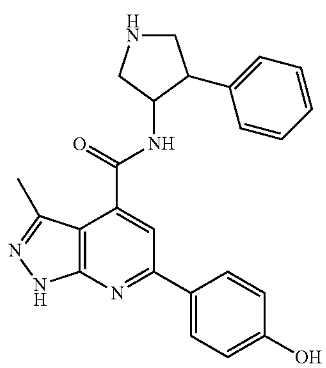 [SMILES: Cc1n[nH]c2nc(-c3ccc(O)cc3)cc(C(=O)NC3CNCC3c3ccccc3)c12] | LC5 | 414.29 | 0.76 |
| 46 | (4-Amino-4-propyl-piperidin-1-yl)-[6-(4-hydroxy-phenyl)-3-methyl-1H-pyrazolo[3,4-b]pyridin-4-yl]-methanone | 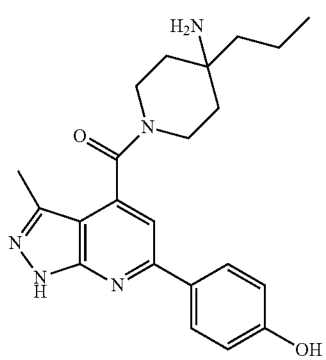 [SMILES: CCCC1(N)CCN(C(=O)c2cc(-c3ccc(O)cc3)nc3[nH]nc(C)c23)CC1] | LC5 | 394.28 | 0.71 |

-continued

| Exp. No. | Name | Structure | LC/MS method | m/z [M + H]⁺ | R_t [min] |
|---|---|---|---|---|---|
| 47 | (3-Amino-3-propyl-pyrrolidin-1-yl)-[6-(4-hydroxy-phenyl)-3-methyl-1H-pyrazolo[3,4-b]pyridin-4-yl]-methanone | 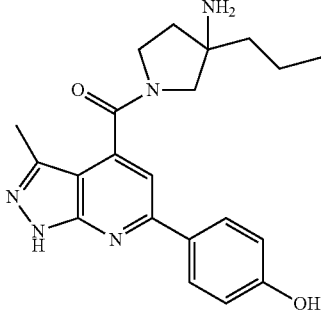 [SMILES: CCCC1(N)CCN(C(=O)c2cc(-c3ccc(O)cc3)nc3[nH]nc(C)c23)C1] | LC5 | 380.24 | 0.68 |
| 48 | (3-Amino-3-propyl-piperidin-1-yl)-[6-(4-hydroxy-phenyl)-3-methyl-1H-pyrazolo[3,4-b]pyridin-4-yl]-methanone | 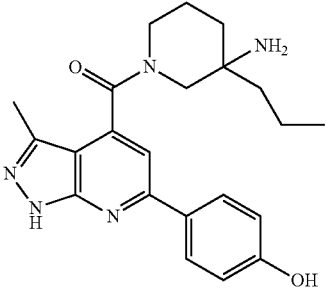 [SMILES: CCCC1(N)CCCN(C(=O)c2cc(-c3ccc(O)cc3)nc3[nH]nc(C)c23)C1] | LC5 | 394.33 | 0.73 |
| 49 | 6-(4-Hydroxy-phenyl)-3-methyl-1H-pyrazolo[3,4-b]pyridine-4-carboxylic acid (4-ethyl-piperidin-4-yl)-amide | 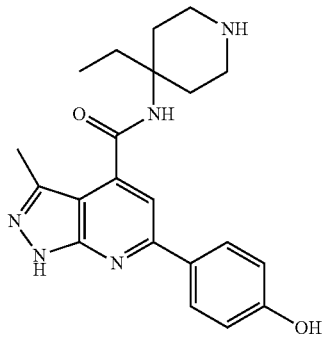 [SMILES: CCC1(NC(=O)c2cc(-c3ccc(O)cc3)nc3[nH]nc(C)c23)CCNCC1] | LC8 | 380.35 | 2.23 |
| 50 | 6-(4-Hydroxy-phenyl)-3-methyl-1H-pyrazolo[3,4-b]pyridine-4-carboxylic acid (2-isopropylamino-ethyl)-amide | 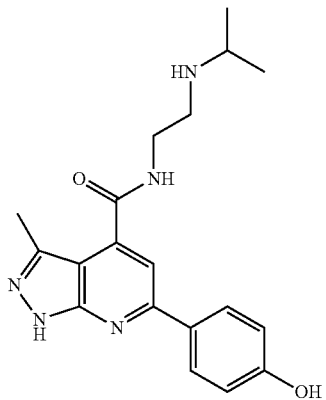 [SMILES: Cc1n[nH]c2nc(-c3ccc(O)cc3)cc(C(=O)NCCNC(C)C)c12] | LC1 | 354.27 | 0.77 |

-continued

| Exp. No. | Name | Structure | LC/MS method | m/z [M + H]+ | Rt [min] |
|---|---|---|---|---|---|
| 51 | 6-(4-Hydroxy-phenyl)-3-methyl-1H-pyrazolo[3,4-b]pyridine-4-carboxylic acid [2-amino-1-(3-methoxy-phenyl)-ethyl]-amide | 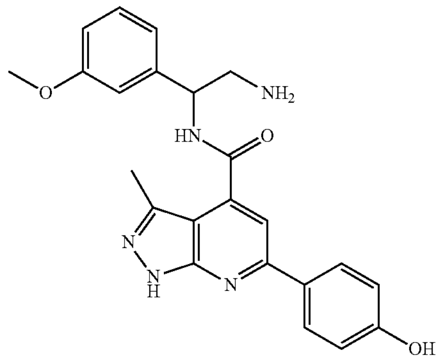 [SMILES: COc1cccc(C(CN)NC(=O)c2cc(-c3ccc(O)cc3)nc3[nH]nc(C)c23)c1] | LC1 | 418.22 | 0.89 |
| 52 | 6-(4-Hydroxy-phenyl)-3-methyl-1H-pyrazolo[3,4-b]pyridine-4-carboxylic acid (2-amino-1-p-tolyl-ethyl)-amide | 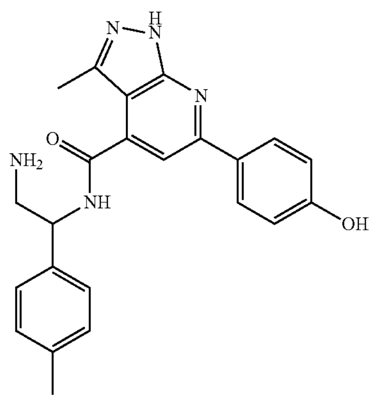 [SMILES: Cc1ccc(C(CN)NC(=O)c2cc(-c3ccc(O)cc3)nc3[nH]nc(C)c23)cc1] | LC1 | 402.22 | 0.92 |

Example 53

[6-(4-Hydroxy-phenyl)-3-methyl-1H-pyrazolo[3,4-b]pyridin-4-yl]-piperazin-1-yl-methanone

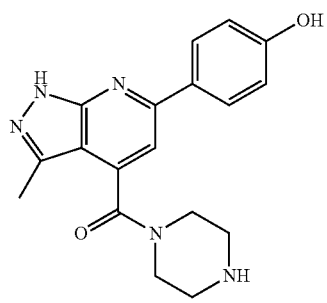 [SMILES: Cc1n[nH]c2nc(-c3ccc(O)cc3)cc(C(=O)N3CCNCC3)c12]

(a) 6-(4-Hydroxy-phenyl)-3-methyl-1H-pyrazolo[3,4-b]pyridine-4-carboxylic acid

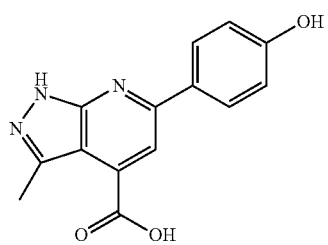 [SMILES: Cc1n[nH]c2nc(-c3ccc(O)cc3)cc(C(=O)O)c12]

1.4 g of 6-(4-hydroxy-phenyl)-3-methyl-1H-pyrazolo[3,4-b]pyridine-4-carboxylic acid methyl ester were dissolved in 50 mL of a mixture of 2N LiOH and methanol (1:1). After the reaction was complete, methanol was removed in vacuo, water was added and the solution acidified to pH 1 by addition of hydrochloric acid. The resulting precipitate was filtered off to give 1.25 g of the title compound.

LC/MS (Method LC6): $R_t$=1.00 min; m/z 270.09 [M+H]+.

(b) 4-[6-(4-Hydroxy-phenyl)-3-methyl-1H-pyrazolo[3,4-b]pyridine-4-carbonyl]-piperazine-1-carboxylic acid tert-butyl ester

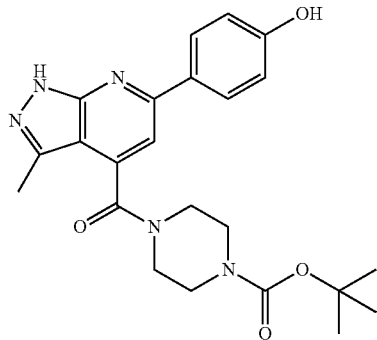 [SMILES: Cc1n[nH]c2nc(-c3ccc(O)cc3)cc(C(=O)N3CCN(C(=O)OC(C)(C)C)CC3)c12]

400 mg of 6-(4-hydroxy-phenyl)-3-methyl-1H-pyrazolo[3,4-h]pyridine-4-carboxylic acid, 300 mg tert.butyl 1-piperazine carboxylate were dissolved in 4 mL of dry DMF. 535 mg of TOTU were added. If necessary, additional piperazine and TOTU was added. Water was added and the resulting precipitate was filtered off and purified by recrystallization (acetonitrile/water, then methanol/water, then ethyl acetate/heptane) to give 236 mg (36%) of the desired product.

LC/MS (Method LC6): $R_t$=1.42 min; m/z=438.28 [M+H]$^+$.

(c) [6-(4-Hydroxy-phenyl)-3-methyl-1H-pyrazolo[3,4-b]pyridin-4-yl]-piperazin-1-yl-methanone

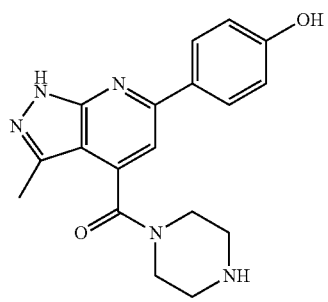 [SMILES: Cc1n[nH]c2nc(-c3ccc(O)cc3)cc(C(=O)N3CCNCC3)c12]

164 mg of 4-[6-(4-hydroxy-phenyl)-3-methyl-1H-pyrazolo[3,4-b]pyridine-4-carbonyl]-piperazine-1-carboxylic acid tert-butyl ester were dissolved in 2 mL of isopropanol.

2 mL of hydrochloric acid (5N in isopropanol) were added. After complete conversion, water was added and the solution was lyophilized. The product was taken up in water and lyophilized twice to remove excess hydrochloric acid to give 159 mg (100%) of the desired product as the hydrochloride salt.

LC/MS (Method LC7): $R_t$=0.78 min; m/z=338.26 [M+H]$^+$.

Example 54

4-[6-(4-Hydroxy-phenyl)-3-methyl-1H-pyrazolo[3,4-b]pyridine-4-carbonyl]-piperazine-1-carboxylic acid amide

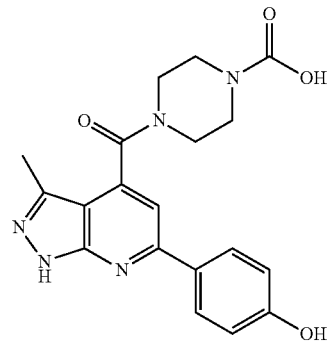 [SMILES: Cc1n[nH]c2nc(-c3ccc(O)cc3)cc(C(=O)N3CCN(C(=O)O)CC3)c12]

4-[6-(4-Hydroxy-phenyl)-3-methyl-1H-pyrazolo[3,4-b]pyridine-4-carbonyl]-piperazine-1-carboxylic acid amide was prepared following a similar procedure as described for the synthesis of example 53, [6-(4-Hydroxy-phenyl)-3-methyl-1H-pyrazolo[3,4-b]pyridin-4-yl]-piperazin-1-yl-methanone, using the respective amine as starting material.

LC/MS (Method LC7): $R_t$=0.83 min; m/z=381.26 [M+H]$^+$.

Example 55

[3-Cyclopropyl-6-(4-hydroxy-phenyl)-1H-pyrazolo[3,4-b]pyridin-4-yl]-piperazin-1-yl-methanone

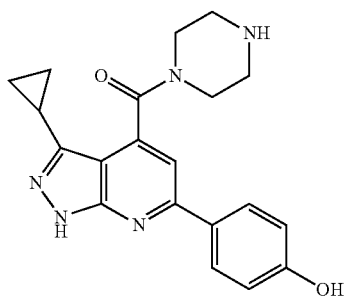 [SMILES: O=C(c1cc(-c2ccc(O)cc2)nc2[nH]nc(C3CC3)c12)N1CCNCC1]

[3-Cyclopropyl-6-(4-hydroxy-phenyl)-1H-pyrazolo[3,4-b]pyridin-4-yl]-piperazin-1-yl-methanone was prepared following a similar procedure as described for the synthesis of example 53, [6-(4-Hydroxy-phenyl)-3-methyl-1H-pyrazolo[3,4-b]pyridin-4-yl]-piperazin-1-yl-methanone, using 3-cyclopropyl-6-(4-hydroxy-phenyl)-1H-pyrazolo[3,4-b]pyridine-4-carboxylic acid (obtained as described in example 41, steps (a) and (c) employing 5-cyclopropyl-1H-pyrazol-3-ylamine, pyruvic acid methyl ester and 4-hydroxybenzaldehyde as the starting materials) and tert.butyl 1-piperazine carboxylate as starting materials.

LC/MS (Method LC7): $R_t$=0.86 min; m/z=364.28 [M+H]$^+$.

Example 56

(2,2-Dimethyl-piperazin-1-yl)-[6-(2-fluoro-4-hydroxy-phenyl)-3-methyl-1H-pyrazolo[3,4-b]pyridin-4-yl]-methanone

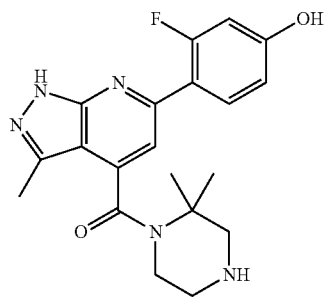 [SMILES: Cc1n[nH]c2nc(-c3ccc(O)cc3F)cc(C(=O)N3CCNCC3(C)C)c12]

(a) 4-[6-(2-Fluoro-4-Hydroxy-phenyl)-3-methyl-1-(tetrahydro-pyran-2-yl)-1H-pyrazolo[3,4-b]pyridine-4-carbonyl]-3,3-dimethyl-piperazine-1-carboxylic acid tert-butyl ester

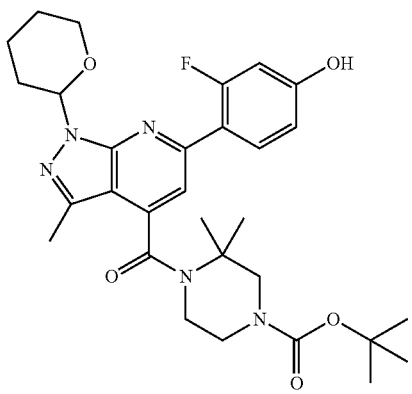 [SMILES: Cc1nn(C2CCCCO2)c2nc(-c3ccc(O)cc3F)cc(C(=O)N3CCN(C(=O)OC(C)(C)C)CC3(C)C)c12]

To a suspension of 6-(2-fluoro-4-Hydroxy-phenyl)-3-methyl-1-(tetrahydro-pyran-2-yl)-1H-pyrazolo[3,4-b]pyridine-4-carboxylic acid (150 mg) in dry dichloromethane (3 mL), N,N-diisopropylethylamine (70 µL), 2-bromo-1-ethylpyridinium tetrafluoroborate (221 mg) and 1-Boc-3,3-dimethylpiperazine (87 mg) were added. The solution was stirred for 30 min. Upon complete conversion, the solution is evaporated in vacuo and 3 mL of 30% sodium methoxide in methanol were added. The mixture was stirred for 30 min, the pH was adjusted to 5 by addition of 2M hydrochloric acid. Ethyl acetate was added and the organic layer was extracted with saturated sodium bicarbonate, 20% aqueous ammonium chloride solution and multiple times with water. The organic layer was dried over sodium sulfate and evaporated to dryness to give 132 mg (58%) of the title compound.

LC/MS (Method LC1): $R_t$=1.34 min; m/z=568.32 [M+H]$^+$.

(b) (2,2-Dimethyl-piperazin-1-yl)-[6-(2-fluoro-4-hydroxy-phenyl)-3-methyl-1H-pyrazolo[3,4-b]pyridin-4-yl]-methanone

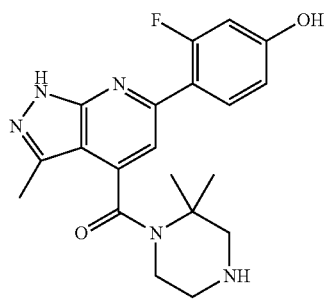 [SMILES: Cc1n[nH]c2nc(-c3ccc(O)cc3F)cc(C(=O)N3CCNCC3(C)C)c12]

130 mg of 4-[6-(2-fluoro-4-Hydroxy-phenyl)-3-methyl-1-(tetrahydro-pyran-2-yl)-1H-pyrazolo[3,4-b]pyridine-4-carbonyl]-3,3-dimethyl-piperazine-1-carboxylic acid tert-butyl ester were dissolved in 4.6 mL of 4M hydrochloric acid in dioxane. After complete conversion, dioxan was removed in vacuo, water was added and the solution was extracted twice with dichloromethane/isopropanol (10/1). The aqueous layer was lyophilized, taken up in water three times and lyophilized again to give 96 mg (100%) of the title compound as the hydrochloride salt.

LC/MS (Method LC1): Rt=0.84 min; m/z=384.22 [M+H]$^+$.

The following examples have been prepared following a similar procedure as described for Example 56, (2,2-Dimethyl-piperazin-1-yl)-[6-(2-fluoro-4-hydroxyphenyl)-3-methyl-1H-pyrazolo[3,4-b]pyridin-4-yl]-methanone, starting from 6-(2-fluoro-4-hydroxy-phenyl)-3-methyl-1-(tetrahydro-pyran-2-yl)-1H-pyrazolo[3,4-b]pyridine-4-carboxylic acid (OP1) and using the respective amine precursors.

| Exp. No. | Name | Structure | LC/MS method | m/z [M + H]$^+$ | $R_t$ [min] |
|---|---|---|---|---|---|
| 57 | [6-(2-Fluoro-4-hydroxy-phenyl)-3-methyl-1H-pyrazolo[3,4-b]pyridin-4-yl]-((R)-2-phenyl-piperazin-1-yl)-methanone | 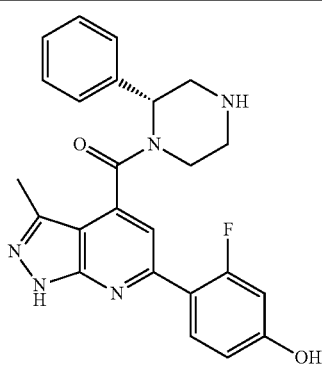 | LC1 | 432.23 | 0.89 |

-continued

| Exp. No. | Name | Structure | LC/MS method | m/z [M + H]⁺ | R$_t$ [min] |
|---|---|---|---|---|---|
| 58 | [6-(2-Fluoro-4-hydroxy-phenyl)-3-methyl-1H-pyrazolo[3,4-b]pyridin-4-yl]-(4-methylamino-piperidin-1-yl)-methanone | 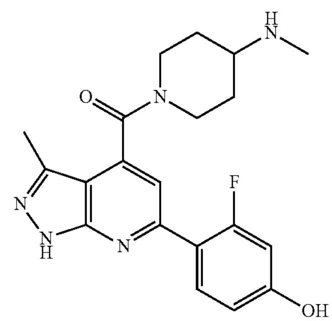 [SMILES: CNC1CCN(C(=O)c2cc(-c3ccc(O)cc3F)nc3[nH]nc(C)c23)CC1] | LC1 | 384.23 | 0.75 |
| 59 | ((S)-3-Aminomethyl-piperidin-1-yl)-[6-(2-fluoro-4-hydroxy-phenyl)-3-methyl-1H-pyrazolo[3,4-b]pyridin-4-yl]-methanone | 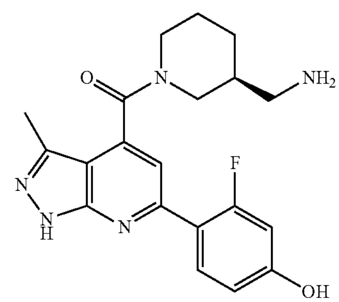 [SMILES: Cc1n[nH]c2nc(-c3ccc(O)cc3F)cc(C(=O)N3CCC[C@@H](CN)C3)c12] | LC8 | 384.32 | 2.08 |
| 60 | [6-(2-Fluoro-4-hydroxy-phenyl)-3-methyl-1H-pyrazolo[3,4-b]pyridin-4-yl]-(2-trifluoromethyl-piperazin-1-yl)-methanone | 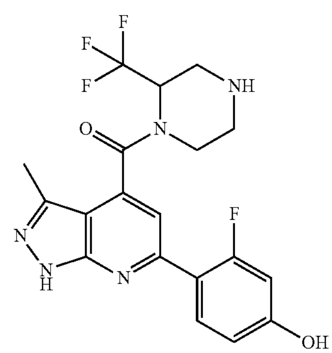 [SMILES: Cc1n[nH]c2nc(-c3ccc(O)cc3F)cc(C(=O)N3CCNCC3C(F)(F)F)c12] | LC5 | 424.19 | 0.74 |
| 61 | 6-(2-Fluoro-4-hydroxy-phenyl)-3-methyl-1H-pyrazolo[3,4-b]pyridine-4-carboxylic acid (1-amino-cycloheptylmethyl)-amide | 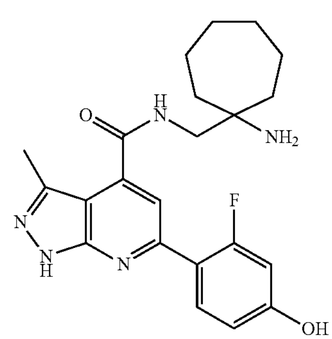 | LC5 | 412.27 | 0.79 |

-continued

| Exp. No. | Name | Structure | LC/MS method | m/z [M + H]+ | R_t [min] |
|---|---|---|---|---|---|
| 62 | 6-(2-Fluoro-4-hydroxy-phenyl)-3-methyl-1H-pyrazolo[3,4-b]pyridine-4-carboxylic acid (3-ethyl-piperidin-3-yl)-amide | 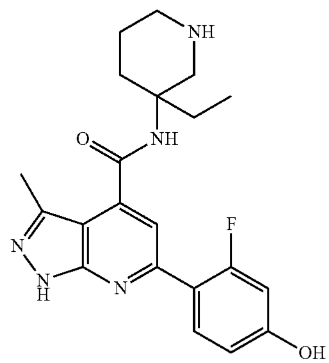 [SMILES: CCC1(NC(=O)c2cc(-c3ccc(O)cc3F)nc3[nH]nc(C)c23)CCCNC1] | LC5 | 398.27 | 0.73 |
| 63 | [6-(2-Fluoro-4-hydroxy-phenyl)-3-methyl-1H-pyrazolo[3,4-b]pyridin-4-yl]-(2,2,5,5-tetramethyl-piperazin-1-yl)-methanone | 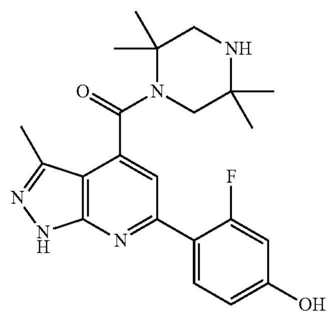 [SMILES: Cc1n[nH]c2nc(-c3ccc(O)cc3F)cc(C(=O)N3CC(C)(C)NCC3(C)C)c12] | LC8 | 412.39 | 2.30 |
| 64 | (4,7-Diaza-spiro[2.5]oct-4-yl)-[6-(2-fluoro-4-hydroxy-phenyl)-3-methyl-1H-pyrazolo[3,4-b]pyridin-4-yl]-methanone | 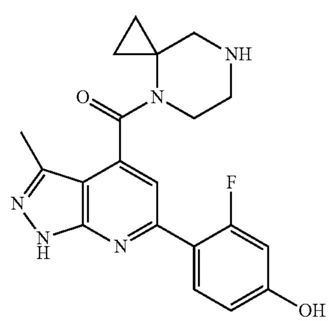 [SMILES: Cc1n[nH]c2nc(-c3ccc(O)cc3F)cc(C(=O)N3CCNCC34CC4)c12] | LC5 | 382.21 | 0.78 |
| 65 | 6-(2-Fluoro-4-hydroxy-phenyl)-3-methyl-1H-pyrazolo[3,4-b]pyridine-4-carboxylic acid (3-amino-1-ethyl-propyl)-amide | 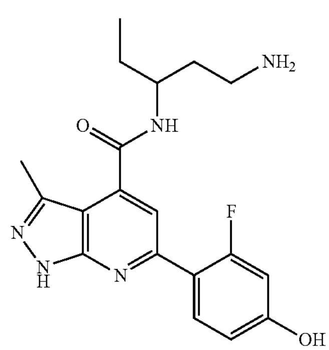 [SMILES: CCC(CCN)NC(=O)c1cc(-c2ccc(O)cc2F)nc2[nH]nc(C)c12] | LC1 | 372.23 | 0.83 |

| Exp. No. | Name | Structure | LC/MS method | m/z [M + H]+ | R_t [min] |
|---|---|---|---|---|---|
| 66 | 6-(2-Fluoro-4-hydroxy-phenyl)-3-methyl-1H-pyrazolo[3,4-b]pyridine-4-carboxylic acid (3-amino-1,1-dimethyl-propyl)-amide | 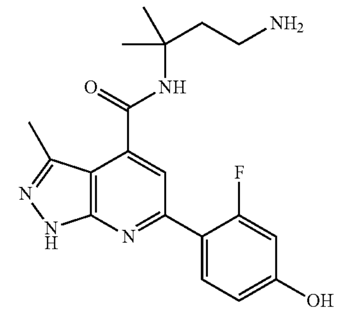 [SMILES: Cc1n[nH]c2nc(-c3ccc(O)cc3F)cc(C(=O)NC(C)(C)CCN)c12] | LC1 | 372.24 | 0.82 |
| 67 | 6-(2-Fluoro-4-hydroxy-phenyl)-3-methyl-1H pyrazolo[3,4-b]pyridine-4-carboxylic acid (3-amino-3-methyl-butyl)-amide | 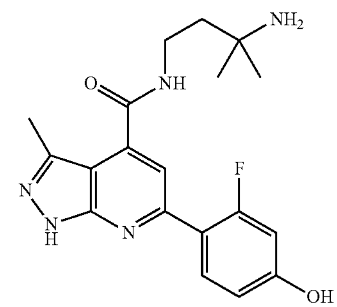 [SMILES: Cc1n[nH]c2nc(-c3ccc(O)cc3F)cc(C(=O)NCCC(C)(C)N)c12] | LC1 | 372.24 | 0.79 |

The following examples have been prepared following a similar procedure as described for Example 56, (2,2-Dimethyl-piperazin-1-yl)-[6-(2-fluoro-4-hydroxyphenyl)-3-methyl-1H-pyrazolo[3,4-b]pyridin-4-yl]-methanone, starting from the respective amine precursors and 6-(4-Hydroxy-phenyl)-3-methyl-1-(tetrahydro-pyran-2-yl)-1H-pyrazolo[3,4-b]pyridine-4-carboxylic acid (see Example 41, step c).

| Exp. No. | Name | Structure | LC/MS method | m/z [M + H]+ | R_t [min] |
|---|---|---|---|---|---|
| 68 | [6-(4-Hydroxy-phenyl)-3-methyl-1H-pyrazolo[3,4-b]pyridin-4-yl]-((S)-3-propyl-piperazin-1-yl)-methanone | 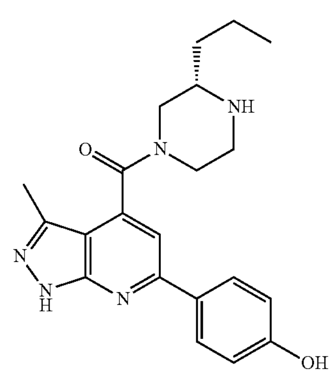 [SMILES: CCC[C@H]1CN(C(=O)c2cc(-c3ccc(O)cc3)nc3[nH]nc(C)c23)CCN1] | LC1 | 380.20 | 0.84 |

| Exp. No. | Name | Structure | LC/MS method | m/z [M + H]⁺ | R_t [min] |
|---|---|---|---|---|---|
| 69 | [6-(4-Hydroxy-phenyl)-3-methyl-1H-pyrazolo[3,4-b]pyridin-4-yl]-[2-(4-methoxy-phenyl)-piperazin-1-yl]-methanone | 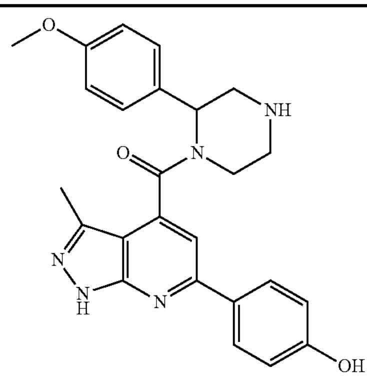 | LC1 | 444.28 | 0.75 |
| 70 | [6-(4-Hydroxy-phenyl)-3-methyl-1H-pyrazolo[3,4-b]pyridin-4-yl]-(5-methyl-2-phenyl-piperazin-1-yl)-methanone | 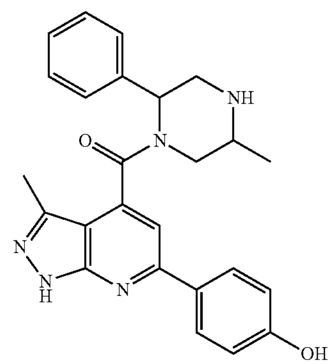 [SMILES: Cc1n[nH]c2nc(-c3ccc(O)cc3)cc(C(=O)N3CC(C)NCC3c3ccccc3)c12] | LC1 | 428.22 | 0.88 |
| 71 | 2,5-Diaza-bicyclo[2.2.2]oct-2-yl-[6-(4-hydroxy phenyl)-3-methyl-1H-pyrazolo[3,4-b]pyridin-4-yl]-methanone | 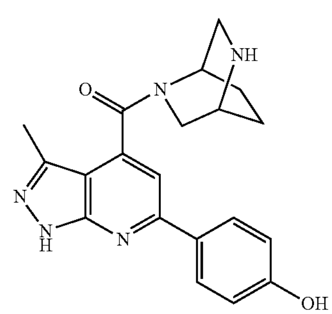 [SMILES: Cc1n[nH]c2nc(-c3ccc(O)cc3)cc(C(=O)N3CC4CCC3CN4)c12] | LC1 | 364.17 | 0.72 |
| 72 | [6-(4-Hydroxy-phenyl)-3-methyl-1H-pyrazolo[3,4-b]pyridin-4-yl]-[2-(3-methoxy-phenyl)-piperazin-1-yl]-methanone | 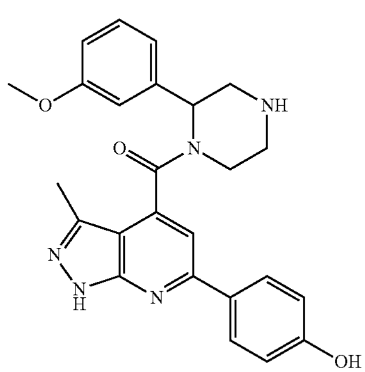 [SMILES: COc1cccc(C2CNCCN2C(=O)c2cc(-c3ccc(O)cc3)nc3[nH]nc(C)c23)c1] | LC1 | 444.20 | 0.89 |

-continued

| Exp. No. | Name | Structure | LC/MS method | m/z [M + H]+ | R_t [min] |
|---|---|---|---|---|---|
| 73 | (trans-2,5-Dimethyl-piperazin-1-yl)-[6-(4-hydroxy-phenyl)-3-methyl-1H-pyrazolo[3,4-b]pyridin-4-yl]-methanone | 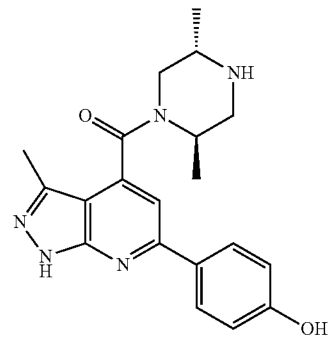 [SMILES: Cc1n[nH]c2nc(-c3ccc(O)cc3)cc(C(=O)N3C[C@H](C)NC[C@H]3C)c12] | LC1 | 366.19 | 0.78 |
| 74 | 6-(4-Hydroxy-phenyl)-3-methyl-1H-pyrazolo[3,4-b]pyridine-4-carboxylic acid piperidin-4-ylamide | 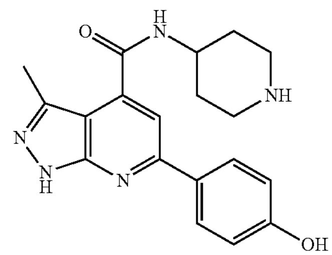 [SMILES: Cc1n[nH]c2nc(-c3ccc(O)cc3)cc(C(=O)NC3CCNCC3)c12] | LC1 | 352.17 | 0.72 |
| 75 | [1,4]Diazepan-1-yl-[6-(4-hydroxy-phenyl)-3-methyl-1H-pyrazolo[3,4-b]pyridin-4-yl]-methanone | 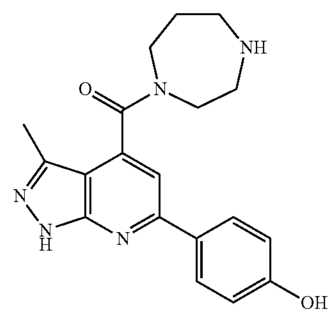 [SMILES: Cc1n[nH]c2nc(-c3ccc(O)cc3)cc(C(=O)N3CCCNCC3)c12] | LC1 | 352.17 | 0.70 |
| 76 | (3-Amino-piperidin-1-yl)-[6-(4-hydroxy-phenyl)-3-methyl-1H-pyrazolo[3,4-b]pyridin-4-yl]-methanone | 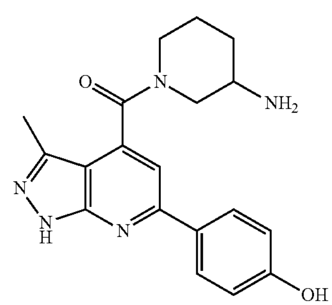 [SMILES: Cc1n[nH]c2nc(-c3ccc(O)cc3)cc(C(=O)N3CCCC(N)C3)c12] | LC1 | 352.17 | 0.75 |
| 77 | 6-(4-Hydroxy-phenyl)-3-methyl-1H-pyrazolo[3,4-b]pyridine-4-carboxylic acid (trans-4-amino-cyclohexyl)-amide | 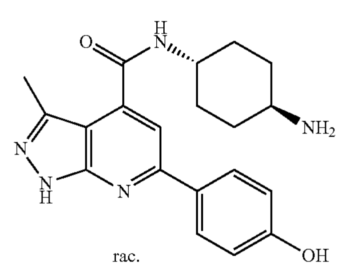 [SMILES: Cc1n[nH]c2nc(-c3ccc(O)cc3)cc(C(=O)N[C@H]3CC[C@H](N)CC3)c12] | LC1 | 366.19 | 0.77 |

| Exp. No. | Name | Structure | LC/MS method | m/z [M + H]+ | R$_t$ [min] |
|---|---|---|---|---|---|
| 78 | 6-(4-Hydroxy-phenyl)-3-methyl-1H-pyrazolo[3,4-b]pyridine-4-carboxylic acid ((trans)-4-methoxy-pyrrolidin-3-yl)-amide | 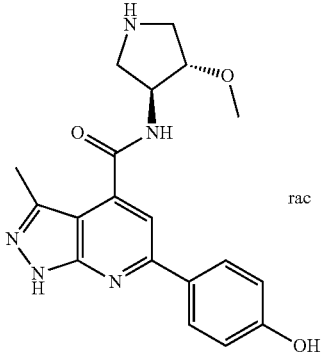 [SMILES: CO[C@H]1CNC[C@@H]1NC(=O)c1cc(-c2ccc(O)cc2)nc2[nH]nc(C)c12] rac | LC1 | 368.18 | 0.79 |
| 79 | [6-(4-Hydroxy-phenyl)-3-methyl-1H-pyrazolo[3,4-b]pyridin-4-yl]-[2-(2-methoxy-phenyl)-piperazin-1-yl]-methanone | 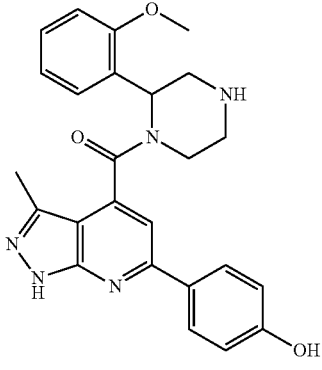 [SMILES: COc1ccccc1C1CNCCN1C(=O)c1cc(-c2ccc(O)cc2)nc2[nH]nc(C)c12] | LC1 | 444.25 | 0.74 |
| 80 | (4,7-Diaza-spiro[2.5]oct-4-yl)-[6-(4-hydroxy-phenyl)-3-methyl-1H-pyrazolo[3,4-b]pyridin-4-yl]-methanone | 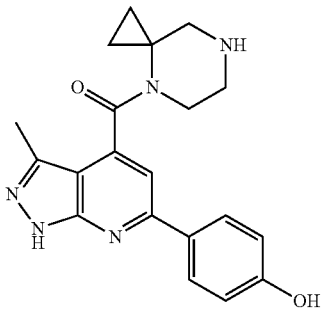 [SMILES: Cc1n[nH]c2nc(-c3ccc(O)cc3)cc(C(=O)N3CCNCC34CC4)c12] | LC1 | 364.17 | 0.64 |
| 81 | ((2R,5S)-2,5-Dimethyl-piperazin-1-yl)-[6-(4-hydroxy-phenyl)-3-methyl-1H-pyrazolo[3,4-b]pyridin-4-yl]-methanone | 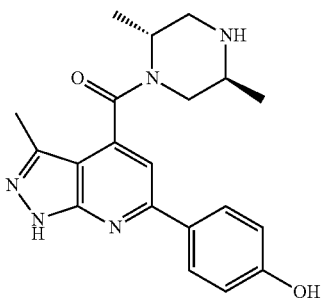 [SMILES: Cc1n[nH]c2nc(-c3ccc(O)cc3)cc(C(=O)N3C[C@H](C)NC[C@H]3C)c12] | LC1 | 366.29 | 0.62 |

| Exp. No. | Name | Structure | LC/MS method | m/z [M + H]+ | R$_t$ [min] |
|---|---|---|---|---|---|
| 82 | [(S)-2-(3-Fluoro-phenyl)-piperazin-1-yl]-[6-(4-hydroxy-phenyl)-3-methyl-1H-pyrazolo[3,4-b]pyridin-4-yl]-methanone | 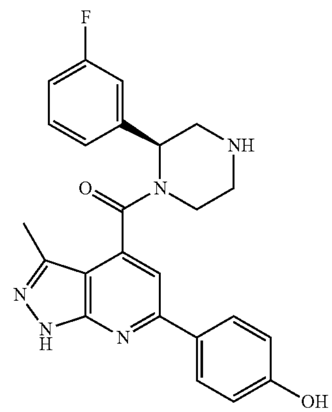 [SMILES: Cc1n[nH]c2nc(-c3ccc(O)cc3)cc(C(=O)N3CCNC[C@@H]3c3cccc(F)c3)c12] | LC1 | 432.24 | 0.76 |
| 83 | ((2R,5R)-2,5-Dimethyl-piperazin-1-yl)-[6-(4-hydroxy-phenyl)-3-methyl-1H-pyrazolo[3,4-b]pyridin-4-yl]-methanone | 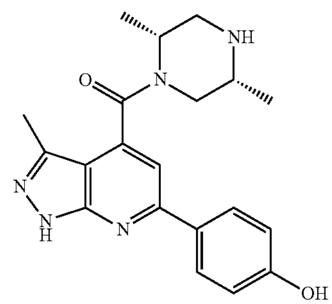 [SMILES: Cc1n[nH]c2nc(-c3ccc(O)cc3)cc(C(=O)N3C[C@@H](C)NC[C@H]3C)c12] | LC1 | 366.23 | 0.62 |
| 84 | [2-(4-Fluoro-phenyl)-piperazin-1-yl]-[6-(4-hydroxy-phenyl)-3-methyl-1H-pyrazolo[3,4-b]pyridin-4-yl]-methanone | 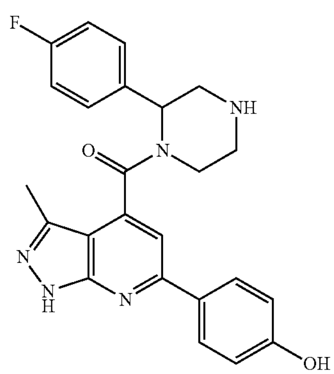 [SMILES: Cc1n[nH]c2nc(-c3ccc(O)cc3)cc(C(=O)N3CCNCC3c3ccc(F)cc3)c12] | LC1 | 432.25 | 0.76 |
| 85 | [2-(2,3-Difluoro-phenyl)-piperazin-1-yl]-[6-(4-hydroxy-phenyl)-3-methyl-1H-pyrazolo[3,4-b]pyridin-4-yl]-methanone | 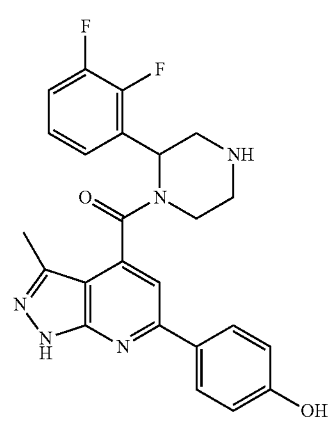 [SMILES: Cc1n[nH]c2nc(-c3ccc(O)cc3)cc(C(=O)N3CCNCC3c3cccc(F)c3F)c12] | LC1 | 450.24 | 0.77 |

| Exp. No. | Name | Structure | LC/MS method | m/z [M + H]⁺ | R_t [min] |
|---|---|---|---|---|---|
| 86 | (3-Cyclopropyl-piperazin-1-yl)-[6-(4-hydroxy-phenyl)-3-methyl-1H-pyrazolo[3,4-b]pyridin-4-yl]-methanone | 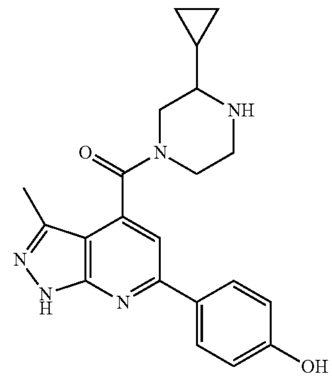 [SMILES: Cc1n[nH]c2nc(-c3ccc(O)cc3)cc(C(=O)N3CCNC(C4CC4)C3)c12] | LC1 | 378.23 | 0.67 |
| 87 | [2-(3,5-Difluoro-phenyl)-piperazin-1-yl]-[6-(4-hydroxy-phenyl)-3-methyl-1H-pyrazolo[3,4-b]pyridin-4-yl]-methanone | 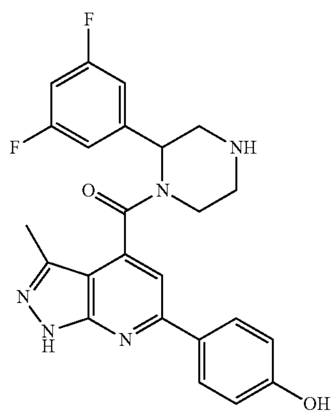 [SMILES: Cc1n[nH]c2nc(-c3ccc(O)cc3)cc(C(=O)N3CCNCC3c3cc(F)cc(F)c3)c12] | LC1 | 450.16 | 0.79 |
| 88 | ((2S,5S)-2,5-Dimethyl-piperazin-1-yl)-[6-(4-hydroxy-phenyl)-3-methyl-1H-pyrazolo[3,4-b]pyridin-4-yl]-methanone | 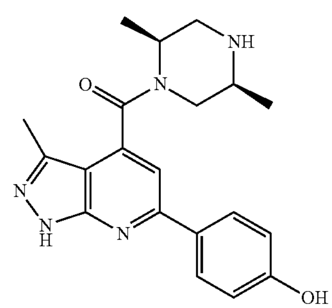 [SMILES: Cc1n[nH]c2nc(-c3ccc(O)cc3)cc(C(=O)N3C[C@H](C)NC[C@@H]3C)c12] | LC1 | 366.21 | 0.62 |
| 89 | [2-(4-Bromo-phenyl)-piperazin-1-yl]-[6-(4-hydroxy-phenyl)-3-methyl-1H-pyrazolo[3,4-b]pyridin-4-yl]-methanone | 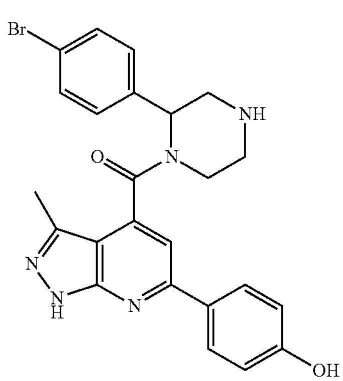 | LC1 | 492.08 | 0.81 |

| Exp. No. | Name | Structure | LC/MS method | m/z [M + H]⁺ | R_t [min] |
|---|---|---|---|---|---|
| 90 | (3-Aminomethyl-azetidin-1-yl)-[6-(4-hydroxy-phenyl)-3-methyl-1H-pyrazolo[3,4-b]pyridin-4-yl]-methanone | 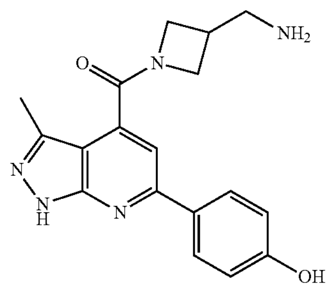 [SMILES: Cc1n[nH]c2nc(-c3ccc(O)cc3)cc(C(=O)N3CC(CN)C3)c12] | LC1 | 338.17 | 0.68 |
| 91 | [2-(3-Fluoro-phenyl)-piperazin-1-yl]-[6-(4-hydroxy-phenyl)-3-methyl-1H-pyrazolo[3,4-b]pyridin-4-yl]-methanone | 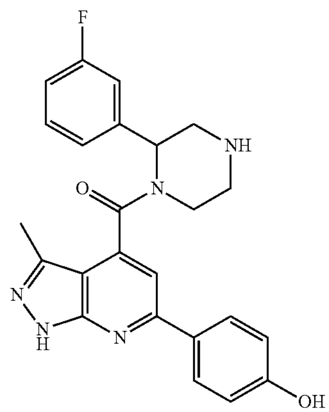 [SMILES: Cc1n[nH]c2nc(-c3ccc(O)cc3)cc(C(=O)N3CCNCC3c3cccc(F)c3)c12] | LC1 | 432.21 | 0.89 |
| 92 | [2-(3,4-Difluoro-phenyl)-piperazin-1-yl]-[6-(4-hydroxy-phenyl)-3-methyl-1H-pyrazolo[3,4-b]pyridin-4-yl]-methanone | 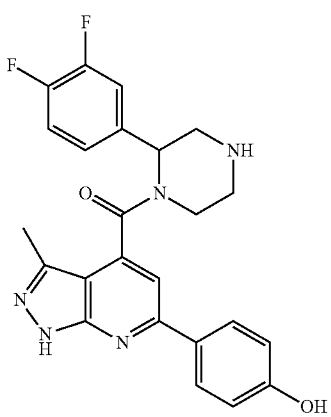 [SMILES: Cc1n[nH]c2nc(-c3ccc(O)cc3)cc(C(=O)N3CCNCC3c3ccc(F)c(F)c3)c12] | LC1 | 450.20 | 0.92 |
| 93 | [6-(4-Hydroxy-phenyl)-3-methyl-1H-pyrazolo[3,4-b]pyridin-4-yl]-[2-(2-trifluoromethyl-phenyl)-piperazin-1-yl]-methanone | 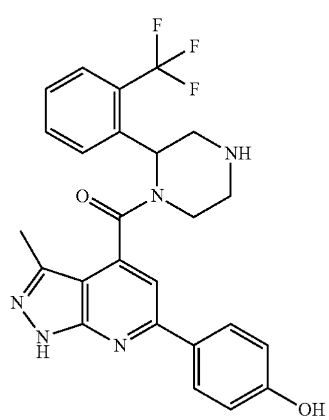 [SMILES: Cc1n[nH]c2nc(-c3ccc(O)cc3)cc(C(=O)N3CCNCC3c3ccccc3C(F)(F)F)c12] | LC1 | 482.22 | 0.93 |

| Exp. No. | Name | Structure | LC/MS method | m/z [M + H]⁺ | R_t [min] |
|---|---|---|---|---|---|
| 94 | [6-(4-Hydroxy-phenyl)-3-methyl-1H-pyrazolo[3,4-b]pyridin-4-yl]-[2-(4-isopropyl-phenyl)-piperazin-1-yl]-methanone | 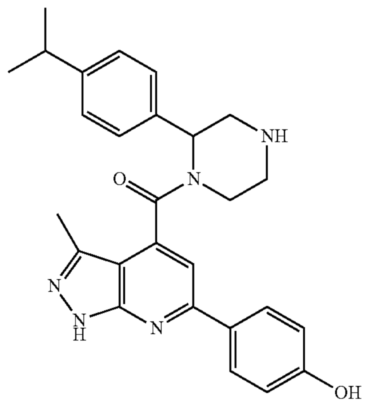 [SMILES: Cc1n[nH]c2nc(-c3ccc(O)cc3)cc(C(=O)N3CCNCC3c3ccc(C(C)C)cc3)c12] | LC1 | 456.26 | 0.98 |
| 95 | [2-(2-Fluoro-phenyl)-piperazin-1-yl]-[6-(4-hydroxy-phenyl)-3-methyl-1H-pyrazolo[3,4-b]pyridin-4-yl]-methanone | 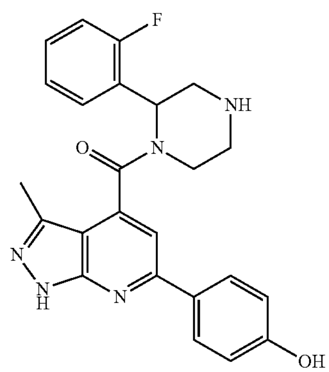 [SMILES: Cc1n[nH]c2nc(-c3ccc(O)cc3)cc(C(=O)N3CCNCC3c3ccccc3F)c12] | LC1 | 432.22 | 0.89 |
| 96 | [2-(2,4-Difluoro-phenyl)-piperazin-1-yl]-[6-(4-hydroxy-phenyl)-3-methyl-1H-pyrazolo[3,4-b]pyridin-4-yl]-methanone | 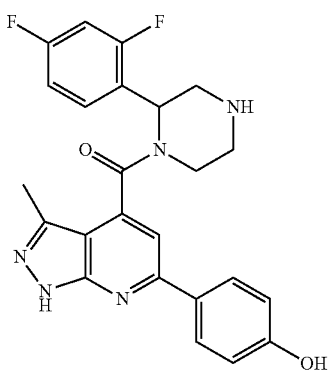 [SMILES: Cc1n[nH]c2nc(-c3ccc(O)cc3)cc(C(=O)N3CCNCC3c3ccc(F)cc3F)c12] | LC1 | 450.21 | 0.90 |
| 97 | [6-(4-Hydroxy-phenyl)-3-methy-1H-pyrazolo[3,4-b]pyridin-4-yl]-[2-(4-trifluoromethyl-phenyl)-piperazin-1-yl]-methanone | 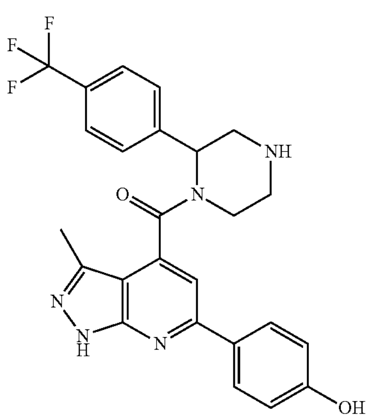 | LC1 | 482.22 | 0.97 |

| Exp. No. | Name | Structure | LC/MS method | m/z [M + H]⁺ | R$_t$ [min] |
|---|---|---|---|---|---|
| 98 | 6-(4-Hydroxy-phenyl)-3-methyl-1H-pyrazolo[3,4-b]pyridine-4-carboxylic acid (azetidin-3-ylmethyl)-amide | 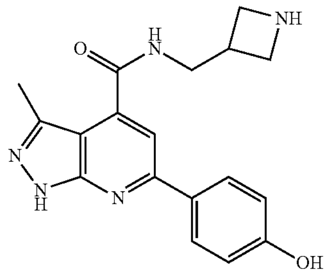 [SMILES: Cc1n[nH]c2nc(-c3ccc(O)cc3)cc(C(=O)NCC3CNC3)c12] | LC1 | 338.21 | 0.72 |
| 99 | [6-(4-Hydroxy-phenyl)-3-methyl-1H-pyrazolo[3,4-[2-(3-trifluoromethyl-phenyl)-piperazin-1-yl]-methanone | 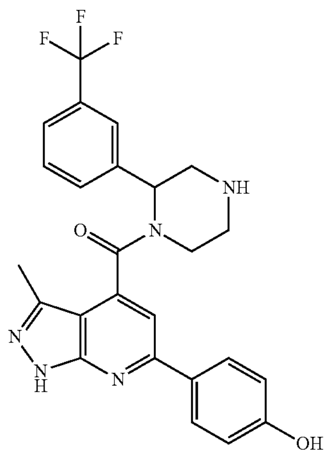 [SMILES: Cc1n[nH]c2nc(-c3ccc(O)cc3)cc(C(=O)N3CCNCC3c3cccc(C(F)(F)F)c3)c12] | LC1 | 482.22 | 0.98 |
| 100 | [2-(2,6-Difluoro-phenyl)-piperazin-1-yl]-[6-(4-hydroxy-phenyl)-3-methyl-1H-pyrazolo[3,4-b]pyridin-4-yl]-methanone | 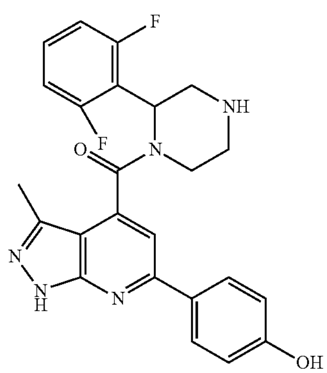 [SMILES: Cc1n[nH]c2nc(-c3ccc(O)cc3)cc(C(=O)N3CCNCC3c3c(F)cccc3F)c12] | LC1 | 450.20 | 0.87 |
| 101 | [2-(3-Bromo-phenyl)-piperazin-1-yl][6-(4-hydroxy-phenyl)-3-methyl-1H-pyrazolo[3,4-b]pyridin-4-yl]-methanone | 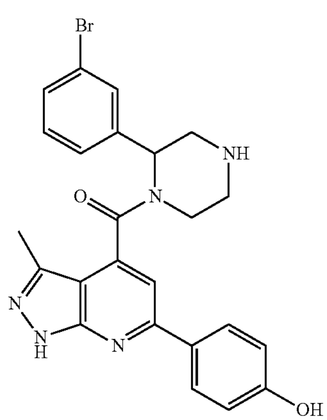 [SMILES: Cc1n[nH]c2nc(-c3ccc(O)cc3)cc(C(=O)N3CCNCC3c3cccc(Br)c3)c12] | LC1 | 492.13 | 0.95 |

-continued

| Exp. No. | Name | Structure | LC/MS method | m/z [M + H]+ | R_r [min] |
|---|---|---|---|---|---|
| 102 | [2-(2-Chloro-phenyl)-piperazin-1-yl]-[6-(4-hydroxy-phenyl)-3-methyl-1H-pyrazolo[3,4-b]pyridin-4-yl]-methanone | 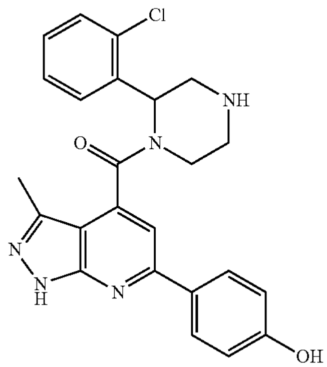 | LC1 | 448.17 | 0.90 |
| 103 | 6-(4-Hydroxy-phenyl)-3-methyl-1H-pyrazolo[3,4-b]pyridine-4-carboxylic acid (cis-4-amino-cyclohexyl)-amide | 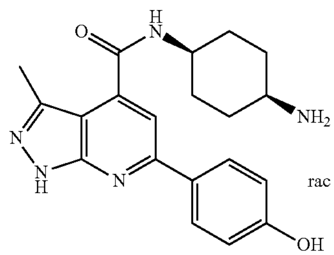 [SMILES: Cc1n[nH]c2nc(-c3ccc(O)cc3)cc(C(=O)N[C@H]3CC[C@@H](N)CC3)c12] | LC1 | 366.21 | 0.78 |
| 104 | 6-(4-Hydroxy-phenyl)-3-methyl-1H-pyrazolo[3,4-b]pyridine-4-carboxylic acid (2-amino-1-phenyl-ethyl)-amide | 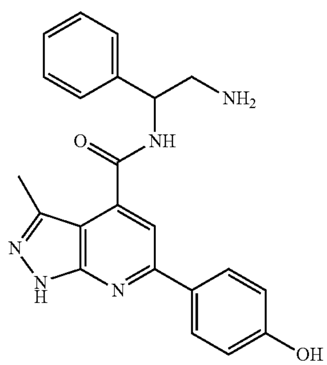 [SMILES: Cc1n[nH]c2nc(-c3ccc(O)cc3)cc(C(=O)NC(CN)c3ccccc3)c12] | LC1 | 388.22 | 0.89 |
| 105 | 6-(4-Hydroxy-phenyl)-3-methyl-1H-pyrazolo[3,4-b]pyridine-4-carboxylic acid (cis-4-amino-cyclohexymethyl)-amide | 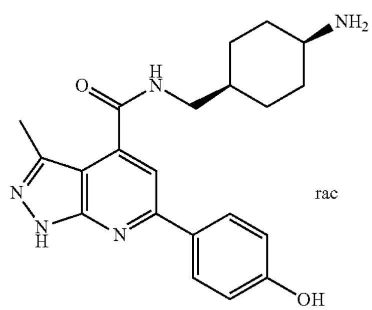 [SMILES: Cc1n[nH]c2nc(-c3ccc(O)cc3)cc(C(=O)NC[C@H]3CC[C@@H](N)CC3)c12] | LC1 | 380.21 | 0.79 |
| 106 | 6-(4-Hydroxy-phenyl)-3-methyl-1H-pyrazolo[3,4-b]pyridine-4-carboxylic acid pyrrolidin-3-ylamide | 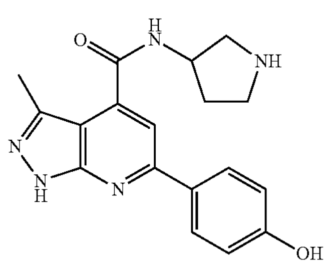 [SMILES: Cc1n[nH]c2nc(-c3ccc(O)cc3)cc(C(=O)NC3CCNC3)c12] | LC1 | 338.17 | 0.73 |

| Exp. No. | Name | Structure | LC/MS method | m/z [M + H]+ | R, [min] |
|---|---|---|---|---|---|
| 107 | 6-(4-Hydroxy-phenyl)-3-methyl-1H-pyrazolo[3,4-b]pyridine-4-carboxylic acid [2-amino-1-(4-fluoro-phenyl)-ethyl]-amide | 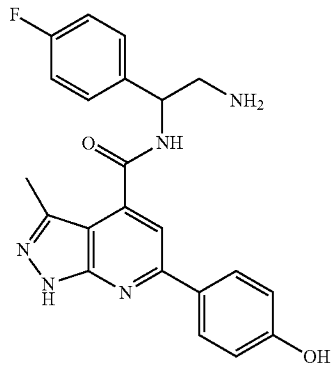 [SMILES: Cc1n[nH]c2nc(-c3ccc(O)cc3)cc(C(=O)NC(CN)c3ccc(F)cc3)c12] | LC1 | 406.20 | 0.90 |
| 108 | (6,9-Diaza-spiro[4.5]dec-6-yl)-[6-(4-hydroxy-phenyl)-3-methyl-1H-pyrazolo[3,4-b]pyridin-4-yl]-methanone | 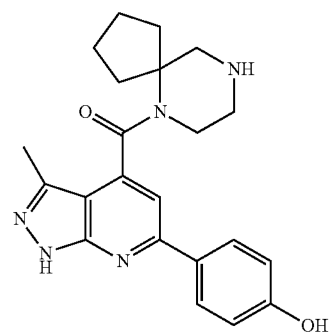 [SMILES: Cc1n[nH]c2nc(-c3ccc(O)cc3)cc(C(=O)N3CCNCC34CCCC4)c12] | LC1 | 392.24 | 0.88 |
| 109 | [6-(4-Hydroxy-phenyl)-3-methyl-1H-pyrazolo[3,4-b]pyridin-4-yl]-(4-methylamino-piperidin-1-yl)-methanone | 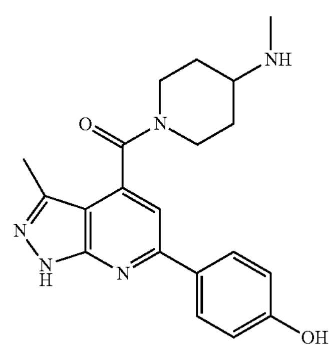 [SMILES: CNC1CCN(C(=O)c2cc(-c3ccc(O)cc3)nc3[nH]nc(C)c23)CC1] | LC1 | 366.25 | 0.71 |
| 110 | ((S)-3-Aminomethyl-piperidin-1-yl)-[6-(4-hydroxy-phenyl)-3-methyl-1H-pyrazolo[3,4-b]pyridin-4-yl]-methanone | 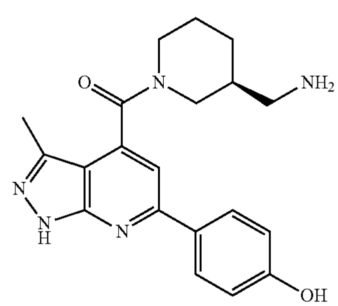 [SMILES: Cc1n[nH]c2nc(-c3ccc(O)cc3)cc(C(=O)N3CCC[C@@H](CN)C3)c12] | LC8 | 366.30 | 1.99 |

| Exp. No. | Name | Structure | LC/MS method | m/z [M + H]+ | R$_t$ [min] |
|---|---|---|---|---|---|
| 111 | 3,8-Diaza-bicyclo[3.2.1]oct-3-yl-[6-(4-hydroxy-phenyl)-3-methyl-1H-pyrazolo[3,4-b]pyridin-4-yl]-methanone | 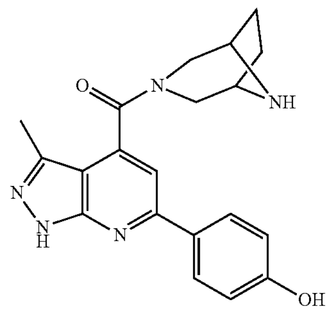 [SMILES: Cc1n[nH]c2nc(-c3ccc(O)cc3)cc(C(=O)N3CC4CCC(C3)N4)c12] | LC1 | 364.25 | 0.75 |
| 112 | ((2S,5R)-2,5-Dimethyl-piperazin-1-yl)-[6-(4-hydroxy-phenyl)-3-methyl-1H-pyrazolo[3,4-b]pyridin-4-yl]-methanone | 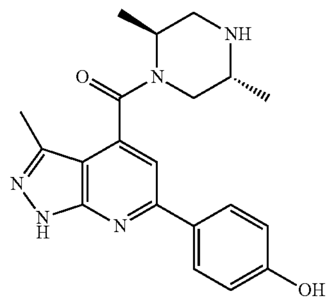 [SMILES: Cc1n[nH]c2nc(-c3ccc(O)cc3)cc(C(=O)N3C[C@@H](C)NC[C@@H]3C)c12] | LC1 | 366.26 | 0.78 |
| 113 | [6-(4-Hydroxy-phenyl)-3-methyl-1H-pyrazolo[3,4-b]pyridin-4-yl]-(2,5,5-trimethyl-piperazin-1-yl)-methanone | 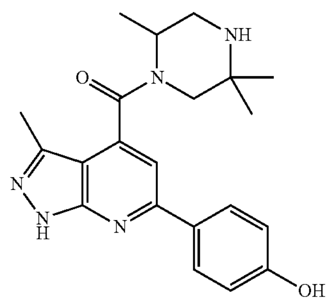 [SMILES: Cc1n[nH]c2nc(-c3ccc(O)cc3)cc(C(=O)N3CC(C)(C)NCC3C)c12] | LC1 | 380.30 | 0.80 |
| 114 | [6-(4-Hydroxy-phenyl)-3-methyl-1H-pyrazolo[3,4-b]pyridin-4-yl]-(2-trifluoromethyl-piperazin-1-yl)-methanone | 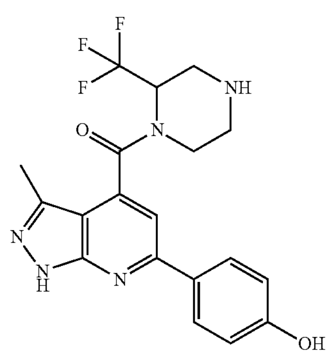 [SMILES: Cc1n[nH]c2nc(-c3ccc(O)cc3)cc(C(=O)N3CCNCC3C(F)(F)F)c12] | LC5 | 406.18 | 0.71 |
| 115 | 6-(4-Hydroxy-phenyl)-3-methyl-1H-pyrazolo[3,4-b]pyridine-4-carboxylic acid (3-ethyl-piperidin-3-yl)-amide | 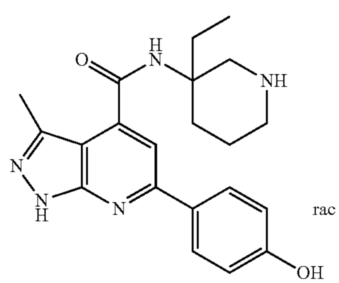 [SMILES: CCC1(NC(=O)c2cc(-c3ccc(O)cc3)nc3[nH]nc(C)c23)CCCNC1] | LC5 | 380.27 | 0.72 |

| Exp. No. | Name | Structure | LC/MS method | m/z [M + H]+ | R_t [min] |
|---|---|---|---|---|---|
| 116 | 6-(4-Hydroxy-phenyl)-3-methyl-1H-pyrazolo[3,4-b]pyridine-4-carboxylic acid (1-amino-cycloheptylmethyl)-amide | 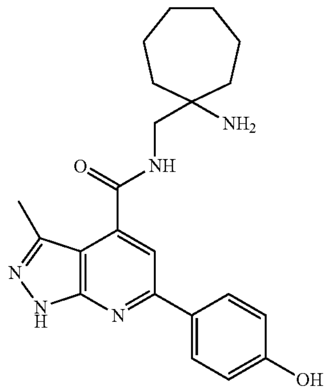 [SMILES: Cc1n[nH]c2nc(-c3ccc(O)cc3)cc(C(=O)NCC3(N)CCCCCC3)c12] | LC5 | 394.29 | 0.77 |
| 117 | (3-Amino-3-methyl-piperidin-1-yl)-[6-(4-hydroxy-phenyl)-3-methyl-1H-pyrazolo[3,4-b]pyridin-4-yl]-methanone | 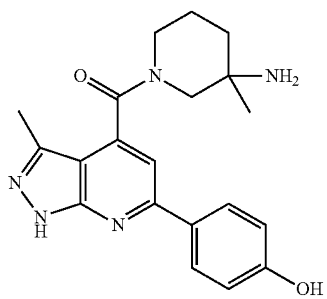 [SMILES: Cc1n[nH]c2nc(-c3ccc(O)cc3)cc(C(=O)N3CCCC(C)(N)C3)c12] | LC1 | 366.32 | 0.77 |
| 118 | 6-(4-Hydroxy-phenyl)-3-methyl-1H-pyrazolo[3,4-b]pyridine-4-carboxylic acid (4-propyl-piperidin-4-yl)-amide | 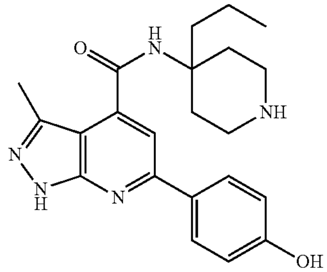 [SMILES: CCCC1(NC(=O)c2cc(-c3ccc(O)cc3)nc3[nH]nc(C)c23)CCNCC1] | LC1 | 394.40 | 0.89 |
| 119 | 6-(4-Hydroxy-phenyl)-3-methyl-1H-pyrazolo[3,4-b]pyridine-4-carboxylic acid (trans-4-p-tolyl-pyrrolidin-3-yl)-amide | 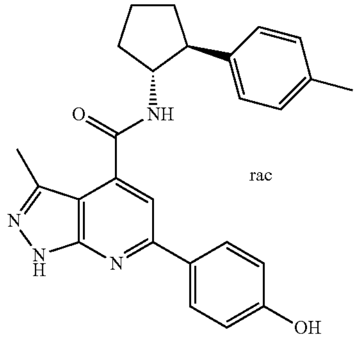 [SMILES: Cc1ccc([C@@H]2CCC[C@H]2NC(=O)c2cc(-c3ccc(O)cc3)nc3[nH]nc(C)c23)cc1] | LC1 | 428.26 | 0.92 |

| Exp. No. | Name | Structure | LC/MS method | m/z [M + H]⁺ | R$_t$ [min] |
|---|---|---|---|---|---|
| 120 | 6-(4-Hydroxy-phenyl)-3-methyl-1H-pyrazolo[3,4-b]pyridine-4-carboxylic acid ((1R,2R)-2-amino-cyclopentyl)-amide | 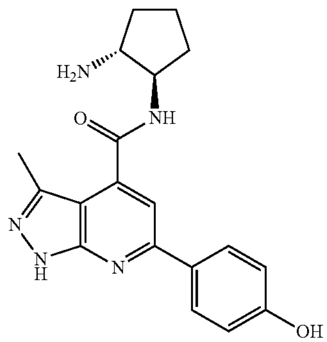 [SMILES: Cc1n[nH]c2nc(-c3ccc(O)cc3)cc(C(=O)N[C@@H]3CCC[C@H]3N)c12] | LC1 | 352.22 | 0.77 |
| 121 | [6-(4-Hydroxy-phenyl)-3-methyl-1H-pyrazolo[3,4-b]pyridin-4-yl]-(2,2,5,5-tetramethyl-piperazin-1-yl)-methanone | 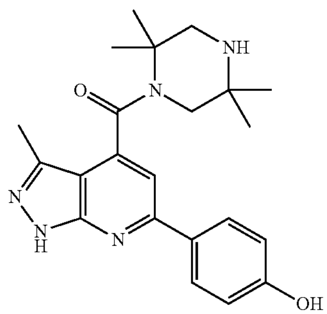 [SMILES: Cc1n[nH]c2nc(-c3ccc(O)cc3)cc(C(=O)N3CC(C)(C)NCC3(C)C)c12] | LC1 | 394.28 | 0.81 |
| 122 | (3-Amino-3-methyl-pyrrolidin-1-yl)-[6-(4-hydroxy-phenyl)-3-methyl-1H-pyrazolo[3,4-b]pyridin-4-yl]-methanone | 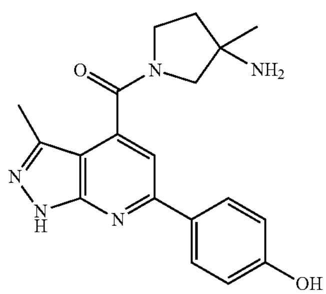 [SMILES: Cc1n[nH]c2nc(-c3ccc(O)cc3)cc(C(=O)N3CCC(C)(N)C3)c12] | LC8 | 352.28 | 1.80 |
| 123 | 6-(4-Hydroxy-phenyl)-3-methyl-1H-pyrazolo[3,4-b]pyridine-4-carboxylic acid (trans-2-amino-cyclohexyl)-amide | 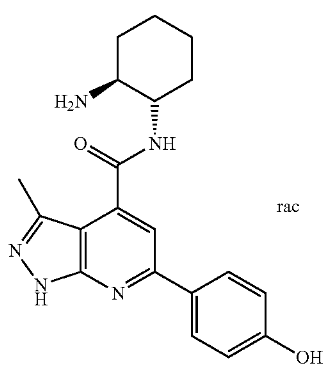 | LC8 | 366.32 | 2.23 |
| 124 | 6-(4-Hydroxy-phenyl)-3-methyl-1H-pyrazolo[3,4-b]pyridine-4-carboxylic acid (3-propyl-piperidin-3-yl)-amide | 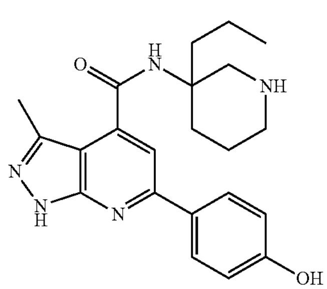 [SMILES: CCCC1(NC(=O)c2cc(-c3ccc(O)cc3)nc3[nH]nc(C)c23)CCCNC1] | LC8 | 394.39 | 2.40 |

| Exp. No. | Name | Structure | LC/MS method | m/z [M + H]+ | R_t [min] |
|---|---|---|---|---|---|
| 125 | 6-(4-Hydroxy-phenyl)-3-methyl-1H-pyrazolo[3,4-b]pyridine-4-carboxylic acid (3-propyl-pyrrolidin-3-yl)-amide | 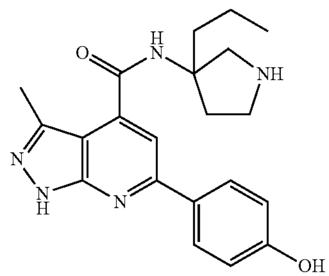 [SMILES: CCCC1(NC(=O)c2cc(-c3ccc(O)cc3)nc3[nH]nc(C)c23)CCNC1] | LC1 | 380.28 | 0.88 |
| 126 | 6-(4-Hydroxy-phenyl)-3-methyl-1H-pyrazolo[3,4-b]pyridine-4-carboxylic acid (cis-2-amino-cyclohexyl)-amide | 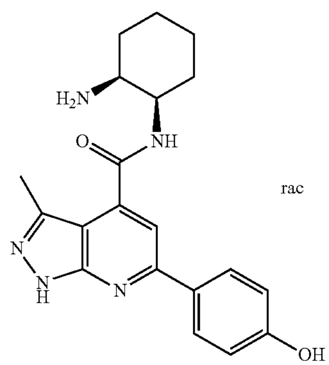 [SMILES: Cc1n[nH]c2nc(-c3ccc(O)cc3)cc(C(=O)N[C@@H]3CCCC[C@@H]3N)c12] | LC1 | 366.20 | 0.82 |
| 127 | 6-(4-Hydroxy-phenyl)-3-methyl-1H-pyrazolo[3,4-b]pyridine-4-carboxylic acid (3-amino-1-ethyl-propyl)-amide | 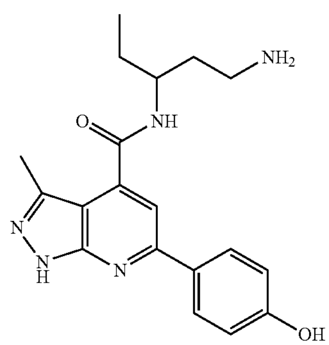 [SMILES: CCC(CCN)NC(=O)c1cc(-c2ccc(O)cc2)nc2[nH]nc(C)c12] | LC1 | 354.24 | 0.81 |
| 128 | 6-(4-Hydroxy-phenyl)-3-methyl-1H-pyrazolo[3,4-b]pyridine-4-carboxylic acid (3-amino-1,1-dimethyl-propyl)-amide | 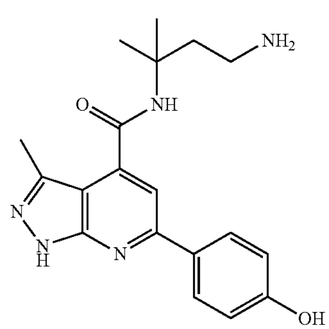 [SMILES: Cc1n[nH]c2nc(-c3ccc(O)cc3)cc(C(=O)NC(C)(C)CCN)c12] | LC1 | 354.23 | 0.80 |

| Exp. No. | Name | Structure | LC/MS method | m/z [M + H]⁺ | R_t [min] |
|---|---|---|---|---|---|
| 129 | 6-(4-Hydroxy-phenyl)-3-methyl-1H-pyrazolo[3,4-b]pyridine-4-carboxylic acid (3-amino-3-methyl-butyl)-amide | 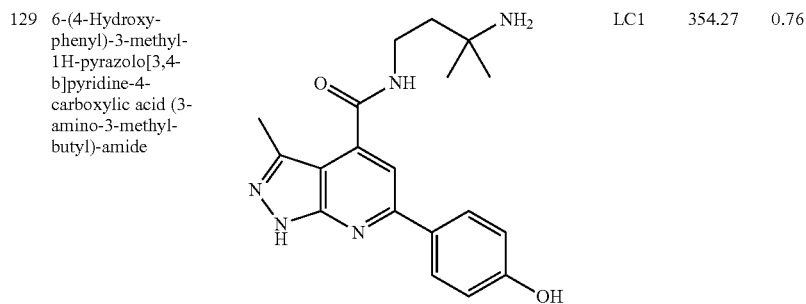 | LC1 | 354.27 | 0.76 |
| 130 | 6-(4-Hydroxy-phenyl)-3-methyl-1H-pyrazolo[3,4-b]pyridine-4-carboxylic acid (trans-4-amino-cyclohexylmethyl)-amide | 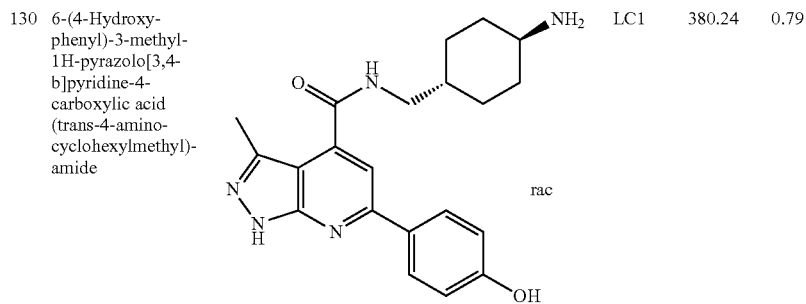 | LC1 | 380.24 | 0.79 |
| 131 | 6-(4-Hydroxy-phenyl)-3-methyl-1H-pyrazolo[3,4-b]pyridine-4-carboxylic acid (3-amino-1-phenyl-propyl)-amide | 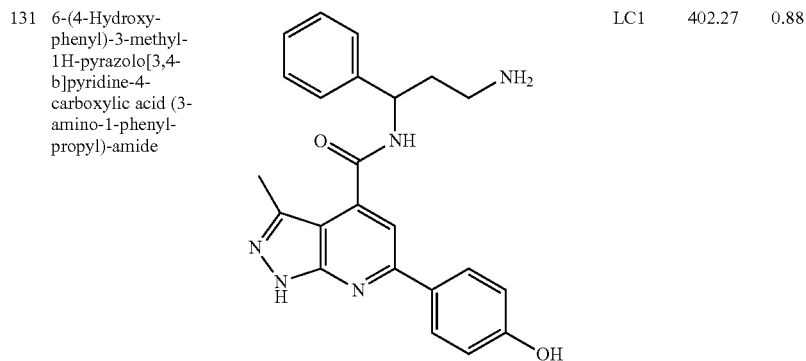 | LC1 | 402.27 | 0.88 |
| 132 | 6-(4-Hydroxy-phenyl)-3-methyl-1H-pyrazolo[3,4-b]pyridine-4-carboxylic acid (2-dimethylamino-1-phenyl-ethyl)-amide | 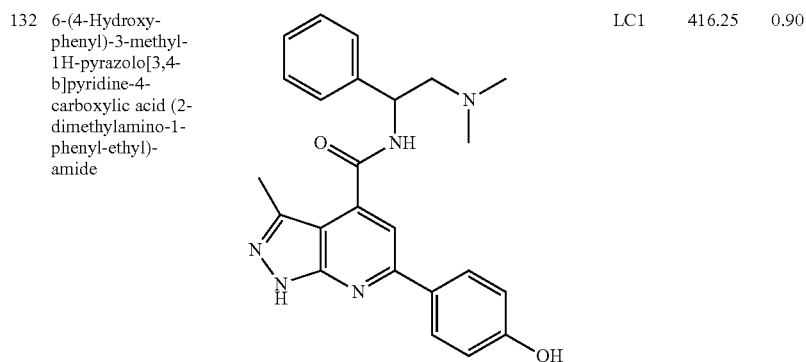 | LC1 | 416.25 | 0.90 |

-continued

| Exp. No. | Name | Structure | LC/MS method | m/z [M + H]+ | R$_t$ [min] |
|---|---|---|---|---|---|
| 133 | 6-(4-Hydroxy-phenyl)-3-methyl-1H-pyrazolo[3,4-b]pyridine-4-carboxylic acid (2-amino-2-methyl-propyl)-amide | 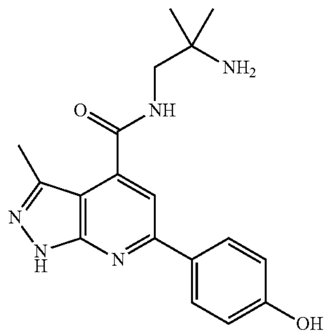 [SMILES: Cc1n[nH]c2nc(-c3ccc(O)cc3)cc(C(=O)NCC(C)(C)N)c12] | LC1 | 340.21 | 0.72 |
| 134 | 6-(4-Hydroxy-phenyl)-3-methyl-1H-pyrazolo[3,4-b]pyridine-4-carboxylic acid (2-amino-1,1,2-trimethyl-propyl)-amide | 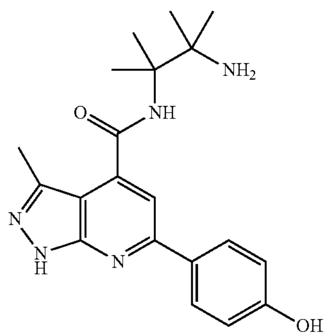 [SMILES: Cc1n[nH]c2nc(-c3ccc(O)cc3)cc(C(=O)NC(C)(C)C(C)(C)N)c12] | LC8 | 368.40 | 2.10 |

Example 135

[6-(2,6-Difluoro-4-hydroxy-phenyl)-3-methyl-1H-pyrazolo[3,4-b]pyridin-4-yl]-(2,2-dimethyl-piperazin-1-yl)-methanone

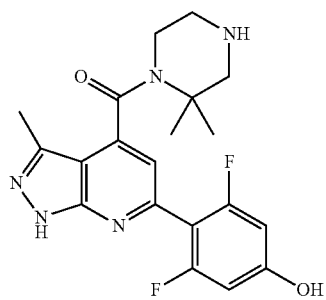 [SMILES: Cc1n[nH]c2nc(-c3c(F)cc(O)cc3F)cc(C(=O)N3CCNCC3(C)C)c12]

[6-(2,6-Difluoro-4-hydroxy-phenyl)-3-methyl-1H-pyrazolo[3,4-b]pyridin-4-yl]-(2,2-dimethyl-piperazin-1-yl)-methanone has been prepared following a similar procedure as described for Example 56, (2,2-Dimethyl-piperazin-1-yl)-[6-(2-fluoro-4-hydroxyphenyl)-3-methyl-1H-pyrazolo[3,4-b]pyridin-4-yl]-methanone, starting from 6-(2,6-difluoro-4-hydroxy-phenyl)-3-methyl-1-(tetrahydro-pyran-2-yl)-1H-pyrazolo[3,4-b]pyridine-4-carboxylic acid.

LC/MS (Method LC1): R$_t$=0.84 min; m/z 402.22 [M+H]+.

The following examples have been prepared following a similar procedure as described for Example 56, (2,2-Dimethyl-piperazin-1-yl)-[6-(2-fluoro-4-hydroxyphenyl)-3-methyl-1H-pyrazolo[3,4-b]pyridin-4-yl]-methanone, starting from the respective amine precursors and 6-(4-hydroxy-2-methyl-phenyl)-3-methyl-1-(tetrahydro-pyran-2-yl)-1H-pyrazolo[3,4-b]pyridine-4-carboxylic acid:

| Exp. No. | Name | Structure | LC/MS method | m/z [M + H]+ | R$_t$ [min] |
|---|---|---|---|---|---|
| 136 | [2-(3,5-Difluoro-phenyl)-piperazin-1-yl]-[6-(4-hydroxy-2-methyl-phenyl)-3-methyl-1H-pyrazolo[3,4-b]pyridin-4-yl]-methanone | 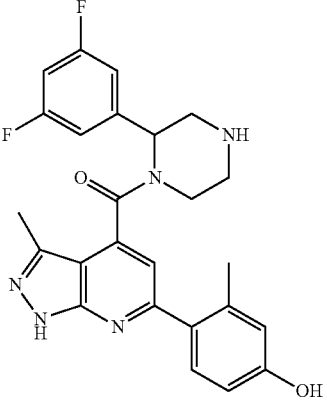 [SMILES: Cc1cc(O)ccc1-c1cc(C(=O)N2CCNCC2c2cc(F)cc(F)c2)c2c(C)n[nH]c2n1] | LC1 | 464.28 | 0.92 |
| 137 | [2-(4-Bromo-phenyl)-piperazin-1-yl]-[6-(4-hydroxy-2-methyl-phenyl)-3-methyl-1H-pyrazolo[3,4-b]pyridin-4-yl]-methanone | 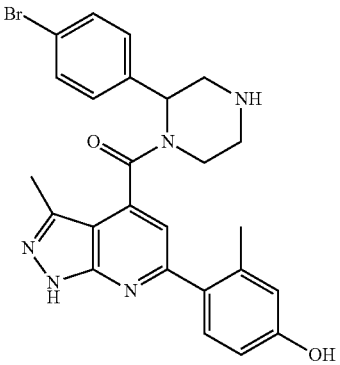 [SMILES: Cc1cc(O)ccc1-c1cc(C(=O)N2CCNCC2c2ccc(Br)cc2)c2c(C)n[nH]c2n1] | LC1 | 506.22 | 0.95 |
| 138 | [2-(4-Fluoro-phenyl)-piperazin-1-yl]-[6-(4-hydroxy-2-methyl-phenyl)-3-methyl-1H-pyrazolo[3,4-b]pyridin-4-yl]-methanone | 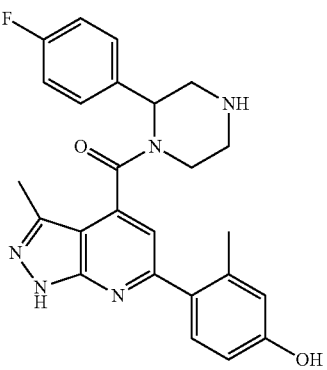 [SMILES: Cc1cc(O)ccc1-c1cc(C(=O)N2CCNCC2c2ccc(F)cc2)c2c(C)n[nH]c2n1] | LC1 | 446.27 | 0.90 |
| 139 | [2-(2,3-Difluoro-phenyl)-piperazin-1-yl]-[6-(4-hydroxy-2-methyl-phenyl)-3-methyl-1H-pyrazolo[3,4-b]pyridin-4-yl]-methanone | 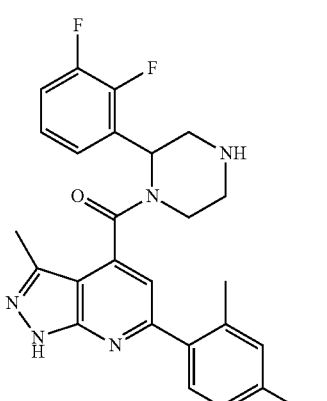 | LC1 | 464.29 | 0.91 |

| Exp. No. | Name | Structure | LC/MS method | m/z [M + H]⁺ | R_t [min] |
|---|---|---|---|---|---|
| 140 | [6-(4-Hydroxy-2-methyl-phenyl)-3-methyl-1H-pyrazolo[3,4-b]pyridin-4-yl]-[2-(4-methoxy-phenyl)-piperazin-1-yl]-methanone | 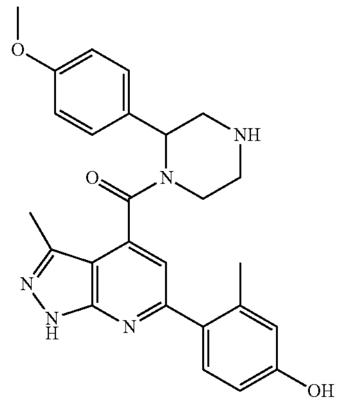 [SMILES: COc1ccc(C2CNCCN2C(=O)c2cc(-c3ccc(O)cc3C)nc3[nH]nc(C)c23)cc1] | LC1 | 458.32 | 0.90 |
| 141 | [(S)-2-(3-Fluoro-phenyl)-piperazin-1-yl]-[6-(4-hydroxy-2-methyl-phenyl)-3-methyl-1H-pyrazolo[3,4-b]pyridin-4-yl]-methanone | 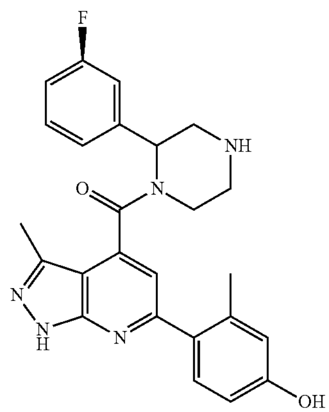 | LC1 | 446.28 | 0.90 |
| 142 | (2,2-Dimethyl-piperazin-1-yl)-[6-(4-hydroxy-2-methyl-phenyl)-3-methyl-1H-pyrazolo[3,4-b]pyridin-4-yl]-methanone | 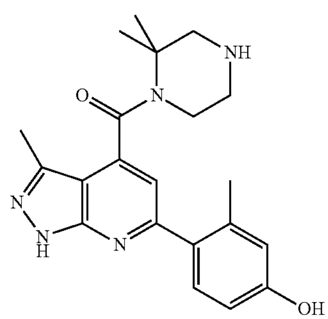 [SMILES: Cc1cc(O)ccc1-c1cc(C(=O)N2CCNCC2(C)C)c2c(C)n[nH]c2n1] | LC5 | 380.29 | 0.69 |
| 143 | 6-(4-Hydroxy-2-methyl-phenyl)-3-methyl-1H-pyrazolo[3,4-b]pyridine-4-carboxylic acid ((3S,4S)-4-methoxy-pyrrolidin-3-yl)-amide | 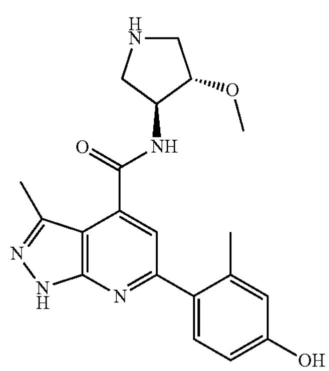 [SMILES: CO[C@H]1CNC[C@@H]1NC(=O)c1cc(-c2ccc(O)cc2C)nc2[nH]nc(C)c12] | LC5 | 382.31 | 0.65 |

| Exp. No. | Name | Structure | LC/MS method | m/z [M + H]⁺ | R$_r$ [min] |
|---|---|---|---|---|---|
| 144 | [6-(4-Hydroxy-2-methyl-phenyl)-3-methyl-1H-pyrazolo[3,4-b]pyridin-4-yl]-(2-trifluoromethyl-piperazin-1-yl)-methanone | 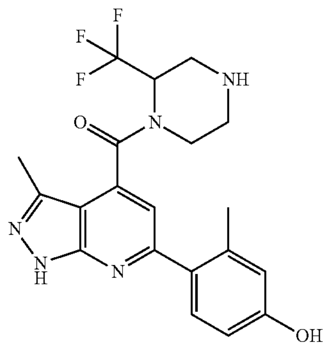 [SMILES: Cc1cc(O)ccc1-c1cc(C(=O)N2CCNCC2C(F)(F)F)c2c(C)n[nH]c2n1] | LC5 | 420.18 | 0.73 |
| 145 | [6-(4-Hydroxy-2-methyl-phenyl)-3-methyl-1H-pyrazolo[3,4-b]pyridin-4-yl]-((S)-3-methyl-piperazin-1-yl)-methanone | 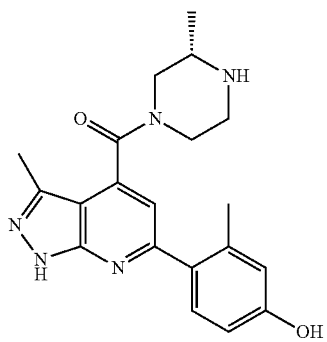 [SMILES: Cc1cc(O)ccc1-c1cc(C(=O)N2CCN[C@@H](C)C2)c2c(C)n[nH]c2n1] | LC5 | 366.22 | 0.60 |
| 146 | [6-(4-Hydroxy-2-methyl-phenyl)-3-methyl-1H-pyrazolo[3,4-b]pyridin-4-yl]-[2-(3-methoxy-phenyl)-piperazin-1-yl]-methanone | 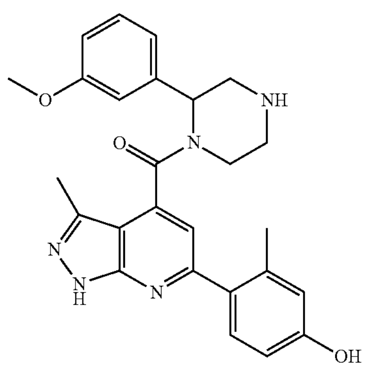 [SMILES: COc1cccc(C2CNCCN2C(=O)c2cc(-c3ccc(O)cc3C)nc3[nH]nc(C)c23)c1] | LC5 | 458.43 | 0.76 |
| 147 | [2-(3-Fluoro-phenyl)-piperazin-1-yl]-[6-(4-hydroxy-2-methyl-phenyl)-3-methyl-1H-pyrazolo[3,4-b]pyridin-4-yl]-methanone | 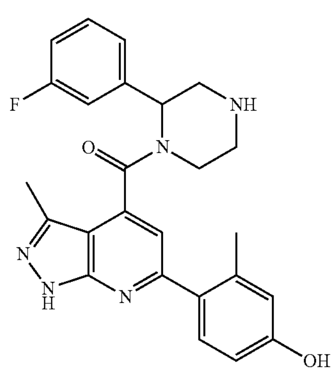 [SMILES: Cc1cc(O)ccc1-c1cc(C(=O)N2CCNCC2c2cccc(F)c2)c2c(C)n[nH]c2n1] | LC5 | 446.38 | 0.76 |

-continued

| Exp. No. | Name | Structure | LC/MS method | m/z [M + H]⁺ | R$_t$ [min] |
|---|---|---|---|---|---|
| 148 | 6-(4-Hydroxy-2-methyl-phenyl)-3-methyl-1H-pyrazolo[3,4-b]pyridine-4-carboxylic acid (1-amino-cycloheptylmethyl)-amide | 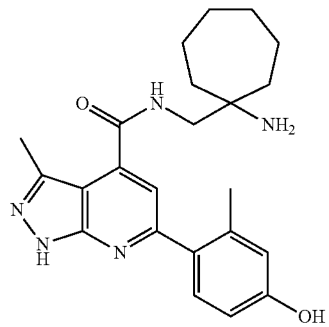 [SMILES: Cc1cc(O)ccc1-c1cc(C(=O)NCC2(N)CCCCCC2)c2c(C)n[nH]c2n1] | LC5 | 408.31 | 0.78 |
| 149 | 6-(4-Hydroxy-2-methyl-phenyl)-3-methyl-1H-pyrazolo[3,4-b]pyridine-4-carboxylic acid (3-ethyl-piperidin-3-yl)-amide | 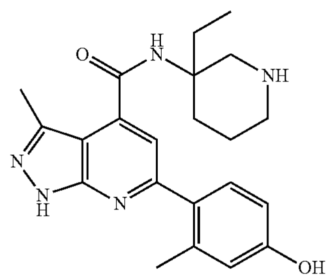 [SMILES: CCC1(NC(=O)c2cc(-c3ccc(O)cc3C)nc3[nH]nc(C)c23)CCCNC1] | LC5 | 394.28 | 0.73 |
| 150 | [6-(4-Hydroxy-2-methyl-phenyl)-3-methyl-1H-pyrazolo[3,4-b]pyridin-4-yl]-((R)-2-phenyl-piperazin-1-yl)-methanone | 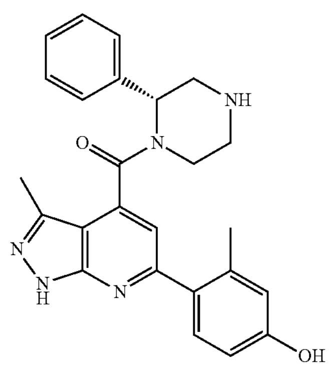 [SMILES: Cc1cc(O)ccc1-c1cc(C(=O)N2CCNC[C@H]2c2ccccc2)c2c(C)n[nH]c2n1] | LC5 | 428.27 | 0.75 |
| 151 | [2-(2-Fluoro-phenyl)-piperazin-1-yl]-[6-(4-hydroxy-2-methyl-phenyl)-3-methyl-1H-pyrazolo[3,4-b]pyridin-4-yl]-methanone | 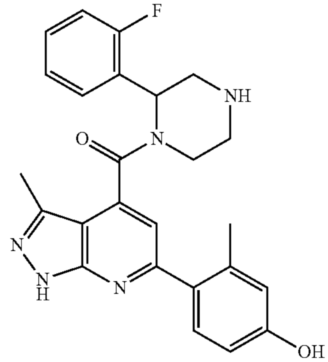 [SMILES: Cc1cc(O)ccc1-c1cc(C(=O)N2CCNCC2c2ccccc2F)c2c(C)n[nH]c2n1] | LC5 | 446.24 | 0.77 |

| Exp. No. | Name | Structure | LC/MS method | m/z [M + H]⁺ | R$_t$ [min] |
|---|---|---|---|---|---|
| 152 | [2-(2,4-Difluoro-phenyl)-piperazin-1-yl]-[6-(4-hydroxy-2-methyl-phenyl)-3-methyl-1H-pyrazolo[3,4-b]pyridin-4-yl]-methanone | 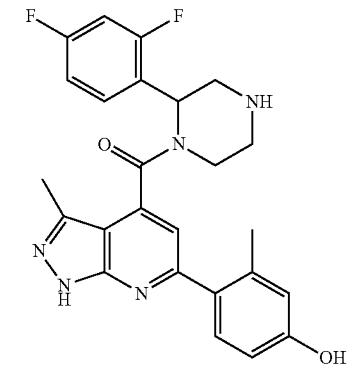 [SMILES: Cc1cc(O)ccc1-c1cc(C(=O)N2CCNCC2c2ccc(F)cc2F)c2c(C)n[nH]c2n1] | LC5 | 464.30 | 0.77 |
| 153 | [2-(2-Chloro-phenyl)-piperazin-1-yl]-[6-(4-hydroxy-2-methyl-phenyl)-3-methyl-1H-pyrazolo[3,4-b]pyridin-4-yl]-methanone | 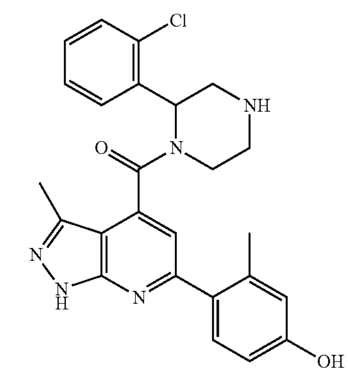 [SMILES: Cc1cc(O)ccc1-c1cc(C(=O)N2CCNCC2c2ccccc2Cl)c2c(C)n[nH]c2n1] | LC5 | 462.25 | 0.77 |
| 154 | [6-(4-Hydroxy-2-methyl-phenyl)-3-methyl-1H-pyrazolo[3,4-b]pyridin-4-yl]-[2-(4-trifluoromethyl-phenyl)-piperazin-1-yl]-methanone | 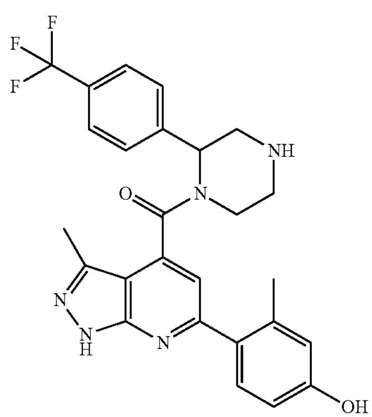 [SMILES: Cc1cc(O)ccc1-c1cc(C(=O)N2CCNCC2c2ccc(C(F)(F)F)cc2)c2c(C)n[nH]c2n1] | LC5 | 496.28 | 0.84 |
| 155 | [6-(4-Hydroxy-2-methyl-phenyl)-3-methyl-1H-pyrazolo[3,4-b]pyridin-4-yl]-(2,2,5,5-tetramethyl-piperazin-1-yl)-methanone | 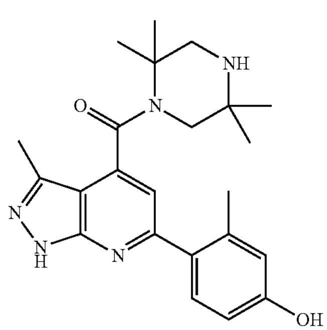 [SMILES: Cc1cc(O)ccc1-c1cc(C(=O)N2CC(C)(C)NCC2(C)C)c2c(C)n[nH]c2n1] | LC1 | 408.27 | 0.84 |

Example 156

(2,2-Dimethyl-piperazin-1-yl)-[6-(4-hydroxy-2,6-dimethyl-phenyl)-3-methyl-1H-pyrazolo[3,4-b]pyridin-4-yl]-methanone

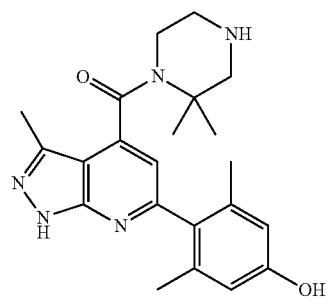 [SMILES: Cc1cc(O)cc(C)c1-c1cc(C(=O)N2CCNCC2(C)C)c2c(C)n[nH]c2n1]

(2,2-Dimethyl-piperazin-1-yl)-[6-(4-hydroxy-2,6-dimethyl-phenyl)-3-methyl-1H-pyrazolo[3,4-b]pyridin-4-yl]-methanone has been prepared following a similar procedure as described for Example 56, (2,2-Dimethyl-piperazin-1-yl)-[6-(2-fluoro-4-hydroxy-phenyl)-3-methyl-1H-pyrazolo[3,4-b]pyridin-4-yl]-methanone, starting from 6-(4-hydroxy-2,6-dimethyl-phenyl)-3-methyl-1-(tetrahydro-pyran-2-yl)-1H-pyrazolo[3,4-b]pyridine-4-carboxylic acid and the respective amine.

LC/MS (Method LC1): $R_t$=0.84 min; m/z=394.26 [M+H]$^+$.

Example 157

[3-Cyclopropyl-6-(4-hydroxy-phenyl)-1H-pyrazolo[3,4-b]pyridin-4-yl]-(2,2-dimethyl-piperazin-1-yl)-methanone

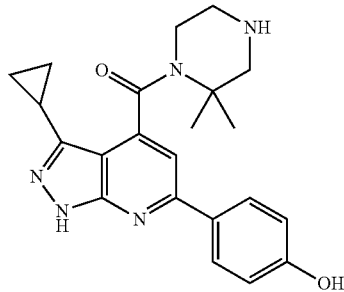 [SMILES: CC1(C)CNCCN1C(=O)c1cc(-c2ccc(O)cc2)nc2[nH]nc(C3CC3)c12]

[3-Cyclopropyl-6-(4-hydroxy-phenyl)-1H-pyrazolo[3,4-b]pyridin-4-yl]-(2,2-dimethyl-piperazin-1-yl)-methanone has been prepared following a similar procedure as described for Example 56, (2,2-Dimethyl-piperazin-1-yl)-[6-(2-fluoro-4-hydroxyphenyl)-3-methyl-1H-pyrazolo[3,4-b]pyridin-4-yl]-methanone, starting from 6-(4-hydroxy-2,6-dimethyl-phenyl)-3-cyclopropyl-1-(tetrahydro-pyran-2-yl)-1H-pyrazolo[3,4-b]pyridine-4-carboxylic acid.

LC/MS (Method LC1): $R_t$=0.86 min; m/z=392.25 [M+H]$^+$.

Example 158

[3-Cyclopropyl-6-(4-hydroxy-phenyl)-1H-pyrazolo[3,4-b]pyridin-4-yl]-((R)-2-phenyl-piperazin-1-yl)-methanone

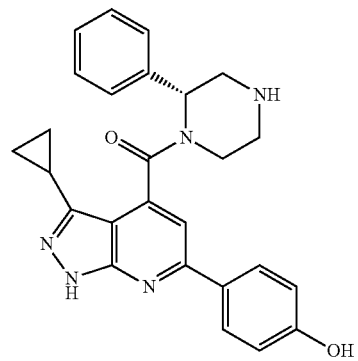 [SMILES: O=C(c1cc(-c2ccc(O)cc2)nc2[nH]nc(C3CC3)c12)N1CCNC[C@H]1c1ccccc1]

[3-Cyclopropyl-6-(4-hydroxy-phenyl)-1H-pyrazolo[3,4-b]pyridin-4-yl]-((R)-2-phenyl-piperazin-1-yl)-methanone has been prepared following a similar procedure as described for Example 56, (2,2-Dimethyl-piperazin-1-yl)-[6-(2-fluoro-4-hydroxyphenyl)-3-methyl-1H-pyrazolo[3,4-b]pyridin-4-yl]-methanone, starting from 6-(4-Hydroxy-2,6-dimethyl-phenyl)-3-cyclopropyl-1-(tetrahydro-pyran-2-yl)-1H-pyrazolo[3,4-b]pyridine-4-carboxylic acid.

LC/MS (Method LC8): $R_t$=2.51 min; m/z=440.34 [M+H]$^+$.

Example 159

3-Ethyl-6-(4-hydroxy-phenyl)-1H-pyrazolo[3,4-b]pyridine-4-carboxylic acid (1-aza-bicyclo[2.2.2]oct-3-yl)-amide

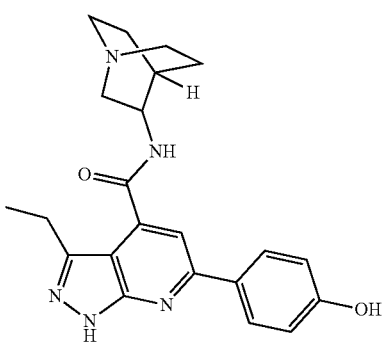 [SMILES: CCc1n[nH]c2nc(-c3ccc(O)cc3)cc(C(=O)NC3CN4CCC3CC4)c12]

To a solution of 1-aza-bicyclo[2.2.2]oct-3-ylamine (17 mg, 0.135 mmol) in 1 mL of DMF, N-methyl morpholine was added (42 mg, 0.42 mmol) followed by 3-ethyl-6-(4-hydroxy-phenyl)-1H-pyrazolo[3,4-b]pyridine-4-carboxylic acid (34 mg, 0.12 mmol) dissolved in 0.5 mL of DMF. Then a solution of TOTU (43 mg, 0.13 mmol) in 0.5 mL DMF was added and the mixture stirred at r.t. over the weekend. The mixture was treated with 0.1 mL TFA, filtered off and purified by prep. HPLC to obtain the desired product 3-ethyl-6-(4-hydroxy-phenyl)-1H-pyrazolo[3,4-b]pyridine-4-carboxylic acid (1-aza-bicyclo[2.2.2]oct-3-yl)-amide as TFA salt. In order to change from TFA salt to HCl salt and deprotection (for compounds bearing BOC-protecting groups) the compound was dissolved in 2 mL of 5-6M HCl iPrOH and the reaction was stirred at r.t. overnight. Then 10 mL of water were added and the mixture was freezed dried to give the desired product 3-ethyl-6-(4-hydroxy-phenyl)-1H-pyrazolo[3,4-b]pyridine-4-carboxylic acid (1-aza-bicyclo[2.2.2]oct-3-yl)-amide as hydrochloride salt (12.7 mg, 23%).

LC/MS (Method LC10): $R_t$=2.07 min; m/z=392.27 [M+H]$^+$.

$^1$H-NMR (500 MHz, d6-DMSO): 1.20 (t, 3H), 1.70-1.80 (m, 1H), 1.91-1.99 (m, 2H), 2.08-2.14 (m, 1H), 2.23 (m, 1H), 2.87 (dd, 2H), 3.12 (dd, 1H), 3.24 (m, 4H), 3.75 (m, 1H), 4.42 (m, 1H), 6.91 (d, 2H), 7.70 (s, 1H), 8.07 (d, 2H), 9.10 (d, 1H), 9.6 (s, 1H), 9.9 (bs, 1H), 13.35 (s, bs, 1H).

The following examples have been prepared following a similar procedure as described for 3-ethyl-6-(4-hydroxy-phenyl)-1H-pyrazolo[3,4-b]pyridine-4-carboxylic acid (1-aza-bicyclo[2.2.2]oct-3-yl)-amide (Example 159), starting from the respective amine precursors and 3-ethyl-6-(4-hydroxy-phenyl)-1H-pyrazolo[3,4-b]pyridine-4-carboxylic acid:

| Exp. No. | Name | Structure | LC/MS method | m/z [M + H]$^+$ | $R_t$ [min] |
|---|---|---|---|---|---|
| 160 | (3-Amino-azetidin-1-yl)-[3-ethyl-6-(4-hydroxy-phenyl)-1H-pyrazolo[3,4-b]pyridin-4-yl]-methanone | 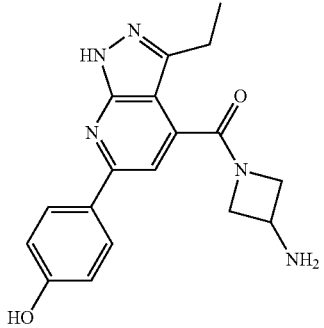 [SMILES: CCc1n[nH]c2nc(-c3ccc(O)cc3)cc(C(=O)N3CC(N)C3)c12] | LC10 | 338.22 | 1.99 |
| 161 | 3-Ethyl-6-(4-hydroxy-phenyl)-1H-pyrazolo[3,4-b]pyridine-4-carboxylic acid ((3S,4S)-4-methoxy-pyrrolidin-3-yl)-amide | 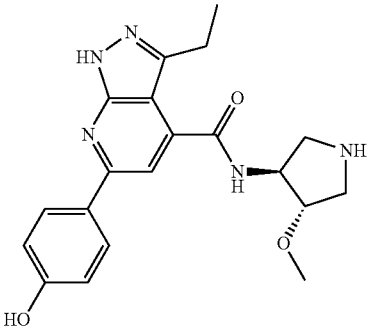 [SMILES: CCc1n[nH]c2nc(-c3ccc(O)cc3)cc(C(=O)N[C@H]3CNC[C@@H]3OC)c12] | LC10 | 382.24 | 2.09 |
| 162 | (S)-3-Ethyl-6-(4-hydroxy-phenyl)-1H-pyrazolo[3,4-b]pyridine-4-carboxylic acid (1-aza-bicyclo-[2.2.2]oct-3-yl)-amide | 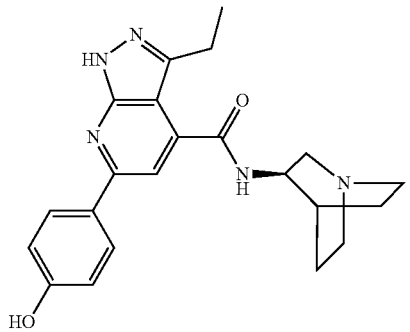 [SMILES: CCc1n[nH]c2nc(-c3ccc(O)cc3)cc(C(=O)N[C@H]3CN4CCC45CCC35)c12] | LC10 | 392.26 | 2.10 |

-continued

| Exp. No. | Name | Structure | LC/MS method | m/z [M + H]+ | R_t [min] |
|---|---|---|---|---|---|
| 163 | 3-Ethyl-6-(4-hydroxy-phenyl)-1H-pyrazolo[3,4-b]pyridine-4-carboxylic acid (8-methyl-8-aza-bicyclo[3.2.1]oct-3-yl)-amide | 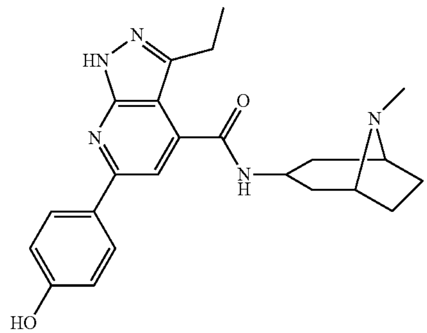 [SMILES: CCc1n[nH]c2nc(-c3ccc(O)cc3)cc(C(=O)NC3CCC4CCC(C3)N4C)c12] | LC10 | 406.27 | 2.04 |
| 164 | 3-Ethyl-6-(4-hydroxy-phenyl)-1H-pyrazolo[3,4-b]pyridine-4-carboxylic acid ((3R)-8-methyl-8-aza-bicyclo-[3.2.1]oct-3-yl)-amide | 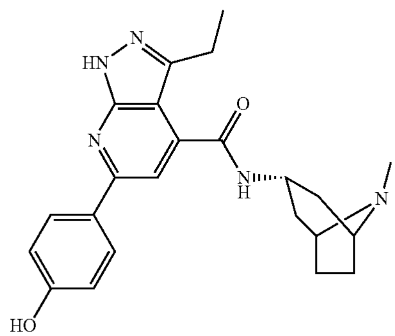 [SMILES: CCc1n[nH]c2nc(-c3ccc(O)cc3)cc(C(=O)N[C@H]3CC4CCC(C3)N(C)C4)c12] | LC10 | 406.28 | 2.04 |
| 165 | [3-Ethyl-6-(4-hydroxy-phenyl)-1H-pyrazolo[3,4-b]pyridin-4-yl]-(3-methyl-piperazin-1-yl)-methanone | 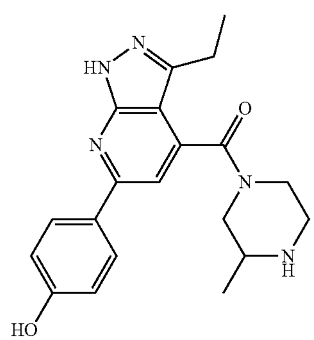 [SMILES: CCc1n[nH]c2nc(-c3ccc(O)cc3)cc(C(=O)N3CCNC(C)C3)c12] | LC10 | 366.25 | 2.07 |
| 166 | (4-Amino-piperidin-1-yl)-[3-ethyl-6-(4-hydroxy-phenyl)-1H-pyrazolo[3,4-b]pyridin-4-yl]-methanone | 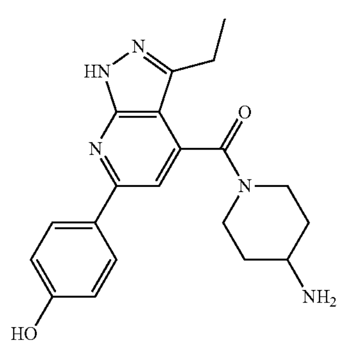 [SMILES: CCc1n[nH]c2nc(-c3ccc(O)cc3)cc(C(=O)N3CCC(N)CC3)c12] | LC10 | 366.26 | 1.97 |

-continued

| Exp. No. | Name | Structure | LC/MS method | m/z [M + H]+ | R_t [min] |
|---|---|---|---|---|---|
| 167 | [3-Ethyl-6-(4-hydroxy-phenyl)-1H-pyrazolo[3,4-b]pyridin-4-yl]-(hexahydro-pyrrolo[3,4-b]pyrrol-1-yl)-methanone | 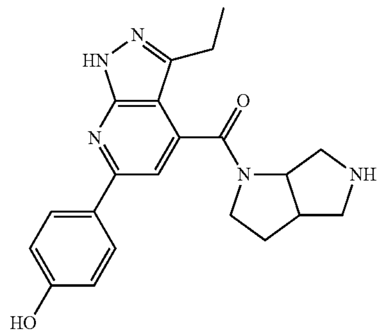 [SMILES: CCc1n[nH]c2nc(-c3ccc(O)cc3)cc(C(=O)N3CCC4CNCC43)c12] | LC10 | 378.25 | 2.07 |
| 168 | 3-Ethyl-6-(4-hydroxy-phenyl)-1H-pyrazolo[3,4-b]pyridine-4-carboxylic acid (5-aza-spiro[3.5]non-8-yl)-amide | 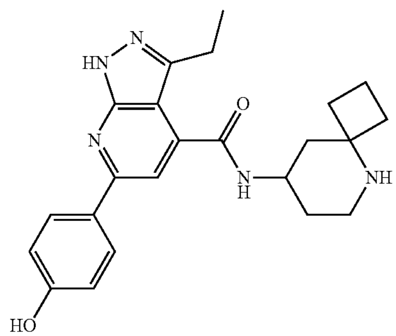 [SMILES: CCc1n[nH]c2nc(-c3ccc(O)cc3)cc(C(=O)NC3CCNC4(CCC4)C3)c12] | LC10 | 406.28 | 2.18 |
| 169 | (2,7-Diaza-spiro[3.5]non-2-yl)-[3-ethyl-6-(4-hydroxy-phenyl)-1H-pyrazolo[3,4-b]pyridin-4-yl]-methanone | 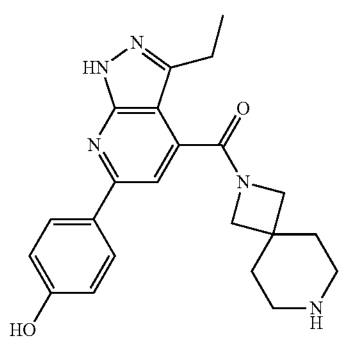 [SMILES: CCc1n[nH]c2nc(-c3ccc(O)cc3)cc(C(=O)N3CC4(CCNCC4)C3)c12] | LC10 | 392.28 | 2.00 |
| 170 | 3-Ethyl-6-(4-hydroxy-phenyl)-1H-pyrazolo[3,4-b]pyridine-4-carboxylic acid (3-amino-cyclohexyl)-amide | 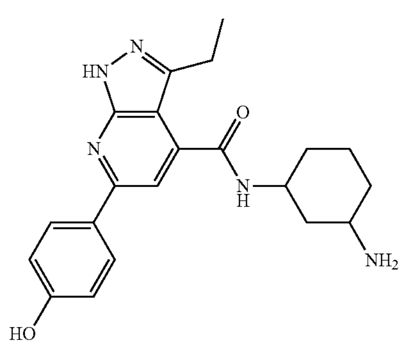 [SMILES: CCc1n[nH]c2nc(-c3ccc(O)cc3)cc(C(=O)NC3CCCC(N)C3)c12] | LC10 | 380.27 | 2.09 |

-continued

| Exp. No. | Name | Structure | LC/MS method | m/z [M + H]⁺ | R_t [min] |
|---|---|---|---|---|---|
| 171 | (2,7-Diaza-spiro[3.5]non-7-yl)-[3-ethyl-6-(4-hydroxy-phenyl)-1H-pyrazolo[3,4-b]pyridin-4-yl]-methanone | 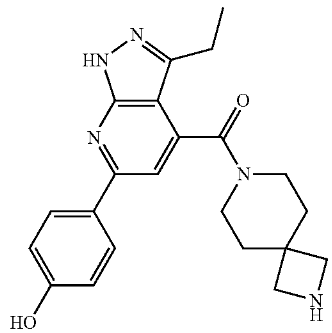 [SMILES: CCc1n[nH]c2nc(-c3ccc(O)cc3)cc(C(=O)N3CCC4(CC3)CNC4)c12] | LC10 | 392.27 | 2.02 |
| 172 | (2,7-Diaza-spiro[4.4]non-2-yl)-[3-ethyl-6-(4-hydroxy-phenyl)-1H-pyrazolo[3,4-b]pyridin-4-yl]-methanone | 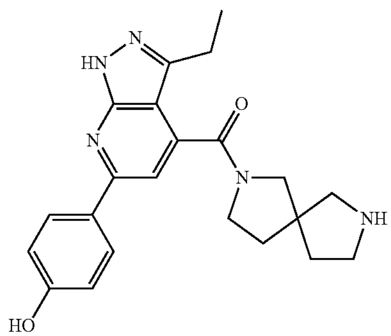 [SMILES: CCc1n[nH]c2nc(-c3ccc(O)cc3)cc(C(=O)N3CCC4(CCNC4)C3)c12] | LC10 | 392.27 | 1.99 |
| 173 | (2,7-Diaza-spiro[4.5]dec-2-yl)-[3-ethyl-6-(4-hydroxy-phenyl)-1H-pyrazolo[3,4-b]pyridin-4-yl]-methanone | 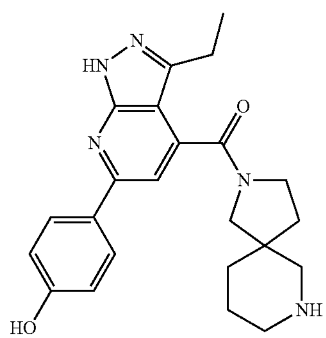 [SMILES: CCc1n[nH]c2nc(-c3ccc(O)cc3)cc(C(=O)N3CCC4(CCCNC4)C3)c12] | LC10 | 406.28 | 2.04 |
| 174 | 3-Ethyl-6-(4-hydroxy-phenyl)-1H-pyrazolo[3,4-b]pyridine-4-carboxylic acid methyl-(1-methyl-piperidin-4-yl)-amide | 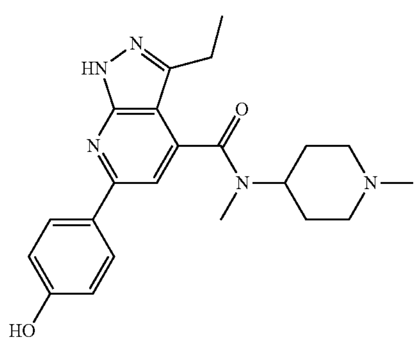 [SMILES: CCc1n[nH]c2nc(-c3ccc(O)cc3)cc(C(=O)N(C)C3CCN(C)CC3)c12] | LC10 | 394.27 | 2.04 |

-continued

| Exp. No. | Name | Structure | LC/MS method | m/z [M + H]+ | R_t [min] |
|---|---|---|---|---|---|
| 175 | 3-Ethyl-6-(4-hydroxy-phenyl)-1H-pyrazolo[3,4-b]pyridine-4-carboxylic acid (1-ethyl-piperidin-3-yl)-amide | 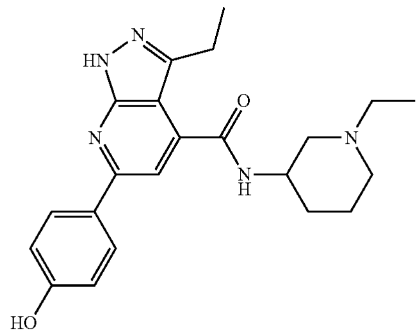 [SMILES: CCc1n[nH]c2nc(-c3ccc(O)cc3)cc(C(=O)NC3CCCN(CC)C3)c12] | LC10 | 394.27 | 2.05 |
| 176 | ((R)-3-Dimethylamino-pyrrolidin-1-yl)-[3-ethyl-6-(4-hydroxy-phenyl)-1H-pyrazolo[3,4-b]pyridin-4-yl]-methanone | 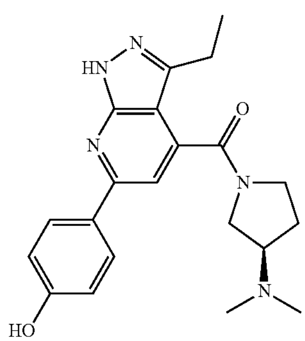 [SMILES: CCc1n[nH]c2nc(-c3ccc(O)cc3)cc(C(=O)N3CC[C@@H](N(C)C)C3)c12] | LC10 | 380.27 | 1.97 |
| 177 | ((S)-3-Dimethylamino-pyrrolidin-1-yl)-[3-ethyl-6-(4-hydroxy-phenyl)-1H-pyrazolo[3,4-b]pyridin-4-yl]-methanone | 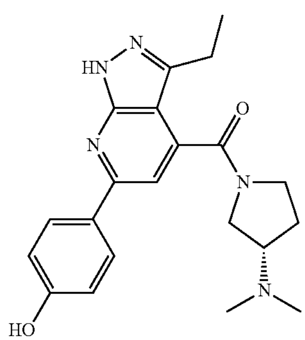 [SMILES: CCc1n[nH]c2nc(-c3ccc(O)cc3)cc(C(=O)N3CC[C@H](N(C)C)C3)c12] | LC10 | 380.27 | 1.99 |
| 178 | [3-Ethyl-6-(4-hydroxy-phenyl)-1H-pyrazolo[3,4-b]pyridin-4-yl]-(3-methylamino-pyrrolidin-1-yl)-methanone | 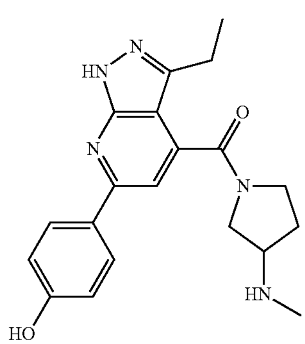 [SMILES: CCc1n[nH]c2nc(-c3ccc(O)cc3)cc(C(=O)N3CCC(NC)C3)c12] | LC10 | 366.25 | 1.99 |

-continued

| Exp. No. | Name | Structure | LC/MS method | m/z [M + H]⁺ | R_t [min] |
|---|---|---|---|---|---|
| 179 | [3-Ethyl-6-(4-hydroxy-phenyl)-1H-pyrazolo[3,4-b]pyridin-4-yl]-((1S,5R)-9-hydroxy-1,5,7-trimethyl-3,7-diaza-bicyclo[3.3.1]non-3-yl)-methanone | 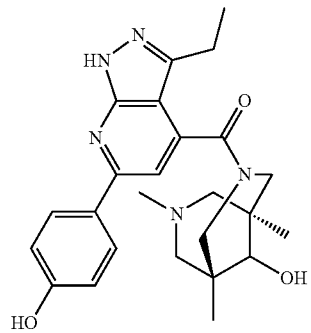 [SMILES: CCc1n[nH]c2nc(-c3ccc(O)cc3)cc(C(=O)N3C[C@]4(C)CN(C)C[C@](C)(C3)C4O)c12] | LC10 | 450.31 | 2.07 |
| 180 | 3-Ethyl-6-(4-hydroxy-phenyl)-1H-pyrazolo[3,4-b]pyridine-4-carboxylic acid (1-methyl-piperidin-3-yl)-amide | 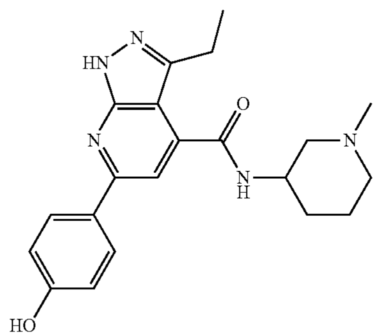 [SMILES: CCc1n[nH]c2nc(-c3ccc(O)cc3)cc(C(=O)NC3CCCN(C)C3)c12] | LC10 | 380.27 | 2.07 |
| 181 | 3-Ethyl-6-(4-hydroxy-phenyl)-1H-pyrazolo[3,4-b]pyridine-4-carboxylic acid (2,3-dihydro-spiro[1H-indene-1,4'-piperidin]-3-yl)-amide | 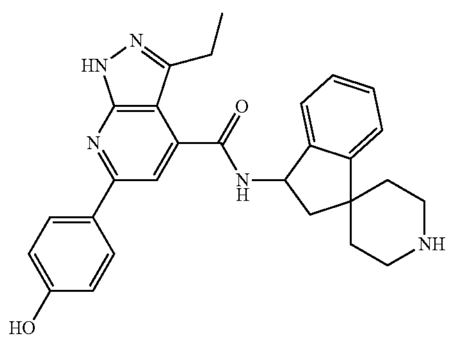 [SMILES: CCc1n[nH]c2nc(-c3ccc(O)cc3)cc(C(=O)NC3CC4(CCNCC4)c4ccccc43)c12] | LC10 | 468.31 | 2.43 |
| 182 | 3-Ethyl-6-(4-hydroxy-phenyl)-1H-pyrazolo[3,4-b]pyridine-4-carboxylic acid (1-methyl-piperidin-4-yl)-amide | 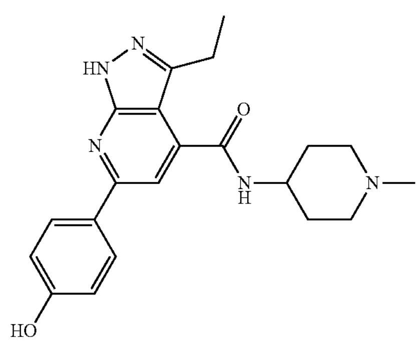 [SMILES: CCc1n[nH]c2nc(-c3ccc(O)cc3)cc(C(=O)NC3CCN(C)CC3)c12] | LC10 | 380.26 | 2.05 |

-continued

| Exp. No. | Name | Structure | LC/MS method | m/z [M + H]⁺ | R_t [min] |
|---|---|---|---|---|---|
| 183 | 3-Ethyl-6-(4-hydroxy-phenyl)-1H-pyrazolo[3,4-b]pyridine-4-carboxylic acid azetidin-3-ylamide | 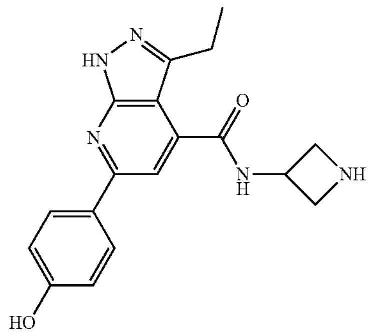 [SMILES: CCc1n[nH]c2nc(-c3ccc(O)cc3)cc(C(=O)NC3CNC3)c12] | LC10 | 338.22 | 1.97 |
| 184 | 3-Ethyl-6-(4-hydroxy-phenyl)-1H-pyrazolo[3,4-b]pyridine-4-carboxylic acid (9-methyl-9-aza-bicyclo[3.3.1]non-3-yl)-amide | 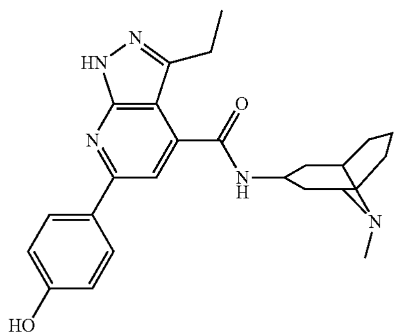 [SMILES: CCc1n[nH]c2nc(-c3ccc(O)cc3)cc(C(=O)NC3CC4CCCC45C(C3)N5C)c12] | LC10 | 420.30 | 2.14 |
| 185 | 3-Ethyl-6-(4-hydroxy-phenyl)-1H-pyrazolo[3,4-b]pyridine-4-carboxylic acid ((R)-6-oxo-piperidin-3-yl)-amide | 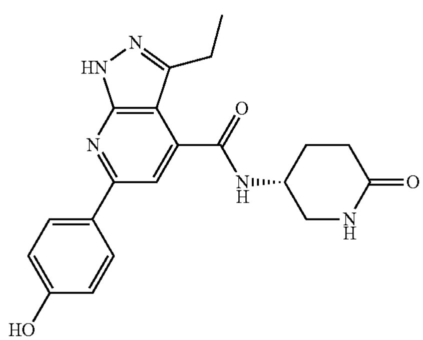 [SMILES: CCc1n[nH]c2nc(-c3ccc(O)cc3)cc(C(=O)N[C@@H]3CCC(=O)NC3)c12] | LC10 | 380.24 | 2.15 |
| 186 | 3-Ethyl-6-(4-hydroxy-phenyl)-1H-pyrazolo[3,4-b]pyridine-4-carboxylic acid (5-oxo-pyrrolidin-2-ylmethyl)-amide | 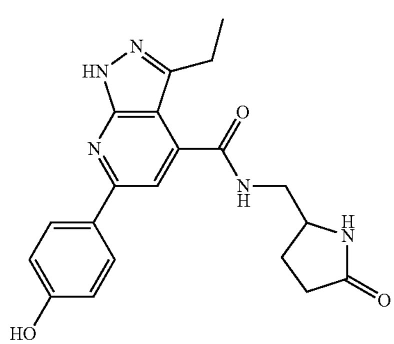 [SMILES: CCc1n[nH]c2nc(-c3ccc(O)cc3)cc(C(=O)NCC3CCC(=O)N3)c12] | LC10 | 380.23 | 2.25 |

-continued

| Exp. No. | Name | Structure | LC/MS method | m/z [M + H]⁺ | R$_t$ [min] |
|---|---|---|---|---|---|
| 187 | (4-Ethyl-[1,4]diazepan-1-yl)-[3-ethyl-6-(4-hydroxy-phenyl)-1H-pyrazolo[3,4-b]pyridin-4-yl]-methanone | 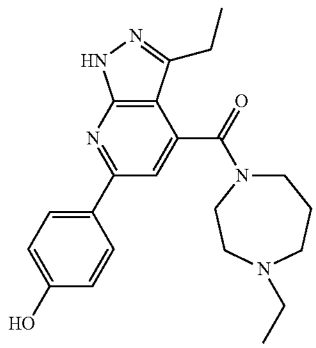 [SMILES: CCc1n[nH]c2nc(-c3ccc(O)cc3)cc(C(=O)N3CCCN(CC)CC3)c12] | LC10 | 394.28 | 2.00 |

The following examples have been prepared following a similar procedure as described for 3-ethyl-6-(4-hydroxy-phenyl)-1H-pyrazolo[3,4-b]pyridine-4-carboxylic acid (1-aza-bicyclo[2.2.2]oct-3-yl)-amide (Example 159), starting from the respective amine precursors and 6-(4-hydroxy-phenyl)-3-methyl-1H-pyrazolo[3,4-b]pyridine-4-carboxylic acid:

| Exp. No. | Name | Structure | LC/MS method | m/z [M + H]⁺ | R$_t$ [min] |
|---|---|---|---|---|---|
| 188 | [6-(4-Hydroxy-phenyl)-3-methyl-1H-pyrazolo[3,4-b]pyridin-4-yl]-((S)-2-methyl-piperazin-1-yl)-methanone | 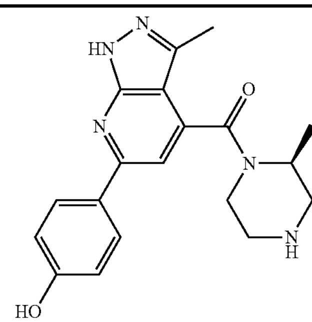 | LC11 | 352.18 | 1.88 |
| 189 | [6-(4-Hydroxy-phenyl)-3-methyl-1H-pyrazolo[3,4-b]pyridin-4-yl]-((R)-3-methyl-piperazin-1-yl)-methanone | 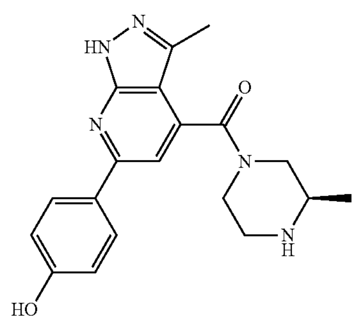 [SMILES: Cc1n[nH]c2nc(-c3ccc(O)cc3)cc(C(=O)N3CCN[C@H](C)C3)c12] | LC11 | 352.17 | 1.92 |
| 190 | [6-(4-Hydroxy-phenyl)-3-methyl-1H-pyrazolo[3,4-b]pyridin-4-yl]-((S)-3-methyl-piperazin-1-yl)-methanone | 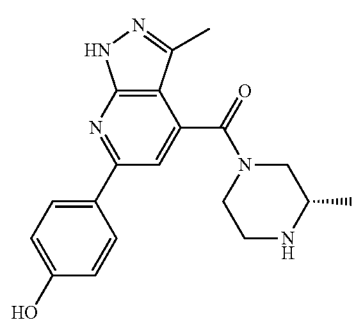 [SMILES: Cc1n[nH]c2nc(-c3ccc(O)cc3)cc(C(=O)N3CCN[C@@H](C)C3)c12] | LC11 | 352.18 | 1.90 |

| Exp. No. | Name | Structure | LC/MS method | m/z [M + H]+ | R_t [min] |
|---|---|---|---|---|---|
| 191 | 6-(4-Hydroxy-phenyl)-3-methyl-1H-pyrazolo[3,4-b]pyridine-4-carboxylic acid (6-amino-spiro[3.3]hept-2-yl)-amide | 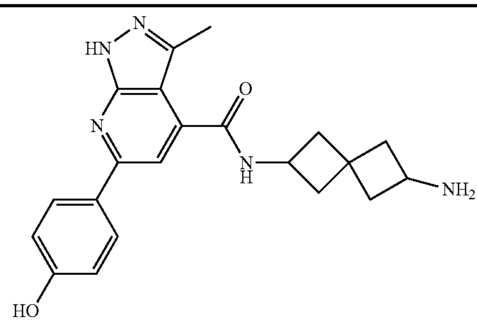 | LC11 | 378.2 | 1.93 |
| 192 | (Hexahydro-pyrrolo[3,4-c]pyrrol-2-yl)-[6-(4-hydroxy-phenyl)-3-methyl-1H-pyrazolo[3,4-b]pyridin-4-yl]-methanone | 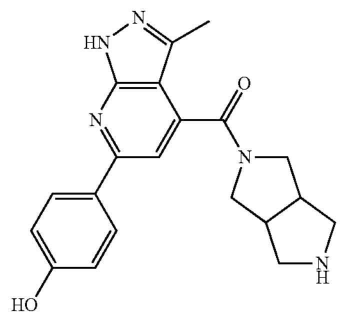 [SMILES: Cc1n[nH]c2nc(-c3ccc(O)cc3)cc(C(=O)N3CC4CNCC4C3)c12] | LC11 | 364.18 | 1.85 |
| 193 | 6-(4-Hydroxy-phenyl)-3-methyl-1H-pyrazolo[3,4-b]pyridine-4-carboxylic acid (2-aza-bicyclo-[2.2.1]hept-5-yl)-amide | 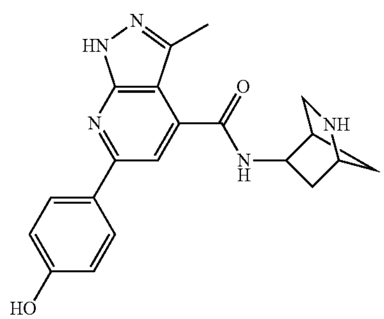 [SMILES: Cc1n[nH]c2nc(-c3ccc(O)cc3)cc(C(=O)NC3CC4CC3CN4)c12] | LC11 | 364.18 | 1.88 |
| 194 | (2,3-Dimethyl-piperazn-1-yl)-[6-(4-hydroxy-phenyl)-3-methyl-1H-pyrazolo[3,4-b]pyridin-4-yl]-methanone | 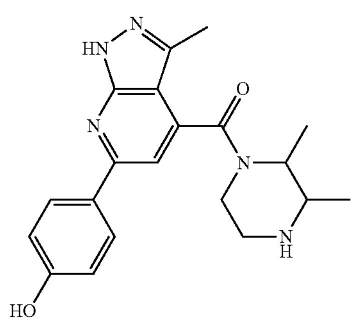 [SMILES: Cc1n[nH]c2nc(-c3ccc(O)cc3)cc(C(=O)N3CCNC(C)C3C)c12] | LC11 | 366.19 | 1.95 |
| 195 | [6-(4-Hydroxy-phenyl)-3-methyl-1H-pyrazolo[3,4-b]pyridin-4-yl]-((R)-3-propyl-piperazin-1-yl)-methanone | 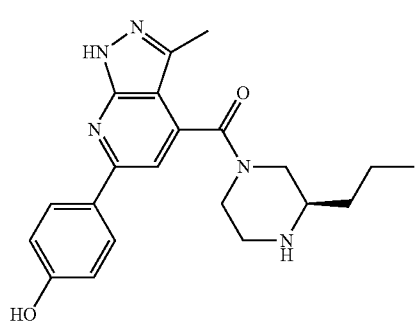 [SMILES: CCC[C@@H]1CN(C(=O)c2cc(-c3ccc(O)cc3)nc3[nH]nc(C)c23)CCN1] | LC11 | 380.20 | 2.08 |

-continued

| Exp. No. | Name | Structure | LC/MS method | m/z [M + H]+ | R_t [min] |
|---|---|---|---|---|---|
| 196 | [6-(4-Hydroxy-phenyl)-3-methyl-1H-pyrazolo[3,4-b]pyridin-4-yl]-(3-trifluoromethyl-piperazin-1-yl)-methanone | 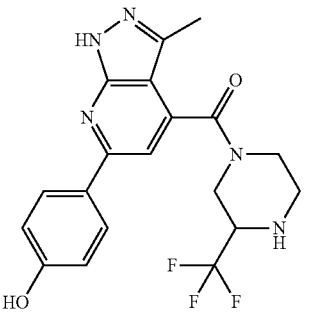 [SMILES: Cc1n[nH]c2nc(-c3ccc(O)cc3)cc(C(=O)N3CCNC(C(F)(F)F)C3)c12] | LC11 | 406.14 | 2.15 |
| 197 | {1-[6-(4-Hydroxy-phenyl)-3-methyl-1H-pyrazolo[3,4-b]pyridine-4-carbonyl]-piperazin-2-yl}-acetic acid methyl ester | 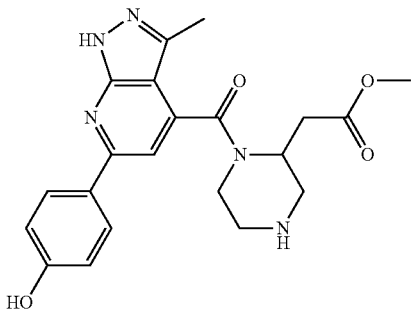 [SMILES: COC(=O)CC1CNCCN1C(=O)c1cc(-c2ccc(O)cc2)nc2[nH]nc(C)c12] | LC11 | 410.18 | 1.97 |
| 198 | (3,3-Dimethyl-piperazin-1-yl)-[6-(4-hydroxy-phenyl)-3-methyl-1H-pyrazolo[3,4-b]pyridin-4-yl]-methanone | 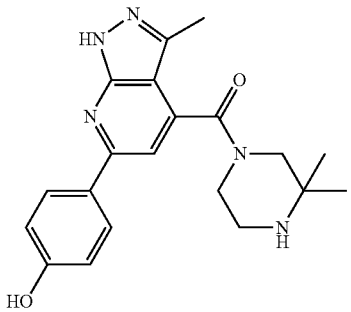 [SMILES: Cc1n[nH]c2nc(-c3ccc(O)cc3)cc(C(=O)N3CCNC(C)(C)C3)c12] | LC10 | 366.27 | 2.00 |
| 199 | (2,2-Dimethyl-piperazin-1-yl)-[6-(4-hydroxy-phenyl)-3-methyl-1H-pyrazolo[3,4-b]pyridin-4-yl]-methanone | 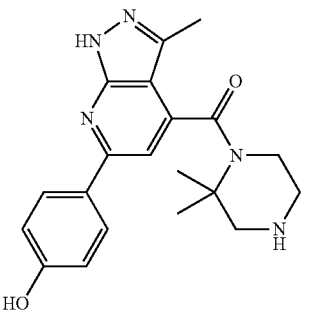 [SMILES: Cc1n[nH]c2nc(-c3ccc(O)cc3)cc(C(=O)N3CCNCC3(C)C)c12] | LC10 | 366.27 | 2.09 |
| 200 | (S)-[6-(4-Hydroxy-phenyl)-3-methyl-1H-pyrazolo[3,4-b]pyridine-4-carboxylic acid (1-aza-bicyclo-[2.2.2]oct-3-yl)-amide | 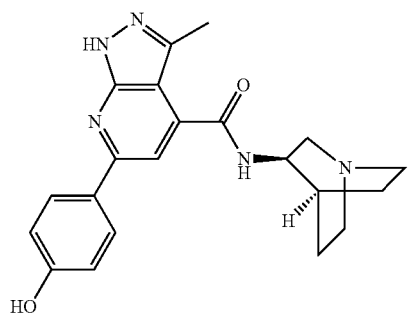 [SMILES: Cc1n[nH]c2nc(-c3ccc(O)cc3)cc(C(=O)N[C@H]3CN4CCC45CC[C@@H]35)c12] | LC12 | 378.28 | 2.18 |

-continued

| Exp. No. | Name | Structure | LC/MS method | m/z [M + H]⁺ | R_t [min] |
|---|---|---|---|---|---|
| 201 | 6-(4-Hydroxy-phenyl)-3-methyl-1H-pyrazolo[3,4-b]pyridine-4-carboxylic acid (3R)-8-methyl-8-aza-bicyclo[3.2.1]oct-3-yl)-amide | 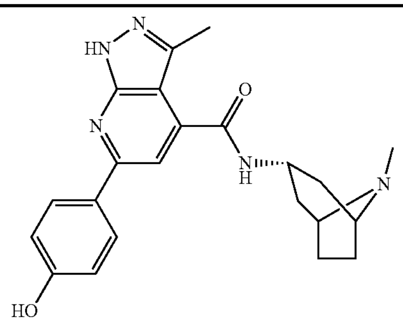 | LC10 | 392.29 | 2.00 |
| 202 | [6-(4-Hydroxy-phenyl)-3-methyl-1H-pyrazolo[3,4-b]pyridin-4-yl]-((S)-2-isopropyl-piperazin-1-yl)-methanone | 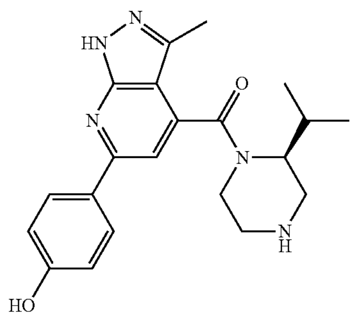 [SMILES: Cc1n[nH]c2nc(-c3ccc(O)cc3)cc(C(=O)N3CCNC[C@@H]3C(C)C)c12] | LC10 | 380.28 | 2.14 |
| 203 | [(R)-3-(1-Amino-cyclopropyl)-pyrrolidin-1-yl]-6-(4-hydroxy-phenyl)-3-methyl-1H-pyrazolo[3,4-b]pyridin-4-yl]-methanone | 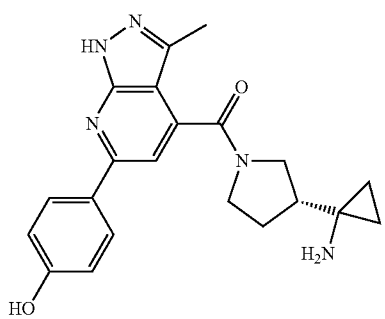 [SMILES: Cc1n[nH]c2nc(-c3ccc(O)cc3)cc(C(=O)N3CC[C@@H](C4(N)CC4)C3)c12] | LC10 | 378.27 | 2.02 |
| 204 | 6-(4-Hydroxy-phenyl)-3-methyl-1H-pyrazo[3,4-b]pyridine-4-carboxylic acid (5-aza-spiro[3.5]non-8-yl)-amide | 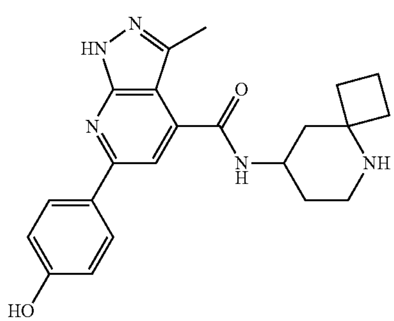 [SMILES: Cc1n[nH]c2nc(-c3ccc(O)cc3)cc(C(=O)NC3CCNC4(CCC4)C3)c12] | LC11 | 392.2 | 1.99 |
| 205 | 6-(4-Hydroxy-phenyl)-3-methyl-1H-pyrazolo[3,4-b]pyridine-4-carboxylic acid [(R)-3-azabicyclo[3.1.0]hexan-1-yl]-amide | 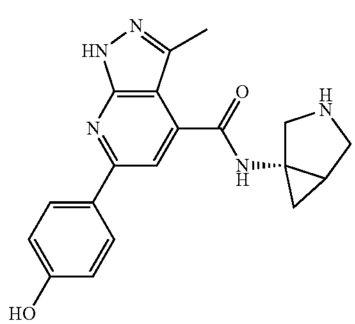 [SMILES: Cc1n[nH]c2nc(-c3ccc(O)cc3)cc(C(=O)N[C@]34CNCC3C4)c12] | LC10 | 350.23 | 1.95 |

| Exp. No. | Name | Structure | LC/MS method | m/z [M + H]+ | R$_t$ [min] |
|---|---|---|---|---|---|
| 206 | (R)-1-[6-(4-Hydroxy-phenyl)-3-methyl-1H-pyrazolo[3,4-b]pyridine-4-carbonyl]-piperazine-2-carboxylic acid methyl ester | 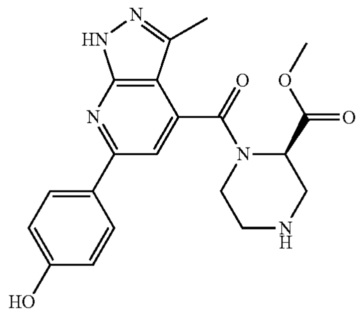 [SMILES: COC(=O)[C@H]1CNCCN1C(=O)c1cc(-c2ccc(O)cc2)nc2[nH]nc(C)c12] | LC10 | 396.24 | 2.04 |
| 207 | 6-(4-Hydroxy-phenyl)-3-methyl-1H-pyrazolo[3,4-b]pyridine-4-carboxylic acid (1-aza-bicyclo[2.2.2]oct-3-yl)-amide | 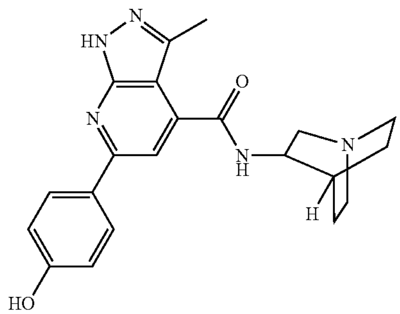 [SMILES: Cc1n[nH]c2nc(-c3ccc(O)cc3)cc(C(=O)NC3CN4CCC45CCC35)c12] | LC10 | 378.26 | 2.04 |
| 208 | 6-(4-Hydroxy-phenyl)-3-methyl-1H-pyrazolo[3,4-b]pyridine-4-carboxylic acid ((R)-6-oxo-piperidin-3-yl)-amide | 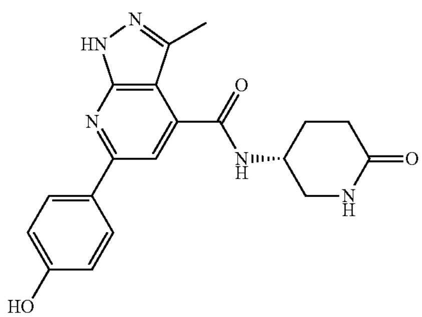 [SMILES: Cc1n[nH]c2nc(-c3ccc(O)cc3)cc(C(=O)N[C@@H]3CCC(=O)NC3)c12] | LC10 | 366.23 | 2.09 |
| 209 | ((S)-3-Butyl-piperazin-1-yl)-[6-(4-hydroxy-phenyl)-3-methyl-1H-pyrazolo[3,4-b]pyridin-4-yl]-methanone | 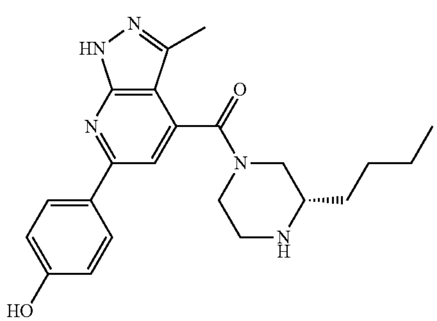 [SMILES: CCCC[C@H]1CN(C(=O)c2cc(-c3ccc(O)cc3)nc3[nH]nc(C)c23)CCN1] | LC10 | 394.27 | 2.22 |
| 210 | ((S)-3-Ethyl-piperazin-1-yl)-[6-(4-hydroxy-phenyl)-3-methyl-1H-pyrazolo[3,4-b]pyridin-4-yl]-methanone | 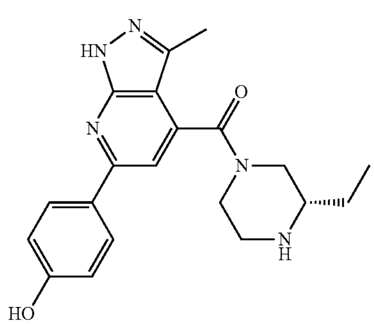 [SMILES: CC[C@H]1CN(C(=O)c2cc(-c3ccc(O)cc3)nc3[nH]nc(C)c23)CCN1] | LC11 | 366.19 | 1.90 |

| Exp. No. | Name | Structure | LC/MS method | m/z [M + H]+ | R_t [min] |
|---|---|---|---|---|---|
| 211 | (R)-4-[6-(4-Hydroxy-phenyl)-3-methyl-1H-pyrazolo[3,4-b]pyridine-4-carbonyl]-piperazine-2-carboxylic acid methyl ester | 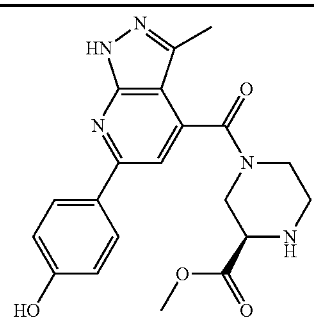 | LC11 | 396.17 | 1.96 |
| 212 | [6-(4-Hydroxy-phenyl)-3-methyl-1H-pyrazolo[3,4-b]pyridin-4-yl]-((R)-3-methoxymethyl-piperazin-1-yl)-methanone | 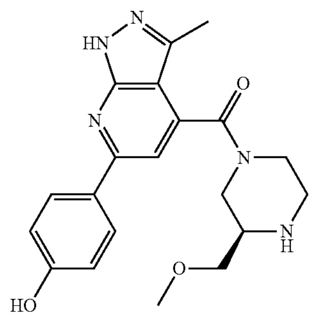 [SMILES: COC[C@H]1CN(C(=O)c2cc(-c3ccc(O)cc3)nc3[nH]nc(C)c23)CCN1] | LC11 | 382.19 | 1.95 |
| 213 | 6-(4-Hydroxy-phenyl)-3-methyl-1H-pyrazolo[3,4-b]pyridine-4-carboxylic acid ((3S,4S)-4-methoxy-pyrrolidin-3-yl)-amide | 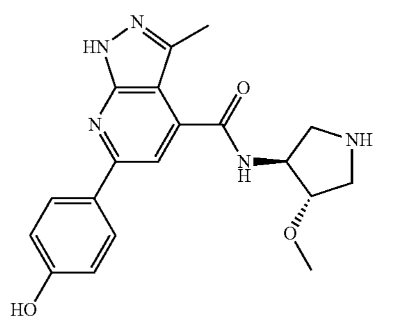 [SMILES: CO[C@H]1CNC[C@@H]1NC(=O)c1cc(-c2ccc(O)cc2)nc2[nH]nc(C)c12] | LC11 | 368.16 | 1.91 |
| 214 | 6-(4-Hydroxy-phenyl)-3-methyl-1H-pyrazolo[3,4-b]pyridine-4-carboxylic acid (3-azabicyclo[3.1.0]hex-6-yl)-amide | 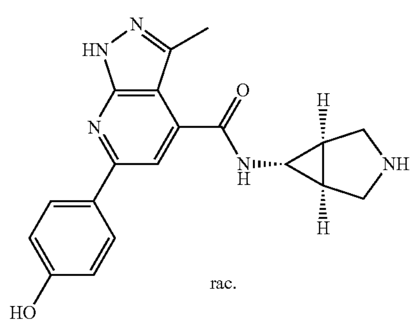 [SMILES: Cc1n[nH]c2nc(-c3ccc(O)cc3)cc(C(=O)N[C@H]3[C@@H]4CNC[C@@H]43)c12] | LC11 | 350.18 | 1.85 |
| 215 | [6-(4-Hydroxy-phenyl)-3-methyl-1H-pyrazolo[3,4-b]pyridin-4-yl]-((S)-3-isobutyl-piperazin-1-yl)-methanone | 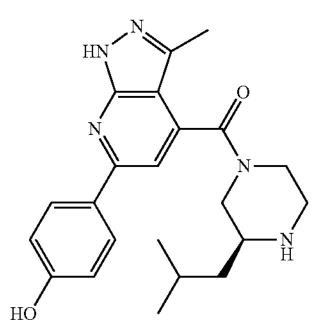 [SMILES: Cc1n[nH]c2nc(-c3ccc(O)cc3)cc(C(=O)N3CCN[C@@H](CC(C)C)C3)c12] | LC11 | 394.22 | 2.14 |

| Exp. No. | Name | Structure | LC/MS method | m/z [M + H]+ | R_t [min] |
|---|---|---|---|---|---|
| 216 | 6-(4-Hydroxy-phenyl)-3-methyl-1H-pyrazolo[3,4-b]pyridine-4-carboxylic acid (pyrrolidin-3-ylmethyl)-amide | 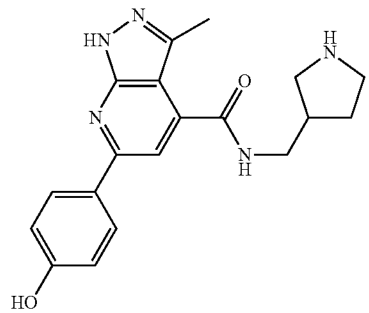 [SMILES: Cc1n[nH]c2nc(-c3ccc(O)cc3)cc(C(=O)NCC3CCNC3)c12] | LC11 | 352.18 | 1.85 |
| 217 | (2-Benzyl-piperazin-1-yl)-[6-(4-hydroxy-phenyl)-3-methyl-1H-pyrazolo[3,4-b]pyridin-4-yl]-methanone | 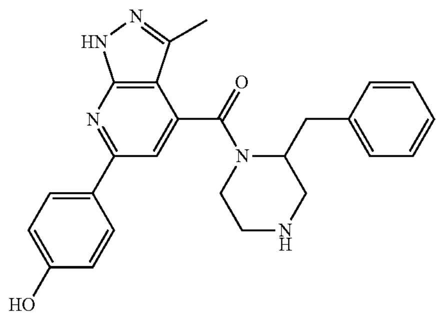 [SMILES: Cc1n[nH]c2nc(-c3ccc(O)cc3)cc(C(=O)N3CCNCC3Cc3ccccc3)c12] | LC11 | 428.2 | 2.19 |
| 218 | 6-(4-Hydroxy-phenyl)-3-methyl-1H-pyrazolo[3,4-b]pyridine-4-carboxylic acid [2-(1-methyl-pyrrolidin-2-yl)-ethyl]-amide | 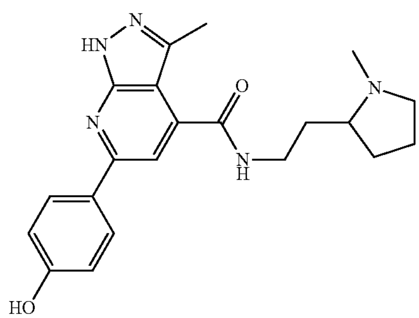 [SMILES: Cc1n[nH]c2nc(-c3ccc(O)cc3)cc(C(=O)NCCC3CCCN3C)c12] | LC11 | 380.19 | 1.88 |
| 219 | 6-(4-Hydroxy-phenyl)-3-methy-1H-pyrazolo[3,4-b]pyridine-4-carboxylic acid (8-methyl-8-aza-bicyclo[3.2.1]oct-3-yl)-amide | 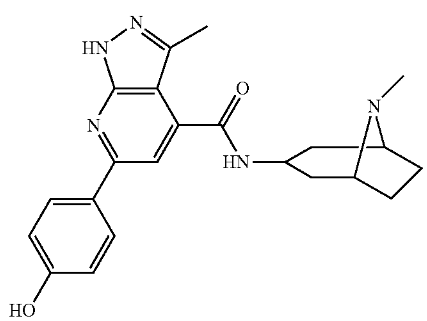 [SMILES: Cc1n[nH]c2nc(-c3ccc(O)cc3)cc(C(=O)NC3CCC4CCC(C3)N4C)c12] | LC11 | 392.2 | 1.92 |
| 220 | 6-(4-Hydroxy-phenyl)-3-methyl-1H-pyrazolo[3,4-b]pyridine-4-carboxylic acid (1-methyl-piperidin-4-yl)-amide | 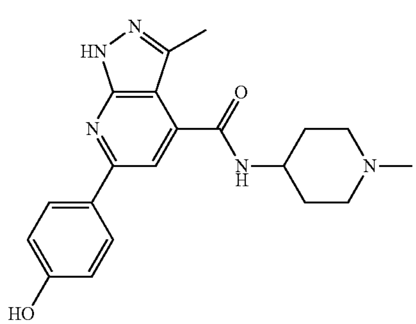 [SMILES: Cc1n[nH]c2nc(-c3ccc(O)cc3)cc(C(=O)NC3CCN(C)CC3)c12] | LC11 | 366.19 | 1.84 |

| Exp. No. | Name | Structure | LC/MS method | m/z [M + H]+ | R_t [min] |
|---|---|---|---|---|---|
| 221 | [6-(4-Hydroxy-phenyl)-3-methyl-1H-pyrazolo[3,4-b]pyridin-4-yl]-(3-methyl-piperazin-1-yl)-methanone | 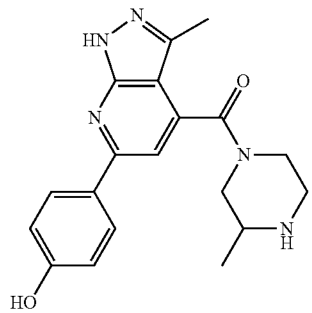 [SMILES: Cc1n[nH]c2nc(-c3ccc(O)cc3)cc(C(=O)N3CCNC(C)C3)c12] | LC11 | 352.18 | 1.91 |
| 222 | 6-(4-Hydroxy-phenyl)-3-methyl-1H-pyrazolo[3,4-b]pyridine-4-carboxylic acid (R)-piperidin-3-ylamide | 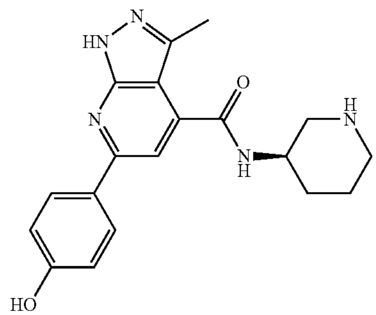 [SMILES: Cc1n[nH]c2nc(-c3ccc(O)cc3)cc(C(=O)N[C@@H]3CCCNC3)c12] | LC11 | 352.18 | 1.89 |
| 223 | 6-(4-Hydroxy-phenyl)-3-methyl-1H-pyrazolo[3,4-b]pyridine-4-carboxylic acid (9-methyl-9-aza-bicyclo[3.3.1]non-3-yl)-amide | 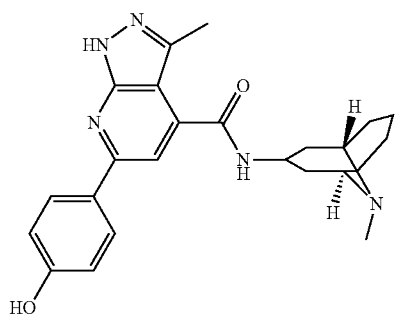 [SMILES: Cc1n[nH]c2nc(-c3ccc(O)cc3)cc(C(=O)NC3C[C@@H]4CCCC45[C@H](C3)N5C)c12] | LC11 | 406.21 | 1.97 |
| 224 | ((R)-2-Benzyl-piperizin-1-yl)-[6-(4-hydroxy-phenyl)-3-methyl-1H-pyrazolo[3,4-b]pyridin-4-yl]-methanone | 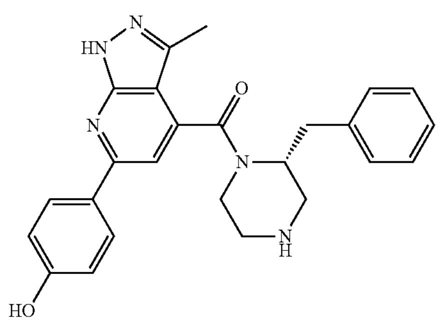 [SMILES: Cc1n[nH]c2nc(-c3ccc(O)cc3)cc(C(=O)N3CCNC[C@H]3Cc3ccccc3)c12] | LC11 | 428.2 | 2.30 |
| 225 | ((S)-2-Benzyl-piperazin-1-yl)-[6-(4-hydroxy-phenyl)-3-methyl-1H-pyrazolo[3,4-b]pyridin-4-yl]-methanone | 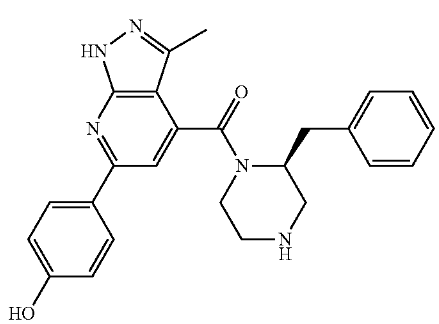 [SMILES: Cc1n[nH]c2nc(-c3ccc(O)cc3)cc(C(=O)N3CCNC[C@@H]3Cc3ccccc3)c12] | LC11 | 428.20 | 2.19 |

| Exp. No. | Name | Structure | LC/MS method | m/z [M + H]+ | R$_t$ [min] |
|---|---|---|---|---|---|
| 226 | (Hexahydro-pyrrolo[3,4-b]pyrrol-1-yl)-[6-(4-hydroxy-phenyl)-3-methyl-1H-pyrazolo[3,4-b]pyridin-4-yl]-methanone | 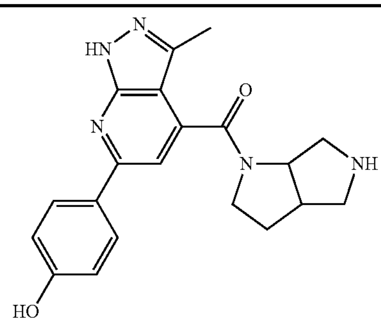 | LC11 | 364.17 | 1.90 |
| 227 | (8-Amino-3-aza-bicyclo[3.2.1]oct-3-yl)-[6-(4-hydroxy-phenyl)-3-methyl-1H-pyrazolo[3,4-b]pyridin-4-yl]-methanone | 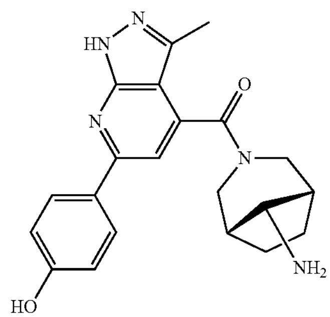 [SMILES: Cc1n[nH]c2nc(-c3ccc(O)cc3)cc(C(=O)N3C[C@H]4CC[C@@H](C3)C4N)c12] | LC11 | 378.19 | 1.88 |
| 228 | 6-(4-Hydroxy-phenyl)-3-methyl-1H-pyrazolo[3,4-b]pyridine-4-carboxylic acid (3-aminomethyl-bicyco[2.2.1]hept-2-yl)-amide | 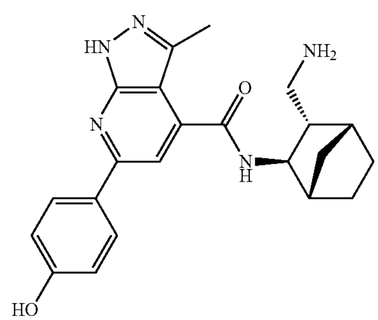 [SMILES: Cc1n[nH]c2nc(-c3ccc(O)cc3)cc(C(=O)N[C@@H]3[C@H]4CC[C@H](C4)[C@H]3CN)c12] | LC11 | 392.19 | 2.16 |
| 229 | [6-(4-Hydroxy-phenyl)-3-methyl-1H-pyrazolo[3,4-b]pyridin-4-yl]-(cis-4-methyl-3-methylamino-piperidin-1-yl)-methanone | 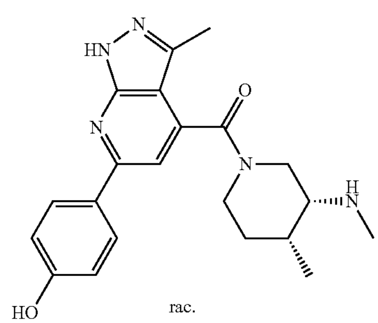 [SMILES: CN[C@H]1CN(C(=O)c2cc(-c3ccc(O)cc3)nc3[nH]nc(C)c23)CC[C@H]1C] | LC11 | 380.2 | 1.97 |
| 230 | [6-(4-Hydroxy-phenyl)-3-methyl-1H-pyrazolo[3,4-b]pyridin-4-yl]-(octahydro-[1,6]naphthyridin-1-yl)-methanone | 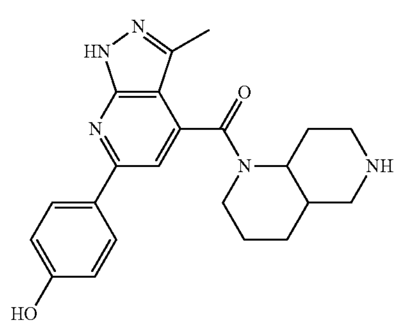 [SMILES: Cc1n[nH]c2nc(-c3ccc(O)cc3)cc(C(=O)N3CCCC4CNCCC43)c12] | LC11 | 392.21 | 1.99 |

| Exp. No. | Name | Structure | LC/MS method | m/z [M + H]+ | R_t [min] |
|---|---|---|---|---|---|
| 231 | 6-(4-Hydroxy-phenyl)-3-methyl-1H-pyrazolo[3,4-b]pyridine-4-carboxylic acid (4-amino-cyclohexyl)-amide | 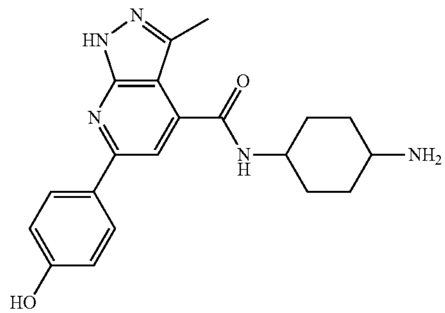 [SMILES: Cc1n[nH]c2nc(-c3ccc(O)cc3)cc(C(=O)NC3CCC(N)CC3)c12] | LC11 | 366.2 | 1.87 |
| 232 | (S)-1-[6-(4-Hydroxy-phenyl)-3-methyl-1H-pyrazolo[3,4-b]pyridine-4-carbonyl]-piperazine-2-carboxylic acid tert-butylamide | 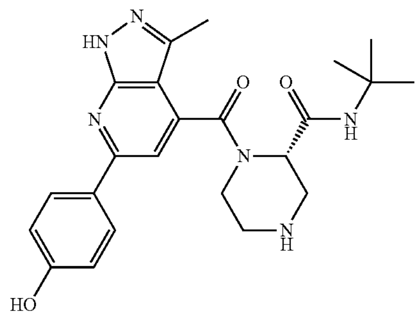 [SMILES: Cc1n[nH]c2nc(-c3ccc(O)cc3)cc(C(=O)N3CCNC[C@H]3C(=O)NC(C)(C)C)c12] | LC11 | 437.21 | 2.15 |
| 233 | [6-(4-Hydroxy-phenyl)-3-methyl-1H-pyrazolo[3,4-b]pyridin-4-yl]-((S)-3-isopropyl-piperazin-1-yl)-methanone | 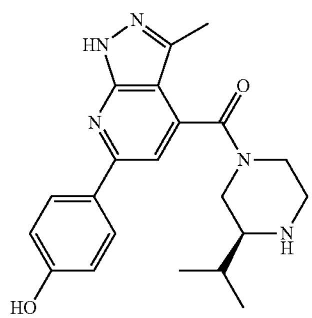 [SMILES: Cc1n[nH]c2nc(-c3ccc(O)cc3)cc(C(=O)N3CCN[C@@H](C(C)C)C3)c12] | LC11 | 380.19 | 2.10 |
| 234 | (2,7-Diaza-spiro[3.5]non-2-yl)-[6-(4-hydroxy-phenyl)-3-methyl-1H-pyrazolo[3,4-b]pyridin-4-yl]-methanone | 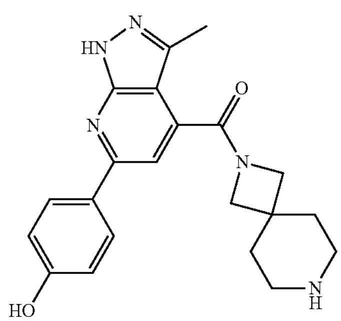 [SMILES: Cc1n[nH]c2nc(-c3ccc(O)cc3)cc(C(=O)N3CC4(CCNCC4)C3)c12] | LC11 | 378.19 | 1.88 |
| 235 | (2,7-Diaza-spiro[4.5]dec-2-yl)-[6-(4-hydroxy-phenyl)-3-methyl-1H-pyrazolo[3,4-b]pyridin-4-yl]-methanone | 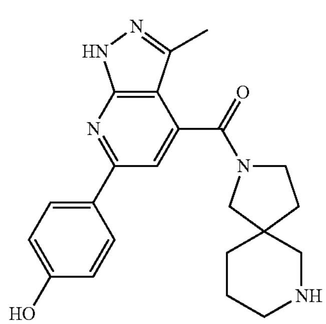 [SMILES: Cc1n[nH]c2nc(-c3ccc(O)cc3)cc(C(=O)N3CCC4(CCCNC4)C3)c12] | LC11 | 392.2 | 1.93 |

| Exp. No. | Name | Structure | LC/MS method | m/z [M + H]⁺ | R_t [min] |
|---|---|---|---|---|---|
| 236 | (3,9-Diaza-spiro[5.5]undec-3-yl)-[6-(4-hydroxy-phenyl)-3-methyl-1H-pyrazolo[3,4-b]pyridin-4-yl]-methanone | 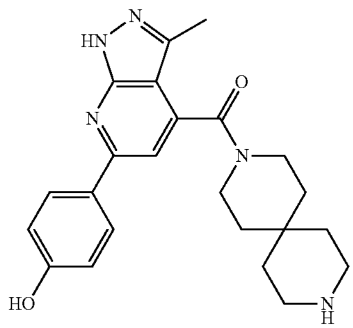 [SMILES: Cc1n[nH]c2nc(-c3ccc(O)cc3)cc(C(=O)N3CCC4(CCNCC4)CC3)c12] | LC11 | 406.22 | 1.93 |
| 237 | 6-(4-Hydroxy-phenyl)-3-methyl-1H-pyrazolo[3,4-b]pyridine-4-carboxylic acid (2,3-dihydro-spiro[1H-indene-1,4'-piperidin]-3-yl)-amide | 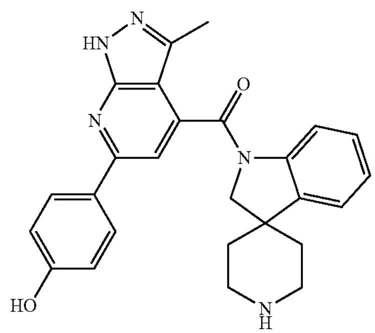 [SMILES: Cc1n[nH]c2nc(-c3ccc(O)cc3)cc(C(=O)N3CC4(CCNCC4)c4ccccc43)c12] | LC11 | 440.19 | 2.50 |
| 238 | ((R)-3-Dimethyamino-pyrrolidin-1-yl)-[6-(4-hydroxy-phenyl)-3-methyl-1H-pyrazolo[3,4-b]pyridin-4-yl]-methanone | 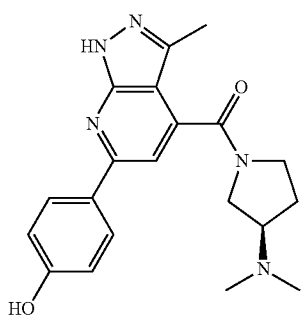 [SMILES: Cc1n[nH]c2nc(-c3ccc(O)cc3)cc(C(=O)N3CC[C@@H](N(C)C)C3)c12] | LC11 | 366.18 | 1.84 |
| 239 | ((S)-3-Dimethylamino-pyrrolidin-1-yl)-[6-(4-hydroxy-phenyl)-3-methyl-1H-pyrazolo,[3,4-b]pyridin-4-yl]-methanone | 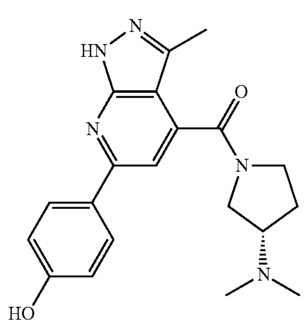 [SMILES: Cc1n[nH]c2nc(-c3ccc(O)cc3)cc(C(=O)N3CC[C@H](N(C)C)C3)c12] | LC11 | 366.18 | 1.80 |

-continued

| Exp. No. | Name | Structure | LC/MS method | m/z [M + H]+ | R_t [min] |
|---|---|---|---|---|---|
| 240 | [6-(4-Hydroxy-phenyl)-3-methyl-1H-pyrazolo[3,4-b]pyridin-4-yl]-(3-methylamino-pyrrolidin-1-yl)-methanone | 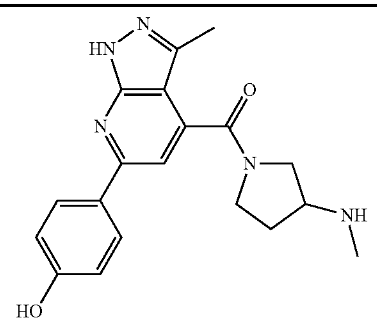 | LC11 | 352.17 | 1.86 |
| 241 | 6-(4-Hydroxy-phenyl)-3-methyl-1H-pyrazolo[3,4-b]pyridine-4-carboxylic acid methyl-piperidin-4-yl-amide | 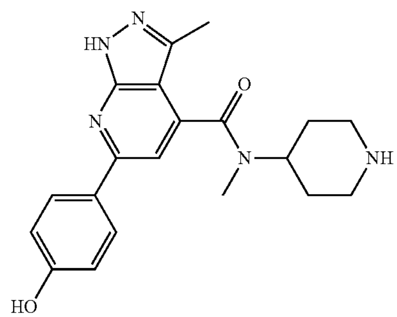 [SMILES: Cc1n[nH]c2nc(-c3ccc(O)cc3)cc(C(=O)N(C)C3CCNCC3)c12] | LC11 | 366.18 | 1.88 |
| 242 | 6-(4-Hydroxy-phenyl)-3-methyl-1H-pyrazolo[3,4-b]pyridine-4-carboxylic acid piperidin-3-ylamide | 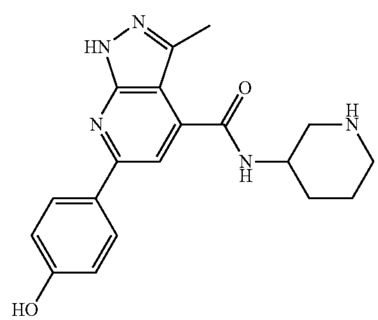 [SMILES: Cc1n[nH]c2nc(-c3ccc(O)cc3)cc(C(=O)NC3CCCNC3)c12] | LC11 | 352.16 | 1.92 |
| 243 | 6-(4-Hydroxy-phenyl)-3-methyl-1H-pyrazolo[3,4-b]pyridine-4-carboxylic acid (piperidin-3-ylmethyl)-amide | 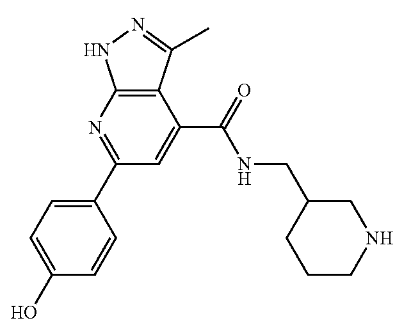 [SMILES: Cc1n[nH]c2nc(-c3ccc(O)cc3)cc(C(=O)NCC3CCCNC3)c12] | LC11 | 366.17 | 1.94 |
| 244 | 6-(4-Hydroxy-phenyl)-3-methyl-1H-pyrazolo[3,4-b]pyridine-4-carboxylic acid (3-methylamino-propyl)-amide | 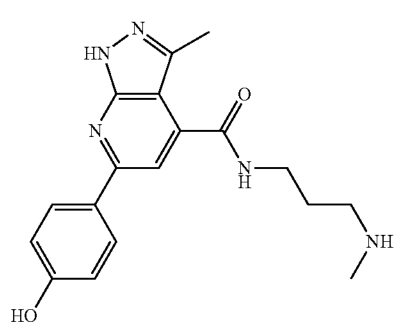 [SMILES: CNCCCNC(=O)c1cc(-c2ccc(O)cc2)nc2[nH]nc(C)c12] | LC11 | 340.16 | 1.88 |

-continued

| Exp. No. | Name | Structure | LC/MS method | m/z [M + H]+ | R$_t$ [min] |
|---|---|---|---|---|---|
| 245 | 6-(4-Hydroxy-phenyl)-3-methyl-1H-pyrazolo[3,4-b]pyridine-4-carboxylic acid (piperidin-2-ylmethyl)-amide | 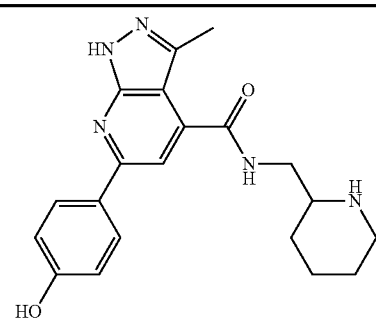 | LC11 | 366.17 | 2.00 |
| 246 | ((S)-3-Amino-pyrrolidin-1-yl)-[6-(4-hydroxy-phenyl)-3-methyl-1H-pyrazolo[3,4-b]pyridin-4-yl]-methanone | 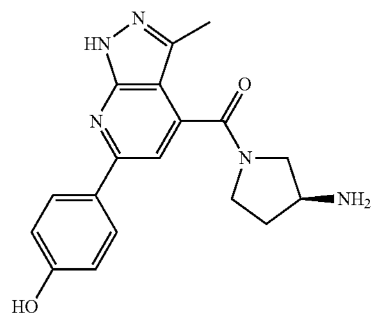 [SMILES: Cc1n[nH]c2nc(-c3ccc(O)cc3)cc(C(=O)N3CC[C@H](N)C3)c12] | LC11 | 338.16 | 1.85 |
| 247 | (3-Amino-azetidin-1-yl)-[6-(4-hydroxy-phenyl)-3-methyl-1H-pyrazolo[3,4-b]pyridin-4-yl]-methanone | 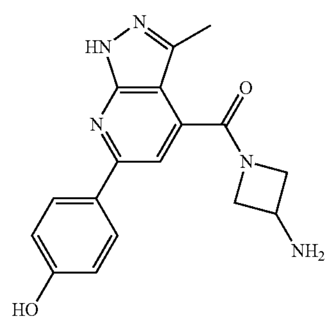 [SMILES: Cc1n[nH]c2nc(-c3ccc(O)cc3)cc(C(=O)N3CC(N)C3)c12] | LC11 | 324.14 | 1.85 |
| 248 | 6-(4-Hydroxy-phenyl)-3-methyl-1H-pyrazolo[3,4-b]pyridine-4-carboxylic acid azetidin-3-ylamide | 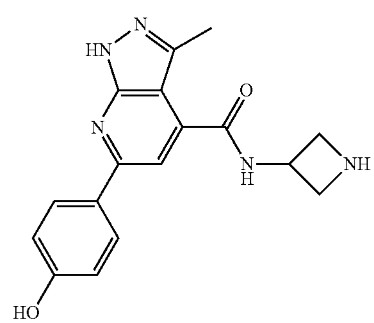 [SMILES: Cc1n[nH]c2nc(-c3ccc(O)cc3)cc(C(=O)NC3CNC3)c12] | LC11 | 324.14 | 1.77 |
| 249 | (4-Amino-piperidin-1-yl)-[6-(4-hydroxy-phenyl)-3-methyl-1H-pyrazolo[3,4-b]pyridin-4-yl]-methanone | 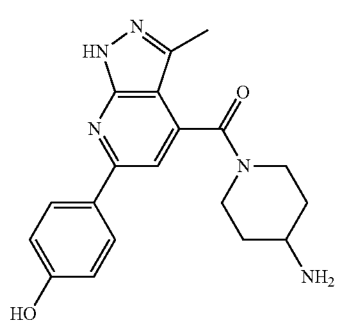 [SMILES: Cc1n[nH]c2nc(-c3ccc(O)cc3)cc(C(=O)N3CCC(N)CC3)c12] | LC11 | 352.17 | 1.84 |

-continued

| Exp. No. | Name | Structure | LC/MS method | m/z [M + H]+ | R_t [min] |
|---|---|---|---|---|---|
| 250 | (3aR,6aS)-Hexahydro-pyrrolo[3,4-c]pyrrol-2-yl-[6-(4-hydroxy-phenyl)-3-methyl-1H-pyrazolo[3,4-b]pyridin-4-yl]-methanone | 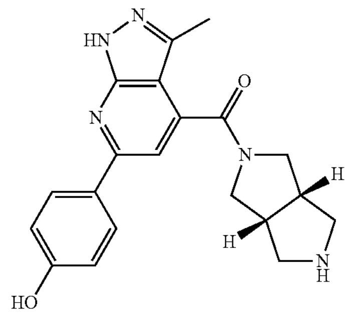 [SMILES: Cc1n[nH]c2nc(-c3ccc(O)cc3)cc(C(=O)N3C[C@H]4CNC[C@H]4C3)c12] | LC11 | 364.16 | 1.86 |
| 251 | 6-(4-Hydroxy-phenyl)-3-methyl-1H-pyrazolo[3,4-b]pyridine-4-carboxylic acid (trans-2-amino-cyclopropyl)-amide | 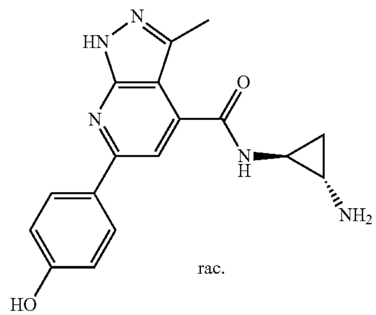 [SMILES: Cc1n[nH]c2nc(-c3ccc(O)cc3)cc(C(=O)N[C@H]3C[C@@H]3N)c12] | LC11 | 324.15 | 1.86 |
| 252 | 6-(4-Hydroxy-phenyl)-3-methyl-1H-pyrazolo[3,4-b]pyridine-4-carboxylic acid (trans-3-amino-cyclobutyl)-amide | 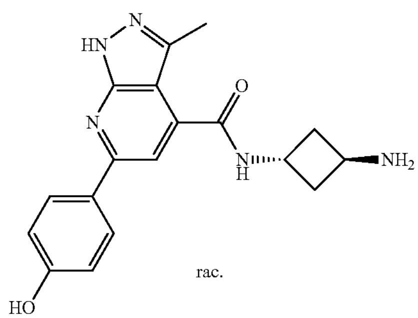 [SMILES: Cc1n[nH]c2nc(-c3ccc(O)cc3)cc(C(=O)N[C@H]3C[C@H](N)C3)c12] | LC11 | 338.17 | 1.84 |
| 253 | [6-(4-Hydroxy-phenyl)-3-methyl-1H-pyrazolo[3,4-b]pyridin-4-yl]-(6-oxa-2,9-diaza-spiro[4.5]dec-2-yl)-methanone | 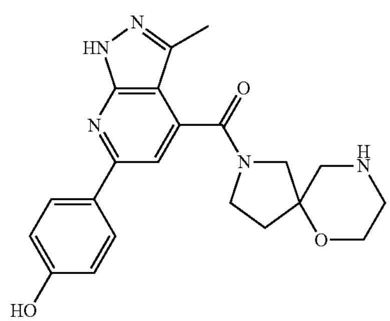 [SMILES: Cc1n[nH]c2nc(-c3ccc(O)cc3)cc(C(=O)N3CCC4(CNCCO4)C3)c12] | LC11 | 394.16 | 1.92 |
| 254 | 6-(4-Hydroxy-phenyl)-3-methyl-1H-pyrazolo[3,4-b]pyridine-4-carboxylic acid (3-amino-cyclohexyl)-amide | 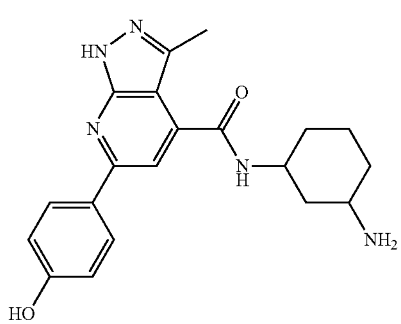 [SMILES: Cc1n[nH]c2nc(-c3ccc(O)cc3)cc(C(=O)NC3CCCC(N)C3)c12] | LC11 | 366.18 | 1.98 |

-continued

| Exp. No. | Name | Structure | LC/MS method | m/z [M + H]⁺ | R_t [min] |
|---|---|---|---|---|---|
| 255 | (2,7-Diaza-spiro[3.5]non-7-yl)-[6-(4-hydroxy-phenyl)-3-methyl-1H-pyrazolo[3,4-b]pyridin-4-yl]-methanone | 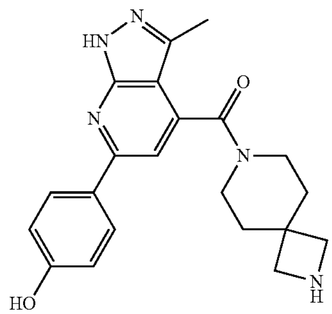 [SMILES: Cc1n[nH]c2nc(-c3ccc(O)cc3)cc(C(=O)N3CCC4(CC3)CNC4)c12] | LC11 | 378.18 | 1.90 |
| 256 | (2,7-Diaza-spiro[4.4]non-2-yl)-[6-(4-hydroxy-phenyl)-3-methyl-1H-pyrazolo[3,4-b]pyridin-4-yl]-methanone | 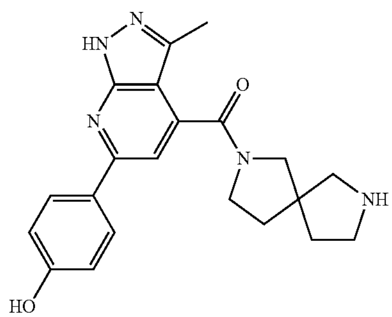 [SMILES: Cc1n[nH]c2nc(-c3ccc(O)cc3)cc(C(=O)N3CCC4(CCNC4)C3)c12] | LC11 | 378.16 | 1.89 |
| 257 | (2,8-Diaza-spiro[4.5]dec-8-yl)-[6-(4-hydroxy-phenyl)-3-methyl-1H-pyrazolo[3,4-b]pyridin-4-yl]-methanone | 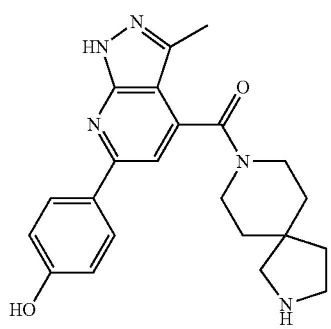 [SMILES: Cc1n[nH]c2nc(-c3ccc(O)cc3)cc(C(=O)N3CCC4(CCNC4)CC3)c12] | LC11 | 392.20 | 1.91 |
| 258 | 6-(4-Hydroxy-phenyl)-3-methy-1H-pyrazolo[3,4-b]pyridin-4-yl]-(1-oxa-4,8-diaza-spiro[5.5]undec-4-yl)-methanone | 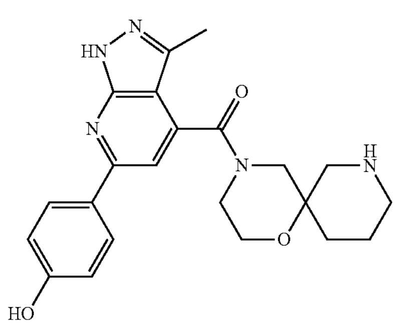 [SMILES: Cc1n[nH]c2nc(-c3ccc(O)cc3)cc(C(=O)N3CCOC4(CCCNC4)C3)c12] | LC11 | 408.18 | 1.97 |

| Exp. No. | Name | Structure | LC/MS method | m/z [M + H]⁺ | R_t [min] |
|---|---|---|---|---|---|
| 259 | [6-(4-Hydroxy-phenyl)-3-methyl-1H-pyrazolo[3,4-b]pyridin-4-yl]-(1-oxa-4,9-diaza-spiro[5.5]undec-9-yl)-methanone | 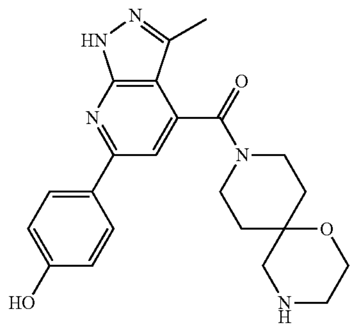 [SMILES: Cc1n[nH]c2nc(-c3ccc(O)cc3)cc(C(=O)N3CCC4(CC3)CNCCO4)c12] | LC11 | 408.18 | 1.95 |
| 260 | (2,8-Diaza-spiro[4.5]dec-2-yl)-[6-(4-hydroxy-phenyl)-3-methyl-1H-pyrazolo[3,4-b]pyridin-4-yl]-methanone | 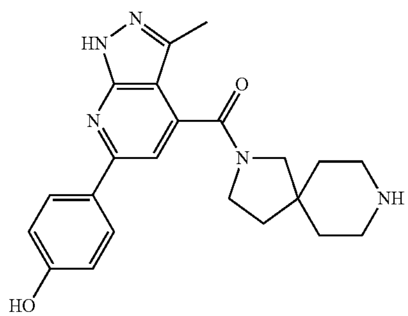 [SMILES: Cc1n[nH]c2nc(-c3ccc(O)cc3)cc(C(=O)N3CCC4(CCNCC4)C3)c12] | LC11 | 392.19 | 1.91 |
| 261 | [6-(4-Hydroxy-phenyl)-3-methyl-1H-pyrazolo[3,4-b]pyridin-4-yl]-(1-oxa-4,9-diaza-spiro[5.5]undec-4-yl)-methanone | 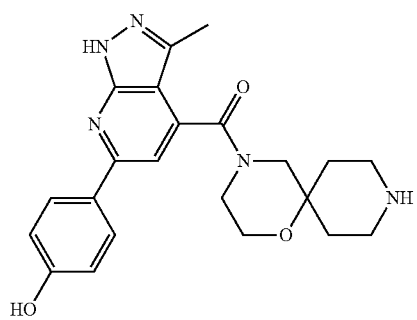 [SMILES: Cc1n[nH]c2nc(-c3ccc(O)cc3)cc(C(=O)N3CCOC4(CCNCC4)C3)c12] | LC11 | 408.18 | 1.96 |
| 262 | [6-(4-Hydroxy-phenyl)-3-methyl-1H-pyrazolo[3,4-b]pyridin-4-yl]-(1-oxa-4,8-diaza-spiro[5.5]undec-8-yl)-methanone | 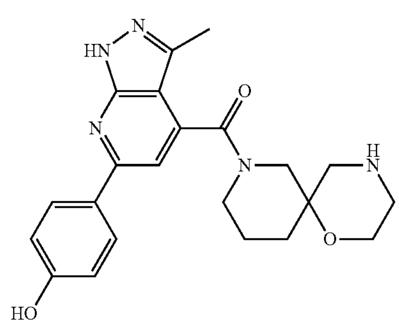 [SMILES: Cc1n[nH]c2nc(-c3ccc(O)cc3)cc(C(=O)N3CCCC4(CNCCO4)C3)c12] | LC11 | 408.17 | 1.98 |

-continued

| Exp. No. | Name | Structure | LC/MS method | m/z [M + H]+ | R_t [min] |
|---|---|---|---|---|---|
| 263 | (2,7-Diaza-spiro[4.5]dec-7-yl)-[6-(4-hydroxy-phenyl)-3-methyl-1H-pyrazolo[3,4-b]pyridin-4-yl]-methanone | 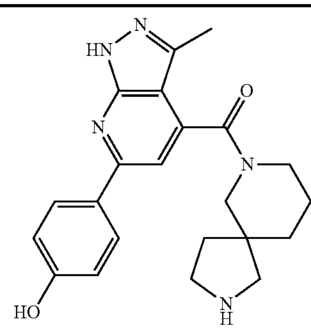 | LC11 | 392.18 | 2.00 |
| 264 | (3-Amino-pyrrolidin-1-yl)-[6-(4-hydroxy-phenyl)-3-methyl-1H-pyrazolo[3,4-b]pyridin-4-yl]-methanone | 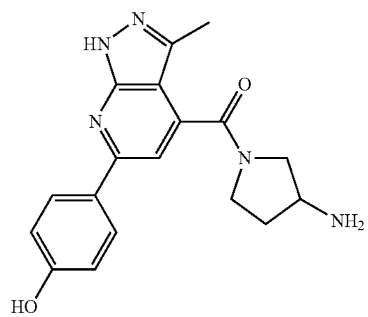 [SMILES: Cc1n[nH]c2nc(-c3ccc(O)cc3)cc(C(=O)N3CCC(N)C3)c12] | LC11 | 338.16 | 1.83 |
| 265 | 1-{4-[6-(4-Hydroxy-phenyl)-3-methyl-1H-pyrazolo[3,4-b]pyridine-4-carbonyl]-piperazin-1-yl}ethanone | 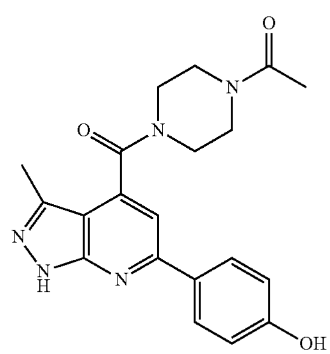 [SMILES: CC(=O)N1CCN(C(=O)c2cc(-c3ccc(O)cc3)nc3[nH]nc(C)c23)CC1] | LC11 | 380.15 | 2.06 |
| 266 | 1-{4-[6-(4-Hydroxy-phenyl)-3-methyl-1H-pyrazolo[3,4-b]pyridine-4-carbonyl]-octahydro-pyrido[1,2-a]pyrazin-4-one | 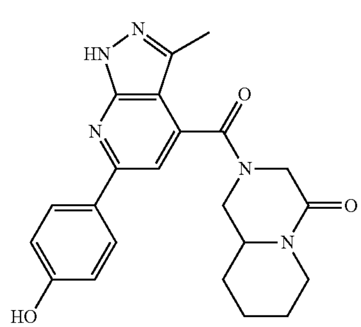 [SMILES: Cc1n[nH]c2nc(-c3ccc(O)cc3)cc(C(=O)N3CC(=O)N4CCCCC4C3)c12] | LC10 | 406.25 | 2.43 |

| Exp. No. | Name | Structure | LC/MS method | m/z [M + H]+ | R_t [min] |
|---|---|---|---|---|---|
| 267 | [6-(4-Hydroxy-phenyl)-3-methyl-1H-pyrazolo[3,4-b]pyridin-4-yl]-[4-(4-methyl-benzoyl)-piperazin-1-yl]-methanone | 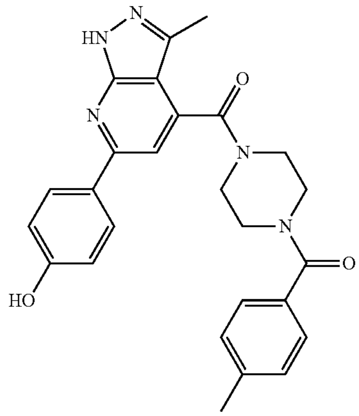 [SMILES: Cc1ccc(C(=O)N2CCN(C(=O)c3cc(-c4ccc(O)cc4)nc4[nH]nc(C)c34)CC2)cc1] | LC10 | 456.26 | 2.72 |
| 268 | (5-Ethyl-2,5-diaza-bicyclo[2.2.1]hept-2-yl)-[6-(4-hydroxy-phenyl)-3-methyl-1H-pyrazolo[3,4-b]pyridin-4-yl]-methanone | 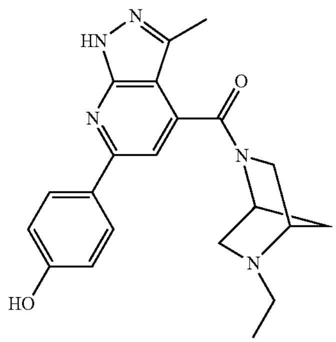 | LC10 | 378.27 | 1.95 |
| 269 | [6-(4-Hydroxy-phenyl)-3-methyl-1H-pyrazolo[3,4-b]pyridin-4-yl]-(4-methyl-[1,4]diazepan-1-yl)-methanone | 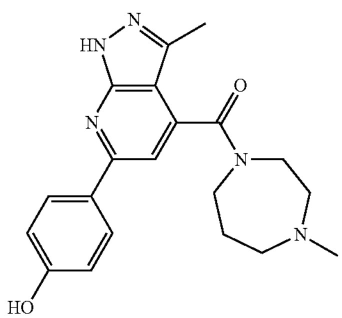 [SMILES: Cc1n[nH]c2nc(-c3ccc(O)cc3)cc(C(=O)N3CCCN(C)CC3)c12] | LC11 | 366.18 | 1.90 |
| 270 | 6-(4-Hydroxy-phenyl)-3-methyl-1H-pyrazolo[3,4-b]pyridine-4-carboxylic acid (3-amino-2,2-dimethyl-propyl)-amide | 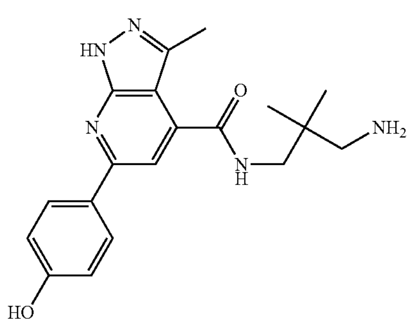 [SMILES: Cc1n[nH]c2nc(-c3ccc(O)cc3)cc(C(=O)NCC(C)(C)CN)c12] | LC10 | 354.26 | 2.05 |

| Exp. No. | Name | Structure | LC/MS method | m/z [M + H]+ | R$_t$ [min] |
|---|---|---|---|---|---|
| 271 | [6-(4-Hydroxy-phenyl)-3-methyl-1H-pyrazolo[3,4-b]pyridin-4-yl]-[4-(2-methanesulfonyl-ethyl)-piperazin-1-yl]-methanone | 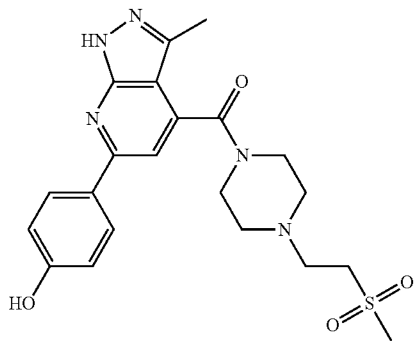 [SMILES: Cc1n[nH]c2nc(-c3ccc(O)cc3)cc(C(=O)N3CCN(CCS(C)(=O)=O)CC3)c12] | LC10 | 444.24 | 1.97 |
| 272 | 6-(4-Hydroxy-phenyl)-3-methyl-1H-pyrazolo[3,4-b]pyridine-4-carboxylic acid methyl-(1-methyl-piperidin-4-yl)-amide | 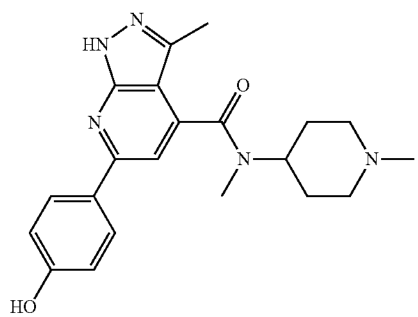 [SMILES: Cc1n[nH]c2nc(-c3ccc(O)cc3)cc(C(=O)N(C)C3CCN(C)CC3)c12] | LC11 | 380.20 | 1.86 |
| 273 | 6-(4-Hydroxy-phenyl)-3-methyl-1H-pyrazolo[3,4-b]pyridine-4-carboxylic acid (1-ethyl-piperidin-3-yl)-amide | 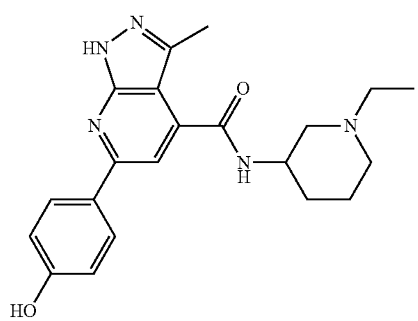 [SMILES: CCN1CCCC(NC(=O)c2cc(-c3ccc(O)cc3)nc3[nH]nc(C)c23)C1] | LC11 | 380.18 | 1.88 |
| 274 | [6-(4-Hydroxy-phenyl)-3-methyl-1H-pyrazolo[3,4-b]pyridin-4-yl]-((1S,5R)-9-hydroxy-1,5,7-trimethyl-3,7-diaza-bicyclo-[3.3.1]non-3-yl)-methanone | 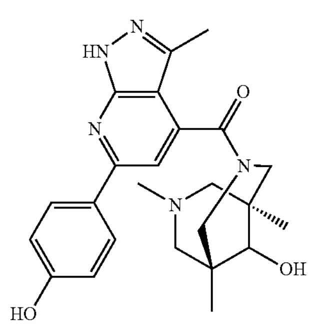 [SMILES: Cc1n[nH]c2nc(-c3ccc(O)cc3)cc(C(=O)N3C[C@]4(C)CN(C)C[C@](C)(C3)C4O)c12] | LC11 | 436.21 | 2.03 |

| Exp. No. | Name | Structure | LC/MS method | m/z [M + H]+ | R_t [min] |
|---|---|---|---|---|---|
| 275 | 6-(4-Hydroxyphenyl)-3-methyl-1H-pyrazolo[3,4-b]pyridine-4-carboxylic acid (1-methyl-piperidin-3-yl)-amide | 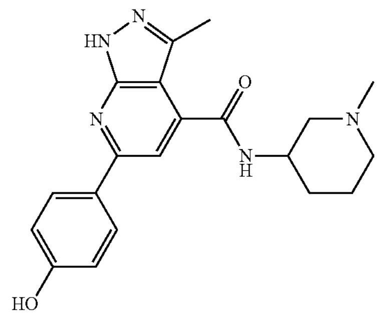 [SMILES: Cc1n[nH]c2nc(-c3ccc(O)cc3)cc(C(=O)NC3CCCN(C)C3)c12] | LC11 | 366.16 | 1.91 |
| 276 | 6-(4-Hydroxyphenyl)-3-methyl-1H-pyrazolo[3,4-b]pyridine-4-carboxylic acid (1,2,2,6,6-pentamethyl-piperidin-4-yl)-amide | 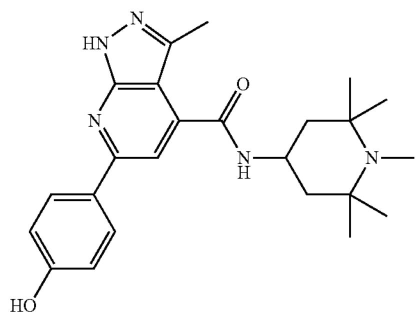 [SMILES: Cc1n[nH]c2nc(-c3ccc(O)cc3)cc(C(=O)NC3CC(C)(C)N(C)C(C)(C)C3)c12] | LC11 | 422.22 | 2.03 |
| 277 | 6-(4-Hydroxyphenyl)-3-methyl-1H-pyrazolo[3,4-b]pyridine-4-carboxylic acid (1-acetyl-piperidin-4-yl)-amide | 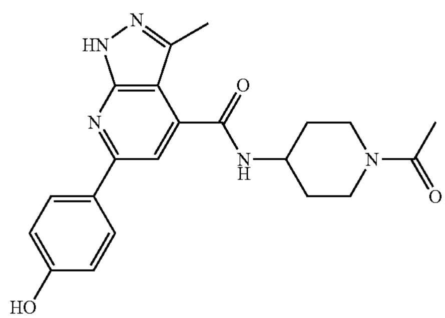 [SMILES: CC(=O)N1CCC(NC(=O)c2cc(-c3ccc(O)cc3)nc3[nH]nc(C)c23)CC1] | LC11 | 394.18 | 2.07 |
| 278 | 6-(4-Hydroxyphenyl)-3-methyl-1H-pyrazolo[3,4-b]pyridine-4-carboxylic acid (5-oxo-pyrrolidin-2-ylmethyl)-amide | 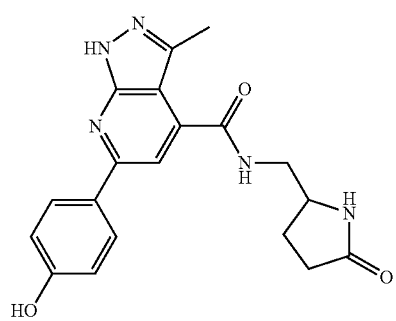 [SMILES: Cc1n[nH]c2nc(-c3ccc(O)cc3)cc(C(=O)NCC3CCC(=O)N3)c12] | LC11 | 366.13 | 1.95 |
| 279 | 6-(4-Hydroxyphenyl)-3-methyl-1H-pyrazolo[3,4-b]pyridine-4-carboxylic acid (1-cyclonexyl-piperidin-4-yl)-amide | 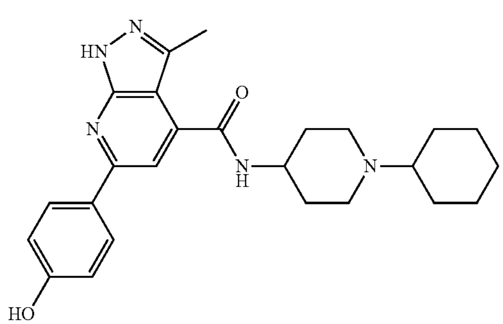 [SMILES: Cc1n[nH]c2nc(-c3ccc(O)cc3)cc(C(=O)NC3CCN(C4CCCCC4)CC3)c12] | LC12 | 434.31 | 2.49 |

| Exp. No. | Name | Structure | LC/MS method | m/z [M + H]+ | R$_t$ [min] |
|---|---|---|---|---|---|
| 280 | [6-(4-Hydroxy-phenyl)-3-methyl-1H-pyrazolo[3,4-b]pyridin-4-yl]-[4-(tetrahydro-furan-2-carbonyl)-piperazn-1-yl]-methanone | 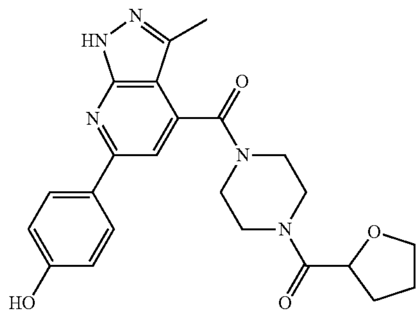 [SMILES: Cc1n[nH]c2nc(-c3ccc(O)cc3)cc(C(=O)N3CCN(C(=O)C4CCCO4)CC3)c12] | LC11 | 436.18 | 2.13 |
| 281 | (4-Ethyl-[1,4]diazepan-1-yl)-[6-(4-hydroxy-phenyl)-3-methyl-1H-pyrazolo[3,4-b]pyridin-4-yl]-methanone | 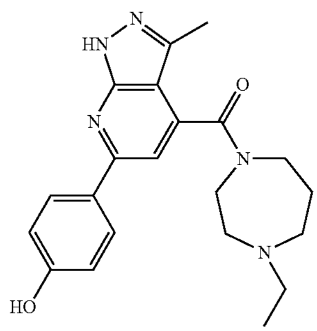 [SMILES: CCN1CCCN(C(=O)c2cc(-c3ccc(O)cc3)nc3[nH]nc(C)c23)CC1] | LC11 | 380.19 | 1.95 |
| 282 | [6-(4-Hydroxy-phenyl)-3-methyl-1H-pyrazolo[3,4-b]pyridin-4-yl]-(3-phenyl-hexahydro-pyrrolo[1,2-a]pyrazin-2-yl)-methanone | 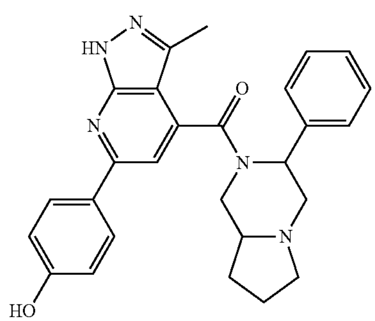 [SMILES: Cc1n[nH]c2nc(-c3ccc(O)cc3)cc(C(=O)N3CC4CCCN4CC3c3ccccc3)c12] | LC11 | 454.19 | 2.19 |
| 283 | 4-Amino-1-[6-(4-hydroxy-phenyl)-3-methyl-1H-pyrazolo[3,4-b]pyridine-4-carbonyl]-piperidine-4-carboxylic acid methyl ester | 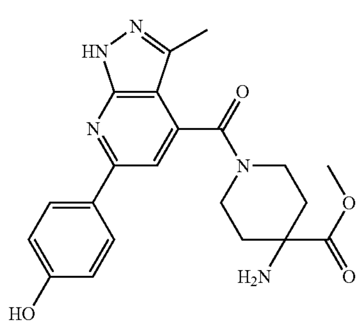 [SMILES: COC(=O)C1(N)CCN(C(=O)c2cc(-c3ccc(O)cc3)nc3[nH]nc(C)c23)CC1] | LC11 | 410.15 | 1.97 |

| Exp. No. | Name | Structure | LC/MS method | m/z [M + H]+ | R_t [min] |
|---|---|---|---|---|---|
| 284 | [6-(4-Hydroxy-phenyl)-3-methyl-1H-pyrazolo[3,4-b]pyridin-4-yl]-(3-methyl-hexahydro-pyrrolo[1,2-a]pyrazin-2-yl methanone | 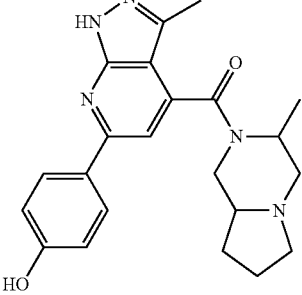 | LC11 | 392.18 | 2.02 |
| 285 | [6-(4-Hydroxy-phenyl)-3-methyl-1H-pyrazolo[3,4-b]pyridin-4-yl]-(3-methyl-octahydro-pyrido[1,2-a]pyrazin-2-yl)-methanone | 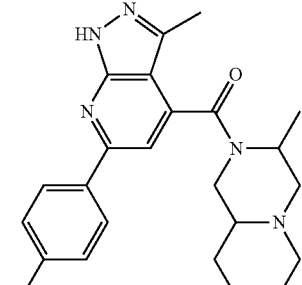 | LC11 | 406.17 | 2.07 |
| 286 | 6-(4-Hydroxy-phenyl)-3-methyl-1H-pyrazolo[3,4-b]pyridine-4-carboxylic acid (2-methyl-2-pyridin-2-yl-3-pyrrolidin-1-yl-propyl)-amide | 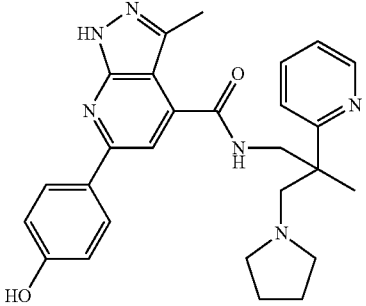 [SMILES: Cc1n[nH]c2nc(-c3ccc(O)cc3)cc(C(=O)NCC(C)(CN3CCCC3)c3ccccn3)c12] | LC10 | 471.34 | 2.22 |
| 287 | [6-(4-Hydroxy-phenyl)-3-methyl-1H-pyrazolo[3,4-b]pyridin-4-yl]-(4-piperidin-1-ylmethyl-piperidin-1-yl)-methanone | 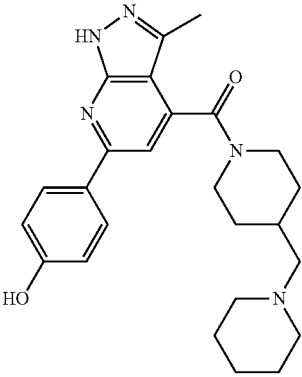 [SMILES: Cc1n[nH]c2nc(-c3ccc(O)cc3)cc(C(=O)N3CCC(CN4CCCCC4)CC3)c12] | LC10 | 434.3 | 2.00 |

The following examples have been prepared following a similar procedure as described for 3-ethyl-6-(4-hydroxy-phenyl)-1H-pyrazolo[3,4-b]pyridine-4-carboxylic acid (1-aza-bicyclo[2.2.2]oct-3-yl)-amide (Example 159), starting from the respective amine precursors and 6-(3-fluoro-4-hydroxy-phenyl)-3-methyl-1H-pyrazolo[3,4-b]pyridine-4-carboxylic acid:

| Exp. No. | Name | Structure | LC/MS method | m/z [M + H]+ | R, [min] |
|---|---|---|---|---|---|
| 288 | 6-(3-Fluoro-4-hydroxy-phenyl)-3-methyl-1H-pyrazolo[3,4-b]pyridine-4-carboxylic acid (6-amino-spiro[3.3]hept-2-yl)-amide | 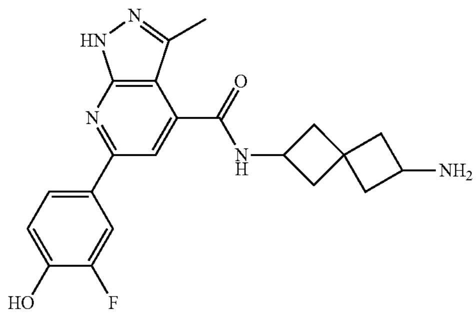 [SMILES: Cc1n[nH]c2nc(-c3ccc(O)c(F)c3)cc(C(=O)NC3CC4(CC(N)C4)C3)c12] | LC10 | 396.26 | 2.07 |
| 289 | [6-(3-Fluoro-4-hydroxy-phenyl)-3-methyl-1H-pyrazolo[3,4-b]pyridin-4-yl]-(hexahydro-pyrrolo[3,4-c]pyrrol-2-yl)-methanone | 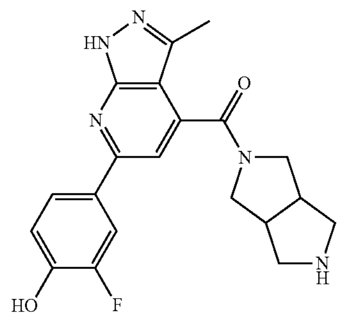 [SMILES: Cc1n[nH]c2nc(-c3ccc(O)c(F)c3)cc(C(=O)N3CC4CNCC4C3)c12] | LC10 | 382.24 | 1.97 |
| 290 | [6-(3-Fluoro-4-hydroxy-phenyl)-3-methyl-1H-pyrazolo[3,4-b]pyridin-4-yl]-((S)-3-methyl-piperazin-1-yl)-methanone | 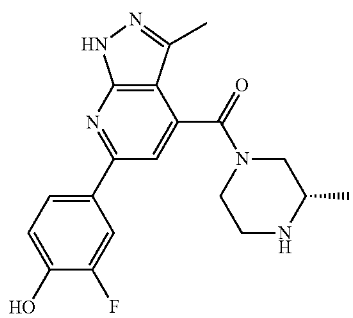 | LC10 | 370.24 | 2.00 |
| 291 | [6-(3-Fluoro-4-hydroxy-phenyl)-3-methyl-1H-pyrazolo[3,4-b]pyridin-4-yl]-((R)-3-propyl-piperazin-1-yl)-methanone | 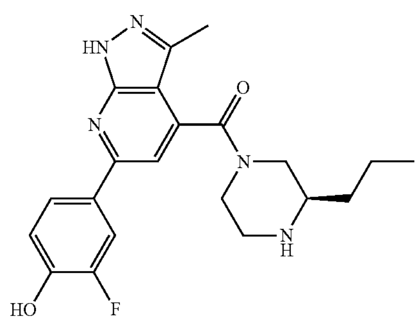 | LC10 | 398.27 | 2.22 |
| 292 | ((S)-3-Amino-pyrrolidin-1-yl)-[6-(3-fluoro-4-hydroxy-phenyl)-3-methyl-1H-pyrazolo[3,4-b]pyridin-4-yl]-methanone | 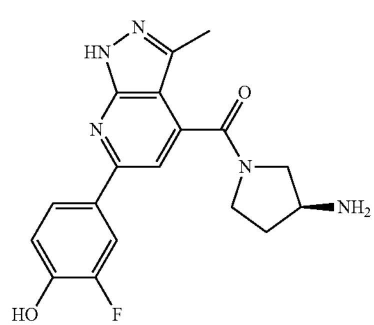 [SMILES: Cc1n[nH]c2nc(-c3ccc(O)c(F)c3)cc(C(=O)N3CC[C@H](N)C3)c12] | LC10 | 356.22 | 1.89 |

| Exp. No. | Name | Structure | LC/MS method | m/z [M + H]+ | R_r [min] |
|---|---|---|---|---|---|
| 293 | [6-(3-Fluoro-4-hydroxy-phenyl)-3-methyl-1H-pyrazolo[3,4-b]pyridin-4-yl]-((S)-3-propyl-piperazin-1-yl)-methanone | 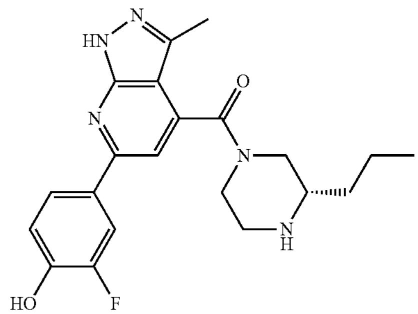 [SMILES: CCC[C@H]1CN(C(=O)c2cc(-c3ccc(O)c(F)c3)nc3[nH]nc(C)c23)CCN1] | LC10 | 398.27 | 2.22 |
| 294 | ((S)-3-Butyl-piperazin-1-yl)-[6-(3-fluoro-4-hydroxy-phenyl)-3-methyl-1H-pyrazolo[3,4-b]pyridin-4-yl]-methanone | 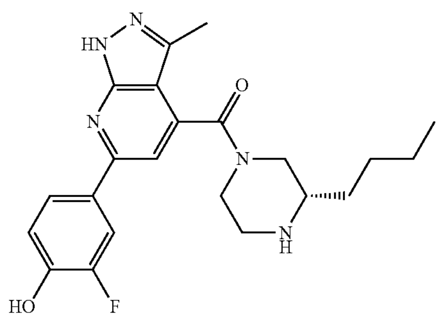 [SMILES: CCCC[C@H]1CN(C(=O)c2cc(-c3ccc(O)c(F)c3)nc3[nH]nc(C)c23)CCN1] | LC10 | 412.29 | 2.29 |
| 295 | ((S)-3-Ethyl-piperazin-1-yl)-[6-(3-fluoro-4-hydroxy-phenyl)-3-methyl-1H-pyrazolo[3,4-b]pyridin-4-yl]-methanone | 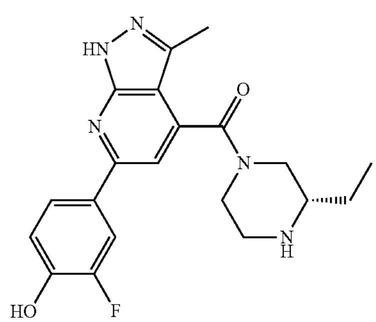 [SMILES: CC[C@H]1CN(C(=O)c2cc(-c3ccc(O)c(F)c3)nc3[nH]nc(C)c23)CCN1] | LC10 | 384.25 | 2.12 |
| 296 | (6,6-Dioxo-octahydro-thieno[3,4-b]pyrazin-1-yl)-[6-(3-fluoro-4-hydroxy-phenyl)-3-methyl-1H-pyrazolo[3,4-b]pyridin-4-yl]-methanone | 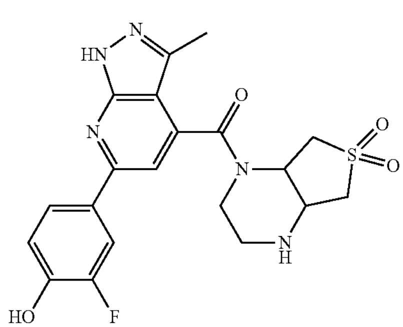 [SMILES: Cc1n[nH]c2nc(-c3ccc(O)c(F)c3)cc(C(=O)N3CCNC4CS(=O)(=O)CC43)c12] | LC10 | 446.21 | 2.14 |

| Exp. No. | Name | Structure | LC/MS method | m/z [M + H]⁺ | R$_t$ [min] |
|---|---|---|---|---|---|
| 297 | (R)-4-[6-(3-Fluoro-4-hydroxy-phenyl)-3-methyl-1H-pyrazolo[3,4-b]pyridine-4-carbonyl]-piperazine-2-carboxylic acid methyl ester | 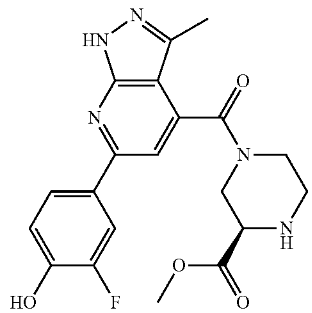 [SMILES: COC(=O)[C@H]1CN(C(=O)c2cc(-c3ccc(O)c(F)c3)nc3[nH]nc(C)c23)CCN1] | LC10 | 414.23 | 2.07 |
| 298 | [6-(3-Fluoro-4-hydroxy-phenyl)-3-methyl-1H-pyrazolo[3,4-b]pyridin-4-yl]-((R)-3-methoxymethyl-piperazin-1-yl)-methanone | 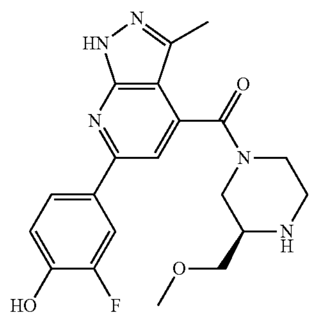 [SMILES: COC[C@H]1CN(C(=O)c2cc(-c3ccc(O)c(F)c3)nc3[nH]nc(C)c23)CCN1] | LC10 | 400.25 | 2.10 |
| 299 | 6-(3-Fluoro-4-hydroxy-phenyl)-3-methyl-1H-pyrazolo[3,4-b]pyridine-4-carboxylic acid (2,3-dihydro-spiro[1H-indene-1,4'-pipendin]-3-yl)-amide | 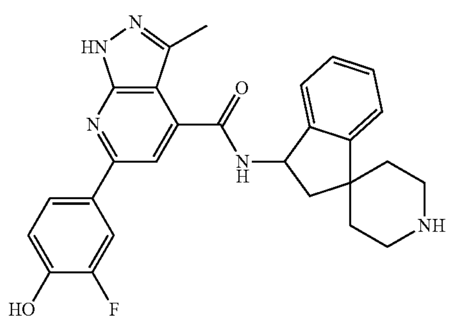 [SMILES: Cc1n[nH]c2nc(-c3ccc(O)c(F)c3)cc(C(=O)NC3CC4(CCNCC4)c4ccccc43)c12] | LC10 | 472.30 | 2.39 |
| 300 | (2-Benzyl-piperazin-1-yl)-[6-(3-fluoro-4-hydroxy-phenyl)-3-methyl-1H-pyrazolo[3,4-b]pyridin-4-yl]-methanone | 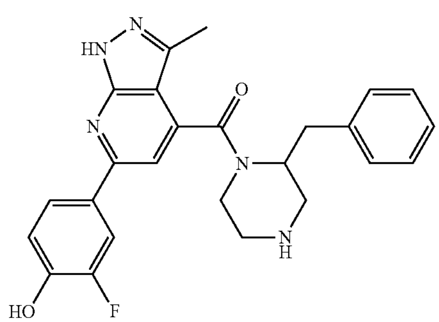 [SMILES: Cc1n[nH]c2nc(-c3ccc(O)c(F)c3)cc(C(=O)N3CCNCC3Cc3ccccc3)c12] | LC10 | 446.28 | 2.37 |
| 301 | 6-(3-Fluoro-4-hydroxy-phenyl)-3-methyl-1H-pyrazolo[3,4-b]pyridine-4-carboxylic acid (8-methyl-8-aza-bicyclo[3.2.1]oct-3-yl)-amide | 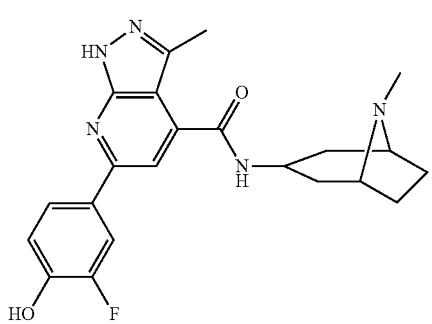 [SMILES: Cc1n[nH]c2nc(-c3ccc(O)c(F)c3)cc(C(=O)NC3CC4CCC(C3)N4C)c12] | LC10 | 410.27 | 2.05 |

| Exp. No. | Name | Structure | LC/MS method | m/z [M + H]+ | R$_t$ [min] |
|---|---|---|---|---|---|
| 302 | 6-(3-Fluoro-4-hydroxy-phenyl)-3-methyl-1H-pyrazolo[3,4-b]pyridine-4-carboxylic acid azetidin-3-ylamide | 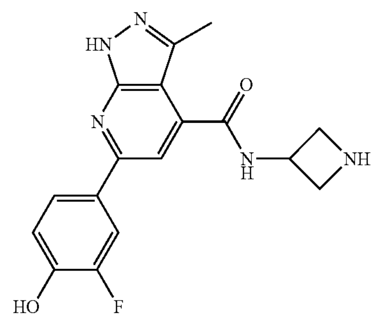 [SMILES: Cc1n[nH]c2nc(-c3ccc(O)c(F)c3)cc(C(=O)NC3CNC3)c12] | LC10 | 342.20 | 1.95 |
| 303 | [6-(3-Fluoro-4-hydroxy-phenyl)-3-methyl-1H-pyrazolo[3,4-b]pyridin-4-yl]-(3-methyl-piperazin-1-yl)-methanone | 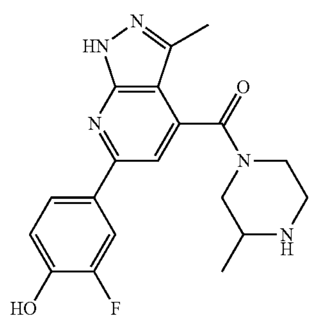 [SMILES: Cc1n[nH]c2nc(-c3ccc(O)c(F)c3)cc(C(=O)N3CCNC(C)C3)c12] | LC10 | 370.24 | 2.04 |
| 304 | (4-Amino-piperidin-1-yl)-[6-(3-fluoro-4-hydroxy-phenyl)-3-methyl-1H-pyrazolo[3,4-b]pyridin-4-yl]-methanone | 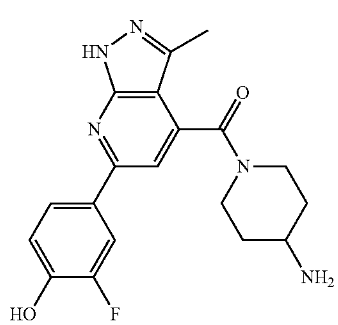 [SMILES: Cc1n[nH]c2nc(-c3ccc(O)c(F)c3)cc(C(=O)N3CCC(N)CC3)c12] | LC10 | 370.24 | 1.93 |
| 305 | 6-(3-Fluoro-4-hydroxy-phenyl)-3-methyl-1H-pyrazolo[3,4-b]pyridine-4-carboxylic acid (R)-piperidin-3-yl-amide | 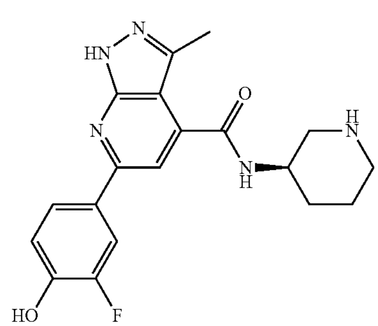 | LC10 | 370.23 | 2.05 |

| Exp. No. | Name | Structure | LC/MS method | m/z [M + H]⁺ | R_t [min] |
|---|---|---|---|---|---|
| 306 | [6-(3-Fluoro-4-hydroxy-phenyl)-3-methyl-1H-pyrazolo[3,4-b]pyridin-4-yl]-(3aR,6aS)-hexahydro-pyrrolo[3,4-c]pyrrol-2-yl-methanone | 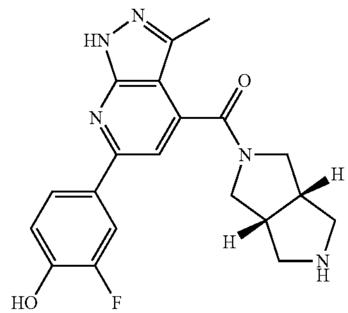 [SMILES: Cc1n[nH]c2nc(-c3ccc(O)c(F)c3)cc(C(=O)N3C[C@H]4CNC[C@H]4C3)c12] | LC10 | 382.24 | 1.92 |
| 307 | 6-(3-Fluoro-4-hydroxy-phenyl)-3-methyl-1H-pyrazolo[3,4-b]pyridine-4-carboxylic acid (trans-2-amino-cyclopropyl)-amide | 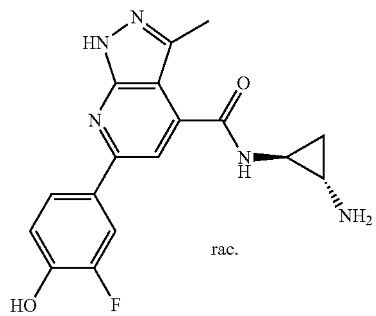 [SMILES: Cc1n[nH]c2nc(-c3ccc(O)c(F)c3)cc(C(=O)N[C@H]3C[C@@H]3N)c12] | LC10 | 342.21 | 1.97 |
| 308 | [6-(3-Fluoro-4-hydroxy-phenyl)-3-methyl-1H-pyrazolo[3,4-b]pyridin-4-yl]-(hexahydro-pyrrolo[3,4-b]pyrrol-1-yl)-methanone | 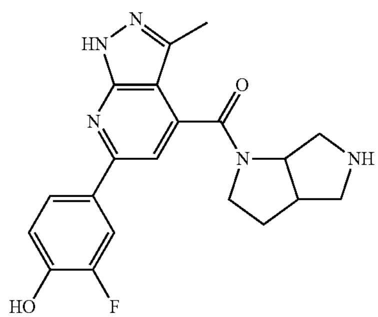 [SMILES: Cc1n[nH]c2nc(-c3ccc(O)c(F)c3)cc(C(=O)N3CCC4CNCC43)c12] | LC10 | 382.24 | 2.02 |
| 309 | 6-(3-Fluoro-4-hydroxy-phenyl)-3-methyl-1H-pyrazolo[3,4-b]pyridine-4-carboxylic acid (trans-3-amino-cyclobutyl)-amide | 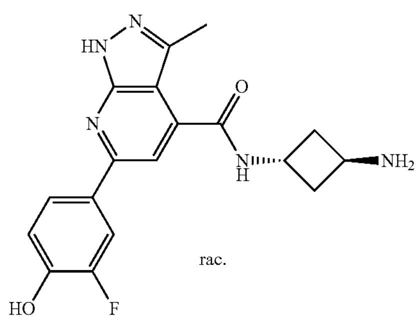 [SMILES: Cc1n[nH]c2nc(-c3ccc(O)c(F)c3)cc(C(=O)N[C@H]3C[C@H](N)C3)c12] | LC10 | 356.23 | 1.93 |
| 310 | (8-Amino-3-aza-bicyclo[3.2.1]oct-3-yl)-[6-(3-fluoro-4-hydroxy-phenyl)-3-methyl-1H-pyrazolo[3,4-b]pyridin-4-yl]-methanone | 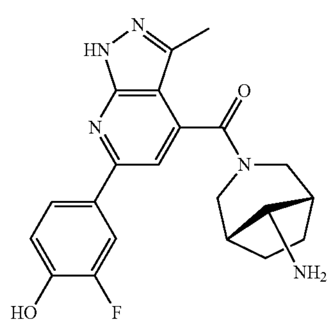 [SMILES: Cc1n[nH]c2nc(-c3ccc(O)c(F)c3)cc(C(=O)N3C[C@H]4CC[C@@H](C3)C4N)c12] | LC10 | 396.26 | 2.07 |

| Exp. No. | Name | Structure | LC/MS method | m/z [M + H]+ | R_t [min] |
|---|---|---|---|---|---|
| 311 | 6-(3-Fluoro-4-hydroxy-phenyl)-3-methyl-1H-pyrazolo[3,4-b]pyridine-4-carboxylic acid (3-aminomethyl-bicyclo[2.2.1]hept-2-yl)-amide | 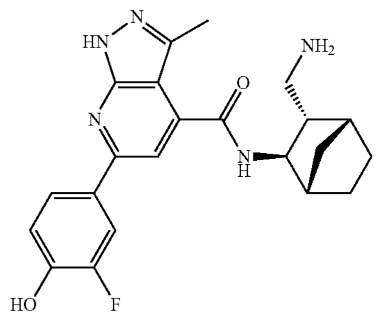 [SMILES: Cc1n[nH]c2nc(-c3ccc(O)c(F)c3)cc(C(=O)N[C@@H]3[C@H]4CC[C@H](C4)[C@H]3CN)c12] | LC10 | 410.27 | 2.25 |
| 312 | [6-(3-Fluoro-4-hydroxy-phenyl)-3-methyl-1H-pyrazolo[3,4-b]pyridin-4-yl]-(cis 4-methyl-3-methylamino-piperidin-1-yl)-methanone | 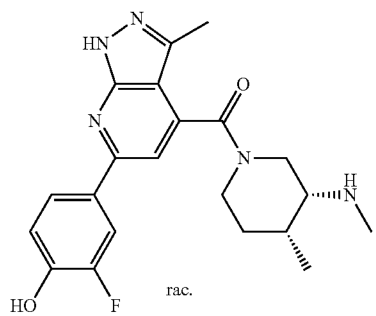 [SMILES: CN[C@H]1CN(C(=O)c2cc(-c3ccc(O)c(F)c3)nc3[nH]nc(C)c23)CC[C@H]1C] | LC10 | 398.26 | 2.09 |
| 313 | [6-(3-Fluoro-4-hydroxy-phenyl)-3-methyl-1H-pyrazolo[3,4-b]pyridin-4-yl]-((S)-2-methyl-piperazin-1-yl)-methanone | 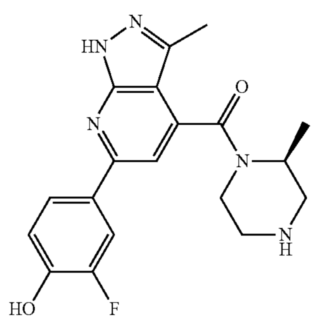 | LC10 | 370.24 | 2.04 |
| 314 | [6-(3-Fluoro-4-hydroxy-phenyl)-3-methyl-1H-pyrazolo[3,4-b]pyridin-4-yl]-(3-trifluoromethyl-piperazin-1-yl)-methanone | 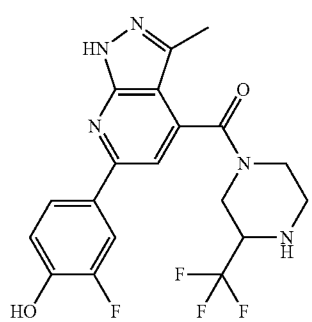 | LC10 | 424.17 | 2.32 |
| 315 | (3-Amino-azetidin-1-yl)-[6-(3-fluoro-4-hydroxy-phenyl)-3-methyl-1H-pyrazolo[3,4-b]pyridin-4-yl]-methanone | 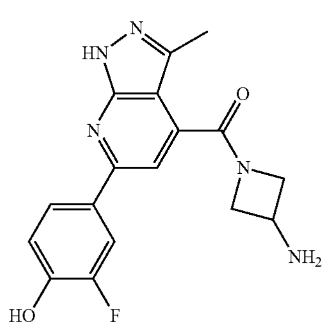 [SMILES: Cc1n[nH]c2nc(-c3ccc(O)c(F)c3)cc(C(=O)N3CC(N)C3)c12] | LC10 | 342.19 | 1.97 |

| Exp. No. | Name | Structure | LC/MS method | m/z [M + H]⁺ | R_t [min] |
|---|---|---|---|---|---|
| 316 | 6-(3-Fluoro-4-hydroxy-phenyl)-3-methyl-1H-pyrazolo[3,4-b]pyridine-4-carboxylic acid [2-(1-methyl-pyrrolidin-2-yl)-ethyl]-amide | 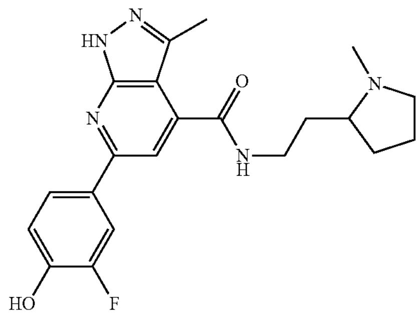 [SMILES: Cc1n[nH]c2nc(-c3ccc(O)c(F)c3)cc(C(=O)NCCC3CCCN3C)c12] | LC10 | 398.23 | 2.09 |
| 317 | (S)-6-(3-Fluoro-4-hydroxy-phenyl)-3-methyl-1H-pyrazolo[3,4-b]pyridine-4-carboxylic acid (1-aza-bicyclo[2.2.2]oct-3-yl)-amide | 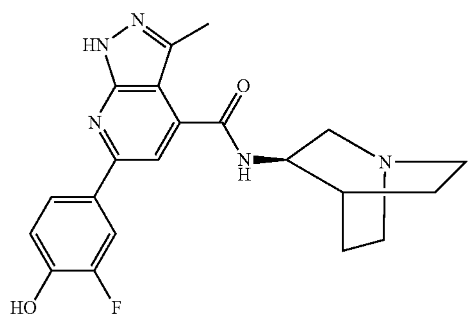 [SMILES: Cc1n[nH]c2nc(-c3ccc(O)c(F)c3)cc(C(=O)N[C@H]3CN4CCC3CC4)c12] | LC10 | 396.23 | 2.04 |
| 318 | 6-(3-Fluoro-4-hydroxy-phenyl)-3-methyl-1H-pyrazolo[3,4-b]pyridine-4-carboxylic acid (3R)-8-methyl-8-aza-bicyclo[3.2.1]oct-3-yl)-amide | 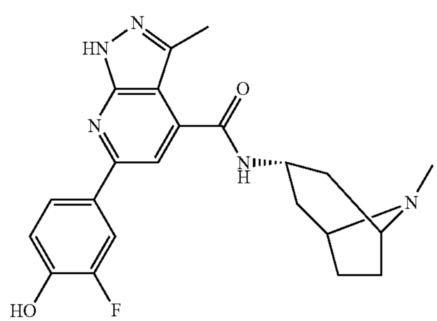 | LC10 | 410.25 | 2.05 |
| 319 | 6-(3-Fluoro-4-hydroxy-phenyl)-3-methyl-1H-pyrazolo[3,4-b]pyridine-4-carboxylic acid (1-methyl-piperidin-4-yl)-amide | 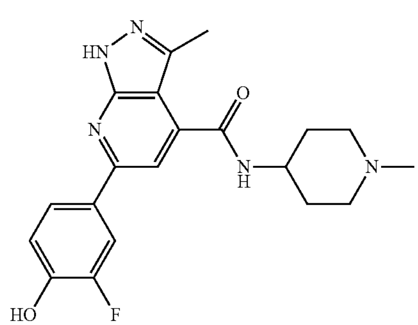 [SMILES: Cc1n[nH]c2nc(-c3ccc(O)c(F)c3)cc(C(=O)NC3CCN(C)CC3)c12] | LC10 | 384.23 | 2.02 |

| Exp. No. | Name | Structure | LC/MS method | m/z [M + H]+ | R_t [min] |
|---|---|---|---|---|---|
| 320 | [6-(3-Fluoro-4-hydroxy-phenyl)-3-methyl-1H-pyrazolo[3,4-b]pyridin-4-yl]-((S)-2-isopropyl-piperazin-1-yl)-methanone | 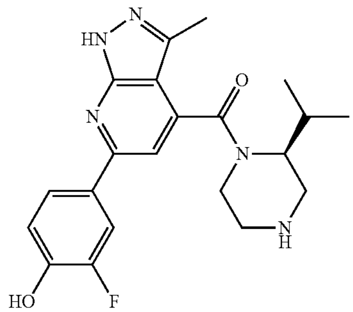 [SMILES: Cc1n[nH]c2nc(-c3ccc(O)c(F)c3)cc(C(=O)N3CCNC[C@@H]3C(C)C)c12] | LC10 | 398.26 | 2.20 |
| 321 | ((R)-2-Benzyl-piperazin-1-yl)-[6-(3-fluoro-4-hydroxy-phenyl)-3-methyl-1H-pyrazolo[3,4-b]pyridin-4-yl]-methanone | 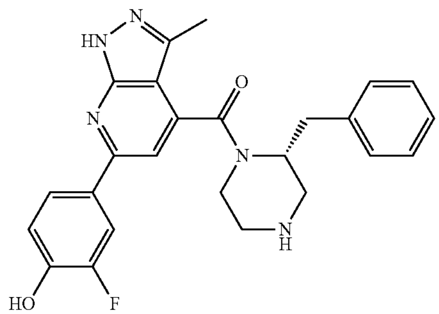 | LC10 | 446.25 | 2.37 |
| 322 | [(R)-3-(1-Amino-cyclopropyl)-pyrrolidin-1-yl]-[6-(3-fluoro-4-hydroxy-phenyl)-3-methyl-1H-pyrazolo[3,4-b]pyridin-4-yl]-methanone | 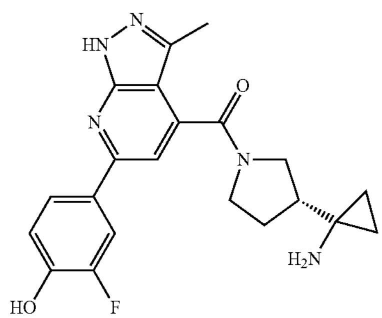 [SMILES: Cc1n[nH]c2nc(-c3ccc(O)c(F)c3)cc(C(=O)N3CC[C@@H](C4(N)CC4)C3)c12] | LC10 | 396.24 | 2.05 |
| 323 | [6-(3-Fluoro-4-hydroxy-phenyl)-3-methyl-1H-pyrazolo[3,4-b]pyridin-4-yl]-(6-oxa-2,9-diaza-spiro[4.5]dec-2-yl)-methanone | 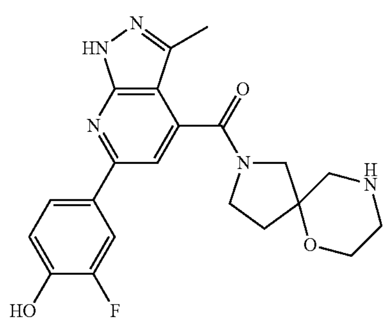 [SMILES: Cc1n[nH]c2nc(-c3ccc(O)c(F)c3)cc(C(=O)N3CCC4(CNCCO4)C3)c12] | LC10 | 412.24 | 2.02 |
| 324 | [6-(3-Fluoro-4-hydroxy-phenyl)-3-methyl-1H-pyrazolo[3,4-b]pyridin-4-yl]-(octahydro-[1,6]naphthyridin-1-yl)-methanone | 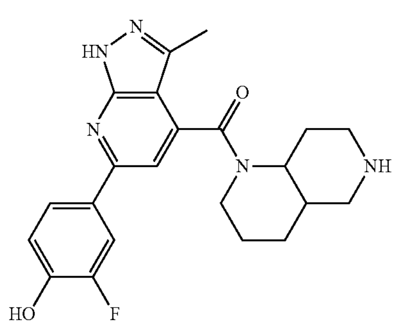 [SMILES: Cc1n[nH]c2nc(-c3ccc(O)c(F)c3)cc(C(=O)N3CCCC4CNCCC43)c12] | LC10 | 410.25 | 2.07 |

| Exp. No. | Name | Structure | LC/MS method | m/z [M + H]⁺ | R_t [min] |
|---|---|---|---|---|---|
| 325 | (S)-1-[6-(3-Fluoro-4-hydroxy-phenyl)-3-methyl-1H-pyrazolo[3,4-b]pyridine-4-carbonyl]-piperazine-2-carboxylic acid tert-butyl-amide | 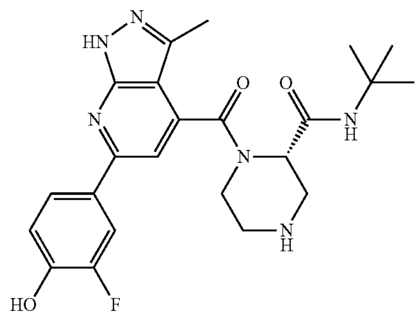 [SMILES: Cc1n[nH]c2nc(-c3ccc(O)c(F)c3)cc(C(=O)N3CCNC[C@H]3C(=O)NC(C)(C)C)c12] | LC10 | 455.27 | 2.32 |
| 326 | [6-(3-Fluoro-4-hydroxy-phenyl)-3-methyl-1H-pyrazolo[3,4-b]pyridin-4-yl]-((S)-3-isopropyl-piperazin-1-yl)-methanone | 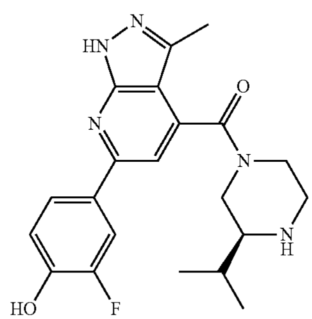 [SMILES: Cc1n[nH]c2nc(-c3ccc(O)c(F)c3)cc(C(=O)N3CCN[C@@H](C(C)C)C3)c12] | LC10 | 398.26 | 2.20 |
| 327 | [6-(3-Fluoro-4-hydroxy-phenyl)-3-methyl-1H-pyrazolo[3,4-b]pyridin-4-yl]-(2-pyridin-3-yl-piperazin-1-yl)-methanone | 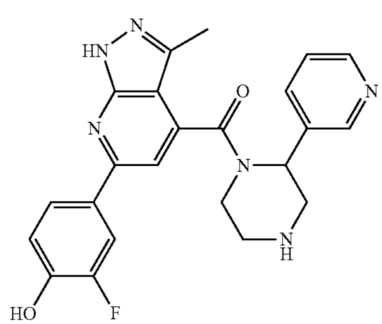 [SMILES: Cc1n[nH]c2nc(-c3ccc(O)c(F)c3)cc(C(=O)N3CCNCC3c3cccnc3)c12] | LC10 | 433.24 | 1.99 |
| 328 | (R)-1-[6-(3-Fluoro-4-hydroxy-phenyl)-3-methyl-1H-pyrazolo[3,4-b]pyridine-4-carbonyl]-piperazine-2-carboxyilc acid methyl ester | 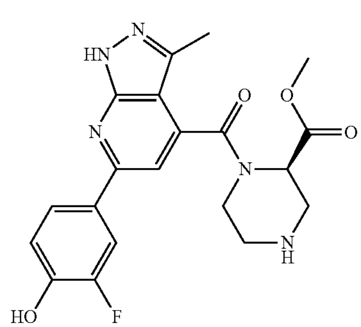 [SMILES: COC(=O)[C@H]1CNCCN1C(=O)c1cc(-c2ccc(O)c(F)c2)nc2[nH]nc(C)c12] | LC10 | 414.21 | 2.12 |

-continued

| Exp. No. | Name | Structure | LC/MS method | m/z [M + H]+ | R_t [min] |
|---|---|---|---|---|---|
| 329 | (2,7-Diaza-spiro[3.5]non-7-yl)-[6-(3-fluoro-4-hydroxy-phenyl)-3-methyl-1H-pyrazolo[3,4-b]pyridin-4-yl]-methanone | 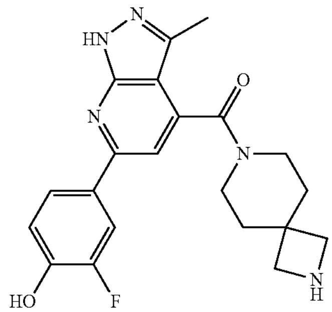 [SMILES: Cc1n[nH]c2nc(-c3ccc(O)c(F)c3)cc(C(=O)N3CCC4(CC3)CNC4)c12] | LC10 | 396.24 | 2.00 |
| 330 | (1,2-Dihydro-5-spiro[3H-indole-3,4'-piperidin]-1-yl)-[6-(3-fluoro-4-hydroxy-phenyl)-3-methyl-1H-pyrazolo[3,4-b]pyridin-4-yl]-methanone | 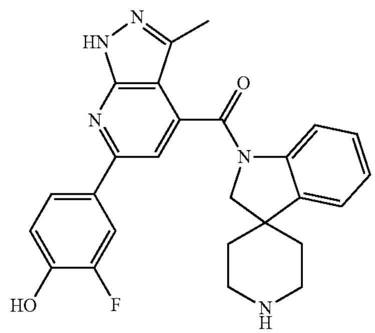 [SMILES: Cc1n[nH]c2nc(-c3ccc(O)c(F)c3)cc(C(=O)N3CC4(CCNCC4)c4ccccc43)c12] | LC10 | 458.26 | 2.45 |
| 331 | 6-(3-Fluoro-4-hydroxy-phenyl)-3-methyl-1H-pyrazolo[3,4-b]pyridine-4-carboxylic acid methyl-(1-methyl-piperidin-4-yl)-amide | 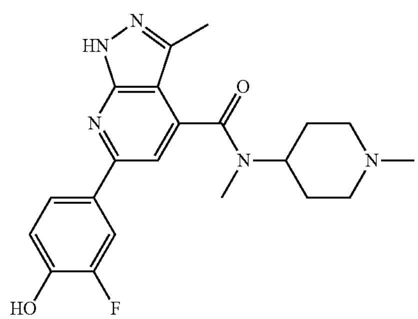 [SMILES: Cc1n[nH]c2nc(-c3ccc(O)c(F)c3)cc(C(=O)N(C)C3CCN(C)CC3)c12] | LC10 | 398.25 | 2.02 |
| 332 | 6-(3-Fluoro-4-hydroxy-phenyl)-3-methyl-1H-pyrazolo[3,4-b]pyridine-4-carboxylic acid (1-ethyl-piperidin-3-yl)-amide | 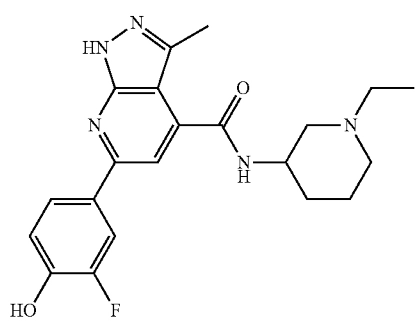 [SMILES: CCN1CCCC(NC(=O)c2cc(-c3ccc(O)c(F)c3)nc3[nH]nc(C)c23)C1] | LC10 | 398.24 | 2.04 |
| 333 | 6-(3-Fluoro-4-hydroxy-phenyl)-3-methyl-1H-pyrazolo[3,4-b]pyridine-4-carboxylic acid (1-aza-bicyclo[2.2.2]oct-3-yl)-amide | 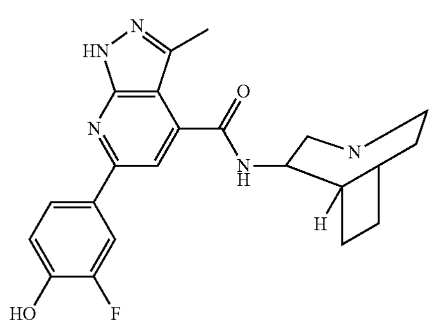 [SMILES: Cc1n[nH]c2nc(-c3ccc(O)c(F)c3)cc(C(=O)NC3CNCCC4CCC43)c12] | LC10 | 396.23 | 2.09 |

-continued

| Exp. No. | Name | Structure | LC/MS method | m/z [M + H]+ | R_t [min] |
|---|---|---|---|---|---|
| 334 | [6-(3-Fluoro-4-hydroxy-phenyl)-3-methyl-1H-pyrazolo[3,4-b]pyridin-4-yl]-((1S,5R)-9-hydroxy-1,5,7-trimethyl-3,7-diazabicyclo[3.3.1]non-3-yl)-methanone | 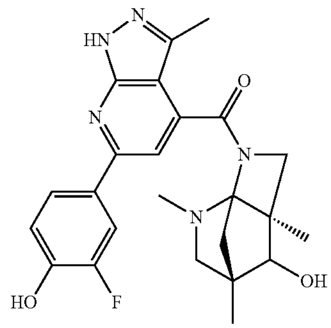 [SMILES: Cc1n[nH]c2nc(-c3ccc(O)c(F)c3)cc(C(=O)N3C[C@@]4(C)C(O)[C@]5(C)CN(C)C34C5)c12] | LC10 | 454.29 | 2.07 |
| 335 | 6-(3-Fluoro-4-hydroxy-phenyl)-3-methyl-1H-pyrazolo[3,4-b]pyridine-4-carboxylic acid methyl-piperidin-4-yl-amide | 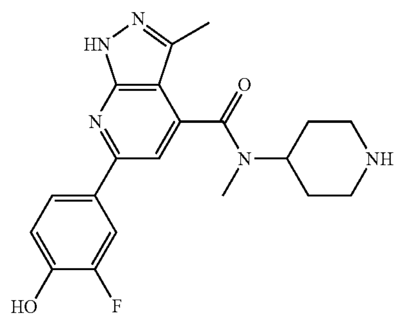 [SMILES: Cc1n[nH]c2nc(-c3ccc(O)c(F)c3)cc(C(=O)N(C)C3CCNCC3)c12] | LC10 | 384.23 | 2.14 |
| 336 | (3-Amino-pyrrolidin-1-yl)-[6-(3-fluoro-4-hydroxy-phenyl)-3-methyl-1H-pyrazolo[3,4-b]pyridin-4-yl]-methanone | 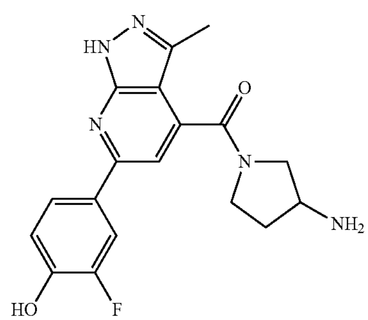 [SMILES: Cc1n[nH]c2nc(-c3ccc(O)c(F)c3)cc(C(=O)N3CCC(N)C3)c12] | LC10 | 356.22 | 1.93 |
| 337 | [6-(3-Fluoro-4-hydroxy-phenyl)-3-methyl-1H-pyrazolo[3,4-b]pyridin-4-yl]-((R)-3-methyl-piperazin-1-yl)-methanone | 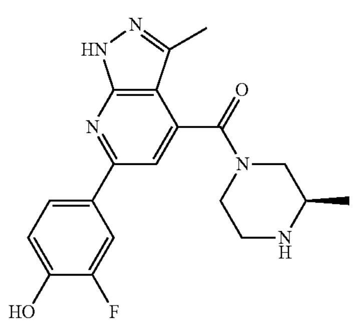 | LC10 | 370.23 | 1.99 |

-continued

| Exp. No. | Name | Structure | LC/MS method | m/z [M + H]+ | R_t [min] |
|---|---|---|---|---|---|
| 338 | 6-(3-Fluoro-4-hydroxy-phenyl)-3-methyl-1H-pyrazolo[3,4-b]pyridine-4-carboxylic acid (4-amino-cyclohexyl)-amide | 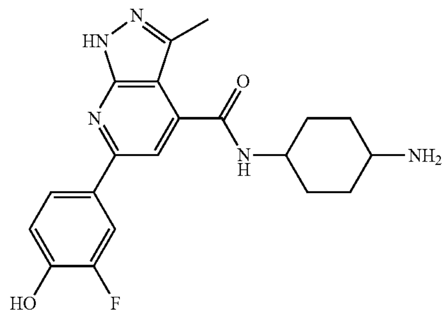 [SMILES: Cc1n[nH]c2nc(-c3ccc(O)c(F)c3)cc(C(=O)NC3CCC(N)CC3)c12] | LC10 | 384.26 | 2.02 |
| 339 | (2,7-Diaza-spiro[3.5]non-2-yl)-[6-(3-fluoro-4-hydroxy-phenyl)-3-methyl-1H-pyrazolo[3,4-b]pyridin-4-yl]-methanone | 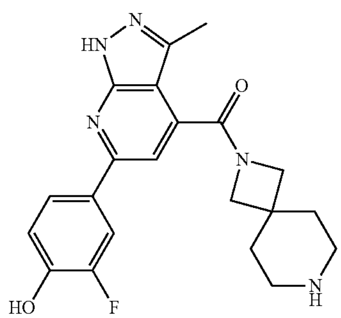 [SMILES: Cc1n[nH]c2nc(-c3ccc(O)c(F)c3)cc(C(=O)N3CC4(CCNCC4)C3)c12] | LC10 | 396.26 | 1.99 |
| 340 | (2,7-Diaza-spiro[4.4]non-2-yl)-[6-(3-fluoro-4-hydroxy-phenyl)-3-methyl-1H-pyrazolo[3,4-b]pyridin-4-yl]-methanone | 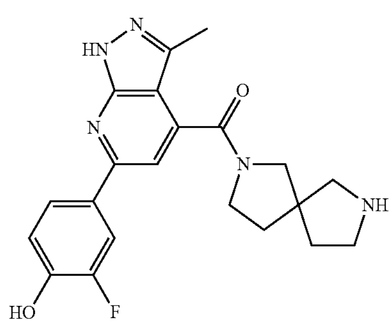 [SMILES: Cc1n[nH]c2nc(-c3ccc(O)c(F)c3)cc(C(=O)N3CCC4(CCNC4)C3)c12] | LC10 | 396.26 | 1.97 |
| 341 | (2,8-Diaza-spiro[4.5]dec-8-yl)-[6-(3-fluoro-4-hydroxy-phenyl)-3-methyl-1H-pyrazolo[3,4-b]pyridin-4-yl]-methanone | 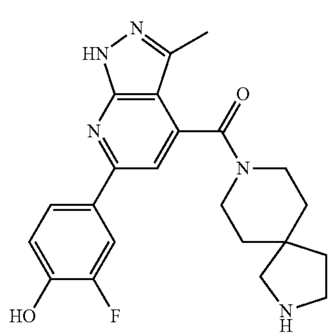 [SMILES: Cc1n[nH]c2nc(-c3ccc(O)c(F)c3)cc(C(=O)N3CCC4(CCNC4)CC3)c12] | LC10 | 410.26 | 2.1 |

-continued

| Exp. No. | Name | Structure | LC/MS method | m/z [M + H]+ | R_t [min] |
|---|---|---|---|---|---|
| 342 | [6-(3-Fluoro-4-hydroxy-phenyl)-3-methyl-1H-pyrazolo[3,4-b]pyridin-4-yl]-(1-oxa-4,9-diaza-spiro[5.5]undec-9-yl)-methanone | 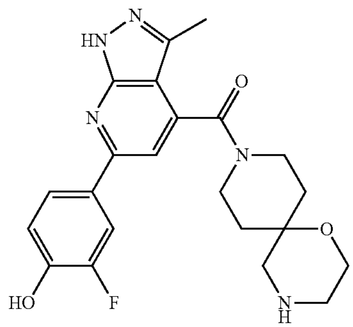 | LC10 | 426.27 | 2.04 |
| 343 | (2,8-Diaza-spiro[4.5]dec-2-yl)-[6-(3-fluoro-4-hydroxy-phenyl)-3-methyl-1H-pyrazolo[3,4-b]pyridin-4-yl]-methanone | 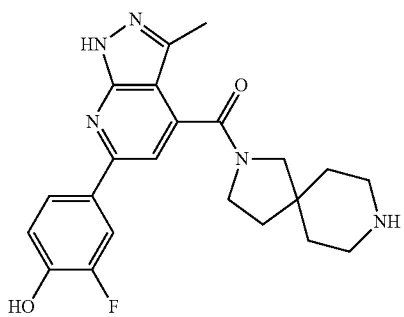 [SMILES: Cc1n[nH]c2nc(-c3ccc(O)c(F)c3)cc(C(=O)N3CCC4(CCNCC4)C3)c12] | LC10 | 410.27 | 2.04 |
| 344 | [6-(3-Fluoro-4-hydroxy-phenyl)-3-methyl-1H-pyrazolo[3,4-b]pyridin-4-yl]-(1-oxa-4,9-diaza-spiro[5.5]undec-4-yl)-methanone | 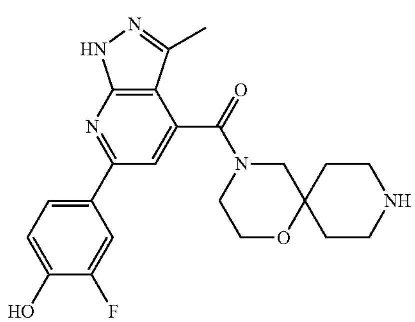 | LC10 | 426.28 | 2.05 |
| 345 | [6-(3-Fluoro-4-hydroxy-phenyl)-3-methyl-1H-pyrazolo[3,4-b]pyridin-4-yl]-(1-oxa-4,8-diaza-spiro[5.5]undec-8-yl)-methanone | 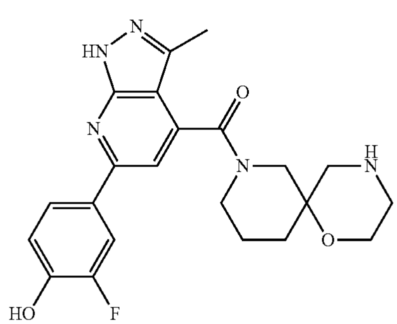 [SMILES: Cc1n[nH]c2nc(-c3ccc(O)c(F)c3)cc(C(=O)N3CCCC4(CNCCO4)C3)c12] | LC10 | 426.26 | 2.14 |

| Exp. No. | Name | Structure | LC/MS method | m/z [M + H]+ | R$_t$ [min] |
|---|---|---|---|---|---|
| 346 | (2,7-Diaza-spiro[4.5]dec-7-yl)-[6-(3-fluoro-4-hydroxy-phenyl)-3-methyl-1H-pyrazolo[3,4-b]pyridin-4-yl]-methanone | 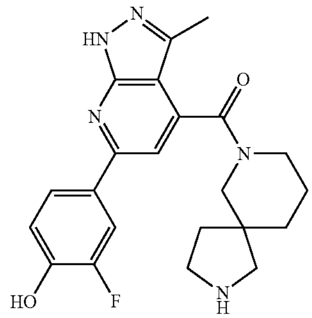 [SMILES: Cc1n[nH]c2nc(-c3ccc(O)c(F)c3)cc(C(=O)N3CCCC4(CCNC4)C3)c12] | LC10 | 410.27 | 2.10 |
| 347 | ((R)-3-Dimethyl-amino-pyrrolidin-1-yl)-[6-(3-fluoro-4-hydroxy-phenyl)-3-methyl-1H-pyrazolo[3,4-b]pyridin-4-yl]-methanone | 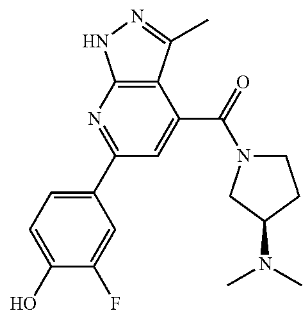 [SMILES: Cc1n[nH]c2nc(-c3ccc(O)c(F)c3)cc(C(=O)N3CC[C@@H](N(C)C)C3)c12] | LC10 | 384.26 | 1.99 |
| 348 | ((S)-3-Dimethyl-amino-pyrrolidin-1-yl)-[6-(3-fluoro-4-hydroxy-phenyl)-3-methyl-1H-pyrazolo[3,4-b]pyridin-4-yl]-methanone | 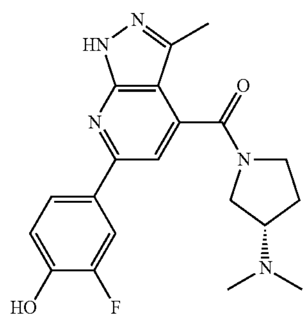 [SMILES: Cc1n[nH]c2nc(-c3ccc(O)c(F)c3)cc(C(=O)N3CC[C@H](N(C)C)C3)c12] | LC10 | 384.25 | 1.95 |
| 349 | 6-(3-Fluoro-4-hydroxy-phenyl)-3-methyl-1H-pyrazolo[3,4-b]pyridine-4-carboxylic acid piperidin-3-ylamide | 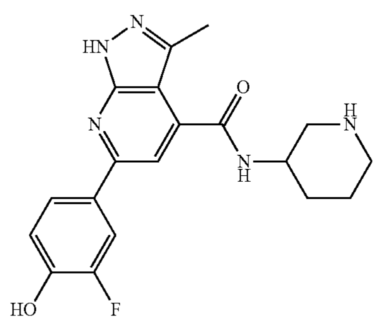 [SMILES: Cc1n[nH]c2nc(-c3ccc(O)c(F)c3)cc(C(=O)NC3CCCNC3)c12] | LC10 | 370.24 | 2.04 |
| 350 | 6-(3-Fluoro-4-hydroxy-phenyl)-3-methyl-1H-pyrazolo[3,4-b]pyridine-4-carboxylic acid (2-aza-bicyclo-[2.2.1]hept-5-yl)-amide | 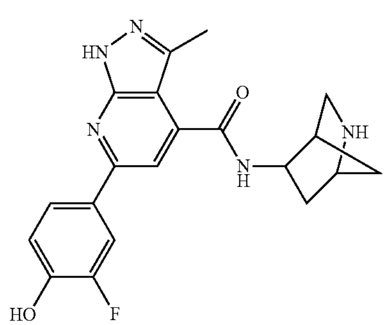 [SMILES: Cc1n[nH]c2nc(-c3ccc(O)c(F)c3)cc(C(=O)NC3CC4CC3CN4)c12] | LC10 | 382.22 | 2.09 |

-continued

| Exp. No. | Name | Structure | LC/MS method | m/z [M + H]+ | R_t [min] |
|---|---|---|---|---|---|
| 351 | [6-(3-Fluoro-4-hydroxy-phenyl)-3-methyl-1H-pyrazolo[3,4-b]pyridin-4-yl]-((S)-3-isobutyl-piperazin-1-yl)-methanone | 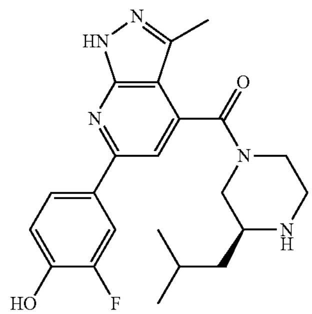 [SMILES: Cc1n[nH]c2nc(-c3ccc(O)c(F)c3)cc(C(=O)N3CCN[C@@H](CC(C)C)C3)c12] | LC10 | 412.26 | 2.27 |
| 352 | (2,3-Dimethyl-piperazin-1-yl)-[6-(3-fluoro-4-hydroxy-phenyl)-3-methyl-1H-pyrazolo[3,4-b]pyridin-4-yl]-methanone | 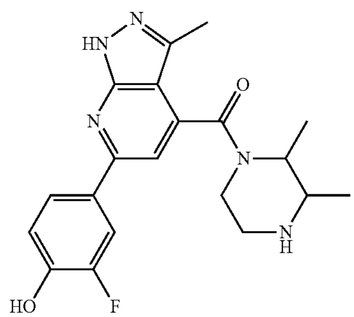 | LC10 | 384.25 | 2.05 |
| 353 | {1-[6-(3-Fluoro-4-hydroxy-phenyl)-3-methyl-1H-pyrazolo[3,4-b]pyridine-4-carbonyl]-piperazin-2-yl}-acetic acid methyl ester | 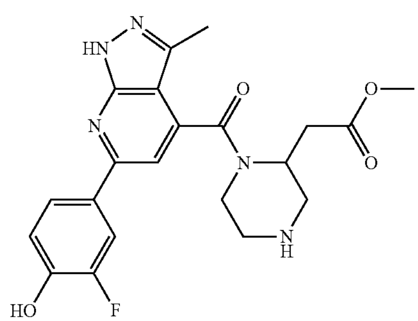 [SMILES: COC(=O)CC1CNCCN1C(=O)c1cc(-c2ccc(O)c(F)c2)nc2[nH]nc(C)c12] | LC10 | 428.23 | 2.14 |
| 354 | 6-(3-Fluoro-4-hydroxy-phenyl)-3-methyl-1H-pyrazolo[3,4-b]pyridine-4-carboxylic acid (pyrrolidin-3-yl-methyl)-amide | 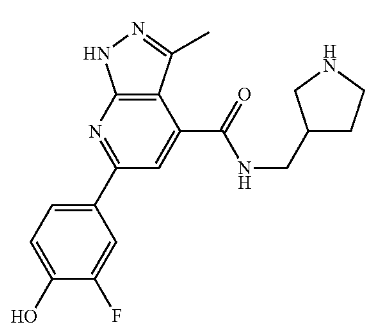 [SMILES: Cc1n[nH]c2nc(-c3ccc(O)c(F)c3)cc(C(=O)NCC3CCNC3)c12] | LC10 | 370.23 | 2.00 |

| Exp. No. | Name | Structure | LC/MS method | m/z [M + H]+ | R_t [min] |
|---|---|---|---|---|---|
| 355 | 6-(3-Fluoro-4-hydroxy-phenyl)-3-methyl-1H-pyrazolo[3,4-b]pyridine-4-carboxylic acid (1-methyl-piperidin-3-yl)-amide | 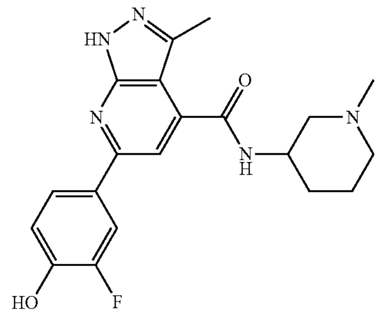 [SMILES: Cc1n[nH]c2nc(-c3ccc(O)c(F)c3)cc(C(=O)NC3CCCN(C)C3)c12] | LC10 | 384.23 | 2.05 |
| 356 | 1-{4-[6-(3-Fluoro-4-hydroxy-phenyl)-3-methyl-1H-pyrazolo[3,4-b]pyridine-4-carbonyl]-piperazin-1-yl}-ethanone | 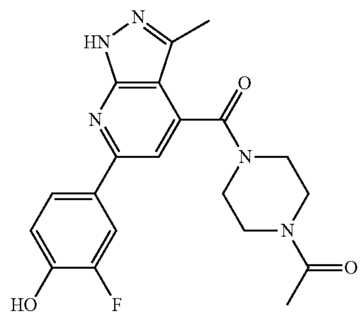 [SMILES: CC(=O)N1CCN(C(=O)c2cc(-c3ccc(O)c(F)c3)nc3[nH]nc(C)c23)CC1] | LC10 | 398.21 | 2.25 |
| 357 | 6-(3-Fluoro-4-hydroxy-phenyl)-3-methyl-1H-pyrazolo[3,4-b]pyridine-4-carboxylic acid (1-acetyl-piperidin-4-yl)-amide | 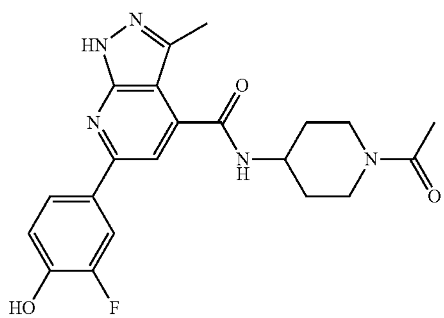 [SMILES: CC(=O)N1CCC(NC(=O)c2cc(-c3ccc(O)c(F)c3)nc3[nH]nc(C)c23)CC1] | LC10 | 412.24 | 2.30 |
| 358 | (5-Ethyl-2,5-diaza-bicyclo[2.2.1]hept-2-yl)-[8-(3-fluoro-4-hydroxy-phenyl)-3-methyl-1H-pyrazolo[3,4-b]pyridin-4-yl]-methanone | 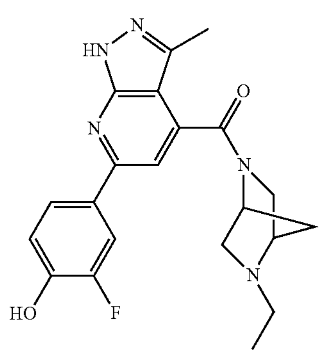 [SMILES: CCN1CC2CC1CN2C(=O)c1cc(-c2ccc(O)c(F)c2)nc2[nH]nc(C)c12] | LC10 | 396.26 | 2.00 |

-continued

| Exp. No. | Name | Structure | LC/MS method | m/z [M + H]+ | R_t [min] |
|---|---|---|---|---|---|
| 359 | 6-(3-Fluoro-4-hydroxy-phenyl)-3-methyl-1H-pyrazolo[3,4-b]pyridine-4-carboxylic acid (5-oxo-pyrrolidin-2-ylmethyl)-amide | 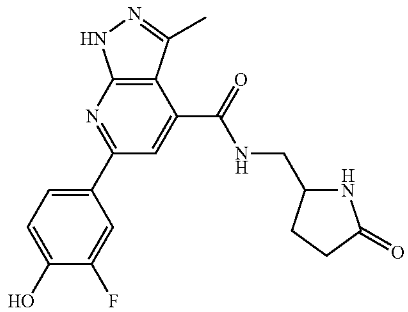 [SMILES: Cc1n[nH]c2nc(-c3ccc(O)c(F)c3)cc(C(=O)NCC3CCC(=O)N3)c12] | LC10 | 384.20 | 2.22 |
| 360 | 6-(3-Fluoro-4-hydroxy-phenyl)-3-methyl-1H-pyrazolo[3,4-b]pyridine-4-carboxylic acid (1-cyclohexyl-piperidin-4-yl)-amide | 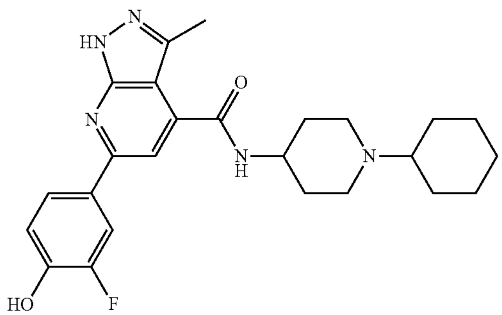 [SMILES: Cc1n[nH]c2nc(-c3ccc(O)c(F)c3)cc(C(=O)NC3CCN(C4CCCCC4)CC3)c12] | LC10 | 452.31 | 2.32 |
| 361 | (R)-6-(3-Fluoro-4-hydroxy-phenyl)-3-methyl-1H-pyrazolo[3,4-b]pyridine-4-carboxylic acid (1-aza-bicyclo-[2.2.2]oct-3-yl)-amide | 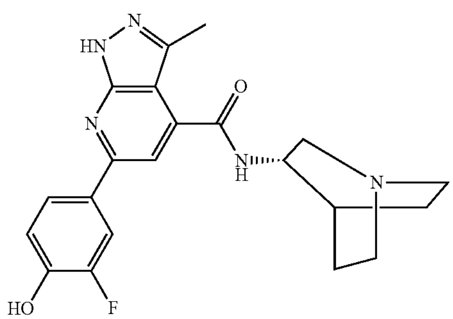 [SMILES: Cc1n[nH]c2nc(-c3ccc(O)c(F)c3)cc(C(=O)N[C@@H]3CN4CCC3CC4)c12] | LC10 | 396.26 | 2.09 |
| 362 | 6-(3-Fluoro-4-hydroxy-phenyl)-3-methyl-1H-pyrazolo[3,4-b]pyridine-4-carboxylic acid [2-methyl-2-(4-methyl-piperazin-1-yl)-propyl]-amide | 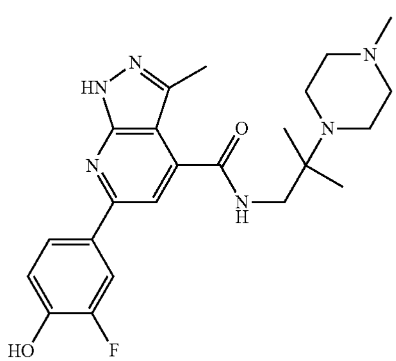 [SMILES: Cc1n[nH]c2nc(-c3ccc(O)c(F)c3)cc(C(=O)NCC(C)(C)N3CCN(C)CC3)c12] | LC10 | 441.32 | 2.05 |

| Exp. No. | Name | Structure | LC/MS method | m/z [M + H]+ | R$_t$ [min] |
|---|---|---|---|---|---|
| 363 | 6-(3-Fluoro-4-hydroxy-phenyl)-3-methyl-1H-pyrazolo[3,4-b]pyridine-4-carboxylic acid (3-amino-2,2-dimethyl-propyl)-amide | 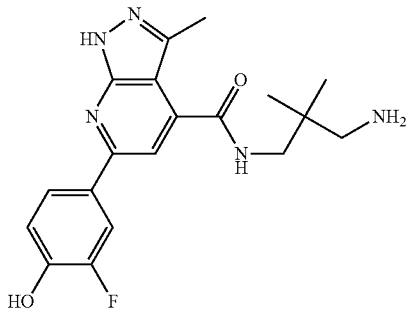 [SMILES: Cc1n[nH]c2nc(-c3ccc(O)c(F)c3)cc(C(=O)NCC(C)(C)CN)c12] | LC10 | 372.23 | 2.05 |
| 364 | 6-(3-Fluoro-4-hydroxy-phenyl)-3-methyl-1H-pyrazolo[3,4-b]pyridine-4-carboxylic acid (1,2,2,6,6-pentamethyl-piperidin-4-yl)-amide | 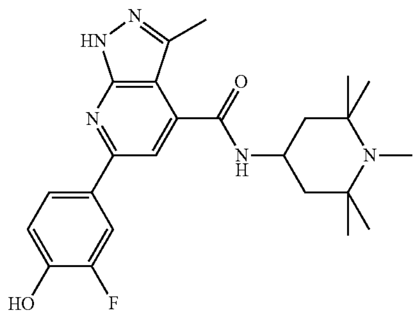 [SMILES: Cc1n[nH]c2nc(-c3ccc(O)c(F)c3)cc(C(=O)NC3CC(C)(C)N(C)C(C)(C)C3)c12] | LC10 | 440.31 | 2.18 |
| 365 | [6-(3-Fluoro-4-hydroxy-phenyl)-3-methyl-1H-pyrazolo[3,4-b]pyridin-4-yl]-(4-methyl-[1,4]diazepan-1-yl)-methanone | 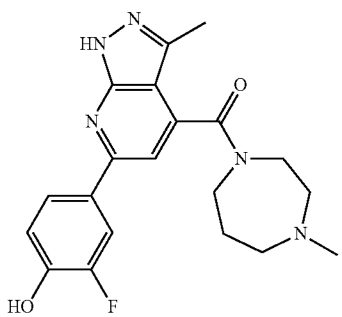 [SMILES: Cc1n[nH]c2nc(-c3ccc(O)c(F)c3)cc(C(=O)N3CCCN(C)CC3)c12] | LC10 | 384.24 | 1.97 |
| 366 | (4-Ethyl-[1,4]-diazepan-1-yl)-[6-(3-fluoro-4-hydroxy-phenyl)-3-methyl-1H-pyrazolo[3,4-b]pyridin-4-yl]-methanone | 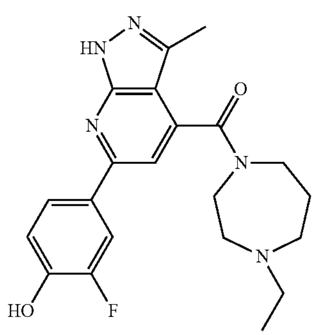 [SMILES: CCN1CCCN(C(=O)c2cc(-c3ccc(O)c(F)c3)nc3[nH]nc(C)c23)CC1] | LC10 | 398.27 | 2.02 |
| 367 | 6-(3-Fluoro-4-hydroxy-phenyl)-3-methyl-1H-pyrazolo[3,4-b]pyridine-4-carboxylic acid (piperidin-2-yl-methyl)-amide | 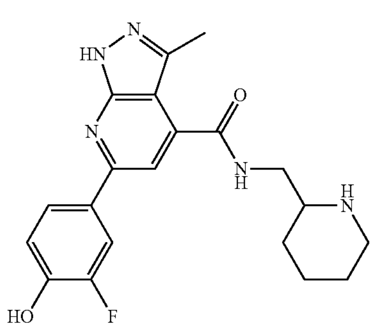 | LC11 | 384.17 | 2.02 |

-continued

| Exp. No. | Name | Structure | LC/MS method | m/z [M + H]⁺ | R_t [min] |
|---|---|---|---|---|---|
| 368 | 4-[6-(3-Fluoro-4-hydroxy-phenyl)-3-methyl-1H-pyrazolo[3,4-b]pyridine-4-carbonyl]-6-isopropylzin-2-one | 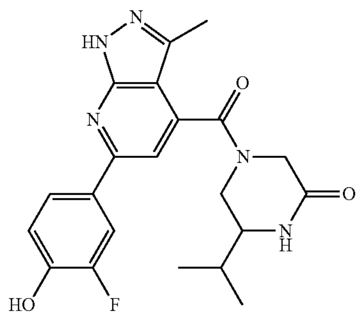 [SMILES: Cc1n[nH]c2nc(-c3ccc(O)c(F)c3)cc(C(=O)N3CC(=O)NC(C(C)C)C3)c12] | LC10 | 412.23 | 2.43 |
| 369 | [6-(3-Fluoro-4-hydroxy-phenyl)-3-methyl-1H-pyrazolo[3,4-b]pyridin-4-yl]-(3-phenyl-hexahydro-pyrrolo[1,2-a]pyrazin-2-yl)-methanone | 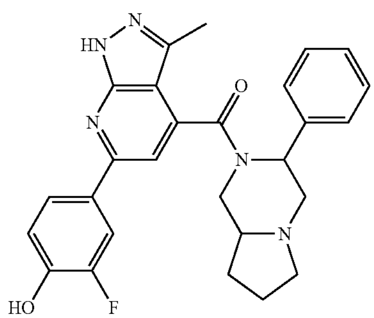 [SMILES: Cc1n[nH]c2nc(-c3ccc(O)c(F)c3)cc(C(=O)N3CC4CCCN4CC3c3ccccc3)c12] | LC10 | 472.26 | 2.32 |
| 370 | 6-(3-Fluoro-4-hydroxy-phenyl)-3-methyl-1H-pyrazolo[3,4-b]pyridine-4-carboxylic acid (2-pyridin-2-yl-2-pyrrolidin-1-yl-propyl)-amide | 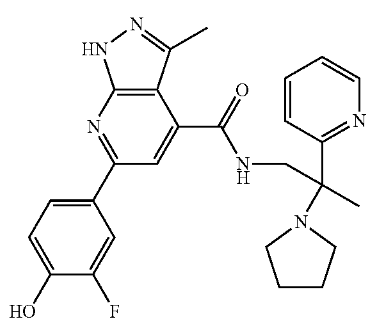 [SMILES: Cc1n[nH]c2nc(-c3ccc(O)c(F)c3)cc(C(=O)NCC(C)(c3ccccn3)N3CCCC3)c12] | LC10 | 475.28 | 2.25 |
| 371 | 6-(3-Fluoro-4-hydroxy-phenyl)-3-methyl-1H-pyrazolo[3,4-b]pyridine-4-carboxylic acid (2-methyl-2-pyridin-2-yl-3-pyrrolidin-1-yl-propyl)-amide | 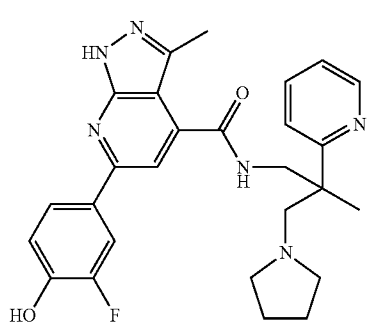 [SMILES: Cc1n[nH]c2nc(-c3ccc(O)c(F)c3)cc(C(=O)NCC(C)(CN3CCCC3)c3ccccn3)c12] | LC10 | 489.30 | 2.25 |

Example 372

[6-(4-Hydroxy-phenyl)-3-methyl-1H-pyrazolo[3,4-b]pyridin-4-yl]-(4-methyl-2-phenyl-piperazin-1-yl)-methanone

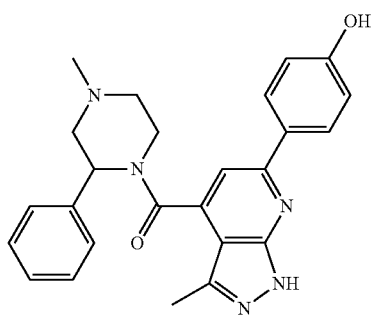 [SMILES: Cc1n[nH]c2nc(-c3ccc(O)cc3)cc(C(=O)N3CCN(C)CC3c3ccccc3)c12]

1-Methyl-3-phenyl-piperazine (31.7 mg, 0.18 mmol) were weighted into a reaction vial and dissolved in 1 ml THF. 1 ml of a DMF stock solution containing N-methylmorpholine (51 mg, 0.5 mmol), 6-(4-Hydroxy-phenyl)-3-methyl-1H-pyrazolo[3,4-b]pyridine-4-carboxylic acid (48 mg, 0.18 mmol), and HOBt (28 mg, 0.21 mmol) was added, followed by EDC (32 mg, 0.21 mmol). The vial was closed with a screw cap and shaken at r.t. over night. The mixture was treated with 0.1 ml TFA, filtered and purified by preparative HPLC to give the TFA salt. Conversion of the TFA salt into the HCl salt (and deprotection of amines containing a BOC-protection group) was achieved by shaking the compound with 2 ml 4M HCl in dioxane at r.t. overnight. Then 5 ml water were added and the mixture was freeze-dried to obtain the final product as the hydrochloride salt (17 mg, 19%).

LC/MS (Method LC10): $R_t$=2.23 min; m/z=428.22 [M+H]$^+$.

$^1$H-NMR (500 MHz, d6-DMSO): 2.30 (s, 1H), 2.63 (s, 3H), 2.85-2.95 (m, 2H), 3.62-3.68 (m, 4H), 4.31-4.43 (m, 1H), 6.22 (m, 1H), 6.90 (d, 2H), 7.2-7.6 (m, 4H), 7.70 (s, 1H), 8.07 (d, 2H).

The following examples have been prepared following a similar procedure as described for [6-(4-hydroxy-phenyl)-3-methyl-1H-pyrazolo[3,4-b]pyridin-4-yl]-(4-methyl-2-phenyl-piperazin-1-yl)-methanone (Example 372), starting from the respective amine precursors and 6-(4-hydroxy-phenyl)-3-methyl-1H-pyrazolo[3,4-b]pyridine-4-carboxylic acid:

| Exp. No. | Name | Structure | LC/MS method | m/z [M + H]$^+$ | $R_t$ [min] |
|---|---|---|---|---|---|
| 373 | 6-(4-Hydroxy-phenyl)-3-methyl-1H-pyrazolo[3,4-b]pyridine-4-carboxylic acid (2,3-dihydro-spiro[1H-indene-1,4'-piperidin]-3-yl)-amide | 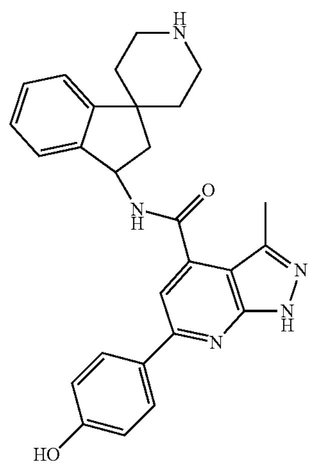 [SMILES: Cc1n[nH]c2nc(-c3ccc(O)cc3)cc(C(=O)NC3CC4(CCNCC4)c4ccccc43)c12] | LC8 | 454.30 | 2.61 |
| 374 | [6-(4-Hydroxy-phenyl)-3-methyl-1H-pyrazolo[3,4-b]pyridin-4-yl]-(2-pyridin-3-yl-piperazin-1-yl)-methanone | 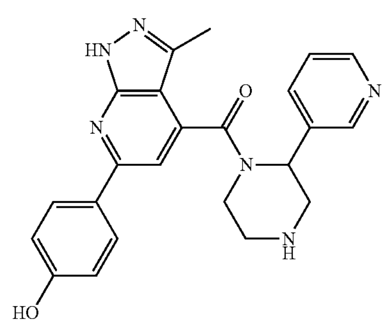 [SMILES: Cc1n[nH]c2nc(-c3ccc(O)cc3)cc(C(=O)N3CCNCC3c3cccnc3)c12] | LC8 | 415.25 | 2.02 |

-continued

| Exp. No. | Name | Structure | LC/MS method | m/z [M + H]+ | R$_t$ [min] |
|---|---|---|---|---|---|
| 375 | (3-Benzyl-piperazin-1-yl)-[6-(4-hydroxy-phenyl)-3-methyl-1H-pyrazolo[3,4-b]pyridin-4-yl]-methanone | 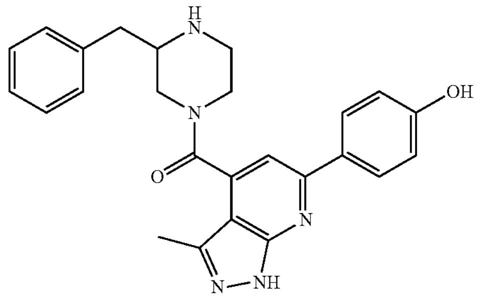 [SMILES: Cc1n[nH]c2nc(-c3ccc(O)cc3)cc(C(=O)N3CCNC(Cc4ccccc4)C3)c12] | LC8 | 428.31 | 2.46 |
| 376 | 6-(4-Hydroxy-phenyl)-3-methyl-1H-pyrazolo[3,4-b]pyridine-4-carboxylic acid [2-dimethylamino-2-(4-methoxy-phenyl)-ethyl]-amide | 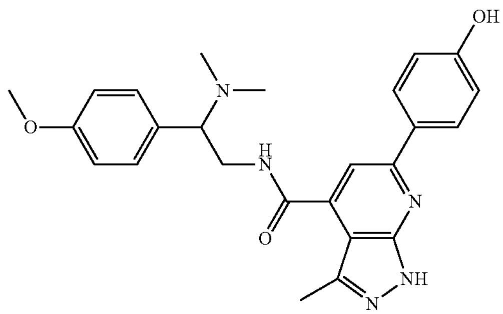 [SMILES: COc1ccc(C(CNC(=O)c2cc(-c3ccc(O)cc3)nc3[nH]nc(C)c23)N(C)C)cc1] | LC10 | 446.26 | 2.18 |
| 377 | 6-(4-Hydroxy-phenyl)-3-methyl-1H-pyrazolo[3,4-b]pyridine-4-carboxylic acid (1-phenyl-2-pyrrolidin-1-yl-ethyl)-amide | 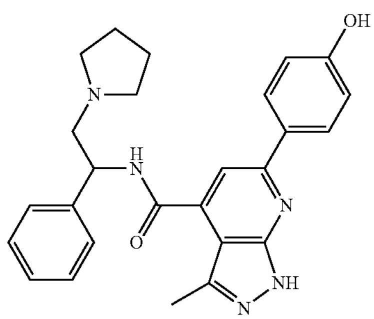 [SMILES: Cc1n[nH]c2nc(-c3ccc(O)cc3)cc(C(=O)NC(CN3CCCC3)c3ccccc3)c12] | LC10 | 442.25 | 2.35 |
| 378 | [2-(4-Chloro-phenyl)-piperazin-1-yl]-[6-(4-hydroxy-phenyl)-3-methyl-1H-pyrazolo[3,4-b]pyridin-4-yl]-methanone | 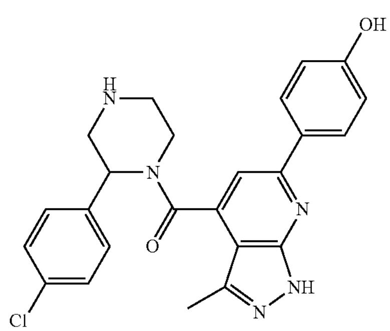 [SMILES: Cc1n[nH]c2nc(-c3ccc(O)cc3)cc(C(=O)N3CCNCC3c3ccc(Cl)cc3)c12] | LC8 | 448.26 | 2.71 |

-continued

| Exp. No. | Name | Structure | LC/MS method | m/z [M + H]+ | R_t [min] |
|---|---|---|---|---|---|
| 379 | {4-[6-(4-Hydroxy-phenyl)-3-methyl-1H-pyrazolo[3,4-b]pyridine-4-carbonyl]-piperazin-1-yl}-pyrrolidin-1-yl-methanone | 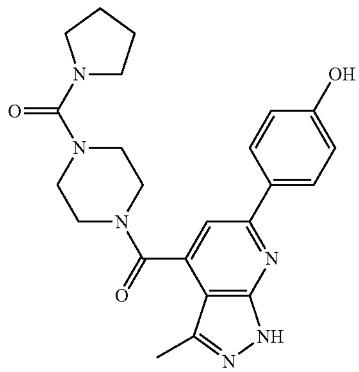 [SMILES: Cc1n[nH]c2nc(-c3ccc(O)cc3)cc(C(=O)N3CCN(C(=O)N4CCCC4)CC3)c12] | LC8 | 435.26 | 2.93 |
| 380 | [4-(Furan-3-carbonyl)-piperazin-1-yl]-[6-(4-hydroxy-phenyl)-3-methyl-1H-pyrazolo[3,4-b]pyridin-4-yl]-methanone | 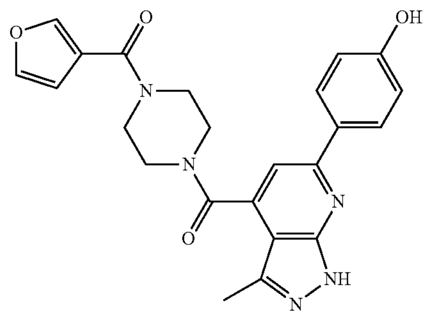 [SMILES: Cc1n[nH]c2nc(-c3ccc(O)cc3)cc(C(=O)N3CCN(C(=O)c4ccoc4)CC3)c12] | LC8 | 432.21 | 2.85 |
| 381 | [6-(4-Hydroxy-phenyl)-3-methyl-1H-pyrazolo[3,4-b]pyridin-4-yl]-[4-(2-methoxy-benzoyl)-piperazin-1-yl]-methanone | 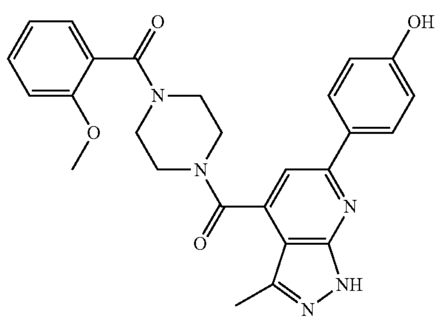 [SMILES: COc1ccccc1C(=O)N1CCN(C(=O)c2cc(-c3ccc(O)cc3)nc3[nH]nc(C)c23)CC1] | LC8 | 472.24 | 3.14 |
| 382 | 6-(4-Hydroxy-phenyl)-3-methyl-1H-pyrazolo[3,4-b]pyridine-4-carboxylic acid (1-phenethyl-piperidin-4-yl)-amide | 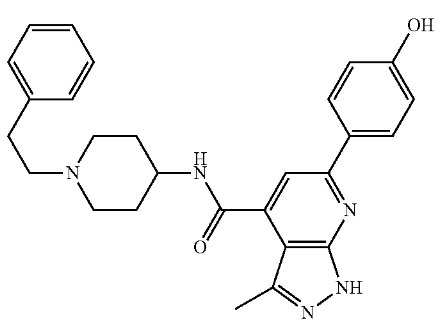 [SMILES: Cc1n[nH]c2nc(-c3ccc(O)cc3)cc(C(=O)NC3CCN(CCc4ccccc4)CC3)c12] | LC8 | 456.32 | 2.70 |

-continued

| Exp. No. | Name | Structure | LC/MS method | m/z [M + H]+ | R_t [min] |
|---|---|---|---|---|---|
| 383 | (S)-Hexahydro-pyrrolo[1,2-a]pyrazin-2-yl-[6-(4-hydroxy-phenyl)-3-methyl-1H-pyrazolo[3,4-b]-pyridin-4-yl]-methanone | 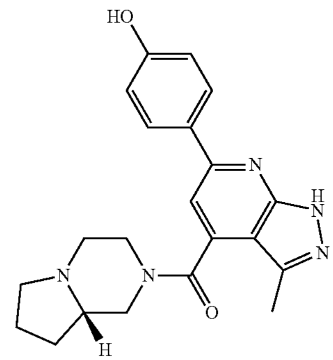 [SMILES: Cc1n[nH]c2nc(-c3ccc(O)cc3)cc(C(=O)N3CCN4CCC[C@H]4C3)c12] | LC8 | 378.27 | 2.05 |
| 384 | 6-(4-Hydroxy-phenyl)-3-methyl-1H-pyrazolo[3,4-b]pyridine-4-car-boxylic acid (1-benzyl-pyrrolidin-3-yl)-amide | 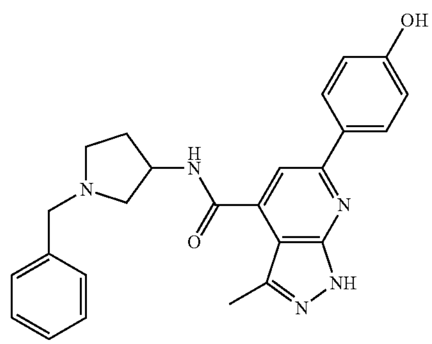 [SMILES: Cc1n[nH]c2nc(-c3ccc(O)cc3)cc(C(=O)NC3CCN(Cc4ccccc4)C3)c12] | LC8 | 428.31 | 2.57 |
| 385 | [6-(4-Hydroxy-phenyl)-3-methyl-1H-pyrazolo[3,4-b]pyridin-4-yl]-(3-phenylamino-pyrrolidin-1-yl)-methanone | 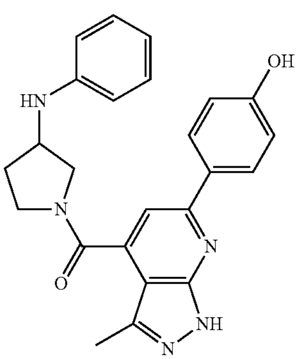 [SMILES: Cc1n[nH]c2nc(-c3ccc(O)cc3)cc(C(=O)N3CCC(Nc4ccccc4)C3)c12] | LC8 | 414.27 | 3.47 |
| 386 | (5-Benzyl-hexa-hydro-pyrrolo[3,4-c]pyrrol-2-yl)-[6-(4-hydroxy-phenyl)-3-methyl-1H-pyra-zolo[3,4-b]pyridin-4-yl]-methanone | 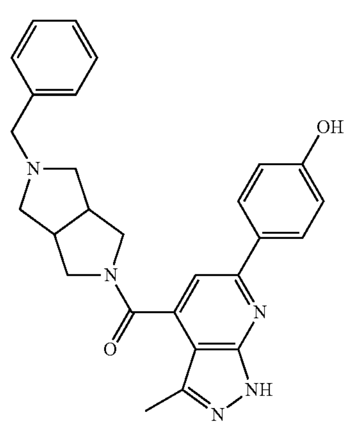 [SMILES: Cc1n[nH]c2nc(-c3ccc(O)cc3)cc(C(=O)N3CC4CN(Cc5ccccc5)CC4C3)c12] | LC8 | 454.30 | 2.47 |

-continued

| Exp. No. | Name | Structure | LC/MS method | m/z [M + H]+ | R_t [min] |
|---|---|---|---|---|---|
| 387 | [6-(4-Hydroxy-phenyl)-3-methyl-1H-pyrazolo[3,4-b]pyridin-4-yl]-[4-(pyridine-4-carbonyl)-[1,4]diazepan-1-yl]-methanone | 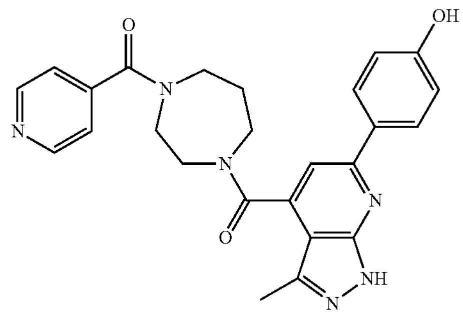 [SMILES: Cc1n[nH]c2nc(-c3ccc(O)cc3)cc(C(=O)N3CCCN(C(=O)c4ccncc4)CC3)c12] | LC8 | 457.29 | 2.31 |
| 388 | 6-(4-Hydroxy-phenyl)-3-methyl-1H-pyrazolo[3,4-b]pyridine-4-carboxylic acid [2-(3-phenyl-pyrrolidin-1-yl)-ethyl]-amide | 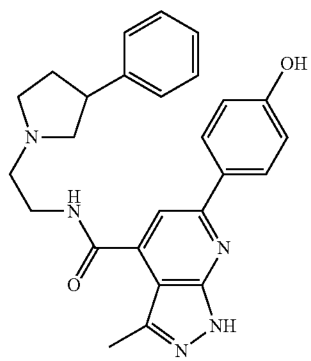 [SMILES: Cc1n[nH]c2nc(-c3ccc(O)cc3)cc(C(=O)NCCN3CCC(c4ccccc4)C3)c12] | LC1 | 442.22 | 0.96 |
| 389 | 6-(4-Hydroxy-phenyl)-3-methyl-1H-pyrazolo[3,4-b]pyridine-4-carboxylic acid (2-pyrrolidin-1-yl-propyl)-amide | 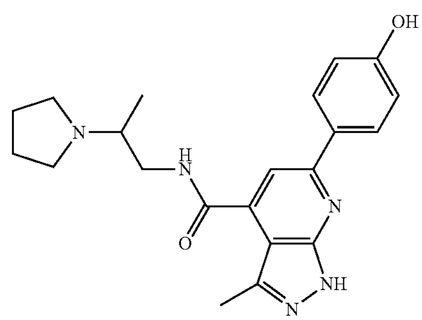 [SMILES: Cc1n[nH]c2nc(-c3ccc(O)cc3)cc(C(=O)NCC(C)N3CCCC3)c12] | LC1 | 380.2 | 0.8 |
| 390 | 6-(4-Hydroxy-phenyl)-3-methyl-1H-pyrazolo[3,4-b]pyridine-4-carboxylic acid [2-(4-phenyl-piperidin-1-yl)-ethyl]-amide | 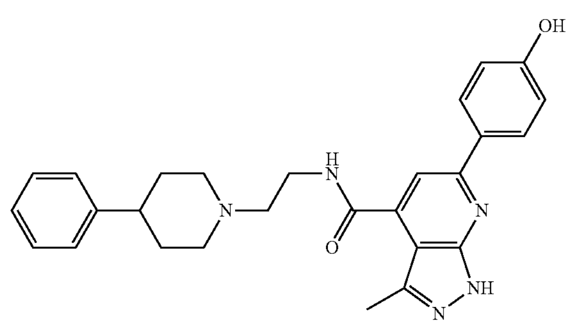 [SMILES: Cc1n[nH]c2nc(-c3ccc(O)cc3)cc(C(=O)NCCN3CCC(c4ccccc4)CC3)c12] | LC1 | 456.25 | 0.99 |

-continued

| Exp. No. | Name | Structure | LC/MS method | m/z [M + H]⁺ | R_f [min] |
|---|---|---|---|---|---|
| 391 | 6-(4-Hydroxy-phenyl)-3-methyl-1H-pyrazolo[3,4-b]pyridine-4-carboxylic acid (2-phenyl-2-pyrrolidin-1-yl-ethyl)-amide | 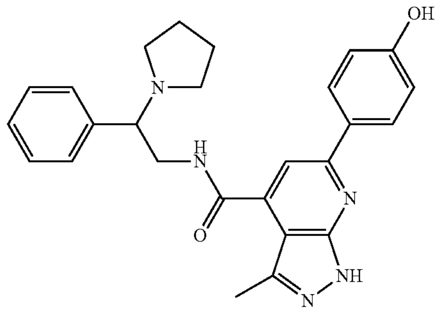 [SMILES: Cc1n[nH]c2nc(-c3ccc(O)cc3)cc(C(=O)NCC(c3ccccc3)N3CCCC3)c12] | LC1 | 442.22 | 0.9 |
| 392 | 6-(4-Hydroxy-phenyl)-3-methyl-1H-pyrazolo[3,4-b]pyridine-4-carboxylic acid (1-benzyl-piperidin-4-yl)-amide | 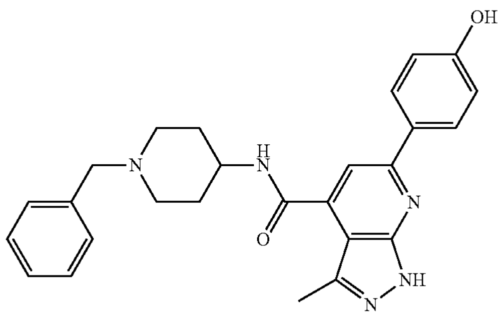 [SMILES: Cc1n[nH]c2nc(-c3ccc(O)cc3)cc(C(=O)NC3CCN(Cc4ccccc4)CC3)c12] | LC1 | 442.24 | 0.89 |
| 393 | 6-(4-Hydroxy-phenyl)-3-methyl-1H-pyrazolo[3,4-b]pyridine-4-carboxylic acid (2-phenyl-2-piperazin-1-yl-ethyl)-amide | 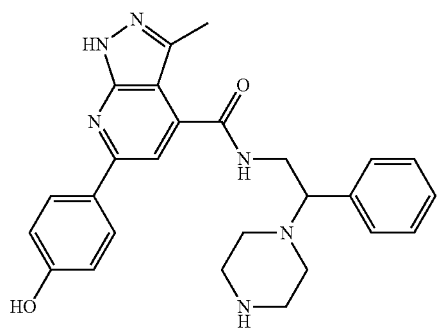 [SMILES: Cc1n[nH]c2nc(-c3ccc(O)cc3)cc(C(=O)NCC(c3ccccc3)N3CCNCC3)c12] | LC1 | 457.25 | 0.88 |
| 394 | 6-(4-Hydroxy-phenyl)-3-methyl-1H-pyrazolo[3,4-b]pyridine-4-carboxylic acid (2-morpholin-4-yl-2-phenyl-ethyl)-amide | 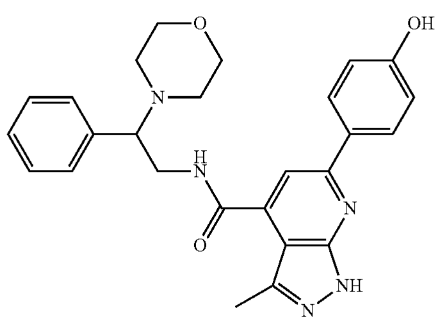 [SMILES: Cc1n[nH]c2nc(-c3ccc(O)cc3)cc(C(=O)NCC(c3ccccc3)N3CCOCC3)c12] | LC1 | 458.23 | 0.88 |
| 395 | 6-(4-Hydroxy-phenyl)-3-methyl-1H-pyrazolo[3,4-b]pyridine-4-carboxylic acid (2-piperidin-4-yl-ethyl)-amide | 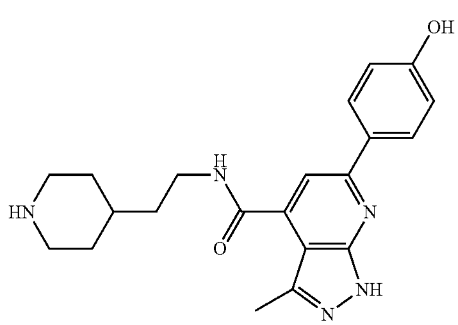 [SMILES: Cc1n[nH]c2nc(-c3ccc(O)cc3)cc(C(=O)NCCC3CCNCC3)c12] | LC12 | 380.43 | 2.19 |

| Exp. No. | Name | Structure | LC/MS method | m/z [M + H]⁺ | R_t [min] |
|---|---|---|---|---|---|
| 396 | 6-(4-Hydroxy-phenyl)-3-methyl-1H-pyrazolo[3,4-b]pyridine-4-carboxylic acid (4-dimethylamino-cyclohexyl)-amide | 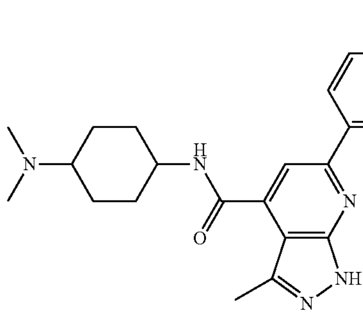 | LC1 | 394.3 | 0.65 |

The following examples have been prepared following a similar procedure as described for [6-(4-hydroxy-phenyl)-3-methyl-1H-pyrazolo[3,4-b]pyridin-4-0]-(4-methyl-2-phenyl-piperazin-1-yl)-methanone (Example 372), starting from the respective amine precursors and 6-(4-hydroxy-phenyl)-3-trifluoroethyl-1H-pyrazolo[3,4-b]pyridine-4-carboxylic acid:

| Exp. No. | Name | Structure | LC/MS method | m/z [M + H]⁺ | Rt [min] |
|---|---|---|---|---|---|
| 397 | [6-(4-Hydroxy-phenyl)-3-trifluoro-methyl-1H-pyrazolo[3,4-b]pyridin-4-yl]-((S)-3-methyl-piperazin-1-yl)-methanone | 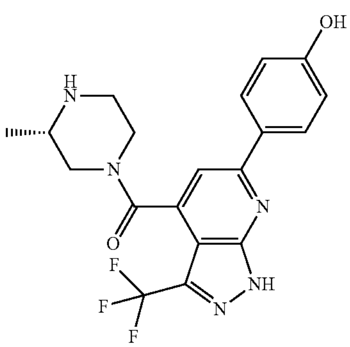 [SMILES: C[C@H]1CN(C(=O)c2cc(-c3ccc(O)cc3)nc3[nH]nc(C(F)(F)F)c23)CCN1] | LC10 | 406.21 | 2.17 |
| 398 | 6-(4-Hydroxy-phenyl)-3-trifluoro-methyl-1H-pyrazolo[3,4-b]pyridine-4-carboxylic acid (R)-piperidin-3-yl-amide | 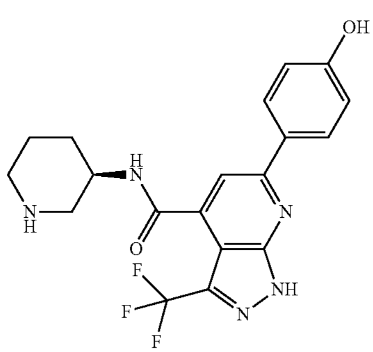 [SMILES: O=C(N[C@@H]1CCCNC1)c1cc(-c2ccc(O)cc2)nc2[nH]nc(C(F)(F)F)c12] | LC10 | 406.20 | 2.14 |

| Exp. No. | Name | Structure | LC/MS method | m/z [M + H]+ | Rt [min] |
|---|---|---|---|---|---|
| 399 | (4-Amino-piperidin-1-yl)-[6-(4-hydroxy-phenyl)-3-trifluoromethyl-1H-pyrazolo[3,4-b]pyridin-4-yl]-methanone | 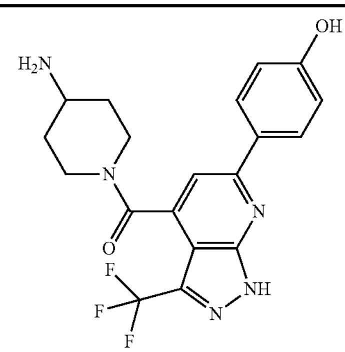 | LC10 | 406.22 | 2.07 |
| 400 | (Hexahydro-pyrrolo[3,4-c]-pyrrol-2-yl)-[6-(4-hydroxy-phenyl)-3-trifluoromethyl-1H-pyrazolo[3,4-b]-pyridin-4-yl]-methanone | 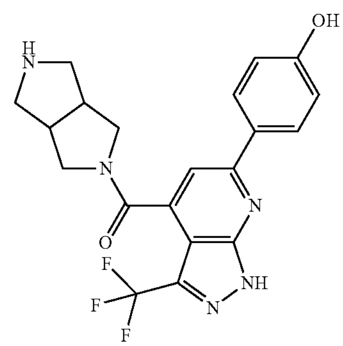 [SMILES: O=C(c1cc(-c2ccc(O)cc2)nc2[nH]nc(C(F)(F)F)c12)N1CC2CNCC2C1] | LC10 | 418.21 | 2.04 |
| 401 | [6-(4-Hydroxy-phenyl)-3-trifluoromethyl-1H-pyrazolo[3,4-b]pyridin-4-yl]-((R)-3-methyl-piperazin-1-yl)-methanone | 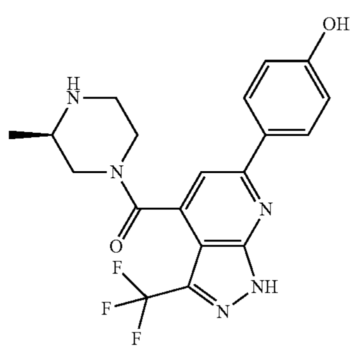 [SMILES: C[C@@H]1CN(C(=O)c2cc(-c3ccc(O)cc3)nc3[nH]nc(C(F)(F)F)c23)CCN1] | LC10 | 406.21 | 2.15 |
| 402 | 6-(4-Hydroxy-phenyl)-3-trifluoromethyl-1H-pyrazolo[3,4-b]pyridine-4-carboxylic acid azetidin-3-ylamide | 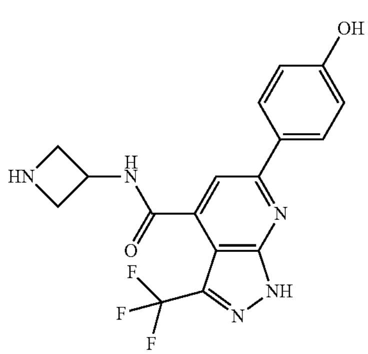 [SMILES: O=C(NC1CNC1)c1cc(-c2ccc(O)cc2)nc2[nH]nc(C(F)(F)F)c12] | LC10 | 378.18 | 2.02 |

| Exp. No. | Name | Structure | LC/MS method | m/z [M + H]+ | Rt [min] |
|---|---|---|---|---|---|
| 403 | (2,7-Diaza-spiro[3.5]non-2-yl)-[6-(4-hydroxy-phenyl)-3-trifluoro-methyl-1H-pyrazolo[3,4-b]pyridin-4-yl]-methanone | 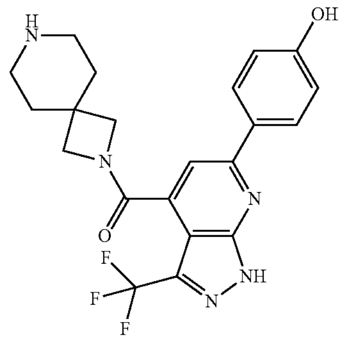 [SMILES: O=C(c1cc(-c2ccc(O)cc2)nc2[nH]nc(C(F)(F)F)c12)N1CC2(CCNCC2)C1] | LC10 | 432.23 | 2.10 |
| 404 | ((S)-3-Amino-pyrrolidin-1-yl)-[6-(4-hydroxy-phenyl)-3-trifluoro-methyl-1H-pyrazolo[3,4-b]pyridin-4-yl]-methanone | 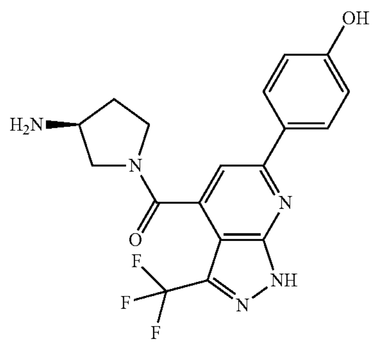 [SMILES: N[C@H]1CCN(C(=O)c2cc(-c3ccc(O)cc3)nc3[nH]nc(C(F)(F)F)c23)C1] | LC10 | 392.20 | 2.04 |
| 405 | (2,7-Diaza-spiro[3.5]non-7-yl)-[6-(4-hydroxy-phenyl)-3-trifluoro-methyl-1H-pyrazolo[3,4-b]pyridin-4-yl]-methanone | 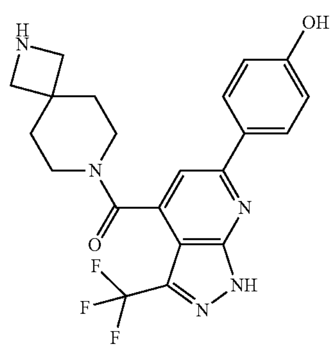 [SMILES: O=C(c1cc(-c2ccc(O)cc2)nc2[nH]nc(C(F)(F)F)c12)N1CCC2(CC1)CNC2] | LC10 | 432.23 | 2.09 |
| 406 | [6-(4-Hydroxy-phenyl)-3-trifluoro-methyl-1H-pyrazolo[3,4-b]pyridin-4-yl]-(3-methyl-amino-pyrrolidin-1-yl)-methanone | 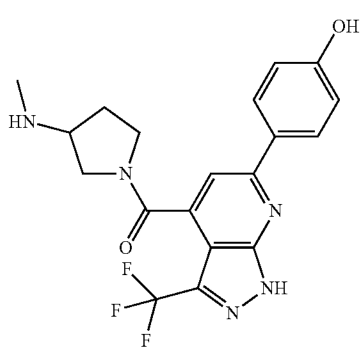 [SMILES: CNC1CCN(C(=O)c2cc(-c3ccc(O)cc3)nc3[nH]nc(C(F)(F)F)c23)C1] | LC10 | 406.21 | 2.07 |

-continued

| Exp. No. | Name | Structure | LC/MS method | m/z [M + H]+ | Rt [min] |
|---|---|---|---|---|---|
| 407 | (2,7-Diaza-spiro-[4.5]dec-2-yl)-[6-(4-hydroxy-phenyl)-3-trifluoro-methyl-1H-pyrazolo[3,4-b]pyridin-4-yl]-methanone | 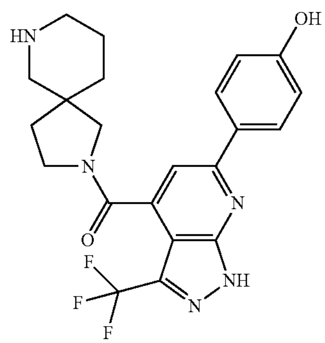 [SMILES: O=C(c1cc(-c2ccc(O)cc2)nc2[nH]nc(C(F)(F)F)c12)N1CCC2(CCCNC2)C1] | LC10 | 446.24 | 2.20 |
| 408 | (Hexahydro-pyrrolo[3,4-b]pyrrol-1-yl)-[6-(4-hydroxy-phenyl)-3-trifluoro-methyl-1H-pyrazolo[3,4-b]pyridin-4-yl]-methanone | 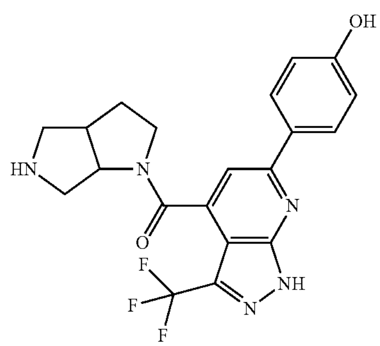 [SMILES: O=C(c1cc(-c2ccc(O)cc2)nc2[nH]nc(C(F)(F)F)c12)N1CCC2CNCC21] | LC10 | 418.20 | 2.15 |
| 409 | (2,8-Diaza-spiro[4.5]dec-2-yl)-[6-(4-hydroxy-phenyl)-3-trifluoro-methyl-1H-pyrazolo[3,4-b]pyridin-4-yl]-methanone | 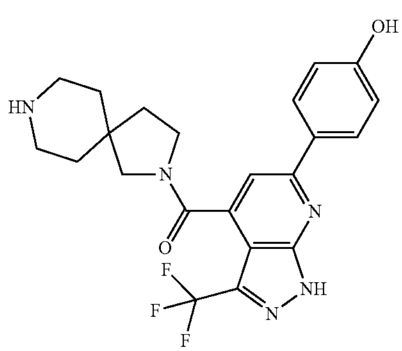 [SMILES: O=C(c1cc(-c2ccc(O)cc2)nc2[nH]nc(C(F)(F)F)c12)N1CCC2(CCNCC2)C1] | LC10 | 446.25 | 2.15 |
| 410 | (2,8-Diaza-spiro[4.5]dec-8-yl)-[6-(4-hydroxy-phenyl)-3-trifluoro-methyl-1H-pyrazolo[3,4-b]pyridin-4-yl]-methanone | 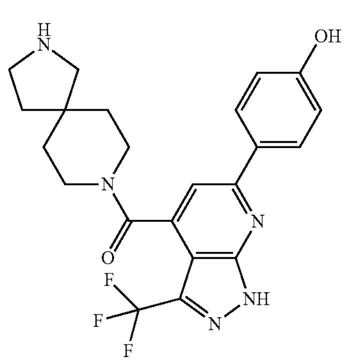 [SMILES: O=C(c1cc(-c2ccc(O)cc2)nc2[nH]nc(C(F)(F)F)c12)N1CCC2(CCNC2)CC1] | LC10 | 446.25 | 2.15 |

-continued

| Exp. No. | Name | Structure | LC/MS method | m/z [M + H]+ | Rt [min] |
|---|---|---|---|---|---|
| 411 | (3,9-Diaza-spiro-[5.5]undec-3-yl)-[6-(4-hydroxy-phenyl)-3-trifluoro-methyl-1H-pyrazolo[3,4-b]pyridin-4-yl]-methanone | 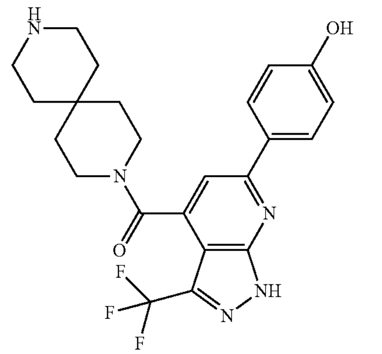 [SMILES: O=C(c1cc(-c2ccc(O)cc2)nc2[nH]nc(C(F)(F)F)c12)N1CCC2(CCNCC2)CC1] | LC10 | 460.27 | 2.15 |
| 412 | 6-(4-Hydroxy-phenyl)-3-trifluoro-methyl-1H-pyrazolo[3,4-b]pyridine-4-carboxylic acid [(S)-1-aza-bicyclo-[2.2.2]oct-3-yl]-amide | 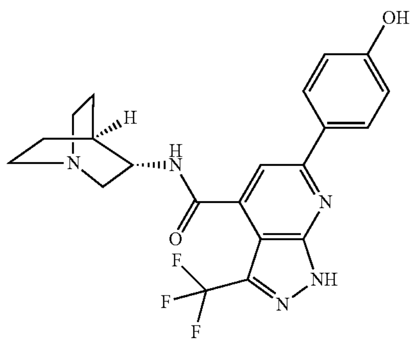 | LC10 | 432.22 | 2.18 |
| 413 | 6-(4-Hydroxy-phenyl)-3-trifluoro-methyl-1H-pyrazolo[3,4-b]pyridine-4-carboxylic acid ((R)-1-aza-bicyclo-[2.2.2]oct-3-yl]-amide | 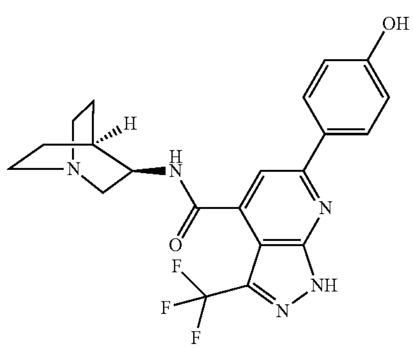 | LC10 | 432.21 | 2.17 |
| 414 | (4-Ethyl-[1,4]diazepan-1-yl)-[6-(4-hydroxy-phenyl)-3-trifluoromethyl-1H-pyrazolo[3,4-b]-pyridin-4-yl]-methanone | 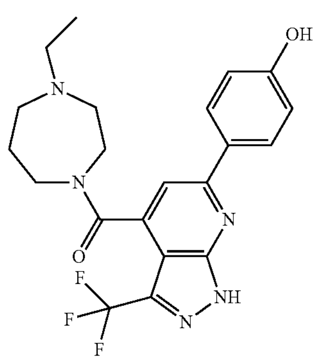 [SMILES: CCN1CCCN(C(=O)c2cc(-c3ccc(O)cc3)nc3[nH]nc(C(F)(F)F)c23)CC1] | LC10 | 494.23 | 2.51 |

Example 415

(4-Amino-4-phenyl-piperidin-1-yl)-[6-(2-fluoro-4-hydroxy-phenyl)-3-methyl-1H-pyrazolo[3,4-b]pyridin-4-yl]-methanone

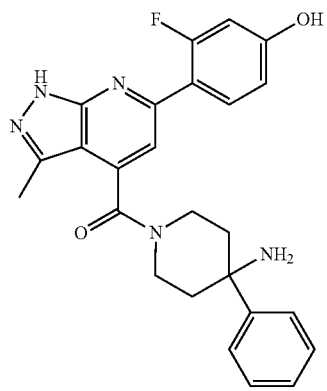 [SMILES: Cc1n[nH]c2nc(-c3ccc(O)cc3F)cc(C(=O)N3CCC(N)(c4ccccc4)CC3)c12]

(a) 6-Bromo-3-methyl-1-(tetrahydro-pyran-2-yl)-1H-pyrazolo[3,4-b]pyridine-4-carboxylic acid ethyl ester

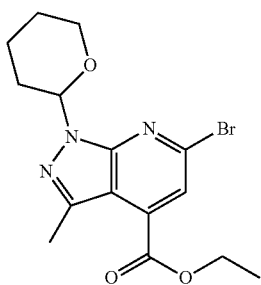 [SMILES: CCOC(=O)c1cc(Br)nc2c1c(C)nn2C1CCCCO1]

A mixture of 6-hydroxy-3-methyl-1H-pyrazolo[3,4-b]pyridine-4-carboxylic acid ethyl ester (13.7 g) and phosphorous oxybromide (19.5 g) in toluene (300 mL) was stirred at 110° C. for 5 h, cooled to r.t., and added dropwise into an ice cold solution of potassium acetate (18.2 g) in water (300 mL). The mixture was extracted twice with ethyl acetate, the combined organic phases were washed with brine, dried over magnesium sulfate and concentrated in vacuo. 6-Bromo-3-methyl-1H-pyrazolo[3,4-b]pyridine-4-carboxylic acid ethyl ester (4.6 g, 26%) were obtained. This material was dissolved in THF (60 mL), and 3,4-dihydro-2H-pyran (1.6 mL) and p-toluenesulfonic acid monohydrate (0.91 g) were added. The solution was stirred at r.t. for 48 h, then 3,4-dihydro-2H-pyran (1.6 mL) were added and the solution stirred again for 48 h. The mixture was poured into water and extracted with ethyl acetate, the organic layer was dried over magnesium sulfate and concentrated in vacuo. The residue was purified by flash chromatography (silica, heptane/ethyl acetate gradient). 2.2 g (38%) of the title compound were obtained.

$^1$H-NMR (500 MHz, $d_6$-DMSO): 1.38 (t, 3H), 1.52-1.63 (m, 2H), 1.73-1.85 (m, 1H), 1.87-1.94 (m, 1H), 1.97-2.06 (m, 1H), 2.37-2.46 (m, 1H), 2.60 (s, 3H), 3.65-3.73 (m, 1H), 3.90-3.96 (m, 1H), 4.43 (q, 2H), 5.92 (dd, 1H), 7.73 (s, 1H).

LC/MS (Method LC1): $R_t$=1.41 min; m/z=286.1 [M+H—$C_5H_9O$]$^+$.

(b) 6-(4-Benzyloxy-2-fluoro-phenyl)-3-methyl-1-(tetrahydro-pyran-2-yl)-1H-pyrazolo[3,4-b]pyridine-4-carboxylic acid

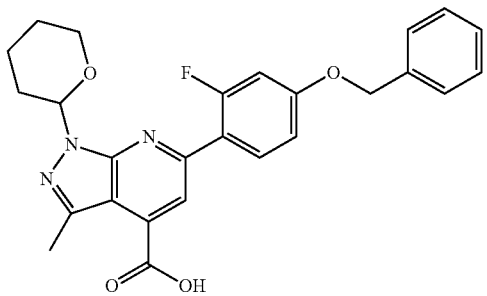 [SMILES: Cc1nn(C2CCCCO2)c2nc(-c3ccc(OCc4ccccc4)cc3F)cc(C(=O)O)c12]

To mixture of 6-bromo-3-methyl-1-(tetrahydro-pyran-2-yl)-1H-pyrazolo[3,4-b]pyridine-4-carboxylic acid ethyl ester (21.0 g), 4-benzyloxy-2-fluorophenylboronic acid (16.8 g) and potassium carbonate (8.7 g) in DME/water (v/v=2/1, 300 mL) was added at r.t. under Ar-atmosphere palladium(0) bis (tri-tert-butylphosphine) (0.99 g) and the mixture was stirred at 85° C. for 90 min. To the mixture water was added and extracted with ethyl acetate. The organic phase was washed several times with water, finally with brine. Methanol was added and the precipitate formed was filtered off, dried in air to give 6-(4-Benzyloxy-2-fluoro-phenyl)-3-methyl-1-(tetrahydro-pyran-2-yl)-1H-pyrazolo[3,4-b]pyridine-4-carboxylic acid ethyl ester (23.0 g, 82% yield). This material was dissolved in isopropanol (100 mL), and 1N sodium hydroxide solution (140 mL) was added. The solution was stirred overnight, filtered, then the filtrate was adjusted to pH2-3 and the precipitate formed was dried in air giving 6-(4-benzyloxy-2-fluoro-phenyl)-3-methyl-1-(tetrahydro-pyran-2-yl)-1H-pyrazolo[3,4-b]pyridine-4-carboxylic acid (18 g, 83%).

$^1$H-NMR (500 MHz, $d_6$-DMSO): 1.54-1.66 (m, 2H), 1.76-1.88 (m, 1H), 1.89-1.94 (m, 1H), 2.03-2.10 (m, 1H), 2.47-2.56 (m, 1H), 2.61 (s, 3H), 3.70-3.77 (m, 1H), 3.91-3.96 (m, 1H), 5.30 (d, 2H), 6.13 (dd, 1H), 7.35-7.47 (m, 3H), 7.49-7.52 (m, 2H), 8.03-8.09 (m, 2H), 8.12-8.16 (m, 1H), 14.0 (br s, 1H).

LC/MS (Method LC1): $R_t$=1.38 min; m/z=462.2 [M+H]$^+$.

(c) {1-[6-(4-Benzyloxy-2-fluoro-phenyl)-3-methyl-1-(tetrahydro-pyran-2-yl)-1H-pyrazolo[3,4-b]pyridine-4-carbonyl]-4-phenyl-piperidin-4-yl}-carbamic acid tert-butyl ester

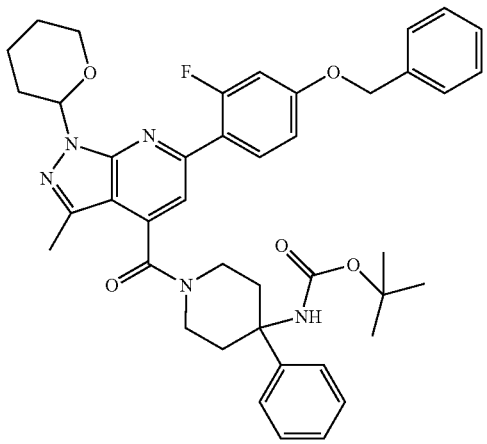 [SMILES: Cc1nn(C2CCCCO2)c2nc(-c3ccc(OCc4ccccc4)cc3F)cc(C(=O)N3CCC(NC(=O)OC(C)(C)C)(c4ccccc4)CC3)c12]

A mixture of 6-(4-benzyloxy-2-fluoro-phenyl)-3-methyl-1-(tetrahydro-pyran-2-yl)-1H-pyrazolo[3,4-b]pyridine-4- carboxylic acid (384 mg), (4-phenylpiperidin-4-yl)-carbamic acid tert-butyl ester (230 mg), DIPEA (427 µL) and BEP (456 mg) in dichloromethane (10 mL) was stirred at r.t. for 5 d. The solvent was distilled off in vacuo, the residue was re-dissolved in MTBE/ethyl acetate (v/v=1/1, 40 mL) and washed once with water, twice with saturated sodium bicarbonate solution, once with 1N sodium hydroxide solution and with brine. After evaporation of the solvents, the residue was purified by flash chromatography (silica, heptane/ethyl acetate gradient) giving 95 mg (16%) of the title compound.

LC/MS (Method LC1): $R_t$=1.47 min; m/z=720.5 [M+H]$^+$.

(d) (4-Amino-4-phenyl-piperidin-1-yl)-[6-(2-fluoro-4-hydroxy-phenyl)-3-methyl-1H-pyrazolo[3,4-b]pyridin-4-yl]-methanone

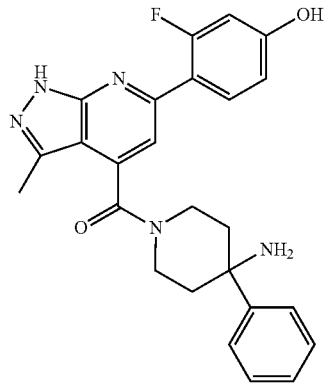 [SMILES: Cc1n[nH]c2nc(-c3ccc(O)cc3F)cc(C(=O)N3CCC(N)(c4ccccc4)CC3)c12]

{1-[6-(4-Benzyloxy-2-fluoro-phenyl)-3-methyl-1-(tetrahydro-pyran-2-yl)-1H-pyrazolo[3,4-b]pyridine-4-carbonyl]-4-phenyl-piperidin-4-yl}-carbamic acid tert-butyl ester (90 mg) was dissolved in methanol (2 mL) and purged with argon, then hydrogen. Palladium (10% on charcoal, 13 mg) was added and the mixture was stirred at 38° C. for 2 h. The catalyst was filtered off, the solvent was evaporated and the residue was dissolved in THF (5 mL) containing HCl (4N in dioxane, 0.14 mL). The solution was stirred at r.t. over night, the precipitate formed was filtered off. The filtrate was concentrated, the residue was re-dissolved in methanol/water (v/v=1/1, 4 mL), and concentrated hydrochloric acid (1 mL) was added. The precipitate formed was filtered off, washed with ethyl acetate and acetone and dried in air. The two filtration solids were combined yielding 45 mg (75%) of the title compound.

LC/MS (Method LC1): $R_t$=0.88 min; m/z=446.2 [M+H]$^+$.

The following examples have been prepared following a similar procedure as described for (4-Amino-4-phenyl-piperidin-1-yl)-[6-(2-fluoro-4-hydroxy-phenyl)-3-methyl-1H-pyrazolo[3,4-b]pyridin-4-yl]-methanone (Example 415), employing the respective amine precursors:

| Exp. No. | Name | Structure | LC/MS method | m/z [M + H]$^+$ | $R_t$ [min] |
|---|---|---|---|---|---|
| 416 | (4-Amino-4-ethyl-piperidin-1-yl)-[6-(2-fluoro-4-hydroxy-phenyl)-3-methyl-1H-pyrazolo[3,4-b]pyridin-4-yl]-methanone | 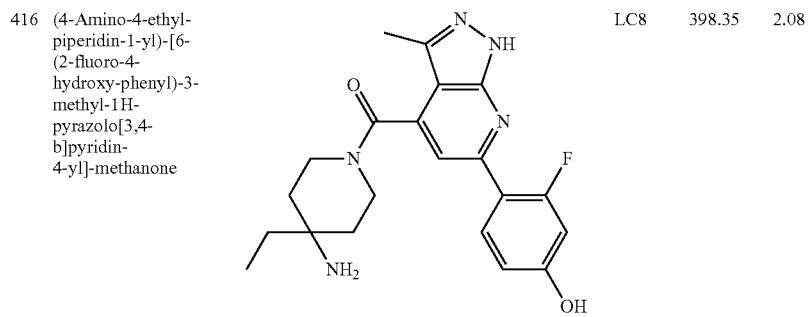 | LC8 | 398.35 | 2.08 |
| 417 | 3,8-Diaza-bicyclo-[3.2.1]oct-8-yl-[6-(2-fluoro-4-hydroxy-phenyl)-3-methyl-1H-pyrazolo[3,4-b]pyridin-4-yl]-methanone | 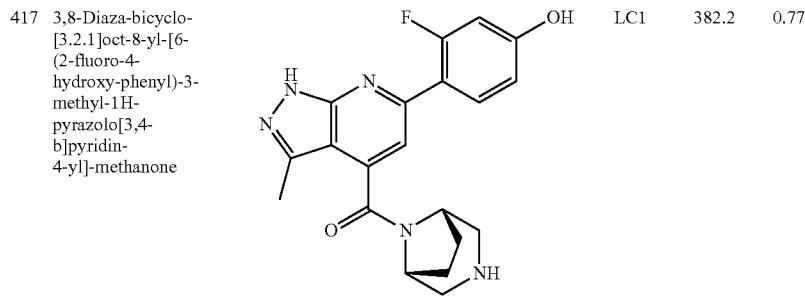 | LC1 | 382.2 | 0.77 |

-continued

| Exp. No. | Name | Structure | LC/MS method | m/z [M + H]⁺ | R_t [min] |
|---|---|---|---|---|---|
| 418 | (4-Amino-4-methyl-piperidin-1-yl)-[6-(2-fluoro-4-hydroxy-phenyl)-3-methyl-1H-pyrazolo[3,4-b]pyridin-4-yl]-methanone | 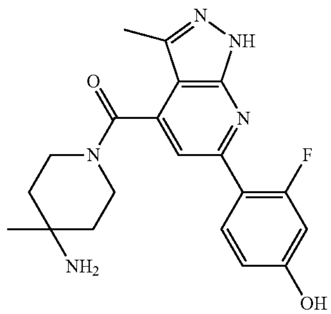 [SMILES: Cc1n[nH]c2nc(-c3ccc(O)cc3F)cc(C(=O)N3CCC(C)(N)CC3)c12] | LC1 | 384.22 | 0.73 |
| 419 | [6-(2-Fluoro-4-hydroxy-phenyl)-3-methyl-1H-pyrazolo[3,4-b]pyridin-4-yl]-(3aR,6aS)-hexahydro-pyrrolo[3,4-c]pyrrol-2-yl-methanone | 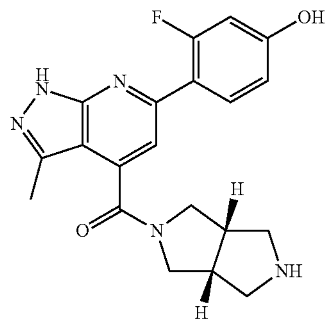 [SMILES: Cc1n[nH]c2nc(-c3ccc(O)cc3F)cc(C(=O)N3C[C@H]4CNC[C@H]4C3)c12] | LC5 | 382.2 | 0.57 |
| 420 | [6-(2-Fluoro-4-hydroxy-phenyl)-3-methyl-1H-pyrazolo[3,4-b]pyridin-4-yl]-((R)-3-propyl-piperazin-1-yl)-methanone | 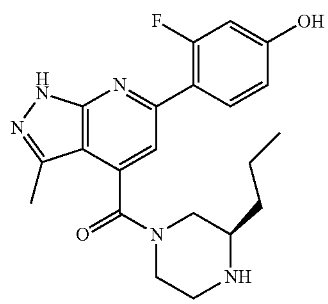 [SMILES: CCC[C@@H]1CN(C(=O)c2cc(-c3ccc(O)cc3F)nc3[nH]nc(C)c23)CCN1] | LC5 | 398.17 | 0.74 |
| 421 | [6-(2-Fluoro-4-hydroxy-phenyl)-3-methyl-1H-pyrazolo[3,4-b]pyridin-4-yl]-(3-phenyl-piperazin-1-yl)-methanone | 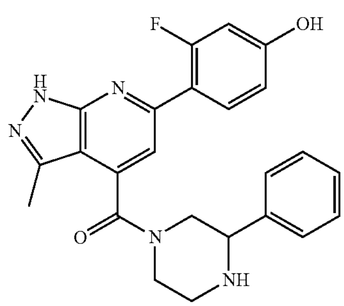 [SMILES: Cc1n[nH]c2nc(-c3ccc(O)cc3F)cc(C(=O)N3CCNC(c4ccccc4)C3)c12] | LC5 | 432.27 | 0.77 |
| 422 | [6-(2-Fluoro-4-hydroxy-phenyl)-3-methyl-1H-pyrazolo[3,4-b]pyridin-4-yl]-((S)-3-propyl-piperazin-1-yl)-methanone | 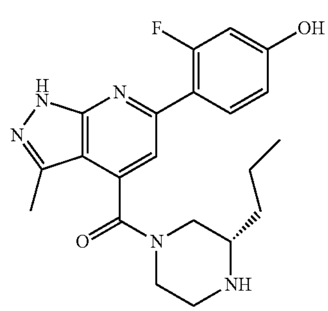 [SMILES: CCC[C@H]1CN(C(=O)c2cc(-c3ccc(O)cc3F)nc3[nH]nc(C)c23)CCN1] | LC5 | 398.24 | 0.73 |

| Exp. No. | Name | Structure | LC/MS method | m/z [M + H]+ | R_t [min] |
|---|---|---|---|---|---|
| 423 | (3-Cyclopropyl-piperazin-1-yl)-[6-(2-fluoro-4-hydroxy-phenyl)-3-methyl-1H-pyrazolo[3,4-b]pyridin-4-yl]-methanone | 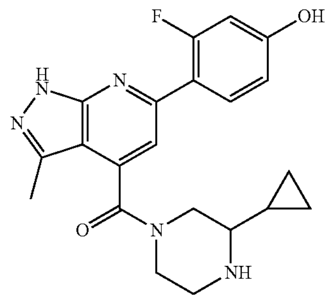 [SMILES: Cc1n[nH]c2nc(-c3ccc(O)cc3F)cc(C(=O)N3CCNC(C4CC4)C3)c12] | LC5 | 396.24 | 0.70 |
| 424 | [6-(2-Fluoro-4-hydroxy-phenyl)-3-methyl-1H-pyrazolo[3,4-b]pyridin-4-yl]-((S)-3-methyl-piperazin-1-yl)-methanone | 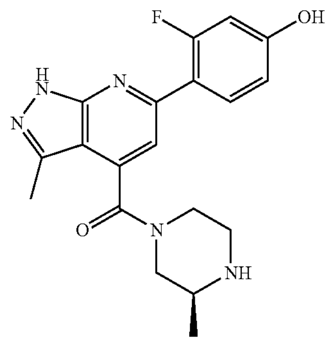 [SMILES: Cc1n[nH]c2nc(-c3ccc(O)cc3F)cc(C(=O)N3CCN[C@@H](C)C3)c12] | LC1 | 370.14 | 0.76 |
| 425 | (3,3-Dimethyl-piperazin-1-yl)-[6-(2-fluoro-4-hydroxy-phenyl)-3-methyl-1H-pyrazolo[3,4-b]pyridin-4-yl]-methanone | 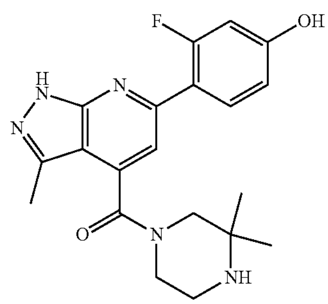 [SMILES: Cc1n[nH]c2nc(-c3ccc(O)cc3F)cc(C(=O)N3CCNC(C)(C)C3)c12] | LC5 | 384.22 | 0.67 |
| 426 | [6-(2-Fluoro-4-hydroxy-phenyl)-3-methyl-1H-pyrazolo[3,4-b]pyridin-4-yl]-((R)-3-methyl-piperazin-1-yl)-methanone | 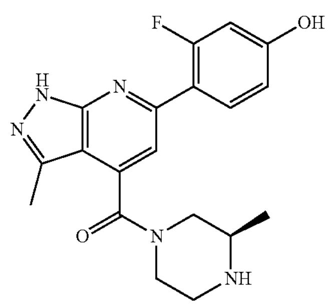 [SMILES: Cc1n[nH]c2nc(-c3ccc(O)cc3F)cc(C(=O)N3CCN[C@H](C)C3)c12] | LC5 | 370.18 | 0.61 |
| 427 | [6-(2-Fluoro-4-hydroxy-phenyl)-3-methyl-1H-pyrazolo[3,4-b]pyridin-4-yl]-(2,5,5-trimethyl-piperazin-1-yl)-methanone | 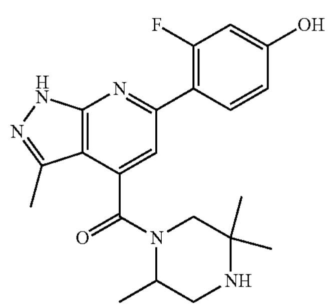 [SMILES: Cc1n[nH]c2nc(-c3ccc(O)cc3F)cc(C(=O)N3CC(C)(C)NCC3C)c12] | LC1 | 398.22 | 0.80 |

| Exp. No. | Name | Structure | LC/MS method | m/z [M + H]+ | Rf [min] |
|---|---|---|---|---|---|
| 428 | ((2R,5R)-2,5-Dimethyl-piperazin-1-yl)-[6-(2-fluoro-4-hydroxy-phenyl)-3-methyl-1H-pyrazolo[3,4-b]pyridin-4-yl]-methanone | 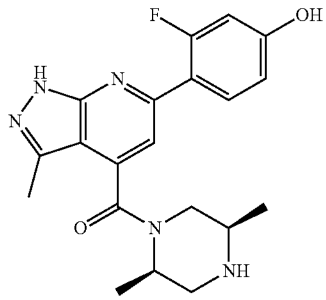 [SMILES: Cc1n[nH]c2nc(-c3ccc(O)cc3F)cc(C(=O)N3C[C@@H](C)NC[C@H]3C)c12] | LC1 | 384.15 | 0.78 |
| 429 | ((2S,5R)-2,5-Dimethyl-piperazin-1-yl)-[6-(2-fluoro-4-hydroxy-phenyl)-3-methyl-1H-pyrazolo[3,4-b]pyridin-4-yl]-methanone | 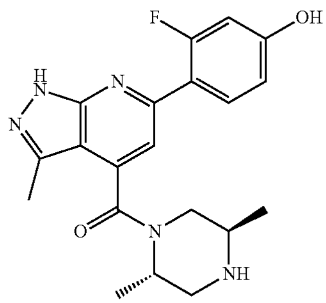 [SMILES: Cc1n[nH]c2nc(-c3ccc(O)cc3F)cc(C(=O)N3C[C@@H](C)NC[C@@H]3C)c12] | LC1 | 384.15 | 0.77 |
| 430 | ((2S,5S)-2,5-Dimethyl-piperazin-1-yl)-[6-(2-fluoro-4-hydroxy-phenyl)-3-methyl-1H-pyrazolo[3,4-b]pyridin-4-yl]-methanone | 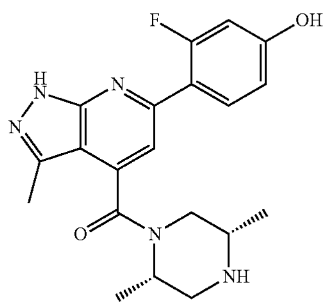 [SMILES: Cc1n[nH]c2nc(-c3ccc(O)cc3F)cc(C(=O)N3C[C@H](C)NC[C@@H]3C)c12] | LC1 | 384.15 | 0.79 |
| 431 | ((S)-2-Ethyl-piperazin-1-yl)-[6-(2-fluoro-4-hydroxy-phenyl)-3-methyl-1H-pyrazolo[3,4-b]pyridin-4-yl]-methanone | 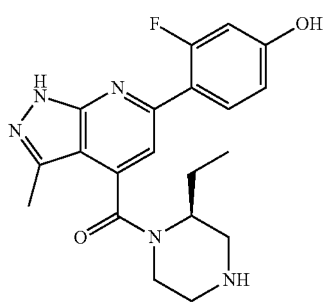 [SMILES: CC[C@H]1CNCCN1C(=O)c1cc(-c2ccc(O)cc2F)nc2[nH]nc(C)c12] | LC1 | 384.16 | 0.80 |
| 432 | (3-Amino-3-trifluoromethyl-pyrrolidin-1-yl)-[6-(2-fluoro-4-hydroxy-phenyl)-3-methyl-1H-pyrazolo[3,4-b]pyridin-4-yl]-methanone | 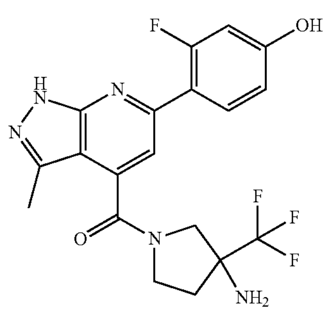 [SMILES: Cc1n[nH]c2nc(-c3ccc(O)cc3F)cc(C(=O)N3CCC(N)(C(F)(F)F)C3)c12] | LC5 | 424.22 | 0.88 |

| Exp. No. | Name | Structure | LC/MS method | m/z [M + H]⁺ | R_t [min] |
|---|---|---|---|---|---|
| 433 | (6,9-Diaza-spiro[4.5]dec-6-yl)-[6-(2-fluoro-4-hydroxy-phenyl)-3-methyl-1H-pyrazolo[3,4-b]pyridin-4-yl]-methanone | 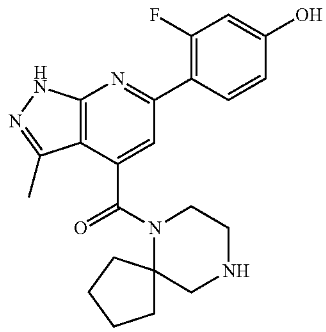 [SMILES: Cc1n[nH]c2nc(-c3ccc(O)cc3F)cc(C(=O)N3CCNCC34CCCC4)c12] | LC5 | 410.12 | 0.89 |
| 434 | [6-(2-Fluoro-4-hydroxy-phenyl)-3-methyl-1H-pyrazolo[3,4-b]pyridin-4-yl]-(2,2,5-trimethyl-piperazin-1-yl)-methanone | 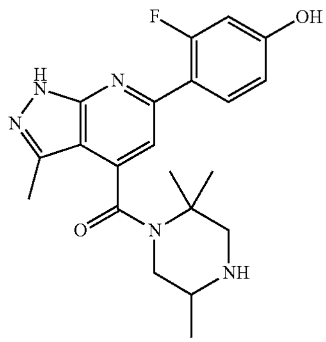 [SMILES: Cc1n[nH]c2nc(-c3ccc(O)cc3F)cc(C(=O)N3CC(C)NCC3(C)C)c12] | LC5 | 398.1 | 0.83 |
| 435 | [6-(2-Fluoro-4-hydroxy-phenyl)-3-methyl-1H-pyrazolo[3,4-b]pyridin-4-yl]-(2-methyl-2-phenyl-piperazin-1-yl)-methanone | 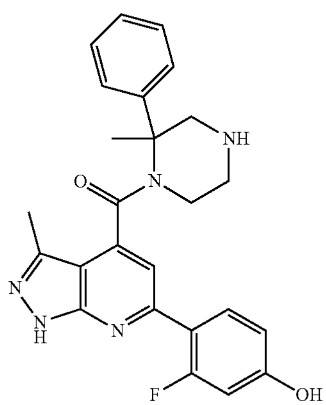 [SMILES: Cc1n[nH]c2nc(-c3ccc(O)cc3F)cc(C(=O)N3CCNCC3(C)c3ccccc3)c12] | LC5 | 446.24 | 0.90 |
| 436 | (2,2-Diethyl-piperazin-1-yl)-[6-(2-fluoro-4-hydroxy-phenyl)-3-methyl-1H-pyrazolo[3,4-b]pyridin-4-yl]-methanone | 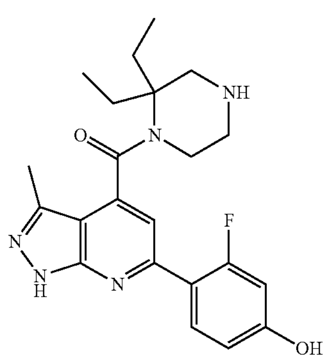 [SMILES: CCC1(CC)CNCCN1C(=O)c1cc(-c2ccc(O)cc2F)nc2[nH]nc(C)c12] | LC9 | 412.29 | 1.34 |

| Exp. No. | Name | Structure | LC/MS method | m/z [M + H]⁺ | R_t [min] |
|---|---|---|---|---|---|
| 437 | (8,8-Dimethyl-6,9-diaza-spiro[4.5]dec-6-yl)-[6-(2-fluoro-4-hydroxy-phenyl)-3-methyl-1H-pyrazolo[3,4-b]pyridin-4-yl]-methanone | 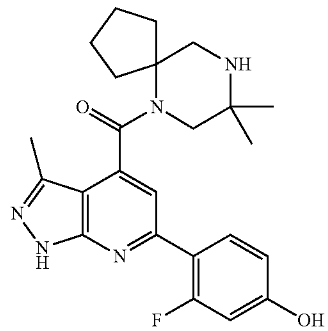 [SMILES: Cc1n[nH]c2nc(-c3ccc(O)cc3F)cc(C(=O)N3CC(C)(C)NCC34CCCC4)c12] | LC9 | 438.44 | 1.13 |
| 438 | [6-(2-Fluoro-4-hydroxy-phenyl)-3-methyl-1H-pyrazolo[3,4-b]pyridin-4-yl]-(8-methyl-6,9-diaza-spiro[4.5]dec-6-yl)-methanone | 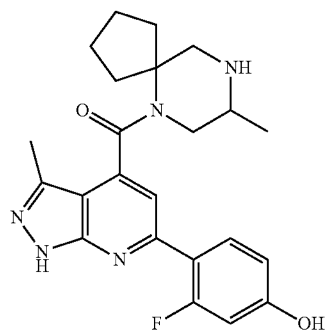 [SMILES: Cc1n[nH]c2nc(-c3ccc(O)cc3F)cc(C(=O)N3CC(C)NCC34CCCC4)c12] | LC9 | 424.34 | 1.11 |
| 439 | (5,8-Diaza-spiro[3.5]non-5-yl)-[6-(2-fluoro-4-hydroxy-phenyl)-3-methyl-1H-pyrazolo[3,4-b]pyridin-4-yl]-methanone | 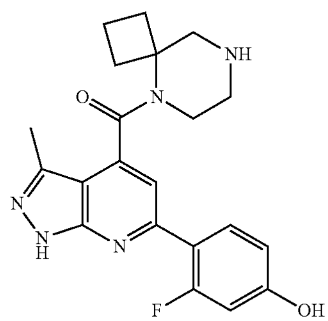 [SMILES: Cc1n[nH]c2nc(-c3ccc(O)cc3F)cc(C(=O)N3CCNCC34CCC4)c12] | LC9 | 396.31 | 1.01 |

Example 440

6-(2-Fluoro-4-hydroxy-phenyl)-3-methyl-1H-pyrazolo[3,4-b]pyridine-4-carboxylic acid (4-phenyl-piperidin-4-yl)-amide

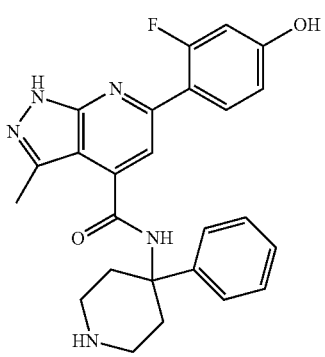 [SMILES: Cc1n[nH]c2nc(-c3ccc(O)cc3F)cc(C(=O)NC3(c4ccccc4)CCNCC3)c12]

(a) 6-(4-Benzyloxy-2-fluoro-phenyl)-3-methyl-1-(tetrahydro-pyran-2-yl)-1H-pyrazolo[3,4-b]pyridine-4-carboxylic acid (1-benzyl-4-phenyl-piperidin-4-yl)-amide

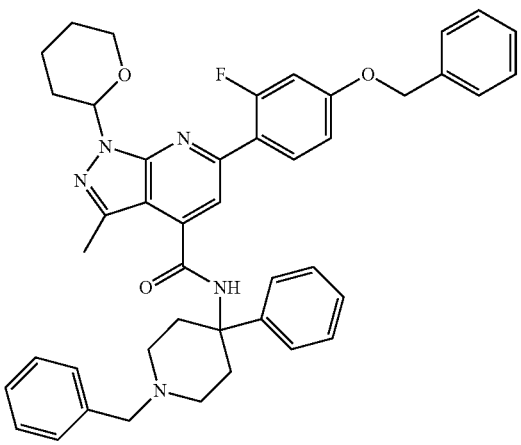 [SMILES: Cc1nn(C2CCCCO2)c2nc(-c3ccc(OCc4ccccc4)cc3F)cc(C(=O)NC3(c4ccccc4)CCN(Cc4ccccc4)CC3)c12]

A mixture of 6-(4-benzyloxy-2-fluoro-phenyl)-3-methyl-1-(tetrahydro-pyran-2-yl)-1H-pyrazolo[3,4-b]pyridine-4-carboxylic acid (304 mg), amine (200 (200 mg), DIPEA (340 µL) and BEP (190 mg) in dichloroethane (6.5 mL) was stirred at r.t. for 90 min. The solvent was distilled off in vacuo, the residue was re-dissolved in ethyl acetate (20 mL) and washed twice with water, twice with saturated sodium bicarbonate solution and with brine, then dried over magnesium sulfate. After evaporation of the solvents, the residue was purified by flash chromatography (silica, heptane/ethyl acetate gradient) giving 278 mg (59%) of the title compound.

LC/MS (Method LC1): $R_t$=1.25 min; m/z=710.4 [M+H]$^+$.

(b) 6-(2-Fluoro-4-hydroxy-phenyl)-3-methyl-1H-pyrazolo[3,4-b]pyridine-4-carboxylic acid (4-phenyl-piperidin-4-yl)-amide

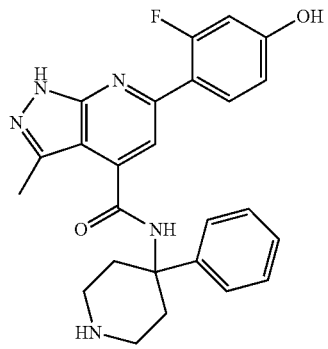 [SMILES: Cc1n[nH]c2nc(-c3ccc(O)cc3F)cc(C(=O)NC3(c4ccccc4)CCNCC3)c12]

6-(4-Benzyloxy-2-fluoro-phenyl)-3-methyl-1-(tetrahydro-pyran-2-yl)-1H-pyrazolo[3,4-b]pyridine-4-carboxylic acid (1-benzyl-4-phenyl-piperidin-4-yl)-amide (275 mg) was dissolved in methanol (10 mL) and purged with argon, then hydrogen. Palladium (10% on charcoal, 82 mg) was added and the mixture was stirred at 40° C. for 2 h, then at r.t. over night. The catalyst was filtered off, the solvent was evaporated and the residue was dissolved in methanol (4 mL) and water (1 ml). Concentrated aqueous hydrochloric acid (1 mL) was added and the solution was stirred for 3 d. The solution was kept at –20° C. in a freezer until a precipitate appeared, which was filtered off and washed with methanol giving 6-(2-Fluoro-4-hydroxy-phenyl)-3-methyl-1H-pyrazolo[3,4-b]pyridine-4-carboxylic acid (4-phenyl-piperidin-4-yl)-amide (144 mg). A second fraction of title compound was obtained by storing the filtrate at –20° C. for a day and filtering off the precipitated product (31 mg, 95% overall yield).

LC/MS (Method LC5): $R_t$=0.80 min; m/z 446.29 [M+H]$^+$.

The following examples have been prepared following a similar procedure as described for 6-(2-Fluoro-4-hydroxy-phenyl)-3-methyl-1H-pyrazolo[3,4-b]pyridine-4-carboxylic acid (4-phenyl-piperidin-4-yl)-amide (Example 440), employing the respective amine precursors:

| Exp. No. | Name | Structure | LC/MS method | m/z [M + H]$^+$ | $R_t$ [min] |
|---|---|---|---|---|---|
| 441 | (2,5-Dipropyl-piperazin-1-yl)-[6-(2-fluoro-4-hydroxy-phenyl)-3-methyl-1H-pyrazolo[3,4-b]pyridin-4-yl]-methanone | 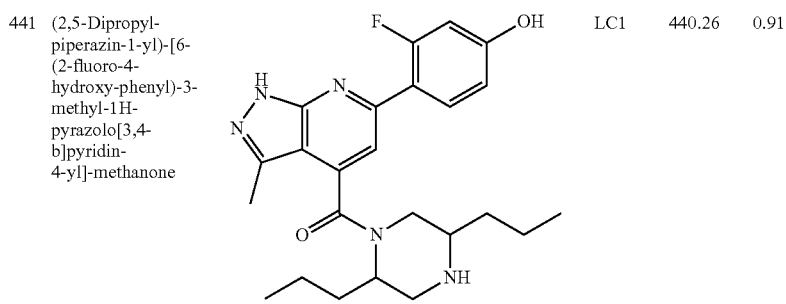 | LC1 | 440.26 | 0.91 |
| 442 | ((cis)-2,3-Dimethyl-piperazin-1-yl)-[6-(2-fluoro-4-hydroxy-phenyl)-3-methyl-1H-pyrazolo[3,4-b]pyridin-4-yl]-methanone | 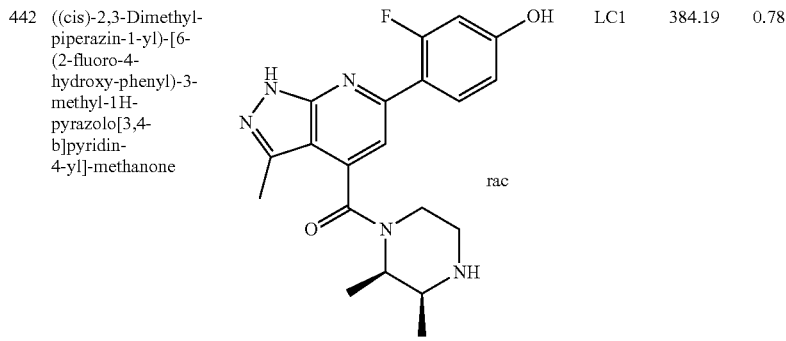 | LC1 | 384.19 | 0.78 |

| Exp. No. | Name | Structure | LC/MS method | m/z [M + H]+ | R$_t$ [min] |
|---|---|---|---|---|---|
| 443 | [6-(2-Fluoro-4-hydroxy-phenyl)-3-methyl-1H-pyrazolo[3,4-b]pyridin-4-yl]-(4aS,8aS)-octahydro-quinoxalin-1-yl-methanone | 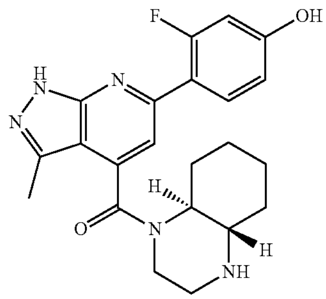 | LC1 | 410.16 | 0.84 |
| 444 | (2,6-Dimethyl-piperazin-1-yl)-[6-(2-fluoro-4-hydroxy-phenyl)-3-methyl-1H-pyrazolo[3,4-b]pyridin-4-yl]-methanone | 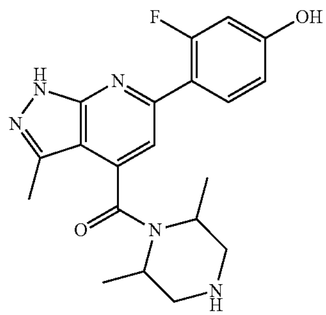 | LC1 | 384.16 | 0.79 |
| 445 | (2,5-Diethyl-piperazin-1-yl)-[6-(2-fluoro-4-hydroxy-phenyl)-3-methyl-1H-pyrazolo[3,4-b]pyridin-4-yl]-methanone | 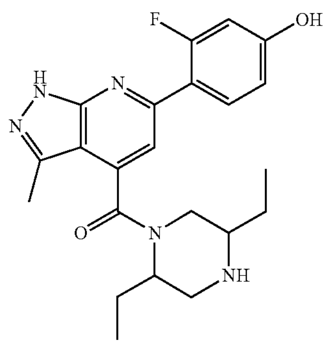 | LC1 | 412.2 | 0.85 |
| 446 | ((2S,5R)-5-Ethyl-2-methyl-piperazin-1-yl)-[6-(2-fluoro-4-hydroxy-phenyl)-3-methyl-1H-pyrazolo[3,4-b]pyridin-4-yl)-methanone | 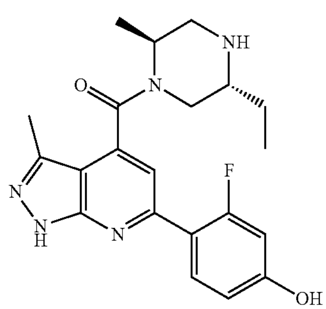 [SMILES: CC[C@@H]1CN(C(=O)c2cc(-c3ccc(O)cc3F)nc3[nH]nc(C)c23)[C@@H](C)CN1] | LC1 | 398.16 | 0.81 |
| 447 | [6-(2-Fluoro-4-hydroxy-phenyl)-3-methyl-1H-pyrazolo[3,4-b]pyridin-4-yl]-(trans-2-methyl-5-phenyl-piperazin-1-yl)-methanone | 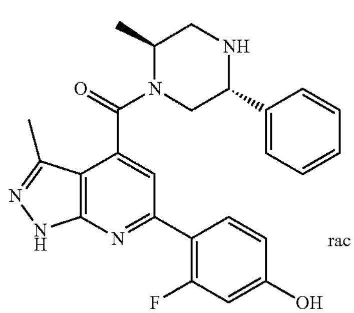 [SMILES: Cc1n[nH]c2nc(-c3ccc(O)cc3F)cc(C(=O)N3C[C@@H](c4ccccc4)NC[C@@H]3C)c12] | LC1 | 446.11 | 0.88 |

-continued

| Exp. No. | Name | Structure | LC/MS method | m/z [M + H]⁺ | R_t [min] |
|---|---|---|---|---|---|
| 448 | [6-(2-Fluoro-4-hydroxy-phenyl)-3-methyl-1H-pyrazolo[3,4-b]pyridin-4-yl]-((2S,5R)-2-methyl-5-propyl-piperazin-1-yl)-methanone | 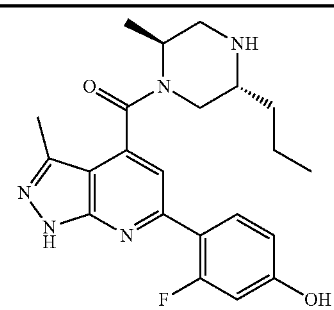 | LC1 | 412.17 | 0.85 |
| 449 | (2-Ethyl-2,5,5-trimethyl-piperazin-1-yl)-[6-(2-fluoro-4-hydroxy-phenyl)-3-methyl-1H-pyrazolo[3,4-b]pyridin-4-yl]-methanone | 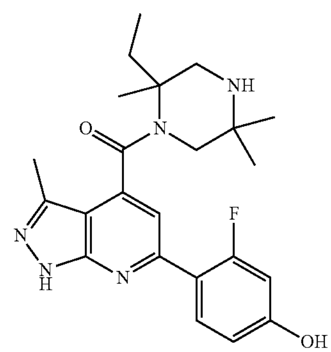 [SMILES: CCC1(C)CNC(C)(C)CN1C(=O)c1cc(-c2ccc(O)cc2F)nc2[nH]nc(C)c12] | LC9 | 426.33 | 1.30 |
| 450 | (2,2-Diethyl-5,5-dimethyl-piperazin-1-yl)-[6-(2-fluoro-4-hydroxy-phenyl)-3-methyl-1H-pyrazolo[3,4-b]pyridin-4-yl]-methanone | 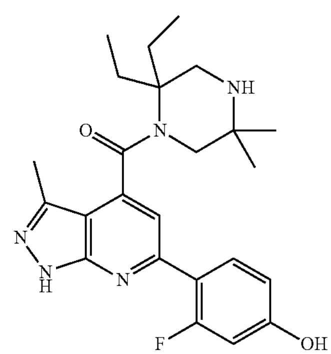 [SMILES: CCC1(CC)CNC(C)(C)CN1C(=O)c1cc(-c2ccc(O)cc2F)nc2[nH]nc(C)c12] | LC9 | 440.31 | 1.18 |
| 451 | (8,8-Dimethyl-6,9-diaza-spiro[4.5]dec-9-yl)-[6-(2-fluoro-4-hydroxy-phenyl)-3-methyl-1H-pyrazolo[3,4-b]pyridin-4-yl]-methanone | 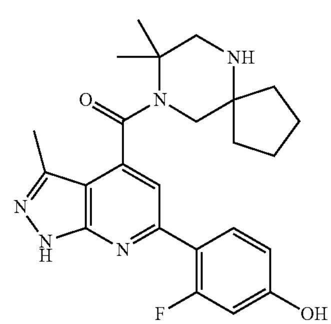 [SMILES: Cc1n[nH]c2nc(-c3ccc(O)cc3F)cc(C(=O)N3CC4(CCCC4)NCC3(C)C)c12] | LC9 | 438.27 | 1.27 |

Example 452

((2S,5R)-2,5-Dimethyl-4-pyridin-2-ylmethyl-piperazin-1-yl)-[6-(2-fluoro-4-hydroxy-phenyl)-3-methyl-1H-pyrazolo[3,4-b]pyridin-4-yl]-methanone

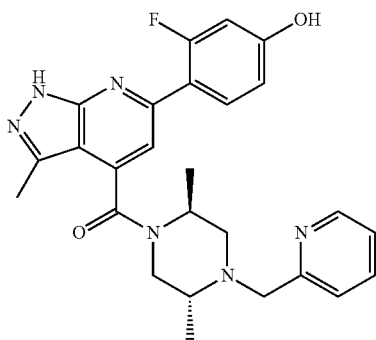 [SMILES: Cc1n[nH]c2nc(-c3ccc(O)cc3F)cc(C(=O)N3C[C@@H](C)N(Cc4ccccn4)C[C@@H]3C)c12]

To a mixture of ((2S,5R)-2,5-Dimethyl-piperazin-1-yl)-[6-(2-fluoro-4-hydroxy-phenyl)-3-methyl-1-(tetrahydro-pyran-2-yl)-1H-pyrazolo[3,4-b]pyridin-4-yl]-methanone (200 mg, precursor of example 543) and pyridine-2-carboxaldehyde (46 mg) in dichloroethane (5 mL) containing acetic acid (7.4 µL) was added sodium triacetoxy borohydride (136 mg) at r.t., then the mixture was stirred at 40° C. overnight. Water was added carefully and the mixture was extracted with dichloromethane. The combined organic phases were dried over magnesium sulfate and concentrated to dryness giving ((2S,5R)-2,5-Dimethyl-4-pyridin-2-ylmethyl-piperazin-1-yl)-[6-(2-fluoro-4-hydroxy-phenyl)-3-methyl-1-(tetrahydro-pyran-2-yl)-1H-pyrazolo[3,4-b]pyridin-4-yl]-methanone. This was dissolved in THF (7 mL) containing conc. hydrochloric acid (1.5 mL) and stirred r.t. overnight. The precipitate formed was filtered off and dried in air. ((2S,5R)-2,5-Dimethyl-4-pyridin-2-ylmethyl-piperazin-1-yl)-[6-(2-fluoro-4-hydroxy-phenyl)-3-methyl-1H-pyrazolo[3,4-b]pyridin-4-yl]-methanone was obtained as a hydrochloride salt (263 mg, 100%).

LC/MS (Method LC1): Rt=0.78 min; m/z 475.4 [M+H]$^+$.

The following examples have been prepared following a similar procedure as described for ((2S,5R)-2,5-Dimethyl-4-pyridin-2-ylmethyl-piperazin-1-yl)-[6-(2-fluoro-4-hydroxy-phenyl)-3-methyl-1H-pyrazolo[3,4-b]pyridin-4-yl]-methanon (Example 452), starting from ((2S,5R)-2,5-Dimethyl-4-pyridin-2-ylmethyl-piperazin-1-yl)-[6-(2-fluoro-4-hydroxy-phenyl)-3-methyl-1H-pyrazolo[3,4-b]pyridin-4-yl]-methanone and the respective aldehydes:

| Exp. No. | Name | Structure | LC/MS method | m/z [M + H]$^+$ | R$_t$ [min] |
|---|---|---|---|---|---|
| 453 | ((2S,5R)-2,5-Dimethyl-4-piperidin-4-ylmethyl-piperazin-1-yl)-[6-(2-fluoro-4-hydroxy-phenyl)-3-methyl-1H-pyrazolo[3,4-b]pyridin-4-yl]-methanone | 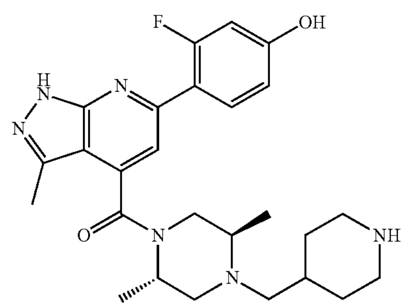 [SMILES: Cc1n[nH]c2nc(-c3ccc(O)cc3F)cc(C(=O)N3C[C@@H](C)N(CC4CCNCC4)C[C@@H]3C)c12] | LC5 | 481.4 | 0.59 |
| 454 | [(2S,5R)-2,5-Dimethyl-4-(tetrahydro-pyran-4-yl-methyl)-piperazin-1-yl]-[6-(2-fluoro-4-hydroxy-phenyl)-3-methyl-1H-pyrazolo[3,4-b]pyridin-4-yl]-methanone | 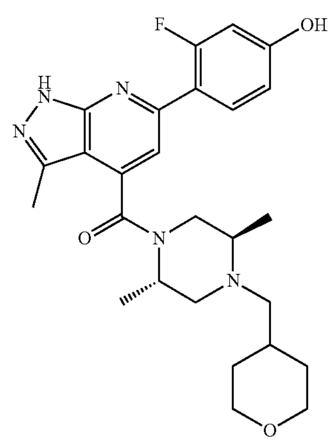 [SMILES: Cc1n[nH]c2nc(-c3ccc(O)cc3F)cc(C(=O)N3C[C@@H](C)N(CC4CCOCC4)C[C@@H]3C)c12] | LC5 | 482.38 | 0.75 |

-continued

| Exp. No. | Name | Structure | LC/MS method | m/z [M + H]+ | R_t [min] |
|---|---|---|---|---|---|
| 455 | [(2S,5R)-2,5-Dimethyl-4-(tetra-hydro-furan-3-ylmethyl)-piperazin-1-yl]-[6-(2-fluoro-4-hydroxy-phenyl)-3-methyl-1H-pyrazolo[3,4-b]pyridin-4-yl]-methanone | 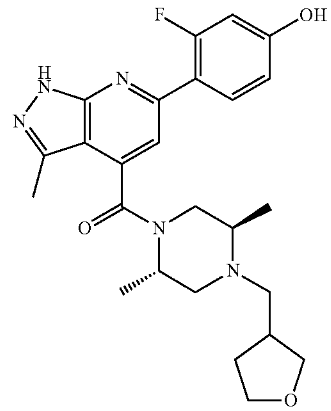 [SMILES: Cc1n[nH]c2nc(-c3ccc(O)cc3F)cc(C(=O)N3C[C@@H](C)N(CC4CCOC4)C[C@@H]3C)c12] | LC5 | 468.38 | 0.74 |

The following enantiomers or diastereomers were obtained after separation of the racemates or diastereomeric mixtures by preparative HPLC using a Waters Alliance 2695 system and chiral columns and solvent mixtures as given in the following tables:

| Exp. No. | Structure and chemical name of racemic mixture | Conditions of chiral sep. | No. of enantiomer | R_t [min] (sep.) | LC/MS method (non-chiral) | m/z [M + H]+ | Rt [min] (non-chiral) |
|---|---|---|---|---|---|---|---|
| 456 | [6-(4-Hydroxy-phenyl)-3-methyl-1H-pyrazolo[3,4-b]pyridin-4-yl]-(3-phenyl-piperazin-1-yl)-methanone | Chiralpak AD/H 141; 4.6 × 250 mm, 1 ml/min, heptane:EtOH:MeOH 5:1:1 + 0.1% DEA | 1 | 9.1 | LC1 | 414.2 | 0.87 |
| 457 | | | 2 | 11.8 | LC1 | 414.2 | 0.87 |

| Exp. No. | Structure and chemical name of racemic mixture | Conditions of chiral sep. | No. of enantiomer | Rt [min] (sep.) | LC/MS method (non-chiral) | m/z [M + H]+ | Rt [min] (non-chiral) |
|---|---|---|---|---|---|---|---|
| 458 459 | 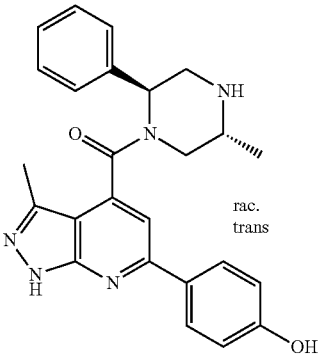 [SMILES: Cc1n[nH]c2nc(-c3ccc(O)cc3)cc(C(=O)N3C[C@@H](C)NC[C@@H]3c3ccccc3)c12] [6-(4-Hydroxy-phenyl)-3-methyl-1H-pyrazolo[3,4-b]pyridin-4-yl]-(trans-5-methyl-2-phenyl-piperazin-1-yl)-methanone | S,S-Whelk 101; 4.6 × 250 mm, 1 ml/min, heptane:EtOH:MeOH 5:1:1 + 0.1% DEA | 1 2 | 13.7 17.0 | LC4 LC4 | 428.1 428.1 | 0.58 0.58 |

| Exp. No. | Structure and chemical name of racemic mixture | Conditions of chiral sep. | No. of enantiomer | Rt [min] (sep.) | LC/MS method (non-chiral) | m/z [M + H]+ | Rt [min] (non-chiral) |
|---|---|---|---|---|---|---|---|
| 460 461 | 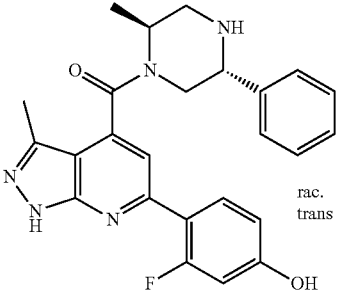 [SMILES: Cc1n[nH]c2nc(-c3ccc(O)cc3F)cc(C(=O)N3C[C@@H](c4ccccc4)NC[C@@H]3C)c12] [6-(2-Fluoro-4-hydroxy-phenyl)-3-methyl-1H-pyrazolo[3,4-b]pyridin-4-yl]-(trans-2-methyl-5-phenyl-piperazin-1-yl)-methanone | Chiracel OJ-H/62; 4.6 × 250 mm, 1 ml/min, heptane:EtOH:MeOH 2:1:1 + 0.1% DEA | 1 2 | 5.3 7.7 | LC5 LC5 | 446.1 446.1 | 0.86 0.86 |

Synthesis of Intermediates

1-Benzyl-4-ethyl-piperidin-4-ylamine was synthesized according to M. Kenki et al., Kyowa Hakko Kogyo Co., Ltd., EP1354882 (2003).

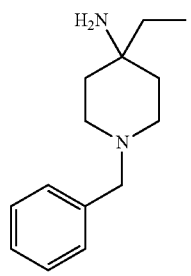 [SMILES: CCC1(N)CCN(Cc2ccccc2)CC1]

In a similar manner as 1-benzyl-4-ethyl-piperidin-4-ylamine the following two intermediates were synthesized:

1-Benzyl-4-methyl-piperidin-4-ylamine

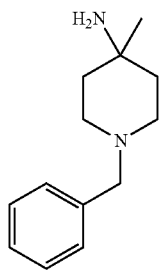

1-Benzyl-4-phenyl-piperidin-4-ylamine

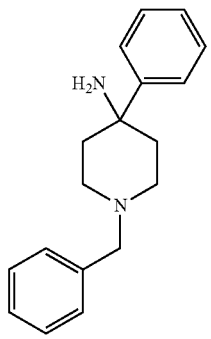 [SMILES: NC1(c2ccccc2)CCN(Cc2ccccc2)CC1]

(4-Ethyl-piperidin-4-yl)-carbamic acid tert-butyl ester was synthesized according to M. Kenki et al., Kyowa Hakko Kogyo Co., Ltd., EP1354882 (2003).

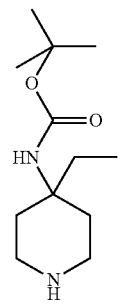 [SMILES: CCC1(NC(=O)OC(C)(C)C)CCNCC1]

In a similar manner as (4-Ethyl-piperidin-4-yl)-carbamic acid tert-butyl ester the following two intermediates were synthesized:

(4-Methyl-piperidin-4-yl)-carbamic acid tert-butyl ester (4-Phenyl-piperidin-4-yl)-carbamic acid tert-butyl ester

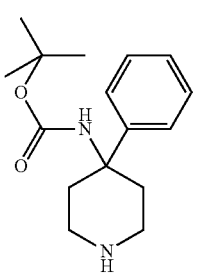 [SMILES: CC(C)(C)OC(=O)NC1(c2ccccc2)CCNCC1]

(4-Propylpiperidin-4-yl)-carbamic acid tert-butyl ester was prepared in a three step synthesis starting from commercial N-benzyl-4-piperidone: Step 1: 4-Allyl-1-benzylpiperidin-4-ylamine was prepared according to B Dhudshia, J Tiburcio, A N Thadani, Chemical Communications (2005) pp. 5551-5553. Step 2 and 3: (4-Allyl-1-benzyl-piperidin-4-yl)-carbamic acid tert-butyl ester and (4-Propyl-piperidin-4-yl)carbamic acid tert-butyl ester were prepared according to M. Kenki et al., Kyowa Hakko Kogyo Co., Ltd., EP1354882 (2003).

471

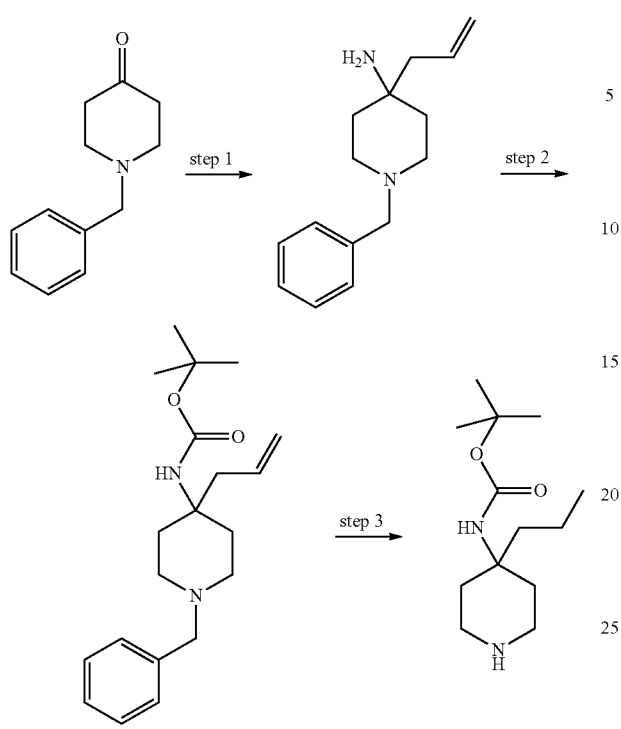

In a similar manner as (4-Propylpiperidin-4-yl)-carbamic acid tert-butyl ester the following two intermediates were synthesized:

(3-Propyl-piperidin-3-yl)-carbamic acid tert-butyl ester

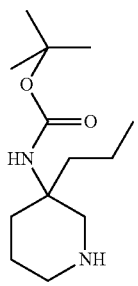

(3-Propyl-pyrrolidin-3-yl)-carbamic acid tert-butyl ester

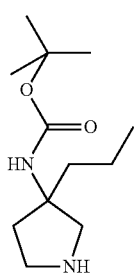

472

1-Benzyl-3,3-dimethyl-piperazine

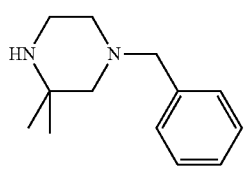

(a) 4-Benzyl-2,2-dimethyl-piperazine-1-carboxylic acid tert-b yl ester

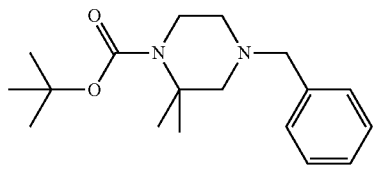 [SMILES: CC(C)(C)OC(=O)N1CCN(Cc2ccccc2)CC1(C)C]

To a solution of 2.20 g of 2,2-Dimethyl-piperazine-1-carboxylic acid tert-butyl ester in 50 ml DCM was added 1.15 ml of benzaldehyde, followed by the addition of 2.61 g of sodium triacetoxyborohydride in small portions. The reaction was stirred at r.t. overnight. To the reaction was then added water. The layers were separated and the organic layer was washed with brine, dried over $Na_2SO_4$, filtered and concentrated in vacuo. 3.30 g (100%) of the title compound were obtained and used without further purification.

LC/MS (Method LC4): Rt=0.67 min; m/z=305.20 $[M+H]^+$.

(b) 1-Benzyl-3,3-dimethyl-piperazine

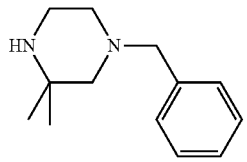

3.30 g 4-Benzyl-2,2-dimethyl-piperazine-1-carboxylic acid tert-butyl ester were dissolved in 50 ml methanol, and 25 ml of 1N aqueous hydrochloric acid were added. After stirring overnight 5 ml of concentrated aqueous hydrochloric acid were added. After 2 h the volatiles were removed in vacuo and 2.40 g (97%) of the title compound were obtained as hydrochloride salt, which could be use without further purification.

LC/MS (Method LC4): Rt=0.15 min; m/z=205.10 $[M+H]^+$.

trans-1-Benzyl-5-methyl-2-phenyl-piperazine

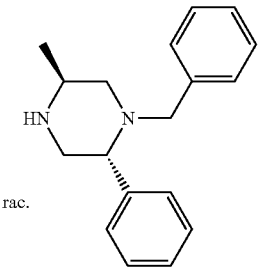 [SMILES: C[C@H]1CN(Cc2ccccc2)[C@H](c2ccccc2)CN1]

trans-1-Benzyl-5-methyl-2-phenyl-piperazine was prepared in analogy to the preparation of benzyl-2,5-dimethylpiperazine (see above) starting form trans-2-Methyl-5-phenyl-piperazine-1-carboxylic acid tert-butyl ester.

LC/MS (Method LC4): Rt=0.64 min; m/z 267.15 [M+H]⁺.

(2R,5S)-2-Ethyl-1-(4-methoxy-benzyl)-5-methyl-piperazine

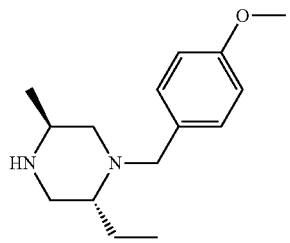 [SMILES: CC[C@@H]1CN[C@@H](C)CN1Cc1ccc(OC)cc1]

(a) (R)-2-(4-Methoxy-benzylamino)-butyric acid methyl ester

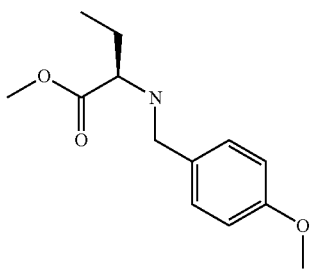

10.0 g of p-methoxybenzaldehyde and 12.98 g of methyl D-homoalaninate-hydrochloride were dissolved in 160 ml of DCM and at 0° C. 11.35 ml of TEA were added. After 10 min at 0° C. 23.36 g of sodium triacetoxyborohydride were added in small portions. The reaction was stirred at r.t. overnight. To the reaction was then added aqueous sodium carbonate solution (10%). The layers were separated and the organic layer was washed with water until neutral, dried over Na₂SO₄, filtered and concentrated in vacuo. 18.72 g of the title compound were obtained and used without further purification.

LC/MS (Method LC4): Rt=0.43 min; m/z=238.15 [M+H]⁺.

(b) (R)-2-R(S)-2-tert-Butoxycarbonylamino-propionyl)-(4-methoxy-benzyl butyric acid methyl ester

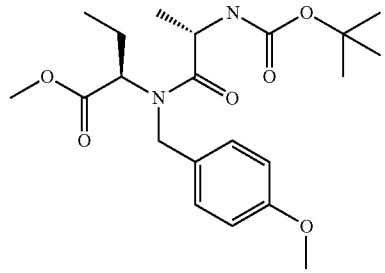 [SMILES: CC[C@H](C(=O)OC)N(Cc1ccc(OC)cc1)C(=O)[C@H](C)NC(=O)OC(C)(C)C]

To a solution of 3.99 g of Boc-L-alanine in 50 ml of DMF were added 12.02 g of HATU, 4.3 ml of Hünig's base and 5.00 g (R)-2-(4-Methoxy-benzylamino)-butyric acid methyl ester. The reaction was stirred overnight, and 6.01 g of HATU and 2.1 ml of Hünig's base were added, and the reaction was stirred for 24 h at r.t. and then for 4 h at 50° C. The reaction was poured unto water, the layers were separated and the aqueous phase was extracted with EtOAc twice. The combined organic layers war washed with 10% aqueous citric acid twice, dried over Na₂SO₄, filtered and concentrated in vacuo. The residue was purified by flash chromatography (silica, heptane/EtOAc) to obtain 7.60 g (88%) of the title compound.

LC/MS (Method LC4): Rt=0.89 min; m/z=409.15 [M+H]⁺.

(c) (3S,6R)-6-Ethyl-1-(4-methoxy-benzyl)-3-methyl-piperazine-2,5-dione

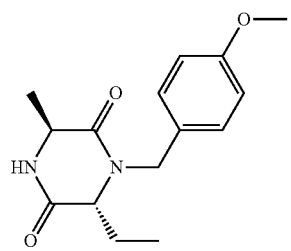 [SMILES: CC[C@@H]1C(=O)N[C@@H](C)C(=O)N1Cc1ccc(OC)cc1]

To a solution of 7.60 g of (R)-2-[((S)-2-tert-Butoxycarbonylamino-propionyl)-(4-methoxy-benzyl)-amino]-butyric acid methyl ester in 116 ml DCM were added 116 ml of TFA at 0° C. during 1 h. After 2 h at 0° C. the reaction mixture was allowed to come to r.t. and stirred for another 1.5 h. The reaction mixture was then concentrated in vacuo, dissolved in EtOAc, and 120 ml of 1M aqueous NaHCO₃-solution were added. After stirring for 1 h, the layers were separated. The organic layer was washed with brine, dried over Na₂SO₄ and concentrated in vacuo to yield 5.34 g (100%) of the title compound, which was used without further purification.

LC/MS (Method LC4): Rt=0.59 min; m/z=277.15 [M+H]⁺.

(d) (2R,5S)-2-Ethyl-1-(4-methoxy-benzyl)-5-methyl-piperazine

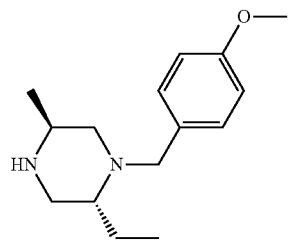 [SMILES: CC[C@@H]1CN[C@@H](C)CN1Cc1ccc(OC)cc1]

To a mixture of (3S,6R)-6-ethyl-1-(4-methoxy-benzyl)-3-methyl-piperazine-2,5-dione (5.34 g) in 130 ml of THF was added 160 ml of a 1 M solution of lithium aluminium hydride in THF. The mixture was stirred overnight and then heated to reflux for 4 h. At 0° C. 5 ml of water, followed by 16 ml of 1 M aqueous KOH-solution were added. The resulting suspension was stirred for 30 min at r.t. and filtered by suction over Celite. The filtrate was concentrated in vacuo and freeze-dried. 3.68 g (77%) of the title compound were obtained and used without further purification.

LC/MS (Method LC4): Rt=0.14 min; m/z=249.20 [M+H]+.

(2R,5S)-1-(4-Methoxy-benzyl)-5-methyl-2-propyl-piperazine

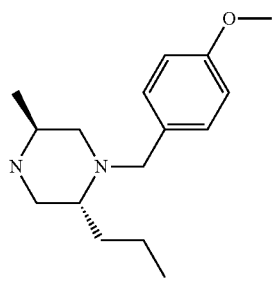 [SMILES: CCC[C@@H]1CN[C@@H](C)CN1Cc1ccc(OC)cc1]

(2R,5S)-1-(4-Methoxy-benzyl)-5-methyl-2-propyl-piperazine was prepared from (R)-2-amino-pentanoic acid methyl ester hydrochloride in analogy to the synthesis of (2R,5S)-2-ethyl-1-(4-methoxy-benzyl)-5-methyl-piperazine.

LC/MS (Method LC4): Rt=0.44 min; m/z=263.25 [M+H]+.

8,8-Dimethyl-6,9-diaza-spiro[4.5]decane-9-carboxylic acid tert-butyl ester

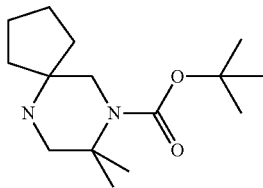 [SMILES: CC(C)(C)OC(=O)N1CC2(CCCC2)NCC1(C)C]

(a) 8,8-Dimethyl-6,9-diaza-spiro[4.5]decan-10-one

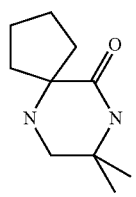

To a solution of 6.1 ml of 1,2-diamino-2-methylpropane in 17 ml water 5.7 ml of 1-hydroxycyclopentane-1-carbonitrile was slowly added. The reaction was kept at reflux for 48 h, and the cooled to r.t. The precipitated product was isolated by suction and washed with water. From the filtrate additional solid could be obtained. The combined solids were freeze-dried and 9.32 g (90%) of the title compound were obtained, which could be used in the next step without further purification.

LC/MS (Method LC4): Rt=0.06 min; m/z=183.10 [M+H]+.

(b) 6-Benzyl-8,8-dimethyl-6,9-diaza-spiro[4.5]decan-10-one

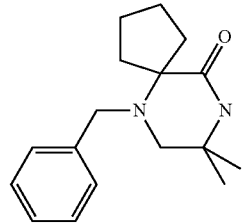 [SMILES: CC1(C)CN(Cc2ccccc2)C2(CCCC2)C(=O)N1]

To a solution of 6.72 g of 8,8-dimethyl-6,9-diaza-spiro[4.5]decan-10-one in 35 ml of DMF were added 4.8 ml of benzyl bromide and 6.9 ml of Hünig's base. The reaction was stirred at r.t overnight. The precipitated product was isolated by suction and washed with DMF and EtOAc. The filtrate was concentrated and the resulting residue was dissolved in EtOAc, washed with water, dried over Na2SO4, filtered and concentrated to yield a second fraction of the product. 9.62 g (96%) of the title compound were obtained.

LC/MS (Method LC4): Rt=0.62 min; m/z=273.20 [M+H]+.

(c) 6-Benzyl-8,8-dimethyl-6,9-diaza-spiro[4.5]decane

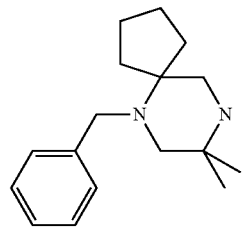 [SMILES: CC1(C)CN(Cc2ccccc2)C2(CCCC2)CN1]

Under Argon atmosphere to a solution of 10.78 g of 6-benzyl-8,8-dimethyl-6,9-diaza-spiro[4.5]decan-10-one in 160 ml of THF 33 ml of a 2.4 M solution of lithium aluminium hydride in THF were slowly added. The reaction was heated to 55° C., and 5 ml of chlorotrimethylsilane were added dropwise. The reaction was kept at 55-60° C. for 2.5 h and then cooled to 0° C. 16 ml of water were added dropwise, and THF was added. The mixture was filtered by suction over celite and the filtrate was concentrated in vacuo. The product was precipitated by treatment with methyl tert-butyl ether. 9.47 g (93%) of the title compound were obtained.

LC/MS (Method LC4): Rt=0.63 min; m/z=259.25 [M+H]+.

(d) 6-Benzyl-8,8-dimethyl-6,9-diaza-spiro[4.5]decane-9-carboxylic acid tert-butyl ester

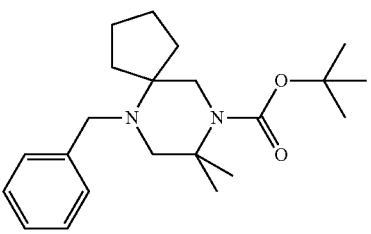 [SMILES: CC(C)(C)OC(=O)N1CC2(CCCC2)N(Cc2ccccc2)CC1(C)C]

4.5 g of 6-benzyl-8,8-dimethyl-6,9-diaza-spiro[4.5]decane were dissolved in 40 ml of DCM and 4.18 g of di-tertbutyl dicarbonate were added. After stirring at r.t. for 1 h the reaction was concentrated in vacuo to yield 6.8 g (100%) of the title compound, which was used without further purification.

LC/MS (Method LC4): Rt=077 min; m/z=359.20 [M+H]⁺.

(e) 8,8-Dimethyl-6,9-diaza-spiro[4.5]decane-9-carboxylic acid tert-butyl ester

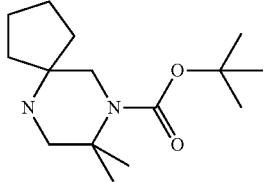 [SMILES: CC(C)(C)OC(=O)N1CC2(CCCC2)NCC1(C)C]

To 7.58 g of 6-benzyl-8,8-dimethyl-6,9-diaza-spiro[4.5]decane-9-carboxylic acid tert-butyl ester in 140 ml of methanol was added 1.13 g Palladium on charcoal (10%) and the mixture was hydrogenated at r.t. and ambient pressure for 16 h. The catalyst was removed by filtration over celite and the filtrate was concentrated in vacuo to yield 5.38 g (95%) of the title compound, which was used without further purification.

LC/MS (Method LC4): Rt=0.66 min; m/z=269.25 [M+H]⁺.

1-Benzyl-2,2,5,5-tetramethyl-piperazine

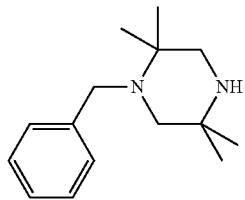 [SMILES: CC1(C)CN(Cc2ccccc2)C(C)(C)CN1]

1-Benzyl-2,2,5,5-tetramethyl-piperazine was synthesized in analogy to 6-benzyl-8,8-dimethyl-6,9-diaza-spiro[4.5]decane starting from 2-methyl-propane-1,2-diamine and acetone cyanohydrin.

LC/MS (Method LC5): Rt=099 min; m/z=233.20 [M+H]⁺.

1-Benzyl-5-ethyl-2,2,5-trimethyl-piperazine

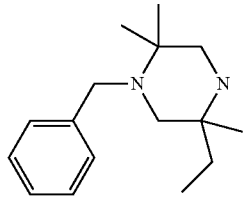 [SMILES: CCC1(C)CN(Cc2ccccc2)C(C)(C)CN1]

1-Benzyl-5-ethyl-2,2,5-trimethyl-piperazine was synthesized in analogy to 6-benzyl-8,8-dimethyl-6,9-diaza-spiro[4.5]decane starting from 2-methylbutane 1,2-diamine and acetone cyanohydrin.

LC/MS (Method LC4): Rt=0.59 min; m/z 247.20 [M+H]⁺.

1-Benzyl-5,5-diethyl-2,2-dimethyl-piperazine

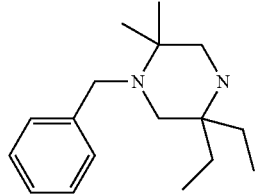 [SMILES: CCC1(CC)CN(Cc2ccccc2)C(C)(C)CN1]

1-Benzyl-5,5-diethyl-2,2-dimethyl-piperazine was synthesized in analogy to 6-benzyl-8,8-dimethyl-6,9-diaza-spiro[4.5]decane starting from 3-(aminomethyl)pentane-3-amine and acetone cyanohydrin.

LC/MS (Method LC4): Rt=0.65 min; m/z 261.20 [M+H]⁺.

8-Methyl-6,9-diaza-spiro[4.5]decane-9-carboxylic acid tert-butyl ester

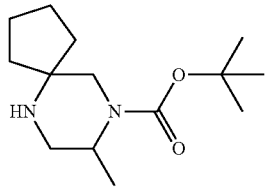 [SMILES: CC1CNC2(CCCC2)CN1C(=O)OC(C)(C)C]

8-Methyl-6,9-diaza-spiro[4.5]decane-9-carboxylic acid tert-butyl ester was synthesized in analogy to 8,8-Dimethyl-6,9-diaza-spiro[4.5]decane-9-carboxylic acid tert-butyl ester starting from 1,2-diamino-propane and 1-hydroxycyclopentane-1-carbonitrile.

LC/MS (Method LC4): Rt=0.56 min; m/z=255.20 [M+H]⁺.

Determination of PKC βII Inhibition

PKC βII Inhibition was Determined According to the Following Protocol:

Active human full-length recombinant PKC βII and the peptide substrate, Fluorescein-RFARKGSLRQKNV, were purchased from Invitrogen GmbH, Darmstadt, Germany. Adenosine-5'-triphosphate (ATP), bovine serum albumine (BSA), dimethylsulphoxide (DMSO), 4-(2-hydroxyethyl)piperazine-1-ethanesulfonic acid (Hepes), Triton X-100, 1,2-Dioleoyl-sn-glycerol (DAG), L-G-Phosphatidyl-L-serine (PS), calcium chloride (CaCl₂), and Pluronic F-68 were purchased from Sigma-Aldrich, Munich, Germany. Magnesium chloride, 1 M sodium hydroxide solution, 1M hydrochloric acid solution and EDTA were obtained from Merck Biosciences, Darmstadt, Germany.

Test compounds were diluted to three times the test concentration in buffer 1 (30 mM Hepes-NaOH, pH 7.4, 0.01% Pluronic F-68 and 3% (v/v) DMSO). The PKC enzyme was diluted to a concentration of 30 ng/ml in buffer 2 (30 mM Hepes-NaOH, pH 7.4, 15 mM MgCl₂, 150 µM CaCl₂, 150 µg/ml PS, 60 µg/ml DAG, and 0.045% (w/v) Triton X-100). The peptide substrate and ATP were diluted to concentrations of 3 µM and 120 µM, respectively, in buffer 2. Two µl of the compound solution were mixed with 2 µl of the diluted enzyme in a 384-well small volume microtiter plate (Greiner, Bio-One, Frickenhausen, Germany), and the kinase reaction was initiated by addition of 2 µl of the solution containing peptide substrate and ATP. After 60 min incubation at 32° C., the reaction was stopped by addition of 20 µl of a solution containing 130 mM Hepes-NaOH, pH 7.4. 0.0195% (v/v) Brij-35, 6.5 mM EDTA. 0.13% chip coating reagent 3 (Caliper Lifescience Inc, Hopkinton, Mass.) and 6.5% (v/v)

DMSO. Phosphorylation of the substrate peptide was then detected on a Caliper 3000 instrument essentially as described by Pommereau et al (J. Biomol. Screening 2004, 9(5), 409-416). Separation conditions were as follows: Pressure −0.8 psi, upstream voltage −3000 V, downstream voltage −800 V. Positive controls (buffer 1 instead of compound) and negative controls (buffer 1 instead of compound and buffer 2 instead of kinase solution) were run in parallel on each plate. Fractional turnover (R) was determined as the height of the peak of the phosphorylated peptide product divided by the sum of the unphosphorylated substrate and phosphorylated product peak heights. Percent-inhibition values for the test compounds were determined using the formula % Inhibition=$100*(1-(R_{compound}-R_{negative\ control})/(R_{positive\ control}-R_{negative\ control})$.

In the following table % inhibition values observed with example compounds at a final concentration of 1.14 µM (±0.15 µM) are listed:

| Exp. No. | % Inhibition |
|---|---|
| 1 | 98 |
| 2 | 69 |
| 3 | 82 |
| 4 | 86 |
| 5 | 74 |
| 6 | 97 |
| 7 | 91 |
| 8 | 32 |
| 9 | 41 |
| 10 | 29 |
| 11 | 101 |
| 12 | 61 |
| 13 | 96 |
| 14 | 94 |
| 15 | 35 |
| 16 | 69 |
| 17 | 95 |
| 18 | 94 |
| 19 | 92 |
| 20 | 110 |
| 21 | 121 |
| 22 | 63 |
| 23 | 95 |
| 24 | 95 |
| 25 | 89 |
| 26 | 97 |
| 27 | 95 |
| 28 | 99 |
| 29 | 99 |
| 30 | 96 |
| 31 | 99 |
| 32 | 98 |
| 33 | 91 |
| 34 | 69 |
| 35 | 52 |
| 36 | 40 |
| 37 | 53 |
| 38 | 80 |
| 39 | 45 |
| 40 | 38 |
| 41 | 95 |
| 42 | 72 |
| 43 | 81 |
| 44 | 83 |
| 45 | 84 |
| 46 | 76 |
| 47 | 70 |
| 48 | 70 |
| 49 | 97 |
| 50 | 81 |
| 51 | 85 |
| 52 | 86 |
| 53 | 92 |
| 54 | 41 |
| 55 | 27 |
| 56 | 96 |
| 57 | 99 |
| 58 | 93 |
| 59 | 80 |
| 60 | 98 |
| 61 | 92 |
| 62 | 100 |
| 63 | 100 |
| 64 | 98 |
| 65 | 94 |
| 66 | 93 |
| 67 | 86 |
| 68 | 88 |
| 69 | 100 |
| 70 | 92 |
| 71 | 95 |
| 72 | 94 |
| 73 | 95 |
| 74 | 47 |
| 75 | 89 |
| 76 | 88 |
| 77 | 60 |
| 78 | 99 |
| 79 | 82 |
| 80 | 91 |
| 81 | 76 |
| 82 | 92 |
| 83 | 104 |
| 84 | 101 |
| 85 | 98 |
| 86 | 96 |
| 87 | 93 |
| 88 | 101 |
| 89 | 92 |
| 90 | 96 |
| 91 | 93 |
| 92 | 95 |
| 93 | 79 |
| 94 | 90 |
| 95 | 99 |
| 96 | 98 |
| 97 | 96 |
| 98 | 89 |
| 99 | 97 |
| 100 | 96 |
| 101 | 99 |
| 102 | 93 |
| 103 | 72 |
| 104 | 94 |
| 105 | 53 |
| 106 | 77 |
| 107 | 83 |
| 108 | 96 |
| 109 | 88 |
| 110 | 65 |
| 111 | 97 |
| 112 | 92 |
| 113 | 93 |
| 114 | 87 |
| 115 | 83 |
| 116 | 76 |
| 117 | 89 |
| 118 | 98 |
| 119 | 91 |
| 120 | 88 |
| 121 | 99 |
| 122 | 89 |
| 123 | 75 |
| 124 | 78 |
| 125 | 52 |
| 126 | 48 |
| 127 | 90 |
| 128 | 91 |
| 129 | 69 |
| 130 | 47 |
| 131 | 68 |
| 132 | 72 |

| Exp. No. | % Inhibition |
|---|---|
| 133 | 89 |
| 134 | 62 |
| 135 | 96 |
| 136 | 100 |
| 137 | 99 |
| 138 | 98 |
| 139 | 99 |
| 140 | 98 |
| 141 | 98 |
| 142 | 98 |
| 143 | 84 |
| 144 | 82 |
| 145 | 92 |
| 146 | 97 |
| 147 | 96 |
| 148 | 85 |
| 149 | 86 |
| 150 | 100 |
| 151 | 96 |
| 152 | 94 |
| 153 | 89 |
| 154 | 94 |
| 155 | 88 |
| 156 | 26 |
| 157 | 91 |
| 158 | 78 |
| 159 | 55 |
| 160 | 49 |
| 161 | 77 |
| 162 | 51 |
| 163 | 57 |
| 164 | 53 |
| 165 | 92 |
| 166 | 87 |
| 167 | 58 |
| 168 | 44 |
| 169 | 84 |
| 170 | 59 |
| 171 | 77 |
| 172 | 67 |
| 173 | 58 |
| 174 | 34 |
| 175 | 46 |
| 176 | 40 |
| 177 | 50 |
| 178 | 71 |
| 179 | 55 |
| 180 | 53 |
| 181 | 77 |
| 182 | 44 |
| 183 | 67 |
| 184 | 22 |
| 185 | 34 |
| 186 | 33 |
| 187 | 58 |
| 188 | 105 |
| 189 | 96 |
| 190 | 101 |
| 191 | 78 |
| 192 | 99 |
| 193 | 94 |
| 194 | 99 |
| 195 | 95 |
| 196 | 75 |
| 197 | 95 |
| 198 | 99 |
| 199 | 99 |
| 200 | 70 |
| 201 | 55 |
| 202 | 101 |
| 203 | 71 |
| 204 | 82 |
| 205 | 92 |
| 206 | 98 |
| 207 | 94 |
| 208 | 88 |
| 209 | 97 |
| 210 | 100 |

| Exp. No. | % Inhibition |
|---|---|
| 211 | 64 |
| 212 | 94 |
| 213 | 94 |
| 214 | 73 |
| 215 | 99 |
| 216 | 92 |
| 217 | 93 |
| 218 | 85 |
| 219 | 89 |
| 220 | 88 |
| 221 | 100 |
| 222 | 97 |
| 223 | 74 |
| 224 | 92 |
| 225 | 85 |
| 226 | 95 |
| 227 | 100 |
| 228 | 91 |
| 229 | 79 |
| 230 | 93 |
| 231 | 84 |
| 232 | 95 |
| 233 | 95 |
| 234 | 94 |
| 235 | 89 |
| 236 | 84 |
| 237 | 59 |
| 238 | 77 |
| 239 | 78 |
| 240 | 94 |
| 241 | 88 |
| 242 | 87 |
| 243 | 78 |
| 244 | 76 |
| 245 | 83 |
| 246 | 88 |
| 247 | 69 |
| 248 | 83 |
| 249 | 82 |
| 250 | 85 |
| 251 | 53 |
| 252 | 72 |
| 253 | 73 |
| 254 | 80 |
| 255 | 90 |
| 256 | 86 |
| 257 | 82 |
| 258 | 78 |
| 259 | 29 |
| 260 | 78 |
| 261 | 70 |
| 262 | 59 |
| 263 | 65 |
| 264 | 88 |
| 265 | 87 |
| 266 | 39 |
| 267 | 32 |
| 268 | 80 |
| 269 | 87 |
| 270 | 87 |
| 271 | 66 |
| 272 | 85 |
| 273 | 83 |
| 274 | 88 |
| 275 | 89 |
| 276 | 66 |
| 277 | 35 |
| 278 | 68 |
| 279 | 78 |
| 280 | 88 |
| 281 | 85 |
| 282 | 73 |
| 283 | 45 |
| 284 | 66 |
| 285 | 76 |
| 286 | 62 |
| 287 | 34 |
| 288 | 59 |

483
-continued

| Exp. No. | % Inhibition |
|---|---|
| 289 | 84 |
| 290 | 96 |
| 291 | 89 |
| 292 | 77 |
| 293 | 89 |
| 294 | 85 |
| 295 | 94 |
| 296 | 32 |
| 297 | 34 |
| 298 | 68 |
| 299 | 92 |
| 300 | 74 |
| 301 | 63 |
| 302 | 82 |
| 303 | 93 |
| 304 | 91 |
| 305 | 83 |
| 306 | 76 |
| 307 | 59 |
| 308 | 60 |
| 309 | 71 |
| 310 | 91 |
| 311 | 74 |
| 312 | 54 |
| 313 | 99 |
| 314 | 35 |
| 315 | 62 |
| 316 | 51 |
| 317 | 68 |
| 318 | 61 |
| 319 | 59 |
| 320 | 72 |
| 321 | 84 |
| 322 | 68 |
| 323 | 42 |
| 324 | 69 |
| 325 | 76 |
| 326 | 83 |
| 327 | 92 |
| 328 | 80 |
| 329 | 72 |
| 330 | 45 |
| 331 | 41 |
| 332 | 63 |
| 333 | 67 |
| 334 | 53 |
| 335 | 61 |
| 336 | 73 |
| 337 | 93 |
| 338 | 68 |
| 339 | 73 |
| 340 | 67 |
| 341 | 53 |
| 342 | 60 |
| 343 | 49 |
| 344 | 64 |
| 345 | 58 |
| 346 | 59 |
| 347 | 35 |
| 348 | 44 |
| 349 | 81 |
| 350 | 77 |
| 351 | 88 |
| 352 | 84 |
| 353 | 70 |
| 354 | 52 |
| 355 | 60 |
| 356 | 31 |
| 357 | 21 |
| 358 | 28 |
| 359 | 36 |
| 360 | 52 |
| 361 | 50 |
| 362 | 80 |
| 363 | 72 |
| 364 | 38 |
| 365 | 41 |
| 366 | 47 |

484
-continued

| Exp. No. | % Inhibition |
|---|---|
| 367 | 36 |
| 368 | 58 |
| 369 | 34 |
| 370 | 48 |
| 371 | 31 |
| 372 | 66 |
| 373 | 96 |
| 374 | 99 |
| 375 | 90 |
| 376 | 64 |
| 377 | 69 |
| 378 | 87 |
| 379 | 86 |
| 380 | 83 |
| 381 | 37 |
| 382 | 67 |
| 383 | 66 |
| 384 | 67 |
| 385 | 24 |
| 386 | 51 |
| 387 | 39 |
| 388 | 54 |
| 389 | 65 |
| 390 | 67 |
| 391 | 84 |
| 392 | 49 |
| 393 | 55 |
| 394 | 23 |
| 395 | 42 |
| 396 | 39 |
| 397 | 73 |
| 398 | 21 |
| 399 | 60 |
| 400 | 62 |
| 401 | 71 |
| 402 | 41 |
| 403 | 55 |
| 404 | 31 |
| 405 | 48 |
| 406 | 47 |
| 407 | 20 |
| 408 | 21 |
| 409 | 23 |
| 410 | 20 |
| 411 | 24 |
| 412 | 23 |
| 413 | 29 |
| 414 | 30 |
| 415 | 90 |
| 416 | 84 |
| 417 | 78 |
| 418 | 30 |
| 419 | 79 |
| 420 | 80 |
| 421 | 51 |
| 422 | 95 |
| 423 | 84 |
| 424 | 100 |
| 425 | 88 |
| 426 | 87 |
| 427 | 99 |
| 428 | 35 |
| 429 | 98 |
| 430 | 92 |
| 431 | 97 |
| 432 | 42 |
| 433 | 98 |
| 434 | 106 |
| 435 | 97 |
| 436 | 100 |
| 437 | 99 |
| 438 | 98 |
| 439 | 99 |
| 440 | 90 |
| 441 | 96 |
| 442 | 97 |
| 443 | 97 |
| 444 | 99 |

-continued

| Exp. No. | % Inhibition |
|---|---|
| 445 | 99 |
| 446 | 98 |
| 447 | 83 |
| 448 | 99 |
| 449 | 99 |
| 450 | 100 |
| 451 | 104 |
| 452 | 83 |
| 453 | 90 |
| 454 | 81 |
| 455 | 92 |
| 456 | 88 |
| 457 | 63 |
| 458 | 44 |
| 459 | 95 |
| 460 | 61 |
| 461 | 99 |

What is claimed is:
1. A compound of formula I

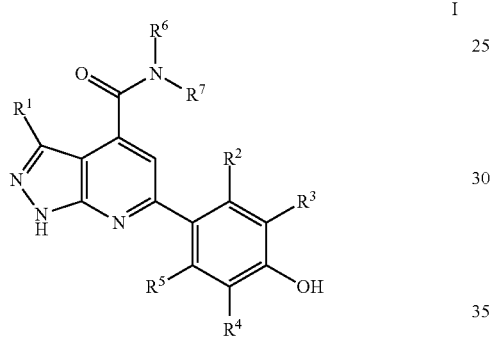

wherein
$R^1$ is $(C_1-C_4)$-alkyl, cyclopropyl, or $CF_3$;
$R^2$ is H, $(C_1-C_4)$-alkyl, halogen or O—$(C_1-C_4)$-alkyl;
$R^3$ is H, $(C_1-C_4)$-alkyl, halogen or O—$(C_1-C_4)$-alkyl;
$R^4$ is H or halogen;
$R^5$ is H, halogen or $(C_1-C_4)$-alkyl;
$R^6$ is H, $(C_1-C_4)$-alkyl or $(C_1-C_4)$-alkylene-phenyl;
$R^7$ is
a) $(C_0-C_6)$-alkyl which is mono-substituted by
  i) a 3- to 8-membered monocyclic heterocycle comprising a ring nitrogen atom and optionally one further ring heteroatom selected from the group consisting of nitrogen and oxygen, which is unsubstituted or substituted by one to five identical or different substituents selected from the group consisting of
    ia) F,
    ib) $(C_1-C_4)$-alkyl, which is unsubstituted or one to fivefold substituted by F,
    ic) O—$(C_1-C_4)$-alkyl, which is unsubstituted or one to fivefold substituted by F,
    id) phenyl, which is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F,
    ie) $(C_1-C_4)$-alkylene-phenyl, which is unsubstituted or one to fivefold substituted by F,
    if) $(C_3-C_8)$-cycloalkyl,
    ig) oxo (═O),
    ih) (CO)—$(C_1-C_4)$-alkyl, and
    ij) $(C_0-C_2)$-alkylene-$NH_2$, $(C_0-C_2)$-alkylene-NH—$(C_1-C_4)$-alkyl, or $(C_0-C_2)$-alkylene-N$((C_1-C_4)$-alkyl$)_2$;
    and wherein $(C_0-C_6)$-alkyl can be further mono-substituted by phenyl or pyridyl, wherein phenyl or pyridyl is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F;
  ii) $(C_3-C_8)$-cycloalkyl which is substituted by one to two identical or different substituents selected from the group consisting of $NH_2$, NH$(C_1-C_4)$-alkyl) and N$((C_1-C_4)$-alkyl$)_2$, and wherein $(C_3-C_8)$-cycloalkyl can be further substituted by one to three identical or different substituents selected from the group consisting of
    iia) F,
    iib) $(C_1-C_4)$-alkyl, wherein $(C_1-C_4)$-alkyl is unsubstituted or one to fivefold substituted by F,
    iic) O—$(C_1-C_4)$-alkyl, which is unsubstituted or one to fivefold substituted by F,
    iid) phenyl, which is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F, and
    iie) $(C_1-C_4)$-alkylene-phenyl, which is unsubstituted or one to fivefold substituted by F;
or
  iii) $NR^8R^9$, wherein
    $R^8$ is H or $(C_1-C_4)$-alkyl, and
    $R^9$ is H or $(C_1-C_6)$-alkyl,
    and wherein $(C_0-C_6)$-alkyl can be further mono-substituted by phenyl, phenylene-$(C_1-C_4)$-alkyl or phenylene-O—$(C_1-C_4)$-alkyl;
b) a bicyclic $(C_6-C_{11})$-cycloalkyl group, which is mono-substituted by $(C_0-C_2)$-alkylene-$NH_2$, $(C_0-C_2)$-alkylene-NH—$(C_1-C_4)$-alkyl, or $(C_0-C_2)$-alkylene-N$((C_1-C_4)$-alkyl$)_2$;
c) a fused bicyclic $(C_6-C_{10})$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F;
d) a spiro bicyclic $(C_7-C_{11})$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F;
e) a bridged bicyclic $(C_7-C_9)$-heterocycloalkyl group containing one nitrogen atom, which is attached via a carbon atom and which is unsubstituted or substituted by one or two identical or different substituents selected from the group consisting of F and $(C_1-C_4)$-alkyl which is unsubstituted or one to fivefold substituted by F; or
f) a tricyclic $(C_{11}-C_{15})$-heterocycloalkyl group containing one nitrogen atom, which is attached via a carbon atom and which consists of a spiro bicyclic ring with an additional fused phenyl ring, and which is unsubstituted or substituted by one or two identical or different substituents selected from the group consisting of F and ($C_1$-$C_4$)-alkyl, which is unsubstituted or one to fivefold substituted by F;

or $R^6$ and $R^7$ together with the N-atom carrying them denote a) a 1,4-piperazinyl of the formula

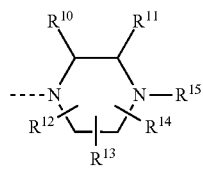

wherein $R^{10}$ is H, or ($C_0$-$C_6$)-alkyl, which is unsubstituted or one to fivefold substituted by F, or mono-substituted by a substituent selected from the group consisting of
  i) O—($C_1$-$C_4$)-alkyl, which is unsubstituted or one to fivefold substituted by F,
  ii) ($C_3$-$C_6$)-cycloalkyl,
  iii) phenyl, which is unsubstituted or substituted by one to two identical or different substituents selected from the group consisting of halogen, $CF_3$, O—($C_1$-$C_4$)-alkyl, $OCF_3$, and ($C_1$-$C_4$)-alkyl,
  iv) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, $CF_3$, $OCF_3$, and
  v) benzo[1,3]dioxole, and
  vi) CO—$R^{16}$;

$R^{11}$ is H or ($C_0$-$C_6$)-alkyl, which is unsubstituted or one to fivefold substituted by F or mono-substituted by a substituent selected from the group consisting of
  i) CO—$R^{17}$,
  ii) ($C_3$-$C_6$)-cycloalkyl,
  iii) phenyl, which is unsubstituted or substituted by one to two identical or different substituents selected from the group consisting of halogen, $CF_3$, O—($C_1$-$C_4$)-alkyl, $OCF_3$, and ($C_1$-$C_4$)-alkyl,
  iv) O—($C_1$-$C_4$)-alkyl, which is unsubstituted or one to fivefold substituted by F,
  v) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, $CF_3$, $OCF_3$, and ($C_1$-$C_4$)-alkyl, and
  vi) oxo (=O);

$R^{12}$ is H, ($C_1$-$C_6$)-alkyl, which is unsubstituted or one to fivefold substituted by F, or phenyl;

$R^{13}$ is H or ($C_1$-$C_6$)-alkyl;

$R^{14}$ is H or ($C_1$-$C_4$)-alkyl;

$R^{15}$ is H, ($C_1$-$C_6$)-alkyl, ($C_3$-$C_6$)-cycloalkyl or CO—$R^{18}$, wherein ($C_1$-$C_6$)-alkyl is unsubstituted or one to fivefold substituted by F, or mono-substituted by a substituent selected from the group consisting of $SO_2$—($C_1$-$C_4$)-alkyl, phenyl, a 5- to 6-membered monocyclic heterocyclic ring comprising one heteroatom selected from the group consisting of nitrogen and oxygen, and a 5- to 6-membered monocyclic heteroaromatic ring comprising one heteroatom selected from the group consisting of nitrogen and oxygen;

$R^{16}$ is O—($C_1$-$C_4$)-alkyl or NH—($C_1$-$C_6$)-alkyl;

$R^{17}$ is O—($C_1$-$C_4$)-alkyl;

$R^{18}$ is ($C_1$-$C_4$)-alkyl, $NH_3$, phenyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen, where phenyl can be further mono-substituted by ($C_1$-$C_4$)-alkyl or O—($C_1$-$C_4$)-alkyl;

b) a four to seven membered monocyclic heterocycloalkyl group containing a nitrogen atom, which is attached via said nitrogen and which is mono-substituted by ($C_0$-$C_6$)-alkylene-$NH_2$, ($C_0$-$C_6$)-alkylene-NH—($C_1$-$C_4$)-alkyl, ($C_0$-$C_6$)-alkylene-NH-phenyl, ($C_0$-$C_6$)-alkylene-N(($C_1$-$C_4$)-alkyl)$_2$, or ($C_0$-$C_6$)-alkylene-N(($C_1$-$C_4$)-alkyl)(phenyl); and wherein said heterocycloalkyl group can be further mono-substituted by ($C_1$-$C_6$)-alkyl, which is unsubstituted or one to fivefold substituted by F, CO—O—($C_1$-$C_4$)-alkyl or phenyl;

c) a 1,4-diazepanyl, which is unsubstituted or mono-substituted by ($C_1$-$C_6$)-alkyl, wherein ($C_1$-$C_6$)-alkyl is unsubstituted or one to fivefold substituted by F, CO-phenyl, or CO-pyridyl;

d) a fused bicyclic ($C_6$-$C_{10}$)-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or substituted by one to two identical or different substituents selected from the group consisting of F, ($C_0$-$C_2$)-alkylene-phenyl, oxo (=O) and ($C_1$-$C_4$)-alkyl, wherein ($C_1$-$C_4$)-alkyl is unsubstituted or one to fivefold substituted by F;

e) a spiro bicyclic ($C_7$-$C_{11}$)-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or mono- or di-substituted by F or ($C_1$-$C_4$)-alkyl, which is unsubstituted or one to fivefold substituted by F;

f) a bridged bicyclic ($C_7$-$C_9$)-heterocycloalkyl group containing one nitrogen atom, which is attached via said nitrogen atom, which is mono-substituted by ($C_0$-$C_2$)-alkylene-$NH_2$, ($C_0$-$C_2$)-alkylene-NH—($C_1$-$C_4$)-alkyl, ($C_0$-$C_2$)-alkylene-N(($C_1$-$C_4$)-alkyl)$_2$ g) a bridged bicyclic ($C_7$-$C_9$)-heterocycloalkyl group containing two nitrogen atoms, which is attached via a nitrogen atom; and which is unsubstituted or substituted by one to four identical or different substituents selected from the group consisting of F, OH, and ($C_1$-$C_4$)-alkyl, which is unsubstituted or one to fivefold substituted by F;

or h) a tricyclic ($C_{11}$-$C_{15}$)-heterocycloalkyl group containing two nitrogen atoms, which is attached via a nitrogen atom and which consists of a spiro bicyclic ring with an additional fused phenyl ring, and which is unsubstituted or substituted by one or two identical or different substituents selected from the group consisting of F and ($C_1$-$C_4$)-alkyl, which is unsubstituted or one to fivefold substituted by F;
wherein the following compounds are disclaimed:
((S)-2-Ethyl-piperazin-1-yl)-[6-(4-hydroxy-phenyl)-3-methyl-1H-pyrazolo[3,4-b]pyridin-4-yl]-methanone,
[6-(4-Hydroxy-phenyl)-3-methyl-1H-pyrazolo[3,4-b]pyridin-4-yl]-(R)-2-methoxymethyl-piperazin-1-yl)-methanone,
6-(4-Hydroxy-phenyl)-3-methyl-1H-pyrazolo[3,4-b]pyridine-4-carboxylic acid phenethyl-(R)-piperidin-3-yl-amide,
[6-(4-Hydroxy-phenyl)-3-methyl-1H-pyrazolo[3,4-b]pyridin-4-yl]-(2-phenyl-piperazin-1-yl)-methanone,
(2-Benzo[1,3]dioxol-5-yl-piperazin-1-yl)-[6-(4-hydroxy-phenyl)-3-methyl-1H-pyrazolo[3,4-b]pyridin-4-yl]-methanone, 6-(4-Hydroxy-phenyl)-3-methyl-1H-pyrazolo[3,4-b]pyridine-4-carboxylic acid (4-methyl-piperidin-4-yl)-amide,
6-(4-Hydroxy-phenyl)-3-methyl-1H-pyrazolo[3,4-b]pyridine-4-carboxylic acid (2,3-dihydro-spiro[1H-indene-1,4'-piperidin]-3-yl)-amide,
[6-(4-Hydroxy-phenyl)-3-methyl-1H-pyrazolo[3,4-b]pyridin-4-0]-(2-pyridin-3-yl-piperazin-1-yl)-methanone,
(3-Benzyl-piperazin-1-yl)-[6-(4-hydroxy-phenyl)-3-methyl-1H-pyrazolo[3,4-b]pyridin-4-yl]-methanone,
[6-(4-Hydroxy-phenyl)-3-methyl-1H-pyrazolo[3,4-b]pyridin-4-yl]-((S)-2-phenyl-piperazin-1-yl)-methanone, and
[6-(4-Hydroxy-phenyl)-3-methyl-1H-pyrazolo[3,4-b]pyridin-4-yl]-((R)-2-phenyl-piperazin-1-yl)-methanone,
in any of its stereoisomeric forms, or a mixture of stereoisomeric forms in any ratio, or a physiologically acceptable salt thereof, or a physiologically acceptable solvate of any of them.

2. The compound of claim 1, wherein
A) $R^1$ is ($C_1$-$C_4$)-alkyl;
$R^2$ is H, halogen or ($C_1$-$C_4$)-alkyl;
$R^3$ is H or halogen;
$R^4$ is H;
$R^5$ is H;
$R^6$ is H;
$R^7$ is
a) ($C_0$-$C_6$)-alkyl which is mono-substituted by
 i) a 3- to 8-membered monocyclic heterocycle comprising a ring nitrogen atom and optionally one further ring heteroatom selected from the group consisting of nitrogen and oxygen, which is unsubstituted or substituted by one to five identical or different substituents selected from the group consisting of
  ia) F,
  ib) ($C_1$-$C_4$)-alkyl, which is unsubstituted or one to fivefold substituted by F,
  ic) O—($C_1$-$C_4$)-alkyl, which is unsubstituted or one to fivefold substituted by F,
  id) phenyl, which is unsubstituted or substituted by one to two identical or different substituents selected from the group consisting of halogen and ($C_1$-$C_4$)-alkyl, wherein ($C_1$-$C_4$)-alkyl is unsubstituted or one to fivefold substituted by F,
  ie) ($C_1$-$C_4$)-alkylene-phenyl, which is unsubstituted or one to fivefold substituted by F,
  if) ($C_3$-$C_8$)-cycloalkyl,
  ig) oxo (=O), and
  ih) (CO)—($C_1$-$C_4$)-alkyl,
  and wherein ($C_0$-$C_6$)-alkyl can be further monosubstituted by phenyl or pyridyl, wherein phenyl or pyridyl is unsubstituted or substituted by one to two identical or different substituents selected from the group consisting of halogen and ($C_1$-$C_4$)-alkyl, wherein ($C_1$-$C_4$)-alkyl is unsubstituted or one to fivefold substituted by F;
 ii) ($C_3$-$C_8$)-cycloalkyl which is substituted by one to two identical or different substituents selected from the group consisting of $NH_2$, NH(($C_1$-$C_4$)-alkyl) and N(($C_1$-$C_4$)-alkyl)$_2$, and wherein ($C_3$-$C_8$)-cycloalkyl can be further substituted by one to three identical or different substituents selected from the group consisting of
  iia) F,
  iib) ($C_1$-$C_4$)-alkyl, wherein ($C_1$-$C_4$)-alkyl is unsubstituted or one to fivefold substituted by F,
  iic) O—($C_1$-$C_4$)-alkyl, which is unsubstituted or one to fivefold substituted by F,
  iid) phenyl, which is unsubstituted or substituted by one to two identical or different substituents selected from the group consisting of halogen and ($C_1$-$C_4$)-alkyl, wherein ($C_1$-$C_4$)-alkyl is unsubstituted or one to fivefold substituted by F, and
  iie) ($C_1$-$C_4$)-alkylene-phenyl, which is unsubstituted or one to fivefold substituted by F;
or
 iii) $NR^8R^9$, wherein
  $R^8$ is H or ($C_1$-$C_4$)-alkyl, and
  $R^9$ is H or ($C_1$-$C_6$)-alkyl,
  and wherein ($C_0$-$C_6$)-alkyl can be further monosubstituted by phenyl, phenylene-($C_1$-$C_4$)-alkyl or phenylene-O—($C_1$-$C_4$)-alkyl;
b) a bicyclic ($C_6$-$C_{11}$)-cycloalkyl group, which is monosubstituted by ($C_0$-$C_2$)-alkylene-$NH_2$, ($C_0$-$C_2$)-alkylene-NH—($C_1$-$C_4$)-alkyl, ($C_0$-$C_2$)-alkylene-N(($C_1$-$C_4$)-alkyl)$_2$;
c) a fused bicyclic ($C_6$-$C_{10}$)-heterocycloalkyl group containing one nitrogen atom, which is attached via a carbon atom and which is unsubstituted or substituted by one or two identical or different substituents selected from the group consisting of F and ($C_1$-$C_4$)-alkyl, which is unsubstituted or one to fivefold substituted by F;
d) a spiro bicyclic ($C_7$-$C_{11}$)-heterocycloalkyl group containing one nitrogen atom, which is attached via a carbon atom and which is unsubstituted or substituted by one or two identical or different substituents selected from the group consisting of F and ($C_7$-$C_{11}$)-alkyl, which is unsubstituted or one to fivefold substituted by F;
e) a bridged bicyclic ($C_7$-$C_9$)-heterocycloalkyl group containing one nitrogen atom, which is attached via a carbon atom and which is unsubstituted or substituted by one or two identical or different substituents selected from the group consisting of F and ($C_1$-$C_4$)-alkyl, which is unsubstituted or one to fivefold substituted by F; or
f) a tricyclic ($C_{11}$-$C_{15}$)-heterocycloalkyl group containing one nitrogen atom, which is attached via a carbon atom and which consists of a spiro bicyclic ring with an additional fused phenyl ring, and which is unsubstituted or substituted by one or two identical or different substituents selected from the group consisting of F and ($C_1$-$C_4$)-alkyl, which is unsubstituted or one to fivefold substituted by F;

or

B) $R^1$ is $(C_1-C_4)$-alkyl;
$R^2$ is H;
$R^3$ is H or halogen;
$R^4$ is H;
$R^5$ is H;
$R^6$ is $(C_1-C_4)$-alkyl or $(C_1-C_4)$-alkylene-phenyl;
$R^7$ is a 5- to 6-membered monocyclic heterocycle comprising a ring nitrogen atom, which is attached via a carbon atom, $(C_1-C_4)$-alkylene-$NH_2$, or $(C_1-C_4)$-alkylene-NH—$(C_1-C_4)$-alkyl;

or

C) $R^1$ is $(C_1-C_4)$-alkyl;
$R^2$ is H, $(C_1-C_4)$-alkyl, halogen or O—$(C_1-C_4)$-alkyl;
$R^3$ is H, $(C_1-C_4)$-alkyl, halogen or O—$(C_1-C_4)$-alkyl;
$R^4$ is H or halogen;
$R^5$ is H, halogen or $(C_1-C_4)$-alkyl;
$R^6$ and $R^7$ together with the N-atom carrying them denote
a) a 1,4-piperazinyl of the formula

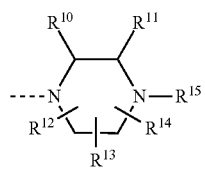

wherein $R^{10}$, $R^{11}$, $R^{12}$, $R^{13}$, $R^{14}$, and $R^{15}$ are as defined in claim 1;
b) a four to seven membered monocyclic heterocycloalkyl group containing a nitrogen atom, which is attached via said nitrogen and which is monosubstituted by $(C_0-C_6)$-alkylene-$NH_2$, $(C_0-C_6)$-alkylene-NH—$(C_1-C_4)$-alkyl, $(C_0-C_6)$-alkylene-NH-phenyl, $(C_0-C_6)$-alkylene-N$((C_1-C_4)$-alkyl$)_2$, or $(C_0-C_6)$-alkylene-N$((C_1-C_4)$-alkyl)(phenyl); and wherein said heterocycloalkyl group can be further mono-substituted by $(C_1-C_6)$-alkyl, which is unsubstituted or one to fivefold substituted by F, CO—O—$(C_1-C_4)$-alkyl or phenyl;
c) a 1,4-diazepanyl, which is unsubstituted or mono-substituted by $(C_1-C_6)$-alkyl, wherein $(C_1-C_6)$-alkyl is unsubstituted or one to fivefold substituted by F, CO-phenyl, or CO-pyridyl;
d) a fused bicyclic $(C_6-C_{10})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or substituted by one to two identical or different substituents selected from the group consisting of F, $(C_3-C_2)$-alkylene-phenyl, oxo (=O), and $(C_1-C_4)$-alkyl, wherein $(C_1-C_4)$-alkyl is unsubstituted or one to fivefold substituted by F;
e) a spiro bicyclic $(C_7-C_{11})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or mono- or di-substituted by F or $(C_1-C_4)$-alkyl, which is unsubstituted or one to fivefold substituted by F;
f) a bridged bicyclic $(C_7-C_9)$-heterocycloalkyl group containing one nitrogen atom, which is attached via said nitrogen atom, which is mono-substituted by $(C_0-C_2)$-alkylene-$NH_2$, $(C_0-C_2)$-alkylene-NH—$(C_1-C_4)$-alkyl, $(C_0-C_2)$-alkylene-N$((C_1-C_4)$-alkyl$)_2$
g) a bridged bicyclic $(C_7-C_9)$-heterocycloalkyl group containing two nitrogen atoms, which is attached via a nitrogen atom; and which is unsubstituted or substituted by one to four identical or different substituents selected from the group consisting of F, OH, and $(C_1-C_4)$-alkyl, which is unsubstituted or one to fivefold substituted by F; or
h) a tricyclic $(C_{11}-C_{15})$-heterocycloalkyl group containing two nitrogen atoms, which is attached via a nitrogen atom and which consists of a spiro bicyclic ring with an additional fused phenyl ring, and which is unsubstituted or substituted by one or two identical or different substituents selected from the group consisting of F and $(C_1-C_4)$-alkyl, which is unsubstituted or one to fivefold substituted by F;

or

D) $R^1$ is $CF_3$;
$R^2$ is H;
$R^3$ is H;
$R^4$ is H;
$R^5$ is H;
$R^6$ is H and
$R^7$ is a) 3-azetidyl or 3-piperidyl;
b) a bridged bicyclic $(C_7-C_9)$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F;

or $R^6$ and $R^7$ together with the N-atom carrying them denote
a) a 1,4-piperazinyl or a 1,4-diazepanyl, which are unsubstituted or mono-substituted by $(C_1-C_4)$-alkyl;
b) a 1-pyrrolidinyl or a 1-piperidyl, which are mono-substituted by $NH_2$, NH$((C_1-C_4)$-alkyl), or N$((C_1-C_4)$-alkyl$)_2$;
c) a fused bicyclic $(C_6-C_{10})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or substituted by one to two identical or different substituents selected from the group consisting of F, $(C_0-C_2)$-alkylene-phenyl, oxo (=O), and $(C_1-C_4)$-alkyl, wherein $(C_1-C_4)$-alkyl is unsubstituted or one to fivefold substituted by F;
d) a spiro bicyclic $(C_7-C_{11})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or mono- or di-substituted by F or $(C_1-C_4)$-alkyl, which is unsubstituted or one to fivefold substituted by F;

or

E) $R^1$ is cyclopropyl;
$R^2$ is H;
$R^3$ is H;
$R^4$ is H;
$R^5$ is H;

R⁶ and R⁷ together with the N-atom carrying them denote a 1,4-piperazinyl, which is unsubstituted or substituted by one to two identical or different substituents selected from the group consisting of (C₁-C₄)-alkyl and phenyl.

3. The compound of claim 1, wherein

A) R¹ is (C₁-C₄)-alkyl;
R² is H, halogen or (C₁-C₄)-alkyl;
R³ is H or halogen;
R⁴ is H;
R⁵ is H;
R⁶ is H;
R⁷ is
  a) (C₀-C₆)-alkyl which is mono-substituted by
    i) a 3- to 8-membered monocyclic heterocycle comprising a ring nitrogen atom and optionally one further ring heteroatom selected from the group consisting of nitrogen and oxygen, which is unsubstituted or substituted by one to five identical or different substituents selected from the group consisting of (C₁-C₄)-alkyl, O—(C₁-C₄)-alkyl, phenyl, phenylene-(C₁-C₄)-alkyl, (C₁-C₄)-alkylene-phenyl, (C₃-C₈)-cycloalkyl, oxo (=O), and (CO)—(C₁-C₄)-alkyl, and wherein (C₀-C₆)-alkyl can be further mono-substituted by phenyl or pyridyl;
    ii) (C₃-C₈)-cycloalkyl which is substituted by one to two identical or different substituents selected from the group consisting of and N((C₁-C₄)-alkyl)₂; NR⁸R⁹, wherein
      R⁸ is H or (C₁-C₄)-alkyl, and
      R⁹ is H or (C₁-C₆)-alkyl,
      and wherein (C₀-C₆)-alkyl can be further mono-substituted by phenyl, phenylene-(C₁-C₄)-alkyl or phenylene-O—(C₁-C₄)-alkyl;
or
R⁷ is
  b) a bicyclic (C₇)-cycloalkyl group, which is mono-substituted by —NH₂, or —CH₂—NH₂;
  c) a fused bicyclic (C₆)-heterocycloalkyl group containing one nitrogen atom, which is attached via a carbon atom
  d) a spiro bicyclic (C₉)-heterocycloalkyl group containing one nitrogen atom, which is attached via a carbon atom;
  e) a bridged bicyclic (C₃-C₈)-heterocycloalkyl group containing one nitrogen atom, which is attached via a carbon atom and which is unsubstituted or monosubstituted by CH₃;
  f) a tricyclic (C₁₄)-heterocycloalkyl group containing one nitrogen atom, which is attached via a carbon atom and which consists of a spiro bicyclic ring with an additional fused phenyl ring;
or
B) R¹ is (C₁-C₄)-alkyl;
R² is H;
R³ is H or halogen;
R⁴ is H;
R⁵ is H;
R⁶ is (C₁-C₄)-alkyl or (C₁-C₄)-alkylene-phenyl;
R⁷ is a 5- to 6-membered monocyclic heterocycle comprising a ring nitrogen atom, which is attached via a carbon atom, (C₁-C₄)-alkylene-NH₂, or (C₁-C₄)-alkylene-NH—(C₁-C₄)-alkyl;
or
C) R¹ is (C₁-C₄)-alkyl;
R² is H, (C₁-C₄)-alkyl, halogen or O—(C₁-C₄)-alkyl;
R³ is H, (C₁-C₄)-alkyl, halogen or O—(C₁-C₄)-alkyl;
R⁴ is H or halogen;
R⁵ is H, halogen or (C₁-C₄)-alkyl;
R⁶ and R⁷ together with the N-atom carrying them denote
  a) a 1,4-piperazinyl of the formula

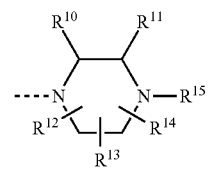

wherein
R¹⁰ is H, or (C₀-C₆)-alkyl, which is unsubstituted or substituted threefold by F or mono-substituted by O—(C₁-C₄)-alkyl, phenyl, a 5- to 6-membered monocyclic heteroaromatic ring comprising one heteroatom selected from the group consisting of nitrogen, oxygen, and sulphur, benzo[1,3]dioxole or CO—R¹⁶; wherein phenyl is unsubstituted or substituted by one to two identical or different substituents selected from the group consisting of halogen, CF₃, O—(C₁-C₄)-alkyl, and (C₁-C₄)-alkyl;
R¹¹ is H or (C₀-C₆)-alkyl, which is unsubstituted or substituted threefold by F or mono-substituted by CO—R¹⁷, (C₃-C₄)-cycloalkyl, phenyl, O—(C₁-C₄)-alkyl or oxo (=O);
R¹² is H, (C₁-C₆)-alkyl or phenyl;
R¹³ is H or (C₁-C₆)-alkyl;
R¹⁴ is H or (C₁-C₄)-alkyl;
R¹⁵ is H, (C₁-C₆)-alkyl, (C₃-C₆)-cycloalkyl or CO—R¹⁸, where (C₁-C₆)-alkyl is unsubstituted or mono-substituted by SO₂—(C₁-C₄)-alkyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen;
R¹⁶ is O—(C₁-C₄)-alkyl or NH—(C₁-C₆)-alkyl;
R¹⁷ is O—(C₁-C₄)-alkyl;
R¹⁸ is (C₁-C₄)-alkyl, NH₂, phenyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen, where phenyl can be further mono-substituted by (C₁-C₄)-alkyl or O—(C₁-C₄)-alkyl;
  b) a 1-azetidinyl, which is mono-substituted by NH₂ or (C₁-C₆)-alkylene-NH₂;
  c) a 1-pyrrolidinyl, which is mono-substituted by NR¹⁹R²⁰ or (C₃-C₄)-alkylene-amine, wherein
    R¹⁹ is H, (C₁-C₄)-alkyl or phenyl;
    R²⁰ is H or (C₁-C₄)-alkyl,
    and 1-pyrrolidinyl can be further mono-substituted by (C₁-C₆)-alkyl or CF₃;
  d) a 1-piperidyl, which is mono-substituted by NR²¹R²² or (C₁-C₄)-alkyl-NH₂, wherein
    R²¹ is H or (C₁-C₄)-alkyl;
    R²² is H;
    and 1-piperidyl can be further mono-substituted by (C₁-C₆)-alkyl, CO—O—(C₁-C₄)-alkyl or phenyl;

e) a 1,4-diazepanyl of the formula

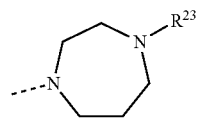

wherein
$R^{23}$ is H, $(C_1-C_6)$-alkyl or CO-4-pyridyl;
f) a fused bicyclic $(C_8-C_{10})$-heterocycloalkyl group containing two nitrogen atoms, which is attached via a nitrogen atom and which can contain one further sulphur atom, wherein said heterocycloalkyl group is unsubstituted or substituted by one to two identical or different substituents selected from the group consisting of $CH_3$, phenyl, methylene-phenyl or oxo (=O);
g) a spiro bicyclic $(C_8-C_{11})$-heterocycloalkyl group containing two nitrogen atoms, which is attached via a nitrogen atom and which can contain one further oxygen atom, wherein said heterocycloalkyl group is unsubstituted or mono- or di-substituted by $CH_3$;
h) a bridged bicyclic $(C_8)$-heterocycloalkyl group containing one nitrogen atom, which is attached via said nitrogen atom, which is substituted by $NH_2$;
i) a bridged bicyclic $(C_7-C_9)$-heterocycloalkyl group containing two nitrogen atoms, which is attached via a nitrogen atom; and which is unsubstituted or substituted by one to four identical or different substituents selected from the group consisting of $CH_3$, $C_2H_5$ and OH;
j) a tricyclic $(C_{14})$-heterocycloalkyl group containing two nitrogen atoms, which is attached via a nitrogen atom and which consists of a spiro bicyclic ring with an additional fused phenyl ring;

or
D) $R^1$ is $CF_3$;
$R^2$ is H;
$R^3$ is H;
$R^4$ is H;
$R^5$ is H;
$R^6$ is H and
$R^7$ is a) 3-azetidyl or 3-piperidyl;
b) a bridged bicyclic $(C_8)$-heterocycloalkyl group containing one nitrogen atom, which is attached via a carbon atom;

or
$R^6$ and $R^7$ together with the N-atom carrying them denote
a) a 1,4-piperazinyl or a 1,4-diazepanyl, which are unsubstituted or mono-substituted by $(C_1-C_4)$-alkyl;
b) a 1-pyrrolidinyl or a 1-piperidyl, which are mono-substituted by $NH_2$ or $NH((C_1-C_4)$-alkyl);
c) a fused bicyclic $(C_8)$-heterocycloalkyl group containing two nitrogen atoms, which is attached via a nitrogen atom;
d) a spiro bicyclic $(C_9-C_{11})$-heterocycloalkyl group containing two nitrogen atoms, which is attached via a nitrogen atom;

or
E) $R^1$ is cyclopropyl;
$R^2$ is H;
$R^3$ is H;
$R^4$ is H;
$R^5$ is H;

$R^6$ and $R^7$ together with the N-atom carrying them denote a 1,4-piperazinyl, which is unsubstituted or substituted by one to two identical or different substituents selected from the group consisting of $(C_1-C_4)$-alkyl and phenyl.

4. The compound of claim 1, wherein
A) $R^1$ is $CH_3$;
$R^2$ is H, F or $CH_3$;
$R^3$ is H or F;
$R^4$ is H;
$R^5$ is H;
$R^6$ is H;
$R^7$ is
a) $(C_0-C_6)$-alkyl which is mono-substituted by
i) azetidyl, pyrrolidinyl, piperidyl, piperazinyl or morpholinyl, which are unsubstituted or substituted by one to five identical or different substituents selected from the group consisting of $CH_3$, $C_2H_5$, $C_3H_7$, O—$CH_3$, O—$C_2H_5$, phenyl, phenylene-methyl, methylene-phenyl, ethylene-phenyl, cyclohexyl, oxo (=O), and (CO)—$CH_3$, and wherein $(C_0-C_6)$-alkyl can be further mono-substituted by phenyl or pyridyl;
ii) $(C_3-C_8)$-cycloalkyl which is substituted by one to two identical or different substituents selected from the group consisting of and $N(CH_3)_2$;
iii) $NR^8R^9$, wherein
$R^8$ is H or $CH_3$, and
$R^9$ is H, $CH_3$, $CH(CH_3)_2$ or $C(CH_3)_3$,
and wherein $(C_0-C_6)$-alkyl can be further mono-substituted by phenyl, phenylene-methyl or phenylene-O-methyl;

or
$R^7$ is
b) a fused bicyclic ring selected from the group consisting of

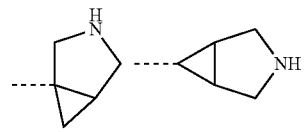

c) a spiro bicyclic ring selected from the group consisting of

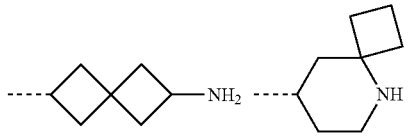

d) a bridged bicyclic ring selected from the group consisting of

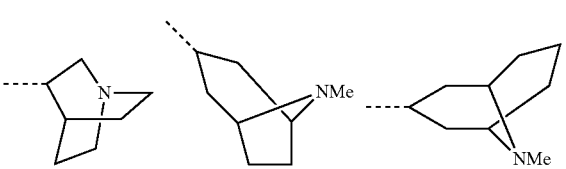

-continued

[structure: bicyclic with -NH2 group]

e) a spiro bicyclic ring with a fused ring selected from the group consisting of

[structure: spiro indane-piperidine]

or

B) R$^1$ is CH$_3$;
R$^2$ is H;
R$^3$ is H or F;
R$^4$ is H;
R$^5$ is H;
R$^6$ is CH$_3$ or (CH$_2$)$_2$-phenyl;
R$^7$ is 4-piperidyl, 4-methyl-4-piperidyl, 3-piperidyl, or t-butyl-aminoethylene;

or

C) R$^1$ is CH$_3$;
R$^2$ is H, CH$_3$, F, Cl or O—CH$_3$;
R$^3$ is H, CH$_3$, F, C$_{1-10}$—CH$_3$ or O—C$_2$H$_5$;
R$^4$ is H or F;
R$^5$ is H, F or CH$_3$;
R$^6$ and R$^7$ together with the N-atom carrying them denote a) a 1,4-piperazinyl of the formula

[structure with R$^{10}$, R$^{11}$, R$^{12}$, R$^{13}$, R$^{14}$, R$^{15}$]

wherein

R$^{10}$ is H, or (C$_0$-C$_4$)-alkyl, which is unsubstituted or substituted threefold by F or mono-substituted by O—CH$_3$, phenyl, pyridyl, furyl, thienyl, benzo[1,3] dioxole or CO—R$^{16}$;
    wherein phenyl is unsubstituted or substituted by one to two identical or different substituents selected from the group consisting of F, Cl, Br, CF$_3$, O—CH$_3$, and CH(CH$_3$)$_2$;
R$^{11}$ is H or (C$_0$-C$_4$)-alkyl, which is unsubstituted or substituted threefold by F or mono-substituted by CO—R$^{17}$, cyclopropyl, phenyl, O—CH$_3$ or oxo (=O);
R$^{12}$ is H, (C$_1$-C$_4$)-alkyl or phenyl;
R$^{13}$ is H or (C$_1$-C$_4$)-alkyl;
R$^{14}$ is H or CH$_3$;
R$^{15}$ is H, (C$_1$-C$_4$)-alkyl, cyclobutyl or CO—R$^{18}$, where (C$_1$-C$_4$)-alkyl is unsubstituted or mono-substituted by SO$_2$—CH$_3$, 4-piperidyl, 2-pyridyl, 4-tetrahydropyranyl or 3-tetrahydrofuryl;
R$^{16}$ is O—CH$_3$ or NH—(C$_1$-C$_4$)-alkyl;
R$^{17}$ is O—CH$_3$;
R$^{18}$ is CH$_3$, NH$_2$, phenyl, 3-fury, 2-tetrahydrofuryl or 1-pyrrolidinyl, where phenyl can be further mono-substituted by CH$_3$ or O—CH$_3$;

b) a 1-azetidinyl, which is mono-substituted by NH$_2$ or (C$_1$-C$_4$)-alkylene-NH$_2$;

c) a 1-pyrrolidinyl, which is mono-substituted by NR$^{19}$R$^{20}$ or 1-cyclopropylamine, wherein
R$^{19}$ is H, CH$_3$ or phenyl;
R$^{20}$ is H or CH$_3$,
    and 1-pyrrolidinyl can be further mono-substituted by (C$_1$-C$_4$)-alkyl or CF$_3$;

d) a 1-piperidyl, which is mono-substituted by NR$^{21}$R$^{22}$ or CH$_2$—NH$_2$, wherein
R$^{21}$ is H or CH$_3$;
R$^{22}$ is H;
    and 1-piperidyl can be further mono-substituted by (C$_1$-C$_4$)-alkyl, CO—OCH$_3$ or phenyl;

e) a 1,4-diazepanyl of the formula

[structure: diazepane with R$^{23}$]

wherein
R$^{23}$ is H, (C$_1$-C$_4$)-alkyl or CO-4-pyridyl;

f) a fused bicyclic ring selected from the group consisting of

[structures: various fused bicyclic ring systems]

-continued

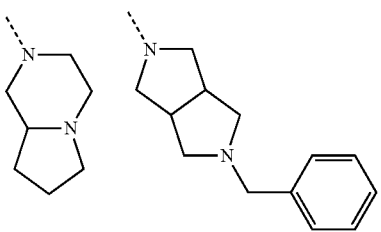

g) a spiro bicyclic ring selected from the group consisting of

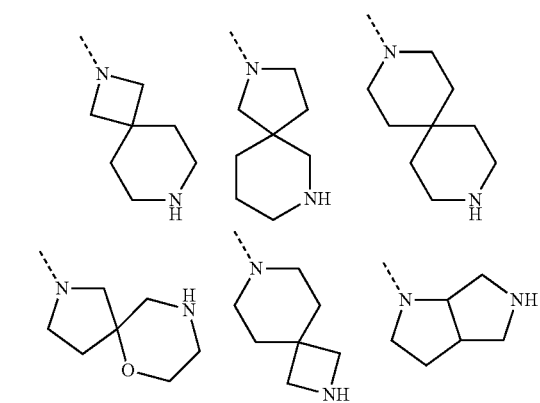

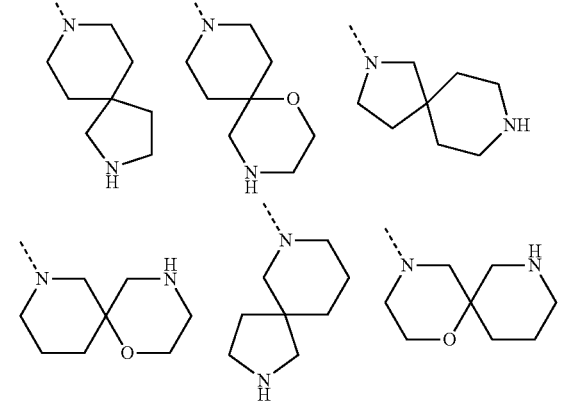

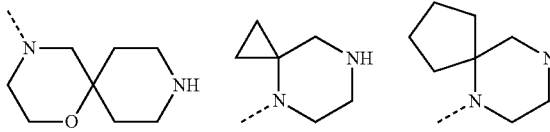

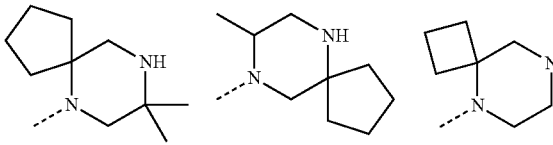

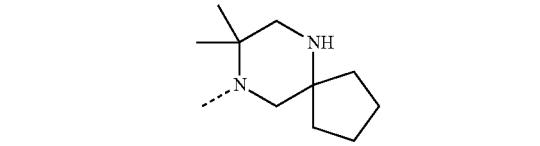

h) a bridged bicyclic ring selected from the group consisting of

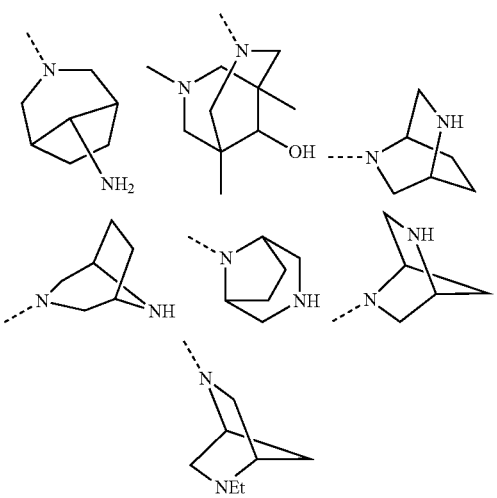

i) a spiro bicyclic ring with a fused ring selected from the group consisting of

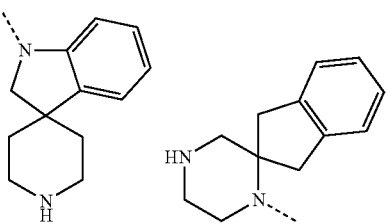

or

D) $R^1$ is $CF_3$;
   $R^2$ is H;
   $R^3$ is H;
   $R^4$ is H;
   $R^5$ is H;
   $R^6$ is H and
   $R^7$ is a) 3-azetidyl or 3-piperidyl;
      b) a bridged bicyclic ring selected from the group consisting of

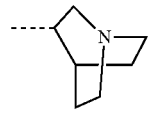

or $R^6$ and $R^7$ together with the N-atom carrying them denote a) a 1,4-piperazinyl or a 1,4-diazepanyl, which are unsubstituted or mono-substituted by $CH_3$ or $C_2H_5$;

b) a 1-pyrrolidinyl or a 1-piperidyl, which are mono-substituted by $NH_2$ or $NH(CH_3)$;

c) a fused bicyclic ring selected from the group consisting of

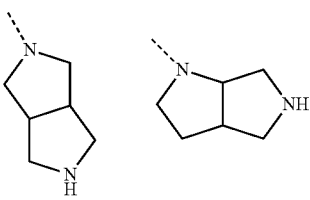

d) a spiro bicyclic ring selected from the group consisting of

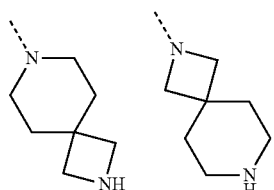

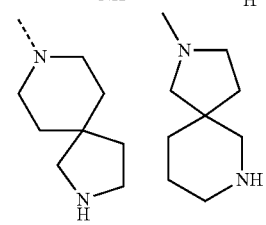

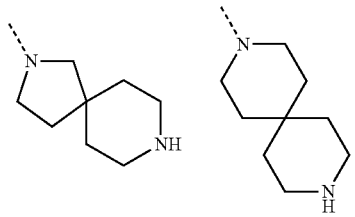

or

E) $R^1$ is $C_2H_5$;
$R^2$ is H;
$R^3$ is H or F;
$R^4$ is H;
$R^5$ is H;
$R^6$ is H and
$R^7$ is a) 3-azetidyl, 3-pyrrolidinyl, 3-piperidyl, 4-piperidyl or methylene-2-pyrrolidinyl, which are unsubstituted or mono-substituted by $CH_3$, $C_2H_5$, $OCH_3$, or oxo (=O);
  b) cyclohexyl, which is mono-substituted by
  c) a bridged bicyclic ring selected from the group consisting of

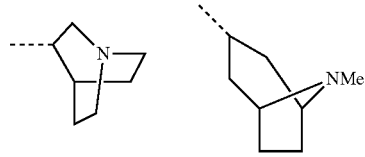

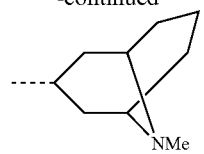

d) a spiro bicyclic ring selected from the group consisting of

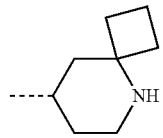

e) a spiro bicyclic ring with a fused ring selected from the group consisting of

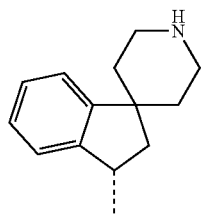

or
$R^6$ is $CH_3$ and
$R^7$ is 4-methyl-4-piperidyl;
or
$R^6$ and $R^7$ together with the N-atom carrying them denote
  a) a 1,4-piperazinyl or a 1,4-diazepanyl, which are unsubstituted or mono-substituted by $CH_3$ or $C_2H_5$;
  b) a 1-azetidinyl, a 1-pyrrolidinyl or a 1-piperidyl, which are mono-substituted by $NH_2$, $NH(CH_3)$ or $N(CH_3)_2$;
  c) a fused bicyclic ring selected from the group consisting of

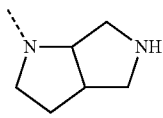

d) a spiro bicyclic ring selected from the group consisting of

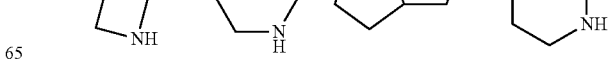

e) a bridged bicyclic ring selected from the group consisting of or

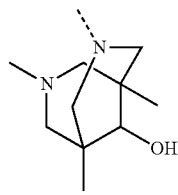

F) $R^1$ is propyl or cyclopropyl;
$R^2$ is H;
$R^3$ is H;
$R^4$ is H;
$R^5$ is H;
$R^6$ and $R^7$ together with the N-atom carrying them denote a 1,4-piperazinyl, which is unsubstituted or substituted by one to two identical or different substituents selected from the group consisting of $CH_3$ and phenyl.

5. The compound of claim 1, wherein
A) $R^1$ is $CH_3$;
$R^2$ is H, F, or $CH_3$;
$R^3$ is H or F;
$R^4$ is H;
$R^5$ is H;
$R^6$ is H;
$R^7$ is
a) 3-azetidinyl,
   3-pyrrolidinyl, which is unsubstituted or mono-substituted by $CH_3$, $C_3H_7$, O—$CH_3$, O—$C_2H_5$, phenyl, phenylene-methyl or methylene-phenyl, 3-piperidyl, which is unsubstituted or mono-substituted by $CH_3$, $C_2H_5$, or $C_3H_7$,
   4-piperidyl, which is unsubstituted or mono-substituted by $CH_3$, $C_2H_5$, $C_3H_7$, phenyl, methylene-phenyl, ethylene-phenyl, cyclohexyl, oxo (=O), and (O)—$CH_3$,
b) ($C_3$-$C_6$)-cycloalkyl which is mono-substituted by $NH_2$ or $N(CH_3)_2$
c) ($C_1$)-alkyl which is mono-substituted by
   i) 3-azetidinyl,
      2-pyrrolidinyl, which is unsubstituted or mono-substituted by oxo (=O),
      2-piperidyl,
      3-piperidyl, which is unsubstituted or mono-substituted by $C_2H_5$;
   ii) ($C_6$-$C_7$)-cycloalkyl, which is mono-substituted by $NH_2$;
d) ($C_2$-$C_4$)-alkyl which is mono-substituted by 1-pyrrolidinyl, 2-pyrrolidinyl, 1-piperazinyl, 1-morpholinyl, 4-piperidyl, which are unsubstituted or mono-substituted by $CH_3$ or phenyl; and wherein ($C_2$-$C_4$)-alkyl can be further mono-substituted by phenyl or pyridyl;
e) ($C_2$-$C_6$)-alkyl which is mono-substituted by $NR^{24}R^{25}$,
   wherein
   $R^{24}$ is H or $CH_3$, and
   $R^{25}$ is H, $CH_3$ or $CH(CH_3)_2$,
   and wherein ($C_2$-$C_6$)-alkyl can be further mono-substituted by phenyl, phenylene-methyl or phenylene-O-methyl;
or
$R^7$ is f) a fused bicyclic ring selected from the group consisting of

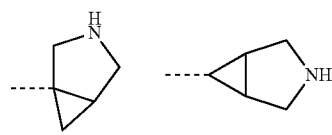

g) a spiro bicyclic ring selected from the group consisting of

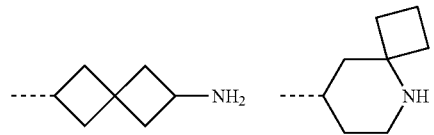

h) a bridged bicyclic ring selected from the group consisting of

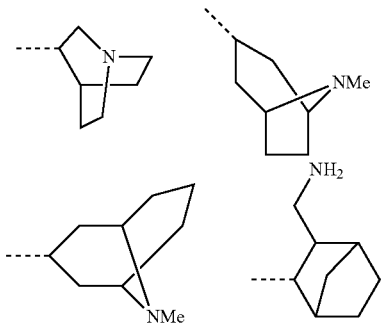

i) a spiro bicyclic ring with a fused ring selected from the group consisting of

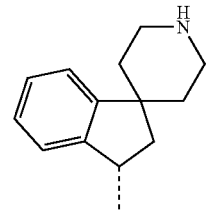

or
B) $R^1$ is $CH_3$;
$R^2$ is H;
$R^3$ is H, F;
$R^4$ is H;
$R^5$ is H;
$R^6$ is $CH_3$, or $(CH_2)_2$-phenyl;
$R^7$ is 4-piperidyl, 4-methyl-4-piperidyl, 3-piperidyl, or t-butyl-aminoethylene;
or
C) $R^1$ is $CH_3$;
$R^2$ is H, $CH_3$, F, Cl, or O—$CH_3$;
$R^3$ is H, $CH_3$, F, $C_{1-10}$—$CH_3$, or O—$C_2H_5$;
$R^4$ is H, or F;
$R^5$ is H, F, or $CH_3$;

$R^6$ and $R^7$ together with the N-atom carrying them denote a) a 1,4-piperazinyl of the formula

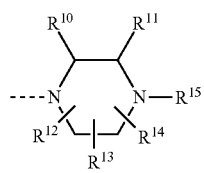

wherein
$R^{11}$ is
 i) H,
 ii) $(C_1$-$C_4)$-alkyl, which is unsubstituted or substituted threefold by F or mono-substituted by O—$CH_3$, or CO—$R^{26}$;
  wherein $R^{26}$ is O—$CH_3$, or NH—$(C_1$-$C_4)$-alkyl;
 iii) phenyl, pyridyl, furyl, thienyl, or benzo[1,3]dioxole, wherein phenyl is unsubstituted or substituted by one to two identical or different substituents selected from the group consisting of F, Cl, Br, $CF_3$, O—$CH_3$, and $CH(CH_3)_2$;
$R^{11}$ is H, or $(C_1$-$C_4)$-alkyl, which is unsubstituted or substituted threefold by F, cyclopropyl, phenyl, methylene-phenyl, $CH_2OCH_3$, or $COOCH_3$;
$R^{12}$ is H, $(C_1$-$C_4)$-alkyl, or phenyl;
$R^{13}$ is H, or $(C_1$-$C_4)$-alkyl;
$R^{14}$ is H, or $CH_3$;
$R^{15}$ is H, $(C_1$-$C_4)$-alkyl, cyclobutyl, or CO—$R^{18}$, where $(C_1$-$C_4)$-alkyl is unsubstituted or mono-substituted by $SO_2$—$CH_3$, 4-piperidyl, 2-pyridyl, 4-tetrahydropyranyl, or 3-tetrahydrofuryl;
$R^{16}$ is O—$CH_3$, or NH—$(C_1$-$C_4)$-alkyl;
$R^{17}$ is O—$CH_3$;
$R^{18}$ is $CH_3$, $NH_2$, phenyl, 3-furyl, 2-tetrahydrofuryl, or 1-pyrrolidinyl, where phenyl can be further mono-substituted by $CH_3$ or O—$CH_3$;
b) a 1-azetidinyl, which is mono-substituted by $NH_2$ or $CH_2$—$NH_2$;
c) a 1-pyrrolidinyl, which is mono-substituted by $NR^{19}R^{20}$ or 1-cyclopropylamine, wherein
$R^{19}$ is H, $CH_3$, or phenyl;
$R^{20}$ is H, or $CH_3$,
 and 1-pyrrolidinyl can be further mono-substituted by $(C_1$-$C_4)$-alkyl or $CF_3$;
d) a 1-piperidyl, which is mono-substituted by $NR^{21}R^{22}$ or CH—, —$NH_2$, wherein
$R^{21}$ is H, or $CH_3$;
$R^{22}$ is H;
 and 1-piperidyl can be further mono-substituted by $(C_1$-$C_4)$-alkyl, CO—$OCH_3$ or phenyl;
e) a 1,4-diazepanyl of the formula

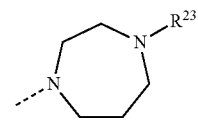

wherein
$R^{23}$ is H, $CH_3$, $C_2H_5$, or CO-4-pyridyl;
f) a fused bicyclic ring selected from the group consisting of

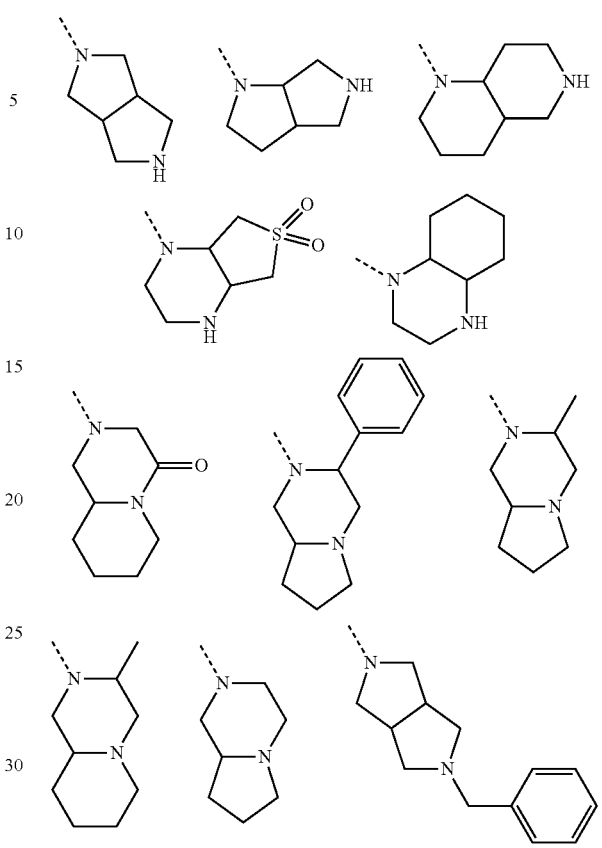

g) a spiro bicyclic ring selected from the group consisting of

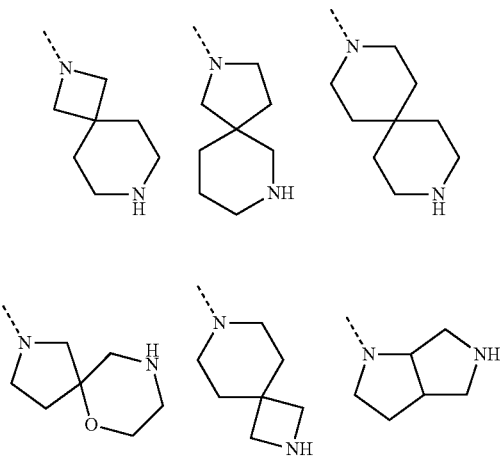

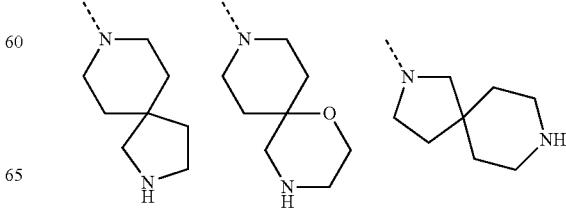

-continued

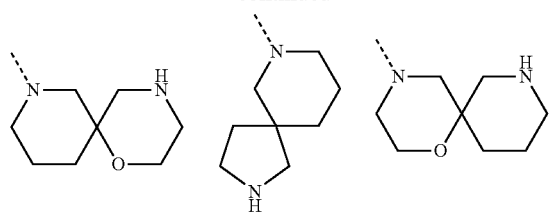

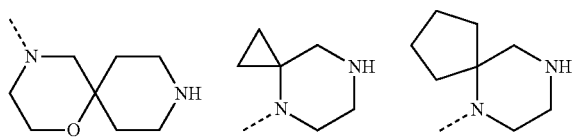

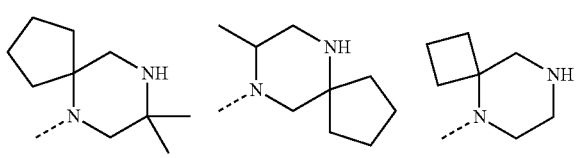

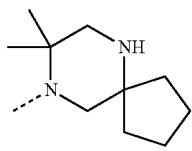

h) a bridged bicyclic ring selected from the group consisting of

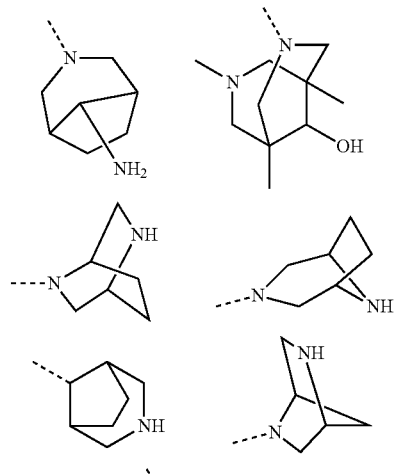

i) a spiro bicyclic ring with a fused ring selected from the group consisting of

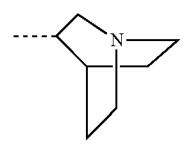

or

D) $R^1$ is $CF_3$;
   $R^2$ is H;
   $R^3$ is H;
   $R^4$ is H;
   $R^5$ is H;
   $R^6$ is H and
   $R^7$ is a) 3-azetidyl, or 3-piperidyl;
      b) a bridged bicyclic ring selected from the group consisting of

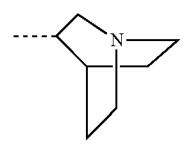

or $R^6$ and $R^7$ together with the N-atom carrying them denote a) a 1,4-piperazinyl or a 1,4-diazepanyl, which are unsubstituted or mono-substituted by $CH_3$ or $C_2H_5$;

b) a 1-pyrrolidinyl or a 1-piperidyl, which is mono-substituted by $NH_2$ or $NH(CH_3)$;

c) a fused bicyclic ring selected from the group consisting of

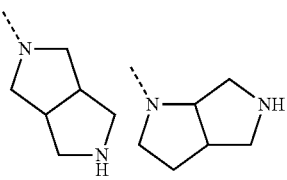

d) a spiro bicyclic ring selected from the group consisting of

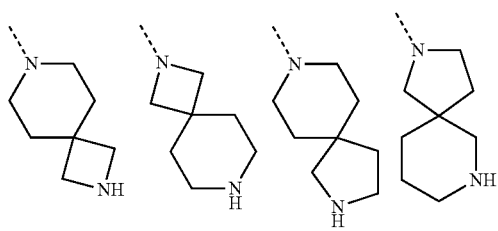

-continued

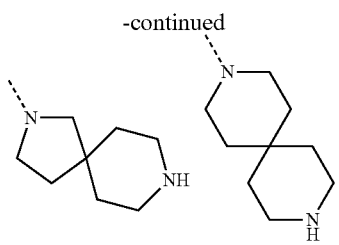

or
E) $R^1$ is $C_2H_5$;
  $R^2$ is H;
  $R^3$ is H, or F;
  $R^4$ is H;
  $R^5$ is H;
  $R^6$ is H and
  $R^7$ is a) 3-azetidyl, 3-pyrrolidinyl, 3-piperidyl, 4-piperidyl or methylene-2-pyrrolidinyl, which are unsubstituted or mono-substituted by $CH_3$, $C_2H_5$, $OCH_3$, or oxo (=O);
    b) cyclohexyl, which is mono-substituted by $NH_2$;
    c) a bridged bicyclic ring selected from the group consisting of

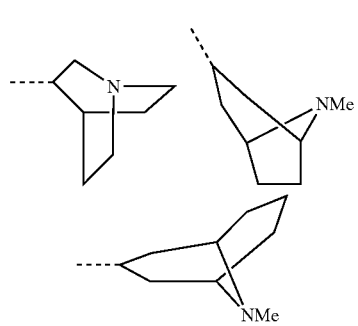

d) a spiro bicyclic ring selected from the group consisting of

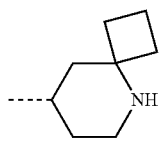

e) a spiro bicyclic ring with a fused ring selected from the group consisting of

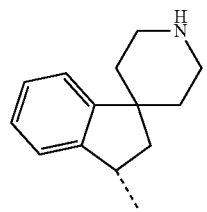

or
  $R^6$ is $CH_3$ and
  $R^7$ is 4-methyl-4-piperidyl;
or
  $R^6$ and $R^7$ together with the N-atom carrying them denote
    a) a 1,4-piperazinyl or a 1,4-diazepanyl, which are unsubstituted or mono-substituted by $CH_3$ or $C_2H_5$;
    b) a 1-azetidinyl, a 1-pyrrolidinyl or a 1-piperidyl, which are mono-substituted by $NH_2$, $NH(CH_3)$ or $N(CH_3)_2$;
    c) a fused bicyclic ring selected from the group consisting of

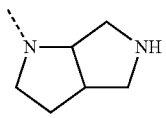

d) a spiro bicyclic ring selected from the group consisting of

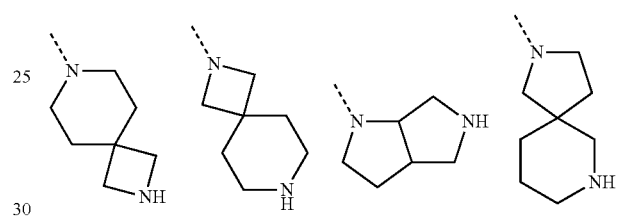

e) a bridged bicyclic ring selected from the group consisting of

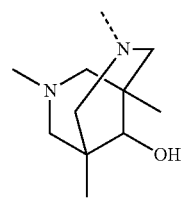

or
F) $R^1$ is propyl or cyclopropyl;
  $R^2$ is H;
  $R^3$ is H;
  $R^4$ is H;
  $R^5$ is H;
  $R^6$ and $R^7$ together with the N-atom carrying them denote a 1,4-piperazinyl, which is unsubstituted or substituted by one to two identical or different substituents selected from the group consisting of $CH_3$ and phenyl.

6. The compound of claim 1, wherein
A) $R^1$ is $CH_3$;
  $R^2$ is H, F, or $CH_3$;
  $R^3$ is H or F;
  $R^4$ is H;
  $R^5$ is H;
  $R^6$ is H;
  $R^7$ is
    a) 3-azetidinyl,
       3-pyrrolidinyl, which is unsubstituted or mono-substituted by $CH_3$, $C_3H_7$, O—$CH_3$, O—$C_2H_5$, phenyl, phenylene-methyl or methylene-phenyl, 3-piperidyl, which is unsubstituted or mono-substituted by $CH_3$, $C_2H_5$, or $C_3H_7$,
4-piperidyl, which is unsubstituted or mono-substituted by $CH_3$, $C_2H_5$, $C_3H_7$, phenyl, methylene-phenyl, ethylene-phenyl, cyclohexyl, oxo (=O), and (CO)—$CH_3$,
b) ($C_3$-$C_6$)-cycloalkyl which is mono-substituted by $NH_2$ or $N(CH_3)_2$
c) ($C_1$)-alkyl which is mono-substituted by
  i) 3-azetidinyl,
    2-pyrrolidinyl, which is unsubstituted or mono-substituted by oxo (=O),
    2-piperidyl,
    3-piperidyl, which is unsubstituted or mono-substituted by $C_2H_5$;
  ii) ($C_6$-$C_7$)-cycloalkyl, which is mono-substituted by $NH_2$;
d) ($C_2$-$C_4$)-alkyl which is mono-substituted by 1-pyrrolidinyl, 2-pyrrolidinyl, 1-piperazinyl, 1-morpholinyl, 4-piperidyl, which are unsubstituted or mono-substituted by $CH^3$ or phenyl; and wherein ($C_2$-$C_4$)-alkyl can be further mono-substituted by phenyl or pyridyl;
e) ($C_2$-$C_6$)-alkyl which is mono-substituted by $NR^{24}R^{25}$,
  wherein
    $R^{24}$ is H or $CH_3$, and
    $R^{25}$ is H, CH3 or $CH(CH_3)_2$,
    and wherein ($C_2$-$C_6$)-alkyl can be further mono-substituted by phenyl, phenylene-methyl or phenylene-O-methyl;
or
B) $R^1$ is $CH_3$;
  $R^2$ is H;
  $R^3$ is H, F;
  $R^4$ is H;
  $R^5$ is H;
  $R^6$ is $CH_3$,
  $R^7$ is 4-piperidyl, 4-methyl-4-piperidyl;
or
C) $R^1$ is $CH_3$;
  $R^2$ is H, $CH_3$, F, Cl;
  $R^3$ is H, $CH_3$, F, Cl;
  $R^4$ is H, or F;
  $R^5$ is H, F, or $CH_3$;
  $R^6$ and $R^7$ together with the N-atom carrying them denote
  a) a 1,4-piperazinyl of the formula

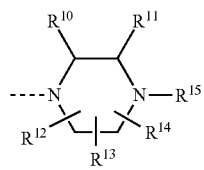

wherein
$R^{10}$ is
  i) H,
  ii) ($C_1$-$C_4$)-alkyl, which is unsubstituted or substituted threefold by F or mono-substituted by O—$CH_3$, or CO—$R^{26}$;
    wherein $R^{26}$ is O—$CH_3$, or NH—($C_1$-$C_4$)-alkyl;
  iii) phenyl, pyridyl, furyl, thienyl, or benzo[1,3]dioxole, wherein phenyl is unsubstituted or substituted by one to two identical or different substituents selected from the group consisting of F, Cl, Br, $CF_3$, O—$CH_3$, and $CH(CH_3)_2$;
$R^{11}$ is H, or ($C_1$-$C_4$)-alkyl, which is unsubstituted or substituted threefold by F, cyclopropyl, phenyl, methylene-phenyl, $CH_2OCH_3$, or $COOCH_3$;
$R^{12}$ is H, ($C_1$-$C_4$)-alkyl, or phenyl;
$R^{13}$ is H, or ($C_1$-$C_4$)-alkyl;
$R^{14}$ is H, or $CH_3$;
$R^{15}$ is H, ($C_1$-$C_4$)-alkyl, cyclobutyl, or CO—$R^{18}$, where ($C_1$-$C_4$)-alkyl is unsubstituted or mono-substituted by $SO_2$—$CH_3$, 4-piperidyl, 2-pyridyl, 4-tetrahydropyranyl, or 3-tetrahydrofuryl;
$R^{16}$ is O—$CH_3$, or NH—($C_1$-$C_4$)-alkyl;
$R^{17}$ is O—$CH_3$;
$R^{18}$ is $CH_3$, $NH_2$, phenyl, 3-furyl, 2-tetrahydrofuryl, or 1-pyrrolidinyl, where phenyl can be further mono-substituted by $CH_3$ or O—$CH_3$;
b) a 1-azetidinyl, which is mono-substituted by $NH_2$ or $CH_2$—$NH_2$;
c) a 1-pyrrolidinyl, which is mono-substituted by $NR^{19}R^{20}$ or 1-cyclopropylamine, wherein
$R^{19}$ is H, $CH_3$, or phenyl;
$R^{20}$ is H, or $CH_3$,
  and 1-pyrrolidinyl can be further mono-substituted by ($C_1$-$C_4$)-alkyl or $CF_3$;
d) a 1-piperidyl, which is mono-substituted by $NR^{21}R^{22}$ or $CH_2$—$NH_2$, wherein
$R^{21}$ is H, or $CH_3$;
$R^{22}$ is H;
  and 1-piperidyl can be further mono-substituted by ($C_1$-$C_4$)-alkyl, CO—$OCH_3$ or phenyl;
e) a 1,4-diazepanyl of the formula

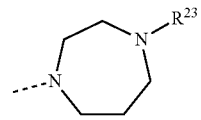

wherein
$R^{23}$ is H, $CH_3$, $C_2H_5$, or CO-4-pyridyl;
f) a fused bicyclic ring selected from the group consisting of

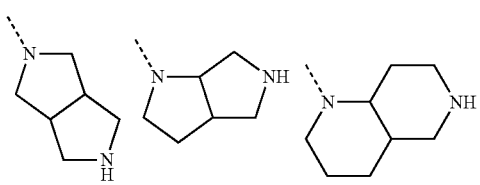

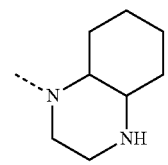

g) a spiro bicyclic ring selected from the group consisting of

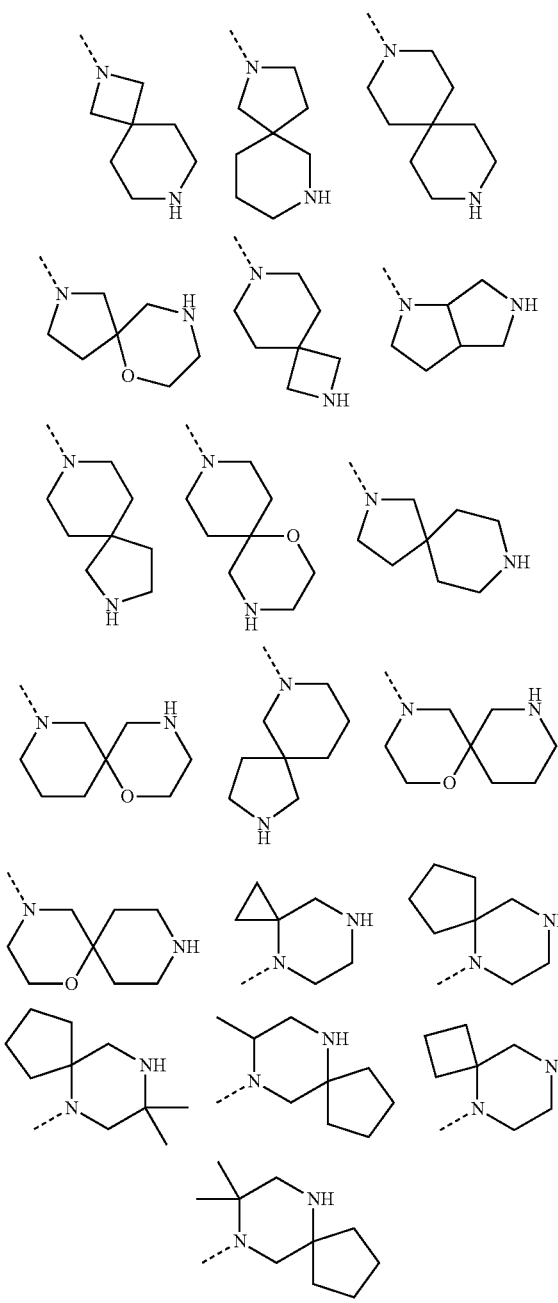

h) a bridged bicyclic ring selected from the group consisting of

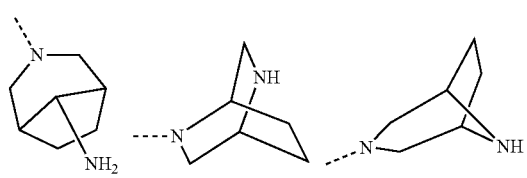

-continued

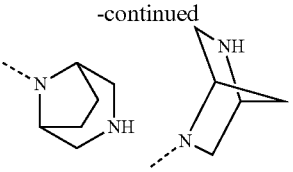

or
D) $R^1$ is $CF_3$;
   $R^2$ is H;
   $R^3$ is H;
   $R^4$ is H;
   $R^5$ is H;
   $R^6$ is H and
   $R^7$ is 3-azetidyl, or 3-piperidyl;
   or
   $R^6$ and $R^7$ together with the N-atom carrying them denote
   a) a 1,4-piperazinyl or a 1,4-diazepanyl, which are unsubstituted or mono-substituted by $CH_3$ or $C_2H_5$;
   b) a 1-pyrrolidinyl or a 1-piperidyl, which is mono-substituted by $NH_2$ or $NH(CH_3)$;
   c) a fused bicyclic ring selected from the group consisting of

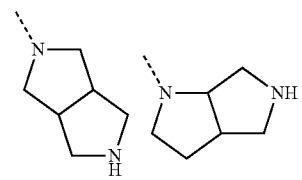

d) a spiro bicyclic ring selected from the group consisting of

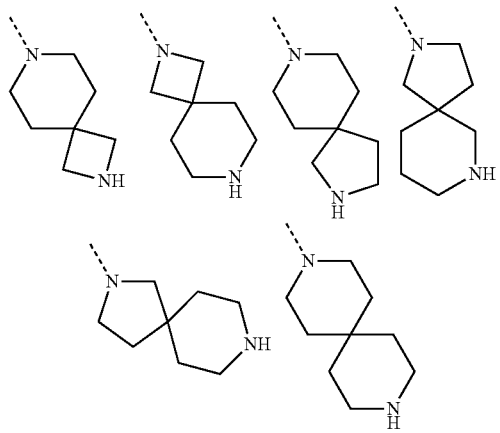

or
E) $R^1$ is $C_2H_5$;
   $R^2$ is H;
   $R^3$ is H;
   $R^4$ is H;
   $R^5$ is H;
   $R^6$ is H and
   $R^7$ is a) 3-azetidyl, 3-pyrrolidinyl, 3-piperidyl, 4-piperidyl or methylene-2-pyrrolidinyl, which are unsubstituted or mono-substituted by $CH_3$, $C_2H_5$, $OCH_3$, or oxo (=O);

b) cyclohexyl, which is mono-substituted by NH-7;
or
$R^6$ is $CH_3$ and
$R^7$ is 4-methyl-4-piperidyl;
or
$R^6$ and $R^7$ together with the N-atom carrying them denote
   a) a 1,4-piperazinyl or a 1,4-diazepanyl, which are unsubstituted or mono-substituted by $CH_3$ or $C_2H_5$;
   b) a 1-azetidinyl, a 1-pyrrolidinyl or a 1-piperidyl, which are mono-substituted by $NH_2$, $NH(CH_3)$ or $N(CH_3)_2$;
   c) a fused bicyclic ring selected from the group consisting of

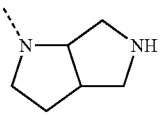

d) a spiro bicyclic ring selected from the group consisting of

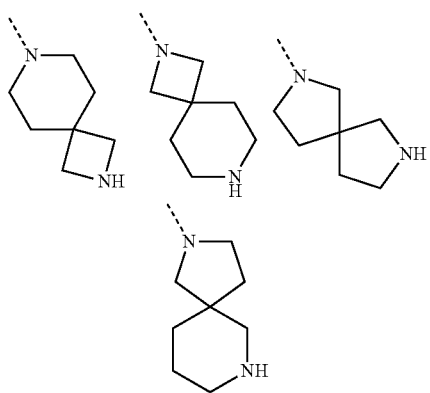

or
F) $R^1$ is propyl or cyclopropyl;
   $R^2$ is H;
   $R^3$ is H;
   $R^4$ is H;
   $R^5$ is H;
   $R^6$ and $R^7$ together with the N-atom carrying them denote a 1,4-piperazinyl, which is unsubstituted or substituted by one to two identical or different substituents selected from the group consisting of $CH_3$ and phenyl.

7. The compound of claim 1, wherein
A) $R^1$ is $CH_3$;
   $R^2$ is H, F, or $CH_3$;
   $R^3$ is H or F;
   $R^4$ is H;
   $R^5$ is H;
   $R^6$ is H; and
   $R^7$ is
   a) 3-azetidinyl,
      3-pyrrolidinyl, which is unsubstituted or mono-substituted by $CH_3$, $C_3H_7$, O—$CH_3$, O—$C_2H_5$, phenyl, phenylene-methyl or methylene-phenyl,
      3-piperidyl, which is unsubstituted or mono-substituted by $CH_3$, $C_2H_5$, or $C_3H_7$,
      4-piperidyl, which is unsubstituted or mono-substituted by $CH_3$, $C_2H_5$, $C_3H_7$, phenyl, methylene-phenyl, ethylene-phenyl, cyclohexyl, oxo (=O), and (O)—$CH_3$,
   b) $(C_3-C_6)$-cycloalkyl which is mono-substituted by $NH_2$ or $N(CH_3)_2$
   c) $(C_1)$-alkyl which is mono-substituted by
      i) 3-azetidinyl,
         2-pyrrolidinyl, which is unsubstituted or mono-substituted by oxo (=O),
         2-piperidyl,
         3-piperidyl, which is unsubstituted or mono-substituted by $C_2H_5$;
      ii) $(C_6-C_7)$-cycloalkyl, which is mono-substituted by $NH_2$;
   d) $(C_2-C_4)$-alkyl which is mono-substituted by 1-pyrrolidinyl, 2-pyrrolidinyl, 1-piperazinyl, 1-morpholinyl, 4-piperidyl, which are unsubstituted or mono-substituted by $CH_3$ or phenyl; and wherein $(C_2-C_4)$-alkyl can be further mono-substituted by phenyl or pyridyl;
   e) $(C_2-C_6)$-alkyl which is mono-substituted by $NR^{24}R^{25}$,
      wherein
      $R^{24}$ is H or $CH_3$, and
      $R^{25}$ is H, $CH_3$ or $CH(CH_3)_2$,
      and wherein $(C_2-C_6)$-alkyl can be further mono-substituted by phenyl, phenylene-methyl or phenylene-O-methyl;
or
$R^6$ and $R^7$ together with the N-atom carrying them denote
   a) a 1,4-piperazinyl of the formula

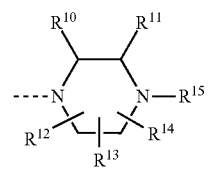

wherein
$R^{10}$ is
   i) H,
   ii) $(C_1-C_4)$-alkyl, which is unsubstituted or substituted threefold by F or mono-substituted by O—$CH_3$, or CO—$R^{26}$;
      wherein $R^{26}$ is O—$CH_3$, or NH—$(C_1-C_4)$-alkyl;
   iii) phenyl, pyridyl, furyl, thienyl, or benzo[1,3]dioxole, wherein phenyl is unsubstituted or substituted by one to two identical or different substituents selected from the group consisting of F, Cl, Br, $CF_3$, O—$CH_3$, and $CH(CH_3)_2$;
$R^{11}$ is H, or $(C_1-C_4)$-alkyl, which is unsubstituted or substituted threefold by F, cyclopropyl, phenyl, methylene-phenyl, $CH_2OCH_3$, or $COOCH_3$;
$R^{12}$ is H, $(C_1-C_4)$-alkyl, or phenyl;
$R^{13}$ is H, or $(C_1-C_4)$-alkyl;
$R^{14}$ is H, or $CH_3$;
$R^{15}$ is H, $(C_1-C_4)$-alkyl, cyclobutyl, or CO—$R^{18}$, where $(C_1-C_4)$-alkyl is unsubstituted or mono-substituted by $SO_2$—$CH_3$, 4-piperidyl, 2-pyridyl, 4-tetrahydropyranyl, or 3-tetrahydrofuryl;
$R^{16}$ is O—$CH_3$, or NH—$(C_1-C_4)$-alkyl;

$R^{17}$ is O—$CH_3$;

$R^{18}$ is $CH_3$, $NH_2$, phenyl, 3-furyl, 2-tetrahydrofuryl, or 1-pyrrolidinyl, where phenyl can be further mono-substituted by $CH_3$ or O—$CH_3$;

b) a 1-azetidinyl, which is mono-substituted by $NH_2$ or $CH_2$—$NH_2$;

c) a 1-pyrrolidinyl, which is mono-substituted by $NR^{19}R^{20}$ or 1-cyclopropylamine, wherein $R^{19}$ is H, $CH_3$, or phenyl;

$R^{20}$ is H, or $CH_3$, and 1-pyrrolidinyl can be further mono-substituted by ($C_1$-$C_4$)-alkyl or $CF_3$;

d) a 1-piperidyl, which is mono-substituted by $NR^{21}R^{22}$ or $CH_2$—$NH_2$, wherein $R^{21}$ is H, or $CH_3$;

$R^{22}$ is H;

and 1-piperidyl can be further mono-substituted by ($C_1$-$C_4$)-alkyl, CO—$OCH_3$ or phenyl;

e) a 1,4-diazepanyl of the formula

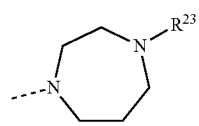

wherein $R^{23}$ is H, $CH_3$, $C_2H_5$, or CO-4-pyridyl;

f) a fused bicyclic ring selected from the group consisting of

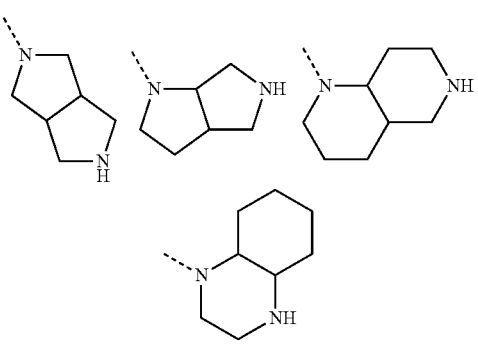

g) a spiro bicyclic ring selected from the group consisting of

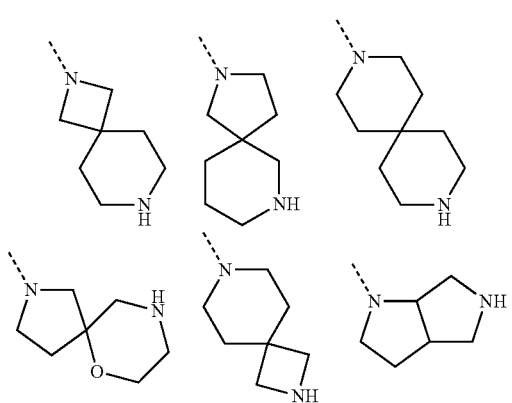

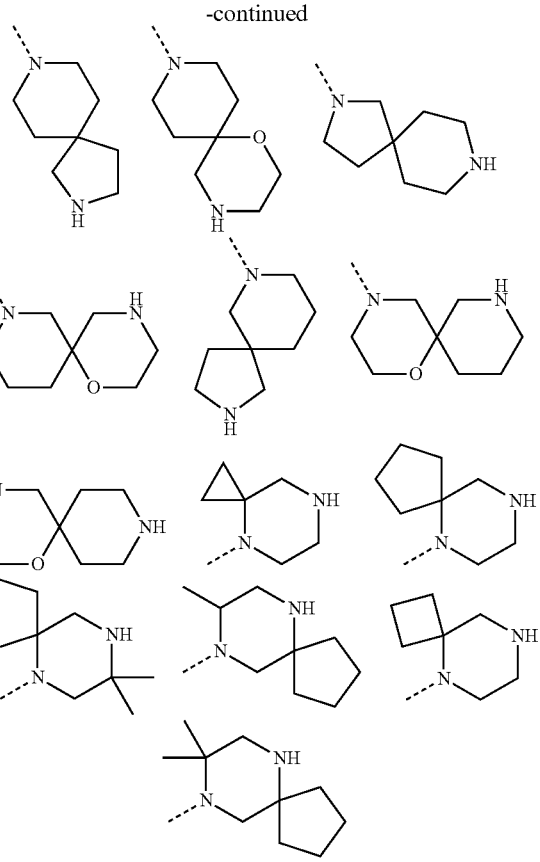

h) a bridged bicyclic ring selected from the group consisting of

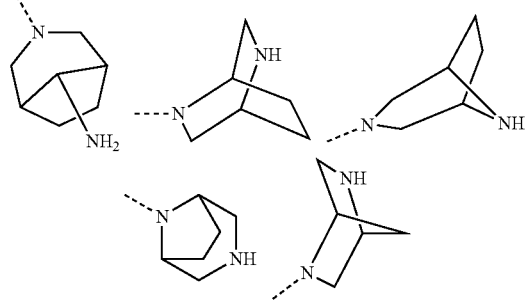

or

B) $R^1$ is $CF_3$, or $C_2H_5$;

$R^2$ is H;

$R^3$ is H;

$R^4$ is H;

$R^5$ is H;

$R^6$ is H and $R^7$ is 3-azetidyl, or 3-piperidyl;

or $R^6$ and $R^7$ together with the N-atom carrying them denote a) a 1,4-piperazinyl or a 1,4-diazepanyl, which are unsubstituted or mono-substituted by $CH_3$ or $C_2H_5$;

b) a 1-pyrrolidinyl or a 1-piperidyl, which is mono-substituted by $NH_2$ or $NH(CH_3)$;

c) a fused bicyclic ring selected from the group consisting of

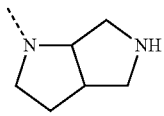

d) a spiro bicyclic ring selected from the group consisting of

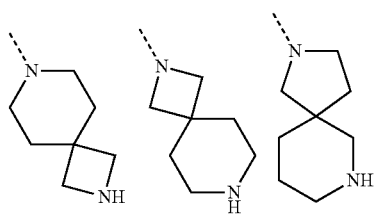

or

C) $R^1$ is propyl or cyclopropyl;
$R^2$ is H;
$R^3$ is H;
$R^4$ is H;
$R^5$ is H;
$R^6$ and $R^7$ together with the N-atom carrying them denote a 1,4-piperazinyl, which is unsubstituted or substituted by one to two identical or different substituents selected from the group consisting of $CH_3$ and phenyl.

8. The compound of claim 1, wherein
A) $R^1$ is $CH_3$;
$R^2$ is H, F, or $CH_3$;
$R^3$ is H or F;
$R^4$ is H;
$R^5$ is H;
$R^6$ is H; and
$R^7$ is
a) 3-pyrrolidinyl, which is unsubstituted or mono-substituted by $CH_3$, $C_3H_7$, O—$CH_3$, O—$C_2H_5$, phenyl or methylene-phenyl,
3-piperidyl, which is unsubstituted or mono-substituted by $CH_3H_5$, or $C_3H_7$,
4-piperidyl, which is unsubstituted or mono-substituted by $CH_3$, $C_2H_5$, $C_3H_7$, phenyl, methylene-phenyl;
b) $(C_3-C_6)$-cycloalkyl which is mono-substituted by $NH_2$ or $N(CH_3)_2$
c) $(C_1)$-alkyl which is mono-substituted by
i) 2-pyrrolidinyl,
2-piperidyl,
3-piperidyl, which is unsubstituted or mono-substituted by $C_2H_5$;
ii) $(C_6-C_7)$-cycloalkyl, which is mono-substituted by $NH_2$;
d) $(C_2-C_4)$-alkyl which is mono-substituted by 1-pyrrolidinyl, 2-pyrrolidinyl, 1-piperazinyl, 1-morpholinyl, 4-piperidyl, which are unsubstituted or mono-substituted by $CH_3$ or phenyl; and wherein $(C_2-C_4)$-alkyl can be further mono-substituted by phenyl or pyridyl;
e) $(C_2-C_6)$-alkyl which is mono-substituted by $NR^{24}R^{25}$, wherein
$R^{24}$ is H or $CH_3$, and
$R^{25}$ is H, $CH_3$ or $CH(CH_3)_2$,
and wherein $(C_2-C_6)$-alkyl can be further mono-substituted by phenyl;
or
$R^6$ and $R^7$ together with the N-atom carrying them denote
a) a 1,4-piperazinyl of the formula

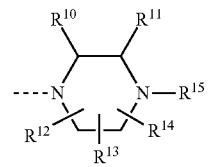

wherein
$R^{10}$ is
a) H,
b) $(C_1-C_3)$-alkyl, $CF_3$
c) phenyl, 3-pyridyl, 2-furyl, 2-thienyl, wherein phenyl is unsubstituted or substituted by one to two identical or different substituents selected from the group consisting of F, Cl, and $CF_3$;
$R^{11}$ is H, $(C_1-C_4)$-alkyl, $CF_3$, cyclopropyl, or phenyl;
$R^{12}$ is H, $(C_1-C_3)$-alkyl, or phenyl;
$R^{13}$ is H, or $(C_1-C_4)$-alkyl;
$R^{14}$ is H, or $CH_3$;
$R^{15}$ is H;
b) a 1-pyrrolidinyl, which is mono-substituted by $NR^{19}R^{20}$, wherein
$R^{19}$ is H, $CH_3$;
$R^{20}$ is H, or $CH_3$,
and 1-pyrrolidinyl can be further mono-substituted by $(C_1-C_4)$-alkyl or $CF_3$;
c) a 1-piperidyl, which is mono-substituted by $NR^{21}R^{22}$ or $CH_2$—$NH_2$, wherein
$R^{21}$ is H, or $CH_3$;
$R^{22}$ is H;
and 1-piperidyl can be further mono-substituted by $(C_1-C_4)$-alkyl, or phenyl;
d) a 1,4-diazepanyl of the formula

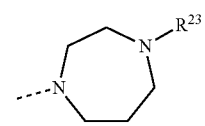

wherein
$R^{23}$ is H;
e) a fused bicyclic ring selected from the group consisting of

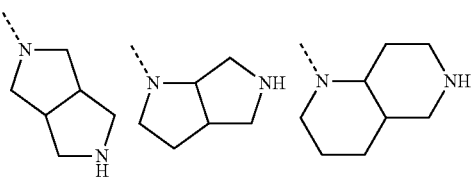

-continued

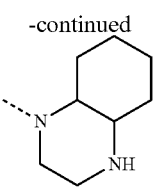

f) a spiro bicyclic ring selected from the group consisting of

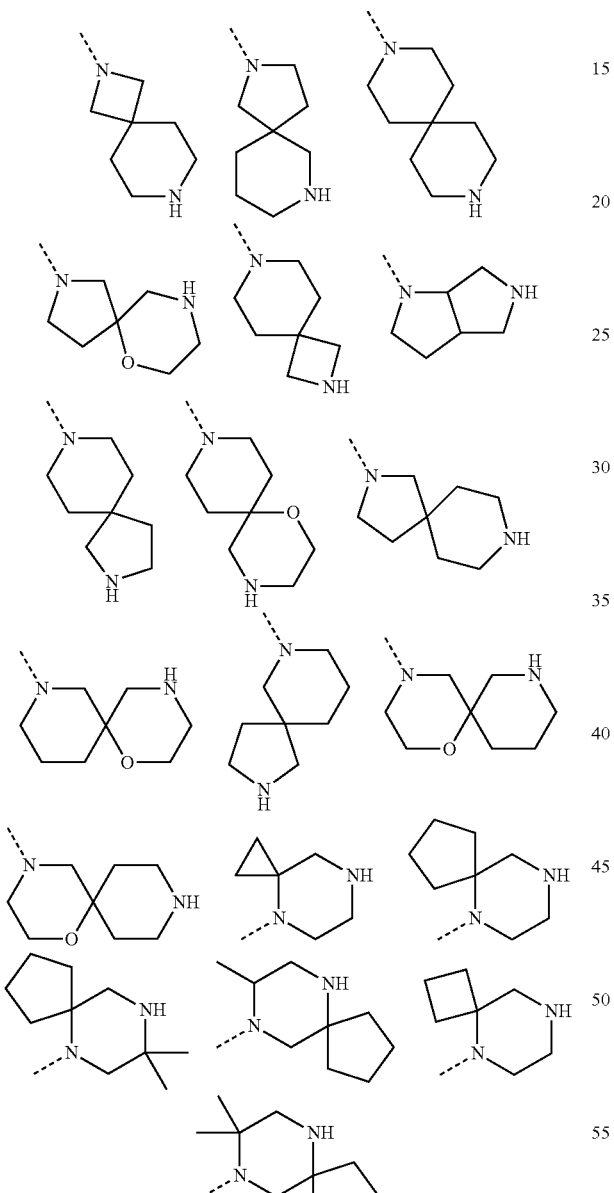

or
B) $R^1$ is $CF_3$, or $C_2H_5$;
$R^2$ is H;
$R^3$ is H;
$R^4$ is H;
$R^5$ is H;
$R^6$ is H and
$R^7$ is 3-azetidyl, or 3-piperidyl;
or
$R^6$ and $R^7$ together with the N-atom carrying them denote
a) a 1,4-piperazinyl or a 1,4-diazepanyl, which are unsubstituted or mono-substituted by $CH_3$ or $C_2H_5$;
b) a 1-pyrrolidinyl or a 1-piperidyl, which is mono-substituted by $NH_2$ or $NH(CH_3)$;
c) a fused bicyclic ring selected from the group consisting of

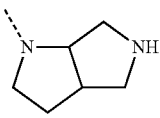

d) a spiro bicyclic ring selected from the group consisting of

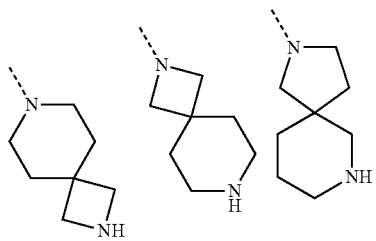

or
C) $R^1$ is propyl or cyclopropyl;
$R^2$ is H;
$R^3$ is H;
$R^4$ is H;
$R^5$ is H;
$R^6$ and $R^7$ together with the N-atom carrying them denote a 1,4-piperazinyl, which is unsubstituted or substituted by one to two identical or different substituents selected from the group consisting of $CH_3$ and phenyl.

9. A pharmaceutical composition comprising at least one compound of formula I

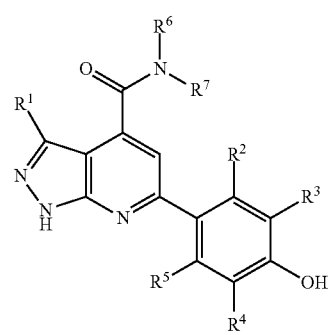

wherein
$R^1$ is $(C_1-C_4)$-alkyl, cyclopropyl, or $CF_3$;
$R^2$ is H, $(C_1-C_4)$-alkyl, halogen or $O—(C_1-C_4)$-alkyl;
$R^3$ is H, $(C_1-C_4)$-alkyl, halogen or $O—(C_1-C_4)$-alkyl;
$R^4$ is H or halogen;

$R^5$ is H, halogen or $(C_1-C_4)$-alkyl;
$R^6$ is H, $(C_1-C_4)$-alkyl or $(C_1-C_4)$-alkylene-phenyl;
$R^7$ is
a) $(C_0-C_6)$-alkyl which is mono-substituted by
   i) a 3- to 8-membered monocyclic heterocycle comprising a ring nitrogen atom and optionally one further ring heteroatom selected from the group consisting of nitrogen and oxygen, which is unsubstituted or substituted by one to five identical or different substituents selected from the group consisting of
      ia) F,
      ib) $(C_1-C_4)$-alkyl, which is unsubstituted or one to fivefold substituted by F,
      ic) O—$(C_1-C_4)$-alkyl, which is unsubstituted or one to fivefold substituted by F,
      id) phenyl, which is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F,
      ie) $(C_1-C_4)$-alkylene-phenyl, which is unsubstituted or one to fivefold substituted by F,
      if) $(C_3-C_8)$-cycloalkyl,
      ig) oxo (=O), and
      ih) (CO)—$(C_1-C_4)$-alkyl, and
      ij) $(C_0-C_7)$-alkylene-NH$_2$, $(C_0-C_2)$-alkylene-NH—$(C_1-C_4)$-alkyl, $(C_0-C_2)$-alkylene-N(($C_1-C_4$)-alkyl)$_2$;
      and wherein $(C_0-C_6)$-alkyl can be further mono-substituted by phenyl or pyridyl, wherein phenyl or pyridyl is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F;
   ii) $(C_3-C_8)$-cycloalkyl which is substituted by one to two identical or different substituents selected from the group consisting of NH(($C_1-C_4$)-alkyl) and N(($C_1-C_4$)-alkyl)$_2$, and wherein $(C_3-C_8)$-cycloalkyl can be further substituted by one to three identical or different substituents selected from the group consisting of
      iia) F,
      iib) $(C_1-C_4)$-alkyl, wherein $(C_1-C_4)$-alkyl is unsubstituted or one to fivefold substituted by F,
      iic) O—$(C_1-C_4)$-alkyl, which is unsubstituted or one to fivefold substituted by F,
      iid) phenyl, which is unsubstituted or substituted by one to two identical or different substituents selected from the group consisting of halogen and $(C_1-C_4)$-alkyl, wherein $(C_1-C_4)$-alkyl is unsubstituted or one to fivefold substituted by F, and
      iie) $(C_1-C_4)$-alkylene-phenyl, which is unsubstituted or one to fivefold substituted by F;
   or
   iii) NR$^8$R$^9$, wherein
      R$^8$ is H or $(C_1-C_4)$-alkyl, and
      R$^9$ is H or $(C_1-C_6)$-alkyl,
      and wherein $(C_0-C_6)$-alkyl can be further mono-substituted by phenyl, phenylene-$(C_1-C_4)$-alkyl or phenylene-O—$(C_1-C_4)$-alkyl;
b) a bicyclic $(C_6-C_{11})$-cycloalkyl group, which is mono-substituted by $(C_0-C_2)$-alkylene-NH$_2$, $(C_0-C_2)$-alkylene-NH-$(C_1-C_4)$-alkyl, or $(C_0-C_2)$-alkylene-N(($C_1-C_4$)-alkyl)$_2$;
c) a fused bicyclic $(C_6-C_{10})$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F;
d) a spiro bicyclic $(C_7-C_{11})$-heterocycloalkyl group containing one nitrogen atom, which is attached via a carbon atom and which is unsubstituted or substituted by one or two identical or different substituents selected from the group consisting of F and $(C_1-C_4)$-alkyl, which is unsubstituted or one to fivefold substituted by F;
e) a bridged bicyclic $(C_7-C_9)$-heterocycloalkyl group containing one nitrogen atom, which is attached via a carbon atom and which is unsubstituted or substituted by one or two identical or different substituents selected from the group consisting of F and $(C_1-C_4)$-alkyl which is unsubstituted or one to fivefold substituted by F; or
f) a tricyclic $(C_{11}-C_{15})$-heterocycloalkyl group containing one nitrogen atom, which is attached via a carbon atom and which consists of a spiro bicyclic ring with an additional fused phenyl ring, and which is unsubstituted or substituted by one or two identical or different substituents selected from the group consisting of F and $(C_1-C_4)$-alkyl, which is unsubstituted or one to fivefold substituted by F;
or
$R^6$ and $R^7$ together with the N-atom carrying them denote
a) a 1,4-piperazinyl of the formula wherein
$R^{10}$ is H, or $(C_0-C_6)$-alkyl, which is unsubstituted or one to fivefold substituted by F, or mono-substituted by a substituent selected from the group consisting of
   i) O—$(C_1-C_4)$-alkyl, which is unsubstituted or one to fivefold substituted by F,
   ii) $(C_3-C_6)$-cycloalkyl,
   iii) phenyl, which is unsubstituted or substituted by one to two identical or different substituents selected from the group consisting of halogen, CF$_3$, O—$(C_1-C_4)$-alkyl, OCF$_3$, and $(C_1-C_4)$-alkyl,
   iv) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, CF$_3$, O—$(C_1-C_4)$-alkyl, OCF$_3$, and $(C_1-C_4)$-alkyl,
   v) benzo[1,3]dioxole, and
   vi) CO—R$^{16}$;
$R^{11}$ is H or $(C_0-C_6)$-alkyl, which is unsubstituted or one to fivefold substituted by F or mono-substituted by a substituent selected from the group consisting of
   i) CO—R$^{17}$,
   ii) $(C_3-C_6)$-cycloalkyl, iii) phenyl, which is unsubstituted or substituted by one to two identical or different substituents selected from the group consisting of halogen, $CF_3$, $OCF_3$, and $(C_1-C_4)$-alkyl,
iv) O—$(C_1-C_4)$-alkyl, which is unsubstituted or one to fivefold substituted by F,
v) a 5- to 6-membered monocyclic heteroaromatic ring comprising one heteroatom selected from the group consisting of nitrogen, oxygen, and sulphur, which is unsubstituted or substituted by one to two identical or different substituents selected from the group consisting of halogen, $CF_3$, $OCF_3$, and $(C_1-C_4)$-alkyl, and
vi) oxo (═O);
$R^{12}$ is H, $(C_1-C_6)$-alkyl, which is unsubstituted or one to fivefold substituted by F, or phenyl;
$R^{13}$ is H or $(C_1-C_6)$-alkyl;
$R^{14}$ is H or $(C_1-C_4)$-alkyl;
$R^{15}$ is H, $(C_1-C_6)$-alkyl, $(C_3-C_6)$-cycloalkyl or CO—$R^{18}$, wherein $(C_1-C_4)$-alkyl is unsubstituted or one to fivefold substituted by F, or mono-substituted by a substituent selected from the group consisting of $SO_2$—$(C_1-C_4)$-alkyl, phenyl, a 5- to 6-membered monocyclic heterocyclic ring comprising one heteroatom selected from the group consisting of nitrogen and oxygen, a 5- to 6-membered monocyclic heteroaromatic ring comprising one heteroatom selected from the group consisting of nitrogen and oxygen;
$R^{16}$ is O—$(C_1-C_4)$-alkyl or NH—$(C_1-C_6)$-alkyl;
$R^{17}$ is O—$(C_1-C_4)$-alkyl;
$R^{18}$ is $(C_1-C_4)$-alkyl, $NH_2$, phenyl, a 5- to 6-membered monocyclic heterocyclic ring comprising one heteroatom selected from the group consisting of nitrogen and oxygen, or a 5- to 6-membered monocyclic heteroaromatic ring comprising one heteroatom selected from the group consisting of nitrogen and oxygen, where phenyl can be further mono-substituted by $(C_1-C_4)$-alkyl or O—$(C_1-C_4)$-alkyl;
b) a four to seven membered monocyclic heterocycloalkyl group containing a nitrogen atom, which is attached via said nitrogen and which is mono-substituted by $(C_0-C_5)$-alkylene-N117, $(C_0-C_6)$-alkylene-NH—$(C_1-C_4)$-alkyl, $(C_0-C_6)$-alkylene-NH-phenyl, $(C_0-C_6)$-alkylene-N$((C_1-C_4)$-alkyl$)_2$, or $(C_0-C_6)$-alkylene-N$((C_1-C_4)$-alkyl$)$(phenyl); and wherein said heterocycloalkyl group can be further mono-substituted by $(C_1-C_6)$-alkyl, which is unsubstituted or one to fivefold substituted by F, CO—O $(C_1-C_4)$-alkyl or phenyl;
c) a 1,4-diazepanyl, which is unsubstituted or mono-substituted by $(C_1-C_6)$-alkyl, wherein $(C_1-C_6)$-alkyl is unsubstituted or one to fivefold substituted by F, CO-phenyl, or CO-pyridyl;
d) a fused bicyclic $(C_6-C_{10})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or substituted by one to two identical or different substituents selected from the group consisting of F, $(C_0-C_2)$-alkylene-phenyl, oxo (═O) and $(C_1-C_4)$-alkyl, wherein $(C_1-C_4)$-alkyl is unsubstituted or one to fivefold substituted by F;
e) a spiro bicyclic $(C_7-C_{11})$-heterocycloalkyl group containing two nitrogen atoms, which is attached via a nitrogen atom and which can contain one further heteroatom selected from the group consisting of nitrogen, oxygen and sulphur, wherein said heterocycloalkyl group is unsubstituted or mono- or di-substituted by F or $(C_1-C_4)$-alkyl, which is unsubstituted or one to fivefold substituted by F;
f) a bridged bicyclic $(C_7-C_9)$-heterocycloalkyl group containing one nitrogen atom, which is attached via said nitrogen atom, which is mono-substituted by $(C_0-C_2)$-alkylene-$NH_2$, $(C_0-C_2)$-alkylene-NH—$(C_1-C_4)$-alkyl, $(C_0-C_2)$-alkylene-N$((C_1-C_4)$-alkyl$)_2$
g) a bridged bicyclic $(C_7-C_9)$-heterocycloalkyl group containing two nitrogen atoms, which is attached via a nitrogen atom; and which is unsubstituted or substituted by one to four identical or different substituents selected from the group consisting of the group consisting of F, OH, and $(C_1-C_4)$-alkyl, which is unsubstituted or one to fivefold substituted by F;
or
h) a tricyclic $(C_{11}-C_{15})$-heterocycloalkyl group containing two nitrogen atoms, which is attached via a nitrogen atom and which consists of a spiro bicyclic ring with an additional fused phenyl ring, and which is unsubstituted or substituted by one or two identical or different substituents selected from the group consisting of F and $(C_1-C_4)$-alkyl, which is unsubstituted or one to fivefold substituted by F;
in any of its stereoisomeric forms, or a mixture of stereoisomeric forms in any ratio, or a physiologically acceptable salt thereof, or a physiologically acceptable solvate of any of them, and a pharmaceutically acceptable carrier.

10. A pharmaceutical composition comprising the compound of claim 1.

11. A method of treating diabetes comprising administering to a human in need thereof a therapeutically effective amount of the compound of claim 1.

* * * * *